(12) United States Patent
Ellsworth et al.

(10) Patent No.: US 9,714,231 B2
(45) Date of Patent: Jul. 25, 2017

(54) PYRROLIDINE GPR40 MODULATORS

(71) Applicant: BRISTOL-MYERS SQUIBB COMPANY, Princeton, NJ (US)

(72) Inventors: Bruce A. Ellsworth, Princeton, NJ (US); Elizabeth A. Jurica, Robbinsville, NJ (US); Jun Shi, Pennington, NJ (US); William R. Ewing, Yardley, PA (US); Xiang-Yang Ye, Princeton, NJ (US); Ximao Wu, Princeton Junction, NJ (US); Zhu Yeheng, Stockton, NJ (US); Sun Chongqing, East Windsor, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 72 days.

(21) Appl. No.: 14/442,642

(22) PCT Filed: Nov. 15, 2013

(86) PCT No.: PCT/US2013/070213
§ 371 (c)(1),
(2) Date: May 13, 2015

(87) PCT Pub. No.: WO2014/078609
PCT Pub. Date: May 22, 2014

(65) Prior Publication Data
US 2016/0280680 A1   Sep. 29, 2016

Related U.S. Application Data

(60) Provisional application No. 61/727,253, filed on Nov. 16, 2012.

(51) Int. Cl.
| | | |
|---|---|---|
| *A61K 31/4025* | (2006.01) | |
| *A61K 31/454* | (2006.01) | |
| *A61K 31/4545* | (2006.01) | |
| *A61K 31/5025* | (2006.01) | |
| *A61K 31/506* | (2006.01) | |
| *C07D 401/12* | (2006.01) | |
| *C07D 401/14* | (2006.01) | |
| *C07D 487/04* | (2006.01) | |
| *A61K 45/06* | (2006.01) | |
| *C07D 207/08* | (2006.01) | |
| *C07D 207/12* | (2006.01) | |
| *C07D 401/10* | (2006.01) | |

(52) U.S. Cl.
CPC ........ *C07D 401/12* (2013.01); *A61K 31/4025* (2013.01); *A61K 31/454* (2013.01); *A61K 31/4545* (2013.01); *A61K 31/506* (2013.01); *A61K 31/5025* (2013.01); *A61K 45/06* (2013.01); *C07D 207/08* (2013.01); *C07D 207/12* (2013.01); *C07D 401/10* (2013.01); *C07D 401/14* (2013.01); *C07D 487/04* (2013.01)

(58) Field of Classification Search
None
See application file for complete search history.

(56) References Cited

U.S. PATENT DOCUMENTS

| | | |
|---|---|---|
| 5,614,492 A | 3/1997 | Habener |
| 8,791,091 B2 | 7/2014 | Turdi et al. |
| 2011/0082165 A1 | 4/2011 | Ellsworth et al. |

FOREIGN PATENT DOCUMENTS

| | | |
|---|---|---|
| GB | 2498976 | 8/2013 |
| WO | WO 2004/099192 A2 | 11/2004 |
| WO | WO 2005/012249 | 2/2005 |
| WO | WO 2011/044073 | 4/2011 |
| WO | WO2012/066077 | 5/2012 |

OTHER PUBLICATIONS

Arbeeny, C. et al., "The Metabolic Syndrome: From Pathophysiology to Novel Treatment Strategies", Curr. Med. Chem.—Imm., Endoc. & Metab. Agents, vol. 1, No. 1, pp. 1-24 (2001).
Barlind, J.G. et al., "Identification and design of a novel series of MGAT2 inhibitors", Bioorganic & Medicinal Chemistry Letters, vol. 23, pp. 2721-2726 (2013).
Bellina, F. et al., "Synthesis and biological activity of pyrrole, pyrroline and pyrrolidine derivatives with two aryl groups on adjacent positions", Tetrahedron, vol. 62, pp. 7213-7256 (2006).
Bertrand, M.B. et al., "Mild Conditions for Pd-Catalyzed Carboamination of N-Protected Hex-4-enylamines and 1-, 3-, and 4-Substituted Pent-4-enylamines. Scope, Limitations, and Mechanism of Pyrrolidine Formation", J. Org. Chem., vol. 73, No. 22, pp. 8851-8860 (2008).
Browning, R.G. et al., "Palladium-catalyzed aryl-amidation. Synthesis of non-racemic N-aryl lactams", Tetrahedron, vol. 60, pp. 359-365 (2004).

(Continued)

*Primary Examiner* — Samantha Shterengarts
(74) *Attorney, Agent, or Firm* — Barry H. Jacobsen; Yong Lu

(57) ABSTRACT

The present invention provides compounds of Formula (I): or a stereoisomer, or a pharmaceutically acceptable salt thereof, wherein all of the variables are as defined herein. These compounds are GPR40 G protein-coupled receptor modulators which may be used as medicaments.

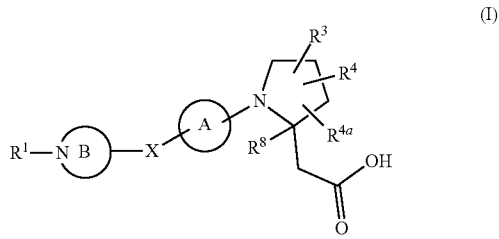

(I)

15 Claims, No Drawings

(56) References Cited

OTHER PUBLICATIONS

Bundgaard, H., Chapter 5: "Design and Application of Prodrugs", A Textbook of Drug Design and Development, pp. 113-191, Krogsgaard-Larsen, P. et al., eds., Harwood Academic Publishers, publ. (1991).

Bundgaard, H., ed., Design of Prodrugs, Elsevier Science Publishers B.V., publ. (1985).

Bundgaard, H., "Prodrugs as a means to improve the delivery of peptide drugs", Advanced Drug Delivery Reviews, vol. 8, pp. 1-38 (1992).

Coldham, I. et al., "Synthesis of Pyrrolidines by Anionic Cyclization onto Allylic Ethers, Alkynes and Carboxylic Groups", Tetrahedron Letters, vol. 38, No. 43, pp. 7621-7624 (1997).

Cordero, F.M. et al., "Synthesis of α-Cyclopropyl-β-homoprolines", J. Org. Chem., vol. 74, No. 11, pp. 4225-4231 (2009).

Deng, Q.-H. et al., "Ruthenium-Catalyzed One-Pot Carbenoid N-H Insertion Reactions and Diastereoselective Synthesis of Prolines", Organic Letters, vol. 10, No. 8, pp. 1529-1532 (2008).

Edfalk, S. et al., "*Gpr40* is Expressed in Enteroendocrine Cells and Mediates Free Fatty Acid Stimulation of Incretin Secretion", Diabetes, vol. 57, pp. 2280-2287 (2008).

Elangbam, C.S., "Review Paper: Current Strategies in the Development of Anti-obesity Drugs and Their Safety Concerns", Vet. Pathol., vol. 46, No. 1, pp. 10-24 (2009).

Evans, G.L. et al., "Synthesis of Ecgoninic Acid and Related Pyrrolidones", Journal of the American Chemical Society, vol. 72, pp. 2727-2728 (1950).

Ford, E.S. et al., "Prevalence of the Metabolic Syndrome Among US Adults: Findings from the Third National Health and Nutrition Examination Survey", Journal of the American Medical Association, vol. 287, No. 3, pp. 356-359 (2002).

Fyfe, M.C.T. et al., "Glucokinase Activators as Potential Antidiabetic Agents Possessing Superior Glucose-Lowering Efficacy", Drugs of the Future, vol. 34, No. 8, pp. 641-653 (2009).

Galliford, C.V. et al., "Catalytic, Three-Component Assembly Reaction for the Synthesis of Pyrrolidines", Organic Letters, vol. 5, No. 19, pp. 3487-3490 (2003).

Hoang, C.T. et al., "Amino Acid Homologation by the Blaise Reaction: A New Entry into Nitrogen Heterocycles", J. Org. Chem., vol. 74, No. 11, pp. 4177-4187 (2009).

Itoh, Y. et al., "Free fatty acids regulate insulin secretion from pancreatic β cells through GPR40", Nature, vol. 422, pp. 173-176 (2003).

Jones, D., "Novel pharmacotherapies for obesity poised to enter market", Nature Reviews: Drug Discovery, vol. 8, pp. 833-834 (2009).

Kakeya, N. et al., "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid", Chem. Pharm. Bull., vol. 32, No. 2, pp. 692-698 (1984).

Kimball, F.S. et al., "Enantiospecific synthesis and cytotoxicity of 7-(4-methoxyphenyl)-6-phenyl-2,3,8,8a-tetrahydroindolizin-5(1H)-one enantiomers", Bioorganic & Medicinal Chemistry, vol. 16, pp. 4367-4377 (2008).

Kimura, M. et al., "Convenient Synthesis of Pyrrolidines by Amphiphilic Allylation of Imines with 2-Methylenepropane-1,3-diols", Angew. Chem. Int. Ed., vol. 47, pp. 5803-5805 (2008).

Larock, R.C., Comprehensive Organic Transformations: A Guide to Functional Group Preparations, pp. xiii-xxviii, VCH Publishers, Inc., publ. (1989).

Larock, R.C. et al., "Synthesis of Pyrrolidines and Piperidines via Palladium-Catalyzed Coupling of Vinylic Halides and Olefinic Sulfonamides", J. Org. Chem., vol. 59, No. 15, pp. 4172-4178 (1994).

Lewis, Sr., R.J., Hawley's Condensed Chemical Dictionary, Thirteenth Edition, John Wiley & Sons, Inc., publ. (1997).

Luly, J.R. et al., "Routes to Mitomycins. New Syntheses of the 2,3,5,8-Tetrahydro-5,8-dioxo-1H-pyrrolo[1,2-a]indole Ring System. An Efficient Synthesis of 7-Methoxymitosene", J. Am. Chem. Soc., vol. 105, No. 9, pp. 2859-2866 (1983).

Luo, S. et al., "The Cotton Centromere Contains a Ty3-*gypsy*-like LTR Retroelement", PLoS ONE, vol. 7, No. 4, pp. 1-10 (2012).

Melnikova, I. et al., "Anti-obesity therapies", Nature Reviews Drug Discovery, 5, pp. 369-370 (2006).

Mizuno, C.S. et al., "Type 2 Diabetes and Oral Antihyperglycemic Drugs", Current Medicinal Chemistry, vol. 15, No. 1, pp. 61-74 (2008).

Mohler, M.L. et al., "Recent and Emerging Anti-Diabetes Targets", Medicinal Research Reviews, vol. 29, No. 1, pp. 125-195 (2009).

Nájera, C. et al., "Catalytic Enantioselective 1,3-Dipolar Cycloaddition Reaction of Azomethine Ylides and Alkenes: The Direct Strategy to Prepare Enantioenriched Highly Substituted Proline Derivatives", Angew. Chem. Int. Ed., vol. 44, pp. 6272-6726 (2005).

NCBI Reference Sequence No. NM_005303, Kristinsson, H. et al., Feb. 20, 2014.

NCBI Reference Sequence No. NM_194057, Shen, X. et al., May 24, 2014.

Ney, J.E. et al., "Synthesis of N-Aryl-2-allylpyrrolidines via Palladium-Catalyzed Carboamination Reactions of γ-(N-Arylamino)alkenes with Vinyl Bromides", Adv. Synth. Catal., vol. 347, pp. 1614-1620 (2005).

Nielsen, N.M. et al., "Glycolamide Esters as Biolabile Prodrugs of Carboxylic Acid Agents: Synthesis, Stability, Bioconversion, and Physicochemical Properties", Journal of Pharmaceutical Sciences, vol. 77, No. 4, pp. 285-298 (1988).

Obici, S., "Minireview: Molecular Targets for Obesity Therapy in the Brain", Endocrinology, vol. 150, No. 6, pp. 2512-2517 (2009).

Paderes, M.C. et al., "Diastereoselective Pyrrolidine Synthesis via Copper Promoted Intramolecular Aminooxygenation of Alkenes: Formal Synthesis of (+)-Monomorine", Organic Letters, vol. 11, No. 9, pp. 1915-1918 (2009).

Pisaneschi, F. et al., "Click Chemistry: A Straightforward Route to Decorated Prolines", Synlett, vol. 18, pp. 2882-2884 (2007).

Qiu, X. et al., "Practical Synthesis of Boc-Protected *cis*-4-Trifluoromethyl and *cis*-4-Difluoromethyl-L-prolines", J. Org. Chem., vol. 67, No. 20, pp. 7162-7164 (2002).

Ray, J.K. et al., "Structurally Designed Novel Furogamma Lactams as Inhibitors for Bacterial Propagations", Bioorganic & Medicinal Chemistry, vol. 2, No. 12, pp. 1417-1421 (1994).

Sasaki, N.A., Chapter 28: "A Novel Synthetic Protocol for the Preparation of Enantiopure 3-, 4-, and 5-Substituted Prolines", Methods in Molecular Medicine: Peptidomimetics Protocols, vol. 23, pp. 489-512, Kazmierski, W.M., ed., Humana Press Inc., publ. (1999).

Schlummer, B. et al., "Brønsted Acid-Catalyzed Intramolecular Hydroamination of Protected Alkenylamines. Synthesis of Pyrrolidines and Piperidines", Organic Letters, vol. 4, No. 9, pp. 1471-1474 (2002).

Semmelhack, M.F., ed., Comprehensive Organic Synthesis: Selectivity, Strategy & Efficiency in Modern Organic Chemistry, vol. 4: "Additions to and Substitutions at C—C π-Bonds", pp. v-vi, Pergamon Press, Inc., publ. (1991).

Shimpukade, B. et al., "Discovery of a Potent and Selective GPR120 Agonist", Journal of Medicinal Chemistry, vol. 55, pp. 4511-4515 (2012).

Simpkins, L.M. et al., "Potent non-nitrile dipeptidic dipeptidyl peptidase IV inhibitors", Bioorganic & Medicinal Chemistry Letters, vol. 17, pp. 6476-6480 (2007).

Smith, M.B. et al., March's Advanced Organic Chemistry: Reactions, Mechanisms, and Structure, Sixth Edition, John Wiley & Sons, Inc. (2007).

Spangenberg, T. et al., "Hydroformylation of Homoallylic Azides: A Rapid Approach toward Alkaloids", Organic Letters, vol. 11, No. 2, pp. 261-264 (2009).

(56) References Cited

OTHER PUBLICATIONS

Stephens, B.E. et al., "A Regio- and Diastereoselective Intramolecular Nitrone Cycloaddition for Practical 3- and 2,3-Disubstituted Piperidine Synthesis from γ-Butyrolactone", J. Org. Chem., vol. 74, No. 1, pp. 254-263 (2009).
Tan, C.P. et al., "Selective Small-Molecule Agonists of G Protein-Coupled Receptor 40 Promote Glucose-Dependent Insulin Secretion and Reduce Blood Glucose in Mice", Diabetes, vol. 57, pp. 2211-2219 (2008).
Testa, B. et al., Hydrolysis in Drug and Prodrug Metabolism: Chemistry, Biochemistry, and Enzymology, pp. xi-xx, Wiley-VCH GmbH & Co., publ. (2003).
Wang, Y.-G. et al., "Organocatalytic Approach to Enantioselective One-Pot Synthesis of Pyrrolidine, Hexahydropyrrolizine, and Octahydroindolizine Core Structures", Organic Letters, vol. 11, No. 9, pp. 2027-2029 (2009).
Widder, K.J. et al., eds., Section III: "Prodrugs", Methods in Enzymology, vol. 112, pp. 309-396, Academic Press, Inc., publ. (1985).
Wolfe, J.P., "Palladium-Catalyzed Carboetherification and Carboamination Reactions of γ-Hydroxy- and γ-Aminoalkenes for the Synthesis of Tetrahydrofurans and Pyrrolidines", Eur. J. Org. Chem., pp. 571-582 (2007).
Yamashima, T., "A putative link of PUFA, GPR40 and adult-born hippocampal neurons for memory", Progress in Neurobiology, vol. 84, pp. 105-115 (2008).
Zhou, J.-Q. et al., "Synthesis of Pyrrolidines and Pyrrolidinones by the Rhodium Complex Catalyzed Cyclization of Unsaturated Amines", J. Org. Chem., vol. 57, pp. 3328-3331 (1992).

PYRROLIDINE GPR40 MODULATORS

CROSS-REFERENCE TO RELATED APPLICATIONS

The present application is a 371 of International Application No. PCT/US2013/070213 filed on Nov. 15, 2013, which claims priority benefit of U.S. provisional application Ser. No. 61/727,253, filed Nov. 16, 2012, each of which is fully incorporated by reference herein.

FIELD OF THE INVENTION

The present invention provides novel carboxylic acid substituted pyrrolidine compounds, and their analogues thereof, which are GPR40 G protein-coupled receptor modulators, compositions containing them, and methods of using them, for example, for the treatment or prophylaxis of diabetes and related conditions.

BACKGROUND OF THE INVENTION

Diabetes mellitus is a progressively debilitating disorder of epidemic proportions leading to various micro- and macrovascular complications and morbidity. The most common type of diabetes, type 2 diabetes, is characterized by increasing insulin resistance associated with inadequate insulin secretion after a period of compensatory hyperinsulinemia. Free fatty acids (FFAs) are evidenced to influence insulin secretion from β cells primarily by enhancing glucose-stimulated insulin secretion (GSIS). G-protein coupled receptors (GPCRs) expressed in β cells are known to modulate the release of insulin in response to changes in plasma glucose levels. GPR40, also known as fatty acid receptor 1 (FFAR1), is a membrane-bound FFA receptor which is preferentially expressed in the pancreatic islets and specifically in β cells and mediates medium to long chain fatty acid induced insulin secretion. GPR40 is also expressed in enteroendocrine cells wherein activation promotes the secretion of gut incretin hormones, such as GLP-1, GIP, CCK and PYY. To decrease medical burden of type 2 diabetes through enhanced glycemic control, GPR40 modulator compounds hold the promise of exerting an incretin effect to promote GSIS as well as potential combination with a broad range of anti-diabetic drugs.

The present invention relates to novel substituted pyrrolidine compounds which have the ability to modulate GPR40. Such compounds are therefore potentially useful for the treatment or prophylaxis of diabetes and related conditions.

SUMMARY OF THE INVENTION

The present invention provides substituted pyrrolidine compounds, and their analogues thereof, which are useful as GPR40 modulators, including stereoisomers, tautomers, pharmaceutically acceptable salts, or solvates thereof.

The present invention also provides processes and intermediates for making the compounds of the present invention or stereoisomers, tautomers, pharmaceutically acceptable salts, or solvates thereof.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of multiple diseases or disorders associated with GPR40, such as diabetes and related conditions, microvascular complications associated with diabetes, the macrovascular complications associated with diabetes, cardiovascular diseases, Metabolic Syndrome and its component conditions, disorders of glucose metabolism, obesity and other maladies.

The compounds of the invention may be used in therapy.

The compounds of the invention may be used for the manufacture of a medicament for the treatment and/or prophylaxis of multiple diseases or disorders associated with GPR40.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the present disclosure provides, inter alia, a compound of Formula (I):

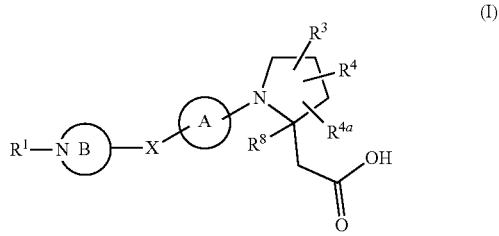

or a stereoisomer, a tautomer, a pharmaceutically acceptable salt, or a solvate thereof, wherein:

X is independently selected from: a bond, O, S, NH, $N(C_{1-4}$ alkyl), $CH_2$, $CH_2CH_2$, $CH(C_{1-4}$ alkyl), $OCH_2$, $CH_2O$, $OCH_2CH_2$, and $CH_2CH_2O$;

ring A is independently

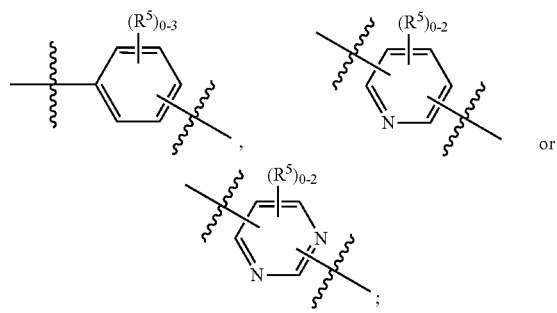

ring B is independently a 4- to 7-membered saturated heterocycle containing carbon atoms, the nitrogen atom shown in the ring B and 0-1 additional heteroatom selected from N, O, and S; and ring B is substituted with 0-4 $R^2$;

$R^1$ is independently $CO_2R^9$, $SO_2R^9$,

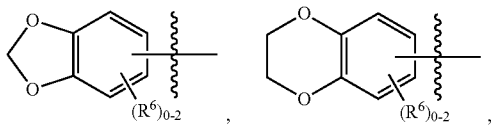

phenyl, benzyl, naphthyl or a 5- to 10-membered heteroaryl containing carbon atoms and 1-4 heteroatoms selected from N, $NR^{11}$, O, and S; wherein said phenyl, benzyl, naphthyl and heteroaryl are each substituted with 0-3 $R^6$;

$R^2$, at each occurrence, is independently selected from: =O, OH, halogen, $C_{1-6}$ alkyl substituted with 0-1 $R^{12}$, $C_{1-6}$ alkoxy substituted with 0-1 $R^{12}$, $C_{1-4}$ haloalkyl substituted with 0-1 $R^{12}$, $C_{1-4}$ haloalkoxy substituted with 0-1 $R^{12}$, $-(CH_2)_m-C_{3-6}$ carbocycle substituted with 0-1 $R^{12}$, and $-(CH_2)_m$-(5- to 10-membered heteroaryl containing carbon atoms and 1-4 heteroatoms selected from N, $NR^{11}$, O, and S); wherein said heteroaryl is substituted with 0-1 $R^{12}$;

when two $R^2$ groups are attached to two different carbon atoms, they may combine to form a 1- to 3-membered carbon atom bridge over ring B;

when two $R^2$ groups are attached to the same carbon, they may combine, together with the carbon atom to which they are attached, to form a 3- to 6-membered carbon atom containing spiro ring;

$R^3$ is independently selected from: H, halogen, CN, OH, $CO_2H$, $C_{1-6}$ alkyl, $C_{2-6}$ alkenyl, $C_{2-6}$ alkynyl, $C_{1-6}$ haloalkyl, $-N(C_{1-4}$ alkyl$)SO_2Ph$, $OR^9$, $SR^9$, $C(O)OR^9$, $CO_2R^9$, $S(O)R^9$, $SO_2R^9$, $CONHR^9$, $CON(C_{1-4}$ alkyl$)_2$, $-(O)_n-(CH_2)_m$-(phenyl substituted with 0-2 $R^{10}$), $-(O)_n-(CH_2)_m$-(5- to 10-membered heteroaryl containing carbon atoms and 1-4 heteroatoms selected from N, $NR^{11}$, O, and S; wherein said heteroaryl is substituted with 0-2 $R^{10}$);

$R^4$ and $R^{4a}$ are independently selected from: H, halogen, $C_{1-6}$ alkyl, $C_{1-6}$ alkoxy, and $-(CH_2)_m-C_{3-6}$ carbocycle;

$R^5$, at each occurrence, is independently selected from: halogen, $C_{1-6}$ alkyl, and $C_{1-6}$ alkoxy;

$R^6$, at each occurrence, is independently selected from: halogen, OH, $C_{1-4}$ alkylthio, CN, $SO_2(C_{1-2}$ alkyl$)$, $N(C_{1-4}$ alkyl$)_2$, $C_{1-4}$ haloalkyl, $C_{1-4}$ haloalkoxy, $C_{1-8}$ alkyl substituted with 0-1 $R^7$, $C_{1-6}$ alkoxy substituted with 0-1 $R^7$, $-(O)_N-(CH_2)_m-(C_{3-10}$ carbocycle substituted with 0-2 $R^7$), and $-(CH_2)_m$-(5- to 10-membered heteroaryl containing carbon atoms and 1-4 heteroatoms selected from N, $NR^{11}$, O, and S); wherein said heteroaryl is substituted with 0-2 $R^7$;

$R^7$, at each occurrence, is independently selected from: halogen, OH, $C_{1-4}$ alkyl, $C_{2-4}$ alkenyl, $C_{1-4}$ alkoxy, $C_{1-4}$ alkylthio, $C_{1-4}$ haloalkyl, $C_{1-4}$ haloalkoxy, $SCF_3$, CN, $NO_2$, $NH_2$, $NH(C_{1-4}$ alkyl$)$, $N(C_{1-4}$ alkyl$)_2$, $SO_2(C_{1-2}$ alkyl$)$, and phenyl;

$R^8$ is independently selected from: H and $C_{1-4}$ alkyl;

$R^9$, at each occurrence, is independently selected from: $C_{1-6}$ alkyl, $C_{1-4}$ haloalkyl, $-(CH_2)_m-(C_{3-6}$ cycloalkyl substituted with 0-2 $R^{10}$), and $-(CH_2)_m$-(phenyl substituted with 0-2 $R^{10}$);

$R^{10}$ and $R^{12}$, at each occurrence, is independently selected from: OH, halogen, CN, $C_{1-4}$ alkyl, $C_{1-4}$ alkoxy, $C_{1-4}$ haloalkyl, $C_{1-4}$ haloalkoxy, $SCF_3$, $NO_2$, $CO_2(C_{1-4}$ alkyl$)$, $SO_2(C_{1-4}$ alkyl$)$, and tetrazolyl;

$R^{11}$, at each occurrence, is independently selected from: H, $C_{1-4}$ alkyl and benzyl;

m, at each occurrence, is independently 0, 1, or 2; and n, at each occurrence, is independently 0 or 1.

In a second aspect, the present disclosure provides a compound of Formula (I), wherein $R^4$ is hydrogen and $R^8$ is hydrogen, further characterized by Formula (II):

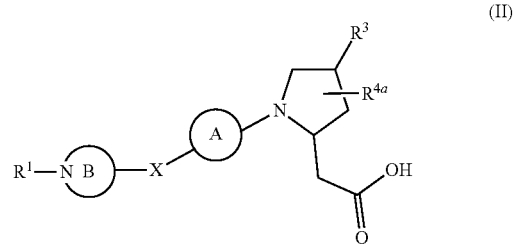

(II)

or a stereoisomer, a tautomer, a pharmaceutically acceptable salt, or a solvate thereof, wherein:

X is independently selected from: a bond, O, S, NH, $N(C_{1-4}$ alkyl$)$, $CH_2$, $CH_2CH_2$, $CH(C_{1-4}$ alkyl$)$, $OCH_2$, $CH_2O$, $OCH_2CH_2$, and $CH_2CH_2O$;

ring A is independently

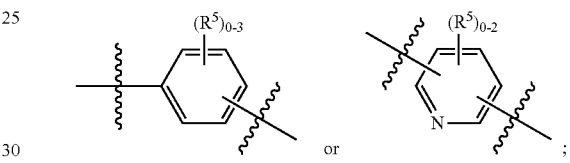

ring B is independently a 4- to 7-membered saturated heterocycle containing carbon atoms and the nitrogen atom shown in ring B; and ring B is substituted with 0-4 $R^2$;

$R^1$ is independently $CO_2(C_{1-4}$ alkyl$)$, $CO_2Bn$,

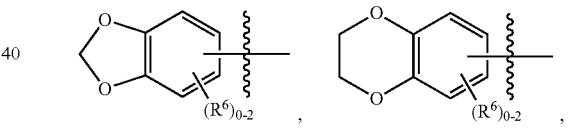

phenyl, benzyl, naphthyl or a 5- to 10-membered heteroaryl containing carbon atoms and 1-4 heteroatoms selected from N, $NR^{11}$, O, and S; wherein said phenyl, benzyl, naphthyl and heteroaryl are each substituted with 0-3 $R^6$;

$R^2$, at each occurrence, is independently selected from: =O, OH, halogen, $C_{1-6}$ alkyl substituted with 0-1 $R^{12}$, $C_{1-6}$ alkoxy substituted with 0-1 $R^{12}$, $C_{1-4}$ haloalkyl, $C_{1-4}$ haloalkoxy, and benzyl;

when two $R^2$ groups are attached to two different carbon atoms, they may combine to form a 1- to 3-membered carbon atom bridge over ring B;

when two $R^2$ groups are attached to the same carbon, they may combine, together with the carbon atom to which they are attached, to form a 3- to 6-membered carbon atom containing spiro ring;

$R^3$ is independently selected from: H, halogen, CN, $SO_2(C_{1-4}$ alkyl$)$, $CONH(C_{1-4}$ alkyl$)$, $CON(C_{1-4}$ alkyl$)_2$, $C_{1-6}$ alkyl, $C_{1-6}$ alkoxy, $C_{1-4}$ alkylthio, $C_{1-4}$ haloalkyl, $C_{1-4}$ haloalkoxy, $-N(C_{1-4}$ alkyl$)SO_2Ph$, $-(O)_n-(CH_2)_m$-(phenyl substituted with 0-2 $R^{10}$), and $-(O)_n-(CH_2)_m$-(a 5- to 10-membered heteroaryl containing carbon atoms and 1-4 heteroatoms selected from N, $NR^{11}$, O, and S; wherein said heteroaryl is substituted with 0-2 $R^{10}$);

$R^{4a}$ is independently selected from: H, halogen, $C_{1-4}$ alkyl, $C_{1-4}$ alkoxy, and —$(CH_2)_m$—$C_{3-6}$ carbocycle;

$R^5$, at each occurrence, is independently selected from: halogen, $C_{1-6}$ alkyl, and $C_{1-6}$ alkoxy;

$R^6$, at each occurrence, is independently selected from: halogen, OH, $C_{1-4}$ alkylthio, CN, $SO_2(C_{1-2}$ alkyl), $N(C_{1-4}$ alkyl)$_2$, $C_{1-4}$ haloalkyl, $C_{1-4}$ haloalkoxy, $C_{1-8}$ alkyl substituted with 0-1 $R^7$, $C_{1-4}$ alkoxy substituted with 0-1 $R^7$, —(O)$_n$—(CH$_2$)$_m$—(C$_{3-6}$ carbocycle substituted with 0-2 $R^7$), —(CH$_2$)$_m$-(naphthyl substituted with 0-2 $R^7$), and —(CH$_2$)$_m$-(5- to 10-membered heteroaryl containing carbon atoms and 1-4 heteroatoms selected from N, NR$^{11}$, O, and S; wherein said heteroaryl is substituted with 0-2 $R^7$);

$R^7$, at each occurrence, is independently selected from: halogen, OH, $C_{1-4}$ alkyl, $C_{2-4}$ alkenyl, $C_{1-4}$ alkoxy, $C_{1-4}$ alkylthio, $C_{1-4}$ haloalkyl, $C_{1-4}$ haloalkoxy, SCF$_3$, CN, NO$_2$, NH$_2$, NH($C_{1-4}$ alkyl), N($C_{1-4}$ alkyl)$_2$, SO$_2(C_{1-2}$ alkyl), and phenyl;

$R^{10}$ and $R^{12}$, at each occurrence, are independently selected from: OH, halogen, CN, $C_{1-4}$ alkyl, $C_{1-4}$ alkoxy, $C_{1-4}$ haloalkyl, $C_{1-4}$ haloalkoxy, SCF$_3$, NO$_2$, CO$_2(C_{1-4}$ alkyl), SO$_2(C_{1-4}$ alkyl), and tetrazolyl;

$R^{11}$, at each occurrence, is independently selected from: H, $C_{1-4}$ alkyl and benzyl;

m, at each occurrence, is independently 0, 1, or 2; and n, at each occurrence, is independently 0 or 1.

In a third aspect, the present disclosure includes a compound of Formula (I) or (II), or a stereoisomer, a tautomer, a pharmaceutically acceptable salt, or a solvate thereof, within the scope of the first or second aspect, wherein:

X is independently selected from: a bond, O, NH, N(CH$_3$), CH$_2$, CH$_2$CH$_2$, CH(CH$_3$), OCH$_2$, CH$_2$O, OCH$_2$CH$_2$, and CH$_2$CH$_2$O;

ring A is independently

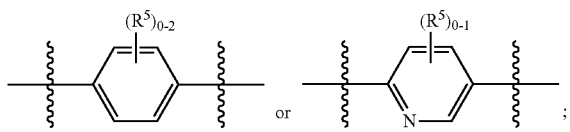

ring B is independently selected from:

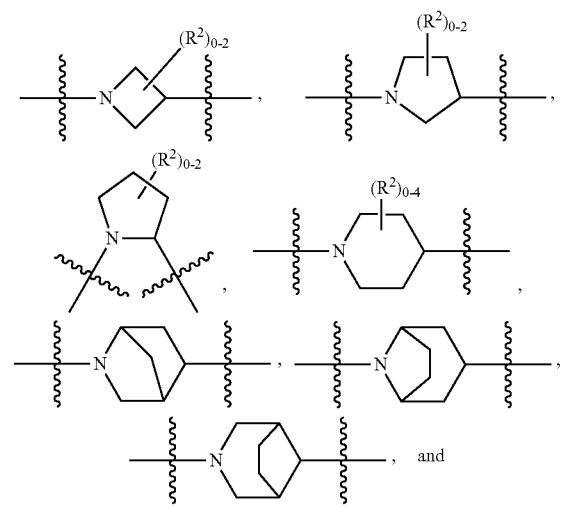

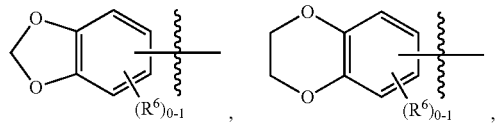

$R^1$ is independently $CO_2(C_{1-4}$ alkyl), CO$_2$Bn,

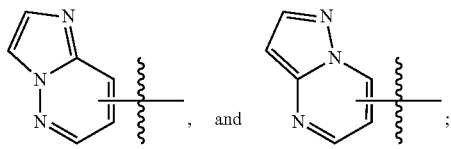

phenyl substituted with 0-3 $R^6$ or a heteroaryl substituted with 0-2 $R^6$; wherein said heteroaryl is selected from: furanyl, oxazolyl, thiazolyl, pyrazolyl, oxadiazolyl, pyridinyl, pyrimidinyl, pyrazinyl,

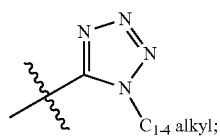

$R^2$, at each occurrence, is independently selected from: OH, halogen, $C_{1-4}$ alkyl substituted with 0-1 $R^{12}$, $C_{1-4}$ alkoxy substituted with 0-1 $R^{12}$, and benzyl;

$R^3$ is independently selected from: H, halogen, CN, SO$_2$($C_{1-4}$ alkyl), CONH($C_{1-4}$ alkyl), CON($C_{1-4}$ alkyl)$_2$, —N($C_{1-4}$ alkyl)SO$_2$Ph, $C_{1-6}$ alkyl, $C_{1-6}$ alkoxy, $C_{1-4}$ haloalkyl, $C_{1-4}$ haloalkoxy, phenyl, benzyl, phenoxy, benzoxy, oxazolyl, 1-$C_{1-4}$ alkyl-pyrazolyl, triazolyl, tetrazolyl, pyridinyl, —O-pyridinyl, pyrimidinyl, —O-pyrimidinyl, and

wherein each said ring moiety is substituted with 0-2 $R^{10}$;

$R^{4a}$ is independently selected from: H, halogen $C_{1-4}$ alkyl, $C_{1-4}$ alkoxy, and $C_{3-6}$ cycloalkyl;

$R^6$, at each occurrence, is independently selected from: halogen, OH, $C_{1-8}$ alkyl substituted with 0-1 OH, $C_{1-4}$ alkoxy, $C_{1-4}$ alkylthio, $C_{1-4}$ haloalkyl, $C_{1-4}$ haloalkoxy, CN, SO$_2(C_{1-2}$ alkyl), N($C_{1-4}$ alkyl)$_2$, $C_{3-6}$ cycloalkyl substituted with 0-2 $C_{1-4}$ alkyl, $C_{5-6}$ cycloalkenyl substituted with 0-2 $C_{1-4}$ alkyl, —O—$C_{3-6}$ cycloalkyl, benzyl, and oxazolyl; and $R^{10}$ and $R^{12}$, at each occurrence, are independently selected from: halogen, CN, $C_{1-4}$ alkyl, $C_{1-4}$ alkoxy, $C_{1-4}$ haloalkyl, $C_{1-4}$ haloalkoxy, SO$_2(C_{1-4}$ alkyl), and CO$_2(C_{1-2}$ alkyl), and tetrazolyl.

In a fourth aspect, the present invention includes a compound of Formula (I) or (II), or a stereoisomer, a tautomer, a pharmaceutically acceptable salt, or a solvate thereof, within the scope of the first, second or third aspect, wherein:

$R^1$ is independently phenyl substituted with 0-3 $R^6$ or a heteroaryl substituted with 0-2 $R^6$; wherein said heteroaryl is selected from; thiazolyl, pyridinyl, pyrimidinyl, pyrazinyl,

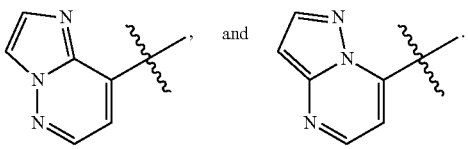 [SMILES: *c1ccnn2ccnc12 ; *c1ccnc2ccnn12]

In a fifth aspect, the present disclosure includes a compound of Formula (I) or (II), or a stereoisomer, a tautomer, a pharmaceutically acceptable salt, or a solvate thereof, within the scope of any of the above aspect, wherein:

X is independently selected from: O, $N(CH_3)$, $CH_2$, $CH_2O$, and $CH_2CH_2O$;

ring B is independently selected from:

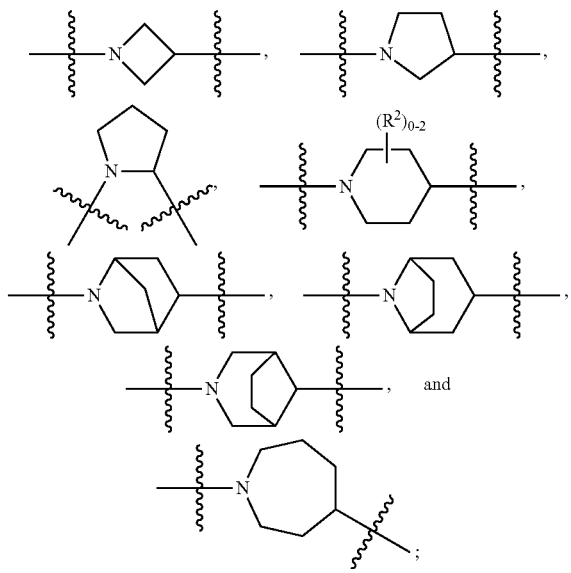

$R^1$, at each occurrence, is independently phenyl substituted with 0-3 $R^6$, pyridinyl substituted with 0-2 $R^6$, pyrazinyl substituted with 0-2 $R^6$, pyrimidinyl substituted with 0-2 $R^6$, thiazolyl substituted with 0-2 $R^6$,

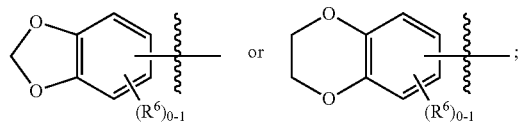

$R^2$, at each occurrence, is independently selected from: OH, halogen, $C_{1-6}$ alkyl substituted with 0-1 CN, $C_{1-6}$ alkoxy, benzyl, and tetrazolylmethyl;

$R^3$, at each occurrence, is independently selected from: H, halogen, CN, $C_{1-6}$ alkyl, $C_{1-6}$ alkoxy, $C_{1-4}$ haloalkyl, $C_{1-4}$ haloalkoxy, phenyl, benzyl, phenoxy, benzoxy, 1-$C_{1-4}$ alkyl-pyrazolyl, triazolyl, tetrazolyl, pyridinyl, —O-pyridinyl, pyrimidinyl, and —O-pyrimidinyl; wherein each said ring moiety is substituted with 0-2 $R^{10}$;

$R^6$, at each occurrence, is independently selected from: halogen, CN, $C_{1-8}$ alkyl, $C_{1-4}$ alkoxy, $C_{1-4}$ haloalkyl, $C_{1-4}$ haloalkoxy, $C_{3-6}$ cycloalkyl substituted with 0-2 $C_{1-4}$ alkyl, $C_{5-6}$ cycloalkenyl substituted with 0-2 $C_{1-4}$ alkyl, —O—$C_{3-6}$ cycloalkyl, benzyl, and oxazolyl; and $R^{10}$, at each occurrence, is independently selected from: halogen, CN, $C_{1-4}$ alkyl, $C_{1-4}$ alkoxy, $C_{1-4}$ haloalkyl, $C_{1-4}$ haloalkoxy, and $CO_2(C_{1-2}$ alkyl).

In a sixth aspect, the present disclosure includes a compound of Formula (I) or (II), or a stereoisomer, a tautomer, a pharmaceutically acceptable salt, or a solvate thereof, within the scope of any of the above aspect, wherein:

ring B is independently selected from:

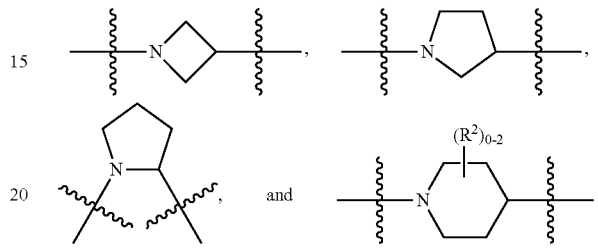

$R^1$, at each occurrence, is independently phenyl substituted with 0-3 $R^6$ or pyridinyl substituted with 0-2 $R^6$;

$R^2$, at each occurrence, is independently selected from: halogen, $C_{1-6}$ alkyl, and $C_{1-6}$ alkoxy;

$R^3$, at each occurrence, is independently selected from: H, halogen, CN, $C_{1-6}$ alkyl, $C_{1-6}$ alkoxy, $C_{1-4}$ haloalkyl, $C_{1-4}$ haloalkoxy, phenyl, benzyl, phenoxy, benzoxy, 1-$C_{1-4}$ alkyl-pyrazolyl, triazolyl, tetrazolyl, pyridinyl, —O-pyridinyl, and —O-pyrimidinyl; wherein said phenyl, benzyl, phenoxy —O-pyridinyl, and —O-pyrimidinyl are each substituted with 0-2 $R^{10}$;

$R^6$, at each occurrence, is independently selected from: halogen, $C_{1-6}$ alkyl, $C_{1-4}$ alkoxy, $C_{1-4}$ haloalkyl, $C_{1-4}$ haloalkoxy, $C_{3-6}$ cycloalkyl substituted with 0-2 $C_{1-4}$ alkyl, $C_{5-6}$ cycloalkenyl substituted with 0-2 $C_{1-4}$ alkyl, and benzyl; and $R^{10}$, at each occurrence, is independently selected from: halogen, CN, $C_{1-4}$ alkyl, $C_{1-4}$ alkoxy, $C_{1-4}$ haloalkyl, and $C_{1-4}$ haloalkoxy.

In a seventh aspect, the present disclosure includes a compound of Formula (III), (IIIa), (IIIb) or (IIIc):

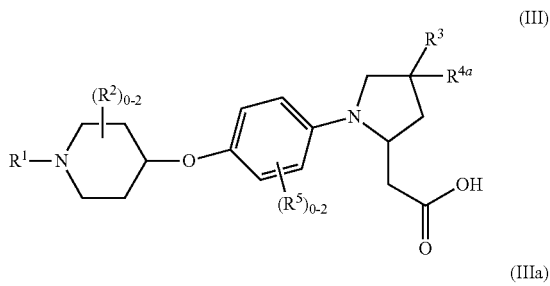

(III)

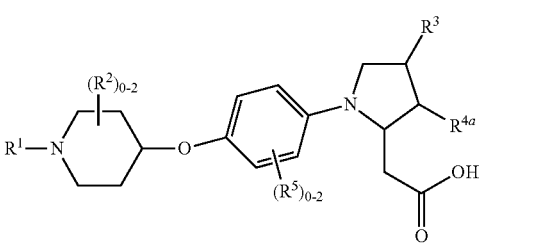

(IIIa)

9

-continued

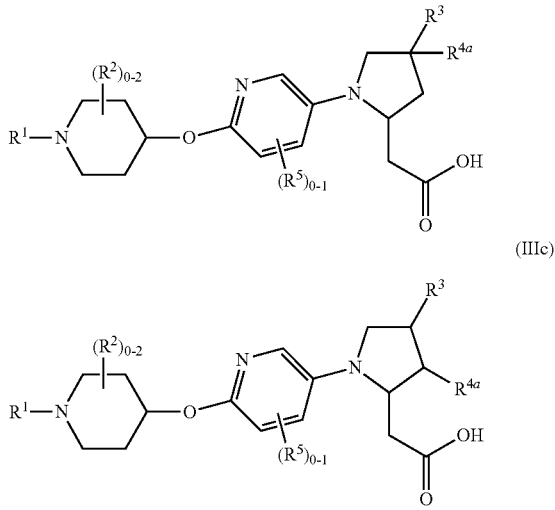

(IIIb)

(IIIc)

or a stereoisomer, a tautomer, a pharmaceutically acceptable salt, or a solvate thereof, wherein:

$R^1$, at each occurrence, is independently phenyl substituted with 0-3 $R^6$ or pyridinyl substituted with 0-2 $R^6$;

$R^2$, at each occurrence, is independently selected from: halogen, $C_{1-4}$ alkyl, and $C_{1-6}$ alkoxy;

$R^3$, at each occurrence, is independently selected from: H, halogen, $C_{1-4}$ alkyl, $C_{1-4}$ alkoxy, $C_{1-4}$ haloalkyl, $C_{1-4}$ haloalkoxy, phenyl, benzyl, phenoxy, pyridinyl, and —O-pyridinyl; wherein said phenyl, benzyl, phenoxy, pyridinyl and —O-pyridinyl are each substituted with 0-1 $R^{10}$;

$R^{4a}$, at each occurrence, is independently selected from: H, halogen, $C_{1-4}$ alkyl, $C_{1-4}$ alkoxy, and cyclopropyl;

$R^5$, at each occurrence, is independently halogen and $C_{1-6}$ alkoxy;

$R^6$, at each occurrence, is independently selected from: halogen, $C_{1-6}$ alkyl, $C_{1-4}$ alkoxy, $C_{3-6}$ cycloalkyl substituted with 0-2 $C_{1-4}$ alkyl, and $C_{5-6}$ cycloalkenyl substituted with 0-2 $C_{1-4}$ alkyl; and $R^{10}$ is independently selected from: halogen, $CF_3$, $OCF_3$, CN, $C_{1-4}$ alkyl, and $C_{1-4}$ alkoxy.

In an eighth aspect, the present disclosure includes a compound of Formula (IV) or (IVa):

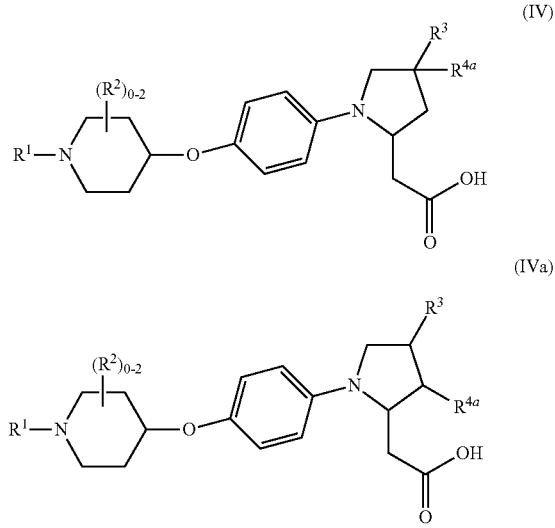

(IV)

(IVa)

or a stereoisomer, a tautomer, a pharmaceutically acceptable salt, or a solvate thereof, within the scope of the seventh aspect.

In a ninth aspect, the present disclosure includes a compound of Formula (IV) or (IVa), or a stereoisomer, a tautomer, a pharmaceutically acceptable salt, or a solvate thereof, within the scope of the seventh or eighth aspect, wherein:

$R^1$ is independently phenyl substituted with 0-3 $R^6$ or pyridinyl substituted with 0-2 $R^6$;

$R^2$ is independently halogen or $C_{1-4}$ alkyl;

$R^3$ is independently selected from: halogen, $C_{1-4}$ alkyl, $C_{1-4}$ alkoxy, $CF_3$, phenyl, benzyl, and phenoxy;

$R^{4a}$ is independently selected from: H, halogen and $C_{1-4}$ alkyl; and $R^6$, at each occurrence, is independently selected from: halogen, $C_{1-4}$ alkyl, and $C_{1-4}$ alkoxy.

In a tenth aspect, the present invention provides a compound selected from the exemplified examples or a stereoisomer, a tautomer, a pharmaceutically acceptable salt, or a solvate thereof.

In another aspect, the present invention provides a compound selected from any subset list of compounds or a single compound from the exemplified examples within the scope of any of the above aspects.

In another aspect, the present disclosure provides a compound of Formula (I):

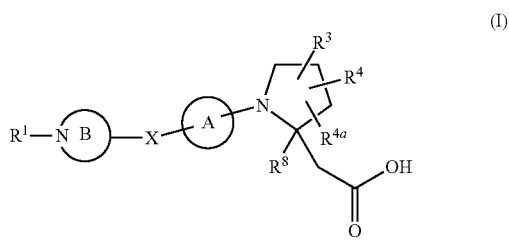

(I)

or a stereoisomer, a tautomer, a pharmaceutically acceptable salt, or a solvate thereof, wherein:

X is independently selected from: a bond, O, S, NH, $N(C_{1-4}$ alkyl), $CH_2$, $CH_2CH_2$, $CH(C_{1-4}$ alkyl), $OCH_2$, $CH_2O$, $OCH_2CH_2$, and $CH_2CH_2O$;

ring A is independently

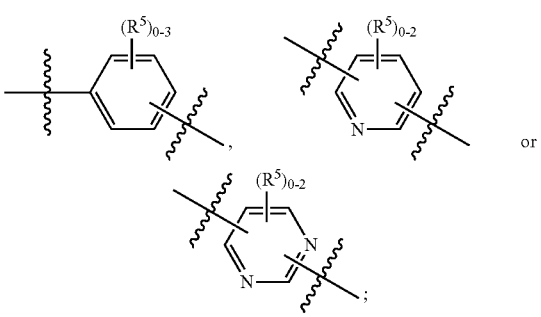

ring B is independently a 4- to 7-membered saturated heterocycle containing carbon atoms, the nitrogen atom shown in the ring B and 0-1 additional heteroatom selected from N, O, and S; and ring B is substituted with 0-4 $R^2$;

$R^1$ is independently $CO_2R^9$, phenyl, benzyl, naphthyl or a 5- to 10-membered heteroaryl containing carbon atoms and 1-4 heteroatoms selected from N, $NR^{11}$, O, and S; wherein said phenyl, benzyl, naphthyl and heteroaryl are each substituted with 0-3 $R^6$;

$R^2$, at each occurrence, is independently selected from: =O, OH, halogen, $C_{1-4}$ alkyl, $C_{1-4}$ alkoxy, and $-(CH_2)_m-$ $C_{3-6}$ carbocycle;

two $R^2$ groups may combine, together with the carbon atoms that they are attached to, to form a bridged ring;

$R^3$ is independently selected from: H, halogen, CN, OH, $CO_2H$, $C_{1-4}$ alkyl, $C_{1-4}$ alkenyl, $C_{1-4}$ alkynyl, $C_{1-4}$ haloalkyl, $OR^9$, $SR^9$, $C(O)OR^9$, $CO_2R^9$, $S(O)R^9$, $SO_2R^9$, $CONHR^9$, $CON(C_{1-4}$ alkyl$)_2$, $-(O)_n-(CH_2)_m$-phenyl, $-(CH_2)_m$-(5- to 10-membered heteroaryl containing carbon atoms and 1-4 heteroatoms selected from N, $NR^{11}$, O, and S); wherein said phenyl and heteroaryl are substituted with 0-2 $R^{10}$;

$R^4$ and $R^{4a}$ are independently selected from: H, halogen, $C_{1-4}$ alkyl, and $-(CH_2)_m-C_{3-6}$ carbocycle;

$R^5$, at each occurrence, is independently selected from: halogen and $C_{1-4}$ alkyl;

$R^6$, at each occurrence, is independently selected from: halogen, OH, $C_{1-4}$ alkylthio, CN, $SO_2(C_{1-2}$ alkyl), $N(C_{1-4}$ alkyl$)_2$, $C_{1-4}$ haloalkyl, $C_{1-4}$ haloalkoxy, $C_{1-6}$ alkyl substituted with 0-1 $R^7$, $C_{1-4}$ alkoxy substituted with 0-1 $R^7$, $-(O)_n-(CH_2)_m-(C_{3-10}$ carbocycle substituted with 0-2 $R^7$), and $-(CH_2)_m$-(5- to 10-membered heteroaryl containing carbon atoms and 1-4 heteroatoms selected from N, $NR^{11}$, O, and S; wherein said heteroaryl is substituted with 0-2 $R^7$;

$R^7$, at each occurrence, is independently selected from: halogen, OH, $C_{1-4}$ alkyl, $C_{2-4}$ alkenyl, $C_{1-4}$ alkoxy, $C_{1-4}$ alkylthio, $C_{1-4}$ haloalkyl, $C_{1-4}$ haloalkoxy, $SCF_3$, CN, $NO_2$, $NH_2$, $NH(C_{1-4}$ alkyl), $N(C_{1-4}$ alkyl$)_2$, $SO_2(C_{1-2}$ alkyl), and phenyl;

$R^8$ is independently selected from: H and $C_{1-4}$ alkyl;

$R^9$, at each occurrence, is independently selected from: $C_{1-4}$ alkyl, $C_{1-4}$ haloalkyl and $-(CH_2)_m$-phenyl;

$R^{10}$, at each occurrence, is independently selected from: halogen, CN, $C_{1-4}$ haloalkyl, $C_{1-4}$ haloalkoxy, $SCF_3$, $NO_2$, and $CO_2(C_{1-4}$ alkyl);

$R^{11}$, at each occurrence, is independently selected from: H, $C_{1-4}$ alkyl and benzyl;

m, at each occurrence, is independently 0, 1, or 2; and n, at each occurrence, is independently 0 or 1.

In another aspect, the present disclosure provides a compound of Formula (I), wherein $R^4$ is hydrogen and $R^8$ is hydrogen, further characterized by Formula (II):

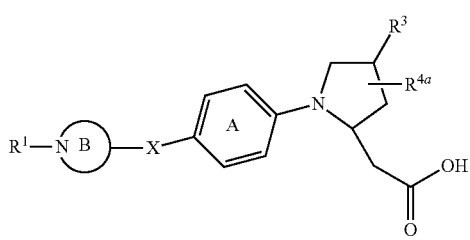

(II)

or a stereoisomer, a tautomer, a pharmaceutically acceptable salt, or a solvate thereof, wherein:

X is independently selected from: a bond, O, S, NH, $N(C_{1-4}$ alkyl), $CH_2$, $CH_2CH_2$, $CH(C_{1-4}$ alkyl), $OCH_2$, $CH_2O$, $OCH_2CH_2$, and $CH_2CH_2O$;

ring A is independently

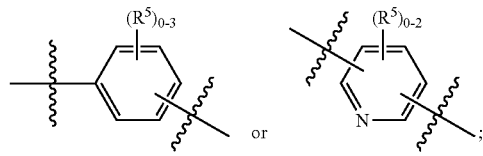

ring B is independently a 4- to 7-membered saturated heterocycle containing carbon atoms and the nitrogen atom shown in ring B; and ring B is substituted with 0-4 $R^2$;

$R^1$ is independently $CO_2(C_{1-4}$ alkyl), $CO_2Bn$, phenyl, benzyl, naphthyl or a 5- to 10-membered heteroaryl containing carbon atoms and 1-4 heteroatoms selected from N, $NR^{11}$, O, and S; wherein said phenyl, benzyl, naphthyl and heteroaryl are each substituted with 0-3 $R^6$;

$R^2$, at each occurrence, is independently selected from: OH, halogen, $C_{1-4}$ alkyl, $C_{1-4}$ alkoxy, and benzyl;

two $R^2$ groups may combine, together with the carbon atoms to which they are attached, to form a bridged ring;

$R^3$ is independently selected from: H, halogen, CN, $SO_2$ $(C_{1-4}$ alkyl), $CONH(C_{1-4}$ alkyl), $CON(C_{1-4}$ alkyl$)_2$, $C_{1-4}$ alkyl, $C_{1-4}$ alkoxy, $C_{1-4}$ alkylthio, $C_{1-4}$ haloalkyl, $C_{1-4}$ haloalkoxy, phenyl, benzyl, phenoxy, and a 5- to 10-membered heteroaryl containing carbon atoms and 1-4 heteroatoms selected from N, $NR^{11}$, O, and S; wherein said phenyl, benzyl, phenoxy and heteroaryl is substituted with 0-2 $R^{10}$;

$R^{4a}$ is independently selected from: H, halogen, $C_{1-4}$ alkyl, and $-(CH_2)_m-C_{3-6}$ carbocycle;

$R^5$, at each occurrence, is independently selected from: halogen and $C_{1-4}$ alkyl;

$R^6$, at each occurrence, is independently selected from: halogen, OH, $C_{1-4}$ alkylthio, CN, $SO_2(C_{1-2}$ alkyl), $N(C_{1-4}$ alkyl$)_2$, $C_{1-4}$ haloalkyl, $C_{1-4}$ haloalkoxy, $C_{1-6}$ alkyl substituted with 0-1 $R^7$, $C_{1-4}$ alkoxy substituted with 0-1 $R^7$, $-(CH_2)_m-(C_{3-6}$ cycloalkyl), $-O(CH_2)_m-(C_{3-6}$ cycloalkyl), $-(CH_2)_m$-(phenyl substituted with 0-2 $R^7$), $-O(CH_2)_m$-(phenyl substituted with 0-2 $R^7$), $-(CH_2)_m$-(naphthyl substituted with 0-2 $R^7$), and $-(CH_2)_m$-(5- to 10-membered heteroaryl containing carbon atoms and 1-4 heteroatoms selected from N, O, and S; wherein said heteroaryl is substituted with 0-2 $R^7$;

$R^7$, at each occurrence, is independently selected from: halogen, OH, $C_{1-4}$ alkyl, $C_{2-4}$ alkenyl, $C_{1-4}$ alkoxy, $C_{1-4}$ alkylthio, $C_{1-4}$ haloalkyl, $C_{1-4}$ haloalkoxy, $SCF_3$, CN, $NO_2$, $NH_2$, $NH(C_{1-4}$ alkyl), $N(C_{1-4}$ alkyl$)_2$, $SO_2(C_{1-2}$ alkyl), and phenyl;

$R^{10}$, at each occurrence, is independently selected from: halogen, CN, $C_{1-4}$ haloalkyl, $C_{1-4}$ haloalkoxy, $SCF_3$, $NO_2$, and $CO_2(C_{1-4}$ alkyl);

$R^{11}$, at each occurrence, is independently selected from: H, $C_{1-4}$ alkyl and benzyl; and m, at each occurrence, is independently 0, 1, or 2.

In another aspect, the present disclosure includes a compound of Formula (I) or (II), or a stereoisomer, a tautomer, a pharmaceutically acceptable salt, or a solvate thereof, wherein:

X is independently selected from: a bond, O, NH, $N(CH_3)$, $CH_2$, $CH_2CH_2$, $CH(CH_3)$, $OCH_2$, $CH_2O$, $OCH_2CH_2$, and $CH_2CH_2O$;

ring A is independently

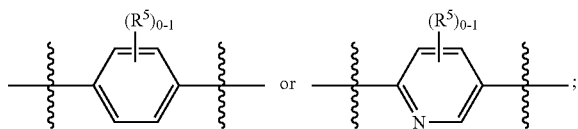

ring B is independently selected from:

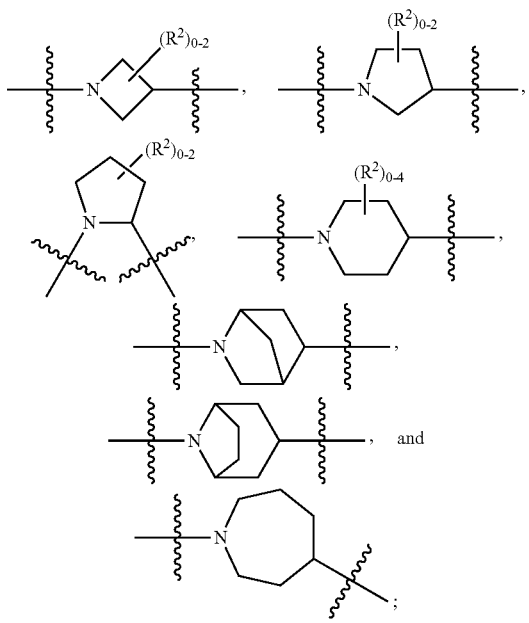

R[1] is independently phenyl substituted with 0-3 R[6] or a heteroaryl substituted with 0-2 R[6]; wherein said heteroaryl is selected from: furanyl, oxazolyl, thiazolyl, pyrazolyl, oxadiazolyl, pyridinyl, pyrimidinyl and pyrazinyl;

R[2], at each occurrence, is independently selected from: OH, halogen, $C_{1-4}$ alkyl, and benzyl;

R[3] is independently selected from: H, halogen, CN, $SO_2(C_{1-4}$ alkyl), $CONH(C_{1-4}$ alkyl), $CON(C_{1-4}$ alkyl)$_2$, $C_{1-4}$ alkyl, $C_{1-4}$ alkoxy, $C_{1-4}$ haloalkyl, $C_{1-4}$ haloalkoxy, phenyl, benzyl, phenoxy, benzoxy, oxazolyl, pyrimidinyl, tetrazolyl, and

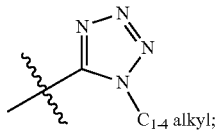

R[4a] is independently selected from: H, halogen and $C_{1-4}$ alkyl; and

R[6], at each occurrence, is independently selected from: halogen, OH, $C_{1-6}$ alkyl substituted with 0-1 OH, $C_{1-4}$ alkoxy, $C_{1-4}$ alkylthio, $C_{1-4}$ haloalkyl, $C_{1-4}$ haloalkoxy, $CH_2OH$, CN, $SO_2(C_{1-2}$ alkyl), $N(C_{1-4}$ alkyl)$_2$, —O—$C_{3-6}$ cycloalkyl, and benzyl.

In another aspect, the present invention includes a compound of Formula (I) or (II), or a stereoisomer, a tautomer, a pharmaceutically acceptable salt, or a solvate thereof, wherein:

R[1] is independently phenyl substituted with 0-3 R[6] or a heteroaryl substituted with 0-2 R[6]; wherein said heteroaryl is selected from: pyridinyl, pyrimidinyl and pyrazinyl.

In another aspect, the present disclosure includes a compound of Formula (I) or (II), or a stereoisomer, a tautomer, a pharmaceutically acceptable salt, or a solvate thereof, wherein:

X is independently selected from: O, $N(CH_3)$, $CH_2$, $CH_2O$, and $CH_2CH_2O$;

ring A is

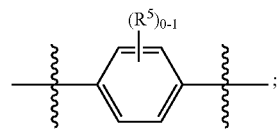

ring B is independently selected from:

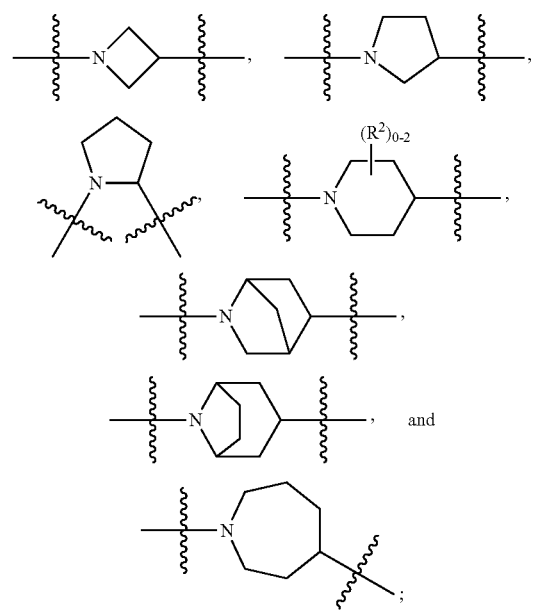

R[1] is independently phenyl substituted with 0-3 R[6], pyridinyl substituted with 0-2 R[6], or pyrazinyl substituted with 0-2 R[6];

R[2], at each occurrence, is independently selected from: OH, halogen, $C_{1-4}$ alkyl, and benzyl;

R[3] is independently selected from: H, halogen, CN, $C_{1-4}$ alkyl, $C_{1-4}$ alkoxy, $CF_3$, $CF_2CF_3$, phenyl, 4-halo-Ph, 4-CN-Ph, 4-$CO_2(C_{1-2}$ alkyl)-Ph, 2-halo-4-CN-Ph, 3-halo-4-halo-Ph, 3-CN-4-CN-Ph, benzyl, phenoxy, benzoxy, 1H-tetrazol-1-yl, and pyrimidin-2-yl; and R[6], at each occurrence, is independently selected from: halogen, CN, $CF_3$, $OCF_3$, $C_{1-4}$ alkyl, $C_{1-4}$ alkoxy, and benzyl.

In another aspect, the present disclosure includes a compound of Formula (I) or (II), or a stereoisomer, a tautomer, a pharmaceutically acceptable salt, or a solvate thereof, wherein:

ring A is

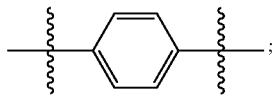

ring B is independently selected from:

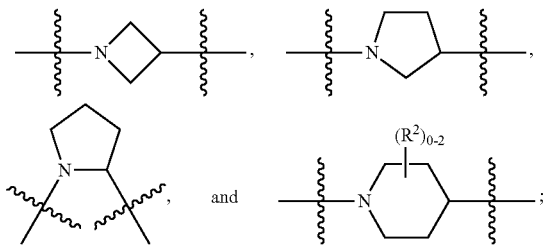

R$^1$ is independently phenyl substituted with 0-3 R$^6$ or pyridinyl substituted with 0-2 R$^6$;

R$^2$ is independently halogen or C$_{1-4}$ alkyl;

R$^3$ is independently selected from: H, halogen, C$_{1-4}$ alkyl, C$_{1-4}$ alkoxy, CF$_3$, phenyl, benzyl, phenoxy, and benzoxy; and R$^6$, at each occurrence, is independently selected from: halogen, OCF$_3$, C$_{1-4}$ alkyl, C$_{1-4}$ alkoxy, and benzyl.

In another aspect, the present disclosure includes a compound of Formula (III):

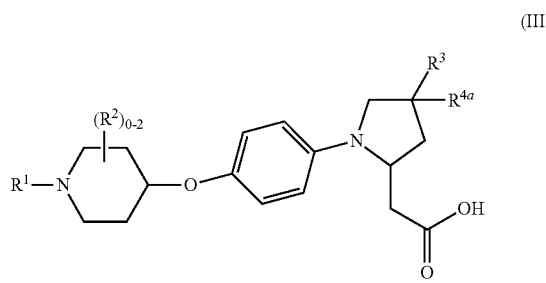

(III)

or a stereoisomer, a tautomer, a pharmaceutically acceptable salt, or a solvate thereof, wherein:

R$^1$ is independently phenyl substituted with 0-3 R$^6$ or pyridinyl substituted with 0-2 R$^6$;

R$^2$ is independently halogen or C$_{1-4}$ alkyl;

R$^3$ is independently selected from: halogen, C$_{1-4}$ alkyl, C$_{1-4}$ alkoxy, CF$_3$, phenyl, benzyl, and phenoxy;

R$^{4a}$ is independently selected from: H, halogen and C$_{1-4}$ alkyl; and

R$^6$, at each occurrence, is independently selected from: halogen, C$_{1-4}$ alkyl, and C$_{1-4}$ alkoxy.

In another embodiment, ring A is independently

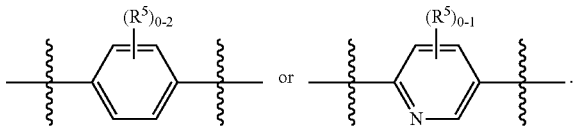

In another embodiment, ring A is

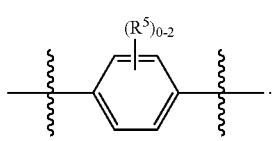

In another embodiment, ring A is

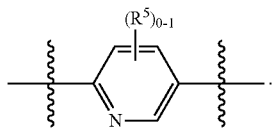

In another embodiment, the compounds of the present invention have hGPR40 EC$_{50}$ values ≤10 μM.

In another embodiment, the compounds of the present invention have hGPR40 EC$_{50}$ values ≤5 μM.

In another embodiment, the compounds of the present invention have hGPR40 EC$_{50}$ values ≤1 μM.

In another embodiment, the compounds of the present invention have hGPR40 EC$_{50}$ values ≤0.5 μM.

In another embodiment, the compounds of the present invention have hGPR40 EC$_{50}$ values ≤0.2 μM.

In another embodiment, the compounds of the present invention have hGPR40 EC$_{50}$ values ≤0.1 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

In another embodiment, the present invention provides a pharmaceutical composition further comprising additional therapeutic agent(s). Examples of additional therapeutic agent(s), according to the present invention include, but are not limited to, anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, or cognition promoting agents, appetite suppressants, treatments for heart failure, treatments for peripheral arterial disease and anti-inflammatory agents.

In a preferred embodiment, the present invention provides pharmaceutical composition, wherein the additional therapeutic agents are, for example, a dipeptidyl peptidase-IV (DPP4) inhibitor (for example a member selected from saxagliptin, sitagliptin, vildagliptin, linagliptin, alogliptin, and "BMS DPP4i"), and/or a sodium-glucose transporter-2 (SGLT2) inhibitor (for example a member selected from dapagliflozin, canagliflozin, empagliflozin and remagliflozin).

In a preferred embodiment, the present invention provides pharmaceutical composition, wherein the additional therapeutic agents are, for example, a DPP4 inhibitor (for example a member selected from saxagliptin, sitagliptin, vildagliptin, linagliptin, alogliptin, and "BMS DPP4i").

In a preferred embodiment, the present invention provides pharmaceutical composition, wherein the additional therapeutic agents are, for example, an SGLT2 inhibitor (for example a member selected from dapagliflozin, canagliflozin, empagliflozin and remagliflozin).

In another embodiment, the present invention provides a method for the treatment and/or prophylaxis of multiple diseases or disorders associated with GPR40, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of the GPR40 that can be prevented, modulated, or treated according to the present invention include, but are not limited to, diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, acute coronary syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), non-cardiac ischemia, pancreatitis, lipid disorders, neurodegenerative disease, cognitive impairment, dementia, and liver diseases such as NASH (Non-Alcoholic SteatoHepatitis), NAFLD (Non-Alcoholic Fatty Liver Disease) and liver cirrhosis.

In another embodiment, the present invention provides a method for the treatment and/or prophylaxis of diabetes, hyperglycemia, gestational diabetes, obesity, dyslipidemia, hypertension and cognitive impairment, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of diabetes, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of hyperglycemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of obesity, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of dyslipidemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of hypertension, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of cognitive impairment, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of multiple diseases or disorders associated with GPR40.

In another embodiment, the present invention also provides the use of a compound of the present invention for the manufacture of a medicament for the treatment and/or prophylaxis of multiple diseases or disorders associated with GPR40.

In another embodiment, the present invention provides a method for the treatment and/or prophylaxis of multiple diseases or disorders associated with GPR40, comprising administering to a patient in need thereof a therapeutically effective amount of a first and second therapeutic agent, wherein the first therapeutic agent is a compound of the present invention. Preferably, the second therapeutic agent, for example, a DPP4 inhibitor (for example a member selected from saxagliptin, sitagliptin, vildagliptin, linagliptin and alogliptin).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders associated with GPR40.

Where desired, the compound of the present invention may be used in combination with one or more other types of anti-diabetic agents and/or one or more other types of therapeutic agents which may be administered orally in the same dosage form, in a separate oral dosage form or by injection. The other type of anti-diabetic agent that may be optionally employed in combination with the GPR40 receptor modulator of the present invention may be one, two, three or more anti-diabetic agents or antihyperglycemic agents which may be administered orally in the same dosage form, in a separate oral dosage form, or by injection to produce an additional pharmacological benefit.

The anti-diabetic agents used in the combination with the GPR40 receptor modulator of the present invention include, but are not limited to, insulin secretagogues or insulin sensitizers, other GPR40 receptor modulators, or other anti-diabetic agents. These agents include, but are not limited to, DPP4 inhibitors (for example, sitagliptin, saxagliptin, alogliptin, linagliptin and vildagliptin), biguanides (for example, metformin and phenformin), sulfonyl ureas (for example, glyburide, glimepiride and glipizide), glucosidase inhibitors (for example, acarbose, miglitol), PPARγ agonists such as thiazolidinediones (for example, rosiglitazone and pioglitazone), PPAR α/γ dual agonists (for example, muraglitazar, tesaglitazar and aleglitazar), glucokinase activators, GPR119 receptor modulators (for example, MBX-2952, PSN821, and APD597), GPR120 receptor modulators (for example, as described in Shimpukade, B. et al., *J. Med. Chem.*, 55(9):4511-4515 (2012)), SGLT2 inhibitors (for example, dapagliflozin, canagliflozin, empagliflozin and remagliflozin), MGAT inhibitors (for example, as described in Barlind, J. G. et al., *Bioorg. Med. Chem. Lett.*, 23(9): 2721-2726 (2013); or US 2013/0143843 A1), amylin analogs such as pramlintide, and/or insulin.

The GPR40 receptor modulator of the present invention may also be optionally employed in combination with agents for treating complication of diabetes. These agents include PKC inhibitors and/or AGE inhibitors.

The GPR40 receptor modulator of the present invention may also be optionally employed in combination with one or more hypophagic and/or weight-loss agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, and the like. The GPR40 receptor modulator of the present invention may also be employed in combination with an agonist of the glucagon-like peptide-1 receptor (GLP-1 R), such as exenatide, liraglutide, GLP-1 (1-36) amide, GLP-1(7-36) amide, GLP-1(7-37), which may be administered via injection, intranasal, or by transdermal or buccal devices.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl". A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in *Hawley's Condensed Chemical Dictionary*, 13th Edition, Lewis, R. J., ed., John Wiley & Sons, Inc., New York (1997). "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, imidazopyridazinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolopyrimidinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, pyrimidinyl, pyrazinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, imidazolopyridinyl, imidazopyridazinyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, pyrazolopyridinyl and pyrazolopyrimidinyl.

Examples of 5- to 6-membered heterocycles include, but are not limited to, pyridinyl, furanyl, thienyl, pyrrolyl, pyrazolyl, pyrazinyl, piperazinyl, piperidinyl, pyrimidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted.

The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), calcium (Ca$^{2+}$)ammonium (R$_n$NH$_m$+ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. et al., *Protecting Groups in Organic Synthesis*, 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, 22nd Edition, Allen, L. V., Jr., ed., Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2nd Edition, reproduced (2006)); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3rd Edition, Academic Press, San Diego, Calif. (2008).

The present invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H (also represented as 'D' for deuterium) and $^3$H, carbon such as $^{11}$C, $^{13}$C, and $^{14}$C, nitrogen, such as $^{13}$N and $^{15}$N, oxygen, such as $^{15}$O, $^{17}$O, and $^{18}$O. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H, may afford certain therapeutic advantages resulting from greater metabolic stability, for example, increase in vivo half-life or reduced dosage requirements, and hence may be preferred in some circumstances. Substitution with positron emitting isotopes, such as $^{11}C$, $^{15}O$, $^{18}F$, and $^{13}N$, can be useful in Positron Emission Topography (PET) studies for examining substrate receptor occupancy. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "Å" for "Angstroms", "° C." for degrees Celsius, "eq" for equivalent or equivalents, "g" for gram or grams, "mg" for milligram or milligrams, "L" for liter or liters, "mL or ml" for milliliter or milliliters, "µL" for microliter or microliters, "N" for normal, "M" for molar, "N" for normal, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "RP-Prep. HPLC" for reverse phase preparative HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

AcCl acetyl chloride
$Ac_2O$ acetic anhydride
AcOH acetic acid
ADDP 1,1'-(azodicarbonyl)dipiperidine
$Ag_2O$ silver oxide
atm atmosphere
9-BBN 9-borabicyclo[3.3.1]nonane
$BF_3.OEt_2$ boron trifluoride diethyl etherate
$BF_3.SMe_2$ boron trifluoride dimethyl sulfide
$BH_3.DMS$ borane dimethyl sulfide complex
Bn benzyl
Boc tert-butyloxycarbonyl
$Boc_2O$ di-tert-butyl dicarbonate
Bu butyl
n-BuOH n-butanol
$Bu_3P$ tributylphosphine
$CDCl_3$ deutero-chloroform
$CD_2Cl_2$ deutero-dichloromethane
cDNA complimentary DNA
$CH_2Cl_2$ or DCM dichloromethane
$CH_3CN$ or MeCN acetonitrile
$CHCl_3$ chloroform
CSA camphorsulfonic acid
$Cs_2CO_3$ cesium carbonate
$Cu(OAc)_2$ copper(II) acetate
CuI copper(I) iodide
$CuBr.SMe_2$ copper(I) bromide dimethylsulfide complex
DAST (diethylamino)sulfur trifluoride
DBAD di-tert-butyl azodicarboxylate
DEAD diethyl azodicarboxylate
DIAD diisopropyl azodicarboxylate
DIPEA diisopropylethylamine
DMAP 4-(dimethylamino)pyridine
DMF dimethyl formamide
DMSO dimethyl sulfoxide
DtBPF 1,1'-bis(di-tert-butylphosphino)ferrocene
EDTA ethylenediaminetetraacetic acid
Et ethyl
$Et_2O$ diethyl ether
EtOAc ethyl acetate
EtOH ethanol
$H_2$ molecular hydrogen
$H_2O_2$ hydrogen peroxide
$H_2SO_4$ sulfuric acid
HCl hydrochloric acid
Hex hexanes
i-Bu isobutyl
i-Pr isopropyl
i-PrOH or IPA isopropanol
KCN potassium cyanide
$K_2CO_3$ potassium carbonate
$K_2HPO_4$ dipotassium phosphate
$KHSO_4$ potassium bisulfate
KI potassium iodide
KOH potassium hydroxide
KOtBu potassium tert-butoxide
$K_3PO_4$ tripotassium phosphate
LAH lithium aluminum hydride
LDA lithium diisopropylamide
L.G. leaving group
LHMDS lithium hexamethyldisilazide
$LiBH_4$ lithium borohydride
LiOH lithium hydroxide
L-Selectride lithium tri-sec-butylborohydride
Me methyl
MeI iodomethane
MeLi methyl lithium
MeOH methanol
$MgSO_4$ magnesium sulfate
MsCl methanesulfonyl chloride
NaDCC sodium dichloroisocyanurate
NaHMDS sodium hexamethyldisilazide
$NaNO_2$ sodium nitrite
$Na_2SO_4$ sodium sulfate
$Na_2S_2O_3$ sodium thiosulfate
$NaBH_4$ sodium borohydride
NaCl sodium chloride
NaCN sodium cyanide
NCS N-chlorosuccinimide
NaH sodium hydride
$NaHCO_3$ sodium bicarbonate
NaOH sodium hydroxide
NaOtBu sodium tert-butoxide
$NH_3$ ammonia NH₄Cl ammonium chloride
NH₄OH ammonium hydroxide
Pd(OAc)₂ palladium(II) acetate
Pd/C palladium on carbon
PdCl₂(dppf) 1,1'-bis(diphenylphosphino)ferrocene-palladium(II)dichloride
PdCl₂(dtbpf) [1,1'-bis(di-tert-butylphosphino)ferrocene]dichloropalladium(II)
PdCl₂(PPh₃)₂ bis(triphenylphosphine)palladium(II) dichloride
Pd₂(dba)₃ tris(dibenzylideneacetone)dipalladium(0)
Pd(Ph₃P)₄ tetrakis(triphenylphosphine)palladium(0)
P.G. protecting group
Ph phenyl
Ph₃P triphenylphosphine
Pr propyl
PS polystyrene
PtO₂ platinum(IV) oxide
SFC supercritical fluid chromatography
SiO₂ silica oxide
SPhos 2-dicyclohexylphosphino-2',6'-dimethoxy-1,1'-biphenyl
SPhos precatalyst chloro(2-dicyclohexylphosphino-2',6'-dimethoxy-1,1'-biphenyl) [2-(2-aminoethylphenyl)]palladium(II)-methyl-t-butyl ether adduct
TBAF tetrabutylammonium fluoride
t-Bu tert-butyl
TBDPS-Cl tert-butylchlorodiphenylsilane
TBS-Cl tert-butyldimethylsilyl chloride
TBSOTf tert-butyldimethylsilyl trifluoromethanesulfonate
TCCA trichloroisocyanuric acid
TEA or NEt₃ triethylamine
TEMPO 2,2,6,6-tetramethyl-1-piperidinyloxy
TFA trifluoroacetic acid
Tf₂O trifluoromethanesulfonic anhydride
THF tetrahydrofuran
TMS-Cl chlorotrimethylsilane
TsCl 4-methylbenzene-1-sulfonyl chloride
TsOH or pTsOH para-toluenesulfonic acid
XPhos 2-dicyclohexylphosphino-2',4',6'-triisopropylbiphenyl The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

The compounds of Formula (I) may be prepared by the exemplary processes described in the following schemes and working examples, as well as relevant published literature procedures that are used by one skilled in the art. Exemplary reagents and procedures for these reactions appear hereinafter and in the working examples. Protection and deprotection in the processes below may be carried out by procedures generally known in the art (see, for example, Wuts, P. G. M. et al., *Protecting Groups in Organic Synthesis*, 4th Edition, Wiley (2007)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); Smith, M. B. et al., *March's Advanced Organic Chemistry: Reactions, Mechanisms, and Structure*. 6th Edition, Wiley & Sons, New York, N.Y. (2007); Katritzky, A. R. et al., eds., *Comprehensive Organic Functional Groups Transformations II*, 2nd Edition, Elsevier Science Inc., Tarrytown, N.Y. (2004); Larock, R. C., *Comprehensive Organic Transformations*, VCH Publishers, Inc., New York, N.Y. (1999), and references therein.

Methods for synthesis of a large variety of substituted pyrrolidine compounds useful as starting materials for the preparation of compounds of the present invention are well known in the art. For examples of methods useful for the preparation of pyrrolidine materials see the following references and citations therein: Katritzky et al., eds., *Comprehensive Heterocyclic Chemistry*, Pergamon Press Inc., New York (1996); Bellina, F. et al., *Tetrahedron*, 62:7213 (2006); Wolfe, J. P., *Eur. J. Org. Chem.*, 571 (2007); Deng, Q.-H. et al., *Organic Letters*, 10:1529 (2008); Pisaneschi, F. et al., *Synlett*, 18:2882 (2007); Najera, C. et al., *Angewandte Chemie, International Edition*, 44(39):6272 (2005); Sasaki, N. A., *Methods in Molecular Medicine*, 23(Peptidomimetics Protocols):489 (1999); Zhou, J.-Q. et al., *Journal of Organic Chemistry*, 57(12):3328 (1992); Coldham, I. et al., *Tetrahedron Letters*, 38(43):7621 (1997); Schlummer, B. et al., *Organic Letters*, 4(9):1471 (2002); Larock, R. C. et al., *Journal of Organic Chemistry*, 59(15):4172 (1994); Galliford, C. V. et al., *Organic Letters*, 5(19):3487 (2003); Kimura, M. et al., *Angewandte Chemie, International Edition*, 47(31):5803 (2008); Ney, J. E. et al., *Adv. Synth. Catal.*, 347:1614 (2005); Paderes, M. C. et al., *Organic Letters*, 11(9):1915 (2009); Wang, Y.-G. et al., *Organic Letters*, 11(9):2027 (2009); Cordero, F. M. et al., *Journal of Organic Chemistry*, 74(11):4225 (2009); Hoang, C. T. et al., *Journal of Organic Chemistry*, 74(11):4177 (2009). Luly, J. R. et al., *Journal of the American Chemical Society*, 105:2859 (1983); Kimball, F. S. et al., *Bioorganic and Medicinal Chemistry*, 16:4367 (2008); Bertrand, M. B. et al., *Journal of Organic Chemistry*, 73(22):8851 (2008); Browning, R. G. et al., *Tetrahedron*, 60:359 (2004); Ray, J. K. et al., *Bioorganic and Medicinal Chemistry*, 2(12):1417 (1994); Evans, G. L. et al., *Journal of the American Chemical Society*, 72:2727 (1950); Stephens, B. E. et al., *Journal of Organic Chemistry*, 74(1):254 (2009); Spangenberg, T. et al., *Organic Letters*, 11(2):261 (2008); Qiu, X.-L. et al., *Journal of Organic Chemistry*, 67(20):7162 (2008).

Compounds of Formula (I) may be synthesized starting with pyrrolidines A via coupling to intermediate B using, for example, CuI and NaOH to give prolinol C, as depicted in Scheme 1. Activation of intermediate C, via methanesulfonyl chloride and base, for example, and displacement with sodium cyanide leads to nitrile D. Removal of P.G. on intermediate D, such as hydrogenolysis (when P.G. is a benzyl ether), gives phenol E. $R^1$ group of intermediate J is appended via displacement of L.G. in intermediate F via amine H using S-Phos precatalyst and base, such as LiH-MDS or, optionally via uncatalyzed displacement of L.G. The hydroxyl of amine J can be activated with, for example, para-toluenesulfonyl chloride and base, such as pyridine, to give tosylate K. Intermediate K and phenol E can be coupled using a base, such as $Cs_2CO_3$, to give intermediate L. The cyano or methyl ester group can be hydrolyzed via NaOH, for example, to provide compounds of Formula (I).

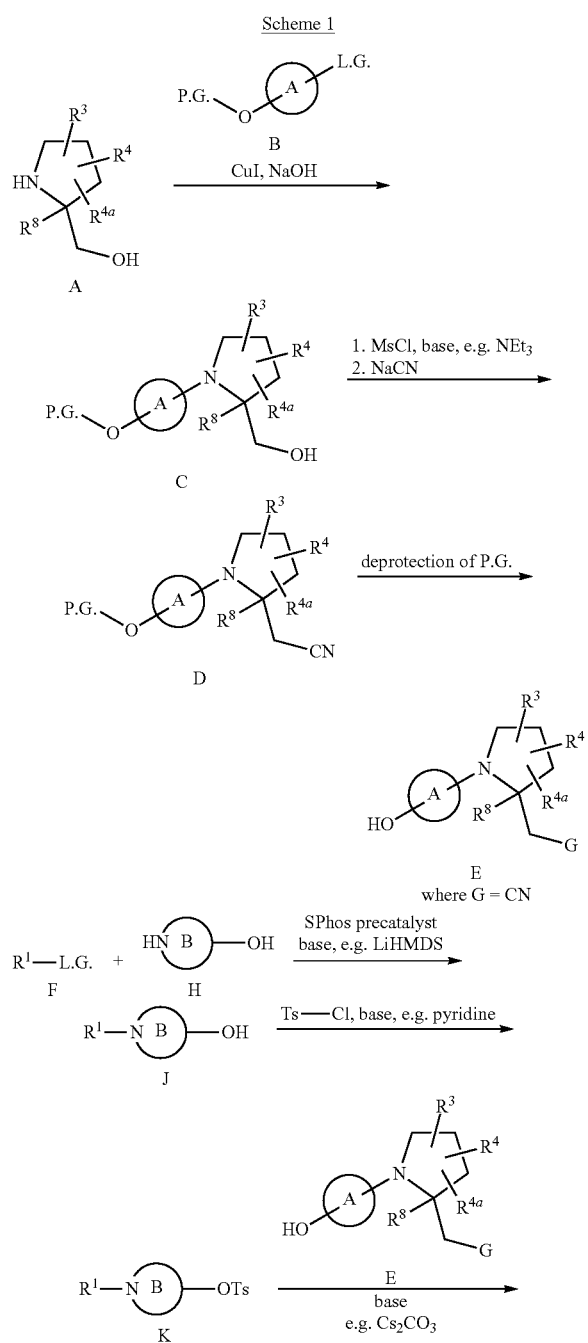

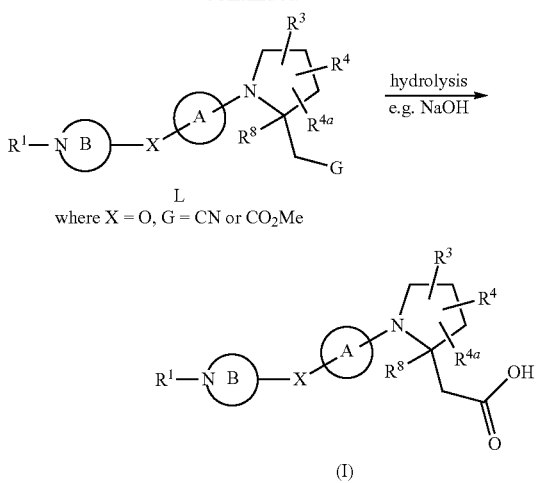

Alternatively, compounds of Formula (I) can be synthesized via reaction of tosylate K with phenol M containing a L.G. using a base (e.g., $Cs_2CO_3$) as depicted in Scheme 2. The resultant intermediates N can be converted to intermediate L via an analogous sequence to that shown in Scheme 1. The cyano or methyl ester group can be hydrolyzed via NaOH, for example, to provide compounds of Formula (I).

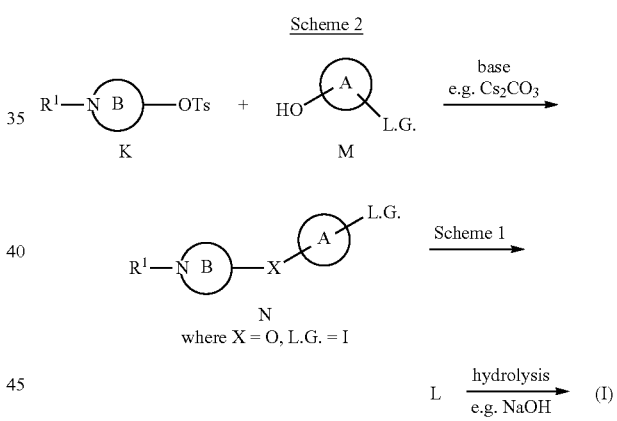

Compounds of Formula (I) may be synthesized by coupling alcohol J with nitrobenzene O using a base, e.g., NaH, to give intermediate P as demonstrated in Scheme 3. The nitrobenzene P can be hydrogenated with hydrogen and Pd/C and then converted to iodide Q using an acid, such as TsOH, KI, and $NaNO_2$. The resultant intermediate N can be converted to intermediate L by analogy to the sequence depicted in Scheme 1. The cyano or methyl ester group can be hydrolyzed via NaOH, for example, to provide compounds of Formula (I).

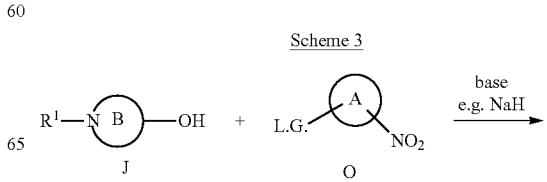

-continued

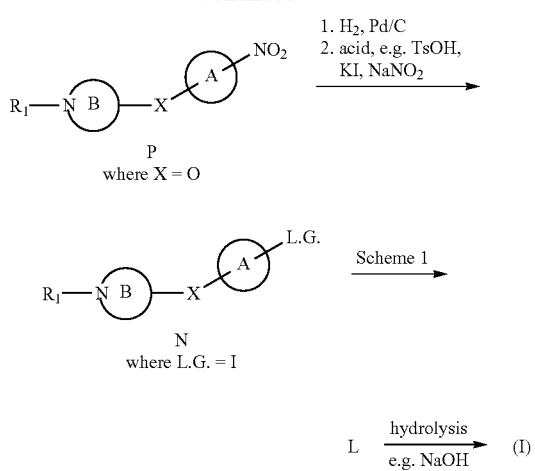

Compounds of Formula (I) can be synthesized by reaction of alcohol J with phenol E via a Mitsunobu reaction using an azodicarboxylate, such as ADDP, and a phosphine (e.g., Bu$_3$P) as demonstrated in Scheme 4 to give compound L. The intermediate L can be converted to compounds of Formula (I) by hydrolysis with base, such as NaOH.

Scheme 4

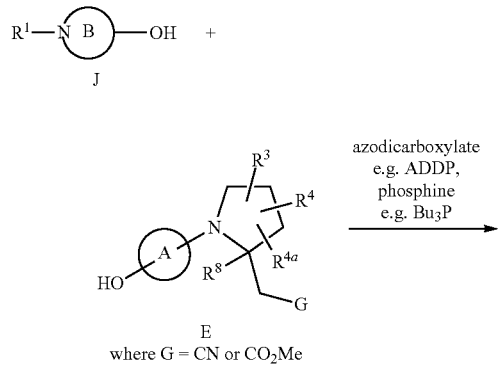

Alternatively, compounds of Formula (I) may be synthesized starting with ethyl 1-benzyl-4-oxopiperidine-3-carboxylate (intermediate R), which can be reacted with R$^2$-L.G., as in intermediate S, using a base, such as KOtBu, to provide β-ketoester T as depicted in Scheme 5. The ester can be removed via decarboxylation with acid, e.g., HCl, to provide piperidinone U. The methyl iodonium salt V can be formed from piperidinone U using MeI. The salt V can be converted to the piperidinone X by reaction with an amine W and base (e.g., K$_2$CO$_3$). The ketone X can be reduced using a hydride source, such as NaBH$_4$, to give alcohol J. Alcohol J can be converted to compounds of Formula (I) according to the sequence depicted in Scheme 1 or Scheme 4.

Scheme 5

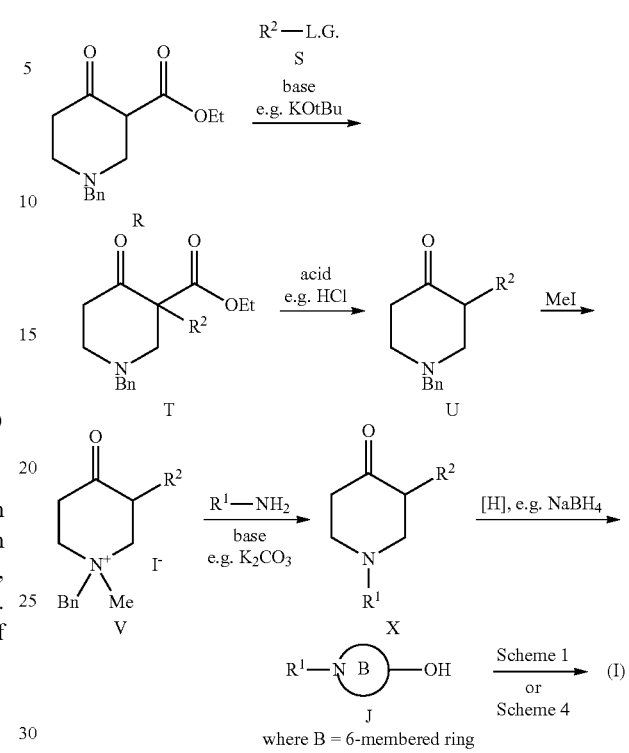

Compounds of Formula (I) can be synthesized starting with aldehyde Y as depicted in Scheme 6. The aldehyde Y can be reacted with boronic acid Z using TsNHNH$_2$ and base, such as K$_2$CO$_3$, to give intermediate AA. P.G. can be removed and the amine can be coupled with a boronic acid AB using NEt$_3$ and Cu(OAc)$_2$ to give intermediate N, which can be converted to compounds of Formula (I) following the route depicted in Scheme 3.

Scheme 6

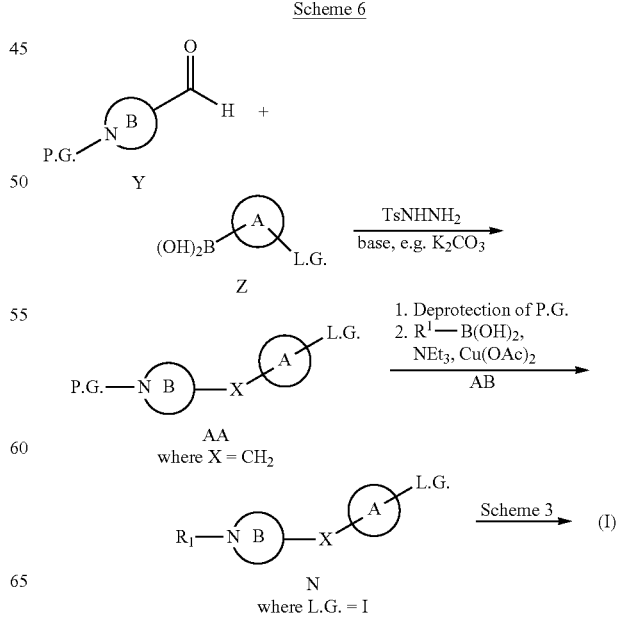

IV. Biology

Diabetes mellitus is a serious disease afflicting over 100 million people worldwide. It is diagnosed as a group of disorders characterized by abnormal glucose homeostasis resulting in elevated blood glucose. Diabetes is a syndrome with interrelated metabolic, vascular, and neuropathic components. The metabolic abnormality is generally characterized by hyperglycemia and alterations in carbohydrate, fat and protein metabolism caused by absent or reduced insulin secretion and/or ineffective insulin secretion. The vascular syndrome consists of abnormalities in the blood vessels leading to cardiovascular, retinal and renal complications. Abnormalities in the peripheral and autonomic nervous systems are also part of diabetic syndrome. Strikingly, diabetes is the fourth leading cause of global death by disease, the largest cause of kidney failure in developed countries, the leading cause of vision loss in industrialized countries and has the greatest prevalence increase in developing countries.

Type 2 diabetes, which accounts for 90% of diabetes cases, is characterized by increasing insulin resistance associated with inadequate insulin secretion after a period of compensatory hyperinsulinemia. The reasons for β cell secondary failure are not completely understood. Acquired pancreatic islet damage or exhaustion and/or genetic factors causing susceptibility to islet secretory insufficiency have been hypothesized.

Free fatty acids (FFAs) are evidenced to influence insulin secretion from β cells primarily by enhancing glucose-stimulated insulin secretion (GSIS). Although glucose is recognized as the major stimulator of insulin secretion from β cells, other stimuli, such as amino acids, hormones, and FFAs, also regulate insulin secretion. Thus, under normal settings, insulin secretion from β cells in response to food intake is evoked by the collective stimuli of nutrients, such as glucose, amino acids, and FFAs, and hormones like the incretin glucagon-like peptide 1 (GLP-1). Fatty acids are also known to stimulate the secretion of several gut satiety hormones, including cholocystokinine (CCK), GLP-1, and peptide YY (PYY).

G-protein coupled receptors (GPCRs) expressed in β cells are known to modulate the release of insulin in response to changes in plasma glucose levels. GPR40, also known as fatty acid receptor 1 (FFAR1), is a membrane-bound FFA receptor which is preferentially expressed in the pancreatic islets and specifically in β cells. GPR40 (e.g., human GPR40, RefSeq mRNA ID NM_005303; e.g., mouse GPR40 RefSeq mRNA ID NM_194057) is a GPCR located at chromosome 19q13.12. GPR40 is activated by medium to long chain fatty acids and thereby triggering a signaling cascade that results in increased levels of $[Ca^2]_i$ in β cells and subsequent stimulation of insulin secretion (Itoh et al., *Nature*, 422:173-176 (2003)). Selective small molecule agonists of GPR40 have been shown to promote GSIS and reduce blood glucose in mice (Tan et al., *Diabetes*, 57:2211-2219 (2008)). Briefly, when activators of GPR40 are administered to either normal mice or mice that are prone to diabetes due to genetic mutation, prior to a glucose tolerance test, improvements in glucose tolerance are observed. A short-lived increase in plasma insulin levels are also observed in these treated mice. It has also been shown that GPR40 agonists restore GSIS in pancreatic β-cells from the neonatal STZ rats suggesting that GPR40 agonists will be efficacious in diabetics with compromised β-cell function and mass. Fatty acids are known to stimulate the secretion of several gut satiety hormones, including cholocystokinine (CCK), GLP-1, and peptide YY (PYY), and GPR40 has been shown to colocalize with cells that secrete such hormones (Edfalk et al., *Diabetes*, 57:2280-2287 (2008) Luo et al., *PLOS ONE*, 7:1-12 (2012)). Fatty acids are also known to play a role in neuronal development and function, and GPR40 has been reported as a potential modulator of the fatty acid effects on neurons (Yamashima, T., *Progress in Neurobiology*, 84:105-115 (2008)).

Given the increase in the worldwide patient population afflicted by type 2 diabetes, there is a need for novel therapies which are effective with minimal adverse events. To decrease medical burden of type 2 diabetes through enhanced glycemic control, GPR40 modulator compounds of the present invention are being investigated here for their incretin effect to promote GSIS as well as the potential combination with a broad range of anti-diabetic drugs.

The term "modulator" refers to a chemical compound with capacity to either enhance (e.g., "agonist" activity) or partially enhance (e.g., "partial agonist" activity) or inhibit (e.g., "antagonist" activity or" inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-diabetic agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index with less propensity for hypoglycemia.

As used herein, the term "patient" encompasses all mammalian species.

As used herein, the term "subject" refers to any human or non-human organism that could potentially benefit from treatment with a GPR40 modulator. Exemplary subjects include human beings of any age with risk factors for metabolic disease. Common risk factors include, but are not limited to, age, sex, weight, family history, or signs of insulin resistance such as acanthosis nigricans, hypertension, dislipidemia, or polycystic ovary syndrome (PCOS).

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to modulate GPR40 and/or to prevent or treat the disorders listed herein. When applied to a combination, the term refers to combined amounts of the active ingredients that result in the preventive or therapeutic effect, whether administered in combination, serially, or simultaneously.

In Vitro GPR40 Assays
FDSS-based Intracellular Calcium Assay

Cell lines expressing GPR40 are generated using the pDEST 3×FLAG® gene expression system and are cultured in culture medium comprising the following components: F12 (GIBCO® #11765), 10% lipid deprived fetal bovine serum, 250 μg/mL zeocin and 500 μg/mL G418. To conduct the fluorescent imaging plate reader (FLIPR)-based calcium flux assay to measure intracellular $Ca^{2+}$ response, cells expressing GPR40 are plated on 384 well plates (BD BIOCOAT® #356697) at a density of 20,000 cells/20 μL medium per well in phenol red and serum-free DMEM (GIBCO® #21063-029) and incubated overnight. Using BD kit #s 80500-310 or -301, the cells are incubated with 20 μL per well of Hank's buffered salt solution with 1.7 mM probenecid and Fluo-3 at 37° C. for 30 min. Compounds are dissolved in DMSO and diluted to desired concentrations with assay buffer and added to the cells as 3× solution (20 μL per well). Run fluorescence/luminescence reader FDSS (Hamamatsu) to read intracellular $Ca^{2+}$ response.

The exemplified Examples disclosed below were tested in the Human GRP40 In Vitro assay described above and found having hGRP40 modulating activity, reported as hGPR40 $EC_{50}$.

GPR40 IP-One HTRF Assays in HEK293/GPR40 Inducible Cell Lines

Human, mouse and rat GPR40-mediated intracellular IP-One HTRF assays were established using human embryonic kidney HEK293 cells stably transfected with a tetracycline-inducible human, mouse or rat GPR40 receptor. Cells were routinely cultured in growth medium containing DMEM (GIBCO® Cat. #12430-047), 10% qualified FBS (Sigma, Cat. #F2442), 200 μg/mL hygromycin (Invitrogen, Cat. #16087-010) and 1.5 μg/mL blasticidin (Invitrogen, Cat. #R210-01). About 12-15 million cells were passed into a T175 tissue culture flask (BD FALCON® 353112) with growth medium and incubated for 16-18 hours (overnight) at 37° C. with 5% $CO_2$. The next day, assay medium was exchanged with growth medium containing 1000 ng/mL of tetracycline (Fluka Analytical, Cat. #87128) to induce GPR40 expression for 18-24 hours at 37° C. incubator with 5% $CO_2$. After induction, the cells were washed with PBS (GIBCO®, Cat. #14190-036) and detached with Cell Stripper (CELLGRO®, Cat. #25-056-CL). 10-20 mL growth medium were added to the flask and cells were collected in 50 mL tubes (FALCON®, Cat. #352098) and spun at 1000 RPM for 5 minutes. Culture medium was aspirated and the cells were resuspended in 10 mL of 1×IP-One Stimulation Buffer from the Cisbio IP-One kit (Cisbio, Cat. #62IPAPEJ). The cells were diluted to 1.4×106 cells/mL in Stimulation Buffer.

Test compounds were 3-fold, 11-point serially diluted in DMSO in a REMP assay plate (Matrix Cat. #4307) by BIOCEL® (Agilent). The compounds were transferred into an Echo plate (LABCYTE®, Cat. #LP-0200) and 20 nL of diluted compounds were transferred to an assay plate (proxiplate from Perkin Elmer, Cat. #6008289) by Echo acoustic nano dispenser (LABCYTE®, model ECHO550). 14 μL of the diluted cells were then added to the assay plate by Thermo (SN 836 330) Combi Drop and incubated at room temperature for 45 minutes. Then 3 μL of IP1 coupled to dye D2 from the Cisbio IP-One kit were added to the assay plate followed by 3 μL of Lumi4-Tb cryptate K from the kit. The plate was further incubated at room for 1 hour before reading on the Envision (Perkin Elmer Model2101) with an HTRF protocol. Activation data for the test compound over a range of concentrations was plotted as percentage activation of the test compound (100%=maximum response). After correcting for background [(sample read−mean of low control)/(mean of high control−mean of low control)] (low control is DMSO without any compound), $EC_{50}$ values were determined. The $EC_{50}$ is defined as the concentration of test compound which produces 50% of the maximal response and was quantified using the 4 parameter logistic equation to fit the data. The maximal Y value observed (% Ymax) was calculated relative to a BMS standard reference compound at a final concentration of 0.625 μM.

Some of the exemplified Examples disclosed below were tested in the Human GRP40 In Vitro assay described above and found having hGRP40 modulating activity reported as hGPR40 IP1 $EC_{50}$.

In Vivo GPR40 Assays
Acute Oral Glucose Tolerance Test

Ten week old C57BL6 mice were housed individually and fasted for 5 hours on the day of study. Tail vein sampling was performed from nicked tails to obtain plasma samples. Baseline plasma samples were taken at t=0. Mice were orally treated with vehicle or compounds co-administered with glucose (2 g/kg). Sampling thereafter from tails of treated mice at 20, 40, 60, 120 and 180 min provided data used for generating glucose excursion curves from which 0-180 min blood glucose excursion profiles were generated. The area under the curve (AUC) allowed for assessment of glucose lowering by compound treatments. Blood samples were collected in EDTA-treated tubes (MICROVETTE® CB300, Sarstedt, Numbrecht, Germany), stored on ice and spun at 6000 rpm for 10 minutes. Plasma glucose was analyzed on the same day using an AU680 Clinical Chemistry Analyzer (Beckman Coulter, Brea, Calif.). Statistical analysis is a one way ANOVA with Dunnett's post hoc test or two-way student's t test where appropriate. P values less than 0.05 were considered statistically significant. Glucose reduction is reported as a % change in AUC (0-180 min) from the vehicle treatment group; for example, "Acute oral glucose tolerance: −50% at 0.3 mg/kg" represents the results of a study as described above, whereupon administration of 0.3 mg/kg of the specified example results in a 50% reduction in glucose AUC (0-180 min) relative to vehicle treated animals.

Acute Oral Glucose Tolerance Test in Rats

Male SPRAGUE DAWLEY® rats (CRL, Wilmington Mass.) were used. Rats were delivered to the vivarium and acclimated for 1 week. Rats were fasted from 5 PM on the night before study. Overnight fasted rats were 180-200 grams at time of study. Tail vein sampling was performed to obtain baseline plasma samples. Rats were randomized to treatment groups based on fasting plasma glucose readings determined by Accu-Chek glucometer (Roche, Indianapolis, Ind.). Rats were dosed at 4 mL/Kg body weight with 40% PEG400 (Sigma, St. Louis, Mo.) 10% CREMOPHOR® (Sigma, St. Louis, Mo.) and 50% distilled water with or without compounds. For rats that received BMS DPP4i combined with GPR40 agonist, administration was performed by co-dosing compounds. Plasma samples were collected one hour after compound dosing to determine baseline changes in glucose and active GLP-1 levels in the presence and absence of BMS DPP4i. Sampling thereafter from tail veins provided time point data to calculate $AUC_{0\text{-}120}$ glucose as a marker of two hour glucose lowering efficacy. Blood samples were collected in EDTA-treated tubes (MICROVETTE® CB300, Sarstedt, Numbrecht, Germany), stored on ice and spun at 6000 rpm for 10 minutes. Plasma glucose was analyzed on the same day using an AU680 Clinical Chemistry Analyzer (Beckman Coulter, Brea, Calif.). Statistical analysis is a one way ANOVA with Dunnett's post hoc test or two-way student's t test where appropriate. P values less than 0.05 were considered statistically significant. Glucose reduction is reported as a % change in AUC (0-120 min) from the vehicle treatment group. Fasting hormone responses are the difference from basal levels 1 hour post dose. Active GLP-1 levels (GLP-1 (7-36) amide and GLP-1 (7-37)) were measured by ELISA (Millipore, Billerica, Mass.).

BMS DPP4i—Reference Compound

BMS DPP4i is disclosed in Simpkins, L. et al., *Bioorganic Medicinal Chemistry Letters*, 17(23):6476-6480 (2007) (compound 48) and in WO 2005/012249 (Example 3). BMS DPP4i has the following formula:

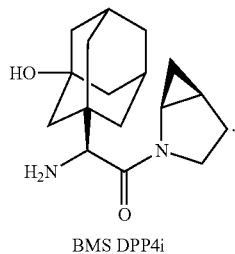

BMS DPP4i

The compounds of the present invention possess activity as modulators of GPR40, and, therefore, may be used in the treatment of diseases associated with GPR40 activity. Via modulation of GPR40, the compounds of the present invention may preferably be employed to modulate the production/secretion of insulin and/or gut hormones, such as GLP-1, GIP, CCK and amylin.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, acute coronary syndrome, delayed wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, fatty liver disease, dyslipidemia, hyperlipidemia, hypertriglyceridemia, hypercholesterolemia, low HDL, high LDL, vascular restenosis, peripheral arterial disease, lipid disorders, liver diseases such as NASH (Non-Alcoholic Steatohepatitis), NAFLD (Non-Alcoholic Fatty Liver Disease) and liver cirrhosis, neurodegenerative disease, cognitive impairment, dementia, and treatment of side-effects related to diabetes, lipodystrophy and osteoporosis from corticosteroid treatment.

Metabolic Syndrome or "Syndrome X" is described in Ford et al., *J. Am. Med. Assoc.*, 287:356-359 (2002) and Arbeeny et al., *Curr. Med. Chem.—Imm., Endoc. & Metab. Agents*, 1:1-24 (2001).

GPR40 is expressed in neuronal cells, and is associated with development and maintenance of neuronal health in brain, as described in Yamashima, T., *Progress in Neurobiology*, 84:105-115 (2008).

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, *Pharmaceutical Press* (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anti-diabetic agent or other pharmaceutically active material.

The compounds of the present invention may be employed in combination with other GPR40 modulators or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, or cognition promoting agents, appetite suppressants, treatments for heart failure, treatments for peripheral arterial disease and anti-inflammatory agents.

Where desired, the compound of the present invention may be used in combination with one or more other types of anti-diabetic agents and/or one or more other types of therapeutic agents which may be administered orally in the same dosage form, in a separate oral dosage form or by injection. The other type of anti-diabetic agent that may be optionally employed in combination with the GPR40 receptor modulator of the present invention may be one, two, three or more anti-diabetic agents or antihyperglycemic agents which may be administered orally in the same dosage form, in a separate oral dosage form, or by injection to produce an additional pharmacological benefit.

The anti-diabetic agents used in the combination with the compound of the present invention include, but are not limited to, insulin secretagogues or insulin sensitizers, other GPR40 receptor modulators, or other anti-diabetic agents. These agents include, but are not limited to, dipeptidyl peptidase IV inhibitors (DPP4i; for example, sitagliptin, saxagliptin, alogliptin, vildagliptin), biguanides (for example, metformin, phenformin), sulfonyl ureas (for example, gliburide, glimepiride, glipizide), glucosidase inhibitors (for example, acarbose, miglitol), PPARγ agonists such as thiazolidinediones (for example, rosiglitazone, pioglitazone), PPAR α/γ dual agonists (for example, muraglitazar, tesaglitazar, aleglitazar), glucokinase activators (as described in Fyfe, M. C. T. et al., *Drugs of the Future,* 34(8):641-653 (2009) and incorporated herein by reference), other GPR40 receptor modulators (e.g., TAK-875), GPR119 receptor modulators (for example, MBX-2952, PSN821, APD597), GPR120 receptor modulators (for example, as described in Shimpukade, B. et al., *J. Med. Chem.,* 55 (9):4511-4515 (2012)), sodium-glucose transporter-2 (SGLT2) inhibitors (for example dapagliflozin, canagliflozin, empagliflozin, remagliflozin), 11b-HSD-1 inhibitors (for example MK-0736, BI35585, BMS-823778, and LY2523199), MGAT inhibitors (for example, as described in Barlind, J. G. et al., *Bioorg. Med. Chem. Lett.,* 23(9):2721-2726 (2013); or US 2013/0143843 A1), amylin analogs such as pramlintide, and/or insulin. Reviews of current and emerging therapies for the treatment of diabetes can be found in: Mohler, M. L. et al., *Medicinal Research Reviews,* 29(1):125-195 (2009), and Mizuno, C. S. et al., *Current Medicinal Chemistry,* 15:61-74 (2008).

The GPR40 receptor modulator of formula I may also be optionally employed in combination with agents for treating complication of diabetes. These agents include PKC inhibitors and/or AGE inhibitors.

The GPR40 receptor modulator of formula I way also be optionally employed in combination with one or more hypophagic agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, and the like. The compound of structure I may also be employed in combination with an agonist of the glucagon-like peptide-1 receptor (GLP-1 R), such as exenatide, liraglutide, GPR-1(1-36) amide, GLP-1(7-36) amide, GLP-1(7-37) (as disclosed in U.S. Pat. No. 5,614,492 to Habener, the disclosure of which is incorporated herein by reference), which may be administered via injection, intranasal, or by transdermal or buccal devices. Reviews of current and emerging therapies for the treatment of obesity can be found in: Melnikova, I. et al.,

*Nature Reviews Drug Discovery*, 5:369-370 (2006); Jones, D., *Nature Reviews: Drug Discovery*, 8:833-834 (2009); Obici, S., *Endocrinology*, 150(6):2512-2517 (2009); and Elangbam, C. S., *Vet. Pathol.*, 46(1):10-24 (2009).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time.

Thus, each component may be administered separately but sufficiently closely in time so as to provide the desired therapeutic effect.

The compounds of the present invention are also useful as standard or reference compounds, for example as a quality standard or control, in tests or assays involving the GPR40 receptor. Such compounds may be provided in a commercial kit, for example, for use in pharmaceutical research involving GPR40 or anti-diabetic activity. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving GPR40.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof; and, (c) a package insert stating that the pharmaceutical composition can be used for the treatment and/or prophylaxis of multiple diseases or disorders associated with GPR40 (as defined previously). In another embodiment, the package insert states that the pharmaceutical composition can be used in combination (as defined previously) with a second therapeutic agent for the treatment and/or prophylaxis of multiple diseases or disorders associated with GPR40. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

VI. Examples

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

HPLC/MS and Preparatory/Analytical HPLC Methods Employed in Characterization or Purification of Examples Analytical HPLC/MS (unless otherwise noted) was performed on Shimadzu SCL-10A liquid chromatographs and Waters MICROMASS® ZQ Mass Spectrometers (Desolvation Gas: Nitrogen; Desolvation Temp. 250° C.; Ion Source Temp: 120° C.; Positive Electrospray conditions) using the following method:

Linear Gradient of 0% to 100% Solvent B over 2 min, with 1 minute hold at 100% B;
UV visualization at 220 nm;
Column: PHENOMENEX® Luna C18 (2) 30 mm×4.60 mm; 5 m particle (Heated to Temp. 40° C.);
Flow rate: 5 ml/min;
Solvent A: 10% MeCN-90% $H_2O$-0.1% TFA; or, 10% MeOH-90% $H_2O$-0.1% TFA; and
Solvent B: 90% MeCN-10% $H_2O$-0.1% TFA; or, 90% MeOH-10% $H_2O$-0.1% TFA.

Preparatory HPLC (unless otherwise noted) was performed on a Shimadzu SCL-10A liquid chromatograph with a linear gradient of 20-100% Solvent B over 10 or 30 min, with either a 2 or 5 min (respectively) hold at 100% Solvent B;
UV visualization at 220 nm;
Column: PHENOMENEX® Luna Axia 5μ C18 30×100 mm;
Flow rate: 20 mL/min;
Solvent A: 10% MeCN-90% $H_2O$-0.1% TFA; and
Solvent B: 90% MeCN-10% $H_2O$-0.1% TFA.

Analytical HPLC (unless otherwise noted) was performed to determine compound purity on a Shimadzu SIL-10A using the following method (Unless otherwise stated, retention times listed in Examples refer the retention times of Column 1):

Linear Gradient of 10% to 100% Solvent B over 15 min;
UV visualization at 220 nm and 254 nm;
Column 1: SunFire C18 3.5 μm, 4.6×150 mm;
Column 2: XBridge Phenyl 3.5 μm, 4.6×150 mm;
Flow rate: 1 ml/min (for both columns);
Solvent A: 5% MeCN-95% $H_2O$-0.05% TFA; and
Solvent B: 95% MeCN-5% $H_2O$-0.05% TFA.
or Linear Gradient of stated starting percentage to 100% Solvent B over 8 min;
UV visualization at 220 nm;
Column: ZORBAX® SB C18 3.5 μm, 4.6×75 mm;
Flow rate: 2.5 ml/min;
Solvent A: 10% MeOH-90% $H_2O$-0.2% $H_3PO_4$; and
Solvent B: 90% MeOH-10% $H_2O$-0.2% $H_3PO_4$.

NMR Employed in Characterization of Examples $^1H$ NMR spectra (unless otherwise noted) were obtained with JEOL® or Bruker FOURIER® transform spectrometers operating at 400 MHz or 500 MHz. $^1H$-nOe experiments were performed in some cases for regiochemistry elucidation with a 400 MHz Bruker FOURIER® Transform spectrometer.

Spectral data are reported as chemical shift (multiplicity, number of hydrogens, coupling constants in Hz) and are reported in ppm (δ units) relative to either an internal standard (tetramethylsilane=0 ppm) for $^1H$ NMR spectra, or are referenced to the residual solvent peak (2.49 ppm for $CD_3SOCD_2H$, 3.30 ppm for $CD_2HOD$, 1.94 for $CHD_2CN$, 7.26 ppm for $CHCl_3$, 5.32 ppm for $CDHCl_2$).

EXAMPLE 1

2-((2R,4R)-1-(4-((1-(2-Fluoro-5-methoxyphenyl) piperidin-4-yl)oxy)phenyl)-4-(trifluoromethyl)pyrrolidin-2-yl)acetic acid, HCl

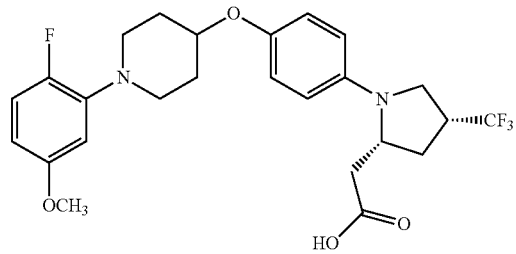

1A. 1-(2-Fluoro-5-methoxyphenyl)piperidin-4-ol: A reaction mixture of 2-bromo-1-fluoro-4-methoxybenzene (0.340 g, 1.66 mmol), piperidin-4-ol (0.419 g, 4.15 mmol) and SPhos (0.027 g, 0.066 mmol) in THF (3.2 mL) was purged with argon. $Pd_2(dba)_3$ (0.030 g, 0.033 mmol) was added followed by a solution of LHMDS (15.2 mL, 15.2 mmol) (1 N in THF). The mixture was purged with argon for several min and then heated to 70° C. for 3 h. The reaction was quenched with sat. aq. $NaHCO_3$ and the resulting solution was diluted with EtOAc, washed with water and brine, dried over $MgSO_4$, and concentrated. Purification via silica chromatography yielded 1A (0.120 g, 0.522 mmol, 32% yield). LC-MS Anal. Calc'd for $C_{12}H_{16}FNO_2$: 225.259, found [M+H] 226.1. $^1H$ NMR (500 MHz, $CDCl_3$) δ 6.93 (dd, J=12.1, 9.1 Hz, 1H), 6.52 (br. s, 1H), 6.42 (d, J=8.0 Hz, 1H), 3.94-3.83 (m, 1H), 3.77 (s, 4H), 3.47-3.28 (m, 2H), 2.85 (t, J=9.6 Hz, 2H), 2.11-1.93 (m, 3H), 1.84-1.70 (m, 2H), 1.46 (d, J=3.9 Hz, 1H).

1B. 1-(2-Fluoro-5-methoxyphenyl)piperidin-4-yl 4-methylbenzenesulfonate: A reaction mixture of 1A (0.120 g, 0.533 mmol) and 4-methylbenzene-1-sulfonyl chloride (0.305 g, 1.60 mmol) in pyridine (5.3 mL) was stirred at 0° C. for 1 h and then warmed to rt for 16 h. The reaction mixture was partitioned between EtOAc and water and the resulting mixture was stirred for 10 min. The organic layer was separated and washed with water. The aqueous phase was extracted with EtOAc (2×). The combined organic layers were washed with water and brine, dried ($MgSO_4$), and concentrated. Purification via silica chromatography yielded 1B (0.140 g, 0.362 mmol, 68% yield) as a white solid. LC-MS Anal. Calc'd for $C_{19}H_{22}FNO_4S$: 379.45, found [M+H] 380.1. $^1H$ NMR (400 MHz, $CDCl_3$) δ 7.83 (d, J=8.3 Hz, 2H), 7.36 (d, J=8.0 Hz, 2H), 6.91 (dd, J=12.1, 8.8 Hz, 1H), 6.47 (dd, J=7.2, 3.0 Hz, 1H), 6.42 (dd, J=8.8, 3.2 Hz, 1H), 4.71 (tt, J=7.4, 3.9 Hz, 1H), 3.76 (s, 3H), 3.27-3.19 (m, 2H), 2.92 (ddd, J=11.8, 7.7, 3.6 Hz, 2H), 2.47 (s, 3H), 2.04-1.88 (m, 4H).

1C. (2R,4R)-1-(tert-Butoxycarbonyl)-4-hydroxypyrrolidine-2-carboxylic acid: A solution of (2R,4R)-4-hydroxypyrrolidine-2-carboxylic acid hydrochloride (50.0 g, 298 mmol) in a 2:1 mixture of THF/water (750 mL) was treated first with a solution of NaOH (32.0 g, 800 mmol) in water (160 mL) and then with Boc$_2$O (98.0 g, 448 mmol). The reaction mixture was stirred at 25° C. for 13 h and then the THF was removed in vacuo. The residue was adjusted to pH 2 by the addition of 10% aq. KHSO$_4$. The acidic solution was extracted with EtOAc (5×). The combined organic extracts were washed with water and brine, dried over anhydrous Na$_2$SO$_4$, and concentrated to give 1C (62.0 g, 268 mmol, 90% yield) as a white solid. LC-MS Anal. Calc'd for C$_{10}$H$_{17}$NO$_5$: 231.11, found [M+H] 232. $^1$H NMR (400 MHz, DMSO-d$_6$) δ 4.16-4.25 (m, 1H), 4.06-4.14 (m, 1H), 3.45-3.54 (m, 1H), 3.07-3.14 (m, 1H), 2.25-2.39 (m, 1H), 1.78-1.86 (m, 1H), 1.32-1.44 (s, 9H).

1D. (2R,4R)-2-Benzyl 1-tert-butyl 4-hydroxypyrrolidine-1,2-dicarboxylate: 1C (62.0 g, 268 mmol) was dissolved in THF (750 mL) and the mixture was cooled to 0° C. NEt$_3$ (56.1 mL, 402 mmol) and benzyl bromide (47.8 mL, 402 mmol) were added sequentially and the reaction mixture was stirred at 25° C. for 12-13 h. Upon completion of the reaction, the solvent was evaporated and the residue was diluted with CH$_2$Cl$_2$. The resultant organic layer was washed with 1.5 N aq. HCl, 10% aq. Na$_2$CO$_3$, water, and brine, dried over anhydrous Na$_2$SO$_4$, and concentrated. Purification via silica chromatography gave 1D (70.0 g, 218 mmol, 81% yield) as a light yellow semisolid. LC-MS Anal. Calc'd for C$_{17}$H$_{23}$NO$_5$: 321.16, found [M+H] 322. $^1$H NMR (300 MHz, CDCl$_3$) δ 7.29-7.43 (m, 5H), 5.10-5.37 (m, 2H), 4.28-4.48 (m, 2H), 3.45-3.79 (m, 2H), 3.21 (d, J=10.0 Hz, 1H), 2.22-2.43 (m, 1H), 2.01-2.18 (m, 1H), 1.28-1.52 (2 s, 9H).

1E. (R)-2-Benzyl 1-tert-butyl 4-oxopyrrolidine-1,2-dicarboxylate: 1D (70.0 g, 218 mmol) was dissolved in acetone (750 mL) and cooled to 10° C. To a separate cooled stirred solution of chromium trioxide (34.8 g, 349 mmol) in water (80 mL), H$_2$SO$_4$ (27.0 mL, 507 mmol) was added and the reaction mixture was stirred for 10 min. The freshly prepared Jones reagent was added dropwise to the solution of the alcohol at 10° C. and the reaction mixture was warmed to rt and stirred for 1 h. The reaction was quenched with MeOH (250 mL), filtered through CELITE®, and the residual solids were rinsed with CHCl$_3$. The filtrate was washed with water and brine, dried over anhydrous Na$_2$SO$_4$, and concentrated. Purification via silica chromatography gave 1E (43.0 g, 135 mmol, 62% yield) as a colorless viscous oil. LC-MS Anal. Calc'd for C$_{17}$H$_{21}$NO$_5$: 319.14, found [M+H-Boc] 221.0. $^1$H NMR (300 MHz, CDCl$_3$) δ 7.32-7.43 (m, 5H), 5.06-5.31 (m, 2H), 4.68-4.96 (2 d, J=8.7 Hz, 1H), 3.91 (d, J=12.8 Hz, 2H), 2.86-3.05 (m, 1H), 2.51-2.65 (m, 1H), 1.33-1.52 (2 s, 9H).

1F. (2R)-2-Benzyl 1-tert-butyl 4-hydroxy-4-(trifluoromethyl) pyrrolidine-1,2-dicarboxylate: To a stirred solution of 1E (43.0 g, 135 mmol) in THF (500 mL) at 0° C., trifluoromethyltrimethylsilane (50.6 mL, 269 mmol) and TBAF (1.0 M in THF) (13.5 mL, 13.5 mmol) were added sequentially. The reaction mixture was warmed to rt and stirred overnight. The reaction mixture was cooled to 0° C., quenched with sat. aq. NH$_4$Cl and stirred at 25° C. for 30 min, followed by the addition of TBAF (1.0 M in THF) (100 mL, 100 mmol). After stirring for 1 h, the product was extracted with EtOAc and the organic layer was washed brine, dried over anhydrous Na$_2$SO$_4$, and concentrated. Purification via silica chromatography gave 1F (40.0 g, 103 mmol, 76% yield) as light yellow viscous oil. LC-MS Anal. Calc'd for C$_{18}$H$_{22}$F$_3$NO$_5$: 389.15, found [M-100] 290. $^1$H NMR (300 MHz, CDCl$_3$) δ 7.29-7.41 (m, 5H), 5.12-5.34 (m, 2H), 4.42-4.65 (2 d, J=9.51 Hz, 1H), 3.60-3.87 (m, 2H), 2.46-2.66 (m, 1H), 2.19 (t, J=15.3 Hz, 1H), 1.32-1.48 (2 s, 9H).

1G. (R)-2-Benzyl 1-tert-butyl 4-(trifluoromethyl)-1H-pyrrole-1,2(2H,5H)-dicarboxylate: To a stirred solution of 1F (20.0 g, 51.4 mmol) in pyridine (460 mL) at 0° C., thionyl chloride (36.0 mL, 493 mmol) was added slowly over a period of 30 min and the reaction mixture was heated to 110° C. for 15 min. The reaction mixture was concentrated, cooled to −10° C., and quenched with water (100 mL). The reaction mixture was extracted with EtOAc, washed with 1.5 N aq. HCl, sat. aq. NaHCO$_3$, and brine, dried over anhydrous Na$_2$SO$_4$, and concentrated. Purification via silica chromatography gave 1G (9.60 g, 25.9 mmol, 50% yield) as a yellow oil. LC-MS Anal. Calc'd for C$_{18}$H$_{20}$F$_3$NO$_4$: 371.13, found [M-100] 272.0. $^1$H NMR (400 MHz, CDCl$_3$) δ 7.31-7.40 (m, 5H), 6.26 (dt, J=15.3, 1.9 Hz, 1H), 5.09-5.29 (m, 3H), 4.30-4.45 (m, 2H), 1.34-1.49 (2 s, 9H).

1H. (2R,4R)-1-(tert-Butoxycarbonyl)-4-(trifluoromethyl) pyrrolidine-2-carboxylic acid: To a solution of 1G (9.50 g, 25.6 mmol) in EtOH (250 mL), was added 10% Pd/C (9.0 g, 85 mmol) and the solution was stirred under H$_2$ (1 atm) at rt overnight. The reaction mixture was filtered through CELITE®, rinsing with MeOH, and concentrated to give 1H (6.50 g, 23.0 mmol, 90% yield) as a white solid. LC-MS Anal. Calc'd for C$_{11}$H$_{16}$F$_3$NO$_4$: 283.10, found [M−H] 282. $^1$H NMR (400 MHz, CDCl$_3$) δ 4.26-4.55 (m, 1H), 3.79-3.98 (m, 1H), 3.41-3.54 (m, 1H), 2.89-3.02 (m, 1H), 2.48-2.67 (m, 1H), 2.13-2.41 (m, 1H), 1.39-1.52 (2 s, 9H).

1I. (2R,4R)-tert-Butyl 2-(hydroxymethyl)-4-(trifluoromethyl)pyrrolidine-1-carboxylate: 1H (6.50 g, 23.0 mmol) was dissolved in anhydrous THF (65 mL) and the mixture was cooled to −10° C. N-Methylmorpholine (2.78 mL, 25.2 mmol) and isobutyl chloroformate (3.32 mL, 25.2 mmol) were added sequentially and the reaction mixture was stirred at −10° C. for 1 h. The reaction mixture was filtered through CELITE® and the solids were rinsed with anhydrous THF. The filtrate was added dropwise to a solution of NaBH$_4$ (2.17 g, 57.4 mmol) in water (20 mL) at 0° C. and then the mixture was warmed to rt and stirred for 1 h. The reaction was quenched with sat. aq. NH$_4$Cl and the solution was extracted with EtOAc, washed with brine, dried (Na$_2$SO$_4$), and concentrated. Purification via silica chromatography gave 1I (4.35 g, 16.2 mmol, 70% yield) as a pale yellow oil. LC-MS Anal. Calc'd for C$_{11}$H$_{18}$F$_3$NO$_3$: 283.10, found [M−H] 282. $^1$H NMR (400 MHz, CDCl$_3$) δ 4.78-4.87 (m, 1H), 3.95-4.06 (m, 1H), 3.77-3.91 (m, 1H), 3.61-3.77 (m, 3H), 3.33 (t, J=10.4 Hz, 1H), 2.75-2.96 (m, 1H), 2.21-2.39 (m, 1H), 1.48 (s, 9H).

1J. ((2R,4R)-4-(Trifluoromethyl)pyrrolidin-2-yl)methanol hydrochloride: To a solution of 1I (4.35 g, 16.2 mmol) in dioxane (10 mL) at 0° C., a 4 M solution of HCl in dioxane (4.91 mL, 19.6 mmol) was added and the reaction mixture was warmed to rt and stirred for 1 h. The reaction mixture was concentrated to give 1J (3.10 g, 15.1 mmol, 93% yield) as a pale yellow oil. $^1$H NMR (400 MHz, DMSO-d$_6$) δ 9.73-9.99 (br. s, 1H), 8.99-9.26 (br. s, 1H), 3.59-3.75 (m, 3H), 3.41-3.55 (m, 3H), 2.50 (m, 1H), 2.22-2.35 (m, 1H), 1.67-1.89 (m, 1H).

1K. ((2R,4R)-4-(Trifluoromethyl)pyrrolidin-2-yl)methanol.(1R)-(−)-10-camphorsulfonic acid salt: To a solution of 1J (3.10 g, 15.1 mmol) in EtOH (30 mL) was added (1R)-(−)-10-camphorsulfonic acid (3.50 g, 15.1 mmol) and the reaction mixture was stirred at rt overnight. The reaction mixture was concentrated and the residue was triturated with Et₂O and stirred at rt for 30 min. The crystals thus obtained were filtered and washed with cold EtOAc and dried to give the salt (4.20 g, 10.5 mmol, 69% yield) as an off-white solid. The solid (3.00 g, 7.47 mmol) was dissolved in EtOAc (30 mL) and heated to 65° C. for 2 h. The solution was cooled to rt to induce crystallization. The mother liquor was decanted to give 1K (2.50 g, 6.23 mmol, 83% yield) as a white crystalline solid. [α]$^{25}_D$: −24.0 (c=1 in MeOH). $^1$H NMR (400 MHz, methanol-d₄) δ 3.81-3.91 (m, 2H), 3.68-3.73 (m, 1H), 3.65 (m, 1H), 3.40-3.51 (m, 2H), 3.28 (d, J=14.8 Hz, 1H), 2.77 (d, J=14.8 Hz, 1H), 2.59-2.68 (m, 1H), 2.38-2.46 (m, 1H), 2.34 (dt, J=18.3, 4.0 Hz, 1H), 1.93-2.10 (m, 3H), 1.89 (d, J=18.3 Hz, 1H), 1.63 (td, J=9.5, 4.9 Hz, 1H), 1.37-1.46 (m, 1H), 1.12 (s, 3H), 0.85 (s, 3H).

1L. ((2R,4R)-1-(4-(Benzyloxy)phenyl)-4-(trifluoromethyl)pyrrolidin-2-yl)methanol: A solution of 1-(benzyloxy)-4-iodobenzene (3.08 g, 9.95 mmol), 1K (3.33 g, 8.29 mmol), and NaOH (0.994 g, 24.9 mmol) in n-BuOH (24.4 mL) was sparged with argon. CuI (0.039 g, 0.21 mmol) was added and the reaction mixture was heated to 90° C. overnight. The reaction mixture was cooled to rt and diluted with water. The product was extracted with CH₂Cl₂ (3×). The combined organic layers were washed with brine, dried (MgSO₄), and concentrated. The crude product was purified via silica chromatography to provide 1L (1.89 g, 5.39 mmol, 65% yield) as an amber oil. LC-MS Anal. Calc'd for C₁₉H₂₀F₃NO₂: 351.36, found [M+H] 352.0. $^1$H NMR (400 MHz, CDCl₃) δ 7.28-7.46 (m, 5H), 6.92 (d, J=9.1 Hz, 2H), 6.70 (d, J=9.1 Hz, 2H), 5.01 (s, 2H), 3.93 (dddd, J=7.4, 5.0, 2.8 Hz, 1H), 3.79 (ddd, J=11.2, 4.4, 4.3 Hz, 1H), 3.57-3.68 (m, 2H), 3.50 (t, J=9.2 Hz, 1H), 2.86-3.05 (m, 1H), 2.23-2.43 (m, 2H), 1.58 (dd, J=7.8, 3.8 Hz, 1H).

1M. 2-((2R,4R)-1-(4-(Benzyloxy)phenyl)-4-(trifluoromethyl)pyrrolidin-2-yl)acetonitrile: 1M (1.22 g, 3.36 mmol, 78% yield) was prepared as a white solid from 1L following the procedure of Example 2. LC-MS Anal. Calc'd for C₂₀H₁₉F₃N₂O: 360.37, found [M+H] 361.0. $^1$H NMR (400 MHz, CDCl₃) δ 7.28-7.47 (m, 5H), 6.94 (d, J=8.8 Hz, 2H), 6.61 (d, J=9.3 Hz, 2H), 5.02 (s, 2H), 4.10-4.22 (dddd, J=8.3, 8.3 5.5, 2.8 Hz, 1H), 3.47-3.62 (m, 2H), 2.99-3.14 (m, 1H), 2.76 (dd, J=16.8, 3.0 Hz, 1H), 2.67 (ddd, J=13.7, 9.3, 7.7 Hz, 1H), 2.41 (dd, J=16.8, 9.1 Hz, 1H), 2.19 (ddd, J=13.6, 8.1, 5.8 Hz, 1H).

1N. 2-((2R,4R)-1-(4-Hydroxyphenyl)-4-(trifluoromethyl)pyrrolidin-2-yl)acetonitrile: To a solution of 1M (1.55 g, 4.31 mmol) in EtOAc (43 mL) was added AcOH (0.49 mL, 8.6 mmol) and 10% Pd/C (0.184 g, 0.173 mmol). The reaction mixture was evacuated and purged with argon (3×) and then evacuated and purged with H₂ (3×) and stirred at rt for 72 h under H₂ (1 atm). The reaction mixture was filtered and concentrated. The crude product was purified by silica chromatography to afford 1N (1.15 g, 4.27 mmol, 99% yield) as a white solid. LC-MS Anal. Calc'd for C₁₃H₁₃F₃N₂O: 270.25, found [M+H] 271.1. $^1$H NMR (400 MHz, CDCl₃) δ 6.80 (d, J=8.6 Hz, 2H), 6.58 (d, J=8.6 Hz, 2H), 4.46 (br. s, 1H), 4.04-4.24 (m, 1H), 3.42-3.64 (m, 2H), 2.98-3.13 (m, 1H), 2.74 (dd, J=16.8, 2.7 Hz, 1H), 2.61-2.71 (m, 1H), 2.41 (dd, J=16.8, 8.7 Hz, 1H), 2.11-2.24 (m, 1H).

1O. Methyl 2-((2R,4R)-1-(4-hydroxyphenyl)-4-(trifluoromethyl)pyrrolidin-2-yl)acetate: To a solution of AcCl (2.00 mL, 28.1 mmol) in CH₂Cl₂ (3.5 mL) at 0° C. was added MeOH (2.5 mL) dropwise. The reaction mixture was stirred at 0° C. for 1 h and 1N (0.130 g, 0.481 mmol) was added. The reaction mixture was slowly warmed to rt and stirred overnight. The reaction mixture was concentrated and diluted with CH₂Cl₂ (20 mL). The organic layer was washed with sat. aq. NaHCO₃, dried (Na₂SO₄), and concentrated. The crude product was purified by silica chromatography to give 1O (0.140 g, 0.462 mmol, 96% yield) as a light brown solid. LC-MS Anal. Calc'd for C₁₄H₁₆F₃NO₃S: 303.277, found [M+H] 304.0. $^1$H NMR (400 MHz, CDCl₃) δ 6.82-6.74 (m, 2H), 6.64-6.55 (m, 2H), 4.37 (br. s, 1H), 4.28-4.16 (m, 1H), 3.69 (s, 3H), 3.47 (dd, J=8.5, 3.2 Hz, 2H), 3.09-2.94 (m, 1H), 2.86 (dd, J=15.8, 3.2 Hz, 1H), 2.60 (ddd, J=13.5, 9.5, 7.6 Hz, 1H), 2.22 (dd, J=15.7, 10.1 Hz, 1H), 1.96 (ddd, J=13.5, 8.0, 5.6 Hz, 1H).

1P. 2-((2R,4R)-1-(4-((1-(2-Fluoro-5-methoxyphenyl)piperidin-4-yl)oxy)phenyl)-4-(trifluoromethyl)pyrrolidin-2-yl) acetate: A solution of 1B (0.140 g, 0.370 mmol), 1O (0.112 g, 0.369 mmol), and Cs₂CO₃ (0.240 g, 0.738 mmol) in DMF (1.1 mL) was stirred at 55° C. overnight. The reaction mixture was cooled to rt and diluted with EtOAc, washed with water and brine, dried (MgSO₄), and concentrated. Purification via silica chromatography gave 1P (0.078 g, 0.14 mmol, 37% yield) as a pale yellow oil. $^1$H NMR (500 MHz, CDCl₃) δ 6.97-6.85 (m, 3H), 6.66-6.59 (m, 2H), 6.53 (dd, J=7.4, 3.0 Hz, 1H), 6.41 (dt, J=8.7, 3.1 Hz, 1H), 4.30 (tt, J=7.4, 3.6 Hz, 1H), 4.27-4.20 (m, 1H), 3.77 (s, 3H), 3.69 (s, 3H), 3.55-3.44 (m, 2H), 3.34 (ddd, J=11.3, 7.4, 3.3 Hz, 2H), 2.95 (ddd, J=11.6, 8.3, 2.9 Hz, 2H), 2.90 (dd, J=15.7, 3.0 Hz, 1H), 2.61 (ddd, J=13.5, 9.4, 7.6 Hz, 1H), 2.23 (dd, J=15.7, 10.2 Hz, 1H), 2.14-2.05 (m, 2H), 2.02-1.90 (m, 4H).

Example 1: A reaction mixture of 1P (0.078 g, 0.15 mmol) and 0.5 M aq LiOH (1.5 mL, 0.76 mmol) in THF (1.5 mL) was stirred at rt for 5 h. 1 N aq. HCl was added until the pH ~2 and the product was extracted with EtOAc. The organic layer was washed with brine, dried (MgSO₄), filtered, and concentrated. The residue was purified via RP-Prep. HPLC. The product was treated with CH₃CN (0.5 mL) and 3 N aq. HCl (0.5 mL) and concentrated. The procedure was repeated (2×) to yield Example 1 (0.032 g, 0.064 mmol, 42% yield) as a colorless oil. LC-MS Anal. Calc'd for C₂₅H₂₈F₄N₂O₄: 496, found [M+H] 497. $^1$H NMR (400 MHz, CDCl₃) δ 7.16-7.03 (m, 2H), 6.94 (d, J=8.8 Hz, 2H), 6.83-6.65 (m, 3H), 4.53 (br. s, 1H), 4.20 (br. s, 1H), 3.88-3.74 (m, 4H), 3.60-3.45 (m, 2H), 3.42-3.29 (m, 2H), 3.14-2.99 (m, 1H), 2.90 (dd, J=16.5, 2.7 Hz, 1H), 2.64 (dt, J=13.7, 8.2 Hz, 1H), 2.47-2.28 (m, 3H), 2.22-2.08 (m, 2H), 2.08-1.96 (m, 3H). Analytical HPLC: RT=10.4 min, HI: 99.0%. hGPR40 EC₅₀=210 nM. hGPR40 IP1 EC₅₀=310 nM.

EXAMPLE 2

2-((2R,4R)-4-Ethoxy-1-(4-((1-(2-fluoro-5-methoxyphenyl)piperidin-4-yl)oxy)phenyl)pyrrolidin-2-yl) acetic acid, HCl

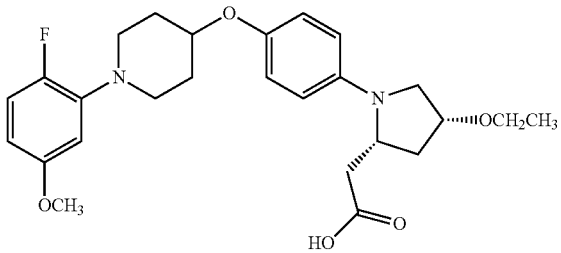 [SMILES: CCO[C@@H]1C[C@H](CC(=O)O)N(c2ccc(OC3CCN(c4cc(OC)ccc4F)CC3)cc2)C1]

2A. 1-(2-Fluoro-5-methoxyphenyl)-4-(4-iodophenoxy) piperidine: A mixture of 4-iodophenol (0.37 g, 1.7 mmol), 1B (0.43 g, 1.1 mmol), and Cs₂CO₃ (1.1 g, 3.4 mmol) in anhydrous DMF (3.8 mL) in a sealed tube was heated to 55°

C. for 16 h. The mixture was diluted with water (3 mL) and extracted with EtOAc (3×). The combined organic layers were dried, filtered, and concentrated. The crude product was purified by silica chromatography to give 2A as a colorless oil (0.38 g, 0.89 mmol, 79% yield). LC-MS Anal. Calc'd for $C_{18}H_{19}FINO_2$: 427.25, found [M+H] 428.0.

2B. (2R,4R)-1-tert-Butyl 2-methyl 4-ethoxypyrrolidine-1,2-dicarboxylate: (2R,4R)-1-tert-Butyl 2-methyl 4-hydroxypyrrolidine-1,2-dicarboxylate (1.00 g, 4.08 mmol) was dissolved in acetone (19.4 mL) and $Ag_2O$ (1.56 g, 6.73 mmol) was added. After 5 min, iodoethane (0.58 mL, 7.1 mmol) was added. The mixture was stirred under argon at rt over the weekend. Additional iodoethane (0.58 mL, 7.1 mmol) was added, followed by $Ag_2O$ (1.56 g, 6.73 mmol) and 4 Å molecular sieves. The reaction mixture was stirred at rt overnight. The reaction mixture was filtered and the filtrate was concentrated. The residue was purified by silica chromatography to give 2B as a colorless oil (0.15 g, 0.56 mmol, 14% yield). $^1$H NMR (500 MHz, $CDCl_3$) δ 4.03-3.97 (m, 1H), 3.70 (s, 3H), 3.66-3.56 (m, 1H), 3.44-3.39 (m, 2H), 2.34-2.17 (m, 2H), 1.46 (s, 3H), 1.41 (s, 6H), 1.13 (t, J=7.0 Hz, 3H).

2C. (2R,4R)-tert-Butyl 4-ethoxy-2-(hydroxymethyl)pyrrolidine-1-carboxylate: To a solution of 2B (152 mg, 0.556 mmol) in THF (2.8 mL) at 0° C. was added 2 M $LiBH_4$ in THF (0.56 mL, 1.1 mmol) dropwise. The reaction mixture was stirred at 0° C. for 15 min and then at rt overnight. The reaction was quenched with sat. aq. $NaHCO_3$ solution and extracted with $CHCl_3$. The combined extracts were washed with sat. aq. $NH_4Cl$ (4 mL), brine (4 mL), dried over $Na_2SO_4$, and concentrated. The residue was purified by silica chromatography to give 2C as a colorless oil (124 mg, 0.510 mmol, 91% yield). $^1$H NMR (500 MHz, $CDCl_3$) δ 4.09-3.91 (m, 2H), 3.87-3.61 (m, 2H), 3.56-3.27 (m, 4H), 2.19 (dd, J=8.3, 5.0 Hz, 1H), 1.76 (d, J=13.2 Hz, 1H), 1.45 (s, 9H), 1.18 (t, J=7.0 Hz, 3H).

2D. ((2R,4R)-4-Ethoxy-1-(4-(1-(2-fluoro-5-methoxyphenyl)piperidin-4-yloxy)phenyl)pyrrolidin-2-yl)methanol: 2C (0.12 g, 0.51 mmol) was dissolved in a 4 N solution of HCl (1.07 mL, 4.29 mmol) in dioxane and stirred for 1 h. The reaction mixture was concentrated to afford ((2R,4R)-4-ethoxypyrrolidin-2-yl)methanol, HCl salt (92 mg, 0.51 mmol, 100% yield) as a white solid. A mixture of 2A (83 mg, 0.19 mmol), ((2R,4R)-4-ethoxypyrrolidin-2-yl)methanol hydrochloride (37 mg, 0.20 mmol) and NaOH (24 mg, 0.61 mmol) in n-BuOH (407 μL) was stirred for a few min under argon. CuI (1 mg, 5 μmol) was added. The reaction mixture was sealed and heated to 90° C. overnight. The mixture was cooled to rt, quenched with sat. aq. $NH_4Cl$ (4 mL), and extracted with $CH_2Cl_2$ (3×3 mL). The combined organic layers were washed with sat. aq. $NH_4Cl$ (2×3 mL), brine, dried over $Na_2SO_4$, and concentrated. The residue was purified by silica chromatography to give 2D as a light yellow oil (32 mg, 0.070 mmol, 35% yield). $^1$H NMR (500 MHz, $CDCl_3$) δ 6.93 (dd, J=12.1, 8.8 Hz, 1H), 6.89 (d, J=9.1 Hz, 2H), 6.62 (d, J=9.1 Hz, 2H), 6.54 (dd, J=7.2, 3.0 Hz, 1H), 6.41 (dt, J=8.8, 3.2 Hz, 1H), 4.28 (tt, J=7.4, 3.7 Hz, 1H), 4.16 (t, J=4.8 Hz, 1H), 3.99-3.92 (m, 2H), 3.77 (s, 3H), 3.70-3.64 (m, 2H), 3.63-3.56 (m, 2H), 3.38-3.32 (m, 2H), 3.32-3.26 (m, 2H), 2.95 (ddd, J=11.7, 8.1, 3.0 Hz, 2H), 2.25 (dd, J=9.2, 5.1 Hz, 1H), 2.09 (tdd, J=7.5, 3.6, 1.8 Hz, 2H), 2.00-1.92 (m, 2H), 1.25 (t, J=7.0 Hz, 3H).

2E. 2-((2S,4R)-4-Ethoxy-1-(4-(1-(2-fluoro-5-methoxyphenyl)piperidin-4-yloxy)phenyl)pyrrolidin-2-yl)acetonitrile: To a solution of 2D (32 mg, 0.072 mmol) in $CH_2Cl_2$ (360 μL) at 0° C. was added $NEt_3$ (24 μL, 0.17 mmol), followed by slow addition of MsCl (11 μL, 0.14 mmol). The reaction mixture was gradually warmed to rt and quenched with sat. aq. $NaHCO_3$. The mixture was extracted with EtOAc (3×3 mL). The combined organic layers were washed with 1 N aq. HCl, sat. aq. $NaHCO_3$, and brine, dried over $MgSO_4$, and concentrated. The crude product was re-dissolved in DMSO (360 μL) and NaCN (14 mg, 0.29 mmol) was added. The reaction mixture was stirred at 50° C. overnight. The reaction mixture was cooled to rt, quenched with water (3 mL), and extracted with $CH_2Cl_2$ (3×2 mL). The combined organic layers were washed with brine, dried over $MgSO_4$, and concentrated. The crude product was purified by silica chromatography to give 2E as a colorless oil (24 mg, 0.053 mmol, 74% yield). LC-MS Anal. Calc'd for $C_{26}H_{32}FN_3O_3$: 453.55, found [M+H] 454.2.

Example 2: 2E (24 mg, 0.053 mmol) was dissolved in EtOH (529 μL) and 6 M aq. KOH (176 μL, 1.06 mmol) was added. The reaction mixture was sealed and heated to 120° C. for 120 min. The solution was cooled to rt and concentrated. The residue was acidified to pH 2 with 1 N aq. HCl and extracted with EtOAc (3×1 mL). The combined organic layers were concentrated and purified via RP-Prep. HPLC. The product was dissolved in $CH_3CN$ (0.5 mL) and 3 N aq. HCl (0.5 mL) and evaporated to dryness. This process was repeated for two more times to afford Example 2 as light yellow solid (15 mg, 0.027 mmol, 51% yield). LC-MS Anal. Calc'd for $C_{26}H_{33}FN_2O_5$: 472.55, found [M+H] 473.2. $^1$H NMR (400 MHz, acetonitrile-$d_3$) δ 7.68-7.43 (m, 3H), 7.27 (dd, J=12.1, 9.3 Hz, 1H), 7.15 (d, J=8.8 Hz, 2H), 7.00 (dt, J=9.3, 3.3 Hz, 1H), 4.86-4.77 (m, 1H), 4.49-4.40 (m, 1H), 4.18 (dt, J=15.1, 7.3 Hz, 1H), 3.90-3.82 (m, 2H), 3.80 (s, 3H), 3.77-3.70 (m, 1H), 3.57 (dd, J=12.1, 4.9 Hz, 2H), 3.51 (q, J=6.8 Hz, 2H), 2.87-2.78 (m, 4H), 2.57-2.43 (m, 2H), 2.30-2.17 (m, 2H), 2.04 (ddd, J=14.0, 9.3, 4.7 Hz, 1H), 1.17 (t, J=7.1 Hz, 3H). Analytical HPLC: RT=9.0 min, HI: 98.2%. hGPR40 $EC_{50}$=120 nM.

EXAMPLE 3

2-((2R,4S)-1-(4-((1-(2-Fluoro-5-methoxyphenyl)piperidin-4-yl)oxy)phenyl)-4-phenylpyrrolidin-2-yl)acetic acid, HCl

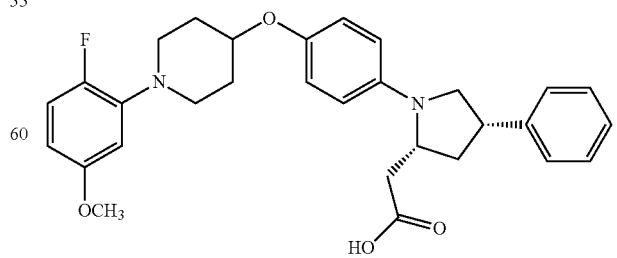

3A. (2R,4S)-1-tert-Butyl 2-methyl 4-phenylpyrrolidine-1,2-dicarboxylate: To a solution of (2R,4S)-4-phenylpyrrolidine-2-carboxylic acid hydrochloride (0.54 g, 2.4 mmol) in MeOH (1.5 mL) at 0° C. was added thionyl chloride (0.18 mL, 2.4 mmol). The reaction mixture was stirred at rt for 10 min and then heated to 80° C. for 2 h. The solvent was removed under reduced pressure to give a grey powder. To a solution of above solid in $CH_2Cl_2$ (20 mL) at 0° C. was added $NEt_3$ (1.0 mL, 7.2 mmol), followed by $Boc_2O$ (0.64 mL, 2.8 mmol). The reaction mixture was stirred at rt overnight and concentrated. The residue was purified by silica chromatography to give 3A as a colorless oil (0.64 g, 2.1 mmol, 87% yield). $^1$H NMR (400 MHz, acetonitrile-$d_3$) δ 7.38-7.31 (m, 2H), 7.26-7.23 (m, 3H), 4.44-4.32 (m, 1H), 4.16-4.05 (m, 1H), 3.77, 3.76 (two s, 3H), 3.50-3.32 (m, 2H), 2.68 (dt, J=12.4, 6.3 Hz, 1H), 2.14-2.03 (m, 1H), 1.48, 1.44 (two s, 9H).

Example 3 (white solid, 9.7 mg) was prepared from 3A following the procedure of Example 2. LC-MS Anal. Calc'd for $C_{30}H_{33}FN_2O_4$: 504.6, found [M+H] 505.3. $^1$H NMR (500 MHz, $D_2O$) δ 9.10 (d, J=7.7 Hz, 2H), 8.92-8.88 (m, 2H), 8.84 (t, J=7.6 Hz, 2H), 8.77-8.72 (m, 1H), 8.67 (d, J=8.5 Hz, 2H), 8.63 (dd, J=11.6, 9.1 Hz, 1H), 8.45 (dd, J=6.6, 2.8 Hz, 1H), 8.29 (dt, J=8.9, 3.1 Hz, 1H), 5.92 (br. s, 1H), 5.59-5.45 (m, 3H), 5.26 (s, 3H), 5.10 (t, J=8.5 Hz, 2H), 4.89-4.80 (m, 2H), 4.40-4.22 (m, 3H), 3.83-3.74 (m, 2H), 3.73-3.65 (m, 1H), 3.64-3.53 (m, 3H). Analytical HPLC: RT =9.6 min, HI: 95.4%. hGPR40 $EC_{50}$=210 nM.

EXAMPLE 4

2-((2R,4R)-1-(4-((1-(2-Fluoro-5-methoxyphenyl)piperidin-4-yl)oxy)phenyl)-4-methoxypyrrolidin-2-yl)acetic acid, HCl

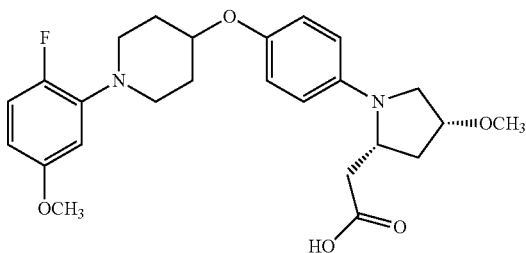 [SMILES: COc1ccc(F)c(N2CCC(Oc3ccc(N4C[C@H](OC)C[C@@H]4CC(=O)O)cc3)CC2)c1]

4A. ((2R,4R)-4-Methoxypyrrolidin-2-yl)methanol, HCl: 4A was prepared from MeI following the procedure of Example 2. LC-MS Anal. Calc'd for $C_6H_{13}NO_2$: 131.17, found [M+H] 132.0. $^1$H NMR (400 MHz, methanol-$d_4$) δ 4.23-4.06 (m, 1H), 3.84-3.73 (m, 2H), 3.71-3.65 (m, 1H), 3.65-3.57 (m, 1H), 3.45 (d, J=12.6 Hz, 1H), 3.33 (s, 3H), 3.26 (dd, J=12.4, 4.3 Hz, 1H), 2.34 (ddd, J=14.4, 9.0, 5.7 Hz, 1H), 1.95-1.75 (m, 1H), 1.18 (t, J=7.1 Hz, 1H).

Example 4 (pale yellow solid, 11.9 mg) was prepared from 4A following the procedure of Example 2. LC-MS Anal. Calc'd for $C_{25}H_{31}FN_2O_5$: 458.53, found [M+H] 459.3. $^1$H NMR (500 MHz, methanol-$d_4$) δ 7.57 (d, J=6.6 Hz, 2H), 7.30 (dd, J=11.7, 9.2 Hz, 1H), 7.26-7.20 (m, 3H), 7.01 (dt, J=9.1, 3.4 Hz, 1H), 4.83 (br. s, 1H), 4.41-4.27 (m, 2H), 4.00-3.92 (m, 1H), 3.90-3.76 (m, 6H), 3.64-3.55 (m, 2H), 3.40 (s, 3H), 2.93 (dt, J=14.0, 7.2 Hz, 1H), 2.81 (br. s, 2H), 2.48-2.38 (m, 2H), 2.24 (td, J=7.2, 3.3 Hz, 2H), 2.09 (ddd, J=14.0, 8.1, 2.9 Hz, 1H). Analytical HPLC: RT=8.2 min, HI: 99.1%. hGPR40 $EC_{50}$=170 nM. hGPR40 IP1 $EC_{50}$=240 nM.

EXAMPLE 5

(S)-2-(4,4-Difluoro-1-(4-((1-(2-fluoro-5-methoxyphenyl)piperidin-4-yl)oxy)phenyl)pyrrolidin-2-yl)acetic acid, TFA

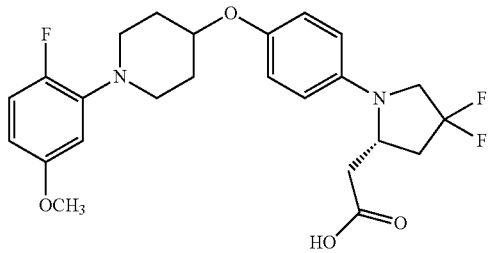 [SMILES: COc1ccc(F)c(N2CCC(Oc3ccc(N4CC(F)(F)C[C@@H]4CC(=O)O)cc3)CC2)c1]

5A. (R)-1-tert-Butyl 2-methyl 4,4-difluoropyrrolidine-1,2-dicarboxylate: To a solution of (R)-1-tert-butyl 2-methyl 4-oxopyrrolidine-1,2-dicarboxylate (1.00 g, 4.11 mmol) in $CH_2Cl_2$ (9 mL) at −78° C. was added DAST (1.8 mL, 14 mmol) over a period of 5 min. After 15 min, the cooling bath was removed and the mixture was stirred at rt for 2 days. The reaction mixture was diluted with $CH_2Cl_2$, cooled to 0° C., and then quenched with sat. aq. $NaHCO_3$. The separated aqueous layer was extracted with $CH_2Cl_2$. The combined organic layers were washed with brine, dried ($Na_2SO_4$), and concentrated. The residue was purified by silica chromatography to give 5A as light yellow oil (841 mg, 3.17 mmol, 77% yield). $^1$H NMR (500 MHz, $CDCl_3$) δ 4.59-4.42 (m, 1H), 3.93-3.73 (m, 5H), 2.79-2.63 (m, 1H), 2.47 (qd, J=13.5, 5.2 Hz, 1H), 1.48, 1.43 (two s, 9H).

Example 5 was prepared from 5A following the procedure of Example 2. LC-MS Anal. Calc'd for $C_{24}H_{27}F_3N_2O_4$: 464.48, found [M+H] 465.2. $^1$H NMR (500 MHz, methanol-$d_4$) δ 7.30 (dd, J=11.6, 9.1 Hz, 1H), 7.19-7.15 (m, 1H), 7.03-6.97 (m, 3H), 6.67 (d, J=9.1 Hz, 2H), 4.62-4.55 (m, 1H), 4.37 (dd, J=10.5, 8.3 Hz, 1H), 3.87-3.81 (m, 5H), 3.74 (dt, J=14.3, 10.7 Hz, 1H), 3.68-3.58 (m, 1H), 3.56-3.49 (m, 2H), 2.82-2.76 (m, 1H), 2.44-2.30 (m, 4H), 2.24-2.14 (m, 3H). Analytical HPLC: RT=8.9 min, HI: 98.9%. hGPR40 $EC_{50}$=66 nM.

EXAMPLE 6

2-((2R,4R)-1-(4-((1-(2-Fluoro-5-methoxyphenyl)piperidin-4-yl)oxy)phenyl)-4-phenoxypyrrolidin-2-yl)acetic acid, HCl

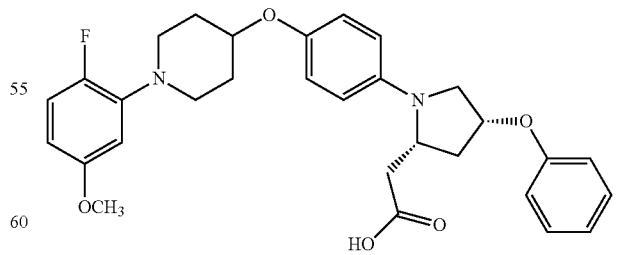

6A. (2R,4S)-1-tert-Butyl 2-methyl 4-hydroxypyrrolidine-1,2-dicarboxylate: 6A was prepared from (2R,4R)-4-hydroxypyrrolidine-2-carboxylic acid hydrochloride following the procedure of Example 3. $^1$H NMR (500 MHz, methanol-$d_4$) δ 4.54-4.49 (m, 1H), 4.48-4.36 (m, 1H), 3.74 (s, 3H), 3.66 (dd, J=11.6, 4.4 Hz, 1H), 3.61-3.43 (m, 1H), 2.35-2.21 (m, 1H), 2.15-2.06 (m, 1H), 1.73-1.65 (m, 1H), 1.49, 1.40 (two s, 9H).

6B. (2R,4R)-1-tert-Butyl 2-methyl 4-phenoxypyrrolidine-1,2-dicarboxylate: To a stirred mixture of 6A (0.500 g, 2.04 mmol), phenol (0.211 g, 2.24 mmol), and Ph$_3$P (0.588 g, 2.24 mmol) in THF (8.6 mL) at rt under argon was added DIAD (0.46 mL, 2.2 mmol). The mixture was stirred at rt overnight. The reaction was quenched with sat. aq. NaHCO$_3$ and extracted with EtOAc (3×5 mL). The combined organic layers were dried (MgSO$_4$), filtered, and concentrated. The residue was purified by silica chromatography to give (2R, 4R)-1-tert-butyl 2-methyl 4-phenoxypyrrolidine-1,2-dicarboxylate as a colorless oil (0.385 g, 1.12 mmol, 59% yield). $^1$H NMR (500 MHz, methanol-d$_4$) δ 7.33-7.25 (m, 2H), 6.98 (q, J=7.2 Hz, 1H), 6.87-6.75 (m, 2H), 4.91 (ddd, J=7.2, 4.7, 2.2 Hz, 1H), 4.60-4.40 (m, 1H), 3.84-3.65 (m, 5H), 2.54-2.42 (m, 2H), 1.50, 1.45 (two s, 9H).

Example 6 (light yellow solid, 12.7 mg) was prepared from 6B following the procedure of Example 2. LC-MS Anal. Calc'd for C$_{30}$H$_{33}$FN$_2$O$_5$: 520.6, found [M+H] 521.3. $^1$H NMR (400 MHz, acetonitrile-d$_3$) δ 7.32 (t, J=8.0 Hz, 2H), 7.29-7.19 (m, 3H), 7.17 (dd, J=6.0, 2.7 Hz, 1H), 7.09 (d, J=8.8 Hz, 2H), 7.03-6.88 (m, 4H), 5.23 (br. s, 1H), 4.68 (br. s, 1H), 4.26 (br. s, 1H), 3.85 (br. s, 2H), 3.79 (s, 3H), 3.74 (t, J=9.3 Hz, 2H), 3.51-3.44 (m, 2H), 2.89 (dt, J=14.3, 7.1 Hz, 1H), 2.84-2.66 (m, 2H), 2.40-2.26 (m, 2H), 2.24-2.05 (m, 3H). Analytical HPLC: RT=9.7 min, HI: 99.6%. hGPR40 EC$_{50}$=190 nM.

EXAMPLE 7

2-((2R,4R)-4-Benzyl-1-(4-((1-(2-fluoro-5-methoxyphenyl)piperidin-4-yl)oxy)phenyl)pyrrolidin-2-yl)acetic acid, HCl

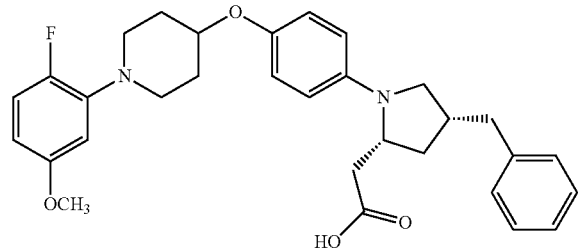 [SMILES: COc1ccc(F)c(N2CCC(Oc3ccc(N4C[C@H](Cc5ccccc5)C[C@@H]4CC(=O)O)cc3)CC2)c1]

and

EXAMPLE 8

2-((2S,4R)-4-Benzyl-1-(4-((1-(2-fluoro-5-methoxyphenyl)piperidin-4-yl)oxy)phenyl)pyrrolidin-2-yl)acetic acid, HCl

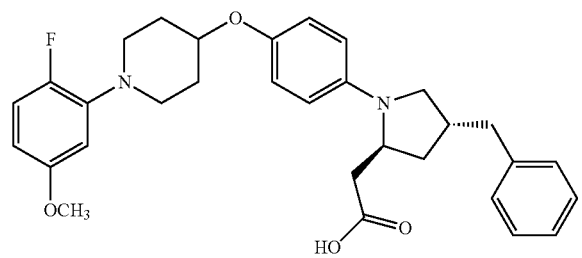 [SMILES: COc1ccc(F)c(N2CCC(Oc3ccc(N4C[C@H](Cc5ccccc5)C[C@H]4CC(=O)O)cc3)CC2)c1]

Example 7 and Example 8 were prepared as single isomers from (2R,4R)-4-benzylpyrrolidine-2-carboxylic acid hydrochloride following the procedure of Example 3. Example 7 (light yellow solid, 9.8 mg). LC-MS Anal. Calc'd for C$_{31}$H$_{35}$FN$_2$O$_4$: 518.63, found [M+H] 519.2. $^1$H NMR (400 MHz, acetonitrile-d$_3$) δ 7.44 (d, J=9.3 Hz, 2H), 7.35-7.28 (m, 2H), 7.28-7.19 (m, 3H), 7.16 (dd, J=11.8, 9.1 Hz, 1H), 7.12-7.08 (m, 2H), 6.97 (dd, J=6.6, 3.3 Hz, 1H), 6.80 (dt, J=8.8, 3.3 Hz, 1H), 4.69 (dt, J=6.6, 3.3 Hz, 1H), 4.25-4.15 (m, 1H), 3.83-3.71 (m, 4H), 3.60 (ddd, J=12.0, 8.7, 3.6 Hz, 2H), 3.34-3.28 (m, 3H), 2.88 (s, 3H), 2.66 (d, J=6.6 Hz, 2H), 2.32-2.21 (m, 3H), 2.10-2.00 (m, 3H). Analytical HPLC: RT=8.8 min, HI: 99.3%. hGPR40 EC$_{50}$=320 nM. Example 8 (light yellow solid, 6.8 mg). LC-MS Anal. Calc'd for C$_{31}$H$_{35}$FN$_2$O$_4$: 518.63, found [M+H] 519.2. $^1$H NMR (400 MHz, acetonitrile-d$_3$) δ 7.49 (d, J=9.3 Hz, 2H), 7.36-7.28 (m, 2H), 7.29-7.17 (m, 3H), 7.10 (dt, J=8.8, 6.0 Hz, 3H), 6.85 (dd, J=6.9, 3.0 Hz, 1H), 6.71 (dt, J=9.2, 3.1 Hz, 1H), 4.66 (dt, J=6.7, 3.5 Hz, 1H), 4.14 (td, J=12.4, 5.5 Hz, 1H), 3.75 (s, 3H), 3.72-3.59 (m, 2H), 3.54-3.45 (m, 2H), 3.26-3.16 (m, 2H), 3.08-2.97 (m, 1H), 2.92-2.77 (m, 2H), 2.75-2.61 (m, 2H), 2.55-2.45 (m, 1H), 2.27-2.16 (m, 2H), 2.04-1.96 (m, 2H), 1.82-1.70 (m, 1H). Analytical HPLC: RT=7.7 min, HI: 100%. hGPR40 EC$_{50}$=420 nM.

EXAMPLE 9

2-((2R,4R)-1-(4-((1-(2-Fluoro-5-methoxyphenyl)piperidin-4-yl)(methyl)amino)phenyl)-4-(trifluoromethyl)pyrrolidin-2-yl)acetic acid, TFA

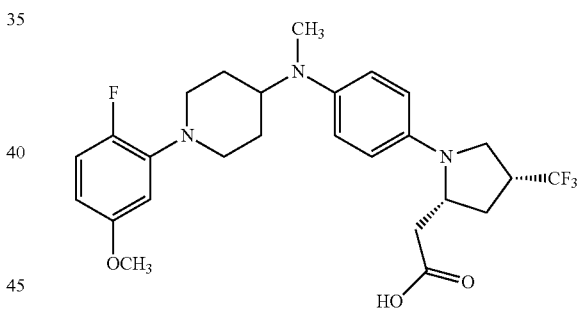

9A. tert-Butyl 1-(2-fluoro-5-methoxyphenyl)piperidin-4-yl(methyl)carbamate: To a solution of 2-bromo-1-fluoro-4-methoxybenzene (325 mg, 1.58 mmol) and tert-butyl methyl (piperidin-4-yl)carbamate (442 mg, 2.06 mmol) in THF (3 mL) purged with argon was added SPhos (52 mg, 0.13 mmol), Pd$_2$(dba)$_3$ (29 mg, 0.032 mmol), and LHMDS (1 M in THF) (3.2 mL, 3.2 mmol). After purging with argon for 2 min, the reaction mixture was heated to 75° C. for 2 h. The reaction was quenched with sat. aq. NaHCO$_3$. The aqueous layer was extracted with EtOAc and the organic layer was washed with brine, dried, and concentrated. Purification via silica chromatography gave 9A (140 mg, 0.414 mmol, 26% yield). LC-MS Anal. Calc'd for C$_{18}$H$_{27}$FN$_2$O$_3$ 338.20, found [M+H] 339.1. $^1$H NMR (400 MHz, CDCl$_3$) δ 6.92 (dd, J=12.1, 8.8 Hz, 1H), 6.54-6.29 (m, 2H), 4.38-3.98 (m, 1H), 3.76 (s, 3H), 3.60-3.35 (m, 2H), 2.89-2.55 (m, 5H), 1.99-1.81 (m, 2H), 1.78-1.59 (m, 2H), 1.48 (s, 9H).

9B. 1-(2-Fluoro-5-methoxyphenyl)-N-methylpiperidin-4-amine, HCl: To a solution of 9A (140 mg, 0.414 mmol) in dioxane (2 mL) was added HCl (4 N in dioxane) (2.10 mL, 8.27 mmol). After stirring for 2 h at rt, the reaction mixture was concentrated and then coevaporated with MeOH to give a white powder as 9B (140 mg, 0.510 mmol, 100% yield). LC-MS Anal. Calc'd for $C_{13}H_{19}FN_2O$, 238.30, found [M+H] 239.1.

9C. 2-((2R,4R)-1-(4-Bromophenyl)-4-(trifluoromethyl)pyrrolidin-2-yl)acetonitrile: 9C was prepared following the procedure of 1N except that 1,4-bromoiodobenzene was used. LC-MS Anal. Calc'd for $C_{13}H_{12}BrF_3N_2$: 333.15, found [M+H] 333.0, 335.0. $^1$H NMR (400 MHz, CDCl$_3$) δ 7.37 (ddd, J=8.8, 3.3, 2.0 Hz, 2H), 6.50 (ddd, J=8.8, 3.3, 2.0 Hz, 2H), 4.17-4.28 (dddd, J=8.2, 8.2, 5.6, 3.2 Hz, 1H), 3.52-3.67 (m, 2H), 3.01-3.17 (m, 1H), 2.78 (dd, J=16.9, 3.0 Hz, 1H), 2.64-2.74 (m, 1H), 2.49 (dd, J=16.8, 8.7 Hz, 1H), 2.24 (ddd, J=13.8, 8.3, 5.7 Hz, 1H).

9D. 2-((2R,4R)-1-(4-((1-(2-Fluoro-5-methoxyphenyl)piperidin-4-yl)(methyl)amino)phenyl)-4-(trifluoromethyl)pyrrolidin-2-yl)acetonitrile: To a vial with 9B (12 mg, 0.044 mmol) in toluene (0.1 mL) was added NaOtBu (10.5 mg, 0.109 mmol). The reaction mixture was stirred for 5 min and then 9C (15 mg, 0.044 mmol) was added. A solution of [1,1'-biphenyl]-2-yldi-tert-butylphosphine (3.9 mg, 0.013 mmol) and Pd(OAc)$_2$ (1.5 mg, 6.6 µmol) in toluene (0.3 mL) was transferred to the mixture. The reaction vessel was purged with argon and heated to 117° C. for 18 h. The reaction was quenched with 1 N aq. HCl (0.1 mL). The crude product was purified by RP-Prep. HPLC to provide 9D (9.0 mg, 0.018 mmol, 9% yield). LC-MS Anal. Calc'd for $C_{26}H_{30}F_4N_4O$: 490.53, found [M+H] 491.2. $^1$H NMR (400 MHz, CDCl$_3$) δ 7.42 (d, J=8.8 Hz, 2H), 7.27 (m, 1H), 7.00 (dd, J=11.9, 8.8 Hz, 1H), 6.76-6.65 (m, 2H), 6.60 (d, J=9.1 Hz, 1H), 4.37-4.13 (m, 1H), 3.84-3.71 (m, 6H), 3.69-3.54 (m, 4H), 3.25 (s, 3H), 3.18-2.97 (m, 3H), 2.78 (d, J=3.0 Hz, 2H), 2.65 (d, J=8.3 Hz, 1H), 2.37-2.27 (m, 1H), 2.20 (d, J=10.9 Hz, 1H), 2.09-1.94 (m, 1H).

Example 9: A vial with 9D (9.0 mg, 0.018 mmol) and aq. KOH (6 N) (0.10 mL, 0.60 mmol) in EtOH (0.1 mL) was heated to 125° C. for 30 min. The reaction mixture was concentrated and then acidified to pH 2 with 1 N aq. HCl. The crude product was purified by RP-Prep. HPLC to provide Example 9 (1.1 mg, 1.5 µmol, 8% yield). LC-MS Anal. Calc'd for $C_{26}H_{31}F_4N_3O_3$: 509.53, found [M+H] 510.2. $^1$H NMR (400 MHz, acetonitrile-d$_3$) δ 7.96-7.73 (m, 1H), 7.52-7.29 (m, 1H), 7.14-6.90 (m, 2H), 6.86-6.57 (m, 1H), 6.61-6.39 (m, 2H), 4.51-4.14 (m, 2H), 3.72 (s, 6H), 3.62-3.34 (m, 2H), 3.29-3.02 (m, 2H), 3.0-2.25 (m, 10H). Analytical HPLC: RT=7.6 min, HI: 86%. hGPR40 EC$_{50}$=290 nM.

EXAMPLE 10

2-((2R,4R)-1-(4-(((S)-1-(2-Fluoro-5-methoxyphenyl)pyrrolidin-3-yl)methoxy)phenyl)-4-(trifluoromethyl)pyrrolidin-2-yl)acetic acid, HCl 10A. (S)-(1-(2-Fluoro-5-methoxyphenyl)pyrrolidin-3-yl)methanol: A mixture of 1-fluoro-2-iodo-4-methoxybenzene (187 mg, 0.741 mmol), (S)-pyrrolidin-3-ylmethanol (150 mg, 1.48 mmol), CuI (14 mg, 0.074 mmol) and K$_3$PO$_4$ monohydrate (342 mg, 1.48 mmol) in dimethylethanolamine (0.7 mL, 7 mmol) was heated to 60° C. for 24 h. The reaction was quenched with sat. aq. NaHCO$_3$. The aqueous layer was extracted with EtOAc and the organic layer was washed with brine, dried (MgSO$_4$), and concentrated. Purification via silica chromatography gave 10A (22 mg, 0.098 mmol, 13% yield). LC-MS Anal. Calc'd for $C_{12}H_{16}FNO_2$: 225.25, found [M+H] 226.3. $^1$H NMR (400 MHz, CDCl$_3$) δ 6.88 (dd, J=13.4, 8.6 Hz, 1H), 6.31-6.08 (m, 2H), 3.80-3.75 (s, 3H), 3.72-3.64 (m, 2H), 3.55-3.43 (m, 2H), 3.42-3.34 (m, 1H), 3.29-3.21 (m, 1H), 2.57-2.44 (m, 1H), 2.15-2.06 (m, 1H), 1.77 (dd, J=12.5, 7.7 Hz, 1H), 1.64 (br. s, 1H).

10B. 2-((2R,4R)-1-(4-(((S)-1-(2-Fluoro-5-methoxyphenyl)pyrrolidin-3-yl)methoxy)phenyl)-4-(trifluoromethyl)pyrrolidin-2-yl)acetonitrile: To a solution of 10A (30 mg, 0.13 mmol), 1N (24 mg, 0.089 mmol), and Ph$_3$P (34.9 mg, 0.133 mmol) in toluene (1 mL) at 0° C. was added DIAD (0.026 mL, 0.13 mmol) dropwise. After the addition, the reaction mixture was stirred at rt overnight. The reaction mixture was loaded onto silica gel column directly. The crude product was purified by silica chromatography to give 10B (70 mg, 0.097 mmol, 100% yield). LC-MS Anal. Calc'd for $C_{25}H_{27}F_4N_3O_2$: 477.49, found [M+H] 478.2.

Example 10: A vial with 10B (42 mg, 0.088 mmol) and aq. KOH (6 N) (0.50 mL, 3.0 mmol) in EtOH (0.5 mL) was heated to 125° C. for 2 h. The reaction mixture was concentrated and acidified to pH 2 with 3 N aq. HCl. The product was extracted with EtOAc and the organic layer was washed with brine, dried, and concentrated. RP-Prep. HPLC gave the desired fraction, which was concentrated. The product was dissolved in CH$_3$CN (0.5 mL) and aq. 3 N HCl (0.5 mL) and evaporated to dryness. This process was repeated two times to afford Example 10 (22 mg, 0.041 mmol, 47% yield). LC-MS Anal. Calc'd for $C_{25}H_{28}F_4N_2O_4$ 496.19, found [M+H] 497.2. $^1$H NMR (400 MHz, acetonitrile-d$_3$) δ 7.82 (br. s, 2H), 7.63 (br. s, 1H), 7.39-7.20 (m, 1H), 7.08 (br. s, 2H), 6.99 (d, J=6.6 Hz, 1H), 4.21 (br. s, 3H), 4.10 (br. s, 1H), 3.91-3.59 (m, 9H), 3.24-2.98 (m, 3H), 2.88 (d, J=16.5 Hz, 1H), 2.71 (m, 1H), 2.44 (m, 1H), 2.31 (m, 1H), 2.15 (m, 1H). Analytical HPLC: RT=11.9 min, HI: 97.9%. hGPR40 EC$_{50}$=940 nM.

EXAMPLE 11

2-((2R,4R)-1-(4-(((R)-1-(2-Fluoro-5-methoxyphenyl)pyrrolidin-3-yl)methoxy)phenyl)-4-(trifluoromethyl)pyrrolidin-2-yl)acetic acid, HCl

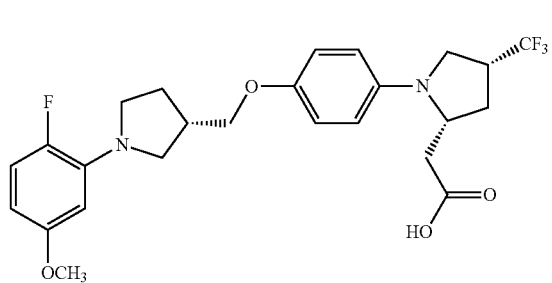 [SMILES: COc1ccc(F)c(N2CC[C@H](COc3ccc(N4C[C@H](C(F)(F)F)C[C@@H]4CC(=O)O)cc3)C2)c1]

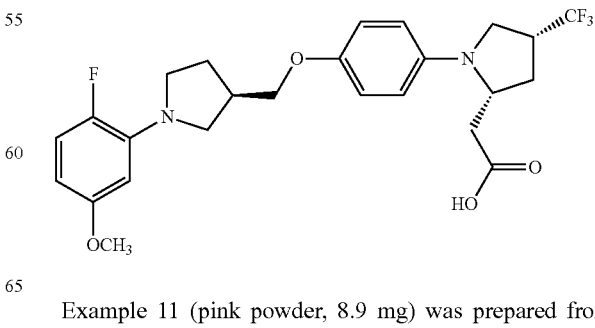

Example 11 (pink powder, 8.9 mg) was prepared from (R)-pyrrolidin-3-ylmethanol following the procedure of Example 10. LC-MS Anal. Calc'd for $C_{25}H_{28}F_4N_2O_4$ 496.19, found [M+H] 497.1. $^1$H NMR (400 MHz, acetonitrile-d$_3$) δ 7.92-7.73 (m, 2H), 7.62 (dd, J=6.3, 3.0 Hz, 1H), 7.31 (dd, J=11.3, 9.1 Hz, 1H), 7.14-6.98 (m, 3H), 4.37-4.07 (m, 4H), 4.00-3.56 (m, 9H), 3.23-3.11 (m, 1H), 3.07-2.96 (m, 2H), 2.85 (dd, J=17.0, 4.9 Hz, 1H), 2.78-2.68 (m, 1H), 2.47 (dd, J=13.7, 7.1 Hz, 1H), 2.36-2.07 (m, 2H). Analytical HPLC: RT=11.5 min, HI: 99.6%. hGPR40 EC$_{50}$=630 nM.

EXAMPLE 12

Isomer 1 and Isomer 2

2-((2R,4R)-1-(4-((1-(2-Fluoro-5-methoxyphenyl)pyrrolidin-3-yl)oxy)phenyl)-4-(trifluoromethyl)pyrrolidin-2-yl)acetic acid, HCl

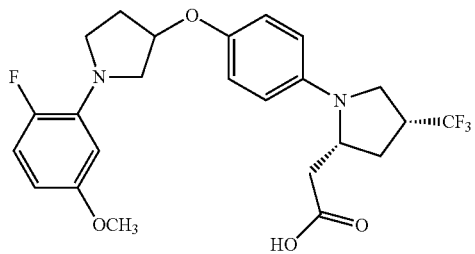 [SMILES: COc1ccc(F)c(N2CCC(Oc3ccc(N4C[C@H](C(F)(F)F)C[C@@H]4CC(=O)O)cc3)C2)c1]

12A. 1-(2-Fluoro-5-methoxyphenyl)pyrrolidin-3-ol: To a solution of 2-bromo-1-fluoro-4-methoxybenzene (500 mg, 2.44 mmol) and DL-pyrrolidin-3-ol (507 μL, 6.10 mmol) in THF (6 mL) purged with argon, was added SPhos (40 mg, 0.098 mmol), Pd$_2$(dba)$_3$ (45 mg, 0.049 mmol), and LHMDS (1 N in THF) (11.7 mL, 11.7 mmol). The reaction mixture was further purged with argon for 2 min and heated to 75° C. for 2.5 h. The reaction was quenched with sat. aq. NaHCO$_3$. The product was extracted with EtOAc and the organic layer was washed with brine, dried (MgSO$_4$), and concentrated. Purification via silica chromatography gave a brown oil as 12A (136 mg, 0.644 mmol, 26% yield). LC-MS Anal. Calc'd for $C_{11}H_{14}FNO_2$ 211.23, found [M+H] 212.1. $^1$H NMR (400 MHz, CDCl$_3$) δ 6.89 (dd, J=13.5, 8.5 Hz, 1H), 6.30-6.03 (m, 2H), 4.64-4.40 (m, 1H), 3.82-3.73 (s, 3H), 3.66-3.49 (m, 2H), 3.44-3.29 (m, 2H), 2.25-2.07 (m, 1H), 2.04-1.88 (m, 2H).

12B. 1-(2-Fluoro-5-methoxyphenyl)pyrrolidin-3-yl 4-methylbenzenesulfonate: To a solution of 12A (68 mg, 0.32 mmol) in CH$_2$Cl$_2$ (1.6 mL) at 0° C. was added TEA (99 μL, 0.71 mmol), Ts-Cl (68 mg, 0.35 mmol) and DMAP (3.9 mg, 0.032 mmol). After the addition, the ice bath was removed. The reaction mixture was stirred at rt for 5 h. The reaction mixture was diluted with water and extracted with CH$_2$Cl$_2$. The combined organic layers were washed with brine, dried (MgSO$_4$), and concentrated. Purification via silica chromatography gave a colorless oil as 12B (74 mg, 0.20 mmol, 63% yield). LC-MS Anal. Calc'd for $C_{18}H_{20}FNO_4S$: 365.11, found [M+H] 366.0.

12C. 2-((2R,4R)-1-(4-((1-(2-Fluoro-5-methoxyphenyl)pyrrolidin-3-yl)oxy)phenyl)-4-(trifluoromethyl)pyrrolidin-2-yl)acetonitrile: A solution of 1N (38.8 mg, 0.144 mmol), 12B (50.0 mg, 0.137 mmol) and Cs$_2$CO$_3$ (89 mg, 0.27 mmol) in DMF (1.3 mL) was stirred at 55° C. for 15 h. The product was extracted with EtOAc and the organic layer was washed with brine, dried (MgSO$_4$), and concentrated. Purification via silica chromatography gave 12C (27 mg, 0.058 mmol, 43% yield). LC-MS Anal. Calc'd for $C_{24}H_{25}F_4N_3O_2$: 463.18, found [M+H] 464.2. $^1$H NMR (400 MHz, CDCl$_3$) δ 7.03-6.82 (m, 3H), 6.67-6.58 (m, 2H), 6.34-6.05 (m, 2H), 4.90 (td, J=4.7, 2.4 Hz, 1H), 4.28-4.10 (m, 1H), 3.93-3.70 (m, 5H), 3.66-3.50 (m, 3H), 3.48-3.40 (m, 1H), 3.17-2.96 (m, 1H), 2.86-2.57 (m, 2H), 2.50-2.35 (m, 1H), 2.28-2.11 (m, 3H).

Example 12, Isomer 1 and Isomer 2: To a solution of 12C (27 mg, 0.058 mmol) in EtOH (0.3 mL) was added aq. KOH (6 N) (0.19 mL, 1.16 mmol). The reaction mixture was heated to 125° C. for 1.5 h. The reaction mixture was cooled to rt and concentrated. The reaction mixture was acidified to pH 2 with 1 N aq. HCl and extracted with EtOAc. The combined organic layers were concentrated and purified by RP-Prep. HPLC. The two isomers were separated by chiral SFC. Isomer 1 was dissolved in 3 N aq. HCl (0.5 mL) and CH$_3$CN (1 mL) and evaporated. The procedure was repeated 2× to give Example 12, Isomer 1 (2.5 mg, 4.8 μmol, 8% yield) as a white powder. LC-MS Anal. Calc'd for $C_{24}H_{26}F_4N_2O_4$: 482.18, found [M+H] 483.1. $^1$H NMR (400 MHz, acetonitrile-d$_3$) δ 7.74 (d, J=9.1 Hz, 2H), 7.17-6.93 (m, 3H), 6.74 (dd, J=7.3, 3.0 Hz, 1H), 6.57-6.37 (m, 1H), 5.24-5.02 (m, 1H), 4.28-4.14 (m, 1H), 4.11-4.00 (m, 1H), 3.97-3.88 (m, 1H), 3.75 (s, 3H), 3.72-3.47 (m, 5H), 3.03 (d, J=8.6 Hz, 1H), 2.84 (dd, J=16.9, 4.5 Hz, 1H), 2.73 (s, 1H), 2.48-2.36 (m, 1H), 2.30 (d, J=12.4 Hz, 2H). Analytical HPLC: RT=11.21 min, HI: 99.7%. hGPR40 EC$_{50}$=2800 nM. Isomer 2 was dissolved in 3 N aq. HCl (0.5 mL) and CH$_3$CN (1 mL) and evaporated. The procedure was repeated (2×) to give Example 12, Isomer 2 (2.0 mg, 3.8 μmol, 7% yield) as a white powder. LC-MS Anal. Calc'd for $C_{24}H_{26}F_4N_2O_4$: 482.18, found [M+H] 483.1. $^1$H NMR (400 MHz, acetonitrile-d$_3$) δ 7.90-7.76 (m, 2H), 7.39 (dd, J=6.6, 3.3 Hz, 1H), 7.20 (dd, J=11.8, 9.1 Hz, 1H), 7.13-7.05 (m, 2H), 6.94-6.71 (m, 1H), 5.28 (br. s, 1H), 4.33-4.17 (m, 1H), 4.15-4.03 (m, 2H), 3.89 (m, 1H), 3.81-3.58 (m, 7H), 3.09 (dd, J=17.3, 8.5 Hz, 1H), 2.95-2.68 (m, 2H), 2.65-2.51 (m, 1H), 2.33 (m, 2H). Analytical HPLC: RT=11.2 min, HI: 99.6%. hGPR40 EC$_{50}$=5400 nM.

EXAMPLE 13

Isomer 1 and Isomer 2

2-((2R,4R)-1-(4-(((2,4-cis)-1-(2-Fluoro-5-methoxyphenyl)-2-methylpiperidin-4-yl)oxy)phenyl)-4-methoxypyrrolidin-2-yl)acetic acid, HCl

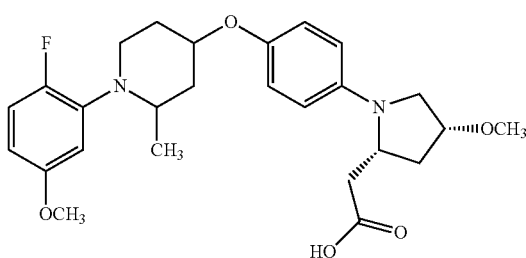 [SMILES: COc1ccc(F)c(N2CCC(Oc3ccc(N4C[C@H](OC)C[C@@H]4CC(=O)O)cc3)CC2C)c1]

Example 13, Isomer 1 and Isomer 2 were prepared from 2-methylpiperidin-4-ol as single isomers following the procedure of Example 17. Example 13, Isomer 1 (colorless foam, 6.3 mg). LC-MS Anal. Calc'd for $C_{26}H_{33}FN_2O_5$ 472.23, found [M+H] 473.0. $^1$H NMR (400 MHz, acetonitrile-$d_3$) δ 8.39-8.12 (m, 1H), 7.79 (d, J=8.3 Hz, 2H), 7.30 (dd, J=12.1, 9.1 Hz, 1H), 7.19-6.92 (m, 3H), 4.90-4.70 (m, 1H), 4.47-4.30 (m, 1H), 4.25-3.99 (m, 2H), 3.95-3.60 (m, 6H), 3.33 (s, 3H), 3.01-2.90 (m, 2H), 2.84 (dt, J=13.5, 6.5 Hz, 2H), 2.70 (d, J=10.9 Hz, 1H), 2.51 (br. s, 1H), 2.41 (br. s, 2H), 2.11 (d, J=2.5 Hz, 1H), 1.36-1.17 (m, 3H). Analytical HPLC: RT=6.6 min, HI: 97%. hGPR40 $EC_{50}$=710 nM. Example 13, Isomer 2 (colorless foam, 5.3 mg). LC-MS Anal. Calc'd for $C_{26}H_{33}FN_2O_5$: 472.23, found [M+H] 473.0. $^1$H NMR (400 MHz, acetonitrile-$d_3$) δ 8.41-8.07 (m, 1H), 7.81 (d, J=9.1 Hz, 2H), 7.32 (dd, J=12.1, 9.1 Hz, 1H), 7.21-7.03 (m, 3H), 4.81 (s, 1H), 4.40 (dd, J=6.4, 3.4 Hz, 1H), 4.19 (br. s, 2H), 3.93-3.78 (m, 4H), 3.76-3.64 (m, 2H), 3.35 (s, 3H), 3.06-2.78 (m, 4H), 2.71 (dd, J=11.2, 2.4 Hz, 1H), 2.54 (d, J=11.6 Hz, 1H), 2.44-2.25 (m, 2H), 2.17-2.05 (m, 1H), 1.40-1.10 (m, 3H). Analytical HPLC: RT=6.6 min, HI: 98.8%. hGPR40 $EC_{50}$=160 nM.

EXAMPLE 14

Isomer 1 and Isomer 2

2-((2R,4R)-1-(4-(((2,4-cis)-1-(2-Fluoro-5-methoxyphenyl)-2-methylpiperidin-4-yl)oxy)phenyl)-4-(trifluoromethyl)pyrrolidin-2-yl)acetic acid, HCl

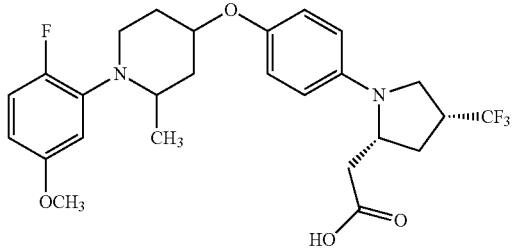 [SMILES: COc1ccc(F)c(N2CCC(Oc3ccc(N4C[C@H](C(F)(F)F)C[C@@H]4CC(=O)O)cc3)CC2C)c1]

Example 14, Isomer 1 and Isomer 2 were prepared from 1K as single isomers following the procedure of Example 13. Example 14, Isomer 1 (colorless foam, 2.2 mg). LC-MS Anal. Calc'd for $C_{26}H_{30}F_4N_2O_4$: 510.21, found [M+H] 511.1. $^1$H NMR (400 MHz, acetonitrile-$d_3$) δ 8.47-8.07 (m, 1H), 7.54-7.21 (m, 3H), 7.07 (d, J=8.8 Hz, 3H), 4.86-4.58 (m, 1H), 4.31-4.14 (m, 1H), 4.09-3.91 (m, 1H), 3.81 (s, 3H), 3.71-3.56 (m, 3H), 3.54-3.37 (m, 1H), 2.96-2.57 (m, 3H), 2.55-2.43 (m, 1H), 2.41-2.03 (m, 5H), 1.43-1.14 (m, 3H). Analytical HPLC: RT=8.6 min, HI: 100%. hGPR40 $EC_{50}$=130 nM. Example 14, Isomer 2 (colorless foam, 2.0 mg). LC-MS Anal. Calc'd for $C_{26}H_{30}F_4N_2O_4$ 510.21, found [M+H] 511.1. $^1$H NMR (400 MHz, acetonitrile-$d_3$) δ 8.43-8.13 (m, 1H), 7.30 (dd, J=12.1, 9.3 Hz, 3H), 7.07 (d, J=8.8 Hz, 3H), 4.85-4.58 (m, 1H), 4.33-4.16 (m, 1H), 4.11-3.96 (m, 1H), 3.83 (s, 3H), 3.81-3.73 (m, 1H), 3.68-3.55 (m, 2H), 3.52-3.37 (m, 2H), 2.94-2.62 (m, 4H), 2.52-2.03 (m, 5H), 1.61-1.08 (m, 3H). Analytical HPLC: RT=8.5 min, HI: 95.2%. hGPR40 $EC_{50}$=280 nM.

EXAMPLE 15

2-((2R,4R)-1-(3-Fluoro-4-((1-(2-fluoro-5-methoxyphenyl)piperidin-4-yl)oxy)phenyl)-4-methoxypyrrolidin-2-yl)acetic acid, HCl

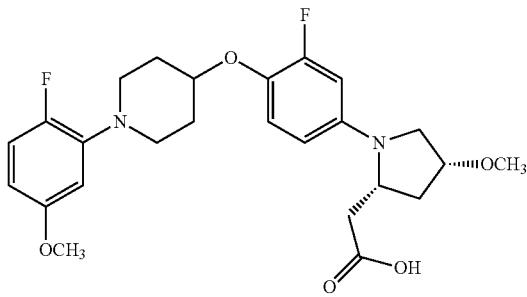 [SMILES: COc1ccc(F)c(N2CCC(Oc3ccc(N4C[C@H](OC)C[C@@H]4CC(=O)O)cc3F)CC2)c1]

Example 15 (white solid, 40 mg) was prepared from 1,2-difluoro-4-nitrobenzene following the procedure of Example 17. LC-MS Anal. Calc'd for $C_{25}H_{30}F_2N_2O_5$: 476.51, found [M+H] 477.3. $^1$H NMR (400 MHz, acetonitrile-$d_3$) δ 7.87 (m, 1H), 7.32 (m, 1H), 7.21 (m, 1H), 7.09-7.06 (m, 3H), 4.69 (s, 1H), 4.25-3.97 (m, 4H), 3.84 (s, 3H), 3.69-3.55 (m, 4H), 3.34 (s, 3H), 2.83-1.96 (m, 9H). Analytical HPLC: RT=8.0 min, HI: 95%. hGPR40 $EC_{50}$=290 nM.

EXAMPLE 16

2-((2R,4R)-1-(4-((1-(2-Fluoro-5-methoxyphenyl)piperidin-4-yl)methyl)phenyl)-4-(trifluoromethyl)pyrrolidin-2-yl)acetic acid, HCl

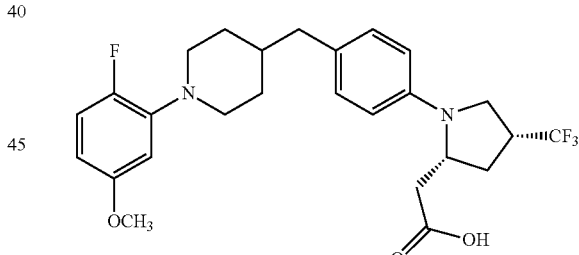

16A. tert-Butyl 4-(4-iodobenzyl)piperidine-1-carboxylate: A solution of tert-butyl 4-formylpiperidine-1-carboxylate (3.70 g, 17.4 mmol) in 1,4-dioxane (45 mL) was treated with 4-methylbenzenesulfonohydrazide (3.23 g, 17.4 mmol) and heated to 50° C. for 3 h and then 80° C. for 1 h. The reaction mixture was cooled to rt and treated with (4-iodophenyl)boronic acid (5.37 g, 21.7 mmol) and $K_2CO_3$ (3.00 g, 21.7 mmol) and heated to 110° C. for 7 h. After cooling, the reaction mixture was diluted with EtOAc and washed with water. The aqueous layer was extracted with EtOAc. The combined organic layers were washed with brine, dried ($MgSO_4$), and concentrated. Purification via silica chromatography gave 16A as a white solid (934 mg, 13% yield). $^1$H NMR (500 MHz, $CDCl_3$) δ 7.60 (d, 2H), 6.88 (d, 2H), 4.09 (m, 2H), 2.62 (m, 2H), 2.47 (m, 2H), 1.60 (m, 3H), 1.57 (s, 9H), 1.10 (m, 2H).

16B. 4 1-(2-Fluoro-5-methoxyphenyl)-4-(4-iodobenzyl)piperidine: To a solution of 16A (362 mg, 0.900 mmol) in CH$_2$Cl$_2$ (8 mL) at rt, TFA (0.97 mL, 13 mmol) was added dropwise. The reaction mixture was stirred at rt for 2.5 h. The reaction mixture was concentrated, diluted with EtOAc, washed with 0.5 N aq. NaOH, water, and brine, dried (MgSO$_4$), and concentrated to give 4-(4-iodobenzyl)piperidine as a white solid, which was used for next reaction without further purification. To a solution of (2-fluoro-5-methoxyphenyl)boronic acid (614 mg, 3.61 mmol) and 4-(4-iodobenzyl)piperidine (272 mg, 0.900 mmol) in CH$_2$Cl$_2$ (9 mL), 4Åmolecular sieves, and NEt$_3$ (0.881 mL, 6.32 mmol) were added and followed by Cu(OAc)$_2$ (328 mg, 1.81 mmol). The reaction mixture was stirred at rt under ambient atmosphere in a loosely capped flask. After 17 h, (2-fluoro-5-methoxyphenyl)boronic acid (154 mg, 0.900 mmol) and Cu(OAc)$_2$ (82 mg, 0.45 mmol) were added and after 24 h, additional (2-fluoro-5-methoxyphenyl)boronic acid (154 mg, 0.900 mmol) was added. After stirring at rt for 40 h, the reaction mixture was diluted with CH$_2$Cl$_2$, stirred for 10 min, and filtered. The filtrate was concentrated. The residue was dissolved in EtOAc, washed with 0.5 N aq. NaOH, water, and brine, dried (MgSO$_4$), and concentrated. Purification via silica chromatography gave 16B as a white solid (102 mg, 27% yield). $^1$H NMR (500 MHz, CDCl$_3$) δ 7.60 (d, 2H), 6.91 (m, 3H), 6.47 (m, 1H), 6.39 (m, 1H), 3.75 (m, 3H), 3.42 (m, 2H), 2.54 (m, 4H), 1.75-1.40 (m, 5H).

Example 16 (white solid, 45 mg) was prepared from 16B following the procedure of Example 2. LC-MS Anal. Calc'd for C$_{26}$H$_{30}$F$_4$N$_2$O$_3$: 494.22, found [M+H] 495.0. $^1$H NMR (400 MHz, acetonitrile-d$_3$) δ 7.91 (m, 1H), 7.52 (m, 2H), 7.26-7.14 (m, 3H), 6.95 (m, 1H), 4.25 (m, 1H), 3.91 (m, 1H), 3.75-3.48 (m, 9H), 2.95-2.55 (m, 5H), 2.28-1.75 (m, 6H). Analytical HPLC: RT=9.0 min, HI: 97%. hGPR40 EC$_{50}$=530 nM. hGPR40 IP1 EC$_{50}$=73 nM.

EXAMPLE 17

Isomer 1 and Isomer 2

2-((2R,4R)-1-(4-(((3,4-trans)-1-(2-Fluoro-5-methoxyphenyl)-3-methylpiperidin-4-yl)oxy)phenyl)-4-methoxypyrrolidin-2-yl)acetic acid, diethylammonium salt

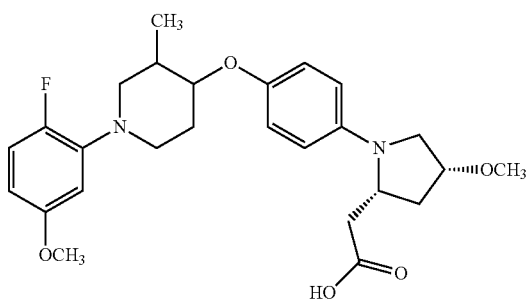 [SMILES: COc1ccc(F)c(N2CCC(Oc3ccc(N4C[C@H](OC)C[C@@H]4CC(=O)O)cc3)C(C)C2)c1]

17A. 1-(2-Fluoro-5-methoxyphenyl)-3-methylpiperidin-4-ol: A mixture of 2-bromo-1-fluoro-4-methoxybenzene (0.422 g, 2.06 mmol), 3-methylpiperidin-4-ol (0.237 g, 2.06 mmol), Pd$_2$(dba)$_3$ (0.038 g, 0.041 mmol) and SPhos (0.034 g, 0.082 mmol) in THF (4.1 mL) was purged with argon. A solution of LHMDS (9.3 mL, 9.3 mmol) (1 N in THF) was added. The vessel was purged with argon and then heated to 70° C. overnight. The reaction mixture was cooled to rt, quenched with 1.5 M aq. K$_2$HPO$_4$, and diluted with EtOAc. The layers were separated and the aqueous layer was extracted with EtOAc. The combined organic layers were washed with brine, dried (MgSO$_4$), and concentrated. The crude product was purified by silica chromatography to separate the cis and trans isomers as pale brown oils. (3,4-trans)-17A (0.157 g, 0.656 mmol, 32% yield). LC-MS Anal. Calc'd for C$_{13}$H$_{18}$FNO$_2$: 239.13, found [M+H] 240.1. $^1$H NMR (500 MHz, CDCl$_3$) δ 6.92 (dd, J=12.1, 8.8 Hz, 1H), 6.50 (dd, J=7.3, 2.9 Hz, 1H), 6.40 (dt, J=8.9, 3.1 Hz, 1H), 3.76 (s, 3H), 3.50-3.42 (m, 1H), 3.37 (ddd, J=11.9, 4.1, 2.5 Hz, 1H), 3.29 (td, J=10.0, 4.5 Hz, 1H), 2.74 (td, J=12.0, 2.8 Hz, 1H), 2.40 (dd, J=11.8, 10.7 Hz, 1H), 2.03 (ddt, J=12.6, 4.3, 3.1 Hz, 1H), 1.87-1.68 (m, 3H), 1.05 (d, J=6.6 Hz, 3H). (3,4-cis)-17A (0.023 g, 0.095 mmol, 5% yield). LC-MS Anal. Calc'd for C$_{13}$H$_{18}$FNO$_2$ 239.13, found [M+H] 240.1. $^1$H NMR (500 MHz, CDCl$_3$) δ 6.93 (dd, J=12.1, 8.8 Hz, 1H), 6.59 (dd, J=7.2, 3.0 Hz, 1H), 6.43 (dt, J=8.8, 3.2 Hz, 1H), 3.94-3.90 (m, 1H), 3.76 (s, 3H), 3.13 (dd, J=7.7, 3.9 Hz, 2H), 3.03 (dd, J=11.7, 4.0 Hz, 1H), 2.94-2.87 (m, 1H), 2.14-2.05 (m, 1H), 2.04-1.96 (m, 1H), 1.89 (ddt, J=13.7, 5.0, 3.9 Hz, 1H), 1.81 (br. s, 1H), 1.04 (d, J=7.2 Hz, 3H).

17B. (3,4-trans)-1-(2-Fluoro-5-methoxyphenyl)-3-methyl-4-(4-nitrophenoxy)piperidine: To a solution of (3,4-trans)-17A (0.0337 g, 0.141 mmol) in DMF (0.70 mL) at 0° C. was added 60% NaH (8.5 mg, 0.21 mmol). The reaction mixture was stirred at 0° C. for 15 min and then warmed to rt and stirred for 30 min. To the mixture was added 1-fluoro-4-nitrobenzene (0.016 mL, 0.16 mmol) and the reaction mixture was heated to 50° C. for 1.5 h. The reaction mixture was cooled to rt and quenched with water. The reaction mixture was diluted with EtOAc and the layers were separated. The organic layer was washed with water (4x), brine, dried (MgSO$_4$), and concentrated. The crude product was purified by silica chromatography to provide 17B (0.0376 g, 0.104 mmol, 74% yield) as a yellow oil. LC-MS Anal. Calc'd for C$_{19}$H$_{21}$FN$_2$O$_4$: 360.38, found [M+H] 360.0. $^1$H NMR (400 MHz, CDCl$_3$) δ 8.24-8.17 (m, 2H), 7.02-6.96 (m, 2H), 6.96-6.89 (m, 1H), 6.51 (dd, J=7.3, 3.0 Hz, 1H), 6.42 (dt, J=8.8, 3.2 Hz, 1H), 4.09 (td, J=9.0, 4.0 Hz, 1H), 3.77 (s, 3H), 3.52-3.40 (m, 2H), 2.95-2.82 (m, 1H), 2.62 (dd, J=12.3, 9.5 Hz, 1H), 2.29-2.16 (m, 2H), 1.96-1.81 (m, 1H), 1.10 (d, J=6.6 Hz, 3H).

17C. 4-(((3,4-trans)-1-(2-Fluoro-5-methoxyphenyl)-3-methylpiperidin-4-yl)oxy)aniline: To a solution of 17B (0.190 g, 0.527 mmol) in MeOH (5.3 mL) was added 10% Pd/C (5.6 mg, 5.3 µmol). The solution was stirred under 55 psi H$_2$ overnight. The reaction mixture was filtered and concentrated to provide 17C (0.173 g, 0.524 mmol, 99% yield) as a colorless oil. LC-MS Anal. Calc'd for C$_{19}$H$_{23}$FN2O$_2$: 330.17, found [M+H] 331.0. $^1$H NMR (500 MHz, CDCl$_3$) δ 6.92 (dd, J=12.1, 8.8 Hz, 1H), 6.82-6.76 (m, 2H), 6.68-6.61 (m, 2H), 6.50 (dd, J=7.4, 3.0 Hz, 1H), 6.39 (dt, J=8.8, 3.2 Hz, 1H), 3.76 (s, 3H), 3.73 (td, J=9.1, 4.3 Hz, 1H), 3.46-3.36 (m, 2H), 2.76 (td, J=11.5, 2.9 Hz, 1H), 2.54 (dd, J=12.0, 9.8 Hz, 1H), 2.18-2.09 (m, 2H), 1.86-1.74 (m, 1H), 1.12 (d, J=6.6 Hz, 3H.

17D. (3,4-trans)-1-(2-Fluoro-5-methoxyphenyl)-4-(4-iodophenoxy)-3-methylpiperidine: 17C (0.173 g, 0.524 mmol) was dissolved in CH$_3$CN (3.0 mL) and pTsOH (0.299 g, 1.57 mmol) was added. The thick suspension was cooled to 0° C. and a solution of NaNO$_2$ (0.072 g, 1.0 mmol) and KI (0.217 g, 1.31 mmol) in water (0.46 mL) was added gradually. The reaction mixture was stirred for 10 min at 0° C. and allowed to warm to rt. After 1 h, to the mixture was added water (40 mL), sat. NaHCO$_3$ (until pH=9-10) and 2 M aq. Na$_2$S$_2$O$_3$.

The product was extracted with CH$_2$Cl$_2$ (3×). The combined organic layers were washed with brine, dried (MgSO$_4$), and concentrated. The crude product was purified by silica chromatography to provide 17D (0.142 g, 0.322 mmol, 61% yield) as a colorless oil. LC-MS Anal. Calc'd for C$_{19}$H$_{21}$FINO$_2$: 441.28, found [M+H] 442.9. $^1$H NMR (400 MHz, CDCl$_3$) δ 7.60-7.52 (m, 2H), 6.93 (dd, J=12.1, 8.8 Hz, 1H), 6.76-6.68 (m, 2H), 6.51 (dd, J=7.4, 3.0 Hz, 1H), 6.41 (dt, J=8.8, 3.0 Hz, 1H), 3.90 (td, J=9.1, 4.4 Hz, 1H), 3.77 (s, 3H), 3.49-3.38 (m, 2H), 2.88-2.76 (m, 1H), 2.58 (dd, J=12.1, 9.3 Hz, 1H), 2.23-2.11 (m, 2H), 1.88-1.76 (m, 1H), 1.09 (d, J=6.6 Hz, 3H).

17E. ((2R,4R)-1-(4-(((3,4-trans)-1-(2-Fluoro-5-methoxyphenyl)-3-methylpiperidin-4-yl)oxy)phenyl)-4-methoxypyrrolidin-2-yl)methanol: 17D (0.071 g, 0.16 mmol), 4A (0.027 g, 0.16 mmol), CuI (0.77 mg, 4.0 µmol), and NaOH (0.019 g, 0.49 mmol) were combined and n-BuOH (0.48 mL) was added. The reaction mixture was heated to 90° C. overnight. The reaction mixture was cooled to rt and diluted with water. The product was extracted with CH$_2$Cl$_2$ (3×). The combined organic layers were washed with brine, dried (MgSO$_4$), and concentrated. The crude product was purified by silica chromatography to provide 17E (0.034 g, 0.077 mmol, 48% yield) as an amber oil. LC-MS Anal. Calc'd for C$_{25}$H$_{33}$FN$_2$O$_4$: 444.54, found [M+H] 445.2. $^1$H NMR (500 MHz, CDCl$_3$) δ 6.96-6.85 (m, 3H), 6.66-6.58 (m, 2H), 6.50 (dd, J=7.4, 3.0 Hz, 1H), 6.39 (dt, J=8.8, 3.2 Hz, 1H), 4.10-4.02 (m, 1H), 3.96-3.85 (m, 2H), 3.76 (s, 3H), 3.75-3.70 (m, 1H), 3.69-3.61 (m, 2H), 3.46-3.41 (m, 2H), 3.40 (s, 3H), 3.29 (dd, J=10.5, 4.7 Hz, 1H), 2.85 (br. s, 1H), 2.81-2.71 (m, 1H), 2.55 (dd, J=12.0, 9.8 Hz, 1H), 2.27-2.19 (m, 2H), 2.19-2.07 (m, 2H), 1.86-1.76 (m, 1H), 1.13 (d, J=6.6 Hz, 3H).

17F. 2-((2S,4R)-1-(4-(((3,4-trans)-1-(2-Fluoro-5-methoxyphenyl)-3-methylpiperidin-4-yl)oxy)phenyl)-4-methoxypyrrolidin-2-yl)acetonitrile: 17E (0.0341 g, 0.077 mmol) was dissolved in CH$_2$Cl$_2$ (0.77 mL) and the solution was cooled to 0° C. MsCl (9.0 µL, 0.12 mmol) and NEt$_3$ (0.021 mL, 0.15 mmol) were added sequentially and the reaction mixture was stirred at 0° C. for 40 min. The reaction mixture was diluted with EtOAc and washed with 1 N aq. HCl, sat. aq. NaHCO$_3$, and brine. The organic layer was dried (MgSO$_4$) and concentrated. The crude product was redissolved in DMSO (0.77 mL) and NaCN (0.015 g, 0.31 mmol) was added. The reaction mixture was stirred at 50° C. overnight and then cooled to rt and quenched with water. The product was extracted with EtOAc (3×). The combined organic layers were washed with brine, dried (MgSO$_4$), and concentrated. The crude product was purified by silica chromatography to afford 17F (0.024 g, 0.052 mmol, 68% yield) as a white solid. LC-MS Anal. Calc'd for C$_{26}$H$_{32}$FN3O$_3$: 453.55, found [M+H] 454.1. $^1$H NMR (400 MHz, CDCl$_3$) δ 6.97-6.85 (m, 3H), 6.55-6.46 (m, 3H), 6.40 (dt, J=8.8, 3.2 Hz, 1H), 4.16-4.06 (m, 2H), 3.77 (s, 4H), 3.76-3.69 (m, 1H), 3.56-3.48 (m, 1H), 3.47-3.33 (m, 5H), 2.91-2.68 (m, 3H), 2.56 (dd, J=12.0, 9.7 Hz, 1H), 2.37-2.31 (m, 1H), 2.27-2.07 (m, 3H), 1.89-1.71 (m, 1H), 1.13 (d, J=6.6 Hz, 3H).

Example 17, Isomer 1 and Isomer 2: 17E (0.024 g, 0.052 mmol) was dissolved in EtOH (0.52 mL) and a 6 M aq. solution of KOH (0.17 mL, 1.0 mmol) was added. The reaction tube was sealed and heated to 120° C. for 2 h. The reaction mixture was cooled to rt and concentrated to remove the EtOH and 3 N aq. HCl was added to acidify the reaction mixture (0.37 mL). The reaction mixture was diluted with CH$_3$CN, filtered, and concentrated. The crude product was purified by RP-Prep. HPLC. The CH$_3$CN was removed by rotary evaporation and the fractions were lyophilized overnight to provide the product as a mixture of diastereomers. The diastereomers were separated by chiral SFC to provide the products as single isomers. Example 17, Isomer 1 (0.0077 g, 0.014 mmol, 27% yield) was recovered as a light brown solid. LC-MS Anal. Calc'd for C$_{26}$H$_{33}$FN$_2$O$_5$: 472.55, found [M+H] 473.2. $^1$H NMR (500 MHz, acetonitrile-d$_3$) δ 8.60 (br. s, 1H), 7.84 (br. s, 1H), 7.76 (d, J=9.1 Hz, 2H), 7.23 (dd, J=12.2, 9.2 Hz, 1H), 7.12 (d, J=9.4 Hz, 2H), 7.02-6.91 (m, 1H), 4.37 (qd, J=6.7, 3.6 Hz, 1H), 4.34-4.27 (m, 1H), 4.24-4.12 (m, 1H), 3.86 (dd, J=12.5, 3.4 Hz, 1H), 3.80 (s, 3H), 3.72-3.64 (m, 3H), 3.61 (dd, J=12.2, 4.3 Hz, 1H), 3.40-3.35 (m, 1H), 3.33 (s, 3H), 3.05-2.85 (m, 5H), 2.81 (dt, J=13.4, 6.6 Hz, 2H), 2.48-2.29 (m, 2H), 2.17-2.06 (m, 1H), 1.34-1.23 (m, 6H), 1.09 (d, J=6.6 Hz, 3H). Analytical HPLC: RT=9.3 min, HI: 94.1%. hGPR40 EC$_{50}$=340 nM. Example 17, Isomer 2 (0.0060 g, 11 µmol, 21% yield) was recovered as a light brown solid. LC-MS Anal. Calc'd for C$_{26}$H$_{33}$FN$_2$O$_5$: 472.55, found [M+H] 473.2. $^1$H NMR (500 MHz, acetonitrile-d$_3$) δ 7.84 (br. s, 1H), 7.76 (d, J=9.1 Hz, 2H), 7.23 (dd, J=12.2, 9.2 Hz, 1H), 7.12 (d, J=9.4 Hz, 2H), 7.02-6.91 (m, 1H), 4.37 (qd, J=6.7, 3.6 Hz, 1H), 4.34-4.27 (m, 1H), 4.24-4.12 (m, 1H), 3.86 (dd, J=12.5, 3.4 Hz, 1H), 3.80 (s, 3H), 3.72-3.64 (m, 3H), 3.61 (dd, J=12.2, 4.3 Hz, 1H), 3.40-3.35 (m, 1H), 3.33 (s, 3H), 3.05-2.85 (m, 5H), 2.81 (dt, J=13.4, 6.6 Hz, 2H), 2.48-2.29 (m, 2H), 2.17-2.06 (m, 1H), 1.34-1.23 (m, 6H), 1.09 (d, J=6.6 Hz, 3H). Analytical HPLC: RT=9.3 min, HI: 93.3%. hGPR40 EC$_{50}$=64 nM.

EXAMPLE 18

Isomer 1 and Isomer 2

2-((2R,4R)-1-(4-(((3,4-trans)-1-(2-Fluoro-5-methoxyphenyl)-3-methylpiperidin-4-yl)oxy)phenyl)-4-(trifluoromethyl)pyrrolidin-2-yl)acetic acid, HCl

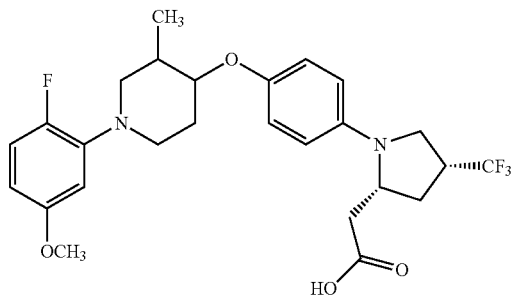

18A. (3,4-trans)-1-(2-Fluoro-5-methoxyphenyl)-4-(4-iodophenoxy)-3-methylpiperidine, Isomer 1 and Isomer 2: 17D (3.27 g, 7.40 mmol) was separated by chiral SFC to provide 18A, Isomer 1 as a colorless oil (1.54 g, 3.49 mmol, 47% yield). LC-MS Anal. Calc'd for C$_{19}$H$_{21}$FINO$_2$: 441.28, found [M+H] 442.9. $^1$H NMR (400 MHz, CDCl$_3$) δ 7.60-7.52 (m, 2H), 6.93 (dd, J=12.1, 8.8 Hz, 1H), 6.76-6.68 (m, 2H), 6.51 (dd, J=7.4, 3.0 Hz, 1H), 6.41 (dt, J=8.8, 3.0 Hz, 1H), 3.90 (td, J=9.1, 4.4 Hz, 1H), 3.77 (s, 3H), 3.49-3.38 (m, 2H), 2.88-2.76 (m, 2H), 2.58 (dd, J=12.1, 9.3 Hz, 1H), 2.23-2.11 (m, 2H), 1.88-1.76 (m, 1H), 1.09 (d, J=6.6 Hz, 3H). 18A, Isomer 2 (1.57 g, 3.55 mmol, 48% yield) was isolated as a colorless oil. LC-MS Anal. Calc'd for C₁₉H₂₁FINO₂ 441.28, found [M+H] 442.9. ¹H NMR (400 MHz, CDCl₃) δ 7.60-7.52 (m, 2H), 6.93 (dd, J=12.1, 8.8 Hz, 1H), 6.76-6.68 (m, 2H), 6.51 (dd, J=7.4, 3.0 Hz, 1H), 6.41 (dt, J=8.8, 3.0 Hz, 1H), 3.90 (td, J=9.1, 4.4 Hz, 1H), 3.77 (s, 3H), 3.49-3.38 (m, 2H), 2.88-2.76 (m, 1H), 2.58 (dd, J=12.1, 9.3 Hz, 1H), 2.23-2.11 (m, 2H), 1.88-1.76 (m, 1H), 1.09 (d, J=6.6 Hz, 3H).

Example 18, Isomer 1 and Isomer 2: Example 18, Isomer 1 (white solid, 40.1 mg) was prepared from 18A, Isomer 1 and 1K following the procedure of Example 17. LC-MS Anal. Calc'd for C₂₆H₃₀F₄N₂O₄: 510.52, found [M+H] 511.3. ¹H NMR (400 MHz, acetonitrile-d₃) δ 8.06 (dd, J=6.1, 3.0 Hz, 1H), 7.82 (d, J=9.1 Hz, 2H), 7.29 (dd, J=12.0, 9.2 Hz, 1H), 7.16 (d, J=9.1 Hz, 2H), 7.06 (dt, J=9.2, 3.3 Hz, 1H), 4.38 (td, J=10.2, 4.4 Hz, 1H), 4.28-4.20 (m, 1H), 4.17-4.06 (m, 1H), 3.86-3.80 (m, 4H), 3.80-3.61 (m, 5H), 3.51 (t, J=11.9 Hz, 1H), 3.11 (dd, J=16.9, 8.3 Hz, 1H), 2.86 (dd, J=17.1, 4.7 Hz, 1H), 2.80-2.69 (m, 1H), 2.54 (d, J=11.9 Hz, 1H), 2.44-2.25 (m, 2H), 1.10 (d, J=6.6 Hz, 3H). Analytical HPLC: RT=11.6 min, HI: 97.2%. hGPR40 EC₅₀=580 nM. Example 18, Isomer 2 (white solid, 38.1 mg) was prepared from 18A, Isomer 2 and 1K following the procedure of Example 17. LC-MS Anal. Calc'd for C₂₆H₃₀F₄N₂O₄: 510.52, found [M+H] 511.3. ¹H NMR (400 MHz, acetonitrile-d₃) δ 7.64 (d, J=7.1 Hz, 2H), 7.50 (br. s, 1H), 7.27 (dd, J=11.4, 9.3 Hz, 1H), 7.15 (d, J=7.1 Hz, 2H), 7.00 (d, J=8.6 Hz, 1H), 4.45-4.24 (m, 2H), 4.08 (dd, J=11.5, 6.2 Hz, 1H), 3.89-3.78 (m, 4H), 3.77-3.61 (m, 4H), 3.47 (t, J=11.4 Hz, 1H), 2.94-2.84 (m, 1H), 2.83-2.70 (m, 2H), 2.64 (br. s, 1H), 2.39 (d, J=12.4 Hz, 1H), 2.31-2.14 (m, 2H), 1.09 (d, J=6.3 Hz, 3H). Analytical HPLC: RT=11.6 min, HI: 95.7%. hGPR40 EC₅₀=69 nM. hGPR40 IP1 EC₅₀=10 nM.

EXAMPLE 19

2-((2R,4R)-1-(4-((1-(3-Methoxyphenyl)piperidin-4-yl)oxy)phenyl)-4-(trifluoromethyl)pyrrolidin-2-yl)acetic acid, HCl

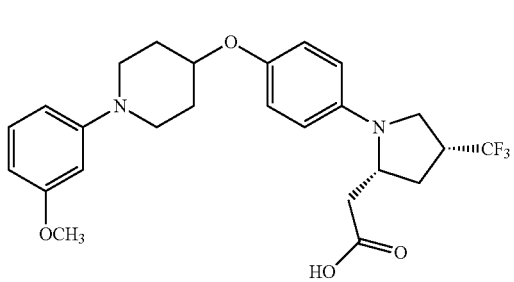

Example 19 (beige solid, 8.4 mg) was prepared from 1-bromo-3-methoxybenzene following the procedure of Example 1. LC-MS Anal. Calc'd for C₂₅H₂₉F₃N₂O₄: 478, found [M+H] 479. ¹H NMR (500 MHz, DMSO-d₆) δ 7.24-7.14 (m, 1H), 7.13-6.96 (m, 1H), 6.91 (d, J=9.1 Hz, 2H), 6.73-6.61 (m, J=9.1 Hz, 3H), 6.55-6.42 (m, 1H), 4.65-4.17 (m, J=3.6 Hz, 3H), 4.16-4.05 (m, 1H), 3.73 (s, 3H), 3.60-3.42 (m, 3H), 3.42-3.26 (m, 2H), 3.21-3.03 (m, 1H), 2.16-1.99 (m, 3H), 1.94-1.83 (m, 1H). Analytical HPLC: RT=8.0 min, HI: 100%. hGPR40 EC₅₀=680 nM.

EXAMPLE 20

2-((2R,4R)-1-(4-((1-(2-Fluorophenyl)piperidin-4-yl)oxy)phenyl)-4-(trifluoromethyl)pyrrolidin-2-yl)acetic acid, TFA

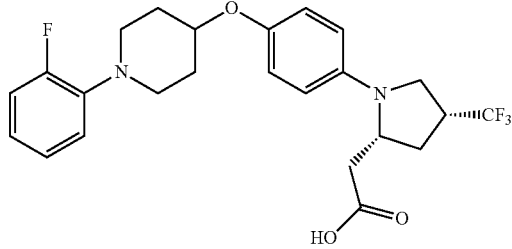

Example 20 (pale yellow oil, 0.011 g) was prepared from 1-bromo-2-fluorobenzene following the procedure of Example 1. LC-MS Anal. Calc'd for C₂₄H₂₆F₄N₂O₃: 466.5, found [M+H] 467.1. ¹H NMR (400 MHz, CDCl₃) δ 7.99 (t, J=7.7 Hz, 1H), 7.61-7.44 (m, 1H), 7.39-7.22 (m, 2H), 6.96 (d, J=8.2 Hz, 2H), 6.79 (br. s, 2H), 5.48 (br. s, 1H), 4.65 (br. s, 1H), 4.34-4.17 (m, J=5.5 Hz, 1H), 4.14-3.93 (m, J=11.3, 11.3 Hz, 2H), 3.58 (d, J=11.0 Hz, 4H), 3.24-2.98 (m, 1H), 2.90 (d, J=15.4 Hz, 1H), 2.75-2.51 (m, 3H), 2.48-2.34 (m, 1H), 2.25 (d, J=13.7 Hz, 2H), 2.14-2.01 (m, 1H). Analytical HPLC: RT=8.7 min, HI: 98.0%. hGPR40 EC₅₀=750 nM.

EXAMPLE 21

2-((2R,4R)-1-(4-((1-(3-Ethoxyphenyl)piperidin-4-yl)oxy)phenyl)-4-(trifluoromethyl)pyrrolidin-2-yl)acetic acid, HCl

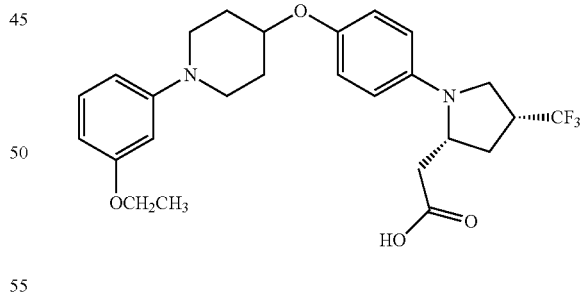

Example 21 (off-white solid, 16.9 mg) was prepared from with 1-bromo-3-ethoxybenzene following the procedure of Example 1. LC-MS Anal. Calc'd for C₂₆H₃₁F₃N₂O₄: 492.2, found [M+H] 493.2. ¹H NMR (500 MHz, DMSO-d₆) δ 7.34 (br. s, 2H), 7.03-6.88 (m, J=7.7 Hz, 4H), 6.78-6.49 (m, 3H), 5.07 (br. s, 1H), 4.50 (br. s, 1H), 4.19-4.08 (m, 1H), 4.05 (q, J=6.8 Hz, 2H), 3.61 (br. s, 2H), 3.54-3.44 (m, 1H), 3.45-3.24 (m, 3H), 2.73-2.61 (m, 1H), 2.60-2.52 (m, 1H), 2.28-2.03 (m, 3H), 2.02-1.80 (m, 3H), 1.33 (t, J=6.9 Hz, 3H). Analytical HPLC: RT=6.6 min, HI: 99.7%. hGPR40 EC₅₀=850 nM.

EXAMPLE 22

2-((2R,4R)-1-(4-((1-Phenylpiperidin-4-yl)oxy)phenyl)-4-(trifluoromethyl)pyrrolidin-2-yl)acetic acid, HCl

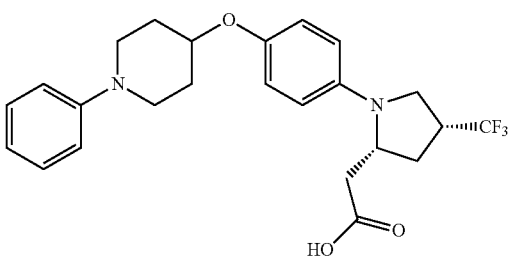 [SMILES: O=C(O)C[C@H]1C[C@@H](C(F)(F)F)CN1c1ccc(OC2CCN(c3ccccc3)CC2)cc1]

Example 22 (colorless oil, 4.5 mg) was prepared from bromobenzene following the procedure of Example 1. LC-MS Anal. Calc'd for $C_{24}H_{27}F_3N_2O_3$: 448.2, found [M+H] 449.1. $^1$H NMR (400 MHz, DMSO-$d_6$) δ 7.67 (br. s, 1H), 7.54-7.39 (m, 3H), 6.97 (d, J=7.7 Hz, 3H), 6.69 (d, J=7.1 Hz, 3H), 4.64-4.40 (m, 1H), 4.19-4.05 (m, 2H), 3.57-3.20 (m, 4H), 3.20-3.04 (m, 2H), 2.99-2.80 (m, 1H), 2.75-2.52 (m, 3H), 2.39-1.97 (m, 2H), 1.96-1.73 (m, 2H). Analytical HPLC: RT=6.7 min, HI: 97.0%. hGPR40 $EC_{50}$=1800 nM.

EXAMPLE 23

2-((2R,4R)-1-(4-((1-(4-Benzyl-2-fluoro-5-methoxyphenyl)piperidin-4-yl)oxy)phenyl)-4-methoxypyrrolidin-2-yl)acetic acid, TFA

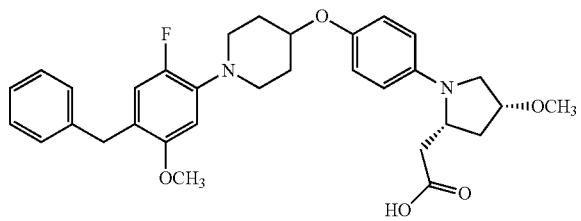 [SMILES: COc1cc(N2CCC(Oc3ccc(N4C[C@H](OC)C[C@@H]4CC(=O)O)cc3)CC2)c(F)cc1Cc1ccccc1]

23A. 5-Fluoro-4-(4-hydroxypiperidin-1-yl)-2-methoxybenzaldehyde: A solution of 4,5-difluoro-2-methoxybenzaldehyde (1.00 g, 5.81 mmol), piperidin-4-ol (0.705 g, 6.97 mmol), and $K_2CO_3$ (4.01 g, 29.0 mmol) in DMF (11.6 mL) was stirred at 100° C. for 16 h and then cooled to rt. The reaction mixture was diluted with EtOAc and water. The product was extracted with EtOAc. The combined organic layers were washed with sat. aq. $NH_4Cl$, water, and brine, dried ($MgSO_4$), and concentrated. Purification via silica chromatography yielded 23A (1.25 g, 4.84 mmol, 83% yield) as a yellow solid. LC-MS Anal. Calc'd for $C_{13}H_{16}FNO_3$: 253.11, found [M+H] 253.9. $^1$H NMR (400 MHz, acetonitrile-$d_3$) δ 10.21 (d, J=2.8 Hz, 1H), 7.54 (d, J=11.4 Hz, 1H), 6.68 (d, J=7.1 Hz, 1H), 3.96 (s, 3H), 3.94-3.90 (m, J=4.0 Hz, 1H), 3.35-3.21 (m, 2H), 3.03-2.85 (m, 2H), 2.14-1.99 (m, J=9.0, 6.3, 2.9 Hz, 2H), 1.90-1.72 (m, 2H).

23B. 1-(2-Fluoro-4-(hydroxy(phenyl)methyl)-5-methoxyphenyl)piperidin-4-ol: A solution of 23A (0.200 g, 0.790 mmol) in anhydrous THF (4.0 mL) was added dropwise to a 1 M solution of phenylmagnesium bromide in THF (2.37 mL, 2.37 mmol) in anhydrous THF (4.0 mL) at −10° C. The reaction mixture was stirred at rt for 2 h and then water (5 mL) and 10% aq. $H_2SO_4$ (5 mL) were added dropwise. The reaction mixture stirred for 20 min and was neutralized with 3 N aq. NaOH. The organic layer was separated and the aqueous layer was extracted with EtOAc. The combined organic layers were washed with water and brine, dried ($MgSO_4$), and concentrated. Purification via silica chromatography yielded 23B (0.28 g, 0.78 mmol, 98% yield) as a yellow solid. LC-MS Anal. Calc'd for $C_{19}H_{22}FNO_3$: 331.16, found [M+H] 332.0. $^1$H NMR (400 MHz, acetonitrile-$d_3$) δ 10.21 (d, J=2.8 Hz, 1H), 7.54 (d, J=11.4 Hz, 1H), 6.68 (d, J=7.1 Hz, 1H), 3.96 (s, 3H), 3.94-3.90 (m, J=4.0 Hz, 1H), 3.35-3.21 (m, 2H), 3.03-2.85 (m, 2H), 2.14-1.99 (m, J=9.0, 6.3, 2.9 Hz, 2H), 1.90-1.72 (m, 2H).

23C. 1-(4-Benzyl-2-fluoro-5-methoxyphenyl)piperidin-4-ol: To a solution of 23B (0.280 g, 0.845 mmol) in $CH_2Cl_2$ (4.2 mL) at −78° C. was added triethylsilane (0.20 mL, 1.3 mmol) followed by $BF_3.OEt_2$ (0.107 mL, 0.845 mmol). After stirring at rt for 3 h, additional triethylsilane (0.20 mL, 1.3 mmol) and $BF_3.OEt_2$ (0.11 mL, 0.85 mmol) were added and the reaction mixture was stirred over the weekend. The layers were separated and the aqueous layer was extracted with EtOAc. The combined organic layers were washed with sat. aq. $NaHCO_3$, brine, and dried ($MgSO_4$), filtered, and concentrated. Purification via silica chromatography yielded 23C (0.073 g, 0.23 mmol, 27% yield) as a yellow solid. LC-MS Anal. Calc'd for $C_{19}H_{22}FNO_2$: 315.16, found [M+H] 316.0. $^1$H NMR (400 MHz, acetonitrile-$d_3$) δ 10.21 (d, J=2.8 Hz, 1H), 7.54 (d, J=11.4 Hz, 1H), 6.68 (d, J=7.1 Hz, 1H), 3.96 (s, 3H), 3.94-3.90 (m, J=4.0 Hz, 1H), 3.35-3.21 (m, 2H), 3.03-2.85 (m, 2H), 2.14-1.99 (m, J=9.0, 6.3, 2.9 Hz, 2H), 1.90-1.72 (m, 2H).

23D. 2-((2S,4R)-1-(4-Hydroxyphenyl)-4-methoxypyrrolidin-2-yl)acetonitrile: 23D was prepared from 4A following the procedure of Example 1. LC-MS Anal. Calc'd for $C_{13}H_{16}N_2O_2$: 232.28, found [M+H] 233.0. $^1$H NMR (400 MHz, $CDCl_3$) δ 6.79 (d, J=8.6 Hz, 2H), 6.47 (d, J=8.8 Hz, 2H), 4.26 (br. s, 1H), 4.15-4.01 (m, 2H), 3.49 (d, J=10.4 Hz, 1H), 3.38 (s, 3H), 3.36 (d, J=5.1 Hz, 1H), 2.82-2.75 (m, 1H), 2.74-2.65 (m, 1H), 2.36-2.30 (m, 1H), 2.26-2.17 (m, 1H).

Example 23 (colorless oil, 0.015 g) was prepared from 23C and 23D following the procedure of Example 1. LC-MS Anal. Calc'd for $C_{32}H_{37}FN_2O_5$: 548.6, found [M+H] 549.1. $^1$H NMR (400 MHz, $CDCl_3$) δ 8.56 (br. s, 1H), 7.39-7.29 (m, 4H), 7.27-7.23 (m, 1H), 7.19 (d, J=6.8 Hz, 1H), 7.14 (d, J=7.3 Hz, 2H), 7.03-6.90 (m, 3H), 4.66 (br. s, 1H), 4.23 (s, 4H), 3.98-3.85 (m, 4H), 3.68 (br. s, 3H), 3.47 (d, J=11.9 Hz, 2H), 3.34 (s, 3H), 2.90-2.67 (m, 3H), 2.56-2.40 (m, 2H), 2.25-2.07 (m, 3H). Analytical HPLC: RT=9.1 min, HI: 99.0%. hGPR40 $EC_{50}$=3200 nM.

EXAMPLE 24

2-((2R,4R)-1-(4-((1-(3-(Trifluoromethoxy)phenyl)piperidin-4-yl)oxy)phenyl)-4-(trifluoromethyl)pyrrolidin-2-yl)acetic acid, HCl

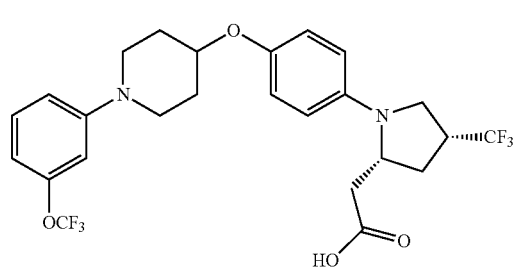 [SMILES: O=C(O)C[C@H]1C[C@@H](C(F)(F)F)CN1c1ccc(OC2CCN(c3cccc(OC(F)(F)F)c3)CC2)cc1]

Example 24 (off-white solid, 29.0 mg) was prepared from 1-chloro-3-(trifluoromethoxy)benzene following the procedure of Example 1. LC-MS Anal. Calc'd for $C_{25}H_{26}F_6N_2O_4$: 532.2, found [M+H] 533.2. $^1$H NMR (500 MHz, DMSO-$d_6$) δ 7.32 (t, J=8.3 Hz, 1H), 7.15-6.97 (m, 1H), 6.97-6.86 (m, 3H), 6.83-6.58 (m, 3H), 5.68 (br. s, 1H), 4.53-4.34 (m, J=3.3 Hz, 1H), 4.20-4.00 (m, 1H), 3.63-3.45 (m, 3H), 3.43-3.30 (m, 2H), 3.13 (t, J=9.4 Hz, 2H), 2.72-2.62 (m, 1H), 2.61-2.52 (m, 1H), 2.21-2.08 (m, J=10.2 Hz, 1H), 1.99 (br. s, 2H), 1.94-1.84 (m, 1H), 1.74-1.60 (m, 2H). Analytical HPLC: RT=10.0 min, HI: 99.8%. hGPR40 $EC_{50}$=4100 nM.

EXAMPLE 25

2-((2S,4R)-4-Fluoro-1-(4-((1-(2-fluoro-5-methoxyphenyl)-3-methylpiperidin-4-yl)oxy)phenyl)pyrrolidin-2-yl)acetic acid, TFA

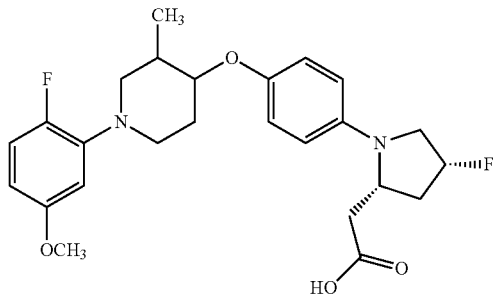 [SMILES: COc1ccc(F)c(N2CCC(Oc3ccc(N4C[C@H](F)C[C@@H]4CC(=O)O)cc3)C(C)C2)c1]

Example 25 (yellow oil, 2.6 mg) was prepared from 18A and (2R,4R)-1-tert-butyl 2-methyl 4-fluoropyrrolidine-1,2-dicarboxylate following the procedure of Example 18. LC-MS Anal. Calc'd for $C_{25}H_{30}F_2N_2O_4$: 460.22, found [M+H] 461.1. $^1$H NMR (500 MHz, CDCl$_3$) δ 7.14 (dd, J=12.0, 9.2 Hz, 1H), 6.95 (d, J=8.8 Hz, 2H), 6.87 (dt, J=9.1, 3.3 Hz, 1H), 6.69 (d, J=7.4 Hz, 2H), 3.81-3.79 (m, 4H), 3.54 (dd, J=11.8, 9.1 Hz, 2H), 3.27 (t, J=11.1 Hz, 1H), 2.93 (br. s, 1H), 2.73 (d, J=10.2 Hz, 1H), 2.45-2.31 (m, 2H), 2.20 (d, J=5.8 Hz, 1H), 1.31-1.25 (m, 1H), 1.22 (d, J=6.6 Hz, 3H). Analytical HPLC: 10.8 min, HI: 95.0%. hGPR40 $EC_{50}$=77 nM.

EXAMPLE 26

Isomer 1 and Isomer 2

2-((2,3-trans,3,4-trans)-1-(4-((1-(2-Fluoro-5-methoxyphenyl)piperidin-4-yl)oxy)phenyl)-3-methyl-4-(trifluoromethyl)pyrrolidin-2-yl)acetic acid, HCl

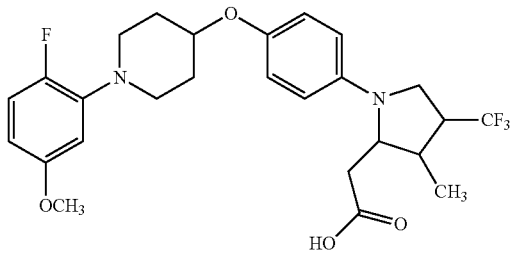 [SMILES: COc1ccc(F)c(N2CCC(Oc3ccc(N4CC(C(F)(F)F)C(C)C4CC(=O)O)cc3)CC2)c1]

26A. 1-(4-Bromophenyl)-4-(trifluoromethyl)pyrrolidin-2-one: A mixture of 1-bromo-4-iodobenzene (4.95 g, 17.5 mmol), 4-(trifluoromethyl)pyrrolidin-2-one (1.07 g, 7.0 mmol), 9,9-dimethyl-4,5-bis(diphenylphosphino)xanthene (365 mg, 0.63 mmol), and Cs$_2$CO$_3$ (3.19 g, 9.80 mmol) in dioxane (14 mL) was purged with argon. Pd$_2$(dba)$_3$ (192 mg, 0.210 mmol) was added. The reaction vial was sealed and heated to 115° C. for 24 h. The reaction mixture was diluted with EtOAc, washed with water and brine, dried (MgSO$_4$), and concentrated. Purification via silica chromatography gave 26A (739 mg, 34% yield). $^1$H NMR (500 MHz, CDCl$_3$) δ 7.51 (m, 4H), 4.04-3.91 (m, 2H), 3.21 (m, 1H), 2.85 (2H, m).

26B. (3,4-trans)-1-(4-Bromophenyl)-3-methyl-4-(trifluoromethyl)pyrrolidin-2-one: To a solution of 26A (739 mg, 2.73 mmol) in THF (13.7 mL) at −78° C., LHMDS (2.78 mL, 2.78 mmol) (1 M in THF) was added. The reaction mixture was stirred at −78° C. for 1 h. MeI (0.20 mL, 3.3 mmol) was added. The cold bath was removed and reaction mixture was warmed to rt slowly and stirred for 2 h. The mixture was quenched with sat. aq. NH$_4$Cl, diluted with EtOAc, washed with water and brine, dried (MgSO$_4$), and concentrated. Purification via silica chromatography gave 26B (white solid, 579 mg, 75% yield). $^1$H NMR (500 MHz, CDCl$_3$) δ 7.51 (m, 4H), 3.93-3.80 (m, 2H), 2.84 (m, 2H), 1.42 (m, 3H).

26C. (3,4-trans)-1-(4-Hydroxyphenyl)-3-methyl-4-(trifluoromethyl)pyrrolidin-2-one: A mixture of 26B (0.500 g, 1.55 mmol), 4,4,4',4',5,5,5',5'-octamethyl-2,2'-bi(1,3,2-dioxaborolane) (0.63 g, 2.5 mmol), potassium acetate (0.487 g, 4.96 mmol) and PdCl$_2$(dppf) (64 mg, 0.078 mmol) in DMF (2.2 mL) was purged with argon. The reaction mixture was heated to 80° C. for 1 h 45 min. The reaction mixture was diluted with EtOAc, washed with water and brine, dried (MgSO$_4$), and concentrated. Purification via silica chromatography gave (3,4-trans)-3-methyl-1-(4-(4,4,5,5-tetramethyl-1,3,2-dioxaborolan-2-yl)phenyl)-4-(trifluoromethyl) pyrrolidin-2-one as a white solid. The solid was dissolved in ethyl acetate (20 mL) and 30% aq. H$_2$O$_2$ (3.17 mL, 31.0 mmol) was added dropwise. The reaction mixture was stirred at rt for 18 h. The reaction mixture was cooled to 0° C. and slowly quenched with aq. sodium sulfite. The mixture was extracted with EtOAc. The extracts were washed with brine, dried (MgSO$_4$), and concentrated. Purification via silica chromatography gave 26C (white solid, 341 mg, 85% yield). $^1$H NMR (500 MHz, CDCl$_3$) δ 7.28 (d, 2H), 6.76 (d, 2H), 6.51 (s, 1H), 3.90-3.80 (m, 2H), 2.84 (m, 2H), 1.42 (m, 3H).

26D. (3,4-trans)-1-(4-((1-(2-Fluoro-5-methoxyphenyl)piperidin-4-yl)oxy)phenyl)-3-methyl-4-(trifluoromethyl)pyrrolidin-2-one: To a solution of 1B (375 mg, 0.910 mmol) and 26C (181 mg, 0.700 mmol) in DMF (1.5 mL), Cs$_2$CO$_3$ (525 mg, 1.61 mmol) was added. The reaction mixture was heated to 55° C. for 19 h. Additional 1B (40 mg, 0.10 mmol) was added and the reaction mixture was stirred at 70° C. for 1 h. The reaction mixture was diluted with EtOAc, washed with water and brine, dried (MgSO$_4$), and concentrated. Purification via silica chromatography gave the desired product (gum, 248 mg, 76% yield). LCMS Anal. Calc'd for $C_{24}H_{26}F_4N_2O_3$: 466.468, found [M+H] 467.3.

26E. Ethyl 2-((2,3-trans,3,4-trans)-1-(4-((1-(2-fluoro-5-methoxyphenyl)piperidin-4-yl)oxy)phenyl)-3-methyl-4-(trifluoromethyl)pyrrolidin-2-yl)acetate: To 26D (140 mg, 0.300 mmol) in THF (2 mL) at −78° C., lithium triethylborohydride (1 M in THF, 1.2 mL, 1.2 mmol) was added. The reaction mixture was stirred at −78° C. After 2.5 h additional lithium triethylborohydride (1 M in THF, 1.2 mL, 1.2 mmol) was added. The reaction mixture was stirred at −78° C. for 6 h 30 min. The reaction was quenched with sat. aq. NaHCO$_3$ (3 mL), warmed to 0° C., and 30% aq. H$_2$O$_2$ (1.5 mL) was added dropwise. The reaction mixture was stirred at 0° C. for 20 min and then diluted with EtOAc. The organic liquid was washed with aq. NaHCO$_3$, water, brine, dried (MgSO$_4$), passed through a silica gel pad, and the pad was rinsed with EtOAc. The organic layer was concentrated to give crude (3,4-trans)-1-(4-((1-(2-fluoro-5-methoxyphenyl)piperidin-4-yl)oxy)phenyl)-3-methyl-4-(trifluoromethyl)pyrrolidin-2-ol which was used for next reaction directly. To a solution of 60% NaH (66.2 mg, 1.66 mmol) in THF (2 mL), triethyl phosphonoacetate (0.36 mL, 1.8 mmol) was added dropwise. The reaction mixture was stirred at rt for 30 min. A solution of (3,4-trans)-1-(4-((1-(2-fluoro-5-methoxyphenyl)piperidin-4-yl)oxy)phenyl)-3-methyl-4-(trifluoromethyl)pyrrolidin-2-ol in THF (1 mL) was added. The reaction mixture was stirred at 65° C. for 18 h and at 70° C. for 1 h. The reaction was quenched with sat. aq. NH$_4$Cl, diluted with EtOAc, washed with water and brine, dried (MgSO$_4$), and concentrated. Purification via silica chromatography gave 26E (viscous oil, 64 mg, 40% yield). LCMS Anal. Calc'd for C$_{28}$H$_{34}$F$_4$N$_2$O$_4$: 538.574, found [M+H] 539.3.

Example 26, Isomer 1 and Isomer 2: To a solution of 26E (64 mg, 0.12 mmol) in THF (4 mL) and MeOH (2 mL), 1 N aq. LiOH (0.96 mL, 0.96 mmol) was added. The reaction mixture was stirred at rt for 6 h. The mixture was concentrated, cooled to 0° C., acidified with 1 N aq. HCl, and extracted with EtOAc. The extracts were dried (MgSO$_4$) and concentrated. The isomers were separated via chiral SFC to provide the products as single isomers. Example 26, Isomer 1 (light brown solid, 31 mg, 43% yield). LC-MS Anal. Calc'd for C$_{26}$H$_{30}$F$_4$N$_2$O$_4$: 510.521, found [M+H] 511.2. $^1$H NMR (400 MHz, acetonitrile-d$_3$) δ 7.92 (m, 1H), 7.73 (d, 2H), 7.31 (m, 1H), 7.14 (d, 2H), 7.04 (m, 1H), 4.82 (s, 1H), 4.09-3.62 (m, 10H), 3.31 (m, 1H), 3.05 (m, 1H), 2.81-2.62 (m, 4H), 2.34 (m, 2H), 1.33 (m, 4H). Analytical HPLC: 8.4 min, HI: 95%. hGPR40 EC$_{50}$=220 nM. hGPR40 IP1 EC$_{50}$=140 nM. Example 26, Isomer 2 (light brown solid, 28 mg, 38% yield). LC-MS Anal. Calc'd for C$_{26}$H$_{30}$F$_4$N$_2$O$_4$: 510.521, found [M+H] 511.2. $^1$H NMR (400 MHz, acetonitrile-d$_3$) δ 7.92 (m, 1H), 7.73 (d, 2H), 7.31 (m, 1H), 7.14 (d, 2H), 7.04 (m, 1H), 4.82 (s, 1H), 4.09-3.62 (10H, m), 3.31 (m, 1H), 3.05 (m, 1H), 2.81-2.62 (m, 4H), 2.34 (m, 2H), 1.33 (m, 4H). Analytical HPLC: RT=8.4 min, HI: 96%. hGPR40 EC$_{50}$=8400 nM.

EXAMPLE 27

Isomer 1 and Isomer 2

2-((2R,4R)-1-(4-(((3,4-trans)-1-(5-Chloro-2-methoxypyridin-4-yl)-3-methylpiperidin-4-yl)oxy)phenyl)-4-(trifluoromethyl)pyrrolidin-2-yl)acetic acid, HCl

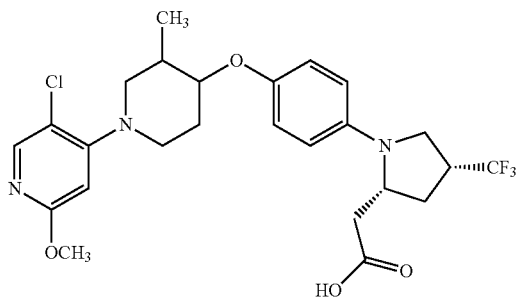 [SMILES: COc1cc(N2CCC(Oc3ccc(N4C[C@H](C(F)(F)F)C[C@@H]4CC(=O)O)cc3)C(C)C2)c(Cl)cn1]

27A. 4-Bromo-5-chloropyridin-2-amine: To a stirred solution of 4-bromopyridin-2-amine (30.0 g, 173 mmol) in DMF (350 mL) at −20° C. was added 1-chloropyrrolidine-2,5-dione (24.3 g, 182 mmol). The reaction mixture was stirred at rt for 24 h. The reaction mixture was poured into cold 1 M aq. NaOH (300 mL) and extracted with Et$_2$O (2×400 mL). The combined extracts were washed with water (3×200 mL), brine (200 mL), dried over Na$_2$SO$_4$, filtered, and concentrated. The crude material was recrystallized from CH$_2$Cl$_2$ to provide 27A as red solid (22.0 g, 106 mmol, 61% yield). LC-MS Anal. Calc'd for C$_5$H$_4$BrClN$_2$: 205.93, found [M+H] 206.9.

27B. 4-Bromo-5-chloro-2-methoxypyridine: To MeOH (390 mL) at 0° C. was added TMS-Cl (49.0 mL, 386 mmol). The reaction mixture was warmed to rt and stirred for 30 min. To this solution was added 27A (20.0 g, 96.0 mmol). The reaction mixture was stirred for 15 min and then NaNO$_2$ (2.74 g, 39.8 mmol) was added to the mixture at rt. The reaction mixture was stirred at 50° C. for 3 h. The reaction mixture was concentrated. The residue was diluted with EtOAc and then basified to pH=11-13 with 1 N aq. NaOH and extracted with EtOAc (3×). The combined organic layers were concentrated. Purification by recrystallization from MeOH and water afforded 27B as white needles (18.0 g, 81.0 mmol, 84% yield). LC-MS Anal. Calc'd for C$_6$H$_5$BrClNO: 220.92, found [M+H] 223.9.

27C. (3,4-cis)-1-Benzyl-3-methylpiperidin-4-ol: To a solution of 1-benzyl-3-methylpiperidin-4-one (24.8 g, 122 mmol) in THF (102 mL) at −78° C. was added dropwise a 1 M solution of L-Selectride (183 mL, 183 mmol) in THF. The reaction mixture was stirred at −78° C. for 1 h 30 min. EtOH (22 mL), water (55 mL) and 1 M aq. NaOH (55 mL) were added sequentially. The reaction mixture was warmed to 0° C. and 30% aq. H$_2$O$_2$ (55 mL) was added dropwise. The cold bath was removed and the reaction mixture was stirred at rt for 2 h. The reaction mixture was diluted with EtOAc and the insoluble white solid was discarded. The organic layer was washed with sat. aq. NaHCO$_3$ and brine, dried (MgSO$_4$), and concentrated to give the crude product as an oil. Purification via silica chromatography gave 27 C as a white solid (22.2 g, 88% yield). $^1$H NMR (500 MHz, CDCl$_3$) δ 7.40-7.20 (m, 5H), 3.84 (s, 1H), 3.55 (s, 2H), 2.60-1.73 (m, 7H), 0.97 (d, 3H).

27D. (3,4-cis)-1-Benzyl-4-((tert-butyldimethylsilyl)oxy)-3-methylpiperidine: To a solution of 27C (21.86 g, 106.5 mmol) and NEt$_3$ (44.5 mL, 320 mmol) in CH$_2$Cl$_2$ (107 mL) at 0° C. was added TBSOTf (29.4 mL, 128 mmol). The reaction mixture was stirred at 0° C. for 1 h. Sat. aq. NaHCO$_3$ (180 mL) was added slowly to the reaction mixture. The mixture was concentrated, diluted with EtOAc, washed with water and brine, dried (MgSO$_4$), and concentrated. Purification via silica chromatography gave 27D as an oil (31.48 g, 92% yield). LC-MS Anal. Calc'd for C$_{19}$H$_{33}$NOSi: 319.56, found [M+H] 320.3.

27E. (3,4-cis)-4-((tert-Butyldimethylsilyl)oxy)-3-methylpiperidine: A mixture of 27D (15.7 g, 49.3 mmol) and 10% Pd/C (3.15 g) in MeOH (493 mL) was stirred at rt under H$_2$ (1 atm) for 24 h. The mixture was filtered through CELITE® and the filtrate was concentrated to give 27E (11.3 g, 100% yield). $^1$H NMR (500 MHz, CDCl$_3$) δ 3.80 (s, 1H), 2.90 (m, 1H), 2.70-2.50 (m, 4H), 1.60-1.50 (m, 3H), 0.86 (s, 9H), 0.80 (d, 3H), 0.00 (s, 6H).

27F. 44(3,4-cis)-4-((tert-Butyldimethylsilyl)oxy)-3-methylpiperidin-1-yl)-5-chloro-2-methoxypyridine: A mixture of 27B (9.70 g, 43.6 mmol), 27E (10.0 g, 43.6 mmol), and K$_2$CO$_3$ (12.0 g, 87.0 mmol) in DMSO (14.5 mL) was vigorously stirred at 110° C. overnight. The reaction mixture was diluted with water and extracted with EtOAc. The organic layer was washed with water and brine, dried (MgSO$_4$), and concentrated. Purification via silica chromatography gave 27F as an oil (14.3 g, 77% yield). LC-MS Anal. Calc'd for C$_{18}$H$_{31}$ClN$_2$O$_2$Si: 370.18, found [M+H] 371.2.

27G. (3,4-cis)-1-(5-Chloro-2-methoxypyridin-4-yl)-3-methylpiperidin-4-ol: To a solution of 27F (10.0 g, 27.0 mmol)) in THF (27 mL) was added a 1 M solution of TBAF in THF (81 mL, 81 mmol). The reaction mixture was stirred at 23° C. for 16 h. Sat. aq. NaHCO$_3$ (100 mL) was added slowly to the reaction mixture. The mixture was extracted with EtOAc (2×100 mL) and the combined organic extracts were washed with water (50 mL) and brine (50 mL), dried (Na$_2$SO$_4$), filtered, and concentrated. Purification via silica chromatography gave 27G as white foam (7.00 g, 99% yield). LC-MS Anal. Calc'd for C$_{12}$H$_{17}$ClN$_2$O$_2$: 256.10, found [M+H] 257.0.

27H. 2-((2R,4R)-1-(4-((3,4-trans)-1-(5-Chloro-2-methoxypyridin-4-yl)-3-methylpiperidin-4-yl)oxy)phenyl)-4-(trifluoromethyl)pyrrolidin-2-yl)acetonitrile: To a solution of 1N (84 mg, 0.31 mmol) and 27G (88 mg, 0.34 mmol) in THF (104 µL) was added Ph$_3$P (114 mg, 0.440 mmol). The reaction vessel was then lowered into a sonication bath and sonicated for several minutes (to allow for mixing) giving a clear and highly viscous solution. While sonicating, DEAD (59 µL, 0.37 mmol) was added dropwise to the reaction mixture and the reaction mixture was sonicated for 120 min. Sat. aq. NaHCO$_3$ (10 mL) was added slowly to the reaction mixture. The mixture was then extracted with EtOAc (2×10 mL) and the combined organic extracts were washed with water (20 mL) and brine (20 mL), dried (Na$_2$SO$_4$), filtered, and concentrated. Purification by silica chromatography gave 27H as a white foam (86 mg, 0.17 mmol, 54% yield). LC-MS Anal. Calc'd for C$_{25}$H$_{28}$ClF$_3$N$_4$O$_2$: 508.18, found [M+H] 509.1.

Example 27, Isomer 1 and Isomer 2: To a stirred solution of 27H (86 mg, 0.17 mmol) in EtOH (1.7 mL) at rt was added 6 N aq. KOH (560 µL, 3.38 mmol). The reaction mixture was stirred at rt for 1 h. 3 N aq. HCl (0.4 mL) was added at 0° C. and the reaction mixture was warmed to rt. The solvent was evaporated and the residue was dissolved in CH$_3$CN, filtered, and concentrated. Purification by RP-Prep. HPLC afforded a diastereomeric mixture. The diastereomers were separated by chiral SFC to provide Example 27, Isomer 1 and Isomer 2 as single isomers. Example 27, Isomer 1 (white solid, 25 mg). LC-MS Anal. Calc'd for C$_{25}$H$_{29}$ClF$_3$N$_3$O$_4$: 527.18, found [M+H] 528.0. $^1$H NMR (400 MHz, acetonitrile-d$_3$) δ 8.00 (s, 1H), 6.98-6.88 (m, 2H), 6.78-6.67 (m, 2H), 6.38 (s, 1H), 4.18 (d, J=7.0 Hz, 1H), 3.87 (s, 3H), 3.59-3.48 (m, 4H), 3.25-3.12 (m, 1H), 2.95-2.85 (m, 1H), 2.80 (dd, J=15.9, 2.9 Hz, 1H), 2.74-2.58 (m, 2H), 2.26 (dd, J=15.8, 9.8 Hz, 2H), 2.20-2.08 (m, 3H), 1.76-1.66 (m, 1H), 1.11 (d, J=4.0 Hz, 3H). HPLC: RT=9.1 min, HI: 95%. hGPR40 EC$_{50}$=440 nM. Example 27, Isomer 2 (white solid, 25 mg). LC-MS Anal. Calc'd for C$_{25}$H$_{29}$ClF$_3$N$_3$O$_4$: 527.18, found [M+H] 528.0. $^1$H NMR (400 MHz, acetonitrile-d$_3$) δ 8.00 (s, 1H), 6.99-6.89 (m, 2H), 6.78-6.65 (m, 2H), 6.38 (s, 1H), 4.24-4.13 (m, 1H), 3.87 (s, 3H), 3.62-3.48 (m, 4H), 3.26-3.11 (m, 1H), 2.96-2.86 (m, 1H), 2.80 (dd, J=15.8, 3.0 Hz, 1H), 2.74-2.58 (m, 2H), 2.26 (dd, J=15.8, 9.8 Hz, 2H), 2.21-2.11 (m, 3H), 1.77-1.66 (m, 1H), 1.11 (d, J=4.0 Hz, 3H). HPLC: RT=9.2 min, HI: 95%. hGPR40 EC$_{50}$=130 nM.

EXAMPLE 28, Isomer 1 and Isomer 2

2-((2R,4R)-1-(4-(((3,4-trans)-1-(5-Chloro-2-methoxypyridin-4-yl)-3-fluoropiperidin-4-yl)oxy)phenyl)-4-(trifluoromethyl)pyrrolidin-2-yl)acetic acid, HCl

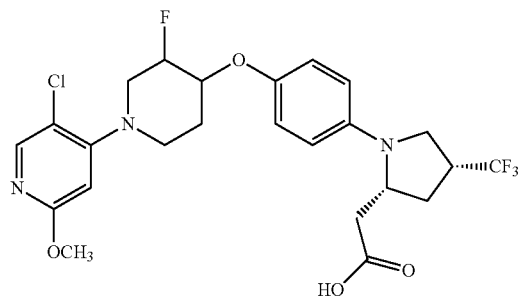 [SMILES: COc1cc(N2CCC(Oc3ccc(N4C[C@H](C(F)(F)F)C[C@@H]4CC(=O)O)cc3)C(F)C2)c(Cl)cn1]

28A. Benzyl 4-((trimethylsilyl)oxy)-5,6-dihydropyridine-1(2H)-carboxylate: To a solution of benzyl 4-oxopiperidine-1-carboxylate (1.27 g, 5.44 mmol) in DMF (4 mL) was added TMS-Cl (0.83 mL, 6.5 mmol) followed by NEt$_3$ (1.52 mL, 10.9 mmol). The resulting heterogeneous mixture was warmed to 80° C. and stirred for 16 h. The cooled mixture was diluted with hexanes (50 mL), washed with sat. NaHCO$_3$ (30 mL) and brine (30 mL), dried over MgSO$_4$, filtered, and concentrated to afford 28A (1.50 g, 4.91 mmol, 90% yield) as a clear oil. $^1$H NMR (400 MHz, CDCl$_3$) δ 7.22-7.08 (m, 5H), 4.98-4.94 (m, 2H), 4.60 (br. s, 1H), 3.77 (q, J=2.3 Hz, 2H), 3.42 (t, J=5.6 Hz, 2H), 1.94 (br. s, 2H), 0.04-0.04 (m, 9H).

28B. Benzyl 3-fluoro-4-oxopiperidine-1-carboxylate: To a solution of 28A (1.52 g, 4.98 mmol) in CH$_3$CN (31.1 mL) at rt was added SELECTFLUOR® (2.12 g, 5.97 mmol) portionwise over 10 min. The mixture was stirred for 2 h and then concentrated to dryness and partitioned between EtOAc and brine. The aqueous layer was extracted with EtOAc and the combined organic layers were washed with brine, dried over MgSO$_4$, filtered, and concentrated to afford 28B (1.20 g, 4.78 mmol, 96% yield) as a solid. $^1$H NMR (400 MHz, CDCl$_3$) δ 7.51-7.30 (m, 5H), 5.27-5.16 (m, 2H), 4.97-4.70 (m, 1H), 4.47 (br. s, 1H), 4.33-4.18 (m, 1H), 3.59-3.28 (m, 2H), 2.72-2.41 (m, 2H).

28C. Benzyl 3-fluoro-4-hydroxypiperidine-1-carboxylate: To a solution of 28B (880 mg, 3.50 mmol) in MeOH (7 mL) was added NaBH$_4$ (130 mg, 3.50 mmol) slowly. Then, 10% aq. KHSO$_4$ (10 mL) was added slowly to the reaction mixture. The mixture was then extracted with EtOAc (2×30 mL), and the combined organic extracts were dried (Na$_2$SO$_4$), filtered, and concentrated to afford 28C (870 mg, 3.44 mmol, 98% yield). LC-MS Anal. Calc'd for C$_{13}$H$_{16}$FNO$_3$: 253.27, found [M+H] 254.2. $^1$H NMR (400 MHz, CDCl$_3$) δ 7.47-7.27 (m, 5H), 5.13 (s, 2H), 4.75-4.52 (m, 1H), 4.07-3.68 (m, 3H), 3.61-3.04 (m, 2H), 2.22 (d, J=5.0 Hz, 1H), 1.93-1.63 (m, 2H).

28D. Benzyl 4-((tert-butyldimethylsilyl)oxy)-3-fluoropiperidine-1-carboxylate: To a solution of 28C (410 mg, 1.62 mmol) in CH$_2$Cl$_2$ (1.62 mL) and NEt$_3$ (670 µL, 4.86 mmol) was added TBSOTf (390 µL, 1.70 mmol) at 0° C. After 1 h, sat. aq. NaHCO$_3$ (10 mL) was added slowly to the reaction mixture. The mixture was extracted with EtOAc (2×30 mL) and the combined organic extracts were dried (Na$_2$SO$_4$), filtered, and concentrated to afford 28D (450 mg, 1.22 mmol, 76% yield). ¹H NMR (400 MHz, CDCl₃) δ 7.36-7.20 (m, 5H), 5.05 (s, 2H), 4.43-4.22 (m, 1H), 4.07-3.96 (m, 1H), 3.88-3.62 (m, 2H), 3.59-3.24 (m, 2H), 1.75-1.50 (m, 2H), 0.84 (s, 9H), 0.02-0.05 (m, 6H).

28E. 4-((tert-Butyldimethylsilyl)oxy)-3-fluoropiperidine: A mixture of 28D (440 mg, 1.20 mmol) and 10% Pd/C (127 mg, 0.120 mmol) in MeOH (12 mL) was purged with H₂ for 30 min and stirred under H₂ (1 atm) at rt for 1 h. The mixture was filtered through CELITE®, washed with EtOAc (30 mL) and MeOH (30 mL) and concentrated to afford 28E (270 mg, 1.16 mmol, 97% yield) as a clear oil. ¹H NMR (400 MHz, CDCl₃) δ 4.50-4.27 (m, 1H), 3.97-3.77 (m, 1H), 3.19-3.05 (m, 1H), 2.93 (ddd, J=13.1, 6.3, 4.1 Hz, 1H), 2.82-2.65 (m, 2H), 2.62-2.46 (m, 1H), 1.73-1.50 (m, 2H), 0.88 (s, 9H), 0.00 (d, J=3.8 Hz, 6H).

28F. 4-(4-((tert-Butyldimethylsilyl)oxy)-3-fluoropiperidin-1-yl)-5-chloro-2-methoxypyridine: A mixture of 28E (194 mg, 0.830 mmol), 27B (185 mg, 0.830 mmol) and SPhos precatalyst (6.0 mg, 8.3 µmol) in THF (1.7 mL) was purged with argon and a 1 M solution of LHMDS in THF (1.0 mL, 1.0 mmol) was added. The reaction mixture was heated to 70° C. for 2 h and then cooled to rt. Sat. aq. NaHCO₃ (10 mL) was added slowly to the reaction mixture. The mixture was then extracted with EtOAc (2×10 mL) and the combined organic extracts were washed with water (20 mL) and brine (20 mL), dried (Na₂SO₄), filtered, and concentrated. Purification by silica chromatography gave 28F (182 mg, 0.490 mmol, 58% yield). LC-MS Anal. Calc'd for C₁₇H₂₈ClFN₂O₂Si: 374.16, found [M+H] 374.9.

28G. 1-(5-Chloro-2-methoxypyridin-4-yl)-3-fluoropiperidin-4-ol: To a solution of 28F (192 mg, 0.510 mmol) in THF (1.0 mL) was added TBAF (610 µL, 0.61 mmol). The reaction mixture was stirred at 23° C. for 2 h. Sat. aq. NaHCO₃ (10 mL) was added slowly to the reaction mixture. The mixture was then extracted with EtOAc (2×10 mL) and the combined organic extracts were washed with water (20 mL) and brine (20 mL), dried (Na₂SO₄), filtered, and concentrated. Purification by silica chromatography gave 28G (110 mg, 0.420 mmol, 82% yield) as a white foam. LC-MS Anal. Calc'd for C₁₁H₂₄ClFN₂O₂: 260.07, found [M+H] 261.0.

28H. 2-((2R)-1-(4-(((3,4-trans)-1-(5-Chloro-2-methoxypyridin-4-yl)-3-fluoropiperidin-4-yl)oxy)phenyl)-4-(trifluoromethyl)pyrrolidin-2-yl)acetonitrile: To a solution of 1N (125 mg, 0.460 mmol) and 28G (110 mg, 0.420 mmol) in THF (1.4 mL) was added Ph₃P (155 mg, 0.590 mmol). The reaction vessel was then lowered into a sonication bath and sonicated for several minutes (to allow for mixing) giving a clear and highly viscous solution. While sonicating, DEAD (80 µL, 0.51 mmol) was added dropwise to the reaction mixture and the reaction mixture was sonicated for 6 h. Sat. aq. NaHCO₃ (10 mL) was added slowly to the reaction mixture. The mixture was then extracted with EtOAc (2×10 mL) and the combined organic extracts were washed with water (20 mL) and brine (20 mL), dried (Na₂SO₄), filtered, and concentrated. Purification by silica chromatography gave 28H white foam (116 mg, 0.230 mmol, 54% yield)). LC-MS Anal. Calc'd for C₂₄H₂₅ClF₄N₄O₂: 512.16, found [M+H] 513.0.

Example 28, Isomer 1 and Isomer 2: To a stirred solution of 28H (110 mg, 0.21 mmol) in EtOH (2.1 mL) at rt was added 6 N aq. KOH (710 µL, 4.29 mmol). The reaction mixture was stirred at 120° C. for 2 h. The EtOH was removed by vacuum and 3 N aq. HCl (2 mL) was added at 0° C. and the reaction mixture was warmed to rt. The solvent was evaporated and the residue was dissolved in CH₃CN and filtered. Purification by RP-Prep. HPLC afforded a diastereomeric mixture. The diastereomers were separated by chiral SFC to provide Example 28, Isomer 1 and Isomer 2 as single isomers. Example 28, Isomer 1 (yellow solid, 24 mg). LC-MS Anal. Calc'd for C₂₄H₂₆ClF₄N₃O₄: 531.16, found [M+H] 532.0. ¹H NMR (400 MHz, acetonitrile-d₃) δ 8.03 (s, 1H), 6.98 (d, J=9.0 Hz, 2H), 6.71 (d, J=9.0 Hz, 2H), 6.42 (s, 1H), 4.90-4.66 (m, 1H), 4.50-4.33 (m, 1H), 4.27-4.15 (m, 1H), 3.87 (s, 3H), 3.74 (dddd, J=16.4, 12.4, 4.1, 1.5 Hz, 1H), 3.58-3.48 (m, 2H), 3.43 (dddd, J=10.3, 8.1, 4.0, 2.0 Hz, 1H), 3.25-3.12 (m, 2H), 3.03 (ddd, J=12.4, 9.4, 3.0 Hz, 1H), 2.81 (dd, J=15.8, 3.0 Hz, 1H), 2.63 (ddd, J=13.4, 9.3, 7.7 Hz, 1H), 2.30-2.19 (m, 2H), 2.06-1.99 (m, 1H), 1.90-1.79 (m, 1H). HPLC: RT=10.0 min, HI: 100%. hGPR40 EC₅₀=330 nM. Example 28, Isomer 2 (yellow solid, 24 mg). LC-MS Anal. Calc'd for C₂₄H₂₆ClF₄N₃O₄: 531.16, found [M+H] 532.0. ¹H NMR (400 MHz, acetonitrile-d₃) δ 8.03 (s, 1H), 6.98 (d, J=9.0 Hz, 2H), 6.71 (d, J=9.0 Hz, 2H), 6.42 (s, 1H), 4.88-4.68 (m, 1H), 4.48-4.35 (m, 1H), 4.25-4.14 (m, 1H), 3.89-3.85 (m, 3H), 3.79-3.67 (m, 1H), 3.60-3.49 (m, 2H), 3.47-3.39 (m, 1H), 3.18 (dt, J=12.5, 7.4 Hz, 2H), 3.04 (ddd, J=12.4, 9.4, 3.0 Hz, 1H), 2.81 (dd, J=15.8, 3.0 Hz, 1H), 2.63 (ddd, J=13.3, 9.3, 7.5 Hz, 1H), 2.31-2.20 (m, 2H), 2.05-1.99 (m, 1H), 1.89-1.80 (m, 1H). HPLC: RT=10.0 min, HI: 100%. hGPR40 EC₅₀=210 nM.

EXAMPLE 29

2-((2R,4R)-1-(4-((1-(4-Ethyl-2-fluoro-5-methoxyphenyl)piperidin-4-yl)oxy)phenyl)-4-methoxypyrrolidin-2-yl)acetic acid, TFA

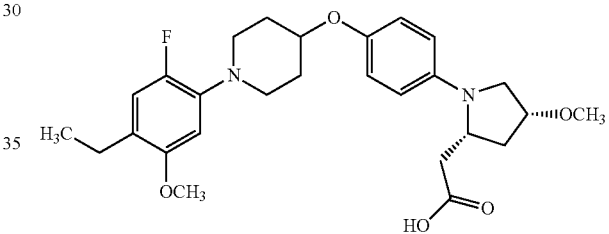

Example 29 (white solid, 6 mg) was prepared from methylmagnesium bromide and 23D following the procedure of Example 23. LC-MS Anal. Calc'd for C₂₇H₃₅FN₂O₅: 486.60, found [M+H] 487.1. ¹H NMR (400 MHz, CDCl₃) δ 7.06 (d, J=11.9 Hz, 2H), 6.94 (d, J=8.8 Hz, 2H), 6.79 (d, J=8.8 Hz, 2H), 4.57 (br. s, 1H), 4.15 (br. s, 2H), 3.92 (s, 4H), 3.63 (d, J=10.6 Hz, 6H), 3.50-3.29 (m, 6H), 2.99-2.62 (m, 4H), 2.58-2.42 (m, 2H), 2.41-2.26 (m, 1H), 2.19 (d, J=15.2 Hz, 3H), 1.29 (t, J=1.0 Hz, 3H). Analytical HPLC: 7.44 min, HI: 96.4%. hGPR40 EC₅₀=1100 nM.

EXAMPLE 30

2-((2R,4R)-1-(4-((1-(2-Fluoro-4-isobutyl-5-methoxyphenyl)piperidin-4-yl)oxy)phenyl)-4-methoxypyrrolidin-2-yl)acetic acid, TFA

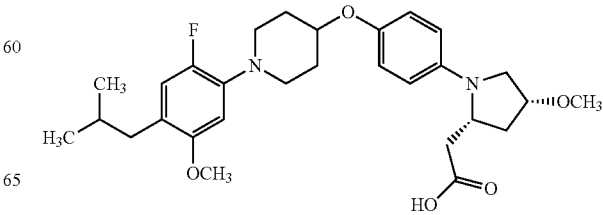

Example 30 (white solid, 6 mg) was prepared from isopropylmagnesium chloride and 23D following the procedure of Example 23. LC-MS Anal. Calc'd for $C_{29}H_{39}FN_2O_5$: 514.60, found [M+H] 515.0. $^1$H NMR (400 MHz, CDCl$_3$) δ 7.17-7.08 (m, 1H), 7.07-7.00 (m, 1H), 6.96 (br. s, 4H), 4.59 (br. s, 1H), 4.19 (br. s, 2H), 3.93 (s, 3H), 3.71 (br. s, 3H), 3.55-3.44 (m, J=12.1 Hz, 1H), 3.39 (s, 5H), 2.94-2.86 (m, 1H), 2.80 (d, J=8.6 Hz, 1H), 2.67 (d, J=7.3 Hz, 2H), 2.49 (d, J=11.4 Hz, 3H), 2.27-2.11 (m, J=8.8 Hz, 3H), 2.06-1.94 (m, 1H), 0.97 (d, J=6.6 Hz, 6H). Analytical HPLC: RT=9.2 min, HI: 99%. hGPR40 EC$_{50}$=840 nM.

EXAMPLE 31

2-((2R,4R)-1-(4-((1-(2-Ethyl-6-fluoro-3-methoxyphenyl)piperidin-4-yl)oxy)phenyl)-4-methoxypyrrolidin-2-yl)acetic acid, TFA

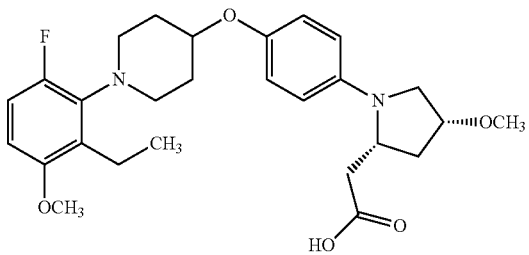 [SMILES: CCc1c(OC)ccc(F)c1N1CCC(Oc2ccc(N3C[C@H](OC)C[C@@H]3CC(=O)O)cc2)CC1]

Example 31 (off-white solid, 14 mg) was prepared from methylmagnesium bromide following the procedure of Example 32. LC-MS Anal. Calc'd for $C_{27}H_{35}FN_2O_5$: 486.60, found [M+H] 486.9. $^1$H NMR (400 MHz, CDCl$_3$) δ 7.20-7.04 (m, 5H), 7.04-6.94 (m, J=8.8 Hz, 3H), 4.34-4.07 (m, 3H), 4.00-3.84 (m, 2H), 3.81 (s, 4H), 3.69-3.54 (m, J=6.1 Hz, 1H), 3.37 (s, 4H), 3.32-2.96 (m, 4H), 2.96-2.59 (m, 6H), 2.28-2.07 (m, 3H), 1.88 (br. s, 1H), 1.11 (t, J=7.5 Hz, 3H). Analytical HPLC: RT=9.3 min, HI: 99%. hGPR40 EC$_{50}$=1100 nM.

EXAMPLE 32

2-((2R,4R)-1-(4-((1-(2-Benzyl-6-fluoro-3-methoxyphenyl)piperidin-4-yl)oxy)phenyl)-4-methoxypyrrolidin-2-yl)acetic acid, TFA

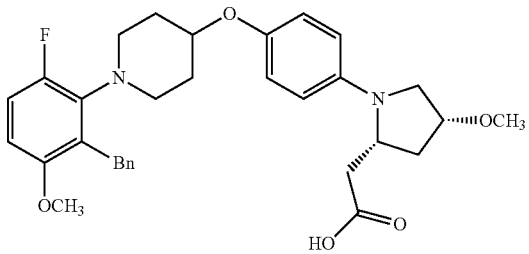 [SMILES: COc1ccc(F)c(N2CCC(Oc3ccc(N4C[C@H](OC)C[C@@H]4CC(=O)O)cc3)CC2)c1Cc1ccccc1]

Example 32 (white solid, 5 mg) was prepared from 2,3-difluoro-6-methoxybenzaldehyde following the procedure of Example 23. LC-MS Anal. Calc'd for $C_{32}H_{37}FN_2O_5$: 548.60, found [M+H] 548.9. $^1$H NMR (400 MHz, CDCl$_3$) δ 7.29 (d, J=8.6 Hz, 3H), 7.23-7.16 (m, 4H), 7.15-7.09 (m, J=6.8, 6.8 Hz, 2H), 6.99 (d, J=8.8 Hz, 4H), 6.95-6.85 (m, 2H), 6.75-6.65 (m, 1H), 4.30-4.11 (m, 5H), 3.93 (d, J=11.9 Hz, 1H), 3.79 (s, 3H), 3.67-3.59 (m, J=12.1, 6.1 Hz, 1H), 3.36 (s, 3H), 3.18 (br. s, 1H), 2.91-2.81 (m, J=7.1 Hz, 3H), 2.80-2.67 (m, J=14.4, 7.2, 7.2 Hz, 2H), 2.24-2.12 (m, J=13.8, 7.7, 2.8 Hz, 1H), 2.10-1.83 (m, 3H), 1.74 (br. s, 2H). Analytical HPLC: RT=9.6 min, HI: 98%. hGPR40 EC$_{50}$=1700 nM.

EXAMPLE 33

Isomer 1 and Isomer 2

2-((2R,4R)-1-(4-(((3,4-trans)-1-(5-Ethoxy-2-fluorophenyl)-3-ethylpiperidin-4-yl)oxy)phenyl)-4-(trifluoromethyl)pyrrolidin-2-yl)acetic acid, HCl

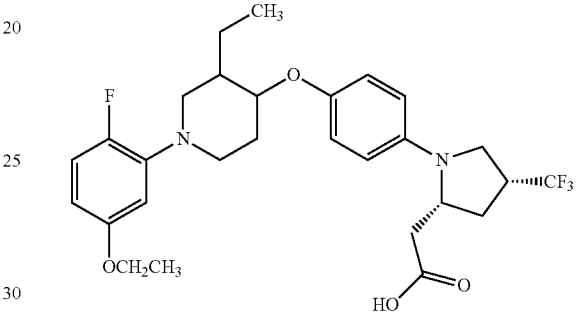

33A. Ethyl 1-benzyl-3-ethyl-4-oxopiperidine-3-carboxylate: To a solution of ethyl 1-benzyl-4-oxopiperidine-3-carboxylate (1.00 g, 3.83 mmol) in CH$_3$CN (9.6 mL) was added a 1 M solution of KOtBu (5.7 mL, 5.7 mmol) in THF and iodoethane (0.031 mL, 0.38 mmol). The reaction mixture was stirred at 60° C. overnight. The reaction mixture was poured into sat. aq. NH$_4$Cl and extracted with EtOAc. The organic layer was washed with brine, dried (Na$_2$SO$_4$), and concentrated to give 33A (0.900 g, 3.11 mmol, 81% yield) as a colorless oil. LC-MS Anal. Calc'd for $C_{17}H_{23}NO_3$: 289.1, found [M+H] 290.0.

33B. 1-Benzyl-3-ethylpiperidin-4-one: To a sealed vial with 33A (800 mg, 2.76 mmol) was added 6 N aq. HCl (8.0 mL, 48 mmol). The reaction mixture was heated to 100° C. for 16 h. The reaction mixture was poured into a solution of 5 N aq. NaOH in ice water and additional 5 N aq. NaOH was added until pH ~8 and the product was extracted with EtOAc. The organic layer was washed with brine, dried (Na$_2$SO$_4$), and concentrated. The crude product was purified by silica chromatography to give a colorless oil as 33B (0.31 g, 1.4 mmol, 52% yield). LC-MS Anal. Calc'd for $C_{14}H_{19}NO$: 217.1, found [M+H] 218.0. $^1$H NMR (400 MHz, CDCl$_3$) δ 7.27 (s, 5H), 3.64-3.31 (m, 2H), 3.02-2.70 (m, 2H), 2.53-2.39 (m, 2H), 2.34-2.25 (m, 2H), 2.18 (dd, J=11.0, 9.5 Hz, 1H), 1.39-0.98 (m, 2H), 0.79 (t, J=7.5 Hz, 3H).

33C. 1-Benzyl-3-ethyl-1-methyl-4-oxopiperidin-1-ium, iodide salt: To a solution of 33B (0.46 g, 2.1 mmol) in acetone (2.1 mL) was added MeI (0.16 mL, 2.6 mmol). The reaction mixture was stirred at rt overnight. The solvents were removed and the crude material was concentrated give a light yellow foam as 33C (0.58 g, 1.6 mmol, 76% yield).

33D. 1-(5-Ethoxy-2-fluorophenyl)-3-ethylpiperidin-4-one: To a solution of 43E (100 mg, 0.644 mmol) in EtOH (1.3 mL) and water (0.6 mL) was added 33C (301 mg, 0.838 mmol) and K$_2$CO$_3$ (13 mg, 0.097 mmol). The reaction mixture was heated to 100° C. overnight. The reaction mixture was poured into water and extracted with $CH_2Cl_2$. The organic layer was washed with brine, dried over $Na_2SO_4$, and concentrated. The crude product was purified by silica chromatography to give a colorless oil as 33D (155 mg, 0.584 mmol, 91% yield). LC-MS Anal. Calc'd for $C_{15}H_{20}FNO_2$: 265.1, found [M+H] 266.0. $^1$H NMR (500 MHz, $CDCl_3$) δ 6.95 (dd, J=12.1, 8.8 Hz, 1H), 6.53 (dd, J=7.4, 3.0 Hz, 1H), 6.44 (dt, J=8.8, 3.2 Hz, 1H), 4.14-3.88 (m, 2H), 3.74-3.48 (m, 2H), 3.25-3.11 (m, 1H), 2.92 (dd, J=11.8, 9.4 Hz, 1H), 2.69 (dddd, J=14.2, 10.0, 5.8, 1.4 Hz, 1H), 2.60-2.40 (m, 2H), 2.07-1.77 (m, 1H), 1.46-1.29 (m, 4H), 1.04-0.83 (m, 3H).

33E. 1-(5-Ethoxy-2-fluorophenyl)-3-ethylpiperidin-4-ol: To a solution of 33D (0.510 g, 1.92 mmol) in MeOH (7.7 mL) in an ice bath was added $NaBH_4$ (0.084 g, 2.2 mmol). After 1 h, the reaction was quenched with 1.5 M aq. $K_2HPO_4$ and concentrated to remove the MeOH. The mixture was diluted with water and extracted with $CH_2Cl_2$. The organic layer was washed with brine, dried ($Na_2SO_4$), and concentrated. The crude product was dissolved in EtOAc and filtered through a plug of silica gel. The crude product was purified by silica chromatography to separate the diastereomers as colorless oils. (3,4-cis)-33E (180 mg, 0.673 mmol, 35% yield). LC-MS Anal. Calc'd for $C_{15}H_{22}FNO_2$: 267.1, found [M+H] 268.0. $^1$H NMR (400 MHz, $CDCl_3$) δ 6.90 (dd, J=12.1, 8.8 Hz, 1H), 6.55 (dd, J=7.3, 3.0 Hz, 1H), 6.39 (dt, J=8.8, 3.2 Hz, 1H), 4.08-3.85 (m, 3H), 3.31-2.96 (m, 3H), 2.82 (t, J=11.0 Hz, 1H), 2.02-1.72 (m, 3H), 1.59-1.33 (m, 5H), 0.99 (t, J=7.5 Hz, 3H). (3,4-trans)-33E (215 mg, 0.804 mmol, 42% yield). LC-MS Anal. Calc'd for $C_{15}H_{22}FNO_2$: 267.1, found [M+H] 268.0$^1$H NMR (400 MHz, $CDCl_3$) δ 6.91 (dd, J=12.4, 8.8 Hz, 1H), 6.51 (dd, J=7.3, 3.0 Hz, 1H), 6.40 (dt, J=8.8, 3.1 Hz, 1H), 3.98 (q, J=6.9 Hz, 2H), 3.59-3.31 (m, 3H), 2.73 (td, J=11.6, 2.8 Hz, 1H), 2.42 (dd, J=11.7, 10.2 Hz, 1H), 2.14-1.94 (m, 1H), 1.91-1.68 (m, 2H), 1.66-1.52 (m, 1H), 1.48-1.13 (m, 4H), 0.98 (t, J=7.6 Hz, 3H).

Example 33, Isomer 1 and Isomer 2 were prepared as single isomers from (3,4-cis)-33E and 10 following the procedure of Example 43. The isomers were separated by chiral SFC. Example 33, Isomer 1 (beige solid, 17.0 mg). LC-MS Anal. Calc'd for $C_{28}H_{34}F_4N_2O_4$: 538.6, found [M+H] 539.0. $^1$H NMR (500 MHz, acetonitrile-$d_3$) δ 7.96-7.67 (m, 3H), 7.30 (dd, J=11.7, 9.2 Hz, 1H), 7.22-7.13 (m, 2H), 7.05 (dt, J=9.1, 3.4 Hz, 1H), 4.51-4.34 (m, 1H), 4.33-4.24 (m, 1H), 4.06 (qd, J=7.0, 1.1 Hz, 2H), 3.95-3.82 (m, 1H), 3.81-3.65 (m, 3H), 3.62-3.53 (m, 1H), 3.50-3.43 (m, 1H), 3.35-3.09 (m, 2H), 2.91 (dd, J=16.8, 8.5 Hz, 1H), 2.81 (d, J=5.8 Hz, 1H), 2.73 (dd, J=16.8, 4.7 Hz, 1H), 2.47-2.37 (m, 2H), 2.31 (dd, J=13.3, 5.9 Hz, 1H), 2.12-1.99 (m, 3H), 1.43-1.25 (m, 3H), 1.13-0.99 (m, 3H). Analytical HPLC RT=12.9 min, HI: 100%. hGPR40 $EC_{50}$=1900 nM. Example 33, Isomer 2 (beige solid, 18.0 mg). LC-MS Anal. Calc'd for $C_{28}H_{34}F_4N_2O_4$: 538.6, found [M+H] 539.0. $^1$H NMR (500 MHz, acetonitrile-$d_3$) δ 7.89-7.67 (m, 3H), 7.30 (dd, J=11.8, 9.4 Hz, 1H), 7.20-7.10 (m, 2H), 7.05 (dt, J=9.2, 3.2 Hz, 1H), 4.51-4.38 (m, 1H), 4.29 (dd, J=13.1, 7.0 Hz, 1H), 4.06 (q, J=7.1 Hz, 2H), 3.88 (dt, J=12.2, 7.8 Hz, 1H), 3.82-3.74 (m, 2H), 3.70 (dd, J=12.0, 2.9 Hz, 1H), 3.62-3.53 (m, 1H), 3.50-3.43 (m, 1H), 3.37-3.10 (m, 2H), 2.91 (dd, J=16.8, 8.3 Hz, 1H), 2.81 (d, J=3.3 Hz, 1H), 2.73 (dd, J=16.8, 4.4 Hz, 1H), 2.46-2.35 (m, 2H), 2.31 (dd, J=13.3, 5.9 Hz, 1H), 2.11-2.00 (m, 3H), 1.43-1.28 (m, 3H), 1.13-1.03 (m, 3H). Analytical HPLC: RT=12.9 min, HI: 100%. hGPR40 $EC_{50}$=430 nM.

EXAMPLE 34

Isomer 1 and Isomer 2

2-((2R,4R)-1-(4-(((3,4-trans)-1-(5-Ethoxy-2-fluorophenyl)-3-isopropylpiperidin-4-yl)oxy)phenyl)-4-(trifluoromethyl)pyrrolidin-2-yl)acetic acid, HCl

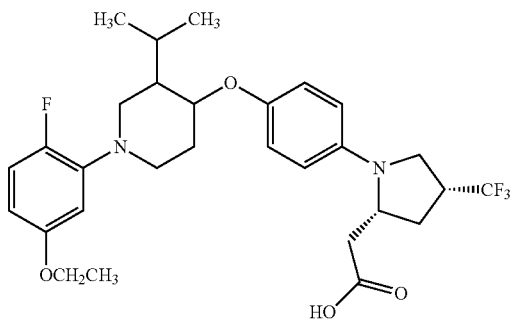 [SMILES: CCOc1ccc(F)c(N2CCC(Oc3ccc(N4C[C@H](C(F)(F)F)C[C@@H]4CC(=O)O)cc3)C(C(C)C)C2)c1]

Example 34, Isomer 1 and Isomer 2 were prepared as single isomers from isopropyl bromide following the procedure of Example 33. Example 34, Isomer 1 (beige solid, 30.0 mg). LC-MS Anal. Calc'd for $C_{29}H_{36}F_4N_2O_4$: 552.3, found [M+H] 553.1. $^1$H NMR (400 MHz, acetonitrile-$d_3$) δ 8.00-7.77 (m, 1H), 7.67-7.49 (m, 2H), 7.29-7.17 (m, 1H), 7.14-7.00 (m, 2H), 6.97-6.76 (m, 1H), 4.65-4.45 (m, 1H), 4.29-4.17 (m, 1H), 4.12-3.97 (m, 3H), 3.74-3.49 (m, 5H), 3.43-3.24 (m, 1H), 2.98-2.90 (m, 1H), 2.88-2.76 (m, 1H), 2.74-2.57 (m, 2H), 2.46-2.30 (m, 2H), 2.28-2.16 (m, 2H), 2.12-2.03 (m, 1H), 1.37 (t, J=6.9 Hz, 3H), 1.04-0.95 (d, J=7.1 Hz, 3H), 0.91-0.82 (d, J=7.1 Hz, 3H). Analytical HPLC: RT=13.2 min, HI: 100%. hGPR40 $EC_{50}$=6800 nM. Example 34, Isomer 2 (beige solid, 26.0 mg). LC-MS Anal. Calc'd for $C_{29}H_{36}F_4N_2O_4$: 552.3, found [M+H] 553.1. $^1$H NMR (400 MHz, acetonitrile-$d_3$) δ 7.89-7.78 (m, 1H), 7.68-7.56 (m, 2H), 7.27-7.17 (m, 1H), 7.11 (d, J=9.3 Hz, 2H), 6.99-6.84 (m, 1H), 4.62-4.47 (m, 1H), 4.29-4.15 (m, 1H), 4.05 (q, J=7.1 Hz, 3H), 3.74-3.53 (m, 5H), 3.45-3.30 (m, 1H), 3.04-2.90 (m, 1H), 2.86 (d, J=4.3 Hz, 1H), 2.77-2.62 (m, 2H), 2.45-2.32 (m, 2H), 2.29-2.17 (m, 2H), 2.12-2.03 (m, 1H), 1.37 (t, J=6.9 Hz, 3H), 0.99 (d, J=7.1 Hz, 3H), 0.89 (d, J=7.1 Hz, 3H). Analytical HPLC: RT=13.2 min, HI: 100%. hGPR40 $EC_{50}$=290 nM.

EXAMPLE 35

Isomer 1 and Isomer 2

2-((2R,4R)-1-(4-(((3,4-trans)-1-(5-Ethoxy-2-fluorophenyl)-3-isobutylpiperidin-4-yl)oxy)phenyl)-4-(trifluoromethyl)pyrrolidin-2-yl)acetic acid, HCl

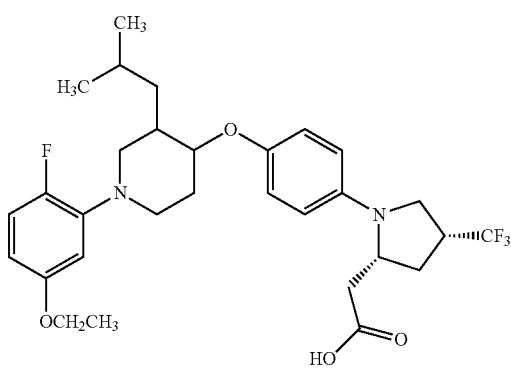 [SMILES: CCOc1ccc(F)c(N2CCC(Oc3ccc(N4C[C@H](C(F)(F)F)C[C@@H]4CC(=O)O)cc3)C(CC(C)C)C2)c1]

Example 35, Isomer 1 and Isomer 2 were prepared as single isomers from isobutyl bromide following the procedure of Example 33. Example 35, Isomer 1 (colorless foam, 2.8 mg). LC-MS Anal. Calc'd for $C_{30}H_{38}F_4N_2O_4$: 566.6, found [M+H] 567.3. $^1$H NMR (400 MHz, acetonitrile-$d_3$) δ 6.99-6.91 (m, 1H), 6.91-6.85 (m, 2H), 6.68 (d, J=9.0 Hz, 2H), 6.52 (dd, J=7.5, 3.1 Hz, 1H), 6.43 (d, J=8.8 Hz, 1H), 4.22-4.07 (m, 1H), 3.98 (q, J=6.9 Hz, 2H), 3.94-3.85 (m, 1H), 3.48 (dd, J=8.4, 1.5 Hz, 2H), 3.45-3.38 (m, 1H), 3.35-3.26 (m, 1H), 3.22-3.06 (m, 1H), 2.88-2.70 (m, 3H), 2.58 (dd, J=12.2, 8.7 Hz, 3H), 2.14-2.05 (m, 2H), 1.71 (br. 2H), 1.52 (m, 1H), 1.33 (t, J=6.9 Hz, 3H), 1.29-1.20 (m, 2H), 0.91 (dd, J=6.5, 3.2 Hz, 6H). Analytical HPLC: RT=13.8 min, HI: 98.8%. hGPR40 $EC_{50}$=1800 nM. Example 35, Isomer 2 (colorless foam, 3.4 mg). LC-MS Anal. Calc'd for $C_{30}H_{38}F_4N_2O_4$: 566.6, found [M+H] 567.3. $^1$H NMR (400 MHz, acetonitrile-$d_3$) δ 6.98-6.92 (m, 1H), 6.92-6.85 (m, 2H), 6.73-6.63 (m, 2H), 6.53 (dd, J=7.5, 3.1 Hz, 1H), 6.43 (d, J=8.8 Hz, 1H), 4.20-4.09 (m, 1H), 3.98 (q, J=7.0 Hz, 2H), 3.95-3.89 (m, 1H), 3.49 (dd, J=8.3, 1.9 Hz, 2H), 3.46-3.38 (m, 1H), 3.36-3.27 (m, 1H), 3.24-3.08 (m, 1H), 2.91-2.80 (m, 1H), 2.79-2.73 (m, 1H), 2.65-2.52 (m, 3H), 1.71 (d, J=5.3 Hz, 3H), 1.53 (d, J=11.4 Hz, 2H), 1.33 (t, J=7.0 Hz, 3H), 1.30-1.22 (m, 2H), 0.91 (dd, J=6.5, 3.2 Hz, 6H). Analytical HPLC: RT=13.73 min, HI: 96.1%. hGPR40 $EC_{50}$=330 nM. hGPR40 IP1 $EC_{50}$=17 nM.

EXAMPLE 36

Isomer 1 and Isomer 2

2-((2R,4R)-1-(4-(((3,4-trans)-3-Benzyl-1-(5-ethoxy-2-fluorophenyl)piperidin-4-yl)oxy)phenyl)-4-(trifluoromethyl)pyrrolidin-2-yl)acetic acid, HCl

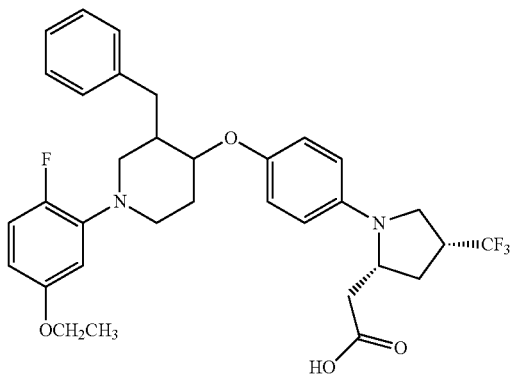 [SMILES: CCOc1ccc(F)c(N2CCC(Oc3ccc(N4C[C@H](C(F)(F)F)C[C@@H]4CC(=O)O)cc3)C(Cc3ccccc3)C2)c1]

Example 36, Isomer 1 and Isomer 2, HCl were prepared from benzyl bromide following the procedure of Example 33. Example 36, Isomer 1 (beige solid, 42 mg). LC-MS Anal. Calc'd for $C_{33}H_{36}F_4N_2O_4$: 600.3 found [M+H] 601.3. $^1$H NMR (400 MHz, acetonitrile-$d_3$) δ 7.39 (br. s, 2H), 7.32-7.25 (m, 2H), 7.25-7.16 (m, 3H), 7.11-7.00 (m, 3H), 6.69 (d, J=9.9 Hz, 1H), 4.36-4.25 (m, 1H), 4.24-4.16 (m, 1H), 4.02-3.93 (m, 2H), 3.92-3.81 (m, 1H), 3.65 (s, 1H), 3.52 (d, J=12.1 Hz, 2H), 3.37 (d, J=12.1 Hz, 2H), 3.18 (d, J=9.9 Hz, 1H), 3.12-3.00 (m, 1H), 2.82 (d, J=4.0 Hz, 2H), 2.74-2.56 (m, 4H), 2.33 (d, J=11.0 Hz, 2H), 2.25-2.06 (m, 2H), 1.33 (t, J=6.9 Hz, 3H). Analytical HPLC: RT=10.9 min, HI: 97.2%. hGPR40 $EC_{50}$=6000 nM. Example 36, Isomer 2 (beige solid, 28 mg). LC-MS Anal. Calc'd for $C_{33}H_{36}F_4N_2O_4$: 600.3 found [M+H] 601.3. $^1$H NMR (400 MHz, acetonitrile-$d_3$) δ 7.34-7.25 (m, 2H), 7.24-7.18 (m, 3H), 7.12 (br. s, 2H), 7.02-6.94 (m, 3H), 6.93-6.81 (m, 1H), 6.56 (d, J=8.8 Hz, 1H), 4.19 (dd, J=8.5, 3.2 Hz, 2H), 3.95 (q, J=6.9 Hz, 2H), 3.72 (d, J=7.9 Hz, 1H), 3.59 (t, J=10.2 Hz, 1H), 3.48-3.25 (m, 3H), 3.22-3.04 (m, 2H), 2.95-2.75 (m, 2H), 2.72-2.54 (m, 3H), 2.48 (br. s, 1H), 2.35-2.19 (m, 2H), 2.16-2.06 (m, 2H), 1.32 (t, J=7.0 Hz, 3H). Analytical HPLC: RT=10.9 min, HI: 95.9%. hGPR40 $EC_{50}$=740 nM.

EXAMPLE 37

2-((2R,4R)-1-(6-((1-(2-Fluoro-5-methoxyphenyl)piperidin-4-yl)(methyl)amino)pyridin-3-yl)-4-methoxypyrrolidin-2-yl)acetic acid, HCl

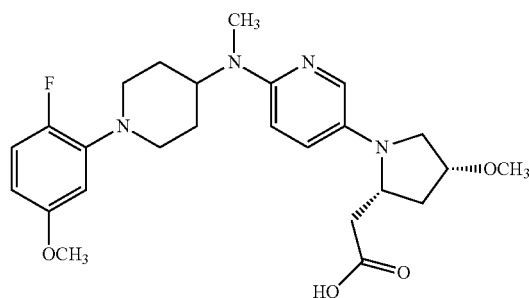 [SMILES: COc1ccc(F)c(N2CCC(N(C)c3ccc(N4C[C@H](OC)C[C@@H]4CC(=O)O)cn3)CC2)c1]

37A. N-(1-(2-Fluoro-5-methoxyphenyl)piperidin-4-yl)-N-methyl-5-nitropyridin-2-amine: To a solution of 9B (0.390 g, 1.64 mmol) and $Cs_2CO_3$ (1.60 g, 4.91 mmol) in DMF (10 mL) was added 2-fluoro-5-nitropyridine (0.465 g, 3.27 mmol). The reaction mixture was heated to 100° C. for 1.5 h. The reaction mixture was cooled to rt, quenched with water, extracted with EtOAc, washed with water and brine, dried ($Na_2SO_4$), and concentrated. The crude product was purified by silica chromatography to give 37A (430 mg, 1.19 mmol, 73% yield) as a colorless oil. LC-MS Anal. Calc'd for $C_{18}H_{21}FN_4O_3$: 360.38 found [M+H] 361.0. $^1$H NMR (400 MHz, $CDCl_3$) δ 9.05 (d, J=2.8 Hz, 1H), 8.21 (dd, J=9.6, 2.8 Hz, 1H), 6.94 (dd, J=11.9, 8.8 Hz, 1H), 6.54 (dd, J=7.3, 3.0 Hz, 1H), 6.48 (d, J=9.3 Hz, 1H), 6.43 (dt, J=8.8, 3.2 Hz, 1H), 5.02-4.78 (m, 1H), 3.77 (s, 3H), 3.64-3.48 (m, 2H), 3.05 (s, 3H), 2.86 (td, J=12.0, 1.8 Hz, 2H), 2.12-1.98 (m, 2H), 1.87-1.75 (m, 2H).

Example 37 (yellow solid, 14 mg) was prepared from 37A following the procedure of Example 17. LC-MS Anal. Calc'd for $C_{25}H_{33}FN_4O_4$: 472.2 found [M+H] 473.0. $^1$H NMR (400 MHz, acetonitrile-$d_3$) δ 8.06 (dd, J=6.1, 3.3 Hz, 1H), 7.70 (dd, J=10.1, 2.5 Hz, 1H), 7.38 (br. s, 1H), 7.30 (dd, J=12.0, 9.2 Hz, 1H), 7.16 (d, J=9.9 Hz, 1H), 7.06 (dt, J=9.1, 3.3 Hz, 1H), 4.84 (br. s, 2H), 4.23-4.04 (m, 4H), 3.81 (s, 3H), 3.72 (d, J=10.6 Hz, 3H), 3.52 (d, J=11.1 Hz, 1H), 3.42-3.29 (m, 3H), 3.20-2.97 (m, 5H), 2.79-2.56 (m, 2H), 2.26 (d, J=5.6 Hz, 1H), 2.15-1.99 (m, 3H). Analytical HPLC: RT=5.80 min, HI: 80.0%. hGPR40 $EC_{50}$=3200 nM.

EXAMPLE 38

2-((2R,4R)-1-(4-(((3,4-trans)-1-(2-Fluoro-5-methoxyphenyl)-3-methylpiperidin-4-yl)oxy)phenyl)-4-isopropoxypyrrolidin-2-yl)acetic acid, TFA

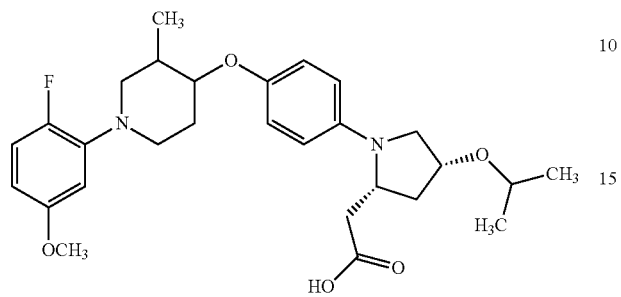

38A. (2R,4R)-1-Benzyl 2-methyl 4-isopropoxypyrrolidine-1,2-dicarboxylate: To a suspension of bismuth (III) bromide (0.022 g, 0.049 mmol) in $CH_3CN$ (2.9 mL) at 0° C. was added triethylsilane (0.12 mL, 0.73 mmol) and the mixture was stirred for 5 min. A solution of (2R,4R)-1-benzyl 2-methyl 4-((tert-butyldimethylsilyl)oxy)pyrrolidine-1,2-dicarboxylate (0.192 g, 0.487 mmol) and acetone (0.18 mL, 2.4 mmol) in $CH_3CN$ (1.5 mL) was added. The reaction mixture was stirred at 0° C. for 1 h and then warmed to rt. The reaction was quenched with 1.5 M aq. $K_2HPO_4$, diluted with EtOAc, and filtered. The layers were separated and the aqueous layer was extracted with EtOAc. The combined organic layers were washed with brine, dried ($MgSO_4$), and concentrated. The crude product was purified by silica chromatography to provide 38A (0.111 g, 0.346 mmol, 71% yield). LC-MS Anal. Calc'd for $C_{17}H_{23}NO_5$: 321.37 found [M+H] 322.0.

38B. (2R,4R)-Benzyl 2-(hydroxymethyl)-4-isopropoxypyrrolidine-1-carboxylate: To a solution of 38A (0.197 g, 0.614 mmol) in THF (3.1 mL) at 0° C. was added a 2 M solution of $LiBH_4$ (0.31 mL, 0.61 mmol) in THF. The reaction mixture was warmed to rt and stirred for 1 h. The reaction was quenched with sat. aq. $NH_4Cl$ and diluted with EtOAc/water. The layers were separated and the organic layer was washed with brine, dried ($MgSO_4$), and concentrated. The crude product was purified by silica chromatography to provide 38B (0.143 g, 0.488 mmol, 79% yield) as a colorless oil. LC-MS Anal. Calc'd for $C_{16}H_{23}NO_4$: 293.36 found [M+H] 294.0.

38C. ((2R,4R)-4-Isopropoxypyrrolidin-2-yl)methanol: To a solution of 38B (0.143 g, 0.488 mmol) in MeOH (4.9 mL) was added 10% Pd/C (0.026 g, 0.049 mmol). The reaction vessel was purged with argon (3×) and then with $H_2$ (3×) and stirred under $H_2$ (1 atm) for 4 h. The reaction mixture was filtered and concentrated to provide 38C as a colorless oil. LC-MS Anal. Calc'd for $C_8H_{17}NO_2$: 159.23 found [M+H] 160.0. $^1$H NMR (500 MHz, $CDCl_3$) δ 4.07 (ddt, J=6.1, 4.7, 3.0 Hz, 1H), 3.68-3.58 (m, 2H), 3.57-3.49 (m, 1H), 3.39 (td, J=9.1, 5.2 Hz, 1H), 3.30 (br. s, 2H), 3.05-2.97 (m, 1H), 2.96-2.87 (m, 1H), 2.09 (ddd, J=13.8, 8.8, 6.1 Hz, 1H), 1.61-1.51 (m, 1H), 1.15 (d, J=6.3 Hz, 6H).

Example 38 was prepared as a single isomer from 38C following the procedure of Example 18. LC-MS Anal. Calc'd for $C_{28}H_{37}FN_2O_5$: 500.60 found [M+H] 501.3. $^1$H NMR (400 MHz, acetonitrile-$d_3$) δ 7.03-6.89 (m, 3H), 6.83 (br. s, 2H), 6.58 (dd, J=7.3, 3.0 Hz, 1H), 6.48 (dt, J=8.3, 3.2 Hz, 1H), 4.35 (br. s, 1H), 3.88 (br. s, 1H), 3.78-3.64 (m, 4H), 3.53-3.33 (m, 4H), 2.90-2.80 (m, 1H), 2.80-2.70 (m, 1H), 2.70-2.55 (m, 2H), 2.37 (ddd, J=13.6, 7.8, 5.8 Hz, 1H), 2.20-2.09 (m, 1H), 2.08-1.95 (m, 3H), 1.77-1.63 (m, 1H), 1.14 (dd, J=6.1, 4.8 Hz, 6H), 1.08 (d, J=6.6 Hz, 3H). Analytical HPLC: RT=10.5 min, HI: 98.9%. hGPR40 $EC_{50}$=69 nM. hGPR40 IP1 $EC_{50}$=73 nM.

EXAMPLE 39

2-((2R,4R)-1-(4-(((3R,4R)-1-(5-Ethoxy-2-fluorophenyl)-3-methylpiperidin-4-yl)oxy)phenyl)-4-(trifluoromethyl)pyrrolidin-2-yl)acetic acid, HCl

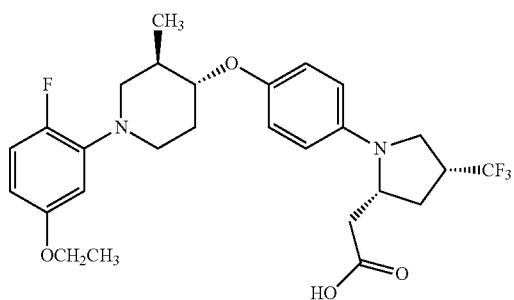 [SMILES: CCOc1ccc(F)c(N2CC[C@@H](Oc3ccc(N4C[C@H](C(F)(F)F)C[C@@H]4CC(=O)O)cc3)[C@H](C)C2)c1]

39A. 4-Fluoro-3-((3,4-trans)-4-(4-iodophenoxy)-3-methylpiperidin-1-yl)phenol, Isomer 2: To a solution of 18A, Isomer 2 (0.244 g, 0.552 mmol) in $CH_2Cl_2$ (1.1 mL) at 0° C. was added $BF_3.SMe_2$ (0.35 mL, 3.3 mmol) dropwise. After 20 min, the reaction mixture was warmed to rt. After stirring for 2.5 h, the reaction mixture was cooled to 0° C. and quenched with MeOH followed by AcCl (0.1 mL), warmed to rt, stirred for 1 h, and concentrated. The reaction mixture was dissolved in EtOAc and washed with 1.5 M aq. $K_2HPO_4$, brine, dried ($MgSO_4$), and concentrated. The crude product was dissolved in EtOAc and filtered through a plug of silica gel, rinsing with EtOAc to provide 39A, Isomer 2 (0.246 g, 0.577 mmol, 104% yield) as a colorless oil. $^1$H NMR (400 MHz, $CDCl_3$) δ 7.60-7.52 (m, 2H), 6.86 (dd, J=12.1, 8.8 Hz, 1H), 6.75-6.68 (m, 2H), 6.44 (dd, J=7.2, 2.9 Hz, 1H), 6.33 (dt, J=8.7, 3.1 Hz, 1H), 4.55 (br. s, 1H), 3.90 (td, J=9.0, 4.0 Hz, 1H), 3.49-3.36 (m, 2H), 2.81 (td, J=11.5, 2.8 Hz, 1H), 2.57 (dd, J=12.1, 9.6 Hz, 1H), 2.22-2.09 (m, 2H), 1.88-1.75 (m, 1H), 1.08 (d, J=6.6 Hz, 3H).

39B. (3,4-trans)-1-(5-Ethoxy-2-fluorophenyl)-4-(4-iodophenoxy)-3-methylpiperidine, Isomer 2: To a solution of 39A, Isomer 2 (0.280 g, 0.654 mmol) in acetone (1.3 mL) was added iodoethane (0.10 mL, 1.2 mmol) and $K_2CO_3$ (0.226 g, 1.64 mmol). The reaction mixture was refluxed overnight. The reaction mixture was filtered and concentrated. A small amount of $K_2CO_3$ precipitated upon concentration so the material was redissolved in $CH_2Cl_2$, filtered, and concentrated. The crude product was purified by silica chromatography to provide 39B, Isomer 2 (0.273 g, 0.600 mmol, 92% yield) as a colorless oil. LC-MS Anal. Calc'd for $C_{20}H_{23}FINO_2$: 159.23 found [M+H] 455.9. $^1$H NMR (400 MHz, $CDCl_3$) δ 7.59-7.52 (m, 2H), 6.91 (dd, J=12.1, 8.8 Hz, 1H), 6.75-6.68 (m, 2H), 6.50 (dd, J=7.5, 2.9 Hz, 1H), 6.40 (dt, J=8.8, 3.2 Hz, 1H), 3.98 (q, J=6.9 Hz, 2H), 3.89 (td, J=9.0, 4.0 Hz, 1H), 3.49-3.37 (m, 2H), 2.81 (td, J=11.5, 2.8 Hz, 1H), 2.57 (dd, J=12.1, 9.6 Hz, 1H), 2.22-2.08 (m, 2H), 1.88-1.76 (m, 1H), 1.40 (t, J=6.9 Hz, 3H), 1.08 (d, J=6.6 Hz, 3H).

Example 39 (white solid, 32.1 mg) was prepared as a single isomer from 39B, Isomer 2 following the procedure of Example 18. LC-MS Anal. Calc'd for $C_{27}H_{32}F_4N_2O_4$: 524.55 found [M+H] 525.0. $^1$H NMR (400 MHz, acetonitrile-$d_3$) δ 7.51-7.44 (m, 2H), 7.30 (dd, J=6.3, 3.0 Hz, 1H), 7.22 (dd, J=11.6, 9.1 Hz, 1H), 7.15-7.08 (m, 2H), 6.92 (dt, J=9.1, 3.4 Hz, 1H), 4.35-4.24 (m, 2H), 4.09-4.00 (m, 2H), 4.00-3.94 (m, 1H), 3.78 (dd, J=12.1, 10.4 Hz, 1H), 3.72-3.55 (m, 4H), 3.34 (t, J=11.6 Hz, 1H), 2.83-2.71 (m, 3H), 2.59-2.45 (m, 1H), 2.36 (dq, J=14.0, 3.5 Hz, 1H), 2.23-2.07 (m, 2H), 1.35 (t, J=6.9 Hz, 3H), 1.09 (d, J=6.8 Hz, 3H). Analytical HPLC: RT=12.3 min, HI: 96.8%. hGPR40 $EC_{50}$=180 nM. hGPR40 IP1 $EC_{50}$=32 nM.

EXAMPLE 40

2-((R)-1-(4-(((3,4-trans)-1-(5-Ethoxy-2-fluorophenyl)-3-methylpiperidin-4-yl)oxy)phenyl)-4,4-dimethylpyrrolidin-2-yl)acetic acid, HCl

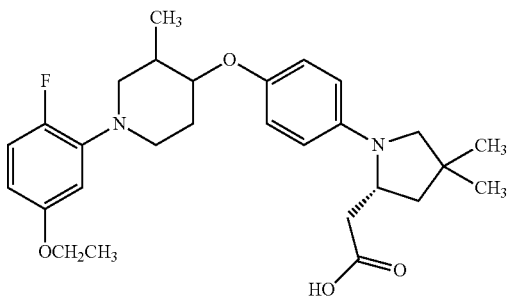 [SMILES: CCOc1ccc(F)c(N2CCC(Oc3ccc(N4CC(C)(C)C[C@@H]4CC(=O)O)cc3)C(C)C2)c1]

40A. (R)-(4,4-Dimethylpyrrolidin-2-yl)methanol: To a solution of LAH (0.207 g, 5.45 mmol) in THF (2.2 mL) at 0° C. was added a solution of (R)-5-(hydroxymethyl)-3,3-dimethylpyrrolidin-2-one (0.156 g, 1.09 mmol) in THF (2.2 mL) dropwise. The flask was rinsed with THF. The reaction mixture was refluxed overnight. The reaction mixture was cooled to 0° C. and carefully quenched with 0.21 mL water, 0.21 mL 15% aq. NaOH, and 0.63 mL water, diluted with EtOAc, and warmed to rt for 30 min. The solids were filtered and the filtrate was concentrated to provide 40A (0.114 g, 0.880 mmol, 81% yield) as a colorless oil. LC-MS Anal. Calc'd for $C_7H_{15}NO$: 129.20 found [M+H] 130.1.

Example 40 (beige solid, 21.3 mg) was prepared as a single isomer from 40A following the procedure from Example 39. LC-MS Anal. Calc'd for $C_{28}H_{37}FN_2O_4$: 484.60 found [M+H] 485.2. $^1$H NMR (400 MHz, acetonitrile-$d_3$) δ 7.78-7.68 (m, 2H), 7.54 (dd, J=6.3, 3.0 Hz, 1H), 7.24 (dd, J=11.7, 9.2 Hz, 1H), 7.19-7.10 (m, 2H), 6.96 (dt, J=9.0, 3.3 Hz, 1H), 4.37 (td, J=9.8, 4.2 Hz, 1H), 4.33-4.24 (m, 1H), 4.05 (q, J=7.1 Hz, 2H), 3.84-3.60 (m, 4H), 3.43 (t, J=11.7 Hz, 1H), 3.29 (d, J=11.9 Hz, 1H), 2.89 (dd, J=16.9, 8.3 Hz, 1H), 2.71 (dd, J=16.7, 4.5 Hz, 1H), 2.68-2.58 (m, 1H), 2.45-2.19 (m, 3H), 2.06 (t, J=12.8 Hz, 1H), 1.42-1.28 (m, 9H), 1.08 (d, J=6.6 Hz, 3H). Analytical HPLC: RT=4.7 min, HI: 98.2%. hGPR40 $EC_{50}$=140 nM. hGPR40 IP1 $EC_{50}$=36 nM.

EXAMPLE 41

2-((2R,4S)-1-(4-(((3,4-trans)-1-(5-Ethoxy-2-fluorophenyl)-3-methylpiperidin-4-yl)oxy)phenyl)-4-phenylpyrrolidin-2-yl)acetic acid, HCl

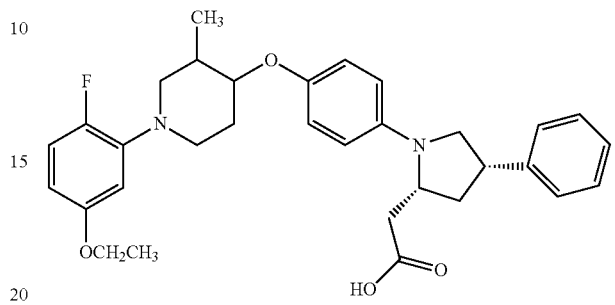

Example 41 (white solid, 24.2 mg) was prepared as a single isomer from 3A following the procedure of Example 39. LC-MS Anal. Calc'd for $C_{32}H_{37}FN_2O_4$: 532.7 found [M+H] 533.1. $^1$H NMR (500 MHz, acetonitrile-$d_3$) δ 7.79 (d, J=8.8 Hz, 2H), 7.53 (d, J=7.4 Hz, 2H), 7.42 (dd, J=6.3, 3.0 Hz, 1H), 7.37 (t, J=7.6 Hz, 2H), 7.31-7.25 (m, 1H), 7.23-7.11 (m, 3H), 6.88 (dt, J=9.1, 3.2 Hz, 1H), 4.40-4.26 (m, 2H), 4.14-3.97 (m, 4H), 3.97-3.85 (m, 1H), 3.75-3.50 (m, 3H), 3.30 (t, J=11.6 Hz, 1H), 3.07 (dd, J=16.8, 8.5 Hz, 1H), 2.89-2.77 (m, 2H), 2.67-2.50 (m, 1H), 2.42-2.25 (m, 2H), 2.24-2.12 (m, 1H), 1.35 (t, J=7.0 Hz, 3H), 1.08 (d, J=6.6 Hz, 3H). Analytical HPLC: RT=10.9 min, HI: 95.7%. hGPR40 $EC_{50}$=230 nM.

EXAMPLE 42

2-((2R,4R)-1-(4-(((2R,4R,6S)-1-(5-Ethoxy-2-fluorophenyl)-2,6-dimethylpiperidin-4-yl)oxy)phenyl)-4-(trifluoromethyl)pyrrolidin-2-yl)acetic acid, HCl

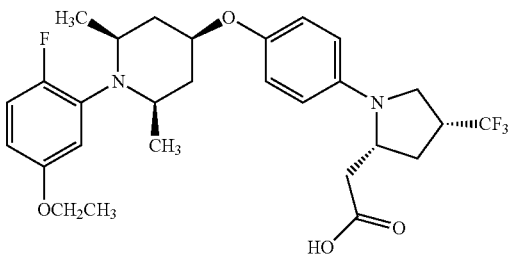 [SMILES: CCOc1ccc(F)c(N2[C@H](C)C[C@H](Oc3ccc(N4C[C@H](C(F)(F)F)C[C@@H]4CC(=O)O)cc3)C[C@@H]2C)c1]

Example 42 was prepared from (2R,4R,6S)-2,6-dimethylpiperidin-4-ol following the procedure of Example 17. LC-MS Anal. Calc'd for $C_{28}H_{34}F_4N_2O_4$: 538.57 found [M+H] 539.0. $^1$H NMR (400 MHz, acetonitrile-$d_3$) δ 7.92 (br. s, 1H), 7.49 (d, J=9.1 Hz, 2H), 7.31 (dd, J=11.7, 9.2 Hz, 1H), 7.18-7.00 (m, 3H), 4.78 (br. s, 1H), 4.36-4.23 (m, 1H), 4.19-4.02 (m, 4H), 3.98 (dd, J=12.0, 7.5 Hz, 1H), 3.76 (dd, J=11.7, 10.2 Hz, 1H), 3.68-3.53 (m, 1H), 2.85-2.68 (m, 3H), 2.49-2.29 (m, 4H), 2.24-2.11 (m, 1H), 1.36 (t, J=6.9 Hz, 3H), 1.19 (d, J=6.3 Hz, 6H). Analytical HPLC: RT=8.0 min, HI: 95.0%. hGPR40 $EC_{50}$=240 nM.

EXAMPLE 43

2-((2R,4R)-4-(Difluoromethoxy)-1-(4-(((3,4-trans)-1-(5-ethoxy-2-fluorophenyl)-3-methylpiperidin-4-yl)oxy)phenyl)pyrrolidin-2-yl)acetic acid, TFA

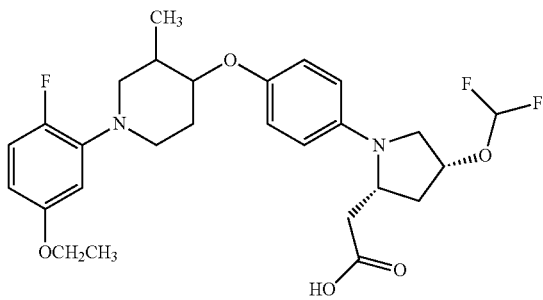 [SMILES: CCOc1ccc(F)c(N2CCC(Oc3ccc(N4C[C@H](OC(F)F)C[C@@H]4CC(=O)O)cc3)C(C)C2)c1]

43A. (2R,4R)-1-Benzyl 2-methyl 4-(difluoromethoxy)pyrrolidine-1,2-dicarboxylate: To a solution of (2R,4R)-1-benzyl 2-methyl 4-hydroxypyrrolidine-1,2-dicarboxylate (2.94 g, 10.5 mmol) and CuI (0.400 g, 2.10 mmol) in $CH_3CN$ (84 mL) at 45° C. was added a solution of 2-(fluorosulfonyl)difluoroacetic acid (2.17 mL, 21.0 mmol) dropwise over 60 min. The reaction mixture was stirred at 45° C. for 60 min and then concentrated. The concentrated reaction mixture was diluted with EtOAc, washed with brine, dried ($MgSO_4$), and concentrated. The crude product was purified by silica chromatography to provide 43A (2.50 g, 7.60 mmol, 72% yield) as a colorless oil. LC-MS Anal. Calc'd for $C_{15}H_{17}F_2NO_5$: 330.0 found [M+H] 329.30. $^1$H NMR (500 MHz, $CDCl_3$) δ 7.41-7.28 (m, 5H), 6.19 (t, J=79.2 Hz, 1H), 5.29-4.99 (m, 2H), 4.84 (dd, J=5.2, 2.8 Hz, 1H), 4.60-4.39 (m, 1H), 3.90-3.79 (m, 1H), 3.78-3.58 (m, 4H), 2.48 (tdd, J=14.5, 9.0, 5.6 Hz, 1H), 2.40-2.31 (m, 1H).

43B. (2R,4R)-Benzyl 4-(difluoromethoxy)-2-(hydroxymethyl)pyrrolidine-1-carboxylate: To a solution of 43A (2.50 g, 7.60 mmol) in THF (38.0 mL) at 0° C. was added a 2 M solution of $LiBH_4$ (7.60 mL, 15.2 mmol) in THF. The reaction mixture was warmed to rt and stirred for 1 h. The reaction was quenched with sat. aq. $NH_4Cl$ and diluted with EtOAc/water. The layers were separated and the organic layer was washed with brine, dried ($MgSO_4$), and concentrated. The crude product was purified by silica chromatography to provide 43B (1.96 g, 6.52 mmol, 86% yield) as a colorless oil. LC-MS Anal. Calc'd for $C_{14}H_{17}F_2NO_4$: 301.29 found [M+H] 302.0.

43C. ((2R,4R)-4-(Difluoromethoxy)pyrrolidin-2-yl)methanol: To a solution of 43B (1.96, 6.52 mmol) in MeOH (65 mL) was added 10% Pd/C (0.173 g, 0.326 mmol). The reaction vessel was purged with argon (3×) and then with $H_2$ (3×) and stirred under $H_2$ (1 atm) overnight. The reaction mixture was filtered and concentrated to provide 43C (1.06 g, 6.32 mmol, 97% yield) as a colorless oil. LC-MS Anal. Calc'd for $C_6H_{11}F_2NO_2$: 167.15 found [M+H] 168.1. $^1$H NMR (500 MHz, $CDCl_3$) δ 6.21 (t, J=74.3 Hz, 1H), 4.75 (ddt, J=7.3, 5.5, 3.7 Hz, 1H), 3.68-3.57 (m, 1H), 3.56-3.43 (m, 1H), 3.38-3.26 (m, 1H), 3.19-3.01 (m, 2H), 2.22 (dt, J=14.3, 7.7 Hz, 1H), 1.69 (ddd, J=14.0, 6.3, 4.0 Hz, 1H).

43D. Methyl 2-((2R,4R)-4-(difluoromethoxy)-1-(4-hydroxyphenyl)pyrrolidin-2-yl)acetate: 43D was prepared from 43C following the procedure of Example 1. LC-MS Anal. Calc'd for $C_{14}H_{17}F_2NO_4$: 301.29 found [M+H] 302.1. $^1$H NMR (500 MHz, $CDCl_3$) δ 6.85-6.70 (m, 2H), 6.52 (d, J=6.3 Hz, 2H), 6.28 (t, J=73.2 Hz, 1H), 4.97 (br. s, 1H), 4.37-4.29 (m, 1H), 4.24-4.13 (m, 1H), 3.71 (s, 3H), 3.60-3.44 (m, 2H), 2.94-2.80 (m, 1H), 2.58 (dd, J=15.3, 10.6 Hz, 1H), 2.40 (ddd, J=14.1, 7.9, 6.1 Hz, 1H), 2.16 (d, J=14.0 Hz, 1H).

43E. 5-Ethoxy-2-fluoroaniline: To a solution of (5-ethoxy-2-fluorophenyl)boronic acid (10.1 g, 55.0 mmol) in MeOH (220 mL) was added 14.8 M aq. $NH_4OH$ (18.6 mL, 275 mmol) and cuprous oxide (1.57 g, 11.0 mmol). The reaction mixture was stirred under air for 7 h. The reaction mixture was concentrated. The crude product was dissolved in EtOAc/hexanes (2:1). The material was filtered through CELITE® and concentrated. The crude material was purified by silica chromatography to provide 43E (4.10 g, 26.4 mmol, 48% yield) as a brown oil. LC-MS Anal. Calc'd for $C_8H_{20}FNO$: 155.17, found [M+H] 156.1. $^1$H NMR (400 MHz, $CDCl_3$) δ 6.86 (dd, J=10.9, 8.8 Hz, 1H), 6.32 (dd, J=7.5, 2.9 Hz, 1H), 6.20 (dt, J=8.8, 3.3 Hz, 1H), 3.94 (q, J=6.9 Hz, 2H), 3.68 (br. s, 2H), 1.37 (t, J=6.9 Hz, 3H).

43F. 1-Benzyl-1,3-dimethyl-4-oxopiperidin-1-ium, iodide salt: To a solution of 1-benzyl-3-methylpiperidin-4-one (14.0 g, 68.9 mmol) in acetone (68.9 mL) at rt was added MeI (8.61 mL, 138 mmol) dropwise. The reaction mixture was concentrated to obtain 43F (24.0 g, 69.5 mmol, 101% yield) as a light yellow foam. LC-MS Anal. Calc'd for $C_{14}H_{20}NO$: 218.15, found [M+H] 219.2.

43G. 1-(5-Ethoxy-2-fluorophenyl)-3-methylpiperidin-4-one: To a solution 43E (7.87 g, 50.7 mmol) in EtOH (103 mL) was added $K_2CO_3$ (1.05 g, 7.61 mmol), 43F (26.3 g, 76.0 mmol), and water (46.6 mL). The reaction mixture was heated to 95° C. overnight. The reaction mixture was cooled to rt and diluted with EtOAc/water. The layers were separated and the aqueous layer was extracted with EtOAc (2×). The combined organic layers were washed with brine, dried ($MgSO_4$), and concentrated. The crude product was purified by silica chromatography to provide 43G (10.12 g, 40.3 mmol, 79% yield) as a colorless oil, which solidified overnight. LC-MS Anal. Calc'd for $C_{14}H_{18}FNO_2$: 251.13, found [M+H] 252.2. $^1$H NMR (400 MHz, $CDCl_3$) δ 6.95 (dd, J=12.1, 8.8 Hz, 1H), 6.52 (dd, J=7.5, 2.9 Hz, 1H), 6.44 (dt, J=8.8, 3.2 Hz, 1H), 3.98 (q, J=7.3 Hz, 2H), 3.75-3.64 (m, 2H), 3.12 (td, J=11.7, 3.5 Hz, 1H), 2.85-2.69 (m, 3H), 2.49 (dt, J=14.1, 3.3 Hz, 1H), 1.40 (t, J=6.9 Hz, 3H), 1.09 (d, J=6.1 Hz, 3H).

43H. (3,4-cis)-1-(5-Ethoxy-2-fluorophenyl)-3-ethylpiperidin-4-ol: To a solution of 43G (4.920 g, 19.58 mmol) in THF (98 mL) at −78° C. was added a 1 M solution of L-Selectride (23.5 mL, 23.5 mmol) in THF. After 1 h, the reaction was quenched with 1 M aq. NaOH (23.5 mL, 23.5 mmol) and warmed to 0° C. 30% aq. $H_2O_2$ (7.40 mL, 72.4 mmol) was added dropwise and the reaction mixture was warmed to rt and stirred for 1 h. The reaction mixture was diluted with EtOAc/water and the layers were separated. The aqueous layer was extracted with EtOAc (2×). The combined organic layers were washed with brine, dried ($MgSO_4$), and concentrated. The crude product was purified by silica chromatography to provide 43H (4.453 g, 17.58 mmol, 90% yield) as a colorless oil. LC-MS Anal. Calc'd for $C_{14}H_{20}FNO_2$: 253.31, found [M+H] 254.0. $^1$H NMR (500 MHz, CDCl$_3$) δ 6.89 (dd, J=12.1, 8.8 Hz, 1H), 6.52 (dd, J=7.3, 2.9 Hz, 1H), 6.37 (dt, J=8.8, 3.2 Hz, 1H), 3.97 (q, J=7.1 Hz, 2H), 3.90 (br. s, 1H), 3.13-3.02 (m, 2H), 3.02-2.95 (m, 1H), 2.84 (dd, J=11.4, 9.8 Hz, 1H), 2.05 (dqt, J=10.1, 6.7, 3.6 Hz, 1H), 2.00-1.91 (m, 1H), 1.91-1.83 (m, 1H), 1.50 (br. s, 1H), 1.38 (t, J=6.9 Hz, 3H), 1.03 (d, J=6.9 Hz, 3H).

43I. (3,4-cis)-1-(5-Ethoxy-2-fluorophenyl)-3-methylpiperidin-4-ol, Isomer 2: 43H (29.2 g, 115 mmol) was purified by chiral SFC. 43I, Isomer 2 (13.5 g, 53.5 mmol, 47% yield) was obtained as a colorless oil after concentration. LC-MS Anal. Calc'd for $C_{14}H_{18}FNO_2$: 251.13, found [M+H] 252.2. $^1$H NMR (400 MHz, CDCl$_3$) δ 6.95 (dd, J=12.1, 8.8 Hz, 1H), 6.52 (dd, J=7.5, 2.9 Hz, 1H), 6.44 (dt, J=8.8, 3.2 Hz, 1H), 3.98 (q, J=7.3 Hz, 2H), 3.75-3.64 (m, 2H), 3.12 (td, J=11.7, 3.5 Hz, 1H), 2.85-2.69 (m, 3H), 2.49 (dt, J=14.1, 3.3 Hz, 1H), 1.40 (t, J=6.9 Hz, 3H), 1.09 (d, J=6.1 Hz, 3H).

43J. Methyl 2-((2R,4R)-4-(difluoromethoxy)-1-(4-(((3,4-trans)-1-(5-ethoxy-2-fluorophenyl)-3-methylpiperidin-4-yl)oxy)phenyl)pyrrolidin-2-yl)acetate, Isomer 2: 43I, Isomer 2 (0.065 g, 0.26 mmol), 43D (0.064 g, 0.21 mmol), and Bu$_3$P (0.084 mL, 0.34 mmol) in toluene (2.1 mL) was added ADDP (0.086 g, 0.34 mmol). The reaction mixture was heated to 60° C. for 75 min. The reaction mixture was poured into hexanes, filtered, and concentrated. The crude product was purified by silica chromatography to provide 43J, Isomer 2 (0.0713 g, 0.133 mmol, 63% yield) as a colorless oil. LC-MS Anal. Calc'd for $C_{28}H_{35}F_3N_2O_5$: 536.58, found [M+H] 537.2. $^1$H NMR (400 MHz, CDCl$_3$) δ 6.96-6.85 (m, 3H), 6.60-6.50 (m, 2H), 6.40 (d, J=8.6 Hz, 1H), 6.48-6.06 (m, 2H), 4.98 (t, J=5.4 Hz, 1H), 4.26-4.16 (m, 1H), 3.98 (q, J=7.0 Hz, 2H), 3.79-3.67 (m, 4H), 3.61-3.48 (m, 2H), 3.48-3.38 (m, 2H), 2.89 (dd, J=15.7, 3.0 Hz, 1H), 2.84-2.70 (m, 1H), 2.66-2.50 (m, 2H), 2.40 (ddd, J=14.2, 8.1, 5.8 Hz, 1H), 2.23-2.08 (m, 3H), 1.83 (d, J=8.8 Hz, 1H), 1.39 (t, J=6.9 Hz, 3H), 1.13 (d, J=6.6 Hz, 3H).

Example 43: To a solution of 43J (0.071 g, 0.13 mmol) in THF (2.4 mL) and water (0.24 mL) was added a 1 M aq. solution of LiOH (1.7 mL, 0.66 mmol) and the reaction mixture was stirred at rt overnight. The reaction mixture was concentrated to remove the THF and hexanes was added. An emulsion formed. The layers were separated as much as possible. Brine was added to the emulsion and the layers separated completely. The combined aqueous and brine layers were acidified to pH 2 with 1 M aq. HCl. The product was extracted with CH$_2$Cl$_2$ (3×) and the combined organic layers were dried (MgSO$_4$) and concentrated to provide the crude product. The crude product was purified by RP-Prep. HPLC to provide Example 43 (0.016 g, 0.025 mmol, 19% yield) as a beige solid as a single isomer. LC-MS Anal. Calc'd for $C_{27}H_{33}F_3N_2O_5$: 522.56, found [M+H] 523.3. $^1$H NMR (400 MHz, acetonitrile-d$_3$) δ 7.00 (dd, J=12.3, 9.0 Hz, 1H), 6.96-6.89 (m, 2H), 6.72 (d, J=9.0 Hz, 2H), 6.68-6.61 (m, 1H), 6.54 (dt, J=8.9, 3.3 Hz, 1H), 4.97-4.90 (m, 1H), 4.16-4.08 (m, 1H), 3.99 (q, J=6.9 Hz, 2H), 3.89 (td, J=9.2, 4.2 Hz, 1H), 3.64-3.55 (m, 1H), 3.55-3.48 (m, 1H), 3.48-3.39 (m, 2H), 3.02-2.91 (m, 1H), 2.84-2.76 (m, 1H), 2.73 (dd, J=12.1, 10.1 Hz, 1H), 2.59-2.45 (m, 2H), 2.23-2.03 (m, 3H), 1.82-1.69 (m, 1H), 1.34 (t, J=6.9 Hz, 3H), 1.09 (d, J=6.6 Hz, 3H). Analytical HPLC: RT=11.7 min, HI: 96.1%. hGPR40 EC$_{50}$=250 nM. hGPR40 IP1 EC$_{50}$=36 nM.

EXAMPLE 44

Isomer 1 and Isomer 2

2-((2R,4R)-1-(4-(((2,3-trans,3,4-trans)-1-(5-Ethoxy-2-fluorophenyl)-2,3-dimethylpiperidin-4-yl)oxy)phenyl)-4-(trifluoromethyl)pyrrolidin-2-yl)acetic acid, HCl

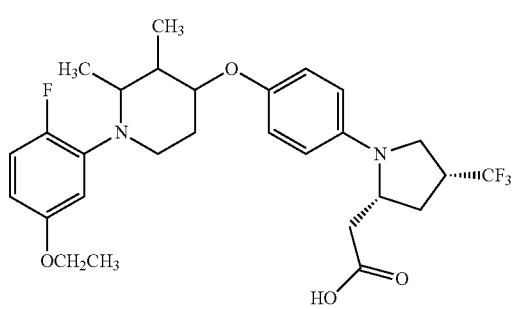 [SMILES: CCOc1ccc(F)c(N2CCC(Oc3ccc(N4C[C@H](C(F)(F)F)C[C@@H]4CC(=O)O)cc3)C(C)C2C)c1]

44A. 1-Benzyl-2,3-dimethylpiperidin-4-one: A mixture of (E)-1-(dimethylamino)-4-methylhex-4-en-3-one, HCl (3.008 g, 15.69 mmol), benzylamine (5.7 mL, 52 mmol), EtOH (11.2 mL), and water (1.6 mL) was stirred overnight at rt. The reaction mixture was diluted with EtOAc and water and the layers were separated. The aqueous layer was extracted with EtOAc and the combined organic layers were washed with brine, dried (MgSO$_4$), and concentrated. The crude product was purified by silica chromatography to provide 44A (2.482 g, 11.42 mmol, 73% yield) as a yellow oil. LC-MS Anal. Calc'd for $C_{14}H_{19}NO$: 217.31, found [M+H] 218.0.

44B. 1-Benzyl-2,3-dimethylpiperidin-4-ol: NaBH$_4$ (0.043 g, 1.1 mmol) was added to a solution of 44B (0.213 g, 0.981 mmol) in MeOH (2 mL) at 0° C. The reaction mixture was warmed to rt and stirred for 1 h. The reaction was quenched with 1.5 M aq. K$_2$HPO$_4$ and concentrated to remove the MeOH. The mixture was diluted with water and CH$_2$Cl$_2$ and the layers were separated. The aqueous layer was extracted with CH$_2$Cl$_2$ and the combined organic layers were washed with brine, dried (MgSO$_4$), and concentrated. The crude product was purified by silica chromatography to isolate two fractions as colorless oils. The first fraction that separated was determined to be (2,3-cis,3,4-cis)-44B (0.100 g, 0.456 mmol, 47% yield). The second fraction was a mixture of inseparable isomers, which was taken on to the next step without further purification (0.0852, 0.388 mmol, 40% yield). LC-MS Anal. Calc'd for $C_{14}H_{21}NO$: 219.32, found [M+H] 220.1.

44C. (2,3-trans,3,4-trans)-1-Benzyl-2,3-dimethylpiperidin-4-yl acetate: To a solution of the mixture of inseparable isomers of 44B (1.61 g, 7.32 mmol) in EtOAc (10 mL) in a pressure vial was added AcCl (0.91 mL, 13 mmol). The reaction mixture was heated to 80° C. for 2 h. The reaction mixture was neutralized with 1.5 M aq. K$_2$HPO$_4$, diluted with EtOAc, and the layers were separated. The organic layer was washed with brine, dried (MgSO$_4$), and concentrated. The material was purified by silica chromatography to provide 44C (0.988 g, 3.78 mmol, 52% yield) as a colorless oil. LC-MS Anal. Calc'd for $C_{16}H_{23}NO_2$: 261.36, found [M+H] 262.1. $^1$H NMR (500 MHz, CDCl$_3$) δ 7.33-7.28 (m, 4H), 7.26-7.20 (m, 1H), 4.45 (td, J=10.3, 4.7 Hz, 1H), 4.01 (d, J=13.8 Hz, 1H), 3.24 (d, J=13.8 Hz, 1H), 2.81

(dt, J=12.4, 3.9 Hz, 1H), 2.23-2.08 (m, 2H), 2.07-1.99 (m, 3H), 1.91-1.81 (m, 1H), 1.64-1.47 (m, 2H), 1.26 (d, J=6.1 Hz, 3H), 0.94 (d, J=6.3 Hz, 3H).

Example 44, Isomer 1 and Isomer 2 were prepared as single isomers from 44C and 1K following the procedure of Example 17. Example 44, Isomer 1 (beige solid, 9.2 mg). LC-MS Anal. Calc'd for $C_{28}H_{34}F_4N_2O_4$: 538.57, found [M+H] 539.0. $^1$H NMR (500 MHz, acetonitrile-$d_3$) δ 14.18 (br. s, 1H), 8.28 (br. s, 1H), 7.58 (br. s, 2H), 7.28 (dd, J=12.1, 9.4 Hz, 1H), 7.10 (d, J=9.1 Hz, 2H), 7.04 (dt, J=9.1, 3.4 Hz, 1H), 4.34 (td, J=10.6, 4.4 Hz, 1H), 4.28-4.16 (m, 1H), 4.11-4.01 (m, 2H), 3.97 (dd, J=11.3, 8.0 Hz, 1H), 3.90-3.73 (m, 2H), 3.72-3.64 (m, 2H), 3.64-3.49 (m, 1H), 3.00-2.88 (m, 1H), 2.87-2.79 (m, 1H), 2.79-2.59 (m, 3H), 2.35-2.17 (m, 2H), 1.38 (t, J=7.0 Hz, 3H), 1.29 (d, J=6.3 Hz, 3H), 1.14 (d, J=6.3 Hz, 3H). Analytical HPLC: RT=4.7 min, HI: 97.1%. hGPR40 $EC_{50}$=500 nM. Example 44, Isomer 2 (beige solid, 9.4 mg). LC-MS Anal. Calc'd for $C_{28}H_{34}F_4N_2O_4$: 538.57, found [M+H] 539.0. $^1$H NMR (500 MHz, acetonitrile-$d_3$) δ 7.94 (br. s, 1H), 7.50 (d, J=8.3 Hz, 2H), 7.30 (dd, J=12.0, 9.2 Hz, 1H), 7.11 (d, J=9.1 Hz, 2H), 7.06 (dt, J=9.3, 3.3 Hz, 1H), 4.35 (td, J=10.6, 4.4 Hz, 1H), 4.30-4.22 (m, 1H), 4.06 (q, J=7.0 Hz, 2H), 3.98 (dd, J=12.0, 7.6 Hz, 1H), 3.91-3.83 (m, 1H), 3.83-3.77 (m, 1H), 3.77-3.67 (m, 2H), 3.63-3.52 (m, 1H), 2.80 (d, J=5.5 Hz, 2H), 2.78-2.70 (m, 1H), 2.59 (br. s, 1H), 2.51 (d, J=12.4 Hz, 1H), 2.33 (dd, J=13.8, 3.9 Hz, 1H), 2.20 (dt, J=12.9, 10.5 Hz, 1H), 1.41-1.34 (m, 3H), 1.26 (d, J=6.3 Hz, 3H), 1.14 (d, J=6.6 Hz, 3H). Analytical HPLC: RT=4.7 min, HI: 96.5%. hGPR40 $EC_{50}$=505 nM.

EXAMPLE 45

2-((2R,4R)-1-(4-((1-(5-Ethoxy-2-fluorophenyl)piperidin-4-yl)oxy)phenyl)-4-(1H-tetrazol-1-yl)pyrrolidin-2-yl)acetic acid, HCl

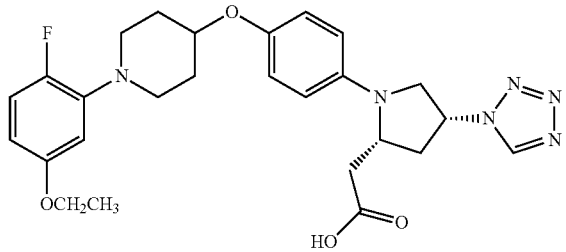 [SMILES: CCOc1ccc(F)c(N2CCC(Oc3ccc(N4C[C@H](n5cnnn5)C[C@@H]4CC(=O)O)cc3)CC2)c1]

45A. 2-((2S,4S)-4-(Benzyloxy)-1-(4-((1-(5-ethoxy-2-fluorophenyl)piperidin-4-yl)oxy)phenyl)pyrrolidin-2-yl)acetonitrile: 45A was prepared from 125A following the procedure of Example 1. LC-MS Anal. Calc'd for $C_{32}H_{36}F_4N_3O_3$: 529.65, found [M+H] 530.3.

45B. 2-((2S,4S)-1-(4-((1-(5-Ethoxy-2-fluorophenyl)piperidin-4-yl)oxy)phenyl)-4-hydroxypyrrolidin-2-yl)acetonitrile: To a solution of 45A (0.145 g, 0.275 mmol) in MeOH (5.5 mL) was added ammonium formate (0.104 g, 1.65 mmol) and 10% Pd/C (0.058 g, 0.055 mmol). The reaction mixture was refluxed overnight. The reaction mixture was filtered and concentrated. The crude product was purified by silica chromatography to provide 45B (0.0756 g, 0.172 mmol, 63% yield) as a colorless oil. LC-MS Anal. Calc'd for $C_{25}H_{30}F_4N_3O_3$: 439.52, found [M+H] 440.2. $^1$H NMR (400 MHz, CDCl$_3$) δ 6.96-6.86 (m, 3H), 6.60-6.50 (m, 3H), 6.40 (dt, J=8.8, 3.2 Hz, 1H), 4.69 (d, J=3.5 Hz, 1H), 4.29 (tt, J=7.4, 3.6 Hz, 1H), 4.21 (ddt, J=9.8, 6.8, 3.4 Hz, 1H), 3.98 (q, J=6.9 Hz, 2H), 3.81 (dd, J=10.1, 4.8 Hz, 1H), 3.39-3.28 (m, 2H), 3.26-3.19 (m, 1H), 2.99-2.88 (m, 2H), 2.74-2.63 (m, 1H), 2.63-2.53 (m, 1H), 2.40-2.31 (m, 1H), 2.30-2.21 (m, 1H), 2.15-2.05 (m, 2H), 2.02-1.88 (m, 2H), 1.82 (d, J=4.2 Hz, 1H), 1.39 (t, J=7.0 Hz, 3H).

45C. 2-((2R,4S)-1-(4-((1-(5-Ethoxy-2-fluorophenyl)piperidin-4-yl)oxy)phenyl)-4-hydroxypyrrolidin-2-yl)acetate: 45B (0.0957 g, 0.218 mmol) was dissolved in EtOH (2.2 mL) and 6 M aq. KOH (0.73 mL, 4.4 mmol) was added. The reaction vessel was sealed and heated to 120° C. for 2 h. The reaction mixture was concentrated to remove the EtOH and 3 N aq. HCl (0.75 mL) was added to acidify the reaction mixture. The aqueous layer was extracted with EtOAc (3×) and the combined organic layers were dried (MgSO$_4$), and concentrated. Only trace amounts of product were isolated. The aqueous layer was lyophilized to provide crude product. AcCl (0.47 mL, 6.5 mmol) was added to EtOH (4.4 mL) dropwise at 0° C. The solution was warmed to rt and stirred for 30 min. The solution was added to the inseparable product/salt mixture and sonicated to help break up the solids. The solution was stirred for 1 h at rt. The reaction mixture was concentrated, redissolved in CH$_2$Cl$_2$, and basified with 1.5 M aq. K$_2$HPO$_4$. The product was extracted with EtOAc (3×) and the combined organic layers were washed with brine, dried (MgSO$_4$), and concentrated. The crude product was purified by silica chromatography to provide 45C (0.0793 g, 0.163 mmol, 75% yield) as a brown oil. LC-MS Anal. Calc'd for $C_{27}H_{35}FN_2O_5$: 486.58, found [M+H] 487.2. $^1$H NMR (500 MHz, CDCl$_3$) δ 6.94-6.87 (m, 3H), 6.60-6.56 (m, 2H), 6.53 (dd, J=7.3, 2.9 Hz, 1H), 6.39 (dt, J=8.8, 3.2 Hz, 1H), 4.60 (sxt, J=4.9 Hz, 1H), 4.31-4.24 (m, 2H), 4.15 (q, J=7.2 Hz, 2H), 3.98 (q, J=7.1 Hz, 2H), 3.65 (dd, J=9.9, 5.2 Hz, 1H), 3.38-3.29 (m, 2H), 3.18 (dd, J=9.6, 3.6 Hz, 1H), 2.93 (ddd, J=11.8, 8.3, 3.0 Hz, 2H), 2.87 (dd, J=15.0, 3.2 Hz, 1H), 2.28-2.20 (m, 1H), 2.19-2.11 (m, 2H), 2.08 (dddd, J=7.6, 5.6, 3.6, 1.7 Hz, 2H), 1.99-1.90 (m, 2H), 1.68 (d, J=5.5 Hz, 1H), 1.39 (t, J=7.0 Hz, 3H), 1.27 (t, J=7.2 Hz, 3H).

45D. Ethyl 2-((2R,4R)-1-(4-((1-(5-ethoxy-2-fluorophenyl)piperidin-4-yl)oxy)phenyl)-4-(1H-tetrazol-1-yl)pyrrolidin-2-yl)acetate: To a solution of 45C (0.047 g, 0.096 mmol), Ph$_3$P (0.038 g, 0.14 mmol), and 1,2,3,4-tetrazole (10.1 mg, 0.144 mmol) in THF (0.96 mL) was added DEAD (0.023 mL, 0.14 mmol). The reaction mixture was stirred overnight at rt. The reaction mixture was concentrated and purified directly by silica chromatography to provide 45D (0.016, 0.029 mmol, 31% yield) as a colorless oil. LC-MS Anal. Calc'd for $C_{28}H_{35}FN_6O_4$: 538.61, found [M+H] 539.3. $^1$H NMR (500 MHz, CDCl$_3$) δ 8.56 (s, 1H), 6.98-6.84 (m, 3H), 6.69-6.61 (m, 2H), 6.53 (dd, J=7.3, 2.9 Hz, 1H), 6.40 (dt, J=8.9, 3.1 Hz, 1H), 5.57-5.48 (m, 1H), 4.40-4.26 (m, 2H), 4.21 (q, J=7.0 Hz, 2H), 4.06 (dd, J=10.5, 5.0 Hz, 1H), 3.98 (q, J=6.9 Hz, 2H), 3.90 (dd, J=10.2, 7.2 Hz, 1H), 3.40-3.27 (m, 2H), 3.06-2.84 (m, 4H), 2.71 (dt, J=14.2, 4.3 Hz, 1H), 2.41 (dd, J=16.1, 10.3 Hz, 1H), 2.16-2.04 (m, 2H), 1.95 (d, J=9.1 Hz, 2H), 1.39 (t, J=7.0 Hz, 3H), 1.28 (t, J=7.2 Hz, 3H).

Example 45 (off-white solid, 9.2 mg) was prepared from 45D following the procedure from Example 1. LC-MS Anal. Calc'd for $C_{26}H_{31}FN_6O_4$: 510.56, found [M+H] 511.2. $^1$H NMR (500 MHz, acetonitrile-$d_3$) δ 8.71 (s, 1H), 7.84 (dd, J=6.2, 2.9 Hz, 1H), 7.71 (d, J=8.8 Hz, 2H), 7.30 (dd, J=11.8, 9.1 Hz, 1H), 7.17 (d, J=9.1 Hz, 2H), 7.04 (dt, J=9.4, 3.3 Hz, 1H), 5.93 (qd, J=δ 0.4, 5.4 Hz, 1H), 4.85 (br. s, 1H), 4.56 (dd, J=12.8, 5.1 Hz, 1H), 4.50-4.41 (m, 1H), 4.22 (dd, J=12.7, 9.1 Hz, 1H), 4.05 (q, J=6.9 Hz, 2H), 3.97-3.86 (m, 2H), 3.72-3.58 (m, 2H), 3.29 (ddd, J=13.8, 7.8, 6.2 Hz, 1H), 3.04-2.90 (m, 2H), 2.87 (dd, J=16.9, 4.5 Hz, 1H), 2.61 (t, J=11.4 Hz, 2H), 2.33 (d, J=11.0 Hz, 2H), 1.37 (t, J=6.9 Hz, 3H). Analytical HPLC: RT=9.9 min, HI: 96.2%. hGPR40 $EC_{50}$=1900 nM.

EXAMPLE 46

2-((2R,4S)-4-(Benzyloxy)-1-(4-((1-(5-ethoxy-2-fluorophenyl)piperidin-4-yl)oxy)phenyl)pyrrolidin-2-yl)acetic acid, HCl

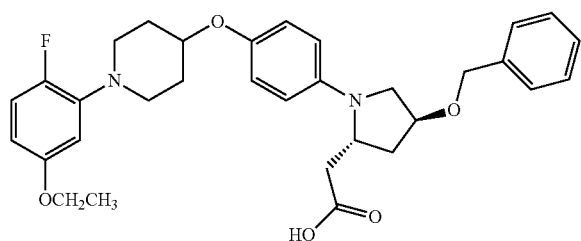 [SMILES: CCOc1ccc(F)c(N2CCC(Oc3ccc(N4C[C@@H](OCc5ccccc5)C[C@@H]4CC(=O)O)cc3)CC2)c1]

Example 46 (beige solid, 29.3 mg) was prepared from 45B following the procedure of Example 1. LC-MS Anal. Calc'd for $C_{32}H_{37}FN_2O_5$: 548.65, found [M+H] 539.0. $^1$H NMR (500 MHz, acetonitrile-$d_3$) δ 7.72 (d, J=9.1 Hz, 2H), 7.45-7.36 (m, 3H), 7.36-7.26 (m, 2H), 7.21 (dd, J=12.2, 9.2 Hz, 1H), 7.17-7.06 (m, 3H), 6.95-6.84 (m, 1H), 4.81-4.73 (m, 1H), 4.67-4.55 (m, 2H), 4.48-4.39 (m, 1H), 4.31-4.21 (m, 2H), 4.02 (q, J=6.9 Hz, 2H), 3.75 (d, J=8.8 Hz, 2H), 3.53-3.42 (m, 3H), 3.07 (dd, J=16.8, 8.8 Hz, 1H), 2.92 (dd, J=16.9, 4.8 Hz, 1H), 2.64 (dd, J=14.0, 5.5 Hz, 1H), 2.53 (br. s, 2H), 2.24 (br. s, 2H), 2.16 (ddd, J=14.0, 12.4, 4.7 Hz, 1H), 1.35 (t, J=6.9 Hz, 3H). Analytical HPLC: RT=10.4 min, HI: 96.1%. hGPR40 $EC_{50}$=650 nM.

EXAMPLE 47

2-((2R)-1-(4-(((3,4-trans)-1-(5-Ethoxy-2-fluorophenyl)-3-methylpiperidin-4-yl)oxy)phenyl)-4-methoxy-4-methylpyrrolidin-2-yl)acetic acid, HCl

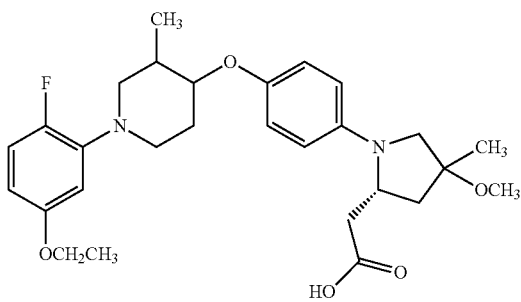 [SMILES: CCOc1ccc(F)c(N2CCC(Oc3ccc(N4CC(C)(OC)C[C@@H]4CC(=O)O)cc3)C(C)C2)c1]

47A. (2R)-tert-Butyl 2-(hydroxymethyl)-4-methoxy-4-methylpyrrolidine-1-carboxylate: To a solution of (R)-1-(tert-butoxycarbonyl)-4-oxopyrrolidine-2-carboxylic acid (1.20 g, 5.23 mmol) in THF (18.7 mL) at −78° C. was added a 1 M solution of methylmagnesium bromide (13.1 mL, 13.1 mmol) in THF dropwise over 30 min. The reaction mixture was stirred at −78° C. for 1 h and then warmed to rt and stirred over the weekend. The reaction was quenched with sat. aq. NH$_4$Cl and acidified with 2 M aq. KH$_2$SO$_4$. The solution was extracted with EtOAc (3×), dried (MgSO$_4$), and concentrated. The product was purified by filtration through silica gel to provide (2R)-1-(tert-butoxycarbonyl)-4-hydroxy-4-methylpyrrolidine-2-carboxylic acid as a brown oil, which was taken forward without further purification. To a solution of (2R)-1-(tert-butoxycarbonyl)-4-hydroxy-4-methylpyrrolidine-2-carboxylic acid in THF (27 mL) at 0° C. was added 60% NaH (0.822 g, 20.5 mmol) in several portions. The reaction mixture was warmed to rt and stirred for 15 min. MeI (2.57 mL, 41.1 mmol) was added in one portion and the reaction mixture was stirred overnight. The reaction was quenched with 1 M aq. NaH$_2$SO$_4$ and acidified to pH 2. The product was extracted with EtOAc (3×), dried (MgSO$_4$), and concentrated to provide (2R)-1-(tert-butoxycarbonyl)-4-methoxy-4-methylpyrrolidine-2-carboxylic acid as a brown oil, which was used without further purification. (2R)-1-(tert-butoxycarbonyl)-4-methoxy-4-methylpyrrolidine-2-carboxylic acid was dissolved in dry THF (26 mL) and cooled to −10° C. 4-Methylmorpholine (0.73 mL, 6.7 mmol) and isobutyl chloroformate (0.87 mL, 6.7 mmol) were then added and the mixture was stirred at −10° C. for 45 min. The mixture was then filtered and added dropwise to a solution of NaBH$_4$ (0.479 g, 12.7 mmol) in water (3.4 mL) cooled to 0° C. The mixture was stirred for 2 h and slowly warmed to rt. The reaction was quenched with sat. NH$_4$Cl and the product was extracted with EtOAc (3×). The combined organic layers were washed with brine, dried (MgSO$_4$), and concentrated. The crude product was purified by silica chromatography to provide 47A (0.657 g, 2.68 mmol, 42% yield) as a colorless oil. LC-MS Anal. Calc'd for $C_{12}H_{23}NO_4$: 245.32, found [M+H] 246.0.

Example 47 (pink solid, 31.5 mg) was prepared as a single isomer from 47A following the procedure of Example 43. LC-MS Anal. Calc'd for $C_{28}H_{37}N_2O_5$: 500.60, found [M+H] 501.4. $^1$H NMR (500 MHz, acetonitrile-$d_3$) δ 7.67 (d, J=9.1 Hz, 2H), 7.51 (dd, J=6.5, 2.9 Hz, 1H), 7.20 (dd, J=12.1, 9.1 Hz, 1H), 7.13 (d, J=9.1 Hz, 2H), 6.89 (dt, J=9.1, 3.3 Hz, 1H), 4.38-4.25 (m, 2H), 4.03 (q, J=6.9 Hz, 2H), 3.97 (d, J=11.8 Hz, 1H), 3.71-3.57 (m, 3H), 3.47 (d, J=12.4 Hz, 1H), 3.33 (t, J=11.8 Hz, 1H), 3.25 (s, 3H), 2.91-2.86 (m, 2H), 2.68-2.58 (m, 1H), 2.53 (dd, J=13.9, 8.4 Hz, 1H), 2.38-2.30 (m, 1H), 2.30-2.18 (m, 2H), 1.48 (s, 3H), 1.35 (t, J=7.0 Hz, 3H), 1.07 (d, J=6.6 Hz, 3H). Analytical HPLC: RT=10.5 min, HI: 96.0%. hGPR40 $EC_{50}$=170 nM. hGPR40 IP1 $EC_{50}$=18 nM.

EXAMPLE 48

Isomer 1 and Isomer 2

2-(1-(4-((1-(2-Fluoro-5-methoxyphenyl)piperidin-4-yl)oxy)phenyl)pyrrolidin-2-yl)acetic acid

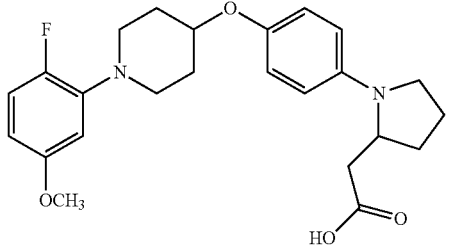 [SMILES: COc1ccc(F)c(N2CCC(Oc3ccc(N4CCCC4CC(=O)O)cc3)CC2)c1]

48A. tert-Butyl 4-(tosyloxy)piperidine-1-carboxylate: To an ice cooled solution of tert-butyl-4-hydroxy-piperdine (3.00 g, 14.9 mmol) in CHCl$_3$ (30 mL), pyridine (3.6 mL, 45 mmol) and TsCl (5.68 g, 29.8 mmol) were added and the reaction mixture was stirred at rt overnight. The reaction mixture was diluted with CHCl$_3$, washed with 1.5 N aq. HCl and brine, dried over Na$_2$SO$_4$, and concentrated. Purification via silica chromatography gave 48A (off-white solid, 2.70 g, 7.61 mmol, 51% yield). LC-MS-Anal. Calc'd for C$_{17}$H$_{25}$NO$_5$S: 355.15, found [M+Na] 377.9. $^1$H NMR (400 MHz, DMSO-d$_6$) δ 7.83 (d, J=7.8 Hz, 2H), 7.49 (d, J=7.8 Hz, 2H), 4.69 (tt, J=8.0, 3.8 Hz, 1H), 3.49 (ddd, J=13.4, 6.5, 4.1 Hz, 2H), 3.15 (t, J=9.4 Hz, 2H), 2.44 (s, 3H), 1.67-1.75 (m, 2H), 1.45-1.54 (m, 2H), 1.38 (s, 9H).

48B. (S)-2-(1-(4-Hydroxyphenyl)pyrrolidin-2-yl)acetonitrile: 48B was prepared from (S)-pyrrolidin-2-ylmethanol following the procedure of Example 1. LC-MS-Anal. Calc'd for C$_{12}$H$_{14}$N$_2$O: 202.25, found [M+H] 203.0. $^1$H NMR (400 MHz, methanol-d$_4$) δ 6.80-6.65 (m, 2H), 6.54 (d, J=8.8 Hz, 2H), 4.07-3.87 (m, 1H), 3.57-3.42 (m, 1H), 3.16-3.05 (m, 1H), 2.75-2.65 (m, 1H), 2.64-2.54 (m, 1H), 2.28-2.11 (m, 2H), 2.09-1.94 (m, 2H).

48C. (S)-tert-Butyl 4-(4-(2-(cyanomethyl)pyrrolidin-1-yl)phenoxy)piperidine-1-carboxylate: To a solution of 48B (1.42 g, 7.03 mmol) in DMF (30 mL), 60% NaH (0.281 g, 7.03 mmol) was added at 0° C. and the reaction mixture was stirred for 10 min. Then 48A (2.50 g, 7.03 mmol) in DMF (10 mL) was added and the reaction mixture was heated to 80° C. for 3 h. The reaction mixture was cooled to 0° C., quenched with sat. aq. NH$_4$Cl solution and extracted with EtOAc. The organic extracts were washed with water and brine, dried over anhydrous Na$_2$SO$_4$, and concentrated. Purified by silica chromatography gave 48C (0.700 g, 1.82 mmol, 25% yield) as a brown solid. LC-MS-Anal. Calc'd for C$_{22}$H$_{31}$N$_3$O$_3$: 385.500, found [M+23] 408.9. $^1$H NMR (400 MHz, DMSO-d$_6$) δ 6.86 (d, J=9.0 Hz, 2H), 6.58 (d, J=9.0 Hz, 2H), 4.28-4.35 (m, 1H), 3.95-4.01 (m, 1H), 3.59-3.67 (m, 2H), 3.39-3.44 (m, 1H), 3.12-3.19 (m, 2H), 3.04-3.09 (m, 1H), 2.66-2.73 (m, 3H), 2.08-2.16 (m, 2H), 1.90-2.01 (m, 2H), 1.80-1.87 (m, 1H), 1.43-1.52 (m, 2H), 1.41 (s, 9H).

48D. (S)-2-(1-(4-(Piperidin-4-yloxy)phenyl)pyrrolidin-2-yl)acetonitrile: To an ice cooled solution of 48C (500 mg, 1.30 mmol) in CH$_2$Cl$_2$ (6 mL) was added TFA (0.30 mL, 3.9 mmol). The reaction mixture was slowly warmed to rt and stirred for 2 h. The reaction mixture was concentrated, dissolved in CH$_2$Cl$_2$, washed with sat. aq. NaHCO$_3$, dried over Na$_2$SO$_4$, and concentrated to give 48D (250 mg, brown oil, 0.841 mmol, 65% yield). LC-MS-Anal. Calc'd for C$_{17}$H$_{23}$N$_3$O: 285.384, found [M+H] 286.9. $^1$H NMR (400 MHz, DMSO-d$_6$) δ 6.80-6.86 (m, 2H), 6.49-6.59 (m, 2H), 4.14-4.22 (m, 1H), 3.93-4.00 (m, 1H), 3.41-3.53 (m, 1H), 2.94-3.09 (m, 2H), 2.57-2.80 (m, 2H), 2.32-2.41 (m, 1H), 2.09-2.22 (m, 2H), 1.76-2.06 (m, 6H), 1.40-1.59 (m, 2H).

48E. (S)-2-(1-(4-((1-(2-Fluoro-5-methoxyphenyl)piperidin-4-yl)oxy)phenyl)pyrrolidin-2-yl)acetonitrile: To a solution of 48D (110 mg, 0.385 mmol) in DMF (5 mL), 2-bromo-1-fluoro-4-methoxybenzene (87 mg, 0.42 mmol), NaOtBu (111 mg, 1.16 mmol), and XPhos (22 mg, 0.039 mmol) were added and the reaction vessel was purged with nitrogen for 20 min. Pd$_2$(dba)$_3$ (35 mg, 0.039 mmol) was added and the reaction mixture was heated to 100° C. in a microwave for 1 h. The reaction mixture was diluted with EtOAc, washed with water and brine, dried over anhydrous Na$_2$SO$_4$, and concentrated. Purification via silica chromatography gave 48E (45 mg, 0.071 mmol, 19% yield) as pale brown oil. LC-MS-Anal. Calc'd for C$_{24}$H$_{28}$FN$_3$O$_2$: 409.22, found [M+H] 410.2. $^1$H NMR (400 MHz, DMSO-d$_6$) δ 7.03 (dd, J=12.6, 9.0 Hz, 1H), 6.89 (d, J=9.0 Hz, 2H), 6.59 (d, J=9.0 Hz, 2H), 6.55 (dd, J=7.5, 3.0 Hz, 1H), 6.45-6.51 (m, 1H), 4.27-4.35 (m, 1H), 3.94-4.02 (m, 1H), 3.72 (s, 3H), 3.39-3.45 (m, 1H), 3.22-3.29 (m, 2H), 3.02-3.11 (m, 1H), 2.90 (ddd, J=11.7, 8.9, 3.0 Hz, 2H), 2.64-2.79 (m, 2H), 2.06-2.19 (m, 2H), 1.89-2.06 (m, 4H), 1.68-1.79 (m, 2H).

Example 48, Isomer 1 and Isomer 2: To a solution of 48E (45 mg, 0.11 mmol) in EtOH (2 mL), was added 6 N aq. KOH (0.92 mL, 5.5 mmol) solution. The reaction vessel was sealed and heated to 100° C. overnight. The EtOH was removed under reduced pressure, the reaction mixture was neutralized with 1.5 N aq. HCl, and the product was extracted with EtOAc (3x). The combined organic layers were washed with water and brine, dried over anhydrous Na$_2$SO$_4$, and concentrated to give the crude product. Purification by RP-Prep. HPLC followed by chiral SFC yielded the products as single isomers. Example 48, Isomer 1 (brown oil, 4.5 mg). LC-MS-Anal. Calc'd for C$_{24}$H$_{29}$FN$_2$O$_4$: 428.21, found [M+H] 429.2. $^1$H NMR (400 MHz, DMSO-d$_6$) δ 7.03 (dd, J=12.6, 8.8 Hz, 1H), 6.87 (d, J=9.0 Hz, 2H), 6.55 (dd, J=7.5, 3.0 Hz, 1H), 6.44-6.52 (m, 3H), 4.21-4.34 (m, 1H), 3.88-4.02 (m, 1H), 3.72 (s, 3H), 3.43-3.50 (m, 1H), 3.14-3.21 (m, 2H), 2.99-3.06 (m, 1H), 2.84-2.94 (m, 2H), 2.54-2.65 (m, 1H), 1.91-2.07 (m, 6H), 1.79-1.87 (m, 1H), 1.69-1.78 (m, 2H). Analytical HPLC: RT=8.6 min, HI: 91.7%. hGPR40 EC$_{50}$=4100 nM. Example 48, Isomer 2 (brown oil, 1.5 mg). LC-MS-Anal. Calc'd for C$_{24}$H$_{29}$FN$_2$O$_4$: 428.21, found [M+H] 429.2. $^1$H NMR (400 MHz, DMSO-d$_6$) δ 7.04 (dd, J=12.6, 8.8 Hz, 1H), 6.89 (d, J=8.8 Hz, 2H), 6.45-6.58 (m, 4H), 4.25-4.33 (m, 1H), 3.92-4.00 (m, 1H), 3.72 (s, 3H), 3.43-3.50 (m, 1H), 3.14-3.21 (m, 2H), 2.99-3.06 (m, 1H), 2.85-2.93 (m, 2H), 2.54-2.65 (m, 1H), 1.88-2.13 (m, 6H), 1.66-1.87 (m, 3H). Analytical HPLC: RT=8.6 min, HI: 91.0%. hGPR40 EC$_{50}$=1400 nM. hGPR40 IP1 EC$_{50}$=2500 nM.

EXAMPLE 49

2-((2R,4R)-1-(6-((1-(2-Fluoro-5-methoxyphenyl)piperidin-4-yl)oxy)pyridin-3-yl)-4-(trifluoromethyl)pyrrolidin-2-yl)acetic acid

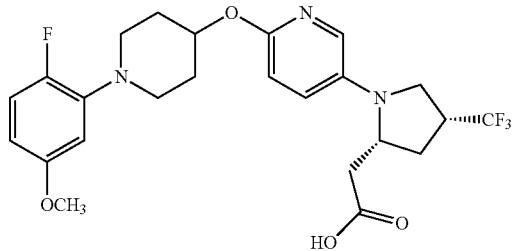 [SMILES: COc1ccc(F)c(N2CCC(Oc3ccc(N4C[C@H](C(F)(F)F)C[C@@H]4CC(=O)O)cn3)CC2)c1]

and

EXAMPLE 50

2-((2S,4R)-1-(6-((1-(2-Fluoro-5-methoxyphenyl)piperidin-4-yl)oxy)pyridin-3-yl)-4-(trifluoromethyl)pyrrolidin-2-yl)acetic acid

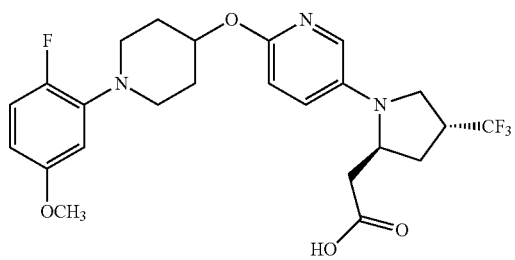 [SMILES: COc1ccc(F)c(N2CCC(Oc3ccc(N4C[C@H](C(F)(F)F)C[C@H]4CC(=O)O)cn3)CC2)c1]

49A. 2-((1-(2-Fluoro-5-methoxyphenyl) piperidin-4-yl)oxy)-5-iodopyridine: To a suspension of 60% NaH (0.128 g, 5.33 mmol) in anhydrous DMF (5 mL) at 0° C. was added a solution of 1A (0.400 g, 1.78 mmol) in anhydrous DMF (5 mL). After stirring at 0° C. for 10 min, 2-chloro-5-iodopyridine (0.850 g, 3.55 mmol) was added and the reaction mixture was heated to 120° C. for 20 h. The reaction was quenched with water and extracted with EtOAc. The combined organic layers were washed with brine, dried over anhydrous $Na_2SO_4$, and concentrated. Purification via silica chromatography gave 49A (0.340 g, 0.794 mmol, 45% yield) as an off-white solid. GC-MS Anal. Calc'd for $C_{17}H_{18}FIN_2O_2$: 428.04, found [M] 428. $^1$H NMR (400 MHz, DMSO-$d_6$) δ 8.38 (dd, J=2.4, 0.6 Hz, 1H), 7.99 (dd, J=8.7, 2.4 Hz, 1H), 7.04 (dd, J=12.6, 8.8 Hz, 1H), 6.73 (dd, J=8.7, 0.6 Hz, 1H), 6.57 (dd, J=7.5, 3.0 Hz, 1H), 6.44-6.49 (m, 1H), 5.01-5.20 (m, 1H), 3.72 (s, 3H), 3.24-3.31 (m, 2H), 2.92 (ddd, J=12.0, 9.4, 3.0 Hz, 2H), 2.05-2.15 (m, 2H), 1.74-1.85 (m, 2H).

Example 49 and Example 50 were prepared from 49A and 1K following the procedure from Example 17. The residue was purified via chiral SFC to give the products as single isomers. Example 49 (brown oil, 12 mg). LC-MS Anal. Calc'd for $C_{24}H_{27}F_4N_3O_4$: 497.19, found [M+H] 498.6. $^1$H NMR (400 MHz, DMSO-$d_6$) δ 12.30 (br. s, 1H), 7.59 (d, J=2.76 Hz, 1H), 7.22 (dd, J=8.9, 3.1 Hz, 1H), 7.03 (dd, J=12.6, 8.8 Hz, 1H), 6.73 (d, J=9.0 Hz, 1H), 6.57 (dd, J=7.4, 2.9 Hz, 1H), 6.45-6.52 (m, 1H), 4.97-5.06 (m, 1H), 4.09-4.17 (m, 1H), 3.72 (s, 3H), 3.36-3.53 (m, 4H), 2.87-2.96 (m, 2H), 2.54-2.66 (m, 3H), 2.15 (dd, J=15.4, 9.9 Hz, 1H), 2.04-2.11 (m, 2H), 1.90 (ddd, J=13.1, 7.1, 5.9 Hz, 1H), 1.72-1.83 (m, 2H). Analytical HPLC: RT=10.6 min, HI: 99.2%. hGPR40 $EC_{50}$=280 nM. Example 50 (brown oil, 3.0 mg). LC-MS Anal. Calc'd for $C_{24}H_{27}F_4N_3O_4$: 497.19, found [M+H] 498.6. $^1$H NMR (400 MHz, DMSO-$d_6$) δ 12.3 (br. s, 1H), 7.53 (d, J=2.8 Hz, 1H), 7.14 (dd, J=9.0, 3.0 Hz, 1H), 7.03 (dd, J=12.6, 8.8 Hz, 1H), 6.73 (d, J=8.8 Hz, 1H), 6.57 (dd, J=70.5, 3.0 Hz, 1H), 6.45-6.51 (m, 1H), 4.93-5.07 (m, 1H), 4.16-4.24 (m, 1H), 3.72 (s, 3H), 3.50-3.61 (m, 2H), 3.19-3.26 (m, 2H), 2.87-2.96 (m, 2H), 2.53-2.57 (m, 2H), 2.15-2.32 (m, 2H), 2.03-2.14 (m, 3H), 1.71-1.83 (m, 2H). Analytical HPLC (25 min gradient, 30 min stop): RT=16.5 min, HI: 98.1%. hGPR40 $EC_{50}$=1500 nM.

EXAMPLE 51

Isomer 1 and Isomer 2

2-((trans)-1-(4-(((3,4-trans)-1-(5-Ethoxy-2-fluorophenyl)-3-methylpiperidin-4-yl)oxy)phenyl)-4-methoxypyrrolidin-2-yl)acetic acid

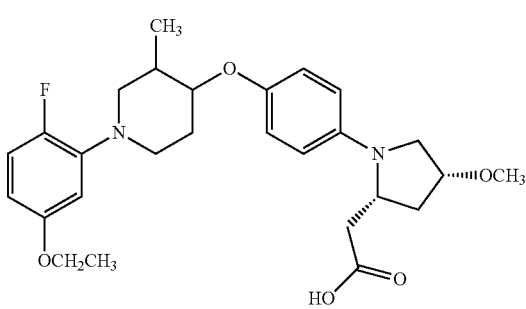 [SMILES: CCOc1ccc(F)c(N2CCC(Oc3ccc(N4C[C@H](OC)C[C@@H]4CC(=O)O)cc3)C(C)C2)c1]

Example 51, Isomer 1 and Isomer 2 were prepared from 43G and 4A following the procedure of Example 17. Example 51, Isomer 1 (brown oil, 12.5 mg). LC-MS Anal. Calc'd for $C_{27}H_{35}FN_2O_5$: 486.25, found [M+H] 487.2. $^1$H NMR (400 MHz, DMSO-$d_6$) δ 12.20 (br. s, 1H), 7.01 (dd, J=12.5, 8.8 Hz, 1H), 6.89 (d, J=9.0 Hz, 2H), 6.48-6.55 (m, 3H), 6.44-6.48 (m, 1H), 4.04-4.09 (m, 1H), 3.97-4.03 (m, 1H), 3.97 (q, J=7.0 Hz, 2H), 3.81 (td, J=8.8, 4.1 Hz, 1H), 3.34-3.41 (m, 2H), 3.28 (s, 3H), 3.25-3.28 (m, 1H), 2.73-2.83 (m, 1H), 2.54-2.70 (m, 3H), 2.39 (dd, J=15.2, 10.4 Hz, 1H), 2.11-2.20 (m, 1H), 1.98-2.10 (m, 2H), 1.92-1.98 (m, 1H), 1.53-1.65 (m, 1H), 1.30 (t, J=6.9 Hz, 3H), 1.05 (d, J=6.5 Hz, 3H). Analytical HPLC (25 min gradient, 30 min stop): RT=19.5 min, HI: 99.4%. hGPR40 $EC_{50}$=1600 nM. Example 51, Isomer 2 (brown oil, 9.5 mg). LC-MS Anal. Calc'd for: $C_{27}H_{35}FN_2O_5$: 486.25, found [M+H] 487.4. $^1$H NMR (400 MHz, DMSO-$d_6$) δ 12.20 (br. s, 1H), 7.01 (dd, J=12.5, 8.8 Hz, 1H), 6.89 (d, J=9.0 Hz, 2H), 6.49-6.54 (m, 3H), 6.44-6.48 (m, 1H), 4.04-4.10 (m, 1H), 3.97-4.03 (m, 1H), 3.97 (q, J=6.9 Hz, 2H), 3.81 (td, J=9.2, 4.0 Hz, 1H), 3.34-3.41 (m, 2H), 3.29 (s, 3H), 3.24-3.28 (m, 1H), 2.73-2.83 (m, 1H), 2.54-2.69 (m, 3H), 2.39 (dd, J=15.2, 10.4 Hz, 1H), 2.11-2.21 (m, 1H), 1.87-2.11 (m, 3H), 1.53-1.66 (m, 1H), 1.30 (t, J=7.0 Hz, 3H), 1.05 (d, J=6.8 Hz, 3H). Analytical HPLC (25 min gradient, 30 min stop): RT=19.6 min, HI: 98.4%. hGPR40 $EC_{50}$=160 nM. hGPR40 IP1 $EC_{50}$=63 nM.

EXAMPLE 52

Isomer 2

2-((2R,4R)-1-(4-(((3,4-cis)-1-(2-Fluoro-5-methoxyphenyl)-3-methylpiperidin-4-yl)oxy)phenyl)-4-methoxypyrrolidin-2-yl)acetic acid

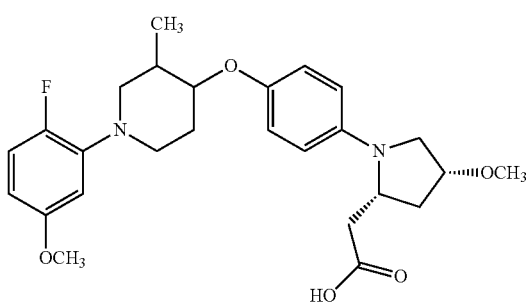 [SMILES: COc1ccc(F)c(N2CCC(Oc3ccc(N4C[C@H](OC)C[C@@H]4CC(=O)O)cc3)C(C)C2)c1]

Example 52, Isomer 2 (brown solid, 8.8 mg) was prepared as a single isomer from (3,4-cis)-17A following the procedure of Example 17. LC-MS-Anal. Calc'd for $C_{26}H_{33}FN_2O_5$: 472.24, found: [M−H] 471.2. $^1$H NMR (400 MHz, DMSO-$d_6$) δ 7.02 (dd, J=12.6, 8.8 Hz, 1H), 6.91 (d, J=9.0 Hz, 2H), 6.45-6.59 (m, 4H), 4.26-4.32 (m, 1H), 4.04-4.09 (m, 1H), 3.95-4.02 (m, 1H), 3.73 (s, 3H), 3.26-3.29 (m, 4H), 2.94-3.10 (m, 5H), 2.60-2.69 (m, 1H), 2.32-2.43 (m, 1H), 2.11-2.20 (m, 2H), 1.98-2.02 (m, 1H), 1.89-1.96 (m, 1H), 1.74-1.82 (m, 1H), 1.05 (d, J=6.8 Hz, 3H). Analytical HPLC: RT=10.8 min, HI: 93.5%. hGPR40 $EC_{50}$=600 nM. hGPR40 IP1 $EC_{50}$=140 nM.

EXAMPLE 53

Isomer 1 and Isomer 2

2-((2S)-4,4-Difluoro-1-(4-((1-(2-fluoro-5-methoxyphenyl)-3-methylpiperidin-4-yl)oxy)phenyl)pyrrolidin-2-yl)acetic acid, HCl

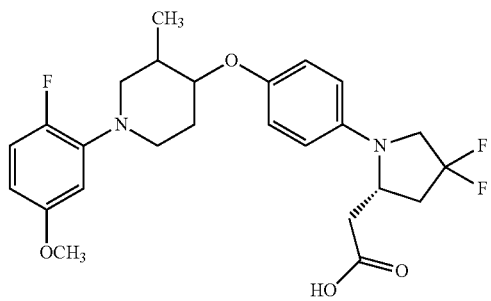 [SMILES: COc1ccc(F)c(N2CCC(Oc3ccc(N4CC(F)(F)C[C@@H]4CC(=O)O)cc3)C(C)C2)c1]

Example 53, Isomer 1 (pink solid, 22.5 mg) was prepared as a single isomer from 5A and 18A, Isomer 1 following the procedure of Example 18. LC-MS Anal. Calc'd for $C_{25}H_{29}F_3N_2O_4$: 478.51, found [M+H] 479.1. $^1$H NMR (500 MHz, acetonitrile-$d_3$) δ 8.05 (dd, J=6.1, 3.0 Hz, 1H), 7.53 (d, J=9.1 Hz, 2H), 7.29 (dd, J=12.0, 9.2 Hz, 1H), 7.11 (d, J=9.1 Hz, 2H), 7.06 (dt, J=9.4, 3.3 Hz, 1H), 4.46-4.38 (m, 1H), 4.33 (td, J=10.1, 4.3 Hz, 1H), 4.20 (q, J=12.4 Hz, 1H), 3.89-3.81 (m, 2H), 3.81 (s, 3H), 3.76-3.69 (m, 1H), 3.69-3.63 (m, 1H), 3.52 (t, J=12.0 Hz, 1H), 3.03-2.88 (m, 3H), 2.88-2.80 (m, 1H), 2.79-2.64 (m, 1H), 2.60-2.45 (m, 1H), 2.36 (dd, J=13.9, 3.4 Hz, 1H), 1.10 (d, J=6.6 Hz, 3H). Analytical HPLC: RT=11.5 min, HI: 94.5%. hGPR40 $EC_{50}$=410 nM. Example 53, Isomer 2 (pink solid, 22.2 mg) was prepared as a single isomer from 5A and 18A, Isomer 2 following the procedure of Example 18. LC-MS Anal. Calc'd for $C_{25}H_{29}F_3N_2O_4$: 478.51, found [M+H] 479.1. $^1$H NMR (500 MHz, acetonitrile-$d_3$) δ 8.05 (br. s, 1H), 7.58 (d, J=8.5 Hz, 2H), 7.29 (dd, J=12.0, 9.2 Hz, 1H), 7.12 (d, J=8.5 Hz, 2H), 7.06 (d, J=8.8 Hz, 1H), 4.47-4.38 (m, 1H), 4.35 (br. s, 1H), 4.23 (q, J=12.2 Hz, 1H), 3.93-3.82 (m, 2H), 3.81-3.77 (m, 3H), 3.77-3.60 (m, 2H), 3.53 (t, J=11.6 Hz, 1H), 3.07-2.89 (m, 3H), 2.85 (dd, J=16.9, 4.0 Hz, 1H), 2.80-2.65 (m, 1H), 2.52 (d, J=10.7 Hz, 1H), 2.36 (d, J=12.4 Hz, 1H), 1.10 (d, J=6.1 Hz, 3H). Analytical HPLC: RT=11.5 min, HI: 97.7%. hGPR40 $EC_{50}$=49 nM. hGPR40 IP1 $EC_{50}$=49 nM.

EXAMPLE 54

Isomer 1 and Isomer 2

2-((2R,4R)-1-(4-((1-(2-Fluoro-5-methoxyphenyl)-3,3-dimethylpiperidin-4-yl)oxy)phenyl)-4-(trifluoromethyl)pyrrolidin-2-yl)acetic acid, diethylammonium salt

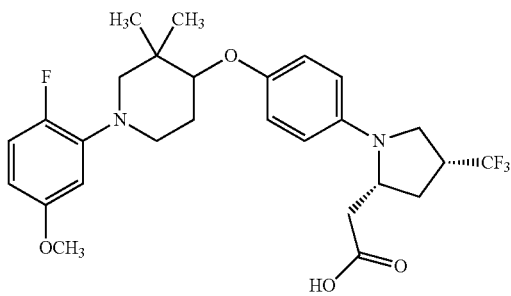 [SMILES: COc1ccc(F)c(N2CCC(Oc3ccc(N4C[C@H](C(F)(F)F)C[C@@H]4CC(=O)O)cc3)C(C)(C)C2)c1]

Example 54, Isomer 1 and Isomer 2 were prepared as single isomers from 3,3-dimethylpiperidin-4-ol and 1K following the procedure of Example 17. Example 54, Isomer 1 (beige solid, 7.9 mg). LC-MS Anal. Calc'd for $C_{27}H_{32}F_4N_2O_4$: 524.55, found [M+H] 525.2. $^1$H NMR (500 MHz, acetonitrile-$d_3$) δ 8.54 (br. s, 1H), 7.78 (d, J=8.8 Hz, 2H), 7.25-7.19 (m, 1H), 7.17-7.08 (m, 3H), 6.75 (dt, J=8.9, 3.1 Hz, 1H), 4.32-4.20 (m, 2H), 4.13-4.03 (m, 1H), 3.78 (s, 3H), 3.75-3.61 (m, 2H), 3.58-3.46 (m, 1H), 3.36 (d, J=12.1 Hz, 1H), 3.30-3.20 (m, 1H), 3.14-3.00 (m, 2H), 2.99-2.89 (m, 4H), 2.84 (dd, J=17.1, 4.4 Hz, 1H), 2.78-2.70 (m, 1H), 2.41-2.24 (m, 2H), 2.12-2.02 (m, 1H), 1.34-1.24 (m, 9H), 1.20 (s, 3H). Analytical HPLC: RT=13.1 min, HI: 95.0%. hGPR40 $EC_{50}$=370 nM. Example 54, Isomer 2 (beige solid, 6.4 mg). LC-MS Anal. Calc'd for $C_{27}H_{32}F_4N_2O_4$: 524.55, found [M+H] 525.2. $^1$H NMR (500 MHz, acetonitrile-$d_3$) δ 8.53 (br. s, 1H), 7.77 (d, J=8.5 Hz, 2H), 7.18-7.09 (m, 4H), 6.72 (dt, J=5.9, 3.1 Hz, 1H), 4.35-4.21 (m, 2H), 4.13-4.03 (m, 1H), 3.80 (s, 3H), 3.77-3.63 (m, 2H), 3.55-3.45 (m, 1H), 3.33 (d, J=12.4 Hz, 1H), 3.22 (ddd, J=11.1, 7.7, 3.4 Hz, 1H), 3.09 (dd, J=16.8, 8.8 Hz, 1H), 3.03-2.93 (m, 5H), 2.87 (dd, J=16.8, 4.4 Hz, 1H), 2.81-2.71 (m, 1H), 2.38-2.24 (m, 2H), 2.12-2.01 (m, 1H), 1.33 (t, J=7.3 Hz, 6H), 1.26 (s, 3H), 1.22 (s, 3H). Analytical HPLC: RT=13.1 min, HI: 96.7%. hGPR40 $EC_{50}$=1100 nM.

EXAMPLE 55

2-((2R,4R)-1-(4-(((3S,4R,5R)-1-(2-Fluoro-5-methoxyphenyl)-3,5-dimethylpiperidin-4-yl)oxy)phenyl)-4-methoxypyrrolidin-2-yl)acetic acid, HCl

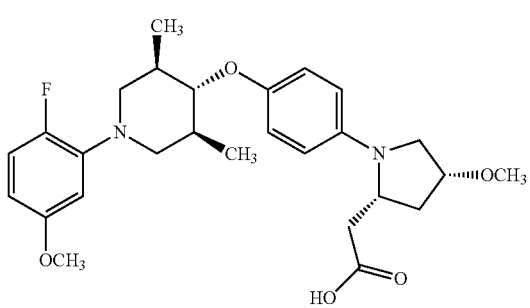 [SMILES: COc1ccc(F)c(N2C[C@@H](C)[C@H](Oc3ccc(N4C[C@H](OC)C[C@@H]4CC(=O)O)cc3)[C@@H](C)C2)c1]

Example 55 (white solid, 8.2 mg) was prepared from (3S,4R,5R)-3,5-dimethylpiperidin-4-ol following the procedure of Example 17. LC-MS Anal. Calc'd for $C_{27}H_{35}FN_2O_5$: 486.58, found [M+H] 487.1. $^1$H NMR (500 MHz, acetonitrile-$d_3$) δ 7.48 (br. s, 2H), 7.22-7.01 (m, 4H), 6.74-6.61 (m, 1H), 4.36-4.25 (m, 1H), 4.16-4.08 (m, 1H), 3.94 (t, J=10.0 Hz, 1H), 3.77 (s, 3H), 3.76-3.73 (m, 1H), 3.59 (dd, J=12.0, 6.5 Hz, 1H), 3.50 (dd, J=11.7, 2.3 Hz, 2H), 3.33 (s, 3H), 2.99-2.81 (m, 4H), 2.73-2.61 (m, 1H), 2.44-2.33 (m, 1H), 2.10 (ddd, J=13.4, 8.2, 5.1 Hz, 2H), 0.99-0.91 (m, 6H). Analytical HPLC: RT=9.7 min, HI: 95.5%. hGPR40 $EC_{50}$=980 nM.

EXAMPLE 56

2-((2R,4R)-1-(4-(((3S,4S,5R)-1-(2-Fluoro-5-methoxyphenyl)-3,5-dimethylpiperidin-4-yl)oxy)phenyl)-4-methoxypyrrolidin-2-yl)acetic acid, HCl

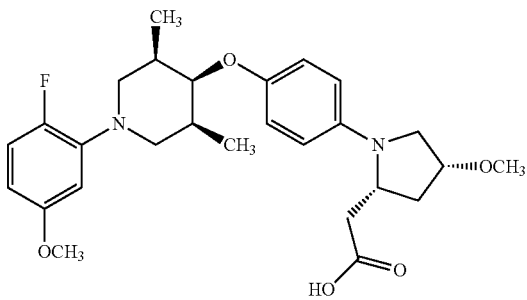 [SMILES: COc1ccc(F)c(N2C[C@@H](C)[C@@H](Oc3ccc(N4C[C@H](OC)C[C@@H]4CC(=O)O)cc3)[C@@H](C)C2)c1]

Example 56 (beige solid, 7.2 mg) was prepared from (3S,4S,5R)-3,5-dimethylpiperidin-4-ol following the procedure of Example 17. LC-MS Anal. Calc'd for $C_{27}H_{35}FN_2O_5$: 486.58, found [M+H] 487.2. $^1$H NMR (500 MHz, acetonitrile-$d_3$) δ 7.80 (br. s, 1H), 7.56 (d, J=8.3 Hz, 2H), 7.27 (dd, J=12.0, 9.2 Hz, 1H), 7.17 (d, J=9.1 Hz, 2H), 6.99 (dt, J=8.9, 3.1 Hz, 1H), 4.65 (s, 1H), 4.37-4.30 (m, 1H), 4.20-4.12 (m, 1H), 3.87-3.82 (m, 1H), 3.81 (s, 3H), 3.66 (dd, J=12.4, 6.9 Hz, 1H), 3.61 (t, J=12.0 Hz, 2H), 3.38 (dd, J=11.7, 3.7 Hz, 2H), 3.33 (s, 3H), 2.93-2.72 (m, 5H), 2.13-2.05 (m, 1H), 0.95 (d, J=6.9 Hz, 6H). Analytical HPLC: RT=8.9 min, HI: 96.6%. hGPR40 $EC_{50}$=2500 nM.

EXAMPLE 57

2-((2R,4R)-4-Methoxy-1-(4-((1-(5-methoxy-2-methylphenyl)piperidin-4-yl)oxy)phenyl)pyrrolidin-2-yl)acetic acid, TFA

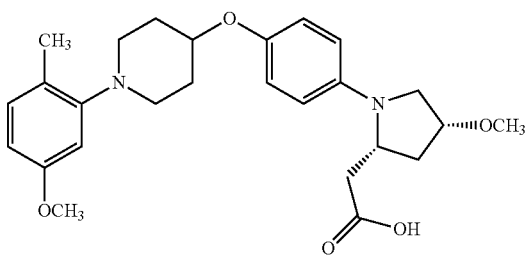 [SMILES: COc1ccc(C)c(N2CCC(Oc3ccc(N4C[C@H](OC)C[C@@H]4CC(=O)O)cc3)CC2)c1]

57A. 1-(5-Methoxy-2-methylphenyl)piperidin-4-one: To a round bottom flask was added 5-methoxy-2-methylaniline (265 mg, 1.93 mmol), $K_2CO_3$ (40 mg, 0.29 mmol), and EtOH (2.5 mL). Then to this mixture at 100° C. was added a slurry of 1-benzyl-1-methyl-4-oxopiperidin-1-ium, iodide salt (960 mg, 2.90 mmol) in water (1 mL) over 20 min. The reaction mixture was stirred at 100° C. for 1 h. The reaction mixture was cooled to rt and extracted with $CH_2Cl_2$ (2×20 mL). The combined organic layers were washed with brine (20 mL), dried ($MgSO_4$), filtered, and concentrated. The residue was purified via silica chromatography to give 57A (120 mg, 0.550 mmol, 28% yield) as a colorless oil. LC-MS Anal. Calc'd for $C_{13}H_{17}NO_2$: 219.1, found [M+H] 220.1. $^1$H NMR (400 MHz, CDCl$_3$) δ 7.15 (d, J=8.1 Hz, 1H), 6.69-6.54 (m, 2H), 3.81 (s, 3H), 3.23 (t, J=6.1 Hz, 4H), 2.63 (t, J=6.1 Hz, 4H), 2.33 (s, 3H).

57B. 1-(5-Methoxy-2-methylphenyl)piperidin-4-ol: To a round bottom flask was added 57A (110 mg, 0.49 mmol), THF (2 mL) and NaBH$_4$ (19 mg, 0.49 mmol). The reaction mixture was stirred at rt for 30 min. The reaction was quenched with water (1 mL). The reaction mixture was then partitioned between EtOAc (30 mL) and water (15 mL). The organic layer was separated, washed with brine (10 mL), dried over MgSO$_4$, filtered, and concentrated. The crude product was purified by silica chromatography to give 57B (95 mg, 0.43 mmol, 87% yield) as a colorless oil. LC-MS Anal. Calc'd for $C_{13}H_{19}NO_2$: 221.3, found [M+H] 222.2. $^1$H NMR (500 MHz, CDCl$_3$) δ 7.09 (d, J=8.3 Hz, 1H), 6.62 (d, J=2.8 Hz, 1H), 6.55 (dd, J=8.3, 2.5 Hz, 1H), 3.86 (d, J=3.3 Hz, 4H), 3.18-3.06 (m, 2H), 2.79-2.65 (m, 2H), 2.27-2.23 (m, 3H), 2.10-1.99 (m, 2H), 1.75 (dtd, J=12.7, 9.3, 3.7 Hz, 2H), 1.48 (br. s, 1H).

57C. 2-((2S,4R)-4-Methoxy-1-(4-(1-(5-methoxy-2-methylphenyl)piperidin-4-yloxy)phenyl)pyrrolidin-2-yl)acetonitrile: To a round bottom flask was added 57B (38.1 mg, 0.172 mmol), 23D (40 mg, 0.17 mmol), toluene (1 mL), Bu$_3$P (0.068 mL, 0.28 mmol), and ADDP (70 mg, 0.28 mmol). The reaction mixture was heated to 50° C. for 2 h. The reaction mixture was treated with heptane and filtered. The filtrate was concentrated and the residue was purified via silica chromatography to give 57C (35 mg, 0.080 mmol, 47% yield) as a colorless oil. LC-MS Anal. Calc'd for $C_{26}H_{33}N_3O_3$: 435.3, found [M+H] 436.1.

Example 57: To a 1-dram vial was added 57C (35 mg, 0.080 mmol), EtOH (0.5 mL), and 6 N aq. KOH (0.27 mL, 1.6 mmol). The reaction mixture was capped and stirred at 130° C. for 2 h. The reaction mixture was treated with 1 N aq. HCl until the pH was <4. Then the solution was extracted with EtOAc (30 mL). The EtOAc solution was washed with water (10 mL) and brine (10 mL), dried over MgSO$_4$, filtered, and concentrated. The residue was purified by RP-Prep. HPLC to give Example 57 (27 mg, 0.055 mmol, 71% yield). LC-MS Anal. Calc'd for $C_{26}H_{34}N_2O_5$: 454.2, found [M+H] 455.1. $^1$H NMR (500 MHz, DMSO-d$_6$) δ 07 (d, J=8.3 Hz, 1H), 6.91 (d, J=9.1 Hz, 2H), 6.60 (br. s, 1H), 6.58-6.48 (m, 3H), 4.36-4.25 (m, 1H), 4.07 (t, J=4.8 Hz, 1H), 4.00 (t, J=9.1 Hz, 1H), 3.72 (s, 3H), 3.40 (d, J=10.7 Hz, 1H), 3.33-3.27 (m, 4H), 3.06 (d, J=5.0 Hz, 2H), 2.78 (d, J=8.3 Hz, 2H), 2.63 (dd, J=15.1, 2.8 Hz, 1H), 2.56 (t, J=5.5 Hz, 1H), 2.41 (dd, J=15.4, 10.5 Hz, 1H), 2.22-2.13 (m, 4H), 2.03 (br. s, 2H), 1.81-1.70 (m, 2H). Analytical HPLC (Acquity): RT=1.2 min, HI: 100%. hGPR40 $EC_{50}$=160 nM. hGPR40 IP1 $EC_{50}$=83 nM.

EXAMPLE 58

2-((2R,4R)-1-(4-(1-(2-Bromo-5-methoxyphenyl)piperidin-4-yloxy)phenyl)-4-methoxypyrrolidin-2-yl)acetic acid, TFA

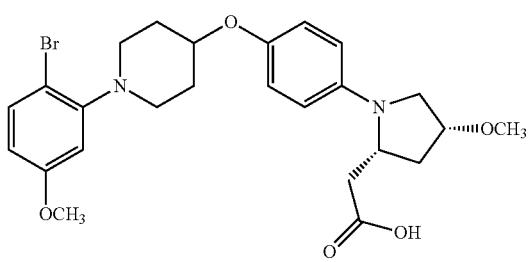 [SMILES: COc1ccc(Br)c(N2CCC(Oc3ccc(N4C[C@H](OC)C[C@@H]4CC(=O)O)cc3)CC2)c1]

Example 58 (5 mg) was prepared from 2-bromo-5-methoxyaniline following the procedure of Example 57. LC-MS Anal. Calc'd for $C_{25}H_{31}BrN_2O_5$: 518.1, found [M+H] 519.2, 521.2. $^1$H NMR (500 MHz, DMSO-d6) δ 7.47 (d, J=8.8 Hz, 1H), 6.91 (d, J=8.5 Hz, 2H), 6.70 (d, J=2.2 Hz, 1H), 6.59 (dd, J=8.7, 2.1 Hz, 1H), 6.53 (d, J=8.5 Hz, 2H), 4.35-4.26 (m, 1H), 4.07 (t, J=4.4 Hz, 1H), 4.00 (t, J=8.7 Hz, 1H), 3.76 (s, 3H), 3.39 (br. s, 1H), 3.32-3.27 (m, 4H), 3.18 (d, J=4.1 Hz, 2H), 2.85 (t, J=8.9 Hz, 2H), 2.68-2.60 (m, 1H), 2.41 (dd, J=15.1, 10.5 Hz, 1H), 2.25-2.13 (m, 1H), 2.02 (d, J=13.2 Hz, 3H), 1.82-1.71 (m, 2H). Analytical HPLC (Acquity): RT=1.7 min, HI: 100%. hGPR40 $EC_{50}$=140 nM.

EXAMPLE 59

2-((2R,4R)-1-(4-(1-(2-Cyclopropyl-5-methoxyphenyl)piperidin-4-yloxy)phenyl)-4-methoxypyrrolidin-2-yl)acetic acid, TFA

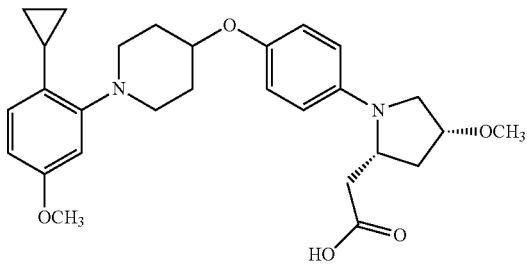 [SMILES: COc1ccc(C2CC2)c(N2CCC(Oc3ccc(N4C[C@H](OC)C[C@@H]4CC(=O)O)cc3)CC2)c1]

59A. 1-Cyclopropyl-4-methoxy-2-nitrobenzene: To a vial was added 1-bromo-4-methoxy-2-nitrobenzene (700 mg, 3.02 mmol), potassium cyclopropyltrifluoroborate (536 mg, 3.62 mmol), $K_3PO_4$ (2.01 mL, 6.03 mmol), $PdCl_2$(dtbpf) (98 mg, 0.15 mmol), and THF (10 mL). The reaction vessel was purged with argon and then sealed and stirred at 90° C. overnight. The reaction mixture was partitioned between water (25 mL) and EtOAc (50 mL). The organic layer was separated, washed with water (25 mL) and brine (25 mL), dried over $MgSO_4$, filtered, and concentrated. The residue was purified via silica chromatography to give 59A (60 mg, 0.31 mmol, 10% yield) as a light brown oil. $^1$H NMR (400 MHz, CDCl$_3$) δ 7.28 (d, J=2.9 Hz, 1H), 7.06-7.02 (m, 1H), 6.98-6.94 (m, 1H), 3.77 (s, 3H), 2.30-2.18 (m, 1H), 0.96-0.87 (m, 2H), 0.58-0.49 (m, 2H).

59B. 2-Cyclopropyl-5-methoxyaniline. To a round bottom 3-neck flask was added 59A (60 mg, 0.31 mmol), EtOH (2 mL), and $PtO_2$ (18 mg, 0.078 mmol). The reaction mixture was stirred under $H_2$ (1 atm) for 1 h. The reaction mixture was filtered through CELITE®. The filtrate was concentrated to give 59B (50 mg, 0.31 mmol, 99% yield) as a light brown oil. LC-MS Anal. Calc'd for $C_{10}H_{13}NO$: 163.1, found [M+H] 164.1.

Example 59 (3 mg) was prepared from 59B following the procedure of Example 57. LC-MS Anal. Calc'd for $C_{28}H_{36}N_2O_5$: 480.3, found [M+H] 481.3. $^1$H NMR (500 MHz, DMSO-d$_6$) δ 6.90 (d, J=8.0 Hz, 2H), 6.70 (d, J=8.3 Hz, 1H), 6.57 (s, 1H), 6.52 (d, J=8.3 Hz, 3H), 4.29 (br. s, 1H), 4.06 (br. s, 1H), 3.99 (t, J=8.8 Hz, 1H), 3.71 (s, 3H), 3.29 (s, 3H), 3.22-3.17 (m, 3H), 2.94-2.71 (m, 3H), 2.58 (br. s, 1H), 2.41-2.28 (m, 1H), 2.13 (td, J=14.6, 6.9 Hz, 2H), 2.07-1.99 (m, 3H), 1.77 (d, J=9.4 Hz, 2H), 0.91 (d, J=8.0 Hz, 2H), 0.60 (d, J=5.0 Hz, 2H). Analytical HPLC (Acquity): RT=1.5 min, HI: 99.2%. hGPR40 $EC_{50}$=290 nM. hGPR40 IP1 $EC_{50}$=38 nM.

EXAMPLE 60

2-((2R,4R)-1-(4-(1-(2-Isopropyl-5-methoxyphenyl)piperidin-4-yloxy)phenyl)-4-methoxypyrrolidin-2-yl)acetic acid, TFA

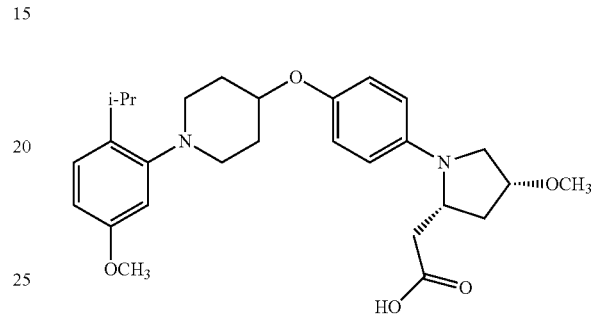

60A. 4-Methoxy-2-nitro-1-(prop-1-en-2-yl)benzene: To a sealed tube was added 1-bromo-4-methoxy-2-nitrobenzene (800 mg, 3.45 mmol), 4,4,5,5-tetramethyl-2-(prop-1-en-2-yl)-1,3,2-dioxaborolane (0.78 mL, 4.1 mmol), $PdCl_2$(dtbpf) (110 mg, 0.17 mmol), 3 M aq. $K_3PO_4$ (2.3 mL, 6.9 mmol), and THF (10 mL). The reaction vessel was purged with argon and then sealed and stirred at 90° C. overnight. The reaction mixture was partitioned between EtOAc (50 mL) and water (20 mL). The organic layer was separated, washed with water (25 mL) and brine (25 mL), dried over $MgSO_4$, filtered, and concentrated. The residue was purified via silica chromatography to give 60A (460 mg, 2.38 mmol, 69% yield) as a light brown oil. $^1$H NMR (400 MHz, CDCl$_3$) δ 7.42-7.37 (m, 1H), 7.25 (d, J=8.6 Hz, 1H), 7.10 (dd, J=8.6, 2.6 Hz, 1H), 5.25-5.10 (m, 1H), 4.93 (t, J=1.1 Hz, 1H), 3.90-3.86 (m, 3H), 2.12-2.03 (m, 3H).

60B. 2-Isopropyl-5-methoxyaniline: To a round bottom 3-neck flask was added 60A (450 mg, 2.33 mmol), EtOH (3 mL) and $PtO_2$ (130 mg, 0.58 mmol). The reaction mixture was stirred under $H_2$ (1 atm) at rt for 2 h. The reaction mixture was filtered through CELITE®. The filtrate was concentrated to give 60B (370 mg, 2.24 mmol, 96% yield). LCMS Anal. Calc'd for $C_{10}H_{15}NO$: 165.1, found [M+H] 166.1.

Example 60 (18 mg) was prepared from 60B following the procedure of Example 57. LC-MS Anal. Calc'd for $C_{28}H_{38}N_2O_5$: 482.3, found [M+H] 483.3. $^1$H NMR (500 MHz, DMSO-d$_6$) δ 7.97 (s, 1H), 7.17 (d, J=9.1 Hz, 1H), 6.92 (d, J=8.8 Hz, 2H), 6.67 (s, 2H), 6.54 (d, J=8.3 Hz, 2H), 4.29 (s, 2H), 4.07 (t, J=5.0 Hz, 1H), 4.00 (t, J=8.7 Hz, 1H), 3.73 (s, 3H), 3.41 (d, J=10.5 Hz, 1H), 3.35-3.24 (m, 5H), 2.99 (s, 2H), 2.81-2.76 (m, 1H), 2.63 (dd, J=15.3, 2.9 Hz, 1H), 2.41 (dd, J=15.1, 10.5 Hz, 1H), 2.22-2.10 (m, 1H), 2.07-1.95 (m, 3H), 1.77 (s, 2H), 1.15 (d, J=6.9 Hz, 6H). Analytical HPLC (Acquity): RT=1.6 min, HI: 97.0%. hGPR40 $EC_{50}$=190 nM.

EXAMPLE 61

2-((2R,4R)-1-(4-(1-(2-Cyclopentyl-5-methoxyphenyl)piperidin-4-yloxy)phenyl)-4-methoxypyrrolidin-2-yl)acetic acid

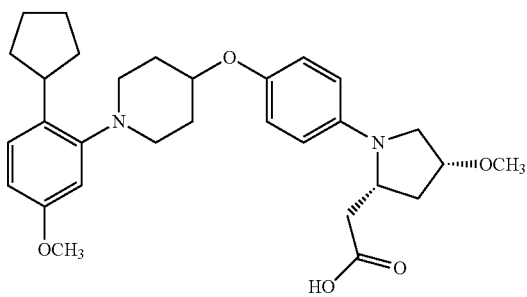 [SMILES: COc1ccc(C2CCCC2)c(N2CCC(Oc3ccc(N4C[C@H](OC)C[C@@H]4CC(=O)O)cc3)CC2)c1]

Example 61 (10 mg) was prepared from cyclopent-1-en-1-ylboronic acid following the procedure of Example 60. LC-MS Anal. Calc'd for $C_3H_{40}N_2O_5$: 508.3, found [M+H] 509.3. $^1$H NMR (500 MHz, DMSO-$d_6$) δ 7.16 (d, J=8.0 Hz, 1H), 6.90 (d, J=8.3 Hz, 2H), 6.71-6.60 (m, 2H), 6.51 (d, J=8.0 Hz, 2H), 4.27 (br. s, 1H), 4.06 (br. s, 1H), 3.99 (br. s, 1H), 3.72 (br. s, 3H), 3.42-3.37 (m, 3H), 3.29 (br. s, 4H), 2.99 (br. s, 2H), 2.75-2.71 (m, 1H), 2.62 (d, J=14.9 Hz, 1H), 2.38 (t, J=12.8 Hz, 1H), 2.15 (br. s, 1H), 2.06-1.89 (m, 5H), 1.77 (d, J=18.2 Hz, 4H), 1.64 (br. s, 2H), 1.45 (br. s, 2H). Analytical HPLC (Acquity): RT=1.9 min, HI: 97.4%. hGPR40 $EC_{50}$=120 nM. hGPR40 IP1 $EC_{50}$=16 nM.

EXAMPLE 62

2-((2R,4R)-1-(4-(1-(2-(3,3-Dimethylbutyl)-5-methoxyphenyl)piperidin-4-yloxy)phenyl)-4-methoxypyrrolidin-2-yl)acetic acid

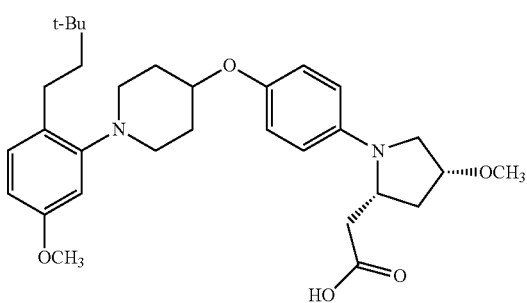 [SMILES: COc1ccc(CCC(C)(C)C)c(N2CCC(Oc3ccc(N4C[C@H](OC)C[C@@H]4CC(=O)O)cc3)CC2)c1]

Example 62 (27 mg) was prepared from (3,3-dimethylbut-1-en-1-yl)boronic acid following the procedure of Example 60. LC-MS Anal. Calc'd for $C_{31}H_{44}N_2O_5$: 524.3, found [M+H] 525.3. $^1$H NMR (500 MHz, DMSO-$d_6$) δ 7.07 (d, J=8.3 Hz, 1H), 6.90 (d, J=7.7 Hz, 2H), 6.63 (br. s, 1H), 6.59 (d, J=8.3 Hz, 1H), 6.51 (d, J=7.7 Hz, 2H), 4.28 (br. s, 1H), 4.06 (br. s, 1H), 3.99 (t, J=8.7 Hz, 1H), 3.71 (br. s, 3H), 3.42-3.40 (m, 2H), 3.29 (br. s, 5H), 2.98 (br. s, 2H), 2.78-2.70 (m, 1H), 2.62 (d, J=15.1 Hz, 1H), 2.49 (br. s, 1H), 2.39 (t, J=12.7 Hz, 1H), 2.44-2.32 (m, 1H), 2.14 (d, J=5.2 Hz, 1H), 2.02 (d, J=12.4 Hz, 3H), 1.73 (d, J=8.0 Hz, 2H), 1.47-1.33 (m, 2H), 0.96 (br. s, 9H). Analytical HPLC (Acquity): RT=2.1 min, HI: 96.9%. hGPR40 $EC_{50}$=89 nM. hGPR40 IP1 $EC_{50}$=13 nM.

EXAMPLE 63

2-((2R,4R)-1-(4-(1-(2-Fluoro-5-(trifluoromethoxy)phenyl)piperidin-4-yloxy)phenyl)-4-methoxypyrrolidin-2-yl)acetic acid, TFA

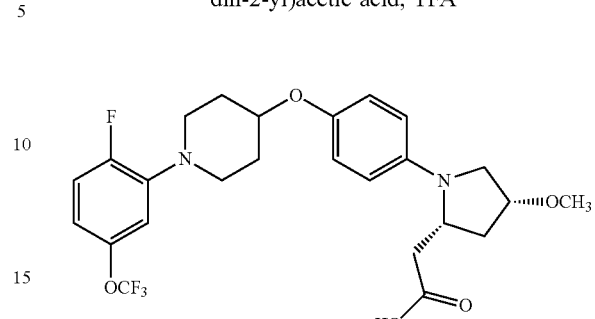

63A. 1-(2-Fluoro-5-(trifluoromethoxy)phenyl)piperidin-4-ol: To a vial was added 2-bromo-1-fluoro-4-(trifluoromethoxy)benzene (2.36 g, 9.12 mmol), a solution of 1 M LHMDS in THF (18.2 mL, 18.2 mmol), piperidin-4-ol (0.92 g, 9.1 mmol), $Pd_2(dba)_3$ (0.17 g, 0.18 mmol), and SPhos (0.15 g, 0.37 mmol). The reaction vessel was purged with argon, capped, and stirred at 70° C. overnight. The reaction mixture was diluted with EtOAc (50 mL) and washed with water (2×40 mL) and brine (40 mL). The organic layer was separated, dried over $MgSO_4$, filtered, and concentrated. The residue was purified via silica chromatography to give 63A (350 mg, 1.25 mmol, 14% yield). LC-MS Anal. Calc'd for $C_{12}H_{13}F_4NO_2$: 279.1, found [M+H] 280.0. $^1$H NMR (400 MHz, $CDCl_3$) δ 6.99-6.84 (m, 1H), 6.79-6.59 (m, 2H), 3.80 (br. s, 1H), 3.37-3.21 (m, 2H), 2.80 (ddd, J=12.2, 9.4, 3.1 Hz, 2H), 2.04-1.86 (m, 2H), 1.68 (dtd, J=12.9, 9.0, 3.7 Hz, 2H).

Example 63 (18 mg) was prepared from 63A following the procedure of Example 57. LC-MS Anal. Calc'd for $C_{25}H_{28}F_4N_2O_5$: 512.2, found [M+H] 513.3. $^1$H NMR (500 MHz, DMSO-$d_6$) δ 7.26 (dd, J=12.4, 8.8 Hz, 1H), 7.00 (d, J=7.4 Hz, 1H), 6.96-6.85 (m, 3H), 6.52 (d, J=8.8 Hz, 2H), 4.32 (dt, J=7.4, 3.9 Hz, 1H), 4.10-4.04 (m, 1H), 3.99 (t, J=8.8 Hz, 1H), 3.42-3.37 (m, 2H), 3.30-3.24 (m, 4H), 2.96 (t, J=9.1 Hz, 2H), 2.63 (dd, J=15.4, 2.2 Hz, 1H), 2.56 (t, J=5.5 Hz, 1H), 2.40 (dd, J=15.1, 10.5 Hz, 1H), 2.21-2.12 (m, 1H), 2.02 (d, J=13.5 Hz, 3H), 1.83-1.64 (m, 2H). Analytical HPLC (Acquity): RT=2.0 min, HI: 96.9%. hGPR40 $EC_{50}$=2600 nM.

EXAMPLE 64

Isomer 1 and Isomer 2

2-((2R,4R)-1-(4-(((3,4-trans)-1-(2-Methyl-5-methoxyphenyl)-3-methylpiperidin-4-yl)oxy)phenyl)-4-methoxypyrrolidin-2-yl)acetic acid

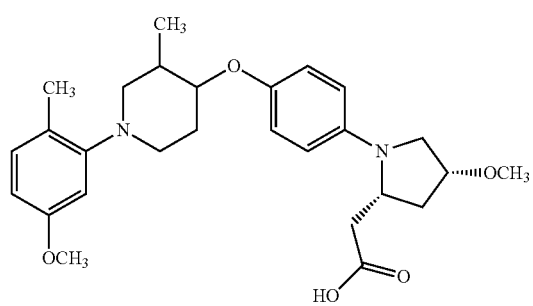 [SMILES: COc1ccc(C)c(N2CCC(Oc3ccc(N4C[C@H](OC)C[C@@H]4CC(=O)O)cc3)C(C)C2)c1]

64A. 1-Benzyl-1,3-dimethyl-4-oxopiperidin-1-ium, iodide salt: To a solution of 1-benzyl-3-methylpiperidin-4-one (5.00 g, 24.6 mmol) in acetone (24.60 mL) at rt was added MeI (2.00 mL, 32.0 mmol) dropwise. The reaction mixture was stirred for overnight. The reaction mixture was concentrated to obtain 64A (8.49 g, 24.6 mmol, 100% yield) as a light yellow foam, which was easily scrapable. LC-MS Anal. Calc'd for $C_{14}H_{20}NO$: 218.31, found [M+H] 219.1.

64B. 1-(5-Methoxy-2-methylphenyl)-3-methylpiperidin-4-one: To a round bottom flask was added 5-methoxy-2-methylaniline (840 mg, 6.12 mmol) and EtOH (10 mL). The reaction mixture was heated to 100° C. Then 64A (2000 mg, 9.19 mmol) was dissolved in water (5 mL) and this solution was added to the reaction over 20 min. The reaction mixture was stirred at 100° C. for 2 h. The reaction mixture was partitioned between EtOAc (200 mL) and water (100 mL). The organic layer was separated, washed with water (50 mL) and brine (50 mL), dried over $MgSO_4$, filtered, and concentrated. The residue was purified via silica chromatography to give 64B (670 mg, 2.87 mmol, 47% yield) as a colorless oil. LC-MS Anal. Calc'd for $C_{14}H_{19}NO_2$: 233.1, found [M+H] 234.1. $^1$H NMR (400 MHz, $CDCl_3$) δ 7.11 (d, J=8.1 Hz, 1H), 6.62-6.53 (m, 2H), 3.78 (s, 3H), 3.44-3.30 (m, 2H), 3.03 (td, J=11.7, 3.4 Hz, 1H), 2.85-2.65 (m, 3H), 2.55-2.44 (m, 1H), 2.31 (s, 3H), 1.09 (d, J=6.6 Hz, 3H).

64C. (3,4-cis)-1-(5-Methoxy-2-methylphenyl)-3-methylpiperidin-4-ol: To a round bottom flask was added 64B (670 mg, 2.87 mmol) and THF (12 mL). The reaction mixture was cooled to −78° C. Then a 1 M solution of L-Selectride in THF (4.3 mL, 4.3 mmol) was added to the reaction mixture and the reaction mixture was stirred at −78° C. for 1 h. The reaction was quenched with 1 N aq. NaOH (4.3 mL, 4.3 mmol). The reaction mixture was brought to rt, 30% aq. $H_2O_2$ (4.3 mL, 42.2 mmol) was added, and the reaction mixture was stirred for 15 min. The reaction mixture was diluted with EtOAc (40 mL) and washed with water (20 mL). The organic layer was separated and washed with water (20 mL) and brine (20 mL), dried over $MgSO_4$, filtered, and concentrated. The diastereomers were separated by chiral SFC to provide the products as single isomers. 64C, Isomer 1 (270 mg, 0.014 mmol, 39% yield) was recovered as a colorless oil. LC-MS Anal. Calc'd for $C_{14}H_{21}NO_2$: 235.3, found [M+H] 236.2. $^1$H NMR (400 MHz, $CDCl_3$) δ 87.15-6.97 (m, 1H), 6.63 (d, J=2.6 Hz, 1H), 6.53 (dd, J=8.1, 2.6 Hz, 1H), 4.00-3.86 (m, 1H), 3.79 (s, 3H), 3.06-2.91 (m, 1H), 2.88-2.72 (m, 3H), 2.24 (s, 3H), 2.06 (dt, J=6.2, 3.3 Hz, 1H), 1.97-1.83 (m, 2H), 1.40 (d, J=4.4 Hz, 1H), 1.06 (d, J=7.0 Hz, 3H). 64C, Isomer 2 (270 mg, 0.014 mmol, 39% yield) was recovered as a colorless oil. LC-MS Anal. Calc'd for $C_{14}H_{21}NO_2$: 235.3, found [M+H] 236.2. $^1$H NMR (400 MHz, $CDCl_3$) δ 7.06 (d, J=8.1 Hz, 1H), 6.62 (d, J=2.6 Hz, 1H), 6.52 (dd, J=8.1, 2.6 Hz, 1H), 3.95-3.86 (m, 1H), 3.77 (s, 3H), 3.04-2.91 (m, 1H), 2.86-2.72 (m, 3H), 2.23 (s, 3H), 2.05 (dt, J=6.3, 3.2 Hz, 1H), 1.96-1.85 (m, 2H), 1.36 (d, J=4.4 Hz, 1H), 1.05 (d, J=7.0 Hz, 3H).

Example 64, Isomer 1 and Isomer 2: Example 64, Isomer 1 (63 mg) was prepared as a single isomer from 64C, Isomer 1 following the procedure of Example 43. LC-MS Anal. Calc'd for $C_{27}H_{36}N_2O_5$: 468.6, found [M+H] 469.4. $^1$H NMR (500 MHz, DMSO-$d_6$) δ 7.07 (d, J=8.3 Hz, 1H), 6.91 (d, J=8.3 Hz, 2H), 6.65-6.47 (m, 4H), 4.08 (br. s, 1H), 4.00 (t, J=8.9 Hz, 1H), 3.83 (br. s, 1H), 3.72 (s, 3H), 3.41 (d, J=10.7 Hz, 1H), 3.35-3.26 (m, 4H), 3.07 (br. s, 2H), 2.72 (br. s, 1H), 2.63 (d, J=15.1 Hz, 1H), 2.56 (t, J=5.5 Hz, 1H), 2.41 (dd, J=15.0, 10.6 Hz, 1H), 2.19 (s, 4H), 2.10 (d, J=10.5 Hz, 1H), 2.01 (d, J=14.0 Hz, 2H), 1.64 (d, J=10.7 Hz, 1H), 1.06 (d, J=6.3 Hz, 3H). Analytical HPLC (Acquity): RT=1.5 min, HI: 99.0%. hGPR40 $EC_{50}$=240 nM. Example 64, Isomer 2 (7 mg) was prepared as a single isomer from 64C, Isomer 2 following the procedure of Example 43. LC-MS Anal. Calc'd for $C_{27}H_{36}N_2O_5$: 468.6, found [M+H] 469.4. $^1$H NMR (500 MHz, DMSO-$d_6$) δ 7.06 (d, J=8.3 Hz, 1H), 6.91 (d, J=8.3 Hz, 2H), 6.65-6.37 (m, 4H), 4.07 (br. s, 1H), 4.03-3.96 (m, 1H), 3.82 (br. s, 1H), 3.71 (s, 3H), 3.41 (d, J=10.5 Hz, 1H), 3.32-3.24 (m, 4H), 3.07 (d, J=8.3 Hz, 2H), 2.70 (br. s, 1H), 2.63 (d, J=15.4 Hz, 1H), 2.56 (t, J=5.4 Hz, 1H), 2.41 (dd, J=14.9, 10.7 Hz, 1H), 2.25-2.13 (m, 4H), 2.08 (d, J=8.0 Hz, 1H), 2.04-1.93 (m, 2H), 1.63 (d, J=10.5 Hz, 1H), 1.06 (d, J=6.3 Hz, 3H). Analytical HPLC (Acquity): RT=1.5 min, HI: 100%. hGPR40 $EC_{50}$=120 nM.

EXAMPLE 65

Isomer 1 and Isomer 2

2-((2R,4R)-1-(4-(1-(2-(2,2-Dimethylcyclopentyl)-5-methoxyphenyl)piperidin-4-yloxy)phenyl)-4-methoxypyrrolidin-2-yl)acetic acid

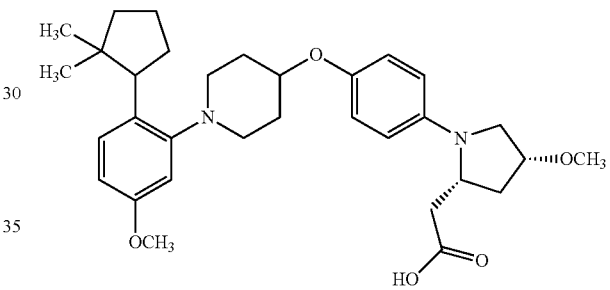

65A. 5,5-Dimethylcyclopent-1-enyl trifluoromethanesulfonate: To a solution of 2,2-dimethylcyclopentanone (3.36 mL, 26.7 mmol) in THF (70 mL) at −78° C., a 2 M solution of LDA in THF/n-heptane (15.8 mL, 28.5 mmol) was added dropwise. The reaction mixture was stirred at −78° C. for 1 h and then a solution of N-phenyl-bis(trifluoromethanesulfonimide) (10.0 g, 28.1 mmol) in THF (20 mL) was added. The reaction mixture was stirred at −78° C. for 1 h, warmed slowly to rt, and stirred overnight. The mixture was diluted with hexanes (200 mL), washed with sat. aq. $NaHCO_3$ (30 mL), and brine (20 mL), dried ($MgSO_4$), and concentrated. The crude product was purified by silica chromatography to give 65A (6.00 g, 24.6 mmol, 92% yield) as a colorless oil. $^1$H NMR (500 MHz, $CDCl_3$) δ 5.54 (t, J=2.7 Hz, 1H), 2.35 (td, J=7.0, 2.5 Hz, 2H), 1.84 (t, J=6.9 Hz, 2H), 1.14 (s, 6H).

65B. 2-(5,5-Dimethylcyclopent-1-en-1-yl)-4,4,5,5-tetramethyl-1,3,2-dioxaborolane: A mixture of 65A (7.57 g, 31.0 mmol), 4,4,4',4',5,5,5',5'-octamethyl-2,2'-bi(1,3,2-dioxaborolane) (8.66 g, 34.1 mmol), $PdCl_2(PPh_3)_2$ (0.653 g, 0.930 mmol), $Ph_3P$ (0.732 g, 2.79 mmol) and sodium phenate (5.40 g, 46.5 mmol) in toluene (100 mL) was heated to 50° C. under argon for 2 h 10 min. The reaction mixture was diluted with EtOAc, washed with water and brine, dried ($MgSO_4$), and concentrated. The crude product was purified by silica chromatography to give 65B (5.47 g, 24.6 mmol, 79% yield) as a colorless liquid. $^1$H NMR (500 MHz, $CDCl_3$) δ 6.37 (t, J=2.2 Hz, 1H), 2.36 (td, J=7.4, 2.2 Hz, 2H), 1.64 (t, J=7.1 Hz, 2H), 1.25 (s, 12H), 1.11 (s, 6H).

65C. 2-(2,2-Dimethylcyclopentyl)-5-methoxyaniline: 65C (219.2 mg, 2.01 mmol) was prepared from 65B following the procedure of Example 60. LC-MS Anal. Calc'd for $C_{14}H_{21}NO$: 219.3, found [M+H] 220.2.

65D. 2-(2,2-Dimethylcyclopentyl)-5-methoxyaniline, Isomer 1 and Isomer 2: 65C was subjected to chiral SFC to give two single isomers. 65D, Isomer 1: LC-MS Anal. Calc'd for $C_{19}H_{29}NO_2$: 303.2, found [M+H] 304.3. $^1$H NMR (400 MHz, CDCl$_3$) δ 7.13 (d, J=8.6 Hz, 1H), 6.69 (d, J=2.6 Hz, 1H), 6.62 (dd, J=8.6, 2.9 Hz, 1H), 3.80-3.76 (m, 3H), 3.10-2.98 (m, 1H), 2.95-2.80 (m, 2H), 2.76-2.66 (m, 1H), 2.59-2.46 (m, 1H), 2.03-1.56 (m, 12H), 0.96 (s, 3H), 0.65 (s, 3H). 65D, Isomer 2: LC-MS Anal. Calc'd for $C_{19}H_{29}NO_2$ 303.2, found [M+H] 304.2. $^1$H NMR (400 MHz, CDCl$_3$) δ 7.13 (d, J=8.6 Hz, 1H), 6.69 (d, J=2.6 Hz, 1H), 6.62 (dd, J=8.6, 2.9 Hz, 1H), 3.78 (s, 3H), 3.15-2.98 (m, 1H), 2.96-2.80 (m, 2H), 2.59-2.41 (m, 1H), 2.07-1.55 (m, 11H), 1.55-1.51 (m, 2H), 0.96 (s, 3H), 0.65 (s, 3H).

Example 65, Isomer 1 and Isomer 2: Example 65, Isomer 1 (22 mg) was prepared as a single isomer from 65D, Isomer 1 following the procedure of Example 43. LC-MS Anal. Calc'd for $C_{32}H_{44}N_2O_5$: 536.3, found [M+H] 537.4. $^1$H NMR (500 MHz, DMSO-d$_6$) δ 7.12 (d, J=9.1 Hz, 1H), 6.91 (d, J=8.0 Hz, 2H), 6.70 (s, 1H), 6.65 (d, J=8.0 Hz, 1H), 6.53 (d, J=6.9 Hz, 2H), 4.07 (br. s, 1H), 3.99 (t, J=8.7 Hz, 1H), 3.73 (br. s, 4H), 3.46 (br. s, 1H), 3.40 (d, J=10.2 Hz, 2H), 3.34 (t, J=9.4 Hz, 1H), 3.29 (br. s, 4H), 2.84 (br. s, 1H), 2.63 (d, J=15.7 Hz, 1H), 2.56 (br. s, 1H), 2.46-2.34 (m, 1H), 2.16 (d, J=4.7 Hz, 1H), 2.09-1.96 (m, 2H), 1.90 (t, J=8.4 Hz, 2H), 1.82-1.62 (m, 4H), 1.56 (d, J=7.4 Hz, 2H), 0.95 (br. s, 3H), 0.62 (br. s, 3H). Analytical HPLC (Acquity): RT=2.2 min, HI: 100%. hGPR40 EC$_{50}$=33 nM. hGPR40 IP1 EC$_{50}$=10 nM. Example 65, Isomer 2 (13 mg) was prepared as a single isomer from 65B, Isomer 2 following the procedure of Example 43. LC-MS Anal. Calc'd for $C_{32}H_{44}N_2O_5$: 536.3, found [M+H] 537.4. $^1$H NMR (500 MHz, DMSO-d$_6$) δ 7.12 (d, J=8.3 Hz, 1H), 6.91 (d, J=7.7 Hz, 2H), 6.69 (br. s, 1H), 6.65 (d, J=8.0 Hz, 1H), 6.51 (d, J=7.7 Hz, 2H), 4.07 (br. s, 1H), 3.99 (br. s, 1H), 3.73 (br. s, 3H), 3.43-3.32 (m, 6H), 3.29 (br. s, 4H), 2.84 (br. s, 1H), 2.63 (d, J=15.1 Hz, 1H), 2.52 (br. s, 1H), 2.45-2.34 (m, 1H), 2.15 (d, J=5.5 Hz, 1H), 2.02 (d, J=13.8 Hz, 2H), 1.90 (t, J=8.3 Hz, 2H), 1.83-1.60 (m, 4H), 1.59-1.51 (m, 2H), 0.95 (br. s, 3H), 0.62 (br. s, 3H). Analytical HPLC (Acquity): RT=2.2 min, HI: 98.9%. hGPR40 EC$_{50}$=120 nM.

EXAMPLE 66

2-((2R,4R)-4-(2-Cyanophenoxy)-1-(4-(1-(5-ethoxy-2-fluorophenyl)piperidin-4-yloxy)phenyl)pyrrolidin-2-yl)acetic acid

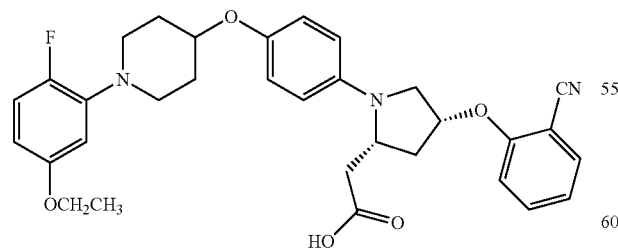

A 0.1 M solution of 45C (1.0 mL, 0.10 mmol) in THF was combined with 2-hydroxybenzonitrile (1.5 eq, 0.150 mmol), polystyrene-bound Ph$_3$P (1.5 eq, 0.150 mmol, loading=3 mmol/g, 50 mg), and DIAD (1.5 eq, 0.15 mmol, 0.029 mL) and stirred under a nitrogen atmosphere at rt for 16 h. The mixture was diluted with THF, filtered through a 45 μM syringe filter, and dried under a stream of nitrogen. The crude mixture was then dissolved in THF (1.8 mL) and 1 M aq. LiOH (180 μL, 0.18 mmol) was added. The reaction mixture was stirred at rt for 16 h. The crude material was purified by RP-Prep.

HPLC to give Example 66 (23 mg, 0.040 mmol, 40% yield). LC-MS Anal. Calc'd for $C_{32}H_{34}FN_3O_5$: 559.25 found [M+H] 560.3. $^1$H NMR (500 MHz, 1:1 methanol-d$_4$: CDCl$_3$) δ 7.49-7.48 (m, 2H), 7.12-7.03 (m, 2H), 6.93-6.84 (m, 3H), 6.57 (d, J=9.4 Hz, 2H), 6.54 (dd, J=7.4, 3.0 Hz, 1H), 6.42 (dt, J=8.9, 3.2 Hz, 1H), 5.24 (br. s, 1H), 4.32-4.20 (m, 2H), 3.96 (q, J=7.1 Hz, 2H), 3.64 (d, J=3.5 Hz, 2H), 3.28 (d, J=3.0 Hz, 2H), 2.95-2.86 (m, 3H), 2.84-2.75 (m, 1H), 2.53 (ddd, J=14.1, 8.2, 5.4 Hz, 1H), 2.37 (d, J=14.4 Hz, 1H), 2.07 (br. s, 2H), 1.97-1.85 (m, 2H), 1.36 (t, J=6.9 Hz, 3H). Analytical HPLC (Acquity): RT=2.0 min, HI: 95.2%. hGPR40 EC$_{50}$=1400 nM.

EXAMPLE 67

2-((2R,4R)-1-(4-(1-(5-Ethoxy-2-fluorophenyl)piperidin-4-yloxy)phenyl)-4-(o-tolyloxy)pyrrolidin-2-yl)acetic acid

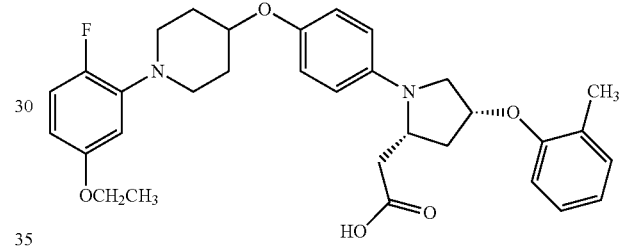

Example 67 (22.6 mg, 0.019 mmol 19% yield) was prepared from o-cresol following the procedure of Example 66. LC-MS Anal. Calc'd for $C_{32}H_{37}FN_2O_5$: 548.27 found [M+H] 549.28. $^1$H NMR (500 MHz, 1:1 methanol-d$_4$: CDCl$_3$) δ 7.17-7.08 (m, 2H), 6.92-6.86 (m, 3H), 6.86-6.79 (m, 2H), 6.56 (d, J=8.9 Hz, 2H), 6.55-6.52 (m, 1H), 6.42 (dt, J=8.5, 3.2 Hz, 1H), 5.12-5.05 (m, 1H), 4.31-4.22 (m, 3H), 3.96 (q, J=7.3 Hz, 2H), 3.30-3.26 (m, 2H), 2.94-2.87 (m, 3H), 2.80-2.71 (m, 1H), 2.47 (ddd, J=14.0, 8.1, 5.7 Hz, 1H), 2.32 (d, J=14.4 Hz, 1H), 2.19 (s, 3H), 2.18-2.15 (m, 1H), 2.06 (br. s, 2H), 1.95-1.84 (m, 2H), 1.36 (t, J=6.9 Hz, 3H). Analytical HPLC (Acquity): RT=2.1 min, HI: 96.7%. hGPR40 EC$_{50}$=950 nM.

EXAMPLE 68

2-((2R,4R)-4-(3-Cyanophenoxy)-1-(4-(1-(5-ethoxy-2-fluorophenyl)piperidin-4-yloxy)phenyl)pyrrolidin-2-yl)acetic acid

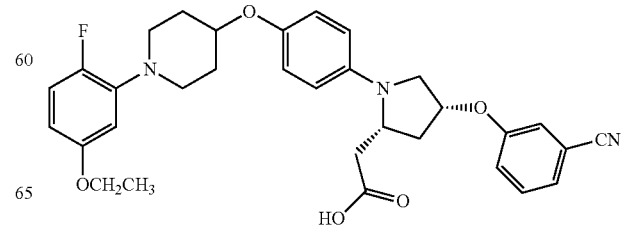

Example 68 (23 mg, 0.04 mmol, 41% yield) was prepared from 3-hydroxybenzonitrile following the procedure of Example 66. LC-MS Anal. Calc'd for $C_{32}H_{34}FN_3O_5$: 559.25 found [M+H] 560.26. $^1$H NMR (500 MHz, methanol-$d_4$) δ 7.49-7.42 (m, 2H), 7.30 (d, J=7.9 Hz, 1H), 7.26-7.21 (m, 2H), 6.96-6.87 (m, 3H), 6.64-6.53 (m, 3H), 6.45 (dt, J=8.8, 3.0 Hz, 1H), 4.36-4.21 (m, 3H), 3.99 (q, J=6.9 Hz, 2H), 3.37 (s, 1H), 3.01 (s, 1H), 2.98-2.86 (m, 4H), 2.64 (dd, J=15.6, 10.7 Hz, 1H), 2.57-2.45 (m, 1H), 2.30 (d, J=14.4 Hz, 1H), 2.09 (br. s, 2H), 1.99-1.88 (m, 2H), 1.39 (t, J=6.9 Hz, 3H). Analytical HPLC (Acquity): RT=2.3 min, HI: 98.5%. hGPR40 $EC_{50}$=310 nM.

EXAMPLE 69

2-((2R,4R)-4-(3-Chlorophenoxy)-1-(4-(1-(5-ethoxy-2-fluorophenyl)piperidin-4-yloxy)phenyl)pyrrolidin-2-yl)acetic acid

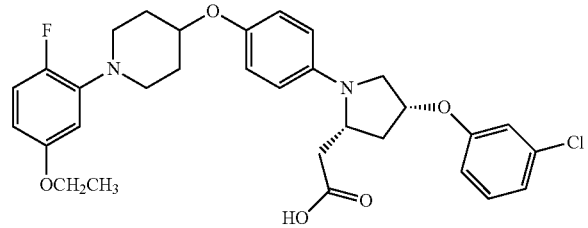 [SMILES: CCOc1ccc(F)c(N2CCC(Oc3ccc(N4C[C@H](Oc5cccc(Cl)c5)C[C@@H]4CC(=O)O)cc3)CC2)c1]

Example 69 (21 mg, 0.036 mmol, 36% yield) was prepared from 3-chlorophenol following the procedure of Example 66. LC-MS Anal. Calc'd for $C_{31}H_{34}ClFN_2O_5$: 568.2 found [M+H] 569.22. $^1$H NMR (500 MHz, 1:1 methanol-$d_4$:CDCl$_3$) δ 7.22 (t, J=8.2 Hz, 1H), 6.95-6.85 (m, 5H), 6.85-6.79 (m, 1H), 6.58 (d, J=8.9 Hz, 2H), 6.54 (dd, J=7.4, 3.0 Hz, 1H), 6.43 (dt, J=8.8, 3.0 Hz, 1H), 5.07 (br. s, 1H), 4.44-4.30 (m, 2H), 4.30-4.19 (m, 2H), 3.97 (q, J=6.9 Hz, 2H), 3.29 (br. s, 2H), 2.95-2.83 (m, 3H), 2.64 (dd, J=15.9, 10.9 Hz, 1H), 2.46 (ddd, J=14.0, 8.1, 5.7 Hz, 1H), 2.27 (d, J=14.4 Hz, 1H), 2.07 (br. s, 2H), 1.96-1.83 (m, 2H), 1.36 (t, J=7.2 Hz, 3H). Analytical HPLC (Acquity): RT=2.1 min, HI: 98.7%. hGPR40 $EC_{50}$=160 nM.

EXAMPLE 70

2-((2R,4R)-1-(4-(1-(5-Ethoxy-2-fluorophenyl)piperidin-4-yloxy)phenyl)-4-(3-methoxyphenoxy)pyrrolidin-2-yl)acetic acid

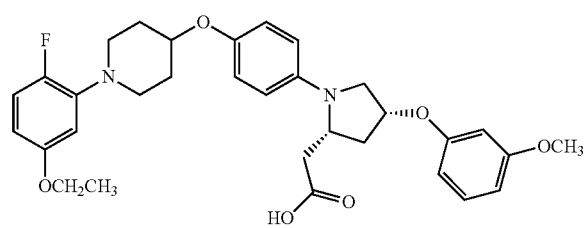 [SMILES: CCOc1ccc(F)c(N2CCC(Oc3ccc(N4C[C@H](Oc5cccc(OC)c5)C[C@@H]4CC(=O)O)cc3)CC2)c1]

Example 70 (20.6 mg, 0.037 mmol, 37% yield) was prepared from 3-methoxyphenol following the procedure of Example 66. LC-MS Anal. Calc'd for $C_{32}H_{37}FN_2O_6$: 564.26 found [M+H] 566.27. $^1$H NMR (500 MHz, 1:1 methanol-$d_4$:CDCl$_3$) δ 7.17 (t, J=8.2 Hz, 1H), 6.93-6.85 (m, 3H), 6.57 (d, J=8.9 Hz, 2H), 6.54 (dd, J=7.4, 3.0 Hz, 1H), 6.51 (dt, J=8.2, 2.8 Hz, 2H), 6.46 (s, 1H), 6.42 (dt, J=8.8, 3.0 Hz, 1H), 5.06 (t, J=4.2 Hz, 1H), 4.30-4.19 (m, 2H), 3.96 (q, J=6.9 Hz, 2H), 3.77 (s, 3H), 3.58-3.54 (m, 2H), 3.28 (d, J=3.0 Hz, 2H), 2.95-2.82 (m, 3H), 2.69 (dd, J=15.9, 10.4 Hz, 1H), 2.44 (ddd, J=13.9, 8.2, 5.7 Hz, 1H), 2.28 (d, J=13.9 Hz, 1H), 2.11-2.03 (m, 2H), 1.95-1.86 (m, 2H), 1.36 (t, J=7.2 Hz, 3H). Analytical HPLC (Acquity): RT=2.0 min, HI: 94.6%. hGPR40 $EC_{50}$=110 nM. hGPR40 IP1 $EC_{50}$=8 nM.

EXAMPLE 71

2-((2R,4R)-1-(4-(1-(5-Ethoxy-2-fluorophenyl)piperidin-4-yloxy)phenyl)-4-(3-(trifluoromethyl)phenoxy)pyrrolidin-2-yl)acetic acid

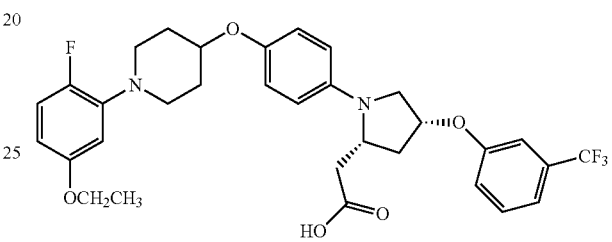

Example 71 (23.9 mg, 0.040 mmol, 40% yield) was prepared from 3-(trifluoromethyl)phenol following the procedure of Example 66. LC-MS Anal. Calc'd for $C_{32}H_{34}F_4N_2O_5$: 602.24 found [M+H] 603.25. $^1$H NMR (500 MHz, 1:1 methanol-$d_4$:CDCl$_3$) δ 7.43 (t, J=7.9 Hz, 1H), 7.21 (d, J=7.9 Hz, 1H), 7.16-7.10 (m, 2H), 6.93-6.85 (m, 3H), 6.58 (d, J=9.4 Hz, 2H), 6.54 (dd, J=6.9, 3.0 Hz, 1H), 6.42 (dt, J=8.9, 3.2 Hz, 1H), 5.17-5.12 (m, 1H), 4.31-4.21 (m, 2H), 3.96 (q, J=7.3 Hz, 2H), 3.64-3.61 (m, 3H), 3.30-3.27 (m, 2H), 2.95-2.87 (m, 2H), 2.65 (dd, J=15.9, 10.4 Hz, 1H), 2.49 (ddd, J=14.1, 8.2, 5.4 Hz, 1H), 2.28 (d, J=13.9 Hz, 1H), 2.12-2.03 (m, 2H), 1.95-1.86 (m, 2H), 1.36 (t, J=6.9 Hz, 3H). Analytical HPLC (Acquity): RT=2.1 min, HI: 96.2%. hGPR40 $EC_{50}$=250 nM.

EXAMPLE 72

2-((2R,4R)-1-(4-(1-(5-Ethoxy-2-fluorophenyl)piperidin-4-yloxy)phenyl)-4-(m-tolyloxy)pyrrolidin-2-yl)acetic acid

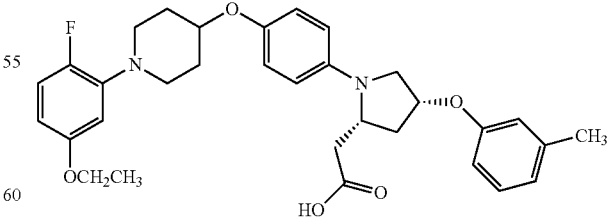

Example 72 (13.5 mg, 0.025 mmol, 24% yield) was prepared from m-cresol following the procedure of Example 66. LC-MS Anal. Calc'd for $C_{32}H_{37}FN_2O_5$: 548.27 found [M+H] 549.27. $^1$H NMR (500 MHz, 1:1 methanol-$d_4$: CDCl$_3$) δ 7.15 (t, J=7.7 Hz, 1H), 6.93-6.85 (m, 3H), 6.76 (d, J=7.4 Hz, 1H), 6.73 (s, 1H), 6.70 (d, J=8.4 Hz, 1H), 6.57 (d, J=8.9 Hz, 2H), 6.54 (dd, J=7.4, 3.0 Hz, 1H), 6.42 (dt, J=8.8, 3.0 Hz, 1H), 5.07 (br. s, 1H), 4.30-4.19 (m, 3H), 3.97 (q, J=6.9 Hz, 3H), 3.31-3.27 (m, 2H), 2.94-2.83 (m, 3H), 2.70 (dd, J=15.9, 10.4 Hz, 1H), 2.43 (ddd, J=13.9, 8.2, 5.7 Hz, 1H), 2.31 (s, 3H), 2.29-2.23 (m, 1H), 2.11-2.03 (m, 2H), 1.95-1.87 (m, 2H), 1.36 (t, J=6.9 Hz, 3H). Analytical HPLC (Acquity): RT=2.3 min, HI: 92.0%. hGPR40 $EC_{50}$=170 nM.

EXAMPLE 73

2-((2R,4R)-4-(4-Chlorophenoxy)-1-(4-(1-(5-ethoxy-2-fluorophenyl)piperidin-4-yloxy)phenyl)pyrrolidin-2-yl)acetic acid

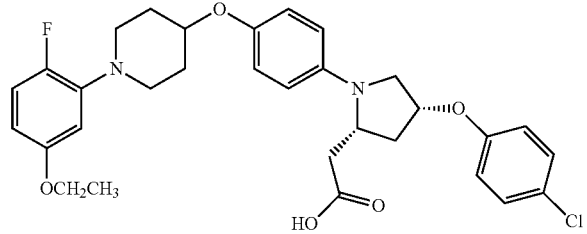 [SMILES: CCOc1ccc(F)c(N2CCC(Oc3ccc(N4C[C@H](Oc5ccc(Cl)cc5)C[C@@H]4CC(=O)O)cc3)CC2)c1]

Example 73 (18.1 mg, 0.032 mmol, 32% yield) was prepared from 4-chlorophenol following the procedure of Example 66. LC-MS Anal. Calc'd for $C_{31}H_{34}ClFN_2O_5$: 568.21 found [M+H] 569.22. $^1$H NMR (500 MHz, 1:1 methanol-$d_4$:CDCl$_3$) δ 7.26-7.20 (m, 2H), 6.93-6.83 (m, 5H), 6.57 (d, J=8.9 Hz, 2H), 6.54 (dd, J=6.9, 3.0 Hz, 1H), 6.43 (dt, J=8.8, 3.0 Hz, 1H), 5.08-5.03 (m, 1H), 4.30-4.19 (m, 2H), 3.96 (q, J=6.9 Hz, 2H), 3.58-3.55 (m, 2H), 3.30-3.26 (m, 2H), 2.95-2.82 (m, 3H), 2.64 (dd, J=15.9, 10.9 Hz, 1H), 2.44 (ddd, J=14.0, 8.3, 5.4 Hz, 1H), 2.26 (d, J=14.4 Hz, 1H), 2.07 (br. s, 2H), 1.95-1.84 (m, 2H), 1.36 (t, J=6.9 Hz, 3H). Analytical HPLC (Acquity): RT=2.1 min, HI: 98.7%. hGPR40 $EC_{50}$=1600 nM.

EXAMPLE 74

2-((2R,4R)-1-(4-(1-(5-Ethoxy-2-fluorophenyl)piperidin-4-yloxy)phenyl)-4-(p-tolyloxy)pyrrolidin-2-yl)acetic acid

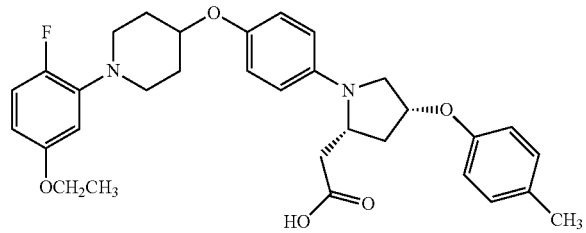 [SMILES: CCOc1ccc(F)c(N2CCC(Oc3ccc(N4C[C@H](Oc5ccc(C)cc5)C[C@@H]4CC(=O)O)cc3)CC2)c1]

Example 74 (18.7 mg, 0.030 mmol, 34% yield) was prepared from p-cresol following the procedure of Example 66. LC-MS Anal. Calc'd for $C_{32}H_{37}FN_2O_5$: 548.27 found [M+H] 549.27. $^1$H NMR (500 MHz, 1:1 methanol-$d_4$:CDCl$_3$) δ 7.07 (d, J=7.9 Hz, 2H), 6.93-6.86 (m, 3H), 6.80 (d, J=8.9 Hz, 2H), 6.58-6.52 (m, 3H), 6.43 (dt, J=8.8, 3.0 Hz, 1H), 5.04 (t, J=5.0 Hz, 1H), 4.32 (br. s, 1H), 4.30-4.18 (m, 2H), 3.96 (q, J=6.9 Hz, 2H), 3.58-3.52 (m, 2H), 3.30-3.26 (m, 1H), 2.94-2.82 (m, 3H), 2.69 (dd, J=15.9, 10.4 Hz, 1H), 2.42 (ddd, J=13.9, 8.2, 5.7 Hz, 1H), 2.29-2.24 (m, 4H), 2.11-2.04 (m, 2H), 1.95-1.86 (m, 2H), 1.36 (t, J=6.9 Hz, 3H). Analytical HPLC (Acquity): RT=2.3 min, HI: 98.2%. hGPR40 $EC_{50}$=1200 nM.

EXAMPLE 75

2-((2R,4R)-1-(4-(1-(5-Ethoxy-2-fluorophenyl)piperidin-4-yloxy)phenyl)-4-(pyridin-2-yloxy)pyrrolidin-2-yl)acetic acid, TFA

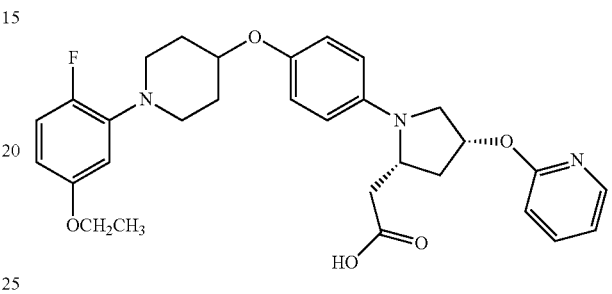

Example 75 (23.1 mg, 0.043 mmol, 43% yield) was prepared from pyridin-2-ol following the procedure of Example 66. LC-MS Anal. Calc'd for $C_{30}H_{34}FN_3O_5$: 535.25 found [M+H] 536.26. $^1$H NMR (500 MHz, 1:1 methanol-$d_4$:CDCl$_3$) δ 7.79 (dd, J=6.9, 1.5 Hz, 1H), 7.50-7.46 (m, 1H), 6.99-6.93 (m, 2H), 6.93-6.85 (m, 3H), 6.61-6.56 (m, 2H), 6.46 (dt, J=8.8, 3.0 Hz, 1H), 6.42 (t, J=6.4 Hz, 1H), 5.41-5.35 (m, 1H), 4.40 (tt, J=7.2, 3.4 Hz, 1H), 4.17-4.10 (m, J=7.9 Hz, 1H), 3.97 (q, J=6.9 Hz, 2H), 3.81-3.76 (m, 1H), 3.75-3.65 (m, 1H), 3.37-3.33 (m, 2H), 2.99-2.87 (m, 4H), 2.32 (dd, J=15.9, 9.9 Hz, 1H), 2.18-2.07 (m, 3H), 1.99-1.90 (m, 2H), 1.36 (t, J=6.9 Hz, 3H). Analytical HPLC (Acquity): RT=2.0 min, HI: 95.1%. hGPR40 $EC_{50}$=420 nM.

EXAMPLE 76

2-((2R,4R)-1-(4-(1-(5-Ethoxy-2-fluorophenyl)piperidin-4-yloxy)phenyl)-4-(pyridin-3-yloxy)pyrrolidin-2-yl)acetic acid

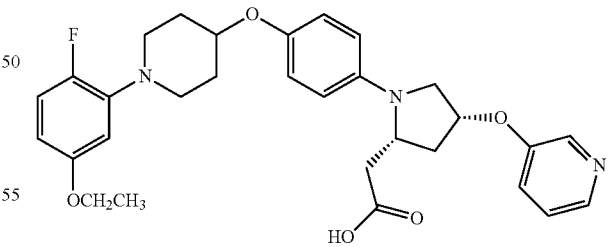

Example 76 (13.4 mg, 0.025 mmol, 25% yield) was prepared from pyridin-3-ol following the procedure of Example 66. LC-MS Anal. Calc'd for $C_{30}H_{34}FN_3O_5$: 535.25 found [M+H] 536.25. $^1$H NMR (500 MHz, DMSO-$d_6$) δ 8.20 (d, J=4.5 Hz, 1H), 7.46 (dd, J=8.4, 1.5 Hz, 1H), 7.36 (dd, J=8.4, 4.5 Hz, 1H), 7.00 (dd, J=12.4, 8.9 Hz, 1H), 6.91 (d, J=8.9 Hz, 2H), 6.60-6.49 (m, 3H), 6.46 (dt, J=8.7, 3.3 Hz, 1H), 5.26 (t, J=4.7 Hz, 1H), 4.30 (dt, J=7.6, 3.9 Hz, 1H), 3.97 (q, J=6.9 Hz, 3H), 3.62-3.49 (m, 3H), 3.30-3.21 (m, 2H), 2.93-2.84 (m, 3H), 2.78-2.70 (m, 1H), 2.48-2.41 (m, 1H), 2.12 (d, J=14.4 Hz, 1H), 2.00 (br. s, 2H), 1.80-1.68 (m, 2H), 1.30 (t, J=6.9 Hz, 3H). Analytical HPLC (Acquity): RT=1.5 min, HI: 95.9%. hGPR40 EC$_{50}$=860 nM.

EXAMPLE 77

2-((2R,4R)-1-(4-(1-(5-Ethoxy-2-fluorophenyl)piperidin-4-yloxy)phenyl)-4-(3-(trifluoromethoxy)phenoxy)pyrrolidin-2-yl)acetic acid

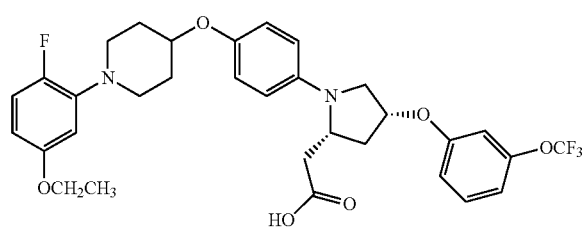 [SMILES: CCOc1ccc(F)c(N2CCC(Oc3ccc(N4C[C@H](Oc5cccc(OC(F)(F)F)c5)C[C@@H]4CC(=O)O)cc3)CC2)c1]

Example 77 (11.2 mg, 0.018 mmol, 18% yield) was prepared from 3-(trifluoromethoxy)phenol following the procedure of Example 66. LC-MS Anal. Calc'd for C$_{32}$H$_{34}$F$_4$N$_2$O$_6$: 618.24 found [M+H] 619.24. $^1$H NMR (500 MHz, 1:1 methanol-d$_4$:CDCl$_3$) δ 7.32 (t, J=8.2 Hz, 1H), 6.94-6.85 (m, 4H), 6.82 (d, J=7.9 Hz, 1H), 6.78 (s, 1H), 6.58 (d, J=8.9 Hz, 2H), 6.54 (dd, J=7.4, 3.0 Hz, 1H), 6.43 (dt, J=8.7, 3.3 Hz, 1H), 5.13-5.07 (m, 1H), 4.35 (br. s, 1H), 4.30-4.20 (m, 2H), 3.96 (q, J=6.9 Hz, 2H), 3.61-3.60 (m, 1H), 3.30-3.26 (m, 2H), 2.95-2.83 (m, 3H), 2.63 (dd, J=15.9, 10.4 Hz, 1H), 2.47 (ddd, J=14.0, 8.3, 5.9 Hz, 1H), 2.28 (d, J=14.4 Hz, 1H), 2.07 (m, 2H), 1.96-1.85 (m, 2H), 1.36 (t, J=6.9 Hz, 3H). Analytical HPLC (Acquity): RT=2.2 min, HI: 95.6%. hGPR40 EC$_{50}$=140 nM.

EXAMPLE 78

2-((2R,4R)-1-(4-(1-(5-Ethoxy-2-fluorophenyl)piperidin-4-yloxy)phenyl)-4-(pyrimidin-2-yloxy)pyrrolidin-2-yl)acetic acid, TFA

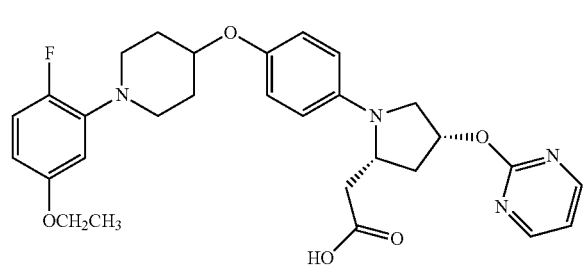 [SMILES: CCOc1ccc(F)c(N2CCC(Oc3ccc(N4C[C@H](Oc5ncccn5)C[C@@H]4CC(=O)O)cc3)CC2)c1]

Example 78 (6.8 mg, 0.013 mmol, 12% yield) was prepared from pyrimidin-2-ol following the procedure of Example 66. LC-MS Anal. Calc'd for C$_{29}$H$_{33}$FN$_4$O$_5$: 536.24 found [M+H] 537.25. $^1$H NMR (500 MHz, methanol-d$_4$) δ 7.10 (t, J=4.7 Hz, 1H), 6.96-6.87 (m, 3H), 6.66-6.57 (m, 3H), 6.47 (dt, J=8.8, 3.0 Hz, 1H), 5.73 (t, J=5.2 Hz, 1H), 4.37-4.24 (m, 2H), 3.99 (q, J=6.9 Hz, 2H), 3.78-3.65 (m, 4H), 3.01-2.85 (m, 5H), 2.81-2.68 (m, 1H), 2.58 (ddd, J=14.5, 8.3, 5.9 Hz, 1H), 2.34 (d, J=14.4 Hz, 1H), 2.10 (br. s, 2H), 2.00-1.89 (m, 2H), 1.39 (t, J=7.2 Hz, 3H). Analytical HPLC (Acquity): RT=1.7 min, HI: 95.6%. hGPR40 EC$_{50}$=1600 nM.

EXAMPLE 79

2-((2R,4R)-4-(2-Chlorophenoxy)-1-(4-(1-(5-ethoxy-2-fluorophenyl)piperidin-4-yloxy)phenyl)pyrrolidin-2-yl)acetic acid

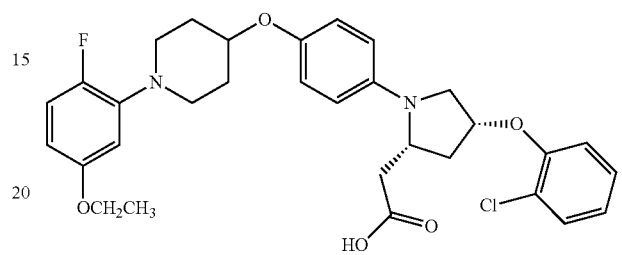

Example 79 (16.8 mg, 0.030 mmol, 30% yield) was prepared from 2-chlorophenol following the procedure of Example 66. LC-MS Anal. Calc'd for C$_{31}$H$_{34}$ClFN$_2$O$_5$: 568.21 found [M+H] 569.22. $^1$H NMR (500 MHz, methanol-d$_4$) δ 7.37 (dd, J=7.7, 1.7 Hz, 1H), 7.25 (td, J=7.8, 1.7 Hz, 1H), 7.08-7.01 (m, 1H), 6.98-6.86 (m, 4H), 6.61-6.54 (m, 3H), 6.45 (dt, J=8.9, 3.2 Hz, 1H), 5.18 (t, J=4.7 Hz, 1H), 4.34-4.24 (m, 3H), 3.99 (q, J=7.1 Hz, 2H), 3.37 (s, 1H), 3.03-2.85 (m, 6H), 2.49 (ddd, J=14.1, 8.2, 5.4 Hz, 1H), 2.39 (d, J=14.4 Hz, 1H), 2.16-2.06 (m, 2H), 1.98-1.87 (m, 2H), 1.38 (t, J=6.9 Hz, 3H). Analytical HPLC (Acquity): RT=2.1 min, HI: 96.9%. hGPR40 EC$_{50}$=740 nM.

EXAMPLE 80

2-((2R,4R)-1-(4-(1-(5-Ethoxy-2-fluorophenyl)piperidin-4-yloxy)phenyl)-4-(N-methylphenylsulfonamido)pyrrolidin-2-yl)acetic acid, TFA

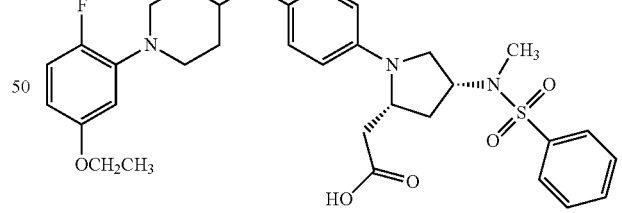

Example 80 (8.5 mg, 0.014 mmol, 14% yield) was prepared from N-methylbenzene sulfonamide following the procedure of Example 66. LC-MS Anal. Calc'd for C$_{32}$H$_{38}$FN$_3$O$_6$S: 611.25 found [M+H] 612.25. $^1$H NMR (500 MHz, 1:1 methanol-d$_4$:CDCl$_3$) δ 7.63 (d, J=1.5 Hz, 4H), 6.91 (dd, J=12.1, 8.7 Hz, 1H), 6.86 (d, J=9.4 Hz, 2H), 6.64-6.53 (m, 3H), 6.45 (dt, J=8.9, 3.0 Hz, 1H), 4.49 (quin, J=8.4 Hz, 1H), 4.32 (dt, J=7.3, 3.5 Hz, 1H), 3.97 (q, J=6.9 Hz, 3H), 3.36-3.33 (m, 2H), 3.29-3.18 (m, 2H), 2.98-2.91 (m, 2H), 2.88 (s, 3H), 2.84 (d, J=2.5 Hz, 1H), 2.34 (dt, J=13.0, 7.6 Hz, 1H), 2.18-2.04 (m, 3H), 1.97-1.87 (m, 2H), 1.79 (dt, J=12.9, 8.7 Hz, 1H), 1.36 (t, J=6.9 Hz, 4H). Analytical HPLC (Acquity): RT=1.9 min, HI: 96.9%. hGPR40 EC$_{50}$=4600 nM.

EXAMPLE 81

2-((2R,4R)-1-(4-(1-(5-Ethoxy-2-fluorophenyl)piperidin-4-yloxy)phenyl)-4-(1H-1,2,3-triazol-1-yl)pyrrolidin-2-yl)acetic acid

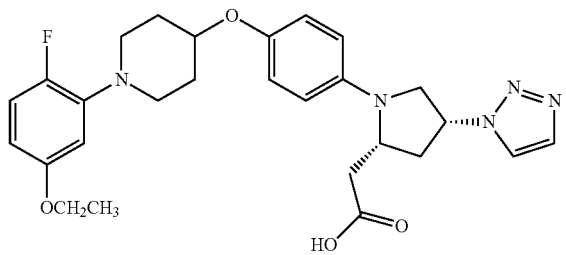 [SMILES: CCOc1ccc(F)c(N2CCC(Oc3ccc(N4C[C@H](n5ccnn5)C[C@@H]4CC(=O)O)cc3)CC2)c1]

Example 81 (13.7 mg, 0.027 mmol, 27% yield) was prepared from 1H-1,2,3-triazole following the procedure of Example 66. LC-MS Anal. Calc'd for C$_{27}$H$_{32}$FN$_5$O$_4$: 509.24 found [M+H] 510.29. $^1$H NMR (500 MHz, 1:1 methanol-d$_4$:CDCl$_3$) δ 7.66-7.63 (m, 2H), 6.94-6.85 (m, 3H), 6.64 (d, J=8.9 Hz, 2H), 6.55 (dd, J=7.2, 2.7 Hz, 1H), 6.43 (dt, J=8.8, 3.0 Hz, 1H), 5.33-5.26 (m, 1H), 4.33-4.23 (m, 3H), 4.06 (dd, J=10.2, 4.7 Hz, 1H), 3.97 (q, J=6.9 Hz, 2H), 3.79 (dd, J=10.2, 7.2 Hz, 1H), 3.28 (d, J=3.0 Hz, 1H), 2.96-2.86 (m, 3H), 2.81 (dd, J=16.1, 2.7 Hz, 1H), 2.66 (dt, J=13.9, 4.0 Hz, 1H), 2.28 (dd, J=15.9, 10.4 Hz, 1H), 2.12-2.03 (m, 2H), 1.96-1.86 (m, 2H), 1.36 (t, J=6.9 Hz, 3H). Analytical HPLC (Acquity): RT=1.9 min, HI: 96.4%. hGPR40 EC$_{50}$=1000 nM.

EXAMPLE 82

2-((2R,4R)-1-(4-((1-(2-Cyclobutyl-5-methoxyphenyl)piperidin-4-yl)oxy)phenyl)-4-methoxypyrrolidin-2-yl)acetic acid, HCl

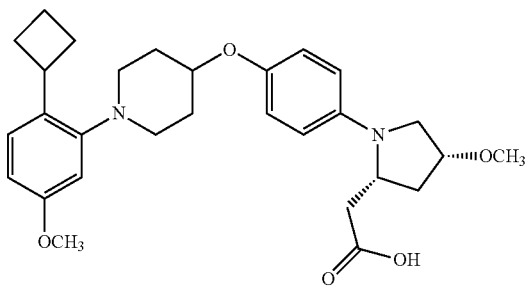 [SMILES: COc1ccc(C2CCC2)c(N2CCC(Oc3ccc(N4C[C@H](OC)C[C@@H]4CC(=O)O)cc3)CC2)c1]

Example 82 (beige solid, 13 mg) was prepared from potassium cyclobutyltrifluoroborate following the procedure of Example 59. LC-MS Anal. Calc'd for C$_{29}$H$_{38}$N$_2$O$_5$: 494.3, found [M+H] 495.3. $^1$H NMR (400 MHz, acetonitrile-d$_3$) δ 7.54 (d, J=2.6 Hz, 1H), 7.21-6.68 (m, 6H), 4.61 (br. s, 1H), 4.26-3.96 (m, 1H), 3.84-3.67 (m, 3H), 3.65-3.56 (m, 2H), 3.54-3.44 (m, 1H), 3.40-3.16 (m, 12H), 2.75-2.48 (m, 2H), 2.44-2.20 (m, 4H), 2.10 (br. s, 3H), 1.97 (br. s, 1H). Analytical HPLC: RT=8.4 min, HI: 95.0%. hGPR40 EC$_{50}$=310 nM.

EXAMPLE 83

Isomer 1 and Isomer 2

2-((2R,4R)-1-(4-(((3,4-trans)-1-(5-Fluoro-2-methoxypyridin-4-yl)-3-methylpiperidin-4-yl)oxy)phenyl)-4-methoxypyrrolidin-2-yl)acetic acid, Isomer 1 and Isomer 2

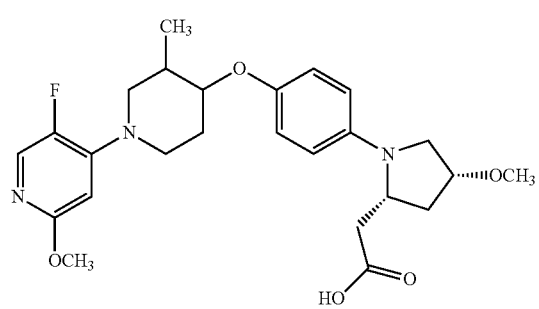 [SMILES: COc1cc(N2CCC(Oc3ccc(N4C[C@H](OC)C[C@@H]4CC(=O)O)cc3)C(C)C2)c(F)cn1]

83A. (3,4-trans)-1-Benzyl-3-methylpiperidin-4-ol: To a solution of 1-benzyl-3-methylpiperidin-4-one (1.00 g, 4.92 mmol) in MeOH (3 mL) and water (7 mL), 85% aq. phosphoric acid (0.33 mL, 5.7 mmol) was added and the reaction mixture was cooled to −10° C. NaBH$_4$ (373 mg, 9.86 mmol) was added in three portions over 1 h and the reaction mixture was slowly warmed to rt and stirred overnight. The reaction was quenched with water, diluted with EtOAc, and the layers were separated. The aqueous layer was extracted with EtOAc. The combined organic layers were washed with brine, dried (Na$_2$SO$_4$), and concentrated to provide 83A (1.00 g, 4.87 mmol, 99% yield) as a pale yellow oil. LC-MS Anal. Calc'd for C$_{13}$H$_{19}$NO: 205.30, found [M+H] 206.0. $^1$H NMR (400 MHz, CDCl$_3$) δ 7.29-7.32 (m, 5H), 3.48 (s, 2H), 3.11-3.18 (m, 1H), 2.76-2.89 (m, 2H), 1.99-2.06 (m, 1H), 1.90 (m, 1H), 1.54-1.67 (m, 4H), 0.94 (d, J=5.2 Hz, 3H).

83B. (3,4-trans)-3-Methylpiperidin-4-ol: To a solution of 83A (1.0 g, 4.9 mmol) in MeOH (5 mL) and THF (5 mL), 10% Pd/C (0.259 g, 0.244 mmol) was added and the reaction mixture was stirred at rt under H$_2$ (1 atm) for 3 h. The reaction mixture was filtered through a pad of CELITE® and washed with MeOH. The filtrate was concentrated to provide 83B (0.47 g, 4.1 mmol, 84% yield) as a brown oil. LC-MS Anal. Calc'd for C$_6$H$_{13}$NO:115.1, found [M+H] 116.2. $^1$H NMR (400 MHz, DMSO-d$_6$) δ 2.72-2.97 (m, 4H), 2.40 (m, 1H), 2.03 (dd, J=12.24, 10.86 Hz, 1H), 1.67-1.76 (m, 1H), 1.15-1.28 (m, 2H), 0.98 (d, J=6.8 Hz, 3H).

83C. (3,4-trans)-1-(5-Fluoro-2-methoxypyridin-4-yl)-3-methylpiperidin-4-ol: To a solution of 83B (0.45 g, 3.9 mmol) in DMSO (1.3 mL), 4-bromo-5-fluoro-2-methoxypyridine (0.805 g, 3.91 mmol) and K$_2$CO$_3$ (0.810 g, 5.86 mmol) were added and the reaction mixture was heated to 110° C. The reaction was quenched with water and extracted with EtOAc (3×). The combined organic layers were washed with brine, dried (Na$_2$SO$_4$), and concentrated. The crude product was purified by silica chromatography to provide 83C (0.57 g, 2.4 mmol, 61% yield) as a white solid. LC-MS Anal. Calc'd for C$_{12}$H$_{17}$FN$_2$O$_2$: 240.1, found [M+H] 241.1.

¹H NMR (400 MHz, CDCl₃) δ 7.26-7.77 (d, J=5.2 Hz, 1H), 6.12 (d, J=6.4 Hz, 1H), 3.85 (s, 3H), 3.66-3.70 (m, 2H), 3.32-3.36 (m, 1H), 2.82-2.89 (m, 1H), 2.49-2.55 (m, 1H), 2.00-2.04 (m, 1H), 1.65-1.74 (m, 2H), 1.51-1.57 (m, 1H), 1.03 (d, J=7.00 Hz, 3H).

Example 83, Isomer 1 and Isomer 2 were prepared from 83C as single isomers following the procedure of Example 17. Example 83, Isomer 1 (off-white solid, 15.4 mg). LC-MS Anal. Calc'd for C₂₅H₃₂FN₃O₅: 473.2, found [M+H] 474.2. ¹H NMR (400 MHz, DMSO-d₆) δ 7.86 (d, J=5.46 Hz, 1H), 6.89 (d, J=9.04 Hz, 2H), 6.51 (d, J=9.10 Hz, 2H), 6.29 (d, J=6.71 Hz, 1H), 4.04-4.09 (m, 1H), 3.96-4.02 (m, 1H), 3.85-3.93 (m, 1H), 3.78 (s, 3H), 3.56-3.63 (m, 2H), 3.38-3.41 (m, 1H), 3.29-3.37 (m, 4H), 2.94-3.02 (m, 1H), 2.72-2.79 (m, 1H), 2.58-2.64 (m, 1H), 2.32-2.43 (m, 1H), 1.99-2.19 (m, 3H), 1.86-1.94 (m, 1H), 1.47-1.59 (m, 1H), 1.04 (d, J=6.65 Hz, 3H). Analytical HPLC: RT=7.5 min, HI: 97.2%. hGPR40 EC₅₀=4800 nM. Example 83, Isomer 2 (off-white solid, 12.2 mg). LC-MS Anal. Calc'd for C₂₅H₃₂FN₃O₅: 473.2, found [M+H] 474.2. ¹H NMR (400 MHz, DMSO-d₆) δ 7.86 (d, J=5.46 Hz, 1H), 6.88 (d, J=8.97 Hz, 2H), 6.51 (d, J=8.97 Hz, 2H), 6.28 (d, J=6.65 Hz, 1H), 4.04-4.08 (m, 1H), 3.85-4.02 (m, 2H), 3.78 (s, 3H), 3.55-3.62 (m, 2H), 3.38-3.41 (m, 1H), 3.28 (s, 3H), 3.26-3.28 (m, 1H), 2.94-3.02 (m, 1H), 2.71-2.79 (m, 1H), 2.56-2.63 (m, 1H), 2.32-2.40 (m, 1H), 1.99-2.19 (m, 3H), 1.85-1.92 (m, 1H), 1.48-1.59 (m, 1H), 1.04 (d, J=6.65 Hz, 3H). Analytical HPLC: RT=7.6 min, HI: 94.9%. hGPR40 EC₅₀=370 nM.

EXAMPLE 84

Isomer 1 and Isomer 2

2-((2R,4R)-1-(4-(((3,4-trans)-1-(5-Chloro-2-methoxypyridin-4-yl)-3-methylpiperidin-4-yl)oxy)phenyl)-4-methoxypyrrolidin-2-yl)acetic acid, TFA

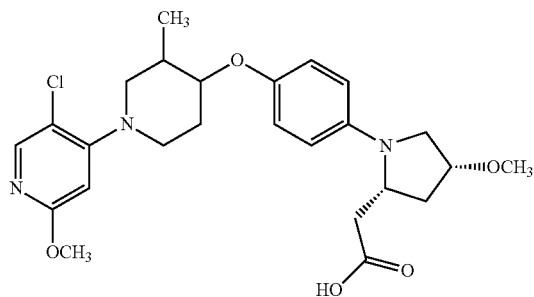 [SMILES: COc1cc(N2CCC(Oc3ccc(N4C[C@H](OC)C[C@@H]4CC(=O)O)cc3)C(C)C2)c(Cl)cn1]

84A. (3,4-trans)-tert-Butyl 4-hydroxy-3-methylpiperidine-1-carboxylate: To a solution of 83B (2.8 g, 24 mmol) in 1 M aq. NaOH (73 mL, 73 mmol) and THF (8 mL) at 0° C., Boc₂O (6.21 mL, 26.7 mmol) was added followed by water (80 mL) and THF (22 mL). The mixture was stirred at 0° C. for 30 min and then warmed to rt and stirred for 12 h. The reaction mixture was diluted with CH₂Cl₂, washed with water and brine, dried (Na₂SO₄), and concentrated. The crude product was purified by silica chromatography to provide 84A (3.7 g, 17 mmol, 71% yield) as a colorless oil. ¹H NMR (400 MHz, CDCl₃) δ 4.10-4.18 (m, 2H), 3.25-3.37 (m, 1H), 2.79-2.90 (m, 1H), 1.88-1.97 (m, 1H), 1.38-1.56 (m, 12H), 1.02 (d, J=6.56 Hz, 3H).

84B. (3,4-trans)-tert-Butyl 4-(((2S,4R)-2-(cyanomethyl)-4-methoxypyrrolidin-1-yl)phenoxy)-3-methylpiperidine-1-carboxylate: 84B (pale yellow oil, 300 mg) was prepared from 84A following the procedure of Example 17. LC-MS Anal. Calc'd for C₂₄H₃₅N₃O₄: 429.2, found [M+H] 430.2. ¹H NMR (400 MHz, CDCl₃) δ 6.50 (d, J=9.04 Hz, 2H), 6.87 (d, J=9.04 Hz, 2H), 4.05-4.12 (m, 2H), 3.84-3.92 (m, 2H), 3.72-3.79 (m, 1H), 3.48-3.52 (m, 1H), 3.36-3.40 (m, 1H), 3.38 (s, 3H), 2.96-3.06 (m, 1H), 2.67-2.83 (m, 3H), 2.31-2.37 (m, 1H), 2.15-2.24 (m, 1H), 1.80-2.02 (m, 2H), 1.49-1.53 (m, 1H), 1.46 (s, 9H), 1.05 (d, J=6.65 Hz, 3H).

84C. 2-((2S,4R)-4-Methoxy-1-(4-(((3,4-trans)-3-methylpiperidin-4-yl)oxy)phenyl)pyrrolidin-2-yl)acetonitrile, HCl: To a solution of 84B (150 mg, 0.349 mmol) in dioxane (0.5 mL), a 4 M solution of HCl in dioxane (0.20 mL, 0.80 mmol) was added at 0° C. and the reaction mixture was slowly warmed to rt and stirred for 5 h. The reaction mixture was concentrated to give 84C (120 mg, 0.328 mmol, 94% yield) as a semisolid.

84D. 2-((2S,4R)-1-(4-(((3,4-trans)-1-(5-Chloro-2-methoxypyridin-4-yl)-3-methylpiperidin-4-yl)oxy)phenyl)-4-methoxypyrrolidin-2-yl)acetonitrile, Isomer 1 and Isomer 2: To a solution of 84C (100 mg, 0.273 mmol) in DMSO (91 µL), K₂CO₃ (189 mg, 1.37 mmol) was added followed by 27B (60.8 mg, 0.273 mmol). The reaction mixture was heated to 110° C. overnight. The reaction mixture was diluted with EtOAc and washed with water and brine, dried (Na₂SO₄), and concentrated. The crude product was purified by RP-Prep. HPLC followed by chiral SFC to recover 84D, Isomer 1 and Isomer 2 as single isomers. 84D, Isomer 1 (22 mg, 0.047 mmol, 17% yield) was isolated as a pale yellow oil. LC-MS Anal. Calc'd for C₂₅H₃₁ClN₄O₃: 470.99, found [M+H] 471.0. ¹H NMR (400 MHz, CDCl₃) δ 7.96 (s, 1H), 6.89-6.91 (m, 2H), 6.50-6.54 (m, 2H), 6.26 (s, 1H), 4.05-4.13 (m, 2H), 3.88 (s, 3H), 3.80 (td, J=8.66, 4.08 Hz, 1H), 3.58-3.65 (m, 2H), 3.51 (d, J=10.60 Hz, 1H), 3.36-3.41 (m, 4H), 2.88-2.96 (m, 1H), 2.68-2.79 (m, 3H), 2.31-2.37 (m, 1H), 2.15-2.25 (m, 1H), 2.01-2.15 (m, 2H), 1.69-1.80 (m, 1H), 1.12 (d, J=6.71 Hz, 3H). 84D, Isomer 2 (24 mg, 0.051 mmol, 19% yield) pale yellow oil. LC-MS Anal. Calc'd for C₂₅H₃₁ClN₄O₃: 470.99, found [M+H] 471.0. ¹H NMR (400 MHz, CDCl₃) δ 7.96 (s, 1H), 6.89-6.91 (m, 2H), 6.50-6.54 (m, 2H), 6.26 (s, 1H), 4.06-4.13 (m, 2H), 3.87 (s, 3H), 3.80 (td, J=8.64, 4.17 Hz, 1H), 3.58-3.65 (m, 2H), 3.48-3.53 (m, 1H), 3.35-3.41 (m, 4H), 2.89-2.96 (m, 1H), 2.68-2.79 (m, 3H), 2.31-2.37 (m, 1H), 2.02-2.25 (m, 3H), 1.70-1.80 (m, 1H), 1.12 (d, J=6.71 Hz, 3H).

Example 84, Isomer 1 and Isomer 2 were prepared as single isomers from 84D, Isomer 1 and Isomer 2 following the procedure of Example 2. Example 84, Isomer 1 (brown solid, 12 mg). LC-MS Anal. Calc'd for C₂₅H₃₂ClN₃O₅: 489.2, found [M+H] 490.3. ¹H NMR (400 MHz, DMSO-d₆) δ 8.03 (s, 1H), 6.90 (d, J=8.0 Hz, 2H), 6.52 (d, J=8.01 Hz, 2H), 6.41 (s, 1H), 4.04-4.09 (m, 1H), 3.96-4.02 (m, 1H), 3.85-3.93 (m, 1H), 3.78 (s, 3H), 3.56-3.63 (m, 2H), 3.38-3.41 (m, 1H), 3.29-3.37 (m, 4H), 2.94-3.02 (m, 1H), 2.72-2.79 (m, 1H), 2.58-2.64 (m, 1H), 2.32-2.43 (m, 1H), 1.99-2.19 (m, 3H), 1.86-1.94 (m, 1H), 1.47-1.59 (m, 1H), 1.04 (d, J=6.68 Hz, 3H). Analytical HPLC (12 min gradient, 15 min stop): RT=10.8 min, HI: 95.7%. hGPR40 EC₅₀=730 nM. Example 84, Isomer 2 (brown solid, 10 mg). LC-MS Anal. Calc'd for C₂₅H₃₂ClN₃O₅: 489.2, found[M+H] 490.3. ¹H NMR (400 MHz, DMSO-d₆) δ 8.31 (s, 1H), 6.88 (d, J=8.97 Hz, 2H), 6.51 (d, J=8.97 Hz, 2H), 6.40 (s, 1H), 4.04-4.08 (m, 1H), 3.85-4.02 (m, 2H), 3.78 (s, 3H), 3.55-3.62 (m, 2H), 3.38-3.41 (m, 1H), 3.28 (s, 3H), 3.26-3.28 (m, 1H), 2.94-3.02 (m, 1H), 2.71-2.79 (m, 1H), 2.56-2.63 (m, 1H), 2.32-2.40 (m, 1H), 1.99-2.19 (m, 3H), 1.85-1.92 (m, 1H), 1.48-

1.59 (m, 1H), 1.04 (d, J=6.65 Hz, 3H). Analytical HPLC (25 min gradient, 30 min stop): RT=17.4 min, HI: 98.3%. hGPR40 $EC_{50}$=180 nM.

EXAMPLE 85

2-((2R,4R)-1-(4-((1-(5-Ethoxy-2-fluorophenyl)piperidin-4-yl)oxy)phenyl)-4-(trifluoromethyl)pyrrolidin-2-yl)acetic acid

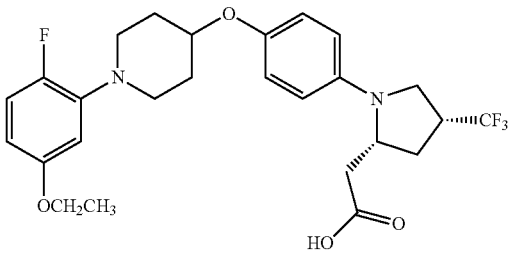 [SMILES: CCOc1ccc(F)c(N2CCC(Oc3ccc(N4C[C@H](C(F)(F)F)C[C@@H]4CC(=O)O)cc3)CC2)c1]

85A. 1-(5-Ethoxy-2-fluorophenyl)piperidin-4-ol: A mixture of 4-ethoxy-1,2-difluorobenzene (17.5 mL, 126 mmol), piperidin-4-ol (39.2 g, 379 mmol), DMSO (42 mL), and pyridine (21.1 mL) in a flask equipped with a reflux condenser under nitrogen was heated to 140° C. for 48 h. The reaction mixture was diluted with 4/1 hexanes/EtOAc and washed with 2% aq. $NaHCO_3$, water, and brine. The organic layer was dried ($MgSO_4$) and concentrated. The crude product was purified by silica chromatography to provide 85A (10.6 g, 44.2 mmol, 35% yield) as a yellow oil. LC-MS Anal. Calc'd for $C_{13}H_{18}FNO_2$: 239.29, found [M+H] 240.1. $^1$H NMR (400 MHz, $CDCl_3$) δ 6.90 (dd, J=12.3, 8.8 Hz, 1H), 6.51 (dd, J=7.4, 3.0 Hz, 1H), 6.39 (dt, J=8.8, 3.2 Hz, 1H), 3.97 (q, J=7.0 Hz, 2H), 3.89-3.78 (m, 1H), 3.41-3.30 (m, 2H), 2.82 (ddd, J=12.2, 9.5, 3.0 Hz, 2H), 2.04-1.95 (m, 2H), 1.74 (dtd, J=12.9, 9.2, 3.7 Hz, 2H), 1.53-1.46 (m, 1H), 1.39 (t, J=6.9 Hz, 3H).

85B. 1-(5-Ethoxy-2-fluorophenyl)piperidin-4-yl 4-methylbenzenesulfonate: To a solution of 85A (10.4 g, 43.4 mmol) and TsCl (12.4 g, 65.1 mmol) in $CH_2Cl_2$ (108 mL), pyridine (35.1 mL, 434 mmol) was added dropwise. The reaction mixture was stirred at rt overnight. The reaction mixture was diluted with EtOAc, washed with water and brine, dried ($MgSO_4$), and concentrated. The crude product was purified by silica chromatography to provide 85B (13.4 g, 34.1 mmol, 79% yield) as a colorless oil. LC-MS Anal. Calc'd for $C_2H_{24}FNO_4S$: 393.47, found [M+H] 394.1. $^1$H NMR (400 MHz, $CDCl_3$) δ 7.86-7.78 (m, 2H), 7.39-7.31 (m, 2H), 6.88 (dd, J=12.1, 8.8 Hz, 1H), 6.46 (dd, J=7.4, 3.0 Hz, 1H), 6.39 (dt, J=8.9, 3.2 Hz, 1H), 4.69 (tt, J=7.4, 3.8 Hz, 1H), 3.96 (q, J=6.9 Hz, 2H), 3.22 (ddd, J=11.8, 7.3, 4.0 Hz, 2H), 2.90 (ddd, J=11.8, 7.6, 3.9 Hz, 2H), 2.46 (s, 3H), 2.03-1.86 (m, 4H), 1.38 (t, J=6.9 Hz, 3H).

85C. 1-(5-Ethoxy-2-fluorophenyl)-4-(4-iodophenoxy)piperidine: A solution of 4-iodophenol (5.62 g, 25.6 mmol), 85B (6.704 g, 17.04 mmol), and $Cs_2CO_3$ (16.7 g, 51.1 mmol) in anhydrous DMF (43 mL) was heated to 55° C. for 16 h. The reaction mixture was diluted with EtOAc and water and extracted with EtOAc (3×). The combined organic layers were washed with water, dried ($MgSO_4$), and concentrated. The crude product was purified by silica chromatography to provide 85C (3.99 g, 9.04 mmol, 53% yield) as a white solid. LC-MS Anal. Calc'd for $C_{19}H_{21}FINO_2$: 441.28, found [M+H] 442.0. $^1$H NMR (400 MHz, $CDCl_3$) δ 7.61-7.51 (m, 2H), 6.91 (dd, J=12.1, 8.8 Hz, 1H), 6.76-6.67 (m, 2H), 6.53 (dd, J=7.4, 3.0 Hz, 1H), 6.40 (dt, J=8.8, 3.2 Hz, 1H), 4.42 (tt, J=7.2, 3.6 Hz, 1H), 3.98 (q, J=6.9 Hz, 2H), 3.31 (ddd, J=11.6, 7.8, 3.5 Hz, 2H), 2.98 (ddd, J=11.8, 8.0, 3.5 Hz, 2H), 2.17-2.05 (m, 2H), 2.02-1.90 (m, 2H), 1.39 (t, J=6.9 Hz, 3H).

Example 85 (brown oil, 28 mg) was prepared from 1K and 85C following the procedure of Example 2. LC-MS Anal. Calc'd for $C_{26}H_{30}F_4N_2O_4$: 510.52, found [M+H] 511.2. $^1$H NMR (400 MHz, DMSO-$d_6$) δ 7.01 (dd, J=8.8, 12.5 Hz, 1H), 6.91 (d, J=8.1 Hz, 2H), 6.65 (d, J=8.1 Hz, 2H), 6.54 (dd, J=2.9, 7.5 Hz, 1H), 6.47 (td, J=3.2, 8.8 Hz, 1H), 4.37-4.30 (m, 1H), 4.15-4.06 (m, 1H), 3.98 (d, J=7.0 Hz, 2H), 3.52-3.45 (m, 1H), 3.27-3.19 (m, 4H), 2.93-2.85 (m, 4H), 2.13-1.97 (m, 3H), 1.93-1.85 (m, 1H), 1.79-1.69 (m, 2H), 1.34-1.27 (t, J=7.0 Hz, 3H). Analytical HPLC (25 min gradient, 30 min stop): RT=18.6 min, HI: 95.0%. hGPR40 $EC_{50}$=320 nM. hGPR40 IP1 $EC_{50}$=70 nM.

EXAMPLE 86

2-((2R,4R)-4-Methoxy-1-(4-((1-(6-methoxyimidazo[1,2-b]pyridazin-8-yl)piperidin-4-yl)oxy)phenyl)pyrrolidin-2-yl)acetic acid, TFA

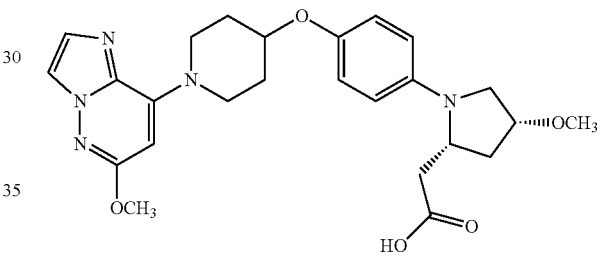

86A. tert-Butyl 4-(4-((2S,4R)-2-(cyanomethyl)-4-methoxypyrrolidin-1-yl)phenoxy)piperidine-1-carboxylate: 86A was prepared from piperidin-4-ol following the procedure of Example 84. LC-MS Anal. Calc'd for $C_{23}H_{33}N_3O_4$: 415.53, found [M+H] 416.4.

86B. Methyl 2-((2R,4R)-4-methoxy-1-(4-(piperidin-4-yloxy)phenyl)pyrrolidin-2-yl)acetate: To a solution of MeOH (15 mL) and $CH_2Cl_2$ (20 mL) at 0° C. was added AcCl (10.0 mL, 141 mmol). The reaction mixture was warmed to rt and stirred for 30 min. This solution was added to 86A (0.500 g, 1.203 mmol) and the reaction mixture was stirred at rt for 1 h. The reaction mixture was diluted with $CH_2Cl_2$ and washed with sat. aq. $NaHCO_3$ and brine. The organic layer was dried ($Na_2SO_4$), filtered, and concentrated to give 86B (0.320 g, 0.918 mmol, 76% yield) as a light brown gummy oil. LC-MS Anal. Calc'd for $C_{19}H_{28}N_2O_4$: 348.44, found [M+H] 349.2.

86C. Methyl 2-((2R,4R)-1-(4-((1-(6-chloroimidazo[1,2-b]pyridazin-8-yl)piperidin-4-yl)oxy)phenyl)-4-methoxypyrrolidin-2-yl)acetate: To a solution of 86B (0.150 g, 0.430 mmol) in DMF (5 mL) was added to 8-bromo-6-chloroimidazo[1,2-b]pyridazine (0.150 g, 0.646 mmol) and $K_2CO_3$ (0.178 g, 1.29 mmol). The reaction mixture was heated to 100° C. for 4 h. The reaction mixture was concentrated, diluted with water, and extracted with EtOAc (3×). The organic layer was dried ($Na_2SO_4$) and concentrated. The crude product was purified by silica chromatography to afford 86C (0.060 g, 0.120 mmol, 28% yield) as a light brown gummy oil. LC-MS Anal. Calc'd for $C_{25}H_{30}ClN_5O_4$: 499.99, found [M+H] 500. $^1$H NMR (400 MHz, CDCl$_3$) δ 7.76 (d, J=1.2 Hz, 1H), 7.54 (d, J=1.2 Hz, 1H), 6.92 (d, J=9.0 Hz, 2H), 6.57 (d, J=9.1 Hz, 2H), 6.11 (s, 1H), 4.48-4.41 (m, 1H), 4.32-4.22 (m, 2H), 4.22-4.14 (m, 1H), 4.14-4.06 (m, 3H), 3.73 (s, 3H), 3.54-3.48 (m, 1H), 3.41-3.39 (m, 1H), 3.39 (s, 3H), 2.90-2.82 (m, 1H), 2.69 (d, J=10.4 Hz, 1H), 2.21-2.11 (m, 4H), 2.03-1.95 (m, 2H).

Example 86: To a solution of 86C (0.025 g, 0.050 mmol) in MeOH (2 mL) was added sodium methoxide (0.027 g, 0.50 mmol). The reaction mixture was stirred at 100° C. overnight. The reaction mixture was concentrated and the crude product was acidified with 1.5 M aq. HCl to pH 2 and the product was extracted with EtOAc (3×). The combined organic layers were dried (Na$_2$SO$_4$) and concentrated. The crude product was purified by RP-Prep. HPLC to provide Example 86 (0.010 g, 0.020 mmol, 40% yield) as a light brown gummy oil. LC-MS Anal. Calc'd for $C_{25}H_{31}N_5O_5$: 481.54, found [M$^+$] 482.6. $^1$H NMR (400 MHz, DMSO-d$_6$) δ 7.88 (d, J=1.2 Hz, 1H), 7.42 (d, J=1.1 Hz, 1H), 6.91 (d, J=9.0 Hz, 2H), 6.51 (d, J=9.1 Hz, 2H), 5.92 (s, 1H), 4.45-4.39 (m, 3H), 4.06 (t, J=4.9 Hz, 2H), 3.85 (s, 3H), 3.74-3.68 (m, 2H), 3.30-3.29 (m, 2H), 3.28 (s, 3H), 2.67 (td, J=1.9, 3.7 Hz, 1H), 2.63 (dd, J=2.6, 15.2 Hz, 1H), 2.33-2.30 (m, 1H), 2.19-2.11 (m, 3H), 1.72-1.62 (m, 2H). Analytical HPLC (XBridge Phenyl column, 12 min gradient, 15 min stop): RT=7.0 min, HI: 95.0%. hGPR40 EC$_{50}$=4700 nM.

EXAMPLE 87

2-((2R,4R)-1-(4-((1-(5-Chloro-2-methoxypyridin-4-yl)piperidin-4-yl)oxy)phenyl)-4-methoxypyrrolidin-2-yl)acetic acid, TFA

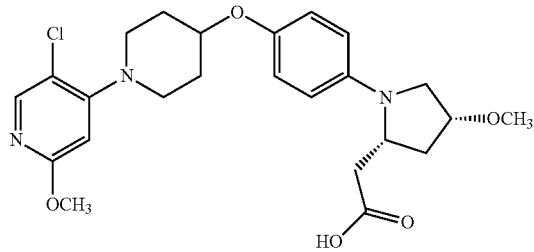 [SMILES: COc1cc(N2CCC(Oc3ccc(N4C[C@H](OC)C[C@@H]4CC(=O)O)cc3)CC2)c(Cl)cn1]

Example 87 (brown solid, 5.8 mg) was prepared from 112A and 4A following the procedure of Example 2. LC-MS Anal. Calc'd for $C_{24}H_{30}ClN_3O_5$: 475.97, found [M$^+$] 476.2. $^1$H NMR (500 MHz, DMSO-d$_6$) δ 7.97 (s, 1H), 6.94-6.88 (m, 2H), 6.86-6.70 (m, 2H), 6.29 (s, 1H), 4.38 (m, 1H), 4.21 (dd, J=3.2, 7.1 Hz, 1H), 4.15-4.05 (m, 1H), 3.89 (s, 3H), 3.43-3.35 (m, 4H), 3.16 (s, 3H), 2.98-2.16 (m, 2H), 2.65-2.60 (m, 1H), 2.51-2.50 (m, 1H), 2.44-2.40 (m, 1H), 2.10-2.04 (m, 3H), 2.02-1.80-1.74 (m, 2H). Analytical HPLC (XBridge Phenyl column, 12 min gradient, 15 min stop): RT=8.9 min, HI: 95.0%. hGPR40 EC$_{50}$=350 nM.

EXAMPLE 88

2-((2S,3S,4R)-1-(4-((1-(5-Ethoxy-2-fluorophenyl)piperidin-4-yl)oxy)phenyl)-3-ethyl-4-methoxypyrrolidin-2-yl)acetic acid, TFA

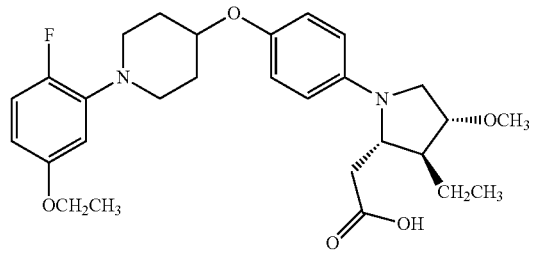 [SMILES: CCOc1ccc(F)c(N2CCC(Oc3ccc(N4C[C@H](OC)[C@@H](CC)[C@@H]4CC(=O)O)cc3)CC2)c1]

Example 88 (colorless foam, 44 mg) was prepared from ethylmagnesium bromide following the procedure of Example 118. LC-MS Anal. Calc'd for $C_{28}H_{37}FN_2O_5$: 500.2, found [M+H] 501.2. $^1$H NMR (500 MHz, DMSO-d$_6$) δ 7.01 (dd, J=12.4, 8.8 Hz, 1H), 6.90 (d, J=9.1 Hz, 2H), 6.54 (dd, J=7.4, 3.0 Hz, 3H), 6.47 (dt, J=8.9, 3.1 Hz, 1H), 4.39-4.22 (m, 1H), 3.98 (q, J=7.1 Hz, 2H), 3.82-3.61 (m, 2H), 3.42-3.33 (m, 2H), 3.31-3.22 (m, 5H), 2.97-2.81 (m, 2H), 2.64-2.55 (m, 1H), 2.49-2.38 (m, 1H), 2.07-1.94 (m, 3H), 1.81-1.67 (m, 2H), 1.36-1.14 (m, 5H), 0.93 (t, J=7.3 Hz, 3H). Analytical HPLC: RT=10.4 min, HI: 97.2%. hGPR40 EC$_{50}$=250 nM.

EXAMPLE 89

2-((2S,3S,4R)-1-(4-((1-(5-Ethoxy-2-fluorophenyl)piperidin-4-yl)oxy)phenyl)-3-isopropyl-4-methoxypyrrolidin-2-yl)acetic acid, TFA

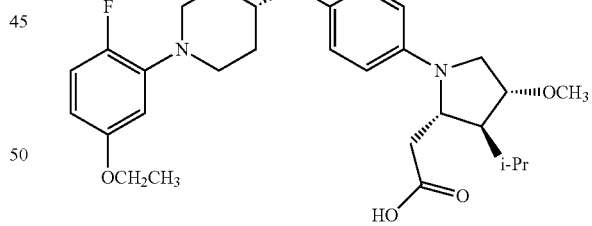

Example 89 (47 mg, 31% yield) was prepared from isopropylmagnesium bromide following the procedure of Example 118. LC-MS Anal. Calc'd for $C_{29}H_{39}FN_2O_5$: 514.2, found [M+H] 515.2. $^1$H NMR (500 MHz, DMSO-d$_6$) δ 7.00 (dd, J=12.4, 8.8 Hz, 1H), 6.89 (d, J=9.1 Hz, 2H), 6.58-6.49 (m, 3H), 6.46 (dt, J=8.8, 3.2 Hz, 1H), 4.35-4.23 (m, 1H), 3.97 (q, J=7.0 Hz, 2H), 3.91-3.80 (m, 2H), 3.42-3.29 (m, 2H), 3.29-3.20 (m, 5H), 2.96-2.83 (m, 2H), 2.56 (dd, J=14.9, 3.0 Hz, 1H), 2.40 (dd, J=14.7, 10.3 Hz, 1H), 2.06-1.93 (m, 3H), 1.78-1.67 (m, 2H), 1.61-1.49 (m, 1H), 1.30 (t, J=7.0 Hz, 3H), 0.85 (dd, J=6.9, 4.7 Hz, 6H). Analytical HPLC: RT=10.9 min, HI: 97.7%. hGPR40 EC$_{50}$=320 nM.

EXAMPLE 90

2-((2S,3S,4R)-3-Cyclopropyl-1-(4-((1-(5-ethoxy-2-fluorophenyl)piperidin-4-yl)oxy)phenyl)-4-methoxy-pyrrolidin-2-yl)acetic acid, TFA

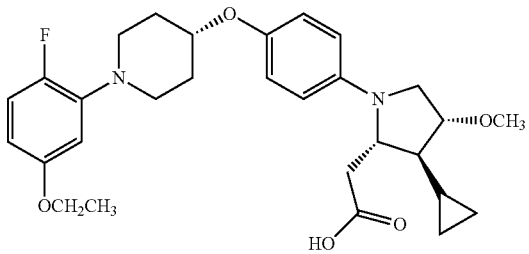

Example 90 (62 mg, 22% yield) was prepared from cyclopropylmagnesium bromide following the procedure of Example 118. LC-MS Anal. Calc'd for $C_{29}H_{37}FN_2O_5$: 512.2, found [M+H] 513.1. $^1$H NMR (400 MHz, DMSO-$d_6$) δ 7.01 (dd, J=12.5, 8.8 Hz, 1H), 6.90 (d, J=9.0 Hz, 2H), 6.60-6.51 (m, 3H), 6.47 (dt, J=8.7, 3.0 Hz, 1H), 4.29 (dt, J=7.7, 3.9 Hz, 1H), 3.97 (q, J=6.8 Hz, 2H), 3.88 (d, J=4.2 Hz, 1H), 3.81 (d, J=7.7 Hz, 1H), 3.52-3.36 (m, 2H), 3.27 (s, 5H), 2.89 (t, J=8.9 Hz, 2H), 2.58 (dd, J=15.2, 3.1 Hz, 1H), 2.41 (dd, J=15.2, 10.6 Hz, 1H), 2.01 (d, J=12.1 Hz, 2H), 1.82-1.64 (m, 2H), 1.54 (d, J=9.5 Hz, 1H), 1.30 (t, J=7.0 Hz, 3H), 0.64-0.53 (m, 1H), 0.44 (ddd, J=16.4, 8.4, 4.3 Hz, 2H), 0.30-0.11 (m, 2H). Analytical HPLC: RT=10.8 min, HI: 98.9%. hGPR40 $EC_{50}$=190 nM.

EXAMPLE 91

2-((2S,3S,4R)-1-(6-(((3,4-trans)-1-(5-Chloro-2-methoxypyridin-4-yl)-3-methylpiperidin-4-yl)oxy)pyridin-3-yl)-4-methoxy-3-methylpyrrolidin-2-yl)acetic acid, HCl

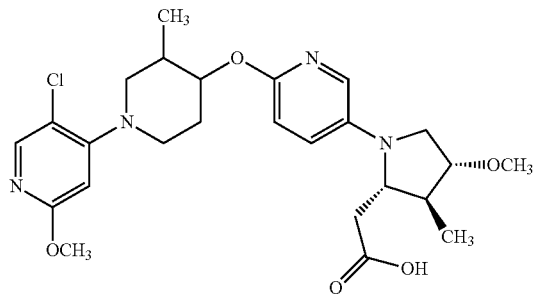 [SMILES: COc1cc(N2CCC(Oc3ccc(N4C[C@H](OC)[C@@H](C)[C@@H]4CC(=O)O)cn3)C(C)C2)c(Cl)cn1]

Example 91 (green powder, 17 mg) was prepared as a single isomer from 132A and 118F following the procedure of Example 118. LC-MS Anal. Calc'd for $C_{25}H_{33}ClN_4O_5$: 504.2, found [M+H] 505.1. $^1$H NMR (400 MHz, DMSO-$d_6$) δ 8.04 (s, 1H), 7.64-7.38 (m, 1H), 7.27-7.07 (m, 1H), 6.95-6.71 (m, 1H), 6.44 (s, 1H), 4.79-4.53 (m, 2H), 3.83 (s, 3H), 3.73-3.58 (m, 2H), 3.55-3.47 (m, 2H), 3.43 (s, 2H), 3.29 (s, 3H), 3.01-2.88 (m, 1H), 2.76-2.56 (m, 2H), 2.39-2.26 (m, 1H), 2.25-2.15 (m, 1H), 2.06-1.93 (m, 1H), 1.71-1.55 (m, 1H), 0.97 (dd, J=13.8, 6.9 Hz, 6H). Analytical HPLC: RT=7.64 min, HI: 96.5%. hGPR40 $EC_{50}$=190 nM. hGPR40 IP1 $EC_{50}$=18 nM.

EXAMPLE 92

2-((2S,3S,4R)-3-Cyclobutyl-1-(4-((1-(5-ethoxy-2-fluorophenyl)piperidin-4-yl)oxy)phenyl)-4-methoxy-pyrrolidin-2-yl)acetic acid, TFA

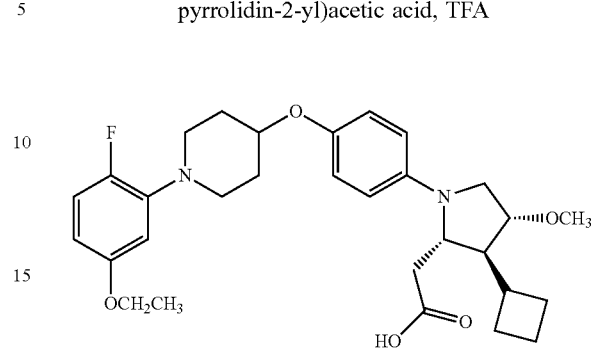

Example 92 (23 mg) was prepared from cyclobutylmagnesium bromide following the procedure of Example 118. LC-MS Anal. Calc'd for $C_{30}H_{39}FN_2O_5$: 526.2. found [M+H] 527.3. $^1$H NMR (500 MHz, DMSO-$d_6$) δ 7.06-6.82 (m, 3H), 6.63-6.35 (m, 3H), 4.40-4.18 (m, 1H), 3.98 (q, J=7.1 Hz, 2H), 3.63 (d, J=3.9 Hz, 2H), 3.37-3.16 (m, 8H), 2.95-2.79 (m, 3H), 2.64-2.55 (m, 2H), 2.48-2.38 (m, 1H), 2.25-1.87 (m, 5H), 1.83-1.56 (m, 5H), 1.31 (t, J=6.9 Hz, 3H). hGPR40 $EC_{50}$=3700 nM.

EXAMPLE 93

2-((2R,4R)-1-(4-(((3,4-trans)-1-(5-Chloro-2-methoxypyridin-4-yl)-3-(cyanomethyl)piperidin-4-yl)oxy)phenyl)-4-methoxypyrrolidin-2-yl)acetic acid, TFA

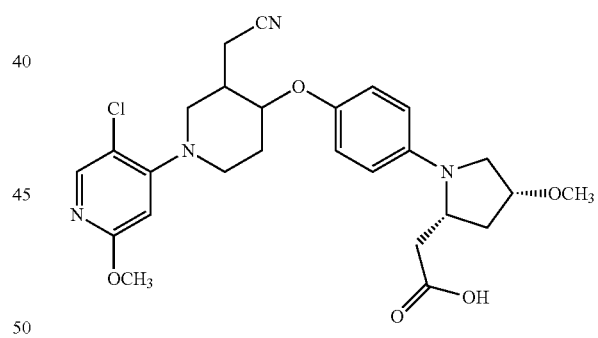

93A. Methyl 2-((2R,4R)-1-(4-hydroxyphenyl)-4-methoxypyrrolidin-2-yl)acetate: 93A was prepared from 23D following the procedure of Example 1. LC-MS Anal. Calc'd for $C_{14}H_{19}NO_4$: 265.31, found: [M+H] 266.1. $^1$H NMR (400 MHz, CDCl$_3$) δ 6.90-6.69 (m, 2H), 6.50 (d, J=7.3 Hz, 2H), 4.46 (s, 1H), 4.17-4.09 (m, 1H), 4.09-4.01 (m, 1H), 3.70 (s, 3H), 3.52-3.40 (m, 1H), 3.36 (s, 3H), 3.35-3.33 (m, 1H), 2.82 (d, J=14.7 Hz, 1H), 2.61 (dd, J=15.3, 10.5 Hz, 1H), 2.24-2.08 (m, 2H).

93B. (3,4-cis)-1-tert-Butyl 3-ethyl 4-hydroxypiperidine-1,3-dicarboxylate: To a 1 L flask with tap water (240 mL) was added sucrose (24.0 g, 11.1 mmol) and baker's yeast (24.0 g, 11.1 mmol). The mixture was stirred at 32° C. for 30 min and then 1-tert-butyl 3-ethyl 4-oxopiperidine-1,3-dicarboxylate (3.00 g, 11.1 mmol) was added. The reaction mixture was stirred at 32° C. for 60 h. The reaction mixture was filtered thought CELITE® and the paste was washed with CH$_2$Cl$_2$ (3×). The filtrate was extracted with CH$_2$Cl$_2$ (3×) and the combined organic layers were washed with water, dried, and concentrated. The crude product was purified by silica chromatography to provide 93B (2.22 g, 8.12 mmol, 74% yield) as a white solid. LC-MS Anal. Calc'd for C$_{13}$H$_{23}$NO$_5$: 273.33, found [M+Na] 296.1. $^1$H NMR (400 MHz, CDCl$_3$) δ 4.27 (br. s, 1H), 4.18 (q, J=7.0 Hz, 2H), 4.00 (br. s, 1H), 3.76-3.63 (m, 1H), 3.39 (br. s, 1H), 3.27 (ddd, J=13.5, 11.3, 3.2 Hz, 1H), 2.98 (br. s, 1H), 2.67-2.55 (m, 1H), 1.87-1.76 (m, 1H), 1.69-1.63 (m, 1H), 1.46 (s, 9H), 1.27 (t, J=7.2 Hz, 3H).

93C. (3,4-cis)-tert-Butyl 4-hydroxy-3-(hydroxymethyl)piperidine-1-carboxylate: To a solution of 93B (1.48 g, 5.41 mmol) in THF (54 mL) at 0° C. was added LAH (0.247 g, 6.50 mmol) in portions. After the addition, the reaction mixture was slowly warmed to rt. The reaction mixture was stirred for 7 h and then cooled to 0° C. Water (0.2 mL), 15% aq. NaOH (0.2 mL), and water (0.6 mL) were added sequentially to the reaction mixture. After stirring for 0.5 h, the mixture was filtered through CELITE® and concentrated. The crude material was dissolved in EtOAc, washed with brine, dried, and concentrated. The crude product was purified by silica chromatography to provide 93C (1.00 g, 4.32 mmol, 80% yield) as a colorless oil. LC-MS Anal. Calc'd for C$_{11}$H$_{21}$NO$_4$: 231.29, found [M-t-Bu+H] 176.1. $^1$H NMR (400 MHz, CDCl$_3$) δ 4.21-4.14 (m, 1H), 3.83-3.70 (m, 2H), 3.52 (dd, J=13.2, 4.0 Hz, 2H), 3.44-3.32 (m, 2H), 3.23 (br. s, 1H), 1.88-1.78 (m, 1H), 1.69 (d, J=4.4 Hz, 2H), 1.44 (s, 9H).

93D. (3,4-cis)-3-(Hydroxymethyl)piperidin-4-ol, TFA: To a solution of 93C (1.00 g, 4.32 mmol) in CH$_2$Cl$_2$ (22 mL) was added TFA (3.33 mL, 43.2 mmol). The reaction mixture was stirred for 2 h at rt and concentrated to give 93D (1.70 g, 4.73 mmol, 100% yield) as a colorless foam. LC-MS Anal. Calc'd for C$_6$H$_{13}$NO$_2$: 131.1. found: [M+H] 132.0.

93E. (3,4-cis)-1-(5-Chloro-2-methoxypyridin-4-yl)-3-(hydroxymethyl)piperidin-4-ol: To a solution of 93D (1.55 g, 4.32 mmol) and K$_2$CO$_3$ (2.69 g, 19.4 mmol) in DMSO (14.4 mL) was added 27B (1.01 g, 4.54 mmol). The reaction mixture was stirred at 110° C. for 16 h. The reaction mixture was diluted with EtOAc and the organic layer was washed with water and brine, dried over Na$_2$SO$_4$, and concentrated. The crude product was purified by silica chromatography to provide 93E (0.680 g, 2.49 mmol, 58% yield) as a colorless oil. LC-MS Anal. Calc'd for C$_{12}$H$_{17}$ClN$_2$O$_3$: 272.1, found: [M+H] 273.1. $^1$H NMR (400 MHz, CDCl$_3$) δ 7.95 (s, 1H), 6.30 (s, 1H), 4.28-4.20 (m, 1H), 3.93 (d, J=4.8 Hz, 2H), 3.87 (s, 3H), 3.23-3.14 (m, 4H), 2.97 (d, J=6.6 Hz, 1H), 2.71 (br. s, 1H), 2.13-2.06 (m, 1H), 1.98-1.88 (m, 2H).

93F. (3,4-cis)-3-(((tert-Butyldiphenylsilyl)oxy)methyl)-1-(5-chloro-2-methoxypyridin-4-yl)piperidin-4-ol, Isomer 1: To a solution of 93E (0.68 g, 2.5 mmol) in DMF (13 mL) was added imidazole (0.25 g, 3.7 mmol) and TBDPS-Cl (0.71 mL, 2.7 mmol). The reaction mixture was stirred at rt for 2 h. The reaction mixture was diluted with EtOAc and the organic layer was washed with water and brine, dried over Na$_2$SO$_4$, and concentrated. The crude product was purified by silica chromatography to provide 93F (0.90 g, 1.8 mmol, 71% yield) as a colorless oil. The racemic material was purified by chiral SFC. 93F, Isomer 1 (0.99 g, 1.9 mmol, 36% yield) was obtained as a colorless oil.

LC-MS Anal. Calc'd for C$_{28}$H$_{35}$ClN$_2$O$_3$Si: 510.2, found: [M+H] 511.1. $^1$H NMR (400 MHz, CDCl$_3$) δ 7.93 (s, 1H), 7.72-7.59 (m, 4H), 7.49-7.32 (m, 6H), 6.24 (s, 1H), 4.22 (d, J=3.1 Hz, 1H), 3.99 (dt, J=12.3, 6.1 Hz, 2H), 3.89-3.84 (m, 4H), 3.25-3.18 (m, 1H), 3.18-3.14 (m, 1H), 3.13-3.04 (m, 2H), 2.11-2.01 (m, 1H), 1.91-1.82 (m, 2H), 1.06 (s, 9H).

93G. Methyl 2-((2R,4R)-1-(4-(((3,4-trans)-3-(((tert-butyldiphenylsilyl)oxy)methyl)-1-(5-chloro-2-methoxypyridin-4-yl)piperidin-4-yl)oxy)phenyl)-4-methoxypyrrolidin-2-yl)acetate: To a solution of 93A (96 mg, 0.19 mmol), 93F (52 mg, 0.20 mmol), and Bu$_3$P (74 μL, 0.30 mmol) in toluene (2.3 mL) was added ADDP (76 mg, 0.30 mmol). The reaction mixture was sonicated for 2 h. The reaction mixture was poured into hexanes (5 mL), filtered, and concentrated. The crude product was purified by silica chromatography to provide 93G (73 mg, 0.096 mmol, 51% yield) as a colorless oil. LC-MS Anal. Calc'd for C$_{42}$H$_{52}$ClN$_3$O$_6$Si: 757.3, found: [M+H] 758.1. $^1$H NMR (400 MHz, CDCl$_3$) δ 7.97 (s, 1H), 7.69-7.63 (m, 2H), 7.60 (dd, J=8.0, 1.4 Hz, 2H), 7.45-7.33 (m, 4H), 7.33-7.27 (m, 2H), 6.86 (d, J=9.0 Hz, 2H), 6.52 (d, J=9.0 Hz, 2H), 6.25 (s, 1H), 4.24 (td, J=8.4, 4.2 Hz, 1H), 4.18-4.11 (m, 1H), 4.08 (t, J=4.8 Hz, 1H), 3.98-3.84 (m, 5H), 3.71 (s, 3H), 3.60 (dd, J=12.0, 1.9 Hz, 1H), 3.53-3.44 (m, 2H), 3.41-3.33 (m, 4H), 2.95-2.78 (m, 3H), 2.63 (dd, J=15.4, 10.6 Hz, 1H), 2.29-2.21 (m, 1H), 2.19-2.07 (m, 3H), 1.86-1.72 (m, 1H), 1.06 (s, 9H).

93H. Methyl 2-((2R,4R)-1-(4-(((3,4-trans)-1-(5-chloro-2-methoxypyridin-4-yl)-3-(hydroxymethyl)piperidin-4-yl)oxy)phenyl)-4-methoxypyrrolidin-2-yl)acetate, Isomer 1: To a solution of 93G (500 mg, 0.659 mmol) in THF (3.3 mL) was added a 1 M solution of TBAF (989 μL, 0.989 mmol) in THF. The reaction mixture was stirred for 1 h and diluted with EtOAc. The organic layer was washed with water and brine, dried over Na$_2$SO$_4$, and concentrated. The crude product was purified by silica chromatography to provide 93H (313 mg, 0.602 mmol, 91% yield). LC-MS Anal. Calc'd for C$_{26}$H$_{34}$ClN$_3$O$_6$: 519.2, found [M+H] 520.0. $^1$H NMR (400 MHz, CDCl$_3$) δ 7.99 (s, 1H), 7.00-6.84 (m, 2H), 6.55 (d, J=8.8 Hz, 2H), 6.31 (s, 1H), 4.28-4.08 (m, 3H), 3.99-3.80 (m, 4H), 3.76-3.67 (m, 3H), 3.59 (dd, J=12.0, 2.1 Hz, 1H), 3.53-3.43 (m, 2H), 3.41-3.32 (m, 4H), 2.91-2.76 (m, 3H), 2.65 (dd, J=15.5, 10.5 Hz, 1H), 2.33-2.10 (m, 4H), 1.95-1.81 (m, 1H), 1.61 (s, 1H).

93I. Methyl 2-((2R,4R)-1-(4-(((3,4-trans)-1-(5-chloro-2-methoxypyridin-4-yl)-3-(cyanomethyl)piperidin-4-yl)oxy)phenyl)-4-methoxypyrrolidin-2-yl)acetate: To a solution of 93H (54 mg, 0.10 mmol) in CH$_2$Cl$_2$ (1.3 mL) at 0° C. was added TEA (43 μL, 0.31 mmol) and MsCl (16 μL, 0.21 mmol). After 0.5 h, the reaction was quenched with water and diluted with CH$_2$Cl$_2$. The layers were separated and the organic layer was washed with 1 N aq. HCl, 1.5 M aq. K$_2$HPO$_4$, and brine, dried over MgSO$_4$, and concentrated. The crude material was dissolved in DMSO (0.6 mL) and NaCN (9.8 mg, 0.20 mmol) was added. The reaction mixture was stirred at 50° C. overnight. The reaction was quenched with water, diluted with EtOAc, washed with water and brine, dried over Na$_2$SO$_4$, and concentrated. The crude product was purified by silica chromatography to provide 93I (27 mg, 0.051 mmol, 100% yield) as a colorless oil. LC-MS Anal. Calc'd for C$_{27}$H$_{33}$ClN$_4$O$_5$: 528.2, found [M+H]: 529.1. $^1$H NMR (400 MHz, CDCl$_3$) δ 8.00 (s, 1H), 6.98-6.82 (m, 2H), 6.63-6.47 (m, 2H), 6.30 (s, 1H), 4.24-4.00 (m, 3H), 3.90 (s, 3H), 3.76-3.60 (m, 4H), 3.57-3.45 (m, 2H), 3.41-3.29 (m, 4H), 2.98-2.56 (m, 6H), 2.48-2.34 (m, 1H), 2.24-2.09 (m, 3H), 1.86 (d, J=9.9 Hz, 1H).

Example 93 (23 mg, 71% yield) was prepared as a single isomer from 93I following the procedure of Example 1. LC-MS Anal. Calc'd for $C_{26}H_{31}ClN_4O_5$: 514.2, found [M+H] 515.3. $^1$H NMR (500 MHz, DMSO-$d_6$) δ 8.05 (s, 1H), 6.93 (d, J=8.0 Hz, 2H), 6.54 (d, J=8.3 Hz, 2H), 6.45 (s, 1H), 4.11-4.03 (m, 2H), 3.97 (br. s, 1H), 3.82 (s, 3H), 3.60 (d, J=11.6 Hz, 2H), 3.48-3.35 (m, 2H), 3.32-3.25 (m, 4H), 2.95-2.90 (m, 1H), 2.86-2.76 (m, 2H), 2.62 (d, J=14.9 Hz, 1H), 2.55 (s, 1H), 2.40 (dd, J=15.0, 10.6 Hz, 1H), 2.24-2.07 (m, 2H), 2.01 (d, J=13.8 Hz, 1H), 1.63 (d, J=9.9 Hz, 1H). Analytical HPLC (Acquity): RT=1.5 min, HI: 99.2%. hGPR40 $EC_{50}$=2300 nM.

EXAMPLE 94

2-((2R,4R)-1-(4-(((3,4-trans)-3-((1H-Tetrazol-1-yl)methyl)-1-(5-chloro-2-methoxypyridin-4-yl)piperidin-4-yl)oxy)phenyl)-4-methoxypyrrolidin-2-yl)acetic acid, TFA

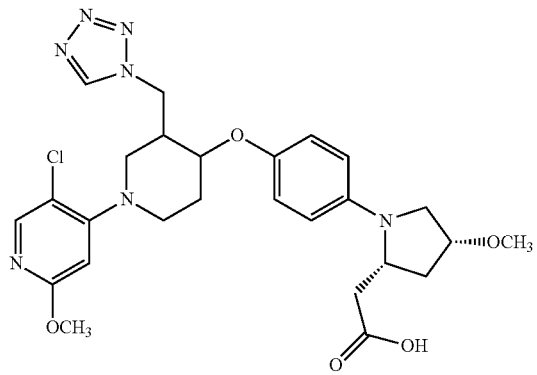 [SMILES: COc1cc(N2CCC(Oc3ccc(N4C[C@H](OC)C[C@@H]4CC(=O)O)cc3)C(Cn3cnnn3)C2)c(Cl)cn1]

94A. Methyl 2-((2R,4R)-1-(4-(((3,4-trans)-3-(1H-tetrazol-1-yl)methyl)-1-(5-chloro-2-methoxypyridin-4-yl)piperidin-4-yl)oxy)phenyl)-4-methoxypyrrolidin-2-yl)acetate: To a solution of 93H (25 mg, 0.048 mmol), 1,2,3,4-tetrazole (3.7 mg, 0.053 mmol), and $Ph_3P$ (19 mg, 0.072 mmol) in THF (0.48 mL) was added DEAD (11 μL, 0.072 mmol). The reaction mixture was stirred overnight. The reaction mixture was diluted with EtOAc and the organic layer was washed with 0.5 N aq. HCl, sat. aq. $NaHCO_3$, and brine, dried over $Na_2SO_4$, and concentrated. The crude product was purified by silica chromatography to give 94A (20 mg, 0.035 mmol, 73% yield) as a colorless oil. LC-MS Anal. Calc'd for $C_{27}H_{34}ClN_7O_5$: 571.2, found [M+H] 572.2.

Example 94 (5.6 mg, 23% yield) was prepared as a single isomer from 94A following the procedure of Example 1. LC-MS Anal. Calc'd for $C_{26}H_{32}ClN_7O_5$: 557.2, found [M+H] 558.2. $^1$H NMR (500 MHz, DMSO-$d_6$) δ 9.01 (s, 1H), 7.99 (s, 1H), 6.92 (d, J=8.0 Hz, 2H), 6.52 (d, J=8.0 Hz, 2H), 6.37 (s, 1H), 5.07-4.98 (m, 1H), 4.96-4.88 (m, 1H), 4.15 (br. s, 1H), 4.06 (br. s, 1H), 3.99 (t, J=8.9 Hz, 1H), 3.80 (s, 3H), 3.38 (t, J=9.9 Hz, 2H), 3.32-3.22 (m, 4H), 2.93 (br. s, 1H), 2.77 (d, J=10.2 Hz, 1H), 2.62 (d, J=15.1 Hz, 1H), 2.55 (t, J=5.0 Hz, 2H), 2.44-2.33 (m, 1H), 2.22-2.10 (m, 2H), 2.01 (d, J=14.0 Hz, 1H), 1.65 (d, J=10.5 Hz, 1H). Analytical HPLC (Acquity): RT=1.5 min, HI: 98.0%. hGPR40 $EC_{50}$=3400 nM.

EXAMPLE 95

2-((2S,3S,4R)-1-(6-((1-(5-Ethoxy-2-fluorophenyl)piperidin-4-yl)oxy)pyridin-3-yl)-4-methoxy-3-methylpyrrolidin-2-yl)acetic acid, TFA

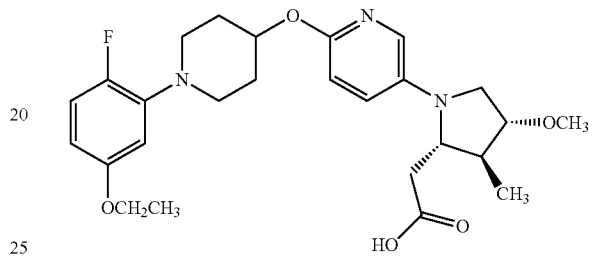

95A. 2-((1-(5-Ethoxy-2-fluorophenyl)piperidin-4-yl)oxy)-5-iodopyridine: To a solution of 85A (1.00 g, 4.18 mmol) in N-methyl-2-pyrrolidone (10 mL) was added $K_2CO_3$ (1.73 g, 12.5 mmol). After 10 minutes of stirring, 2-fluoro-5-iodopyridine (1.86 g, 8.36 mmol) was added and the reaction mixture was heated in a microwave reactor at 200° C. for 90 min. The reaction mixture was diluted with water and extracted with EtOAc (3×). The combined organic layers were washed with brine, dried ($MgSO_4$), and concentrated. The crude product was purified by silica chromatography to provide 96B (0.190 g, 0.421 mmol, 10% yield). LC-MS Anal. Calc'd for $C_{18}H_{20}FIN_2O_2$: 442.27, found [M+H] 443.0. $^1$H NMR (400 MHz, $CDCl_3$) δ 8.32 (dd, J=2.3, 0.6 Hz, 1H), 7.79 (dd, J=8.8, 2.4 Hz, 1H), 6.92 (dd, J=12.1, 8.8 Hz, 1H), 6.59 (dd, J=8.6, 0.7 Hz, 1H), 6.55 (dd, J=7.3, 2.9 Hz, 1H), 6.44-6.39 (m, J=8.9, 3.2, 3.2 Hz, 1H), 5.21-5.11 (m, J=8.0, 4.0, 4.0 Hz, 1H), 4.00 (q, J=1.0 Hz, 2H), 3.42-3.30 (m, 2H), 3.05-2.94 (m, J=12.0, 8.7, 3.3 Hz, 2H), 2.22-2.09 (m, J=9.3, 6.5, 3.3 Hz, 2H), 2.03-1.89 (m, 2H), 1.40 (t, J=7.0 Hz, 3H).

Example 95: Example 95 was prepared from 95A and 118F following the procedure of Example 2. The final compound was converted from a TFA salt to a free base by adjusting to a pH of 8 with sat. aq. $NaHCO_3$, extracting with $CH_2Cl_2$ (3×), drying ($MgSO_4$), concentrating to dryness, and lyophilizing to yield Example 95 (0.017 g, 0.035 mmol, 15% yield) as an off-white solid. LC-MS Anal. Calc'd for $C_{26}H_{34}FN_3O_5$: 487.56, found [M+H] 488.2. $^1$H NMR (400 MHz, acetonitrile-$d_3$) δ 7.70 (dd, J=9.7, 3.3 Hz, 1H), 7.44 (d, J=3.3 Hz, 1H), 7.33 (d, J=9.5 Hz, 1H), 7.13 (dd, J=11.9, 9.0 Hz, 1H), 6.94 (dd, J=6.8, 3.1 Hz, 1H), 6.76 (dt, J=8.9, 3.4 Hz, 1H), 5.03-4.90 (m, 1H), 4.03 (q, J=7.0 Hz, 2H), 3.82-3.70 (m, 2H), 3.62 (ddd, J=12.3, 9.0, 3.4 Hz, 2H), 3.54-3.44 (m, 2H), 3.42-3.27 (m, 5H), 2.74-2.62 (m, 2H), 2.52-2.41 (m, J=7.3 Hz, 1H), 2.39-2.26 (m, 2H), 2.20-2.05 (m, 2H), 1.35 (t, J=6.9 Hz, 3H), 0.99 (d, J=7.3 Hz, 3H). Analytical HPLC: RT=7.8 min, HI: 97.2%. hGPR40 $EC_{50}$=510 nM.

EXAMPLE 96

2-((2R,4R)-1-(4-((1-(5-Fluoro-2-methoxypyridin-4-yl)piperidin-4-yl)oxy)phenyl)-4-methoxypyrrolidin-2-yl)acetic acid, diethylammonium salt

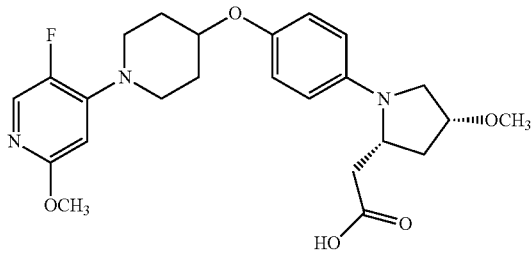 [SMILES: COc1cc(N2CCC(Oc3ccc(N4C[C@H](OC)C[C@@H]4CC(=O)O)cc3)CC2)c(F)cn1]

Example 96 was prepared from piperidin-4-ol following the procedure of Example 83. LC-MS Anal. Calc'd for $C_{24}H_{30}FN_3O_5$: 459.51, found [M+H] 460.2. $^1$H NMR (400 MHz, DMSO-$d_6$) δ 7.87 (d, J=5.4 Hz, 1H), 6.88 (d, J=8.8 Hz, 2H), 6.51 (d, J=8.8 Hz, 2H), 6.29 (d, J=6.6 Hz, 1H), 4.34 (m, 1H), 4.07-3.93 (m, 3H), 3.78 (s, 3H), 3.54-3.44 (m, 2H), 3.30 (m, 3H), 3.26 (m, 3H), 2.77 (q, J=7.1 Hz, 2H), 2.38-2.33 (m, 1H), 2.16 (m, 1H), 2.0-1.93 (m, 4H). Analytical HPLC (XBridge Phenyl): RT=6.8 min, HI: 96.0%. hGPR40 $EC_{50}$=840 nM. hGPR40 IP1 $EC_{50}$=520 nM.

EXAMPLE 97

2-((2S,3S,4R)-1-(6-((1-(5-Chloro-2-methoxypyridin-4-yl)piperidin-4-yl)oxy)pyridin-3-yl)-4-methoxy-3-methylpyrrolidin-2-yl)acetic acid

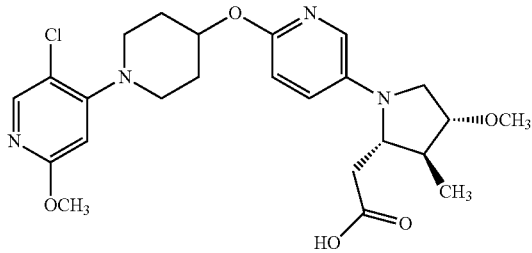 [SMILES: COc1cc(N2CCC(Oc3ccc(N4C[C@H](OC)[C@@H](C)[C@@H]4CC(=O)O)cn3)CC2)c(Cl)cn1]

97A. 5-Chloro-4-(4-((5-iodopyridin-2-yl)oxy)piperidin-1-yl)-2-methoxypyridine: To a solution of 112A (0.331 g, 1.36 mmol) in DMF (4 mL) at 0° C. was added 60% NaH (0.163 g, 4.08 mmol) and the reaction mixture was stirred at rt for 10 min. 2-Fluoro-5-iodopyridine (0.606 g, 2.72 mmol) was added to the reaction mixture, which was stirred at rt for 15 min. The solvent was removed under reduced pressure and the reaction mixture was diluted with water and extracted with EtOAc (3×). The combined organic layers were washed with brine, dried (MgSO$_4$), and concentrated. The crude product was purified by silica chromatography to provide 97A (0.460 g, 0.929 mmol, 68% yield) as a white solid. LC-MS Anal. Calc'd for $C_{16}H_{17}ClIN_3O_2$: 445.68, found [M+H] 445.9. $^1$H NMR (400 MHz, CDCl$_3$) δ 8.32 (dd, J=2.3, 0.6 Hz, 1H), 7.98 (s, 1H), 7.79 (dd, J=8.7, 2.3 Hz, 1H), 6.59 (dd, J=8.7, 0.6 Hz, 1H), 6.29 (s, 1H), 5.26-5.15 (m, J=7.6, 3.8, 3.8 Hz, 1H), 3.89 (s, 3H), 3.47-3.34 (m, 2H), 3.13-3.01 (m, J=11.9, 8.3, 3.3 Hz, 2H), 2.22-2.10 (m, 2H), 2.03-1.90 (m, J=12.6, 8.3, 4.0, 4.0 Hz, 2H).

Example 97 was prepared from 97A and 118F following the procedure of Example 2. The final compound was converted to a neutral compound following the procedure of Example 95 to yield Example 97 (0.015 g, 0.030 mmol, 20% yield) as an off-white solid. LC-MS Anal. Calc'd for $C_{24}H_{31}ClN_4O_5$: 490.98, found [M+H] 491.2. $^1$H NMR (400 MHz, acetonitrile-$d_3$) δ 7.95 (s, 1H), 7.46 (d, J=3.1 Hz, 1H), 7.04 (dd, J=8.9, 3.2 Hz, 1H), 6.64 (d, J=8.8 Hz, 1H), 6.33 (s, 1H), 5.08-4.95 (m, J=7.8, 7.8, 3.9, 3.9 Hz, 1H), 3.81 (s, 3H), 3.70-3.59 (m, 2H), 3.44-3.32 (m, 5H), 3.30 (s, 3H), 3.08-2.96 (m, J=12.2, 8.7, 3.1 Hz, 2H), 2.70-2.48 (m, 2H), 2.39-2.27 (m, 1H), 2.14-2.01 (m, 2H), 1.88-1.73 (m, 2H), 0.97 (d, J=1.0 Hz, 3H). Analytical HPLC: RT=6.8 min, HI: 97.6%. hGPR40 $EC_{50}$=110 nM.

EXAMPLE 98

2-((2S,3S,4R)-1-(4-(((3,4-trans)-1-(5-Chloro-2-methoxypyridin-4-yl)-3-methylpiperidin-4-yl)oxy)-3-fluorophenyl)-4-methoxy-3-methylpyrrolidin-2-yl)acetic acid

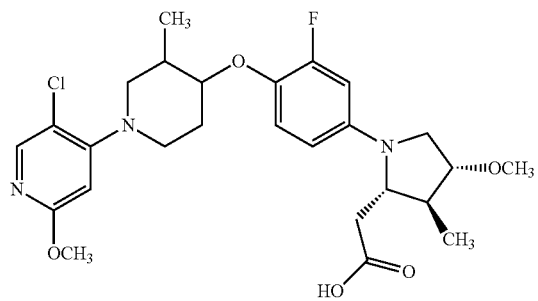 [SMILES: COc1cc(N2CCC(Oc3ccc(N4C[C@H](OC)[C@@H](C)[C@@H]4CC(=O)O)cc3F)C(C)C2)c(Cl)cn1]

98A. 5-Chloro-4-((3,4-trans)-4-(2-fluoro-4-iodophenoxy)-3-methylpiperidin-1-yl)-2-methoxypyridine: To a solution of 119A, Isomer 1 (220 mg, 0.857 mmol) and 2-fluoro-4-iodophenol (204 mg, 0.857 mmol) in toluene (6 mL) was added Bu$_3$P (0.317 mL, 1.29 mmol). While stirring, ADDP (324 mg, 1.29 mmol) was added in three portions. The reaction mixture was heated to 50° C. for 3 h and then stirred at rt for 16 h. Hexanes (50 mL) were added to the mixture and a white solid was formed. The mixture was filtered and the filtrate was collected, concentrated, and purified by silica chromatography to afford 98A (286 mg, 0.600 mmol, 70% yield) as white oil. LC-MS Anal. Calc'd for $C_{18}H_{19}ClFIN_2O_2$: 476, found [M+H] 477.0. $^1$H NMR (400 MHz, CD$_2$Cl$_2$) δ 7.95 (s, 1H), 7.38-7.47 (m, 2H), 6.77-6.88 (m, 1H), 6.29 (s, 1H), 3.93-4.03 (m, 1H), 3.86 (s, 3H), 3.48-3.60 (m, 2H), 2.79-2.94 (m, 1H), 2.65 (dd, J=9.24, 12.54 Hz, 1H), 2.16 (tdd, J=2.26, 4.40, 13.09 Hz, 2H), 1.84 (d, J=10.34 Hz, 1H), 1.13 (d, J=6.60 Hz, 3H).

98B. ((2R,3S,4R)-1-(4-(((3,4-trans)-1-(5-Chloro-2-methoxypyridin-4-yl)-3-methylpiperidin-4-yl)oxy)-3-fluorophenyl)-4-methoxy-3-methylpyrrolidin-2-yl)methanol: A mixture of 98A (180 mg, 0.378 mmol), 118F (54.8 mg, 0.378 mmol), CuI (10 mg, 0.057 mmol), and NaOH (52 mg, 1.3 mmol) was purged with argon. n-BuOH (2 mL) was added and the reaction mixture was stirred at 90° C. for 12 h. The reaction was quenched with water (10 mL) and extracted with CH₂Cl₂ (3×). The combined organic extracts were washed with brine, dried (Na₂SO₄), and purified by silica chromatography to afford 98B (447 mg, 0.142 mmol, 72% yield) as a yellow oil. LC-MS Anal. Calc'd for C₂₅H₃₃ClFN₃O₄: 493.0, found [M+H] 494.1. ¹H NMR (400 MHz, CD₂Cl₂) δ 7.94 (s, 1H), 6.93 (t, J=9.24 Hz, 1H), 6.40 (dd, J=2.97, 14.20 Hz, 1H), 6.32 (ddd, J=0.99, 2.92, 8.86 Hz, 1H), 6.28 (s, 1H), 3.84-3.86 (m, 4H), 3.66-3.75 (m, 2H), 3.61-3.65 (m, 2H), 3.48-3.56 (m, 3H), 3.41-3.48 (m, 2H), 3.38 (s, 2H), 2.78 (d, J=1.98 Hz, 1H), 2.56-2.65 (m, 2H), 2.44 (d, J=7.26 Hz, 1H), 2.06-2.16 (m, 2H), 1.81 (d, J=10.34 Hz, 1H), 1.16 (d, J=6.60 Hz, 3H), 1.05 (d, J=7.26 Hz, 3H).

98C. ((2R,3S,4R)-1-(4-(((3,4-trans)-1-(5-Chloro-2-methoxypyridin-4-yl)-3-methylpiperidin-4-yl)oxy)-3-fluorophenyl)-4-methoxy-3-methylpyrrolidin-2-yl)methyl methanesulfonate: To a solution of 98B (70 mg, 0.14 mmol) in CH₂Cl₂ (2 mL) at 0° C. was added NEt₃ (0.054 mL, 0.38 mmol) and MsCl (0.024 mL, 0.31 mmol). The reaction mixture was stirred at 0° C. for 40 min. The reaction was quenched with water (5 mL) and extracted with CH₂Cl₂ (3×). The combined organic extracts were washed with 0.5 N aq. HCl, 1.5 M aq. KH₂PO₄, and brine, dried (Na₂SO₄), and concentrated to obtain 98C (65 mg, 0.11 mmol, 80% yield). LC-MS Anal. Calc'd for C₂₆H₃₅ClFN₃O₆S, 571.1, found [M+H] 572.0.

98D. 2-((2S,3S,4R)-1-(4-(((3,4-trans)-1-(5-Chloro-2-methoxypyridin-4-yl)-3-methylpiperidin-4-yl)oxy)-3-fluorophenyl)-4-methoxy-3-methylpyrrolidin-2-yl)acetonitrile: To a mixture of 98C (65 mg, 0.11 mmol) and NaCN (45 mg, 0.91 mmol) was added DMSO (2 mL) and the reaction mixture was stirred at 50° C. for 12 h. The reaction was quenched with water (5 mL) and extracted with EtOAc (3×). The combined organic extracts were washed with brine, dried (Na₂SO₄), and purified by silica chromatography to afford 98D (43 mg, 0.085 mmol, 75% yield) as a colorless oil. LC-MS Anal. Calc'd for C₂₆H₃₂ClFN₄O₃ 502.2, found [M+H] 503.2. ¹H NMR (400 MHz, CD₂Cl₂) δ 7.89-7.99 (m, 1H), 6.96 (t, J=9.13 Hz, 1H), 6.18-6.40 (m, 3H), 3.84 (s, 4H), 3.63-3.76 (m, 3H), 3.43-3.56 (m, 5H), 3.36 (s, 3H), 2.73-2.83 (m, 2H), 2.51-2.66 (m, 2H), 2.03-2.18 (m, 2H), 1.11-1.18 (m, 3H), 1.04 (d, J=7.26 Hz, 3H).

Example 98: To a solution of 98D (40 mg, 0.080 mmol) in EtOH (0.5 mL) was added 6 M aq. KOH (0.27 mL, 1.6 mmol). The reaction mixture was stirred at 125° C. for 5 h. The reaction mixture was acidified to pH 2 with 1 N aq. HCl and extracted with CH₂Cl₂ (3×). The combined organic extracts were washed with brine, dried (Na₂SO₄), and concentrated. The crude product was purified by RP-Prep. HPLC to give Example 98 (15 mg, 0.029 mmol, 36% yield) as an off-white oil as a single isomer. LC-MS Anal. Calc'd for C₂₆H₃₃ClFN₃O₅ 521.2, found [M+H] 522.2. ¹H NMR (400 MHz, CD₂Cl₂) δ 7.93 (s, 1H), 6.95 (t, J=9.24 Hz, 1H), 6.35 (dd, J=2.86, 13.86 Hz, 1H), 6.20-6.29 (m, 2H), 3.84 (s, 3H), 3.62-3.76 (m, 3H), 3.48-3.56 (m, 2H), 3.38-3.45 (m, 3H), 3.34 (s, 3H), 2.73-2.87 (m, 3H), 2.59 (dd, J=9.46, 12.32 Hz, 1H), 2.41 (d, J=7.48 Hz, 1H), 2.00-2.18 (m, 2H), 1.80 (d, J=10.34 Hz, 1H), 1.15 (d, J=6.60 Hz, 3H), 1.01 (d, J=7.26 Hz, 3H). Analytical HPLC (ZORBAX® method, 0% Solvent B start): RT=8.33 min, HI: 100%. hGPR40 EC₅₀=102 nM. hGPR40 IP1 EC₅₀=100 nM.

EXAMPLE 99

2-((2S,3S,4R)-1-(4-((1-(5-Chloro-2-methoxypyridin-4-yl)piperidin-4-yl)oxy)-3-fluorophenyl)-4-methoxy-3-methylpyrrolidin-2-yl)acetic acid

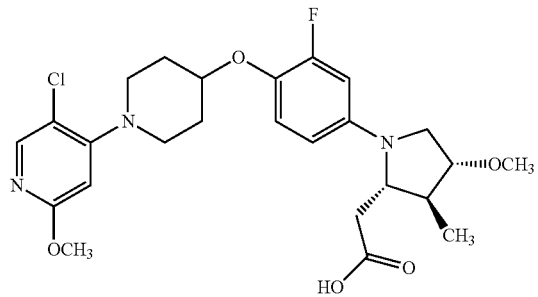 [SMILES: COc1cc(N2CCC(Oc3ccc(N4C[C@H](OC)[C@@H](C)[C@@H]4CC(=O)O)cc3F)CC2)c(Cl)cn1]

Example 99 (yellow solid, 23 mg) was prepared from 112A following the procedure of Example 98. LC-MS Anal. Calc'd for C₂₅H₃₁ClFN₃O₅: 507.2, found [M+H] 508.2. ¹H NMR (400 MHz, CD₂Cl₂) δ 7.95 (s, 1H), 6.96 (t, J=9.13 Hz, 1H), 6.36 (d, J=13.86 Hz, 1H), 6.23-6.31 (m, 2H), 4.21 (td, J=3.71, 7.32 Hz, 1H), 3.86 (s, 3H), 3.60-3.78 (m, 2H), 3.39-3.50 (m, 4H), 3.35 (s, 3H), 2.99 (ddd, J=3.30, 8.14, 11.88 Hz, 2H), 2.78 (br. s, 2H), 2.42 (d, J=6.38 Hz, 1H), 2.00-2.11 (m, 2H), 1.85-1.99 (m, 2H), 1.01 (d, J=7.04 Hz, 3H). Analytical HPLC (ZORBAX® method, 0% Solvent B start): RT=8.1 min, HI: 96%. hGPR40 EC₅₀=289 nM. hGPR40 IP1 EC₅₀=290 nM.

EXAMPLE 100

2-((2S,3S,4R)-1-(4-(((3,4-trans)-1-(5-Ethoxy-2-fluorophenyl)-3-methylpiperidin-4-yl)oxy)-3-fluorophenyl)-4-methoxy-3-methylpyrrolidin-2-yl)acetic acid

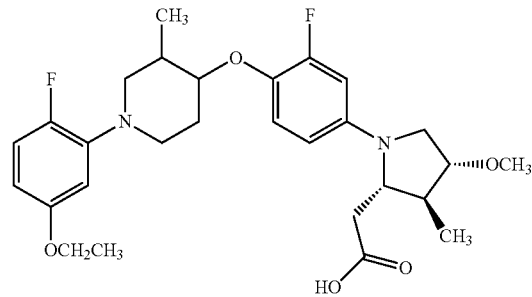 [SMILES: CCOc1ccc(F)c(N2CCC(Oc3ccc(N4C[C@H](OC)[C@@H](C)[C@@H]4CC(=O)O)cc3F)C(C)C2)c1]

Example 100 (yellow oil, 9 mg) was prepared as a single isomer from 43I, Isomer 2 following the procedure of Example 98. LC-MS Anal. Calc'd for C₂₈H₃₆F₂N₂O₅: 518.2, found [M+H] 519.2. ¹H NMR (400 MHz, CD₂Cl₂) δ 6.91-7.00 (m, 1H), 6.85-6.90 (m, 1H), 6.48 (dd, J=2.97, 7.37 Hz, 1H), 6.38 (td, J=3.16, 8.86 Hz, 2H), 6.29 (d, J=8.14 Hz, 1H), 3.96 (q, J=7.04 Hz, 2H), 3.61-3.76 (m, 3H), 3.30-3.49 (m, 7H), 2.69 (t, J=10.34 Hz, 3H), 2.46-2.57 (m, 1H), 2.34-2.45 (m, 1H), 2.01-2.16 (m, 2H), 1.78 (d, J=10.56 Hz, 1H), 1.36 (t, J=7.04 Hz, 3H), 1.24-1.31 (m, 2H), 1.14 (d, J=6.60 Hz, 3H), 1.01 (d, J=5.28 Hz, 2H). Analytical HPLC (ZORBAX® method, 0% Solvent B start): RT=8.4 min, HI: 100%. hGPR40 EC₅₀=110 nM.

EXAMPLE 101

2-((2S,3S,4R)-1-(4-((1-(5-Ethoxy-2-fluorophenyl)piperidin-4-yl)oxy)-3-fluorophenyl)-4-methoxy-3-methylpyrrolidin-2-yl)acetic acid

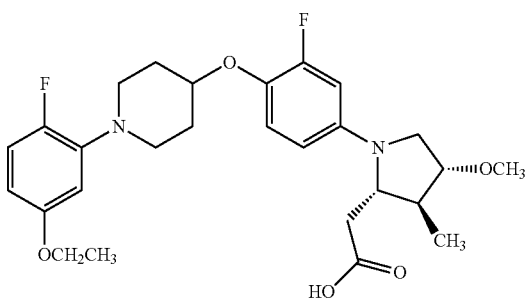 [SMILES: CCOc1ccc(F)c(N2CCC(Oc3ccc(N4C[C@H](OC)[C@@H](C)[C@@H]4CC(=O)O)cc3F)CC2)c1]

Example 101 (yellow oil, 35 mg) was prepared from 85C following the procedure of Example 98. LC-MS Anal. Calc'd for $C_{27}H_{34}F_2N_2O_5$ 504.2, found [M+H] 505.2. $^1$H NMR (400 MHz, $CD_2Cl_2$) δ 6.80-6.97 (m, 2H), 6.48 (dd, J=2.86, 7.26 Hz, 1H), 6.17-6.42 (m, 3H), 4.07 (br. s, 1H), 3.94 (q, J=7.04 Hz, 2H), 3.70 (d, J=15.41 Hz, 1H), 3.60 (br. s, 1H), 3.36-3.46 (m, 2H), 3.21-3.35 (m, 5H), 2.82 (t, J=9.35 Hz, 3H), 2.49-2.68 (m, 1H), 2.39 (br. s, 1H), 1.97 (br. s, 2H), 1.76-1.91 (m, 2H), 1.35 (t, J=7.04 Hz, 3H), 0.89-1.02 (m, 3H). Analytical HPLC (ZORBAX® method, 0% Solvent B start): RT=8.0 min, HI: 100%. hGPR40 $EC_{50}$=180 nM.

EXAMPLE 102

2-((2R,4R)-1-(4-((1-(5-Chloro-2-methoxypyridin-4-yl)piperidin-4-yl)methyl)phenyl)-4-methoxypyrrolidin-2-yl)acetic acid

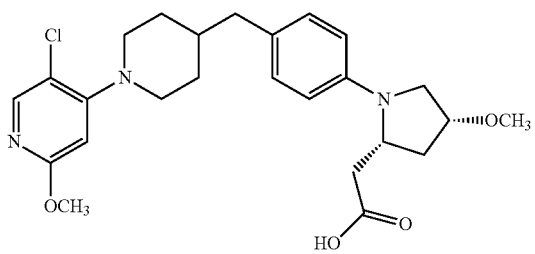 [SMILES: COc1cc(N2CCC(Cc3ccc(N4C[C@H](OC)C[C@@H]4CC(=O)O)cc3)CC2)c(Cl)cn1]

102A. 2-((2S,4R)-1-(4-Bromophenyl)-4-methoxypyrrolidin-2-yl)acetonitrile: 102A was prepared from 4A and 1-bromo-4-iodobenzene following the procedure of Example 2. LC-MS Anal. Calc'd for $C_{13}H_{15}BrN_2O$: 295.18, found [M+H] 295.0, 297.0. $^1$H NMR (400 MHz, $CD_2Cl_2$) δ 7.35-7.29 (m, 2H), 6.53-6.41 (m, 2H), 4.18-4.05 (m, 2H), 3.50 (dt, J=10.8, 1.1 Hz, 1H), 3.41-3.34 (m, 4H), 2.80-2.73 (m, 2H), 2.38-2.28 (m, 1H), 2.26-2.15 (m, 1H).

102B. tert-Butyl 4-(4-((2S,4R)-2-(cyanomethyl)-4-methoxypyrrolidin-1-yl)benzyl)piperidine-1-carboxylate: To a solution of tert-butyl 4-methylenepiperidine-1-carboxylate (178 mg, 0.901 mmol) in THF (3 mL) was added a 0.5 M solution of 9-BBN in THF (1.80 mL, 0.901 mmol) and the reaction mixture was stirred at 68° C. for 1.5 h. The resulting solution was added to a stirring mixture of 102A (266 mg, 0.901 mmol), $K_2CO_3$ (249 mg, 1.80 mmol) and $PdCl_2(dppf)$ (33 mg, 0.045 mmol) in DMF/water (2 mL/0.3 mL) and the reaction mixture was stirred at 65° C. for 5 h. The reaction was quenched with water (5 mL) and extracted with EtOAc (3×). The combined organic extracts were washed with brine, dried ($Na_2SO_4$), and concentrated. The crude product was purified by silica chromatography to provide 102B (120 mg, 0.290 mmol, 32% yield) as colorless oil. LC-MS Anal. Calc'd for $C_{24}H_{35}N_3O_3$: 413.2, found [M+H] 414.0. $^1$H NMR (400 MHz, $CD_2Cl_2$) δ 7.03 (d, J=8.58 Hz, 2H), 6.52 (d, J=8.58 Hz, 2H), 3.95-4.16 (m, 4H), 3.50 (s, 1H), 3.33-3.42 (m, 4H), 2.74 (d, J=9.68 Hz, 2H), 2.43 (d, J=6.60 Hz, 2H), 2.29 (d, J=0.88 Hz, 2H), 2.16-2.24 (m, 1H), 1.49-1.63 (m, 6H), 1.42 (s, 9H).

102C. Methyl 2-((2R,4R)-4-methoxy-1-(4-(piperidin-4-ylmethyl)phenyl)pyrrolidin-2-yl)acetate: 102B (120 mg, 0.290 mmol) was dissolved in a ~3.0 M HCl in $CH_2Cl_2$/MeOH solution [10 mL, prepared by addition of AcCl (2.6 mL) to 3/2 $CH_2Cl_2$/MeOH (10 mL) at 0° C. and then stirring at rt for 30 min]. The resulting solution was stirred at rt overnight and then evaporated. The residue was taken up in $CH_2Cl_2$ (15 mL) and was washed with sat. aq. $NaHCO_3$. The aqueous layer was extracted with $CH_2Cl_2$ (2×) and the combined organic layers were dried ($Na_2SO_4$) and concentrated to yield 102C (99 mg, 0.286 mmol, 98% yield) as a brown oil. LC-MS Anal. Calc'd for $C_{20}H_{30}N_2O_3$: 346.2, found [M+H] 347.0.

102D. Methyl 2-((2R,4R)-1-(4-((1-(5-chloro-2-methoxypyridin-4-yl)piperidin-4-yl)methyl)phenyl)-4-methoxypyrrolidin-2-yl)acetate: A solution of 102C (48 mg, 0.14 mmol), 27B (37 mg, 0.17 mmol), and $K_2CO_3$ (57.4 mg, 0.416 mmol) in DMSO (1.5 mL) was heated to 90° C. overnight. The reaction was quenched with sat. aq. $NaHCO_3$ and extracted with EtOAc (2×). The combined organic extracts were washed with brine, dried ($Na_2SO_4$), and concentrated. The crude product was purified by silica chromatography to provide 102D (25 mg, 0.051 mmol, 37% yield) as yellow oil. LC-MS Anal. Calc'd for $C_{26}H_{34}ClN_3O_4$: 487.1, found [M+H] 488.2.

Example 102 (white oil, 4 mg) was prepared from 102D following the procedure of Example 1. LC-MS Anal. Calc'd for $C_{25}H_{32}ClN_3O_4$: 473.9, found [M+H] 474.1. $^1$H NMR (400 MHz, $CD_2Cl_2$) δ 7.92 (s, 1H), 7.05 (d, J=8.58 Hz, 2H), 6.57 (d, J=8.58 Hz, 2H), 6.24 (s, 1H), 4.08 (br. s, 2H), 3.75-3.91 (m, 4H), 3.49-3.61 (m, 3H), 3.30-3.46 (m, 4H), 2.78-2.94 (m, 1H), 2.43-2.68 (m, 5H), 2.13-2.24 (m, 1H), 1.73 (d, J=12.54 Hz, 3H), 1.34-1.51 (m, 2H). Analytical HPLC (ZORBAX® method, 0% Solvent B start): RT=8.3 min, HI: 94%. hGPR40 $EC_{50}$=952 nM. hGPR40 IP1 $EC_{50}$=950 nM.

EXAMPLE 103

2-((2R,4R)-1-(4-((1-(5-Ethoxy-2-fluorophenyl)piperidin-4-yl)oxy)phenyl)-4-(pentyloxy)pyrrolidin-2-yl)acetic acid, TFA

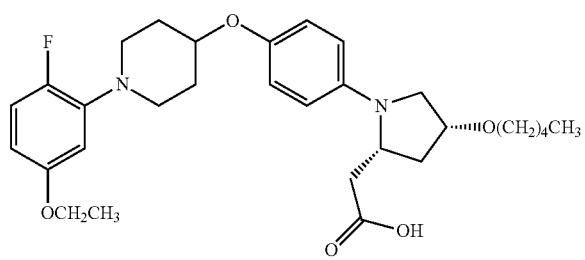

103A. (2R,4R)-tert-Butyl 4-hydroxy-2-(hydroxymethyl)pyrrolidine-1-carboxylate: (2R,4R)-1-(tert-butoxycarbonyl)-4-hydroxypyrrolidine-2-carboxylic acid (6.98 g, 30.2 mmol) was dissolved in anhydrous THF (123 mL) and cooled to −10° C. 4-Methylmorpholine (3.5 mL, 32 mmol) and isobutyl chloroformate (4.2 mL, 32 mmol) were then added and the reaction mixture was stirred at −10° C. for 45 min. The reaction mixture was filtered and added dropwise to a solution of NaBH$_4$ (2.28 g, 60.4 mmol) in water (16 mL) cooled to 0° C. The reaction mixture was stirred for 2 h and slowly warmed to rt. The reaction was quenched with sat. aq. NH$_4$Cl and the product was extracted with EtOAc (3×). The combined organic layers were washed with brine, dried (MgSO$_4$), and concentrated. The crude product was purified by silica chromatography to provide 103A (5.98 g, 27.5 mmol, 91% yield) as a colorless oil, which solidified to a white solid upon standing. LC-MS Anal. Calc'd for C$_{10}$H$_{19}$NO$_4$: 217.26, found [M+H] 218.0. $^1$H NMR (500 MHz, CDCl$_3$) δ 4.35-4.09 (m, 2H), 4.09-3.88 (m, 2H), 3.67-3.33 (m, 3H), 2.44-2.24 (m, 1H), 2.07-1.71 (m, 2H), 1.53-1.40 (m, 9H).

103B. (2R,4R)-tert-Butyl 2-(((tert-butyldiphenylsilyl)oxy)methyl)-4-hydroxypyrrolidine-1-carboxylate: To a solution of 103A (3.00 g, 13.8 mmol) in DMF (69 mL) was added TBDPS-Cl (3.9 mL, 15 mmol) and imidazole (1.41 g, 20.7 mmol). The reaction mixture was stirred at rt for 2 h. The reaction mixture was diluted with EtOAc and washed with water (5×). The organic layer was washed with brine, dried (MgSO$_4$), and concentrated. The crude product was purified by silica chromatography to give 103B (2.58 g, 5.66 mmol, 41% yield) as a colorless oil. LC-MS Anal. Calc'd for C$_{26}$H$_{37}$NO$_4$Si: 455.66, found [M+H] 456.1. $^1$H NMR (500 MHz, CDCl$_3$) δ 7.72-7.60 (m, 4H), 7.48-7.34 (m, 6H), 4.78 (d, J=11.0 Hz, 0.5H), 4.50 (d, J=10.2 Hz, 0.5H), 4.37-4.20 (m, 1.5H), 4.01 (br. s, 1H), 3.89 (d, J=9.4 Hz, 0.5H), 3.62-3.42 (m, 3H), 2.45-2.29 (m, 1H), 2.12-1.96 (m, 1H), 1.54-1.43 (s, 4.5H), 1.29 (s, 4.5H), 1.08 (s, 9H).

103C. (2R,4R)-tert-Butyl 2-(((tert-butyldiphenylsilyl)oxy)methyl)-4-(pentyloxy)pyrrolidine-1-carboxylate: To a solution of 103B (5.00 g, 11.0 mmol) in THF (50 mL) cooled to 0° C. was added 60% NaH (1.58 g, 65.8 mmol). 1-Bromopentane (9.94 g, 65.8 mmol) was added and the reaction mixture was heated to 67° C. for 24 h. The reaction mixture was diluted with water and extracted with EtOAc (3×). The organic layer was washed with brine, dried (Na$_2$SO$_4$), and concentrated. The crude product was purified by silica chromatography to give 103C (4.00 g, 7.61 mmol, 69% yield) as a yellow gummy oil. LC-MS Anal. Calc'd for C$_{31}$H$_{47}$NO$_4$Si: 525.80, found [M+H] 527.0.

103D. (2R,4R)-tert-Butyl 2-(hydroxymethyl)-4-(pentyloxy)pyrrolidine-1-carboxylate: To a solution of 103C (4.35 g, 8.27 mmol) in THF (50 mL) was added a 1 M solution of TBAF in THF (17 mL, 17 mmol) and the reaction mixture was stirred at rt for 4 h. The reaction mixture was diluted with water and extracted with EtOAc (3×50 mL), washed with brine, dried (Na$_2$SO$_4$), and concentrated. The crude product was purified by silica chromatography to give 103D (2.00 g, 6.96 mmol, 84% yield) as a colorless gummy oil.

Example 103 (brown oil, 36.2 mg) was prepared from 85C and 103D following the procedure of Example 2. LC-MS Anal. Calc'd for C$_{36}$H$_{41}$FN$_2$O$_5$: 528.30, found [M+H] 529.3. $^1$H NMR (400 MHz, DMSO-d$_6$) δ 7.01 (dd, J=8.8, 12.5 Hz, 1H), 6.89 (d, J=9.0 Hz, 2H), 6.56-6.43 (m, 4H), 4.32-4.25 (m, 1H), 4.14 (t, J=5.0 Hz, 1H), 3.97 (q, J=7.0 Hz, 2H), 3.96-3.85 (m, 1H), 3.45-3.38 (m, 2H), 3.48-3.38 (m, 5H), 2.92-2.83 (m, 2H), 2.69-2.59 (m, 1H), 2.49-2.41 (m, 1H), 2.18-2.09 (m, 1H), 2.04-1.95 (m, 3H), 1.78-1.67 (m, 2H), 1.56-1.46 (m, 2H), 1.35-1.25 (m, 6H), 0.91-0.83 (m, 3H). Analytical HPLC (25 min gradient, 30 min stop): RT=23.2 min, HI: 99.0%. hGPR40 EC$_{50}$=120 nM.

EXAMPLE 104

2-((2S,3R)-1-(4-((1-(5-Ethoxy-2-fluorophenyl)piperidin-4-yl)oxy)phenyl)-3-methylpyrrolidin-2-yl)acetic acid, TFA

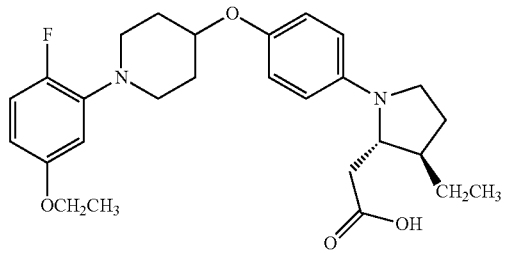 [SMILES: CCOc1ccc(F)c(N2CCC(Oc3ccc(N4CC[C@@H](CC)[C@@H]4CC(=O)O)cc3)CC2)c1]

Example 104 (brown oil, 9.1 mg) was prepared from 85C and (2R,3R)-1-(tert-butoxycarbonyl)-3-methylpyrrolidine-2-carboxylic acid following the procedure of Example 2. LC-MS Anal. Calc'd for C$_{26}$H$_{33}$FN$_2$O$_4$: 456.24, found [M+H] 457.2. $^1$H NMR (400 MHz, DMSO-d$_6$) δ 7.01 (dd, J=8.8, 12.5 Hz, 1H), 6.92 (d, J=8.5 Hz, 2H), 6.56-6.44 (m, 4H), 4.31-4.27 (m, 1H), 3.97 (q, J=7.0 Hz, 2H), 3.60 (d, J=9.5 Hz, 1H), 3.33-3.22 (m, 1H), 3.30-3.21 (m, 3H), 2.93-2.84 (m, 2H), 2.60-2.53 (m, 1H), 2.24-2.14 (m, 3H), 2.06-1.96 (m, 2H), 1.79-1.67 (m, 3H), 1.30 (t, J=7.0 Hz, 3H), 0.99 (d, J=6.2 Hz, 3H). Analytical HPLC (12 min gradient, 15 min stop): RT=9.2 min, HI: 99.0%. hGPR40 EC$_{50}$=250 nM.

EXAMPLE 105

2-((2S,3R)-1-(6-(((3,4-trans)-1-(5-Chloro-2-methoxypyridin-4-yl)-3-methylpiperidin-4-yl)oxy)pyridin-3-yl)-3-methylpyrrolidin-2-yl)acetic acid

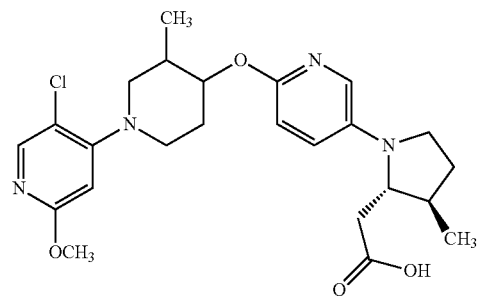 [SMILES: COc1cc(N2CCC(Oc3ccc(N4CC[C@@H](C)[C@@H]4CC(=O)O)cn3)C(C)C2)c(Cl)cn1]

Example 105 (off-white solid, 21.3 mg) was prepared as a single isomer from 132A and (2R,3R)-1-(tert-butoxycarbonyl)-3-methylpyrrolidine-2-carboxylic acid following the procedure of Example 2. LC-MS Anal. Calc'd for C$_{24}$H$_{31}$ClN$_4$O$_4$: 474.20, found [M+H] 475.2. $^1$H NMR (400 MHz, DMSO-d$_6$) δ 8.03 (s, 1H), 7.45 (d, J=2.7 Hz, 1H), 7.04 (dd, J=2.9, 8.9 Hz, 1H), 6.71 (d, J=8.9 Hz, 1H), 6.43 (s, 1H), 4.68 (dt, J=4.1, 9.1 Hz, 1H), 3.80 (s, 3H), 3.58 (d, J=9.6 Hz, 1H), 3.48 (d, J=10.1 Hz, 2H), 3.36-3.26 (m, 1H), 3.21-3.11

(m, 1H), 2.91 (t, J=10.7 Hz, 1H), 2.78-2.61 (m, 1H), 2.49-2.45 (m, 1H), 2.30-2.22 (m, 4H), 2.04-1.93 (m, 1H), 1.67-1.50 (m, 2H), 0.97-1.10 (d, J=6.5 Hz, 3H), 0.94 (d, J=6.4 Hz, 3H). Analytical HPLC (12 min gradient, 15 min stop): RT=9.6 min, HI: 99.0%. hGPR40 $EC_{50}$=60 nM.

EXAMPLE 106

2-((2S,3R,4R)-1-(6-(((3,4-trans)-1-(5-Chloro-2-methoxypyridin-4-yl)-3-methylpiperidin-4-yl)oxy)pyridin-3-yl)-3,4-dimethylpyrrolidin-2-yl)acetic acid

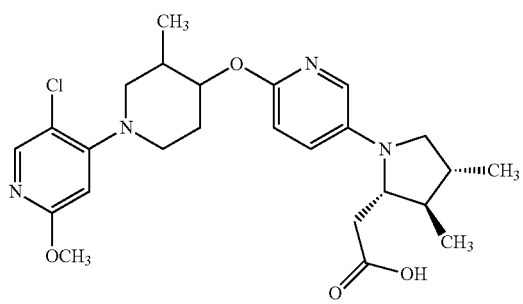 [SMILES: COc1cc(N2CCC(Oc3ccc(N4C[C@H](C)[C@@H](C)[C@@H]4CC(=O)O)cn3)C(C)C2)c(Cl)cn1]

Example 106 (off-white solid, 31.2 mg) was prepared as a single isomer from 132A and (2R,3R,4R)-1-(tert-butoxycarbonyl)-3,4-dimethylpyrrolidine-2-carboxylic acid following the procedure of Example 2. LC-MS Anal. Calc'd for $C_{25}H_{33}ClN_4O_4$: 489.22, found [M+H] 490.1. $^1$H NMR (400 MHz, DMSO-$d_6$) δ 8.03 (s, 1H), 7.46 (d, J=2.9 Hz, 1H), 7.06 (dd, J=3.1, 8.9 Hz, 1H), 6.71 (d, J=8.8 Hz, 1H), 6.43 (s, 1H), 4.70 (dt, J=4.3, 9.4 Hz, 1H), 3.82 (s, 3H), 3.60-3.54 (m, 1H), 3.53-3.45 (m, 2H), 3.39 (dd, J=6.8, 9.4 Hz, 1H), 3.04 (t, J=9.0 Hz, 1H), 2.92 (dt, J=2.5, 11.8 Hz, 1H), 2.71-2.61 (m, 2H), 2.30-2.17 (m, 2H), 2.04-1.94 (m, 1H), 1.81-1.71 (m, 2H), 1.67-1.56 (m, 1H), 1.07 (d, J=6.2 Hz, 3H), 1.05 (d, J=6.1 Hz, 3H), 0.98 (d, J=6.7 Hz, 3H). Analytical HPLC (12 min gradient, 15 min stop): RT=10.5 min, HI: 99.0%. hGPR40 $EC_{50}$=170 nM.

EXAMPLE 107

2-((2R,4R)-1-(4-((1-(5-Ethoxy-2-fluorophenyl)piperidin-4-yl)oxy)phenyl)-4-methoxypyrrolidin-2-yl)acetic acid, TFA

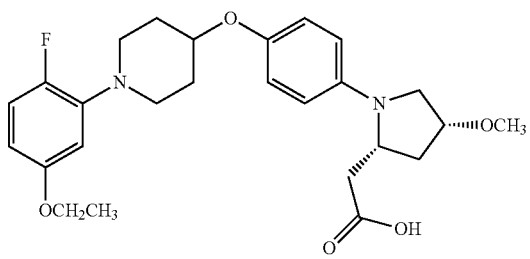 [SMILES: CCOc1ccc(F)c(N2CCC(Oc3ccc(N4C[C@H](OC)C[C@@H]4CC(=O)O)cc3)CC2)c1]

Example 107 (brown solid, 31.8 mg) was prepared from 85C and 4A following the procedure of Example 2. LC-MS Anal. Calc'd for $C_{26}H_{33}FN_2O_5$: 472.24, found [M+H] 473.0. $^1$H NMR (400 MHz, DMSO-$d_6$) δ 7.02 (dd, J=8.8, 12.5 Hz, 1H), 6.91 (d, J=9.0 Hz, 2H), 6.60-6.51 (m, 3H), 6.50-6.44 (m, 1H), 4.34-4.26 (m, 1H), 4.08 (t, J=4.9 Hz, 1H), 3.98 (q, J=7.0 Hz, 2H), 3.94-3.99 (m, 1H), 3.44-3.38 (m, 1H), 3.29 (s, 3H), 3.22-3.31 (m, 3H), 2.95-2.84 (m, 2H), 2.63 (dd, J=2.9, 15.2 Hz, 1H), 2.41 (dd, J=10.4, 15.2 Hz, 1H), 2.23-2.13 (m, 1H), 2.06-1.95 (m, 3H), 1.80-1.68 (m, 2H), 1.31 (t, J=7.0 Hz, 3H). Analytical HPLC (12 min gradient, 15 min stop): RT=10.6 min, HI: 99.0%. hGPR40 $EC_{50}$=160 nM.

EXAMPLE 109

2-((R)-1-(6-(((3,4-trans)-1-(5-Chloro-2-methoxypyridin-4-yl)-3-methylpiperidin-4-yl)oxy)pyridin-3-yl)-4,4-dimethylpyrrolidin-2-yl)acetic acid, TFA

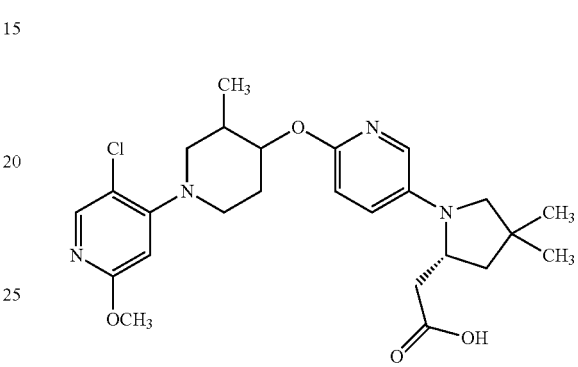

Example 109 (off-white solid, 10 mg) was prepared as a single isomer from 132A and (R)-1-(tert-butoxycarbonyl)-4,4-dimethylpyrrolidine-2-carboxylic acid following the procedure of Example 2. LC-MS Anal. Calc'd for $C_{25}H_{33}ClN_4O_4$: 488.22, found [M+H] 489.0. $^1$H NMR (400 MHz, DMSO-$d_6$) δ 8.02 (s, 1H), 7.46 (d, J=2.9 Hz, 1H), 7.06 (dd, J=3.0, 8.9 Hz, 1H), 6.70 (d, J=8.9 Hz, 1H), 6.43 (s, 1H), 4.72-4.66 (m, 1H), 4.03-3.96 (m, 1H), 3.81 (s, 3H), 3.52-3.45 (m, 2H), 3.21 (d, J=9.5 Hz, 1H), 2.96-2.80 (m, 2H), 2.76-2.62 (m, 2H), 2.27-2.13 (m, 2H), 2.07-1.92 (m, 2H), 1.67-1.57 (m, 2H), 1.12 (s, 3H), 0.99-0.91 (m, 6H). Analytical HPLC (12 min gradient, 15 min stop): RT=10.8 min, HI: 99.0%. hGPR40 $EC_{50}$=230 nM.

EXAMPLE 110

2-((2R,4R)-1-(6-(((3,4-trans)-1-(5-Chloro-2-methoxypyridin-4-yl)-3-methylpiperidin-4-yl)oxy)pyridin-3-yl)-4-methylpyrrolidin-2-yl)acetic acid

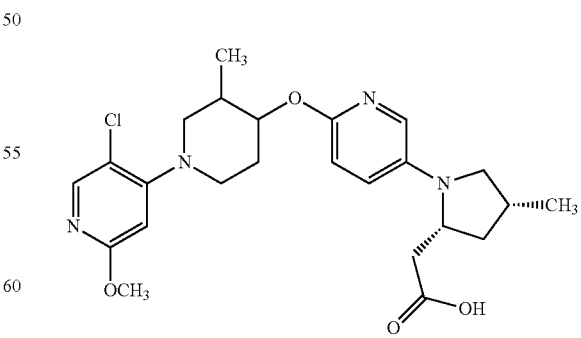

Example 110 (off-white solid, 16 mg) was prepared as a single isomer from 132A and (2R,4R)-1-(tert-butoxycarbonyl)-4-methylpyrrolidine-2-carboxylic acid following the procedure of Example 2. LC-MS Anal. Calc'd for $C_{24}H_{31}ClN_4O_4$: 474.20, found [M+H] 475.0. $^1$H NMR (500 MHz, DMSO-$d_6$) δ 8.04 (s, 1H), 7.49 (d, J=2.9 Hz, 1H), 7.13 (dd, J=2.4, 9.1 Hz, 1H), 6.76 (d, J=8.9 Hz, 1H), 6.44 (s, 1H), 4.74-4.67 (m, 1H), 4.02-3.94 (m, 1H), 3.82 (s, 3H), 3.53-3.46 (m, 2H), 3.38-3.33 (m, 1H), 3.01 (t, J=8.7 Hz, 1H), 2.96-2.88 (m, 1H), 2.77-2.64 (m, 2H), 2.46-2.38 (m, 1H), 2.30-2.18 (m, 2H), 2.14 (dd, J=9.7, 15.2 Hz, 1H), 2.03-1.96 (m, 1H), 1.65-1.59 (m, 1H), 1.49-1.41 (m, 1H), 1.10 (d, J=6.7 Hz, 3H), 0.98 (d, J=6.7 Hz, 3H). Analytical HPLC (12 min gradient, 15 min stop): RT=10.2 min, HI: 98.0%. hGPR40 $EC_{50}$=220 nM.

EXAMPLE 111

2-((2S,3S,4R)-1-(4-(((3,4-trans)-1-(5-Chloro-2-methoxypyridin-4-yl)-3-methylpiperidin-4-yl)oxy)-2-fluorophenyl)-4-methoxy-3-methylpyrrolidin-2-yl) acetic acid

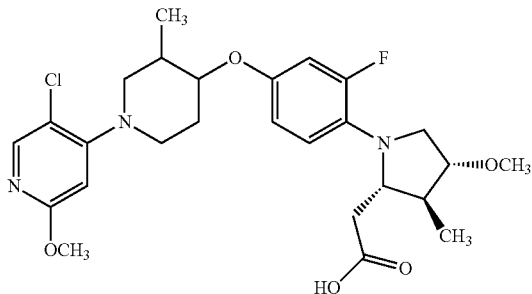 [SMILES: COc1cc(N2CCC(Oc3ccc(N4C[C@H](OC)[C@@H](C)[C@@H]4CC(=O)O)c(F)c3)C(C)C2)c(Cl)cn1]

111A. 5-Chloro-4-((3,4-trans)-4-(3-fluoro-4-iodophenoxy)-3-methylpiperidin-1-yl)-2-methoxypyridine: To a stirred solution of 3-fluoro-4-iodophenol (160 mg, 0.66 mmol), 119A, Isomer 1 (160 mg, 0.60 mmol), and $Ph_3P$ (210 mg, 0.78 mmol) in THF (3.6 mL) at rt was added DBAD (180 mg, 0.78 mmol). The resulting solution was stirred at rt for 24 h and then evaporated. The residue was purified by silica chromatography to afford 111A (190 mg, 0.38 mmol, 64% yield) as a colorless oil. LC-MS Anal. Calc'd for $C_{17}H_{19}ClFIN_2O_2$: 476.71, found [M+H] 477.0, 478.9. $^1$H NMR (400 MHz, $CDCl_3$) δ 7.98 (s, 1H), 7.58 (dd, J=8.7, 7.5 Hz, 1H), 6.68 (dd, J=9.9, 2.7 Hz, 1H), 6.55 (dd, J=8.7, 2.7 Hz, 1H), 6.27 (s, 1H), 3.95 (dt, J=8.6, 4.1 Hz, 1H), 3.89 (s, 3H), 3.51 (m, 2H), 2.89 (m, 1H), 2.65 (dd, J=12.6, 9.3 Hz, 1H), 2.19 (m, 2H) 1.83 (m, 1H), 1.10 (d, J=6.7 Hz, 3H). $^{19}$F NMR δ (376 MHz, $CDCl_3$): −92.0.

111B. ((2R,3S,4R)-1-(4-(((3,4-trans)-1-(5-Chloro-2-methoxypyridin-4-yl)-3-methylpiperidin-4-yl)oxy)-2-fluorophenyl)-4-methoxy-3-methylpyrrolidin-2-yl)methanol: A flask containing 111A (152 mg, 0.312 mmol), 118F (40 mg, 0.25 mmol), NaOH (31 mg, 0.75 mmol), and CuI (9 mg, 0.05 mmol) was evacuated and purged with argon. n-BuOH (1.3 mL) was added under argon and the mixture was degassed by ultrasound irradiation for 5 min. The mixture was heated to 90° C. for 18.5 h. The reaction mixture was cooled to rt and quenched with sat. aq. $NH_4Cl$ (20 mL). The aqueous mixture was extracted with $CH_2Cl_2$ (3×30 mL) and the combined extracts were washed with brine (20 mL). The organic layer was dried ($Na_2SO_4$) and evaporated and the residue was stripped from toluene (10 mL). The crude product was purified by silica chromatography to provide 111B (74 mg, 0.15 mmol, 60% yield) as a brown oil. LC-MS Anal. Calc'd for $C_{25}H_{33}ClFN_3O_4$: 494.00, found [M+H] 494.1, 496. $^1$H NMR (400 MHz, $CDCl_3$) δ 7.97 (s, 1H), 6.83 (t, J=9.3 Hz, 1H), 6.65 (m, 2H), 6.27 (s, 1H), 3.89 (s, 3H), 3.85 (dt, J=8.6, 4.0 Hz, 1H), 3.70 (m, 1H), 3.65-3.46 (m, 5H), 3.39 (s, 3H), 3.38 (m, 2H), 2.86 (m, 1H), 2.64 (dd, J=12.4, 9.2 Hz, 1H), 2.38 (m, 1H), 2.31 (br. s, 1H), 2.17 (m, 2H) 1.81 (m, 1H), 1.18 (d, J=7.1 Hz, 3H), 1.11 (d, J=6.8 Hz, 3H). $^{19}$F NMR δ (376 MHz, $CDCl_3$): −120.4.

111C. 2-((2S,3S,4R)-1-(4-(((3,4-trans)-1-(5-Chloro-2-methoxypyridin-4-yl)-3-methylpiperidin-4-yl)oxy)-2-fluorophenyl)-4-methoxy-3-methylpyrrolidin-2-yl)acetonitrile: To a solution of 111B (74 mg, 0.15 mmol) and MsCl (0.017 mL, 0.22 mmol) in $CH_2Cl_2$ (2.4 mL) at 0° C. was added $NEt_3$ (0.044 mL, 0.31 mmol). The mixture was stirred for 30 min at 0° C. and then for 3 h while warming to rt. The reaction mixture was diluted with EtOAc (40 mL) and washed with 1 M aq. HCl (10 mL), sat. aq. $NaHCO_3$ (20 mL), and brine (20 mL). The EtOAc solution was dried ($Na_2SO_4$) and concentrated. To a solution of the residue in DMSO (0.7 mL) was added KCN (15 mg, 0.22 mmol) and KI (4 mg, 0.02 mmol). The mixture was heated to 65° C. and stirred at this temperature under argon for 5 h. The reaction mixture was cooled to rt, diluted with EtOAc (60 mL), and washed with sat. aq. $NaHCO_3$ (2×20 mL), water (2×20 mL), and brine (20 mL). The organic layer was dried ($Na_2SO_4$) and concentrated. The crude product was purified by silica chromatography to give 111C (44 mg, 0.087 mmol, 59% yield) as a colorless oil. LC-MS Anal. Calc'd for $C_{26}H_{32}ClFN_4O_3$: 502.22, found [M+H] 503.2, 505. $^1$H NMR (400 MHz, $CDCl_3$) δ 7.97 (s, 1H), 6.68 (m, 3H), 6.27 (s, 1H), 3.89 (s, 3H), 3.84 (dt, J=8.7, 4.1 Hz, 1H), 3.77 (m, 1H), 3.62 (m, 1H), 3.56-3.44 (m, 4H), 3.39 (s, 3H), 2.86 (m, 1H), 2.70-2.53 (m, 3H), 2.39 (m, 1H), 2.16 (m, 2H) 1.81 (m, 1H), 1.19 (d, J=7.1 Hz, 3H), 1.12 (d, J=6.7 Hz, 3H). $^{19}$F NMR δ (471 MHz, $CDCl_3$): −122.8.

111D. Methyl 2-((2S,3S,4R)-1-(4-(((3,4-trans)-1-(5-chloro-2-methoxypyridin-4-yl)-3-methylpiperidin-4-yl)oxy)-2-fluorophenyl)-4-methoxy-3-methylpyrrolidin-2-yl)acetate: 111C (44 mg, 0.087 mmol) was dissolved in ~3 M HCl/MeOH/$CH_2Cl_2$/MeOAc solution [6.3 mL, prepared by addition of AcCl (1.3 mL) to a 3/2 $CH_2Cl_2$/MeOH solution (5.0 mL) at 0° C. and then stirring at rt for 20 min]. The resulting solution was allowed to stand at rt for 14.2 h and then diluted with MeCN (6 mL) and evaporated. The residue was taken up in EtOAc (50 mL) and washed with 10% aq. $NaHCO_3$ (30 mL), 5% aq. $NaHCO_3$ (30 mL), and brine (20 mL). The organic layer was dried ($Na_2SO_4$) and concentrated. The crude product was purified by silica chromatography to afford 111D (19 mg, 0.034 mmol, 39% yield) as a colorless oil. LC-MS Anal. Calc'd for $C_{27}H_{35}ClFN_3O_5$: 536.04, found [M+H] 536.2, 538. $^1$H NMR (400 MHz, $CDCl_3$) δ 7.97 (s, 1H), 6.72 (t, J=9.3 Hz, 1H), 6.64 (m, 2H), 6.26 (s, 1H), 3.89 (s, 3H), 3.83 (m, 2H), 3.63 (s, 3H), 3.59-3.47 (m, 4H), 3.42 (m, 1H), 3.37 (s, 3H), 2.85 (m, 1H), 2.63 (m, 2H), 2.51 (dd, J=15.2, 9.0 Hz, 1H), 2.17 (m, 3H), 1.80 (m, 1H), 1.14 (d, J=7.1 Hz, 3H), 1.11 (d, J=6.9 Hz, 3H). $^{19}$F NMR δ (471 MHz, $CDCl_3$): −121.6.

Example 111: To a stirred solution of 111D (34 mg, 0.064 mmol) in THF (1.9 mL) and water (0.19 mL) at rt was added 1 M aq. LiOH (0.19 mL, 0.19 mmol). After stirring at rt for 3.7 h, i-PrOH (0.1 mL) and additional amounts of THF (0.5 mL), water (0.2 mL), and 1 M aq. LiOH (0.1 mL, 0.1 mmol) were added. The reaction mixture was stirred at rt for an additional 11 h and then partially evaporated to remove most of the organic solvents. The remaining solution was partitioned between water (40 mL) and hexanes (15 mL). The layers were separated and the aqueous layer was acidified to pH 3 by dropwise addition of 1 M aq. HCl and extracted with CH$_2$Cl$_2$ (3×30 mL). The combined organic extracts were dried (Na$_2$SO$_4$) and concentrated. The residue was dried under vacuum to give the desired product (33 mg, 0.060 mmol, 97% yield). A portion of this material (23.9 mg) was purified by chiral SFC to afford Example 111 (white solid, 16.3 mg) as a single isomer. LC-MS Anal. Calc'd for C$_{26}$H$_{33}$ClFN$_3$O$_5$: 522.01, found [M+H] 522.2, 524. $^1$H NMR (500 MHz, CD$_2$Cl$_2$) δ 7.96 (s, 1H), 6.98 (t, J=9.2 Hz, 1H), 6.73 (m, 2H), 6.29 (s, 1H), 3.93 (dt, J=9.2, 4.2 Hz, 1H), 3.86 (s, 3H), 3.62-3.43 (m, 5H), 3.34 (s, 3H), 3.24 (dd, J=10.5, 6.1 Hz, 1H), 2.88 (m, 1H), 2.65 (m, 1H), 2.58 (dd, J=16.7, 5.7 Hz, 1H), 2.52 (dd, J=16.7, 2.9 Hz, 1H), 2.20 (m, 1H), 2.13 (m, 2H), 1.80 (m, 1H), 1.19 (d, J=7.1 Hz, 3H), 1.10 (d, J=6.8 Hz, 3H). $^{19}$F NMR δ (471 MHz, CD$_2$Cl$_2$): −120.9. Analytical HPLC (ZORBAX® method, 0% Solvent B start): RT=8.3 min, HI: 100%. hGPR40 EC$_{50}$=110 nM.

EXAMPLE 112

2-((2S,3S,4R)-1-(4-((1-(5-Chloro-2-methoxypyridin-4-yl)piperidin-4-yl)oxy)-2-fluorophenyl)-4-methoxy-3-methylpyrrolidin-2-yl)acetic acid

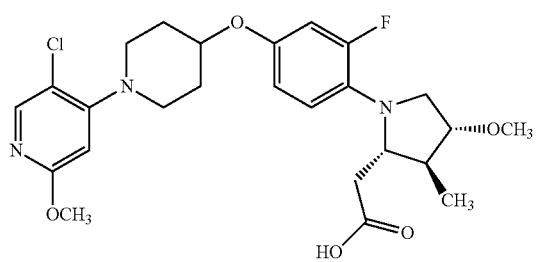 [SMILES: COc1cc(N2CCC(Oc3ccc(N4C[C@H](OC)[C@@H](C)[C@@H]4CC(=O)O)c(F)c3)CC2)c(Cl)cn1]

112A. 1-(5-Chloro-2-methoxypyridin-4-yl)piperidin-4-ol: To a round bottom flask was added 27B (2.8 g, 13 mmol), piperidin-4-ol (1.40 g, 13.8 mmol), K$_2$CO$_3$ (8.70 g, 62.9 mmol) and DMSO (30 mL). The reaction mixture was stirred at 110° C. for 14 h.

The reaction mixture was partitioned between water (150 mL) and EtOAc (150 mL). The organic layer was separated, washed with water (2×100 mL) and brine (100 mL), dried over MgSO$_4$, filtered, and concentrated. The residue was purified by silica chromatography to give 112A (2.7 g, 11 mmol, 88% yield) as a colorless oil. LC-MS Anal. Calc'd for C$_{11}$H$_{15}$ClN$_2$O$_2$: 242.70, found [M+H] 243.1, 245.0. $^1$H NMR (400 MHz, CDCl$_3$) δ 7.97 (s, 1H), 6.27 (s, 1H), 3.94-3.84 (m, 4H), 3.51-3.37 (m, 2H), 2.90 (ddd, J=12.3, 9.2, 3.0 Hz, 2H), 2.07-1.95 (m, 2H), 1.84-1.66 (m, 2H).

Example 112 (white solid, 36.7 mg) was prepared from 112A following the procedure of Example 111. LC-MS Anal. Calc'd for C$_{25}$H$_{31}$ClFN$_3$O$_5$ 507.98, found [M+H] 508.1, 510. $^1$H NMR (400 MHz, CD$_2$Cl$_2$) δ 8.00 (s, 1H), 7.06 (t, J=9.1 Hz, 1H), 6.78 (m, 2H), 6.35 (s, 1H), 4.49 (m, 1H), 3.90 (s, 3H), 3.63 (m, 2H), 3.42 (m, 3H), 3.38 (s, 3H), 3.25 (dd, J=10.4, 5.9 Hz, 1H), 3.11 (m, 2H), 2.64 (dd, J=16.7, 5.5 Hz, 1H), 2.54 (dd, J=16.7, 2.6 Hz, 1H), 2.15 (m, 3H), 2.00 (m, 2H), 1.24 (d, J=6.9 Hz, 3H). $^{19}$F NMR δ (376 MHz, CD$_2$Cl$_2$): −120.6. Analytical HPLC (ZORBAX® method, 0% Solvent B start): RT=8.0 min, HI: 99%. hGPR40 EC$_{50}$=130 nM.

EXAMPLE 113

2-((2S,3S,4R)-1-(4-(((3,4-trans)-1-(5-Ethoxy-2-fluorophenyl)-3-methylpiperidin-4-yl)oxy)-2-fluorophenyl)-4-methoxy-3-methylpyrrolidin-2-yl)acetic acid

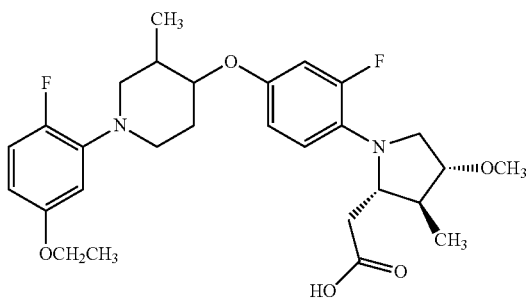 [SMILES: CCOc1ccc(F)c(N2CCC(Oc3ccc(N4C[C@H](OC)[C@@H](C)[C@@H]4CC(=O)O)c(F)c3)C(C)C2)c1]

Example 113 (white solid, 17.0 mg) was prepared as a single isomer from 431 following the procedure of Example 111. LC-MS Anal. Calc'd for C$_{28}$H$_{36}$F$_2$N$_2$O$_5$: 518.59, found [M+H] 519.3. $^1$H NMR (400 MHz, CD$_2$Cl$_2$) δ 7.07 (t, J=9.3 Hz, 1H), 6.94 (dd, J=12.4, 9.1 Hz, 1H), 6.77 (m, 2H), 6.55 (dd, J=7.3, 2.8 Hz, 1H), 6.44 (m, 1H), 4.01 (q, J=7.3 Hz, 2H), 3.92 (m, 2H), 3.63 (m, 2H), 3.44 (m, 3H), 3.38 (s, 3H), 3.24 (dd, J=10.0, 6.1 Hz, 1H), 2.85 (m, 1H) 2.68-2.45 (m, 3H), 2.27-2.08 (m, 2H), 1.83 (m, 1H), 1.41 (t, J=7.0 Hz, 3H), 1.12 (2 d, J=7.2 and 6.4 Hz, 6H). $^{19}$F NMR δ (376 MHz, CD$_2$Cl$_2$): −120.6, −133.6. Analytical HPLC (ZORBAX® method, 0% Solvent B start): RT=8.32 min, HI: 99%. hGPR40 EC$_{50}$=290 nM.

EXAMPLE 114

2-((2S,3S,4R)-1-(4-((1-(5-Ethoxy-2-fluorophenyl)piperidin-4-yl)oxy)-2-fluorophenyl)-4-methoxy-3-methylpyrrolidin-2-yl)acetic acid

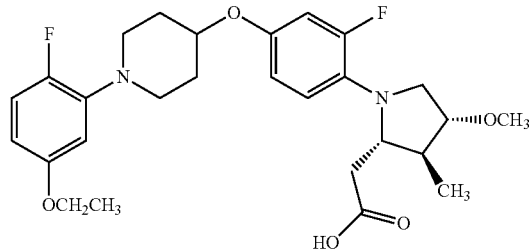 [SMILES: CCOc1ccc(F)c(N2CCC(Oc3ccc(N4C[C@H](OC)[C@@H](C)[C@@H]4CC(=O)O)c(F)c3)CC2)c1]

Example 114 (white solid, 37.1 mg) was prepared from 85A following the procedure for Example 111. LC-MS Anal. Calc'd for C$_{27}$H$_{34}$F$_2$N$_2$O$_5$: 504.57, found [M+H] 505.2. $^1$H NMR (500 MHz, CD$_2$Cl$_2$) δ 7.07 (t, J=9.3 Hz, 1H), 6.94 (dd, J=11.7, 8.9 Hz, 1H), 6.78 (m, 2H), 6.55 (dd, J=7.3, 2.8 Hz, 1H), 6.44 (dt, J=8.8, 3.1 Hz, 1H), 4.44 (m, 1H), 4.01 (q, J=6.9 Hz, 2H), 3.62 (m, 2H), 3.43 (m, 1H), 3.38 (s, 3H), 3.36 (m, 2H), 3.24 (dd, J=10.5, 6.1 Hz, 1H), 3.00 (m, 2H) 2.63 (dd, J=16.6, 5.3 Hz, 1H), 2.54 (dd, J=16.6, 2.4 Hz, 1H), 2.15 (m, 3H), 1.97 (m, 2H), 1.40 (t, J=7.1 Hz, 3H), 1.24 (d, J=6.9 Hz, 3H). $^{19}$F NMR δ (471 MHz, CD$_2$Cl$_2$): −120.6, −133.8. Analytical HPLC (ZORBAX® method, 0% Solvent B start): RT=8.01 min, HI: 99%. hGPR40 EC$_{50}$=320 nM.

EXAMPLE 115

2-((2S,3S,4R)-1-(4-(((3,4-trans)-1-(5-Chloro-2-methoxypyridin-4-yl)-3-methylpiperidin-4-yl)oxy)-2-fluorophenyl)-4-hydroxy-3-methylpyrrolidin-2-yl)acetic acid

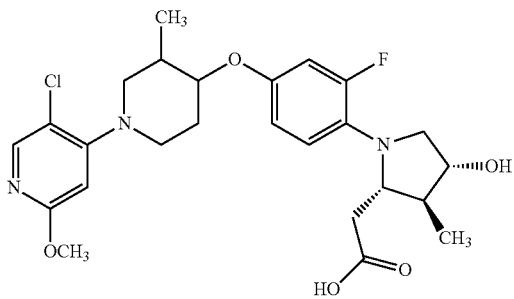 [SMILES: COc1cc(N2CCC(Oc3ccc(N4C[C@H](O)[C@@H](C)[C@@H]4CC(=O)O)c(F)c3)C(C)C2)c(Cl)cn1]

115A. 2-Fluoro-1-iodo-4-methoxybenzene: To a solution of TsOH (7.48 g, 38.7 mmol) in MeCN (51 mL) was added 2-fluoro-4-methoxyaniline (1.86 g, 12.9 mmol) and the resulting suspension was cooled to 12-14° C. A solution of NaNO$_2$ (1.78 g, 25.8 mmol) and KI (5.41 g, 32.3 mmol) in water (7.7 mL) was added slowly. After the addition was complete, the mixture was stirred at 12-14° C. for 10 min and then at rt overnight. The mixture was diluted with water (70 mL) and 1 M aq. K$_2$CO$_3$ was added until pH=9 followed by 2 M aq. Na$_2$S$_2$O$_3$ (25 mL). The aqueous mixture was extracted with ether (3×40 mL) and the combined organic extracts were dried (Na$_2$SO$_4$) and concentrated. The crude product was purified by silica chromatography to afford 115A (1.79 g, 7.03 mmol, 54% yield) as a colorless oil. $^1$H NMR (500 MHz, CDCl$_3$) δ 7.58 (dd, J=8.8, 7.6 Hz, 1H), 6.65 (dd, J=10.0, 2.8 Hz, 1H), 6.52 (dd, J=8.8, 2.8 Hz, 1H), 3.79 (s, 3H). $^{19}$F NMR δ (471 MHz, CDCl$_3$): −92.6.

115B. ((2R,3S,4R)-1-(2-Fluoro-4-methoxyphenyl)-4-methoxy-3-methylpyrrolidin-2-yl)methanol: A flask containing 115A (458 mg, 1.80 mmol), 118F (96 mg, 0.53 mmol), NaOH (87 mg, 2.1 mmol), and CuI (21 mg, 0.11 mmol) was evacuated and backfilled with argon. n-BuOH (2.5 mL) was added under argon and the mixture degassed by ultrasound irradiation under argon for 5 min. The reaction mixture was heated to 90° C. for 24 h. The reaction mixture was cooled to rt and quenched by the addition of sat. aq. NH$_4$Cl (8 mL) and water (20 mL). The aqueous mixture was extracted with CH$_2$Cl$_2$ (3×30 mL) and the combined organic extracts were washed with brine (20 mL). The organic layer was dried (Na$_2$SO$_4$), evaporated, and the residue was stripped from toluene (15 mL). The crude product was purified by silica chromatography to provide 115B (141 mg, 0.52 mmol, 99% yield) as a brownish oil. LC-MS Anal. Calc'd for C$_{14}$H$_{20}$FNO$_3$: 269.31, found [M+H] 270.1.

115C. 2-((2S,3S,4R)-1-(2-Fluoro-4-methoxyphenyl)-4-methoxy-3-methylpyrrolidin-2-yl)acetonitrile: To a solution of 115B (141 mg, 0.52 mmol) and MsCl (0.061 mL, 0.79 mmol) in CH$_2$Cl$_2$ (3.6 mL) at 0° C. was added NEt$_3$ (0.15 mL, 1.1 mmol). The mixture was stirred for 1 h at 0° C. and diluted with EtOAc (70 mL). The EtOAc solution was washed with 0.2 M aq. HCl (30 mL), sat. aq. NaHCO$_3$ (30 mL), and brine (20 mL), dried (Na$_2$SO$_4$), and concentrated. To a solution of the crude product (183 mg) in DMSO (1.1 mL) was added KCN (53 mg, 0.79 mmol) and KI (14 mg, 0.08 mmol). The mixture was heated to 65° C. for 4 h. The reaction mixture was cooled to rt, diluted with 4/1 EtOAc/hexanes (60 mL), and washed with sat. aq. NaHCO$_3$ (2×30 mL), water (2×30 mL), and brine (20 mL). The organic layer was dried (Na$_2$SO$_4$) and concentrated. The crude product was purified by silica chromatography to give 115C (98 mg, 0.35 mmol, 66% yield) as a colorless oil. LC-MS Anal. Calc'd for C$_{15}$H$_{19}$FN$_2$O$_2$: 278.32, found [M+H] 279.1.

115D. Methyl 2-((2S,3S,4R)-1-(2-fluoro-4-methoxyphenyl)-4-methoxy-3-methylpyrrolidin-2-yl)acetate: 115C (97 mg, 0.34 mmol) was dissolved in ~3 M HCl/MeOH/CH$_2$Cl$_2$/MeOAc solution [12.6 mL, prepared by addition of AcCl (2.6 mL) to a 3/2 CH$_2$Cl$_2$/MeOH solution (10.0 mL) at 0° C. and then stirring at rt for 20 min]. The resulting solution was allowed to stand at rt for 15 h and then evaporated. The remaining oily material was stripped from MeOH (2×10 mL) and the residue was dissolved in ~3 M HCl/MeOH/MeOAc solution [12.6 mL, prepared by addition of AcCl (2.6 mL) to MeOH (10.0 mL) at 0° C. and then stirring at rt for 30 min]. The resulting solution was heated to 40° C. and allowed to stand at this temperature for 21 h. The solution was cooled to rt, diluted with MeCN (10 mL), and evaporated. The residue was taken up in EtOAc (70 mL) and washed with 10% aq. Na$_2$CO$_3$ (30 mL), sat. aq. NaHCO$_3$ (20 mL), and brine (20 mL). The organic layer was dried (Na$_2$SO$_4$) and concentrated. The crude product was purified by silica chromatography to afford 115D (100 mg, 0.33 mmol, 97% yield) as a colorless oil. LC-MS Anal. Calc'd for C$_{16}$H$_{22}$FNO$_4$ 311.35, found [M+H] 312.2.

115E. Methyl 2-((2S,3S,4R)-1-(2-fluoro-4-hydroxyphenyl)-4-hydroxy-3-methylpyrrolidin-2-yl)acetate: To a solution of 115D (83 mg, 0.27 mmol) in CH$_2$Cl$_2$ (1.1 mL) at 0° C. was added BF$_3$.SMe$_2$ (0.17 mL, 1.6 mmol). The reaction mixture was stirred at 0° C. for 4 h. After this time, additional amounts of BF$_3$.SMe$_2$ (0.09 mL, 0.9 mmol) and CH$_2$Cl$_2$ (0.5 mL) were added and the reaction mixture was stirred at 0° C. for an additional 3 h. The reaction was quenched with MeOH (5.0 mL) followed by AcCl (0.6 mL) and the resulting reddish solution was stirred at 0° C. for 20 min. Then, the solution was warmed to rt and stirred for 2 h. Additional AcCl (0.6 mL) was added, and the mixture was stirred at rt for 2 h and then evaporated. The residue was taken up in EtOAc (60 mL) and washed with 10% aq. Na$_2$CO$_3$ (20 mL), sat. aq. NaHCO$_3$ (20 mL), and brine (20 mL). The organic layer was dried (Na$_2$SO$_4$) and concentrated. The crude product was purified by silica chromatography to give 115E (16 mg, 0.054 mmol, 20% yield) as a brown oil. LC-MS Anal. Calc'd for C$_{14}$H$_{18}$FNO$_4$: 283.30, found [M+H] 284.1.

115F. Methyl 2-((2S,3S,4R)-4-acetoxy-1-(2-fluoro-4-hydroxyphenyl)-3-methylpyrrolidin-2-yl)acetate: To a solution of 115E (26 mg, 0.092 mmol) in CH$_2$Cl$_2$ (0.5 mL) at rt was added a solution of DMAP (2 mg, 0.02 mmol) in pyridine (23 μL, 0.28 mmol). Ac$_2$O (14 μL, 0.15 mmol) was added to the resulting solution and the reaction mixture was stirred at rt for 1.5 h. The reaction mixture was diluted with EtOAc (8 mL) and quenched with 1 M aq. K$_2$CO$_3$ (6 mL). The biphasic mixture was stirred at rt for 1.5 h and then diluted with CH$_2$Cl$_2$ (50 mL). The pH of the aqueous layer was adjusted to 7.5 by the addition of 1 M aq. HCl and the biphasic mixture was shaken. The layers were separated and the organic layer was washed with water (20 mL) and brine (20 mL), dried (Na$_2$SO$_4$), and concentrated. To a solution of the crude material in MeOH (0.8 mL) and water (0.2 mL) was added ammonium acetate (59 mg, 0.74 mmol) and the resulting mixture was stirred at rt for 48 h. The mixture was diluted with EtOAc (40 mL) and washed with water (20 mL) and brine (20 mL). The organic layer was dried (Na$_2$SO$_4$)

and evaporated. The crude product was purified by silica chromatography to provide 115F (23 mg, 0.070 mmol, 74% yield) as a colorless oil. LC-MS Anal. Calc'd for $C_{16}H_{20}FNO_5$: 325.33, found [M+H] 326.2.

115G. Methyl 2-((2S,3S,4R)-4-acetoxy-1-(4-(((3,4-trans)-1-(5-chloro-2-methoxypyridin-4-yl)-3-methylpiperidin-4-yl)oxy)-2-fluorophenyl)-3-methylpyrrolidin-2-yl)acetate: To a stirred solution of 115F (23 mg, 0.067 mmol), 119A, Isomer 1 (27 mg, 0.10 mmol) and $Ph_3P$ (32 mg, 0.12 mmol) in THF (0.5 mL) at rt was added DBAD (28 mg, 0.12 mmol). The resulting solution was stirred at rt for 36 h and then evaporated. The residue was purified by silica chromatography to afford 115G (28 mg, 0.049 mmol, 73% yield) as a colorless oil. LC-MS Anal. Calc'd for $C_{28}H_{35}ClFN_3O_6$: 564.05, found [M+H] 564.2, 566.

Example 115: To a stirred solution of 115G (28 mg, 0.049 mmol) in THF (1.5 mL), i-PrOH (0.3 mL), and water (0.3 mL) at rt was added 1 M aq. LiOH (0.30 mL, 0.30 mmol). After stirring at rt for 5 h, the reaction mixture was partially evaporated to remove most of the organic solvents. The remaining solution was partitioned between water (40 mL) and hexanes (15 mL). The layers were separated and the aqueous layer was acidified to pH 3 by dropwise addition of 1 M aq. HCl and extracted with $CH_2Cl_2$ (3×30 mL). The combined organic extracts were dried ($Na_2SO_4$) and concentrated to afford Example 115 (23 mg, 0.044 mmol, 89% yield) as a white solid as a single isomer. LC-MS Anal. Calc'd for $C_{25}H_{31}ClFN_3O_5$: 507.98, found [M+H] 508.2, 510. $^1$H NMR (500 MHz, $CD_2Cl_2$) δ 7.96 (s, 1H), 7.04 (t, J=9.3 Hz, 1H), 6.74 (m, 2H), 6.29 (s, 1H), 4.06 (q, J=5.7 Hz, 1H), 3.94 (dt, J=8.9, 4.0 Hz, 1H), 3.86 (s, 3H), 3.51 (m, 3H), 3.42 (m, 1H), 3.29 (dd, J=10.7, 6.8 Hz, 1H), 2.88 (m, 1H), 2.65 (m, 1H), 2.61 (dd, J=16.7, 5.4 Hz, 1H), 2.52 (dd, J=16.7, 2.8 Hz, 1H), 2.21 (m, 1H), 2.13 (m, 1H), 2.04 (m, 1H), 1.79 (m, 1H), 1.20 (d, J=6.8 Hz, 3H), 1.10 (d, J=6.7 Hz, 3H). $^{19}$F NMR δ (471 MHz, $CD_2Cl_2$): −120.4. Analytical HPLC (ZORBAX® method, 0% Solvent B start): RT=7.60 min, HI: 99%. hGPR40 $EC_{50}$=1619 nM. hGPR40 IP1 $EC_{50}$=1600 nM.

EXAMPLE 117

2-((2S,3S,4R)-1-(6-(((3,4-trans)-1-(5-Ethoxy-2-fluorophenyl)-3-methylpiperidin-4-yl)oxy)pyridin-3-yl)-4-methoxy-3-methylpyrrolidin-2-yl)acetic acid, HCl

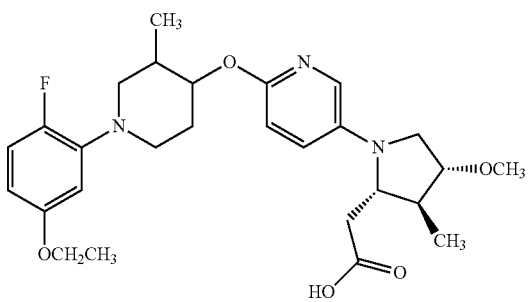 [SMILES: CCOc1ccc(F)c(N2CCC(Oc3ccc(N4C[C@H](OC)[C@@H](C)[C@@H]4CC(=O)O)cn3)C(C)C2)c1]

117A. 2-(((3R,4R)-1-(5-Ethoxy-2-fluorophenyl)-3-methylpiperidin-4-yl)oxy)-5-iodopyridine: To a solution of 43I, Isomer 2 (0.325 g, 1.28 mmol), 5-iodopyridin-2-ol (0.425 g, 1.92 mmol) and $Bu_3P$ (0.51 mL, 2.1 mmol) in toluene (16 mL) was added ADDP (0.517 g, 2.05 mmol). The reaction mixture was sonicated for 99 min. The reaction mixture was poured into hexanes, filtered, and concentrated. The crude product was purified by silica chromatography to provide 117A (0.414 g, 0.906 mmol, 71% yield) as a colorless oil. LC-MS Anal. Calc'd for $C_{19}H_{22}FIN_2O_2$: 456.29, found [M+H] 457.1. $^1$H NMR (500 MHz, $CDCl_3$) δ 8.30 (dd, J=2.3, 0.7 Hz, 1H), 7.78 (dd, J=8.7, 2.3 Hz, 1H), 6.91 (dd, J=12.4, 8.8 Hz, 1H), 6.59 (dd, J=8.7, 0.7 Hz, 1H), 6.52 (dd, J=7.3, 2.9 Hz, 1H), 6.39 (dt, J=8.8, 3.0 Hz, 1H), 4.78 (td, J=9.6, 4.4 Hz, 1H), 4.02-3.94 (m, 2H), 3.48-3.40 (m, 2H), 2.87 (td, J=11.7, 2.8 Hz, 1H), 2.57 (dd, J=12.1, 10.2 Hz, 1H), 2.29-2.21 (m, 1H), 2.20-2.09 (m, 1H), 1.80 (dddd, J=12.6, 11.3, 10.0, 4.1 Hz, 1H), 1.40 (t, J=7.0 Hz, 3H), 1.01 (d, J=6.9 Hz, 3H).

Example 117 (yellow solid, 31.7 mg) was prepared as a single isomer from 117A and 118F following the procedure of Example 2. LC-MS Anal. Calc'd for $C_{27}H_{36}FN_3O_5$: 456.29, found [M+H] 457.1. $^1$H NMR (500 MHz, acetonitrile-$d_3$) δ 7.98 (dd, J=6.2, 2.9 Hz, 1H), 7.76 (dd, J=9.5, 3.1 Hz, 1H), 7.53 (d, J=2.6 Hz, 1H), 7.35 (d, J=9.7 Hz, 1H), 7.26 (dd, J=12.1, 9.2 Hz, 1H), 7.00 (dt, J=9.2, 3.3 Hz, 1H), 4.95 (td, J=9.8, 4.2 Hz, 1H), 4.04 (q, J=7.0 Hz, 2H), 3.97-3.87 (m, 1H), 3.86-3.76 (m, 2H), 3.76-3.72 (m, 1H), 3.69 (dd, J=12.3, 2.9 Hz, 1H), 3.59-3.47 (m, 3H), 3.32 (s, 3H), 3.05-2.90 (m, 1H), 2.79-2.57 (m, 3H), 2.56-2.48 (m, 1H), 2.44 (q, J=7.1 Hz, 1H), 1.36 (t, J=6.9 Hz, 3H), 1.13 (d, J=6.6 Hz, 3H), 0.99 (d, J=7.3 Hz, 3H). Analytical HPLC: RT=8.7 min, HI: 98.9%. hGPR40 $EC_{50}$=140 nM. hGPR40 IP1 $EC_{50}$=14 nM.

EXAMPLE 118

2-((2S,3S,4R)-1-(4-(((3,4-trans)-1-(5-Ethoxy-2-fluorophenyl)-3-methylpiperidin-4-yl)oxy)phenyl)-4-methoxy-3-methylpyrrolidin-2-yl)acetic acid, HCl

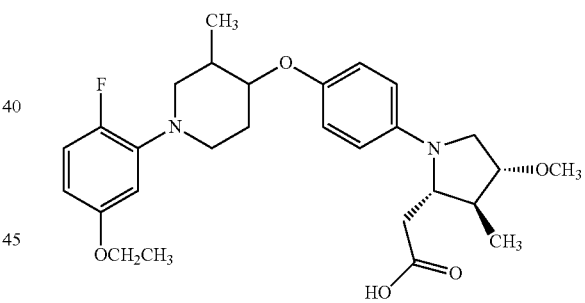

118A. (R)-1-Benzyl 2-methyl 4-((tert-butyldimethylsilyl)oxy)-4,5-dihydro-1H-pyrrole-1,2-dicarboxylate: To a solution of (2S,4R)-methyl 4-hydroxypyrrolidine-2-carboxylate, HCl (10.0 g, 55.3 mmol) in $CH_2Cl_2$ (76 mL) at rt was added imidazole (8.66 g, 127 mmol) and TBS-Cl (9.17 g, 60.8 mmol). The reaction mixture was stirred at rt overnight. The reaction mixture was washed with 10% aq. $Na_2CO_3$ (75 mL). The layers were separated and the aqueous layer was extracted with $CH_2Cl_2$ (75 mL). The combined organic layers were concentrated to a small volume and then toluene was added and the fractions were concentrated to ~75 mL. The toluene phase was washed with water and then used directly in the next step. To the solution of the crude material in toluene cooled to 0° C. was added water (25 mL) followed by NaDCC (6.69 g, 30.4 mmol). After 30 min, the reaction mixture was filtered through CELITE®, washed with toluene (30 mL), and the phases were separated. The organic phase was washed with water, cooled to 0° C., and NEt$_3$ (9.3 mL, 66 mmol) was added. The reaction mixture was stirred for 1 h at 0° C. and then overnight at rt. The organic solution was washed with water (2×), dried (MgSO$_4$), and concentrated. The crude material was used directly in the next step without further purification. To a solution of the crude material in CH$_2$Cl$_2$ (101 mL) at −10° C. was added 2,6-lutidine (11.8 mL, 101 mmol) followed by the dropwise addition of benzyl chloroformate (7.9 mL, 56 mmol) and the reaction mixture was warmed to rt and stirred overnight. Ethylenediamine (0.50 mL, 7.4 mmol) was added to the reaction mixture, which was stirred for 15 min at rt and then washed with 1 N aq. citric acid (60 mL) and 1 N aq. HCl (50 mL). The organic layer was washed with water, 1.5 N aq. KH$_2$PO$_4$, and brine. The organic layer was dried (Na$_2$SO$_4$), filtered, and concentrated. The crude product was purified by silica chromatography to provide 118A (16.3 g, 41.6 mmol, 82% yield) as a colorless oil. LC-MS Anal. Calc'd for C$_{20}$H$_{29}$NO$_5$Si: 391.55, found [M+H] 392.0. $^1$H NMR (500 MHz, CDCl$_3$) δ 7.40-7.29 (m, 5H), 5.69-5.62 (m, 1H), 5.20-5.11 (m, 2H), 4.94 (dt, J=7.7, 3.2 Hz, 1H), 3.98 (dd, J=12.4, 8.0 Hz, 1H), 3.79 (dd, J=12.2, 3.4 Hz, 1H), 3.71-3.62 (m, 3H), 0.88 (s, 9H), 0.07 (d, J=3.3 Hz, 6H).

118B. (2R,3S,4R)-1-Benzyl 2-methyl 4-((tert-butyldimethylsilyl)oxy)-3-methylpyrrolidine-1,2-dicarboxylate: CuBr.SMe$_2$ (4.78 g, 23.2 mmol) was suspended in anhydrous Et$_2$O (51 mL) and cooled to −40° C. A 1.6 M solution of MeLi in Et$_2$O (29.1 mL, 46.5 mmol) was added dropwise via addition funnel. The solution was stirred for 1 h and then a solution of 118A (7.00 g, 17.9 mmol) in Et$_2$O (20.4 mL) was added dropwise via addition funnel. The reaction mixture was stirred for 45 min at −45° C. and then transferred via cannula to a vigorously stirred solution of sat. aq. NH$_4$Cl and stirred for 30 min. The organic layer was separated and washed with sat. aq. NH$_4$Cl. The combined aqueous layers were extracted with hexanes. The combined organic layers were dried (MgSO$_4$) and concentrated. The crude material was purified by silica chromatography to obtain 119B (5.11 g, 12.5 mmol, 70% yield) as a colorless oil. LC-MS Anal. Calc'd for C$_{21}$H$_{33}$NO$_5$Si: 407.58, found [M+H] 408.2. $^1$H NMR (500 MHz, CDCl$_3$) δ 7.40-7.27 (m, 5H), 5.21-5.00 (m, 2H), 4.01-3.90 (m, 1H), 3.87-3.80 (m, 1.6H), 3.77-3.71 (m, 1.8H), 3.59-3.56 (m, 1.6H), 3.36-3.28 (m, 1H), 2.33-2.25 (m, 1H), 1.11 (dd, J=7.2, 2.2 Hz, 3H), 0.86 (s, 9H), 0.08-0.01 (m, 6H).

118C. (2R,3S,4R)-1-Benzyl 2-methyl 4-hydroxy-3-methylpyrrolidine-1,2-dicarboxylate: To a solution of 118B (5.10 g, 12.5 mmol) in THF (42 mL) was added a 1 M solution of TBAF in THF (19 mL, 19 mmol) and the reaction mixture was stirred at rt for 1 h. The reaction mixture was diluted with EtOAc, washed with water and brine, dried (MgSO$_4$), and concentrated. The crude material was purified by silica chromatography to obtain 118C (3.61 g, 12.3 mmol, 98% yield) as a colorless oil, which crystallized to a white solid upon standing. LC-MS Anal. Calc'd for C$_{15}$H$_{19}$NO$_5$: 293.32, found [M+H] 294.0. $^1$H NMR (400 MHz, CDCl$_3$) δ 7.41-7.27 (m, 5H), 5.25-4.97 (m, 2H), 4.09-3.96 (m, 1H), 3.95-3.87 (m, 1H), 3.86-3.70 (m, 3H), 3.69-3.57 (m, 2H), 3.10-2.83 (m, 1H), 2.37 (td, J=6.9, 2.9 Hz, 1H), 1.12 (d, J=7.3 Hz, 3H).

118D. (2R,3S,4R)-1-Benzyl 2-methyl 4-methoxy-3-methylpyrrolidine-1,2-dicarboxylate: To a solution of 118C (0.299 g, 1.02 mmol) in DMF (5.1 mL) at 0° C. was added 60% NaH (0.061 g, 1.5 mmol). The reaction mixture was stirred for 30 min and then MeI (0.064 mL, 1.0 mmol) was added and the reaction mixture was warmed to rt and stirred overnight. The reaction was quenched with water and diluted with EtOAc. The layers were separated and the organic layer was washed with water (4×). The organic layer was washed with brine, dried (MgSO$_4$), and concentrated. The crude product was purified by silica chromatography to provide 118D (0.266 g, 0.867 mmol, 85% yield) as a colorless oil. LC-MS Anal. Calc'd for C$_{16}$H$_{21}$NO$_5$: 307.34, found [M+H] 308.0. $^1$H NMR (500 MHz, CDCl$_3$) δ 7.40-7.27 (m, 5H), 5.25-4.99 (m, 2H), 4.09-3.95 (m, 1H), 3.88-3.77 (m, 1H), 3.76-3.57 (m, 3H), 3.52-3.43 (m, 2H), 3.29 (d, J=5.8 Hz, 3H), 2.57-2.42 (m, 1H), 1.14 (dd, J=7.2, 2.5 Hz, 3H).

118E. (2R,3S,4R)-Benzyl 2-(hydroxymethyl)-4-methoxy-3-methylpyrrolidine-1-carboxylate: To a solution of 118D (0.265 g, 0.863 mmol) in THF (4.3 mL) at 0° C. was added a 2 M solution of LiBH$_4$ (0.86 mL, 1.7 mmol) in THF. The reaction mixture was warmed to rt and stirred overnight. The reaction was quenched with sat. aq. NH$_4$Cl and diluted with EtOAc/water. The layers were separated and the organic layer was washed with brine, dried (MgSO$_4$), and filtered through a plug of silica gel, washing with EtOAc, to provide 118E (0.245 g, 0.878 mmol, 100% yield) as a colorless oil. LC-MS Anal. Calc'd for C$_{15}$H$_{21}$NO$_4$: 279.33, found [M+H] 280.0. $^1$H NMR (500 MHz, CDCl$_3$) δ 7.44-7.31 (m, 6H), 5.26-5.10 (m, 2H), 4.41-4.29 (m, 1H), 3.81 (dd, J=11.7, 5.6 Hz, 2H), 3.67 (br. s, 1H), 3.51-3.43 (m, 1H), 3.42-3.33 (m, 4H), 2.05-1.95 (m, 1H), 1.13 (dd, J=9.8, 7.0 Hz, 3H).

118F. ((2R,3S,4R)-4-Methoxy-3-methylpyrrolidin-2-yl)methanol: To a solution of 118E (0.241 g, 0.863 mmol) in MeOH (8.6 mL) was added 10% Pd/C (0.092 g, 0.086 mmol). The reaction vessel was purged with argon (3×) and then with H$_2$ (3×) and stirred under H$_2$ (1 atm) at rt for 2 h. The reaction mixture was filtered and concentrated to provide 118F (0.129 g, 0.889 mmol, 100% yield) as a colorless oil. LC-MS Anal. Calc'd for C$_7$H$_{15}$NO$_2$: 145.20, found [M+H] 146.1. $^1$H NMR (500 MHz, CDCl$_3$) δ 3.70-3.64 (m, 1H), 3.59-3.52 (m, 1H), 3.47 (dt, J=5.2, 3.6 Hz, 1H), 3.34 (s, 3H), 3.12-3.05 (m, 1H), 3.04-2.99 (m, 1H), 2.88-2.82 (m, 1H), 2.32 (br. s, 2H), 1.95-1.85 (m, 1H), 1.11 (d, J=7.2 Hz, 3H).

Example 118 (tan solid, 54.4 mg) was prepared from 118F and 18A, Isomer 2 following the procedure of Example 2. LC-MS Anal. Calc'd for C$_{28}$H$_{37}$FN$_2$O$_5$: 500.60, found [M+H] 501.1. $^1$H NMR (500 MHz, acetonitrile-d$_3$) δ 8.01 (dd, J=6.3, 3.0 Hz, 1H), 7.76 (d, J=9.1 Hz, 2H), 7.29 (dd, J=12.0, 9.2 Hz, 1H), 7.15 (d, J=9.1 Hz, 2H), 7.05 (dt, J=9.1, 3.3 Hz, 1H), 4.40 (td, J=10.2, 4.4 Hz, 1H), 4.06 (q, J=7.1 Hz, 2H), 3.96 (td, J=6.9, 3.9 Hz, 1H), 3.93-3.83 (m, 3H), 3.82-3.77 (m, 1H), 3.75 (d, J=12.4 Hz, 1H), 3.71-3.64 (m, 1H), 3.59-3.52 (m, 1H), 3.36 (s, 3H), 3.01-2.87 (m, 2H), 2.77 (dd, J=17.5, 5.4 Hz, 1H), 2.58-2.47 (m, 1H), 2.47-2.33 (m, 2H), 1.38 (t, J=7.0 Hz, 3H), 1.24 (d, J=6.6 Hz, 3H), 1.10 (d, J=6.6 Hz, 3H). Analytical HPLC: RT=10.8 min, HI: 95.1%. hGPR40 EC$_{50}$=59 nM. hGPR40 IP1 EC$_{50}$=13 nM.

EXAMPLE 119

2-((2S,3S,4R)-1-(4-(((3,4-trans)-1-(5-Chloro-2-methoxypyridin-4-yl)-3-methylpiperidin-4-yl)oxy)phenyl)-4-methoxy-3-methylpyrrolidin-2-yl)acetic acid, HCl

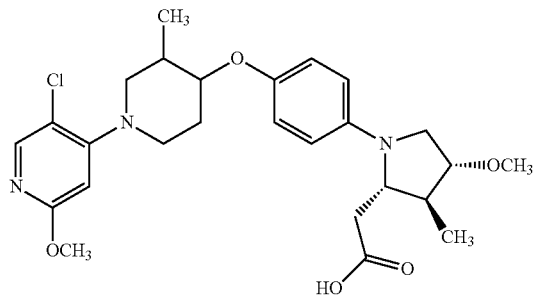 [SMILES: COc1cc(N2CCC(Oc3ccc(N4C[C@H](OC)[C@@H](C)[C@@H]4CC(=O)O)cc3)C(C)C2)c(Cl)cn1]

119A. (3,4-cis)-1-(5-Chloro-2-methoxypyridin-4-yl)-3-methylpiperidin-4-ol, Isomer 1 and Isomer 2: 27G (8.8 g, 34.2 mmol) was separated by chiral SFC to provide 119A, Isomer 1 as a colorless oil (3.00 g, 11.7 mmol, 34% yield). LC-MS Anal. Calc'd for $C_{12}H_{17}ClN_2O_2$: 256.10, found [M+H] 257.0. $^1$H NMR (400 MHz, CDCl$_3$) δ 7.96 (s, 1H), 6.27 (s, 1H), 3.97-3.91 (m, 1H), 3.88 (s, 3H), 3.27-3.17 (m, 1H), 3.16-3.04 (m, 2H), 2.90 (dd, J=11.7, 9.9 Hz, 1H), 2.05 (dd, J=6.9, 2.9 Hz, 1H), 2.00-1.83 (m, 2H), 1.42 (d, J=3.8 Hz, 1H), 1.03 (d, J=7.0 Hz, 3H). 119A, Isomer 2 (3.00 g, 11.7 mmol, 34% yield) was isolated as a colorless oil (3.00 g, 11.7 mmol, 34% yield). LC-MS Anal. Calc'd for $C_{12}H_{17}ClN_2O_2$: 256.10, found [M+H] 257.0. $^1$H NMR (400 MHz, CDCl$_3$) δ 7.96 (s, 1H), 6.27 (s, 1H), 3.97-3.91 (m, 1H), 3.88 (s, 3H), 3.27-3.17 (m, 1H), 3.16-3.04 (m, 2H), 2.90 (dd, J=11.7, 9.9 Hz, 1H), 2.05 (dd, J=6.9, 2.9 Hz, 1H), 2.00-1.83 (m, 2H), 1.42 (d, J=3.8 Hz, 1H), 1.03 (d, J=7.0 Hz, 3H).

119B. 5-Chloro-4-((3,4-trans)-4-(4-iodophenoxy)-3-methylpiperidin-1-yl)-2-methoxypyridine: To a solution of 119A, Isomer 1 (0.519 g, 2.02 mmol), 4-iodophenol (0.579 g, 2.63 mmol), and Bu$_3$P (0.80 mL, 3.2 mmol) in toluene (25 mL) was added ADDP (0.817 g, 3.24 mmol). The reaction mixture was sonicated for 99 min. The reaction mixture was poured into hexanes, filtered, and concentrated. The crude product was purified by silica chromatography to provide 119B (0.482 g, 1.05 mmol, 52% yield) as a colorless oil. LC-MS Anal. Calc'd for $C_{18}H_{20}ClIN_2O_2$: 458.72, found [M+H] 459.0. $^1$H NMR (400 MHz, CDCl$_3$) δ 7.98 (s, 1H), 7.61-7.50 (m, 2H), 6.75-6.66 (m, 2H), 6.27 (s, 1H), 3.99-3.90 (m, 1H), 3.89 (s, 3H), 3.56-3.46 (m, 2H), 2.93-2.82 (m, 1H), 2.65 (dd, J=12.3, 9.0 Hz, 1H), 2.23-2.08 (m, 2H), 1.82 (dtd, J=13.1, 9.7, 3.9 Hz, 1H), 1.10 (d, J=6.6 Hz, 3H).

Example 119 (beige solid, 14.2 mg) was prepared from 119B and 118F following the procedure of Example 17. LC-MS Anal. Calc'd for $C_{26}H_{34}ClN_3O_5$: 504.02, found [M] 504.2. $^1$H NMR (500 MHz, acetonitrile-d$_3$) δ 8.01 (s, 1H), 7.67 (d, J=9.1 Hz, 2H), 7.10 (d, J=9.1 Hz, 2H), 6.47 (s, 1H), 4.29 (td, J=8.5, 4.1 Hz, 1H), 4.04 (s, 3H), 3.98-3.88 (m, 4H), 3.88-3.82 (m, 1H), 3.82-3.76 (m, 1H), 3.41-3.32 (m, 4H), 3.11 (dd, J=13.3, 9.8 Hz, 1H), 2.90 (d, J=5.2 Hz, 1H), 2.80-2.73 (m, 1H), 2.44-2.34 (m, 1H), 2.31-2.23 (m, 1H), 2.16-2.05 (m, 1H), 1.78-1.67 (m, 1H), 1.22 (d, J=6.9 Hz, 3H), 1.07 (d, J=6.6 Hz, 3H). Analytical HPLC: RT=9.3 min, HI: 95.3%. hGPR40 EC$_{50}$=75 nM. hGPR40 IP1 EC$_{50}$=11 nM.

EXAMPLE 120

2-((2R,4R)-1-(4-(((3,4-trans)-1-(2-Fluoro-5-methoxy-d$_3$-phenyl)-3-methylpiperidin-4-yl)oxy)phenyl)-4-(trifluoromethyl)pyrrolidin-2-yl)acetic acid, HCl

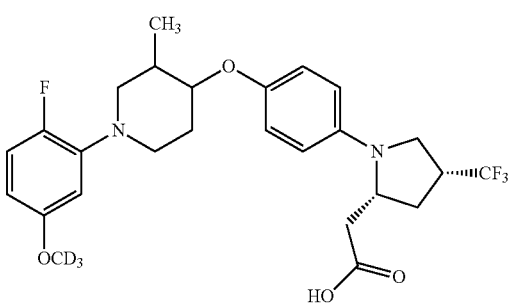

Example 120 (white solid, 37 mg) was prepared from MeI-d$_3$ following the procedure of Example 39. LC-MS Anal. Calc'd for $C_{26}H_{27}D_3F_4N_2O_4$: 513.54, found [M+H] 514.2. $^1$H NMR (500 MHz, acetonitrile-d$_3$) δ 7.63-7.55 (m, 2H), 7.43 (dd, J=6.3, 3.0 Hz, 1H), 7.25 (dd, J=11.7, 9.2 Hz, 1H), 7.18-7.09 (m, 2H), 6.97 (dt, J=9.2, 3.2 Hz, 1H), 4.39-4.26 (m, 2H), 4.05 (dd, J=12.4, 7.2 Hz, 1H), 3.81 (dd, J=12.2, 10.6 Hz, 1H), 3.75-3.60 (m, 4H), 3.42 (t, J=11.8 Hz, 1H), 2.90-2.72 (m, 3H), 2.65-2.52 (m, 1H), 2.43-2.34 (m, 1H), 2.26-2.13 (m, 2H), 1.09 (d, J=6.6 Hz, 3H). Analytical HPLC: RT=11.7 min, HI: 98.5%. hGPR40 EC$_{50}$=77 nM.

EXAMPLE 121

2-((2S,3S,4R)-1-(4-((1-(5-Ethoxy-2-fluorophenyl)piperidin-4-yl)oxy)phenyl)-4-methoxy-3-methylpyrrolidin-2-yl)acetic acid, TFA

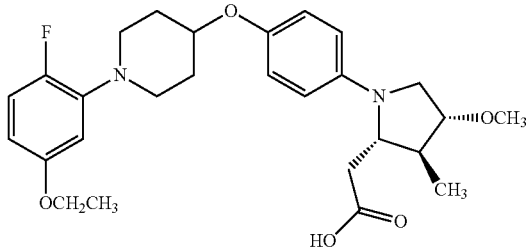

Example 121 (35.2 mg) was prepared from 85C and 118F following the procedure of Example 2. LC-MS Anal. Calc'd for $C_{27}H_{35}FN_2O_5$: 486.58, found [M+H] 487.1. $^1$H NMR (500 MHz, DMSO-d$_6$) δ 7.05-6.96 (m, 1H), 6.88 (d, J=7.7 Hz, 2H), 6.49 (td, J=15.6, 7.8 Hz, 5H), 4.28 (br. s, 1H), 3.96 (d, J=6.3 Hz, 2H), 3.74-3.32 (m, 6H), 3.28 (br. s, 3H), 3.24 (br. s, 2H), 2.64-2.39 (m, 1H), 2.29 (d, J=6.6 Hz, 1H), 2.04-1.93 (m, 2H), 1.79-1.65 (m, J=8.3 Hz, 2H), 1.34-1.25 (m, 3H), 0.94 (d, J=6.6 Hz, 3H). Analytical HPLC (Acquity method): RT=1.8 min, HI: 96.8%. hGPR40 EC$_{50}$=140 nM. hGPR40 IP1 EC$_{50}$=42 nM.

EXAMPLE 122

2-((2R,4S)-1-(4-((1-(5-Ethoxy-2-fluorophenyl)piperidin-4-yl)oxy)phenyl)-4-(3-(trifluoromethyl)phenyl)pyrrolidin-2-yl)acetic acid, TFA

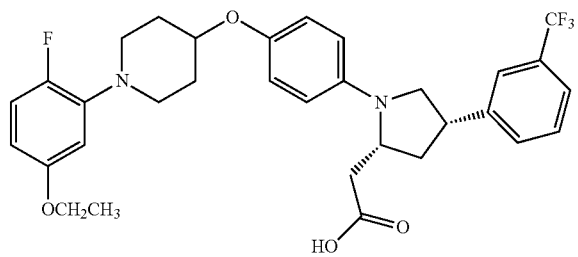 [SMILES: CCOc1ccc(F)c(N2CCC(Oc3ccc(N4C[C@H](c5cccc(C(F)(F)F)c5)C[C@@H]4CC(=O)O)cc3)CC2)c1]

122A. (R)-1-Benzyl 2-methyl 4-oxopyrrolidine-1,2-dicarboxylate: To a solution of (2R,4R)-1-benzyl 2-methyl 4-hydroxypyrrolidine-1,2-dicarboxylate (16.7 g, 59.7 mmol) in CH$_2$Cl$_2$ (149 mL) was added TCCA (13.9 g, 59.7 mmol) followed by the addition of TEMPO (0.093 g, 0.60 mmol). The reaction mixture was warmed to rt and stirred for 15 min. The reaction mixture was filtered and washed with sat. aq. Na$_2$CO$_3$, 0.1 M aq. HCl, and brine. The organic layer was dried (MgSO$_4$) and concentrated. The material was filtered through a plug of silica gel to obtain 122A (12.6 g, 45.3 mmol, 76% yield) as a colorless oil, which solidified upon standing to a pale yellow solid. LC-MS Anal. Calc'd for C$_{14}$H$_{15}$NO$_5$: 277.27, found [M+H] 278.0. $^1$H NMR (500 MHz, CDCl$_3$) δ 7.43-7.28 (m, 5H), 5.27-5.20 (m, 1H), 5.19-5.08 (m, 1H), 4.92-4.78 (m, 1H), 4.07-3.88 (m, 2H), 3.81-3.56 (m, 3H), 3.03-2.87 (m, 1H), 2.61 (dd, J=18.8, 2.6 Hz, 1H).

122B. (R)-7-Benzyl 8-methyl 1,4-dioxa-7-azaspiro[4.4]nonane-7,8-dicarboxylate: 122A (12.6 g, 45.3 mmol) and ethane-1,2-diol (2.5 mL, 45 mmol) were dissolved in toluene (450 mL). TsOH (1.01 g, 5.89 mmol) was added. The resulting mixture was heated to reflux for 18 h. The reaction mixture was cooled to rt, poured into ice-water, extracted with EtOAc (3×), washed with brine, dried (MgSO$_4$), and concentrated under reduced pressure. The crude product was purified by silica chromatography to provide 122B (8.58 g, 26.7 mmol, 59% yield) as a pale yellow oil, which solidified upon standing. LC-MS Anal. Calc'd for C$_{16}$H$_{19}$NO$_6$: 321.33, found [M+H] 322.0. $^1$H NMR (400 MHz, CDCl$_3$) δ 7.42-7.27 (m, 5H), 5.25-4.99 (m, 2H), 4.60-4.42 (m, 1H), 4.02-3.87 (m, 4H), 3.82-3.53 (m, 5H), 2.48-2.34 (m, 1H), 2.29-2.17 (m, 1H).

122C. (S)-2-(7-(4-((1-(5-Ethoxy-2-fluorophenyl)piperidin-4-yl)oxy)phenyl)-1,4-dioxa-7-azaspiro[4.4]nonan-8-yl)acetonitrile: 122C was prepared from 122B and 85C following the procedure of Example 118. LC-MS Anal. Calc'd for C$_{27}$H$_{32}$FN$_3$O$_4$: 481.56, found [M+H] 482.2. $^1$H NMR (500 MHz, CDCl$_3$) δ 6.95-6.87 (m, 3H), 6.53 (dd, J=7.4, 3.0 Hz, 1H), 6.51-6.45 (m, 2H), 6.40 (dt, J=8.8, 3.2 Hz, 1H), 4.29 (tt, J=7.4, 3.6 Hz, 1H), 4.23-4.16 (m, 1H), 4.10-4.05 (m, 1H), 4.05-4.01 (m, 1H), 4.01-3.95 (m, 4H), 3.47-3.43 (m, 1H), 3.42-3.37 (m, 1H), 3.37-3.30 (m, 2H), 2.94 (ddd, J=11.8, 8.3, 3.3 Hz, 2H), 2.80-2.75 (m, 1H), 2.75-2.68 (m, 1H), 2.46 (dd, J=13.3, 8.1 Hz, 1H), 2.22 (dd, J=13.2, 1.4 Hz, 1H), 2.12-2.05 (m, 2H), 1.99-1.90 (m, 2H), 1.39 (t, J=7.0 Hz, 3H).

122D. (S)-2-(1-(4-((1-(5-Ethoxy-2-fluorophenyl)piperidin-4-yl)oxy)phenyl)-4-oxopyrrolidin-2-yl)acetonitrile: To a solution of 122C (1.36 g, 2.82 mmol) in acetone (39 mL) and water (17 mL) (purged with argon for 10 min) was added TsOH (2.14 g, 11.3 mmol). The reaction mixture was heated to 56° C. for 30 h. The reaction mixture was cooled to rt and diluted with EtOAc/water. 1.5 M aq. K$_2$HPO$_4$ was added to basify the reaction mixture and the layers were separated. The aqueous layer was extracted with EtOAc and the combined organic layers were washed with brine, dried (MgSO$_4$), and concentrated. 122D (1.16 g, 2.66 mmol, 94% yield) was isolated as a light brown solid and was used without further purification. LC-MS Anal. Calc'd for C$_{25}$H$_{28}$FN$_3$O$_3$: 437.51, found [M+H] 438.1. $^1$H NMR (400 MHz, CDCl$_3$) δ 7.00-6.95 (m, 2H), 6.91 (dd, J=12.1, 8.8 Hz, 1H), 6.67-6.61 (m, 2H), 6.54 (dd, J=7.4, 3.0 Hz, 1H), 6.40 (dt, J=8.8, 3.1 Hz, 1H), 4.58 (tt, J=8.0, 2.9 Hz, 1H), 4.34 (tt, J=7.4, 3.7 Hz, 1H), 3.98 (q, J=6.9 Hz, 2H), 3.86-3.71 (m, 2H), 3.39-3.28 (m, 2H), 3.05 (dd, J=18.6, 8.5 Hz, 1H), 2.96 (ddd, J=11.9, 8.1, 3.3 Hz, 2H), 2.72 (ddd, J=17.6, 12.3, 2.5 Hz, 2H), 2.57 (dd, J=16.8, 7.6 Hz, 1H), 2.16-2.06 (m, 2H), 2.02-1.89 (m, 2H), 1.40 (t, J=6.9 Hz, 3H).

122E. (S)-5-(Cyanomethyl)-1-(4-((1-(5-ethoxy-2-fluorophenyl)piperidin-4-yl)oxy)phenyl)-2,5-dihydro-1H-pyrrol-3-yltrifluoromethanesulfonate: To a solution of 1 M solution of NaHMDS (0.75 mL, 0.75 mmol) in THF (3.4 mL) at −78° C. was added a solution of 122D (0.300 g, 0.686 mmol) in THF (3.4 mL) dropwise. The reaction mixture was stirred for 30 min and then a solution of 1,1,1-trifluoro-N-phenyl-N-(trifluoromethyl)sulfonyl methanesulfonamide (0.294 g, 0.823 mmol) in THF (3.4 mL) was added dropwise. The reaction mixture was stirred for 2 h at −78° C., quenched with 1.5 M aq. K$_2$HPO$_4$, and extracted with EtOAc (2×). The combined organic layers were washed with brine, dried (MgSO$_4$), and concentrated. The crude product was purified by silica chromatography to provide 122E (0.309 g, 0.543 mmol, 79% yield) as a colorless oil. LC-MS Anal. Calc'd for C$_{26}$H$_{27}$F$_4$N$_3$O$_5$S: 569.57, found [M+H] 570.0. $^1$H NMR (400 MHz, CDCl$_3$) δ 6.98-6.86 (m, 3H), 6.58-6.49 (m, 3H), 6.40 (dt, J=8.8, 3.2 Hz, 1H), 5.93 (q, J=1.8 Hz, 1H), 4.93-4.83 (m, 1H), 4.53 (ddd, J=13.3, 6.7, 1.9 Hz, 1H), 4.36-4.27 (m, 1H), 4.22-4.15 (m, 1H), 3.98 (q, J=7.0 Hz, 2H), 3.39-3.28 (m, 2H), 2.95 (ddd, J=11.8, 8.2, 3.3 Hz, 2H), 2.82-2.78 (m, 2H), 2.15-2.05 (m, 2H), 2.01-1.88 (m, 2H), 1.40 (t, J=6.9 Hz, 3H).

122F. (S)-2-(1-(4-((1-(5-Ethoxy-2-fluorophenyl)piperidin-4-yl)oxy)phenyl)-4-(3-(trifluoromethyl)phenyl)-2,5-dihydro-1H-pyrrol-2-yl)acetonitrile: To a solution of 122E (0.030 g, 0.053 mmol) and (3-(trifluoromethyl)phenyl)boronic acid (0.015 g, 0.079 mmol) in dioxane (0.53 mL) was added a 2 M aq. solution of Na$_2$CO$_3$ (0.066 mL, 0.13 mmol). The reaction vessel was purged with argon for 10 min and then Pd(Ph$_3$P)$_4$ (1.2 mg, 1.1 µmol) was added. The reaction mixture was microwaved at 150° C. for 3 min. The reaction mixture was diluted with EtOAc/water and the layers were separated. The organic layer was washed with brine, dried (MgSO$_4$), and concentrated. The crude product was purified by silica chromatography to provide 122F (0.024 g, 0.043 mmol, 81% yield). LC-MS Anal. Calc'd for $C_{32}H_{31}F_4N_3O_2$: 565.60, found [M+H] 566.3. $^1$H NMR (500 MHz, CDCl$_3$) δ 7.74-7.64 (m, 2H), 7.61 (d, J=8.0 Hz, 1H), 7.56-7.49 (m, 1H), 7.00-6.95 (m, 2H), 6.92 (dd, J=12.1, 8.8 Hz, 1H), 6.67-6.60 (m, 2H), 6.55 (dd, J=7.3, 2.9 Hz, 1H), 6.46-6.37 (m, 2H), 4.98 (td, J=6.3, 2.9 Hz, 1H), 4.81 (ddd, J=13.2, 6.1, 1.9 Hz, 1H), 4.45 (dt, J=13.1, 2.4 Hz, 1H), 4.32 (tt, J=7.4, 3.6 Hz, 1H), 4.03-3.93 (m, 2H), 3.40-3.31 (m, 2H), 2.96 (ddd, J=11.7, 8.1, 3.3 Hz, 2H), 2.92-2.85 (m, 1H), 2.75 (dd, J=16.6, 7.0 Hz, 1H), 2.15-2.07 (m, 2H), 2.02-1.92 (m, 2H), 1.40 (t, J=7.0 Hz, 3H).

122G. 2-((2R,4S)-1-(4-((1-(5-Ethoxy-2-fluorophenyl)piperidin-4-yl)oxy)phenyl)-4-(3-(trifluoromethyl)phenyl)pyrrolidin-2-yl)acetonitrile: To a solution of 122F (0.024 g, 0.043 mmol) in MeOH (2 mL) was added 10% Pd/C (2.3 mg, 2.1 µmol). The reaction vessel was purged with argon (3×) and then H$_2$ (3×) and stirred under H$_2$ (1 atm) at rt. After 1 h, a grey precipitate formed in reaction. EtOAc (2 mL) and additional Pd/C (2.3 mg, 2.2 µmol) was added. The reaction vessel was purged with argon (3×) and then H$_2$ (3×) and stirred under H$_2$ (1 atm) at rt for 2 h. The reaction mixture was filtered and concentrated to provide 122G (0.0221 g, 0.039 mmol, 91% yield) as a pale yellow oil. LC-MS Anal. Calc'd for $C_{32}H_{33}F_4N_3O_2$: 567.62, found [M+H] 568.3.

Example 122 (7.4 mg) was prepared from 122G following the procedure of Example 2. LC-MS Anal. Calc'd for $C_{32}H_{34}F_4N_2O_4$: 586.62, found [M+H] 587.3. $^1$H NMR (500 MHz, DMSO-d$_6$) δ 12.16 (br. s, 1H), 7.75-7.67 (m, 2H), 7.63-7.54 (m, 2H), 7.00 (dd, J=12.4, 8.8 Hz, 1H), 6.90 (d, J=8.8 Hz, 2H), 6.61 (d, J=8.5 Hz, 2H), 6.53 (dd, J=7.4, 2.8 Hz, 1H), 6.46 (dt, J=8.7, 2.9 Hz, 1H), 4.31 (dt, J=7.6, 3.9 Hz, 1H), 4.10 (q, J=7.0 Hz, 1H), 3.97 (q, J=7.1 Hz, 2H), 3.72-3.61 (m, 1H), 3.55-3.44 (m, 3H), 3.29-3.21 (m, 2H), 2.93-2.78 (m, 2H), 2.77-2.68 (m, 1H), 2.20 (dd, J=15.4, 9.9 Hz, 1H), 2.01 (d, J=7.7 Hz, 3H), 1.79-1.68 (m, 2H), 1.30 (t, J=6.9 Hz, 3H). Analytical HPLC (Acquity method): RT=1.9 min, HI: 100%. hGPR40 EC$_{50}$=240 nM.

EXAMPLE 123

2-((2R,4S)-1-(4-((1-(5-Ethoxy-2-fluorophenyl)piperidin-4-yl)oxy)phenyl)-4-(6-methoxypyridin-3-yl)pyrrolidin-2-yl)acetic acid, TFA

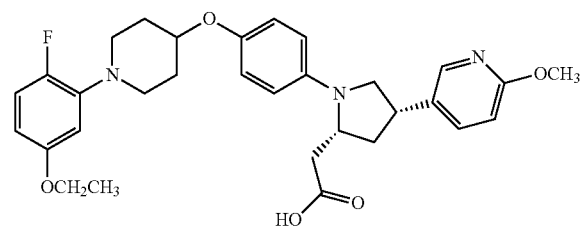 [SMILES: CCOc1ccc(F)c(N2CCC(Oc3ccc(N4C[C@H](c5ccc(OC)nc5)C[C@@H]4CC(=O)O)cc3)CC2)c1]

Example 123 (amber oil, 3.5 mg) was prepared from 122E and (6-methoxypyridin-3-yl)boronic acid following the procedure from Example 122. LC-MS Anal. Calc'd for $C_{31}H_{36}FN_3O_5$: 549.63, found [M+H] 550.0. $^1$H NMR (400 MHz, acetonitrile-d$_3$) δ 8.16 (d, J=2.2 Hz, 1H), 7.85 (dd, J=8.7, 2.5 Hz, 1H), 7.28 (d, J=7.7 Hz, 2H), 7.10-6.97 (m, 3H), 6.88 (d, J=8.7, 0.6 Hz, 1H), 6.71 (dd, J=7.2, 3.0 Hz, 1H), 6.58 (dt, J=8.9, 3.1 Hz, 1H), 4.55 (br. s, 1H), 4.11-4.03 (m, 1H), 4.00 (q, J=7.0 Hz, 3H), 3.92 (s, 3H), 3.91-3.76 (m, 3H), 3.44 (ddd, J=11.6, 7.7, 3.4 Hz, 2H), 3.11 (ddd, J=11.8, 8.1, 3.4 Hz, 2H), 2.91-2.74 (m, 2H), 2.72-2.59 (m, 1H), 2.22-2.12 (m, 3H), 1.34 (t, J=6.9 Hz, 4H). Analytical HPLC: RT=9.4 min, HI: 93.3%. hGPR40 EC$_{50}$=270 nM. hGPR40 IP1 EC$_{50}$=51 nM.

EXAMPLE 124

2-((2R,4R)-1-(4-((1-(5-Ethoxy-2-fluorophenyl)piperidin-4-yl)oxy)phenyl)-4-(3-methoxybenzyl)pyrrolidin-2-yl)acetic acid, TFA

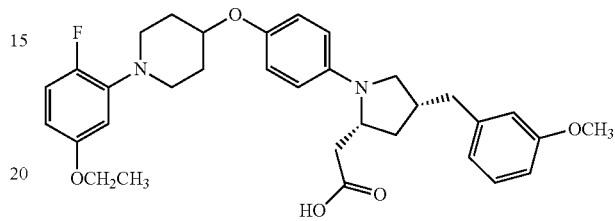

124A. (S)-2-(1-(4-((1-(5-Ethoxy-2-fluorophenyl)piperidin-4-yl)oxy)phenyl)-4-(3-methoxybenzyl)-2,5-dihydro-1H-pyrrol-2-yl)acetonitrile: To a suspension of zinc dust (0.049 g, 0.75 mmol) in anhydrous THF (0.33 mL) was sequentially added with stirring ethylene dibromide (1.7 µL, 0.020 mmol) and TMSCl (1.3 µL, 10 µmol) under argon. The mixture was heated with stirring to 65° C. for 20 min. A solution of 1-(bromomethyl)-3-methoxybenzene (0.070 mL, 0.50 mmol) in THF (0.66 mL) was added dropwise. The mixture was stirred at 65° C. for 2 h, cooled to rt, and used directly in the next step. A microwave vial was charged with 122E (0.031 g, 0.055 mmol) and Pd(Ph$_3$P)$_4$ (1.2 mg, 1.1 µmol) and then purged with argon. THF (0.27 mL) was added followed by the solution of (3-methoxybenzyl)zinc (II) bromide (0.21 mL). The reaction mixture was heated to 50° C. for 2 h. The reaction was quenched with water and diluted with EtOAc. The layers were separated and the aqueous layer was extracted with EtOAc. The combined organic layers were dried (MgSO$_4$), filtered, and concentrated. The crude product was purified by silica chromatography to provide 124A (0.021 g, 0.040 mmol, 73% yield) as a pale yellow oil. LC-MS Anal. Calc'd for $C_{33}H_{36}FN_3O_3$: 541.66, found [M+H] 542.3. $^1$H NMR (400 MHz, CDCl$_3$) δ 6.97-6.87 (m, 4H), 6.86-6.75 (m, 3H), 6.58-6.50 (m, 1H), 6.50-6.43 (m, 2H), 6.40 (dt, J=8.7, 3.0 Hz, 1H), 5.65-5.58 (m, 1H), 4.74 (br. s, 1H), 4.31-4.21 (m, 2H), 3.98 (q, J=6.9 Hz, 2H), 3.93-3.86 (m, 1H), 3.81 (s, 3H), 3.61-3.46 (m, 2H), 3.34 (t, J=7.6 Hz, 2H), 2.99-2.89 (m, 2H), 2.77-2.63 (m, 2H), 2.14-2.02 (m, 2H), 2.01-1.87 (m, 2H), 1.39 (t, J=6.9 Hz, 3H).

Example 124 (beige solid, 12.1 mg) was prepared from 124A following the procedure of Example 122. LC-MS Anal. Calc'd for $C_{33}H_{39}FN_2O_5$: 562.67, found [M+H] 563.2. $^1$H NMR (400 MHz, acetonitrile-d$_3$) δ 7.26-7.11 (m, 3H), 7.03-6.91 (m, 3H), 6.86-6.75 (m, 3H), 6.58 (dd, J=7.4, 3.0 Hz, 1H), 6.46 (dt, J=8.8, 3.2 Hz, 1H), 4.53-4.40 (m, 1H), 4.15-4.02 (m, 1H), 3.98 (q, J=7.0 Hz, 2H), 3.77 (s, 3H), 3.66-3.53 (m, 1H), 3.52-3.40 (m, 1H), 3.37-3.27 (m, 2H), 2.97 (ddd, J=11.9, 8.6, 3.2 Hz, 2H), 2.90-2.70 (m, 4H), 2.56 (dd, J=15.8, 8.1 Hz, 1H), 2.44 (dt, J=12.9, 6.3 Hz, 1H), 2.14-2.03 (m, 2H), 1.90-1.78 (m, 2H), 1.78-1.65 (m, 1H), 1.33 (t, J=6.9 Hz, 3H). Analytical HPLC: RT=9.3 min, HI: 95.3%. hGPR40 EC$_{50}$=380 nM. hGPR40 IP1 EC$_{50}$=47 nM.

EXAMPLE 125

2-((2R,4R)-1-(4-((1-(5-Ethoxy-2-fluorophenyl)piperidin-4-yl)oxy)phenyl)-4-phenoxypyrrolidin-2-yl)acetic acid, TFA

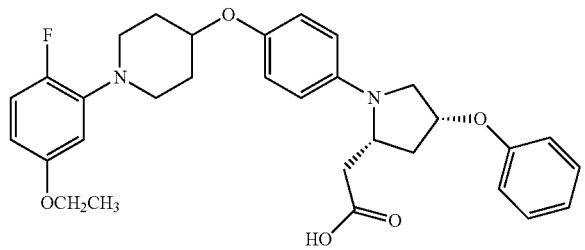 [SMILES: CCOc1ccc(F)c(N2CCC(Oc3ccc(N4C[C@H](Oc5ccccc5)C[C@@H]4CC(=O)O)cc3)CC2)c1]

125A. (2R,4S)-1-tert-Butyl 2-methyl 4-(benzyloxy)pyrrolidine-1,2-dicarboxylate: To a solution of (2R,4S)-1-tert-butyl 2-methyl 4-hydroxypyrrolidine-1,2-dicarboxylate (4.19 g, 17.1 mmol) in DMF (27 mL) at 0° C. was added benzyl bromide (4.5 mL, 38 mmol) followed by Ag$_2$O (4.35 g, 18.8 mmol). The reaction mixture was warmed to rt and stirred for 1 week. The reaction mixture was diluted with ether and filtered. The filtrate was diluted with Et$_2$O and washed with water, brine, dried (MgSO$_4$), and concentrated. The crude product was purified by silica chromatography to provide 125A (5.21 g, 15.6 mmol, 91% yield) as a colorless oil. LC-MS Anal. Calc'd for C$_{18}$H$_{25}$NO$_5$: 335.40, found [M+H] 336.0. $^1$H NMR (500 MHz, CDCl$_3$) δ 7.39-7.27 (m, 5H), 4.57-4.41 (m, 2H), 4.39-4.30 (m, 1H), 4.23-4.12 (m, 1H), 3.76-3.71 (m, 3H), 3.70-3.48 (m, 2H), 2.46-2.29 (m, 1H), 2.12-2.00 (m, 1H), 1.51-1.37 (m, 9H).

125B. 2-((2S,4S)-4-(Benzyloxy)-1-(4-((1-(5-ethoxy-2-fluorophenyl)piperidin-4-yl)oxy)phenyl)pyrrolidin-2-yl)acetonitrile: 125B was prepared from 125A following the procedure of Example 17. LC-MS Anal. Calc'd for C$_{32}$H$_{36}$FN$_3$O$_3$: 529.65, found [M+H] 530.3. $^1$H NMR (500 MHz, CDCl$_3$) δ 7.38-7.27 (m, 5H), 6.95-6.85 (m, 3H), 6.58-6.51 (m, 2H), 6.43-6.35 (m, 1H), 4.59-4.51 (m, 2H), 4.29 (tt, J=7.4, 3.6 Hz, 1H), 3.98 (q, J=7.2 Hz, 2H), 3.38-3.28 (m, 1H), 2.99-2.90 (m, 1H), 2.73-2.64 (m, 1H), 2.54 (dd, J=16.8, 7.4 Hz, 1H), 2.43 (ddd, J=13.1, 7.4, 5.4 Hz, 1H), 2.27 (dt, J=13.3, 5.4 Hz, 1H), 2.15-2.05 (m, 2H), 2.01-1.89 (m, 2H), 1.40 (t, J=6.9 Hz, 3H).

125C. 2-((2S,4S)-1-(4-((1-(5-Ethoxy-2-fluorophenyl)piperidin-4-yl)oxy)phenyl)-4-hydroxypyrrolidin-2-yl)acetonitrile: To a solution of 125B (3.36 g, 6.35 mmol) in MeOH (127 mL) was added ammonium formate (2.40 g, 38.1 mmol) and 10% Pd/C (2.03 g, 1.90 mmol). The reaction mixture was refluxed overnight. The reaction mixture was filtered and concentrated. The crude product was purified by silica chromatography to provide 125C (2.04 g, 4.65 mmol, 73% yield) as a colorless oil. LC-MS Anal. Calc'd for C$_{25}$H$_{30}$FN$_3$O$_3$: 439.52, found [M+H] 440.2. $^1$H NMR (500 MHz, CDCl$_3$) δ 6.95-6.87 (m, 3H), 6.60-6.50 (m, 3H), 6.43-6.37 (m, 1H), 4.74-4.66 (m, 1H), 4.30 (tt, J=7.4, 3.6 Hz, 1H), 4.25-4.17 (m, 1H), 3.98 (q, J=7.0 Hz, 2H), 3.82 (dd, J=10.2, 5.0 Hz, 1H), 3.38-3.29 (m, 2H), 3.27-3.15 (m, 1H), 2.98-2.89 (m, 2H), 2.74-2.65 (m, 1H), 2.63-2.53 (m, 1H), 2.40-2.32 (m, 1H), 2.32-2.20 (m, 1H), 2.17-2.05 (m, 2H), 2.02-1.89 (m, 2H), 1.39 (t, J=7.0 Hz, 3H).

125D. Ethyl 2-((2R,4S)-1-(4-((1-(5-ethoxy-2-fluorophenyl)piperidin-4-yl)oxy)phenyl)-4-hydroxypyrrolidin-2-yl)acetate: 125C (2.04 g, 4.64 mmol) was dissolved in EtOH (46.4 mL) and a 6 M aq. KOH (15 mL, 93 mmol) was added. The reaction mixture was sealed and heated at 120° C. for 2 h. The reaction mixture was cooled to rt and diluted with EtOH (100 mL). The reaction mixture was cooled to 0° C. and 12.1 M aq. HCl (8.1 mL, 97 mmol) was added dropwise to acidify the reaction mixture, which was filtered, and concentrated. In a separate flask, AcCl (9.90 mL, 139 mmol) was added to EtOH (93 mL) dropwise at 0° C. The solution was warmed to rt and stirred for 30 min. The solution was added to the inseparable product/salt mixture of 2-((2R,4S)-1-(4-((1-(5-ethoxy-2-fluorophenyl)piperidin-4-yl)oxy)phenyl)-4-hydroxypyrrolidin-2-yl)acetic acid (2.13 g, 4.64 mmol) and sonicated to help break up the solids. The solution turned yellow and was stirred for 1 h at rt. The reaction mixture was concentrated, redissolved in CH$_2$Cl$_2$, and basified with 1.5 M aq. K$_2$HPO$_4$. The product was extracted with EtOAc (3×) and the combined organic layers were washed with brine, dried (MgSO$_4$), and concentrated. The crude product was purified by silica chromatography to provide 125D (1.94 g, 3.98 mmol, 86% yield) as a brown oil. LC-MS Anal. Calc'd for C$_{27}$H$_{35}$FN$_2$O$_5$: 486.58, found [M+H] 487.2. $^1$H NMR (500 MHz, CDCl$_3$) δ 6.93-6.87 (m, 3H), 6.60-6.56 (m, 2H), 6.53 (dd, J=7.3, 2.9 Hz, 1H), 6.39 (dt, J=8.8, 3.2 Hz, 1H), 4.64-4.56 (m, 1H), 4.28 (tq, J=7.2, 3.7 Hz, 2H), 4.19-4.09 (m, 2H), 3.98 (q, J=7.2 Hz, 2H), 3.65 (dd, J=9.9, 5.2 Hz, 1H), 3.38-3.29 (m, 2H), 3.18 (dd, J=9.8, 3.4 Hz, 1H), 2.97-2.90 (m, 2H), 2.87 (dd, J=15.1, 3.0 Hz, 1H), 2.27-2.20 (m, 1H), 2.19-2.05 (m, 4H), 2.00-1.89 (m, 2H), 1.65 (d, J=5.8 Hz, 1H), 1.39 (t, J=6.9 Hz, 3H), 1.27 (t, J=7.2 Hz, 3H).

Example 125: To a solution of 125D (0.041 g, 0.084 mmol), Ph$_3$P (0.033 g, 0.13 mmol), and phenol (0.012 g, 0.13 mmol) in THF (0.85 mL) was added DEAD (0.020 mL, 0.13 mmol). The reaction mixture was stirred for 2 h at rt. The reaction mixture was concentrated and purified by silica chromatography to obtain ethyl 2-((2R,4R)-1-(4-((1-(5-ethoxy-2-fluorophenyl)piperidin-4-yl)oxy)phenyl)-4-phenoxypyrrolidin-2-yl)acetate as a colorless oil. To a solution of ethyl 2-((2R,4R)-1-(4-((1-(5-ethoxy-2-fluorophenyl)piperidin-4-yl)oxy)phenyl)-4-phenoxypyrrolidin-2-yl)acetate in THF (1.5 mL) and water (0.15 mL) was added a 1 M aq. solution of LiOH (0.84 mL, 0.84 mmol) and the reaction mixture was stirred at rt for 3 days. The reaction mixture was acidified with 3 M aq. HCl (0.11 mL) and concentrated. The crude product was purified by RP-Prep HPLC to provide Example 125 (22.0 mg, 0.034 mmol, 41% yield). LC-MS Anal. Calc'd for C$_{31}$H$_{35}$FN$_2$O$_5$: 534.62, found [M+H] 535.2. $^1$H NMR (500 MHz, DMSO-d$_6$) δ 7.31 (t, J=8.0 Hz, 2H), 7.05-6.93 (m, 4H), 6.90 (d, J=8.8 Hz, 2H), 6.58-6.50 (m, 3H), 6.46 (dt, J=8.7, 3.1 Hz, 1H), 5.16 (t, J=4.7 Hz, 1H), 4.29 (dt, J=7.6, 4.0 Hz, 1H), 4.09 (t, J=8.4 Hz, 1H), 3.97 (q, J=7.0 Hz, 2H), 3.58-3.53 (m, 3H), 3.29-3.21 (m, 2H), 2.93-2.83 (m, 1H), 2.73-2.66 (m, 1H), 2.49-2.38 (m, 2H), 2.09 (d, J=13.8 Hz, 2H), 1.99 (br. s, 2H), 1.78-1.66 (m, 2H), 1.29 (t, J=7.0 Hz, 3H). Analytical HPLC (Acquity): RT=2.0 min, HI: 100%. hGPR40 EC$_{50}$=450 nM.

EXAMPLE 126

2-((2R,4S)-1-(4-((1-(5-Ethoxy-2-fluorophenyl)piperidin-4-yl)oxy)phenyl)-4-(1-methyl-1H-pyrazol-4-yl)pyrrolidin-2-yl)acetic acid, TFA

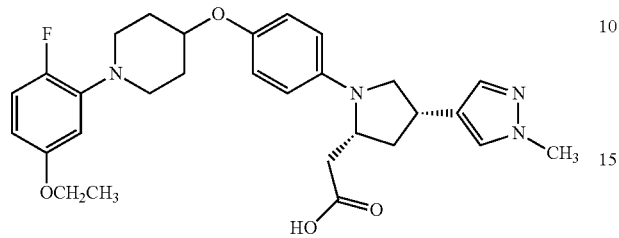

Example 126 was prepared from 122E and 1-methyl-4-(4,4,5,5-tetramethyl-1,3,2-dioxaborolan-2-yl)-1H-pyrazole following the procedure of Example 122. LC-MS Anal. Calc'd for $C_{29}H_{35}FN_4O_4$: 522.61, found [M+H] 523.2. $^1$H NMR (500 MHz, DMSO-$d_6$) δ 7.60 (s, 1H), 7.38 (s, 1H), 7.06-6.98 (m, 1H), 6.91 (d, J=7.7 Hz, 2H), 6.61 (br. s, 2H), 6.55 (d, J=6.9 Hz, 1H), 6.48 (d, J=8.5 Hz, 1H), 4.38-4.27 (m, 1H), 4.10-4.02 (m, 1H), 3.99 (q, J=6.9 Hz, 2H), 3.80 (br. s, 3H), 3.61-3.52 (m, 1H), 3.39-3.32 (m, 1H), 3.28 (d, J=6.6 Hz, 3H), 2.93-2.87 (m, 1H), 2.63 (dd, J=12.5, 6.7 Hz, 1H), 2.58-2.54 (m, 2H), 2.17-2.07 (m, 1H), 2.06-1.96 (m, 2H), 1.86 (q, J=9.3 Hz, 1H), 1.75 (d, J=9.6 Hz, 2H), 1.31 (t, J=6.7 Hz, 3H). Analytical HPLC (Acquity): RT=1.9 min, HI: 100%. hGPR40 $EC_{50}$=810 nM.

EXAMPLE 128

2-((4R)-4-(4-Cyanophenoxy)-1-(4-((1-(5-ethoxy-2-fluorophenyl)piperidin-4-yl)oxy)phenyl)pyrrolidin-2-yl)acetic acid, HCl

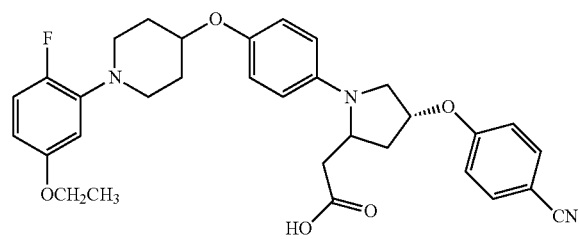 [SMILES: CCOc1ccc(F)c(N2CCC(Oc3ccc(N4C[C@H](Oc5ccc(C#N)cc5)CC4CC(=O)O)cc3)CC2)c1]

Example 128 (beige solid, 1.9 mg) was prepared from 4-cyanophenol and 125C following the procedure of Example 125. LC-MS Anal. Calc'd for $C_{32}H_{34}FN_3O_5$: 559.63, found [M+H] 560.2. $^1$H NMR (500 MHz, acetonitrile-$d_3$) δ 7.85 (dd, J=6.1, 3.0 Hz, 1H), 7.73-7.63 (m, 4H), 7.29 (dd, J=12.0, 9.2 Hz, 1H), 7.18-7.12 (m, 2H), 7.11-7.06 (m, 2H), 7.03 (dt, J=9.1, 3.4 Hz, 1H), 5.42-5.34 (m, 1H), 4.82 (dt, J=5.5, 2.8 Hz, 1H), 4.35-4.25 (m, 1H), 4.05 (q, J=6.9 Hz, 2H), 3.99 (d, J=4.4 Hz, 2H), 3.94-3.84 (m, 2H), 3.68-3.58 (m, 2H), 3.08 (dt, J=14.1, 7.1 Hz, 1H), 2.99-2.91 (m, 1H), 2.90-2.82 (m, 1H), 2.66-2.61 (m, 2H), 2.38-2.23 (m, 3H), 1.37 (t, J=6.9 Hz, 3H). Analytical HPLC: RT=11.1 min, HI: 96.9%. hGPR40 $EC_{50}$=1300 nM.

EXAMPLE 130

2-((2R,4R)-4-Cyano-1-(4-((1-(5-ethoxy-2-fluorophenyl)piperidin-4-yl)oxy)phenyl)pyrrolidin-2-yl)acetic acid, TFA

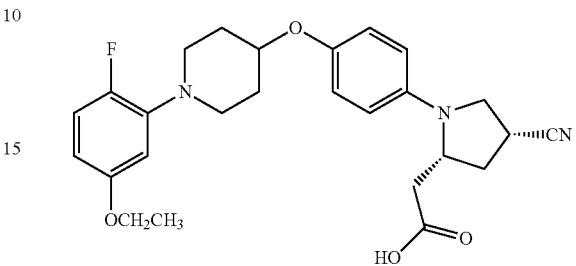

130A. Ethyl 2-((2R,4R)-4-cyano-1-(4-((1-(5-ethoxy-2-fluorophenyl)piperidin-4-yl)oxy)phenyl)pyrrolidin-2-yl)acetate: 125C was dissolved in $CH_2Cl_2$ (1 mL) and cooled to 0° C. MsCl (0.012 mL, 0.15 mmol) and $NEt_3$ (0.029 mL, 0.21 mmol) were added sequentially and the reaction mixture was stirred at 0° C. for 40 min. The reaction mixture was diluted with EtOAc and washed with 1 N aq. HCl, sat. aq. $NaHCO_3$, and brine. The organic layer was dried ($MgSO_4$) and concentrated. The crude product was redissolved in DMSO (1 mL) and NaCN (0.020 g, 0.41 mmol) was added. The reaction mixture was stirred at 50° C. overnight and then heated to 90° C. for 4 h. The reaction mixture was cooled to rt and quenched with water. The product was extracted with EtOAc (3×). The combined organic layers were washed with brine, dried ($MgSO_4$), and concentrated. The crude product was purified by silica chromatography to afford 130A (0.036 g, 0.072 mmol, 70% yield) as a yellow oil. LC-MS Anal. Calc'd for $C_{28}H_{34}FN_3O_4$: 495.59, found [M+H] 496.1. $^1$H NMR (400 MHz, $CDCl_3$) δ 6.96-6.86 (m, 3H), 6.64-6.57 (m, 2H), 6.53 (dd, J=7.4, 3.0 Hz, 1H), 6.40 (dt, J=8.8, 3.2 Hz, 1H), 4.30 (tt, J=7.4, 3.6 Hz, 1H), 4.24-4.11 (m, 3H), 3.98 (q, J=6.9 Hz, 2H), 3.71 (dd, J=9.5, 5.1 Hz, 1H), 3.54 (dd, J=9.5, 7.5 Hz, 1H), 3.40-3.28 (m, 2H), 3.26-3.16 (m, 1H), 3.00-2.86 (m, 3H), 2.68-2.57 (m, 1H), 2.53 (dd, J=16.1, 10.3 Hz, 1H), 2.31-2.20 (m, 1H), 2.16-2.02 (m, 2H), 2.01-1.89 (m, 2H), 1.39 (t, J=7.0 Hz, 3H), 1.28 (t, J=7.2 Hz, 3H).

Example 130 (19.9 mg) was prepared from 130A following the procedure of Example 125. LC-MS Anal. Calc'd for $C_{26}H_{30}FN_3O_4$: 467.53, found [M+H] 468.2. $^1$H NMR (500 MHz, DMSO-$d_6$) δ 7.01 (dd, J=12.7, 8.8 Hz, 1H), 6.92 (d, J=8.8 Hz, 2H), 6.62 (d, J=9.1 Hz, 2H), 6.54 (dd, J=7.4, 2.8 Hz, 1H), 6.47 (dt, J=8.8, 3.0 Hz, 1H), 4.34 (dt, J=7.6, 4.0 Hz, 1H), 4.07-4.01 (m, 1H), 3.98 (q, J=7.1 Hz, 2H), 3.64 (dd, J=9.4, 4.1 Hz, 2H), 3.44-3.39 (m, 1H), 3.31-3.21 (m, 2H), 2.95-2.84 (m, 2H), 2.78-2.69 (m, 1H), 2.59-2.53 (m, 1H), 2.41 (dd, J=15.7, 10.5 Hz, 1H), 2.17-2.08 (m, 1H), 2.00 (br. s, 2H), 1.79-1.69 (m, 2H), 1.31 (t, J=6.9 Hz, 3H). Analytical HPLC (Acquity): RT=1.7 min, HI: 99%. hGPR40 $EC_{50}$=2100 nM.

EXAMPLE 131

2-((2R,3R,4S)-1-(4-(((3,4-trans)-1-(5-Chloro-2-methoxypyridin-4-yl)-3-methylpiperidin-4-yl)oxy)phenyl)-4-methoxy-3-methylpyrrolidin-2-yl)acetic acid

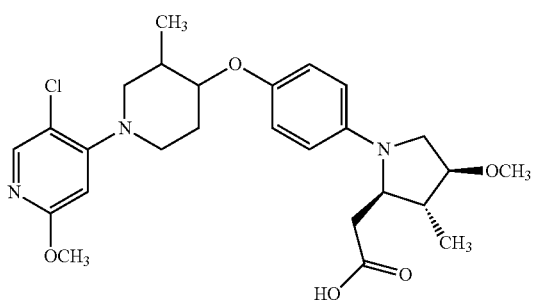 [SMILES: COc1cc(N2CCC(Oc3ccc(N4C[C@@H](OC)[C@H](C)[C@H]4CC(=O)O)cc3)C(C)C2)c(Cl)cn1]

Example 131 (0.5 mg) was prepared from ((2S,3R,4S)-4-methoxy-3-methylpyrrolidin-2-yl)methanol and 119B following the procedure of Example 118. LC-MS Anal. Calc'd for $C_{26}H_{34}ClN_3O_5$: 504.02, found [M] 504.3. $^1$H NMR (500 MHz, DMSO-$d_6$) δ 12.27 (br. s, 1H), 8.02 (s, 1H), 6.88 (d, J=9.1 Hz, 2H), 6.48 (d, J=9.1 Hz, 2H), 6.40 (s, 1H), 3.86 (td, J=8.8, 4.1 Hz, 1H), 3.80 (s, 3H), 3.64 (br. s, 1H), 3.59 (d, J=8.3 Hz, 1H), 3.49-3.42 (m, 2H), 3.39-3.35 (m, 2H), 3.28 (s, 3H), 2.86 (t, J=10.3 Hz, 1H), 2.65 (dd, J=12.2, 9.8 Hz, 1H), 2.58 (dd, J=15.4, 2.8 Hz, 1H), 2.44 (dd, J=15.4, 10.5 Hz, 1H), 2.32-2.25 (m, 1H), 2.12-2.04 (m, 1H), 1.99-1.88 (m, 1H), 1.64-1.52 (m, 1H), 1.08-1.01 (m, 3H), 0.94 (d, J=7.2 Hz, 3H). Analytical HPLC (Acquity): RT=1.7 min, HI: 100%. hGPR40 $EC_{50}$=4700 nM.

EXAMPLE 132

2-((2R,4R)-1-(6-(((3,4-trans)-1-(5-Chloro-2-methoxypyridin-4-yl)-3-methylpiperidin-4-yl)oxy)pyridin-3-yl)-4-methoxypyrrolidin-2-yl)acetic acid

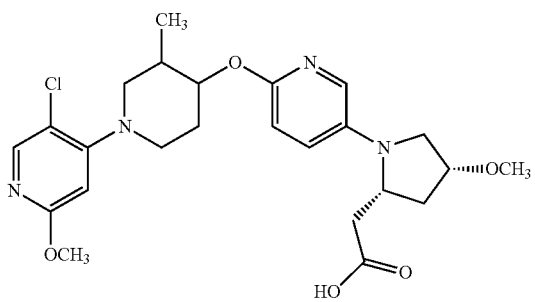 [SMILES: COc1cc(N2CCC(Oc3ccc(N4C[C@H](OC)C[C@@H]4CC(=O)O)cn3)C(C)C2)c(Cl)cn1]

132A. 5-Chloro-4-((3,4-trans)-4-((5-iodopyridin-2-yl)oxy)-3-methylpiperidin-1-yl)-2-methoxypyridine: To a solution of 119A, Isomer 1 (494 mg, 1.92 mmol) and 5-iodopyridin-2-ol (340 mg, 1.54 mmol) in toluene (8 mL) was added Bu$_3$P (0.58 mL, 2.3 mmol). ADDP (582 mg, 2.31 mmol) was added in three portions to the reaction mixture. The reaction mixture was sonicated in a water bath for 1 h, stirred at 60° C. for 2 h, and then stirred at rt for 16 h. The reaction mixture was treated with hexanes (50 mL). After stirring for 5 min, the mixture was filtered and the filtrate was concentrated. The residue was purified by silica chromatography to provide 132A (534 mg, 1.05 mmol, 68% yield) as a white foam. LC-MS Anal. Calc'd for $C_{17}H_{19}ClIN_3O_2$: 459.71, found [M+H] 459.9. $^1$H NMR (400 MHz, CDCl$_3$) δ 8.29 (dd, J=2.4, 0.7 Hz, 1H), 7.96 (s, 1H), 7.77 (dd, J=8.8, 2.4 Hz, 1H), 6.58 (dd, J=8.7, 0.6 Hz, 1H), 6.26 (s, 1H), 4.82 (td, J=9.3, 4.3 Hz, 1H), 3.88 (s, 3H), 3.60-3.46 (m, 2H), 2.97-2.85 (m, 1H), 2.61 (dd, J=12.3, 9.7 Hz, 1H), 2.34-2.23 (m, 1H), 2.20-2.08 (m, 1H), 1.85-1.73 (m, 1H), 1.02 (d, J=6.6 Hz, 3H).

Example 132 (white solid, 8.6 mg) was prepared as a single isomer from 4A and 132A following the procedure of Example 2. LC-MS Anal. Calc'd for $C_{24}H_{31}ClN_4O_5$: 490.2, found [M+H] 491.1. $^1$H NMR (400 MHz, CDCl$_3$) δ 7.91 (s, 1H), 7.50 (d, J=1.8 Hz, 1H), 7.04-6.90 (m, 1H), 6.66 (d, J=8.8 Hz, 1H), 6.21 (s, 1H), 4.67 (td, J=9.0, 4.0 Hz, 1H), 4.14-3.99 (m, 2H), 3.82 (s, 3H), 3.54-3.40 (m, 3H), 3.31 (s, 3H), 3.25-3.31 (m, 2H), 2.94-2.42 (m, 4H), 2.29-1.97 (m, 4H), 1.72 (d, J=10.6 Hz, 1H), 0.99 (d, J=6.8 Hz, 3H). Analytical HPLC: RT=6.3 min, HI: 97.1%. hGPR40 $EC_{50}$=250 nM. hGPR40 IP1 $EC_{50}$=55 nM.

EXAMPLE 133

2-((2R,4R)-1-(6-(((3,4-trans)-1-(5-Chloro-2-methoxypyridin-4-yl)-3-methylpiperidin-4-yl)oxy)pyridin-3-yl)-4-(trifluoromethyl)pyrrolidin-2-yl)acetic acid

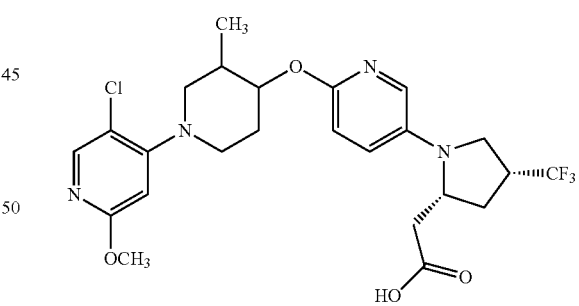

Example 133 (white solid, 6.1 mg) was prepared as a single isomer from 1K and 132A following the procedure of Example 2. LC-MS Anal. Calc'd for $C_{24}H_{28}ClF_3N_4O_4$: 528.2, found [M+H] 529.2. $^1$H NMR (400 MHz, CDCl$_3$) δ 8.00 (s, 1H), 7.65 (d, J=2.6 Hz, 1H), 7.15 (dd, J=9.0, 2.6 Hz, 1H), 6.76 (d, J=8.8 Hz, 1H), 6.29 (s, 1H), 4.78 (td, J=9.1, 4.4 Hz, 1H), 4.33-4.17 (m, 1H), 3.91 (s, 3H), 3.69-3.38 (m, 4H), 3.23-2.76 (m, 3H), 2.70-2.61 (m, 2H), 2.44-2.26 (m, 3H), 2.22-1.99 (m, 2H), 1.86-1.76 (m, 1H), 1.07 (d, J=6.8 Hz, 3H). Analytical HPLC: RT=7.9 min, HI: 94.6%. hGPR40 $EC_{50}$=380 nM. hGPR40 IP1 $EC_{50}$=49 nM.

EXAMPLE 134

2-((2R,4R)-1-(4-(((3,4-trans)-1-(5-Chloro-2-methoxypyridin-4-yl)-3-methylpiperidin-4-yl)oxy)-3-fluorophenyl)-4-(trifluoromethyl)pyrrolidin-2-yl)acetic acid

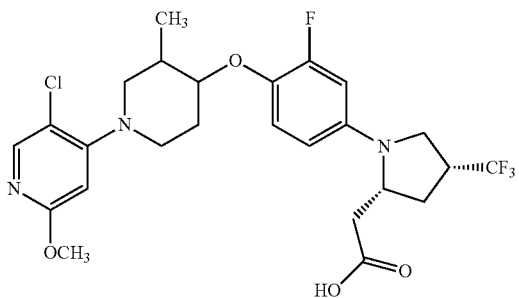 [SMILES: COc1cc(N2CCC(Oc3ccc(N4C[C@H](C(F)(F)F)C[C@@H]4CC(=O)O)cc3F)C(C)C2)c(Cl)cn1]

Example 134 (41.6 mg) was prepared as a single isomer from 1K and 98A following the procedure of Example 98. LC-MS Anal. Calc'd for $C_{25}H_{28}ClF_4N_3O_4$: 545.2, found [M+H] 546.2. $^1$H NMR (500 MHz, DMSO-d$_6$) δ 8.11-7.76 (m, 1H), 7.30-6.87 (m, 1H), 6.70-6.27 (m, 3H), 4.25-4.02 (m, 1H), 3.90-4.30 (br, 1H), 3.83-3.76 (m, 1H), 3.74 (s, 3H), 3.60-3.27 (m, 5H), 2.98-2.75 (m, 1H), 2.76-2.53 (m, 4H), 2.27-1.83 (m, 3H), 1.63 (d, J=10.5 Hz, 1H), 1.08 (d, J=3.3 Hz, 3H). Analytical HPLC (Acquity): RT=2.1 min, HI: 97.5%. hGPR40 $EC_{50}$=580 nM.

EXAMPLE 135

2-((2R,4R)-1-(2-Chloro-4-(((3,4-trans)-1-(5-chloro-2-methoxypyridin-4-yl)-3-methylpiperidin-4-yl)oxy)phenyl)-4-(trifluoromethyl)pyrrolidin-2-yl)acetic acid, HCO$_2$H

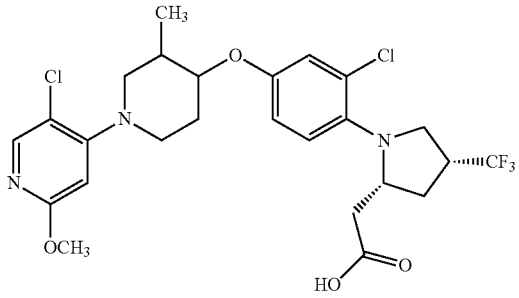 [SMILES: COc1cc(N2CCC(Oc3ccc(N4C[C@H](C(F)(F)F)C[C@@H]4CC(=O)O)c(Cl)c3)C(C)C2)c(Cl)cn1]

135A. 5-Chloro-4-((3,4-trans)-4-(3-chloro-4-iodophenoxy)-3-methylpiperidin-1-yl)-2-methoxypyridine: To a solution of 119A, Isomer 1 (415 mg, 1.62 mmol) and 3-chloro-4-iodophenol (440 mg, 1.73 mmol) in toluene (12 mL) was added Bu$_3$P (0.61 mL, 2.4 mmol). ADDP (612 mg, 2.42 mmol) was added in three portions over 11 min. The reaction mixture was heated to 50° C. for 3 h and then at rt for 16 h. The reaction mixture was treated with hexanes (30 mL). After stirring for 5 min, the mixture was filtered and the filtrate was concentrated. The residue was purified by silica chromatography to give 135A (465 mg, 0.880 mmol, 54% yield) as a glassy residue. LC-MS Anal. Calc'd for $C_{18}H_{19}Cl_2IN_2O_2$: 493.17, found [M+H] 492.9, 494.9.

Example 135 (5.7 mg) was prepared as a single isomer from 135A and 1K following the procedure of Example 2. LC-MS Anal. Calc'd for $C_{25}H_{28}Cl_2F_3N_3O_4$: 561.1, found [M+H] 562.2. $^1$H NMR (500 MHz, DMSO-d$_6$) δ 8.02 (s, 1H), 7.15 (d, J=8.8 Hz, 1H), 7.10 (d, J=2.8 Hz, 1H), 6.97 (dd, J=8.8, 2.8 Hz, 1H), 6.40 (s, 1H), 4.14 (td, J=8.9, 4.3 Hz, 1H), 3.93 (d, J=8.3 Hz, 1H), 3.81 (s, 3H), 3.64 (dd, J=9.9, 5.8 Hz, 1H), 3.49-3.42 (m, 2H), 3.35-3.20 (m, 2H), 2.98-2.84 (m, 2H), 2.71-2.63 (m, 1H), 2.50-2.40 (m, 1H), 2.33 (dd, J=15.4, 3.0 Hz, 1H), 2.18-1.91 (m, 3H), 1.79-1.55 (m, 2H), 1.03 (d, J=6.6 Hz, 3H). Analytical HPLC (Acquity): RT=2.3 min, HI: 92.3%. hGPR40 $EC_{50}$=400 nM.

EXAMPLE 136

2-((2R,4R)-1-(3-Chloro-4-(((3,4-trans)-1-(5-chloro-2-methoxypyridin-4-yl)-3-methylpiperidin-4-yl)oxy)phenyl)-4-(trifluoromethyl)pyrrolidin-2-yl)acetic acid

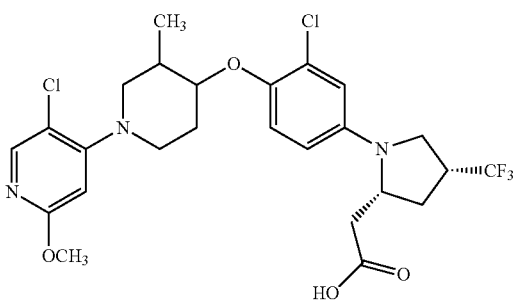 [SMILES: COc1cc(N2CCC(Oc3ccc(N4C[C@H](C(F)(F)F)C[C@@H]4CC(=O)O)cc3Cl)C(C)C2)c(Cl)cn1]

136A. 5-Chloro-4-((3,4-trans)-4-(2-chloro-4-iodophenoxy)-3-methylpiperidin-1-yl)-2-methoxypyridine: To a solution of 119A, Isomer 1 (312 mg, 1.22 mmol) and 2-chloro-4-iodophenol (331 mg, 1.30 mmol) in toluene (8 mL) was added Bu$_3$P (0.455 mL, 1.82 mmol). ADDP (460 mg, 1.823 mmol) was added in three portions over 11 min. After the addition, toluene (2 mL) was added and the reaction mixture was heated to 50° C. for 3 h and then at rt for 16 h. The reaction mixture was treated with hexanes (30 mL). After stirring for 5 min, the mixture was filtered and the filtrate was concentrated. The residue was purified by silica chromatography to provide 136A (427 mg, 0.753 mmol, 62% yield). LC-MS Anal. Calc'd for $C_{18}H_{19}Cl_2IN_2O_2$: 493.17, found [M+H] 492.9, 494.9. $^1$H NMR (400 MHz, CDCl$_3$) δ 7.97 (s, 1H), 7.67 (d, J=2.2 Hz, 1H), 7.47 (dd, J=8.6, 2.2 Hz, 1H), 6.70 (d, J=8.6 Hz, 1H), 6.27 (s, 1H), 4.04 (td, J=8.0, 4.0 Hz, 1H), 3.89 (s, 3H), 3.58-3.43 (m, 2H), 2.91 (ddd, J=12.2, 9.5, 3.0 Hz, 1H), 2.72 (dd, J=12.3, 8.6 Hz, 1H), 2.30-2.11 (m, 2H), 1.96-1.84 (m, 1H), 1.15 (d, J=6.8 Hz, 3H).

Example 136 (50.5 mg) was prepared as a single isomer from 136A and 1K following the procedure of Example 2. LC-MS Anal. Calc'd for $C_{25}H_{28}Cl_2F_3N_3O_4$: 561.1, found [M+H] 562.1. $^1$H NMR (500 MHz, DMSO-d$_6$) δ 8.08-7.86 (m, 1H), 7.11 (d, J=8.8 Hz, 1H), 6.79-6.49 (m, 2H), 6.39 (br. s, 1H), 4.13 (br. s, 1H), 3.99 (br. s, 1H), 3.81 (br. s, 3H), 3.62-3.07 (m, 5H), 2.95-2.51 (m, 4H), 2.40-1.83 (m, 5H), 1.66 (d, J=10.7 Hz, 1H), 1.09 (br. s, 3H). Analytical HPLC (Acquity): RT=2.2 min, HI: 95.3%. hGPR40 $EC_{50}$=500 nM.

EXAMPLE 137

2-((2R,4R)-1-(3-Chloro-4-(((3,4-trans)-1-(5-chloro-2-methoxypyridin-4-yl)-3-methylpiperidin-4-yl)oxy)phenyl)-4-methoxypyrrolidin-2-yl)acetic acid, sodium salt

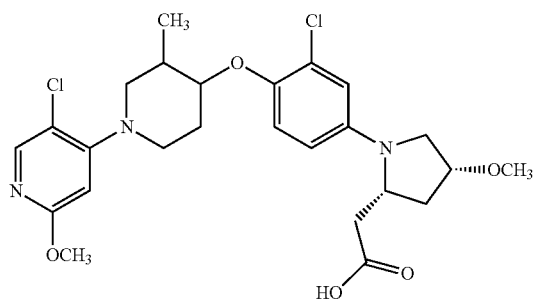 [SMILES: COc1cc(N2CCC(Oc3ccc(N4C[C@H](OC)C[C@@H]4CC(=O)O)cc3Cl)C(C)C2)c(Cl)cn1]

Example 137 (white solid, 55.0 mg) was prepared as a single isomer from 136A and 4A following the procedure of Example 2. LC-MS Anal. Calc'd for $C_{25}H_{31}Cl_2N_3O_5$: 523.2, found [M+H] 524.2. $^1$H NMR (400 MHz, DMSO-$d_6$) δ 8.01 (s, 1H), 7.09 (d, J=9.0 Hz, 1H), 6.58 (d, J=2.9 Hz, 1H), 6.49 (dd, J=9.0, 2.9 Hz, 1H), 6.39 (s, 1H), 4.10-3.87 (m, 3H), 3.81 (s, 3H), 3.51-3.19 (m, 5H), 3.25 (s, 3H), 2.85 (m, 1H), 2.69 (dd, J=12.3, 9.5 Hz, 1H), 2.50 (m, 1H), 2.38 (d, J=10.3 Hz, 1H), 2.15-1.96 (m, 4H), 1.71-1.63 (m, 1H), 1.09 (d, J=6.6 Hz, 3H). Analytical HPLC (50-100% gradient B): RT=9.9 min, HI: 99.2%. hGPR40 $EC_{50}$=230 nM.

EXAMPLE 138

2-((2R,4R)-1-(4-((3,4-trans)-1-(5-Chloro-2-methoxypyridin-4-yl)-3-methylpiperidin-4-yloxy)-2-fluorophenyl)-4-trifluoromethyl)pyrrolidin-2-yl)acetic acid, TFA

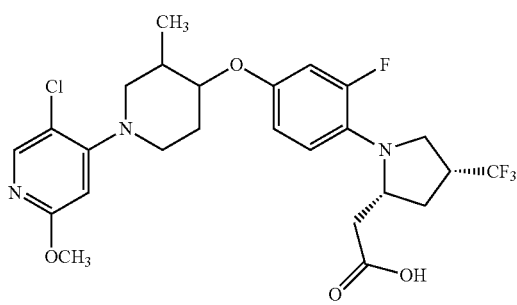 [SMILES: COc1cc(N2CCC(Oc3ccc(N4C[C@H](C(F)(F)F)C[C@@H]4CC(=O)O)c(F)c3)C(C)C2)c(Cl)cn1]

Example 138 (19 mg) was prepared as a single isomer from 111A and 1K following the procedure of Example 111. LC-MS Anal. Calc'd for $C_{25}H_{28}ClF_4N_3O_4$: 545, found [M+H] 546.2. $^1$H NMR (500 MHz, CDCl$_3$) δ 8.11 (s, 1H), 7.07-6.89 (m, 1H), 6.76-6.64 (m, 2H), 6.30 (s, 1H), 4.35-3.9 (m, 5H), 3.91-3.62 (m, 3H), 3.34-2.90 (m, 4H), 2.73-2.35 (m, 3H), 2.30-1.80 (m, 4H), 1.15 (d, J=6.9 Hz, 3H). Analytical HPLC (Acquity): RT=2.17 min, HI: 97.6%. hGPR40 $EC_{50}$=190 nM. hGPR40 IP1 $EC_{50}$=27 nM.

EXAMPLE 139

2-((2R,4R)-1-(4-((3,4-trans)-1-(5-Chloro-2-methoxypyridin-4-yl)-3-methylpiperidin-4-yloxy)-2-fluorophenyl)-4-methoxypyrrolidin-2-yl)acetic acid

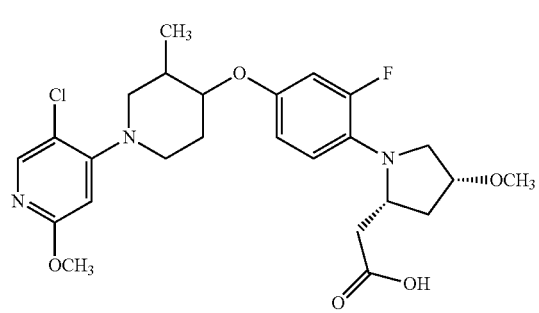 [SMILES: COc1cc(N2CCC(Oc3ccc(N4C[C@H](OC)C[C@@H]4CC(=O)O)c(F)c3)C(C)C2)c(Cl)cn1]

Example 139 (8 mg) was prepared as a single isomer from 111A and 4A following the procedure of Example 111. LC-MS Anal. Calc'd for $C_{25}H_{31}ClFN_3O_5$: 507. found [M+H] 508.1. $^1$H NMR (400 MHz, CDCl$_3$) δ 7.99 (s, 1H), 6.92 (t, J=9.1 Hz, 1H), 6.76-6.64 (m, 2H), 6.28 (s, 1H), 4.11-3.83 (m, 6H), 3.65-3.47 (m, 3H), 3.36 (s, 3H), 3.25 (dd, J=10.5, 6.1 Hz, 1H), 2.94-2.81 (m, 1H), 2.71-2.42 (m, 4H), 2.26-2.06 (m, 2H), 2.01-1.75 (m, 2H), 1.12 (d, J=6.6 Hz, 3H). Analytical HPLC (ZORBAX®, 0% Solvent B start): RT=7.6 min, HI: 99%. hGPR40 $EC_{50}$=230 nM. hGPR40 IP1 $EC_{50}$=22 nM.

EXAMPLE 140

2-((2R,4R)-1-(4-((3,4-trans)-1-(5-Chloro-2-methoxypyridin-4-yl)-3-methylpiperidin-4-yloxy)-2,3-difluorophenyl)-4-(trifluoromethyl)pyrrolidin-2-yl)acetic acid

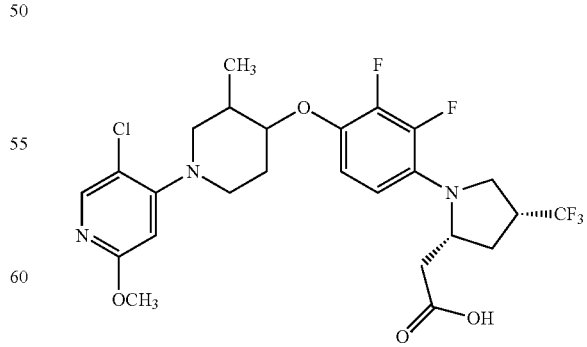

Example 140 (32 mg) was prepared as a single isomer from 2,3-difluoro-4-iodophenol and 1K following the procedure of Example 111. LC-MS Anal. Calc'd for $C_{25}H_{27}ClF_5N_3O_4$: 563, found [M+H] 564.2. $^1$H NMR (500 MHz, DMSO-d$_6$) δ 8.02-7.95 (m, 1H), 7.06-6.86 (m, 1H), 6.79-6.56 (m, 1H), 6.40 (s, 1H), 4.30-3.95 (m, 2H), 3.80 (s, 3H), 3.66-3.05 (m, 4H), 2.94-2.45 (m, 4H), 2.43-1.92 (m, 4H), 1.85-1.59 (m, 2H), 1.06 (d, J=6.6 Hz, 3H). Analytical HPLC (Acquity): RT=2.17 min, HI: 99.7%. hGPR40 EC$_{50}$=250 nM. hGPR40 IP1 EC$_{50}$=72 nM.

EXAMPLE 141

Isomer 1, Isomer 2, and Isomer 3

2-((4R)-1-(4-((3,4-trans)-1-(5-Chloro-2-methoxy-pyridin-4-yl)-3-methylpiperidin-4-yloxy)-2,3-difluorophenyl)-4-methoxypyrrolidin-2-yl)acetic acid

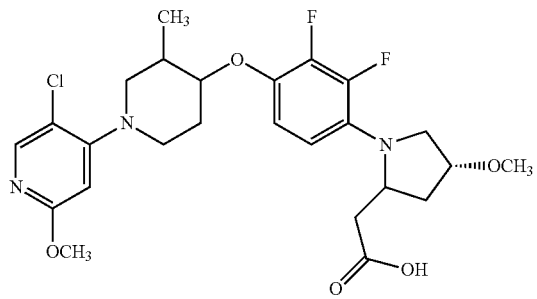 [SMILES: COc1cc(N2CCC(Oc3ccc(N4C[C@H](OC)CC4CC(=O)O)c(F)c3F)C(C)C2)c(Cl)cn1]

Example 141 was prepared from 2,3-difluoro-4-iodophenol and 4A following the procedure of Example 2. The isomers were separated as single isomers using RP-Prep. HPLC. Example 141, Isomer 1 (2.6 mg). LC-MS Anal. Calc'd for $C_{25}H_{30}ClF_2N_3O_5$: 525, found [M+H] 526.4. $^1$H NMR (500 MHz, CDCl$_3$) δ 7.98 (s, 1H), 6.72 (t, J=8.0 Hz, 1H), 6.49 (t, J=8.5 Hz, 1H), 6.27 (s, 1H), 4.21 (m, 1H), 4.10-4.01 (m, 1H), 3.89 (s, 3H), 3.80-3.60 (m, 1H), 3.64 (d, J=10.7 Hz, 1H), 3.53 (d, J=8.8 Hz, 2H), 3.42-3.34 (m, 4H), 2.83 (t, J=10.0 Hz, 1H), 2.73 (dd, J=16.1, 2.6 Hz, 1H), 2.68-2.57 (m, 2H), 2.45-2.35 (m, 1H), 2.24-2.08 (m, 2H), 2.06-1.99 (m, 1H), 1.93-1.83 (m, 1H), 1.17 (d, J=6.6 Hz, 3H). Analytical HPLC (Acquity): RT=1.97 min, HI: 99.0%. hGPR40 EC$_{50}$=410 nM. Example 141, Isomer 2 (1.6 mg). LC-MS Anal. Calc'd for $C_{25}H_{30}ClF_2N_3O_5$: 525, found [M+H] 526.4. $^1$H NMR (500 MHz, DMSO-d$_6$) δ 8.02-7.95 (m, 1H), 7.03-6.96 (m, 1H), 6.80 (t, J=8.5 Hz, 1H), 6.41 (s, 1H), 4.18-4.02 (m, 1H), 3.81 (s, 3H), 3.60-3.52 (m, 1H), 3.51-3.42 (m, 2H), 3.28 (s, 3H), 3.20-3.14 (m, 1H), 3.10-2.95 (m, 3H), 2.93-2.79 (m, 1H), 2.75-2.55 (m, 2H), 2.15-2.06 (m, 1H), 2.05-1.95 (m, 1H), 1.94-1.86 (m, 1H), 1.83-1.75 (m, 1H), 1.72-1.59 (m, 1H), 1.06 (d, J=6.6 Hz, 3H). Analytical HPLC (Acquity): RT=1.93 min, HI: 99.0%. hGPR40 EC$_{50}$=5600 nM. Example 141, Isomer 3 (2.1 mg). LC-MS Anal. Calc'd for $C_{25}H_{30}ClF_2N_3O_5$: 525, found [M+H] 526.4. $^1$H NMR (500 MHz, CDCl$_3$) δ 7.99 (s, 1H), 6.70 (dd, J=15.1, 8.3 Hz, 2H), 6.27 (s, 1H), 3.95-3.85 (m, 4H), 3.60-3.50 (m, 3H), 3.49-3.36 (m, 5H), 2.93-2.79 (m, 3H), 2.74-2.59 (m, 2H), 2.43 (d, J=12.9 Hz, 1H), 2.29-2.06 (m, 2H), 1.94-1.83 (m, 1H), 1.70-1.55 (m, 1H), 1.17 (d, J=6.6 Hz, 3H). Analytical HPLC (Acquity): RT=1.98 min, HI: 99.0%. hGPR40 EC$_{50}$=4700 nM.

EXAMPLE 142

2-((2R,4R)-1-(4-((3,4-trans)-1-(5-Chloro-2-methoxypyridin-4-yl)-3-methylpiperidin-4-yloxy)-3-fluorophenyl)-4-methoxypyrrolidin-2-yl)acetic acid, TFA

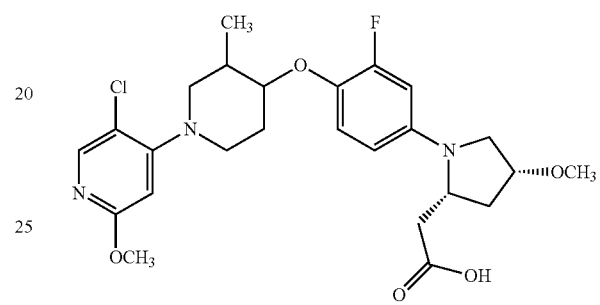

Example 142 (19.4 mg) was prepared as a single isomer from 98A and 4A following the procedure of Example 111. LC-MS Anal. Calc'd for $C_{25}H_{31}ClFN_3O_5$: 507. found [M+H] 508.1. $^1$H NMR (500 MHz, DMSO-d$_6$) δ 8.02-7.95 (m, 1H), 7.07 (t, J=9.4 Hz, 1H), 6.45-6.38 (m, 2H), 6.29 (d, J=9.1 Hz, 1H), 4.05 (br. s, 1H), 4.02-3.92 (m, 1H), 3.86-3.70 (m, 4H), 3.51-3.36 (m, 3H), 3.27 (m, 1H), 2.92-2.70 (m, 4H), 2.69-2.53 (m, 2H), 2.47-2.33 (m, 1H), 2.20-2.08 (m, 1H), 2.07-1.90 (m, 3H), 1.70-1.56 (m, 1H), 1.08 (d, J=6.3 Hz, 3H). Analytical HPLC (Acquity): RT=1.9 min, HI: 99.0%. hGPR40 EC$_{50}$=270 nM. hGPR40 IP1 EC$_{50}$=31 nM.

EXAMPLE 143

2-((2R,4R)-1-(4-1-(5-Ethoxy-2-fluorophenyl)piperidin-4-yloxy)-2-fluorophenyl)-4-trifluomethyl)pyrrolidin-2-yl)acetic acid

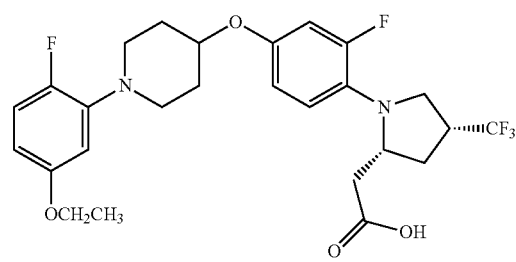 [SMILES: CCOc1ccc(F)c(N2CCC(Oc3ccc(N4C[C@H](C(F)(F)F)C[C@@H]4CC(=O)O)c(F)c3)CC2)c1]

Example 143 (39 mg) was prepared from 85A and 1K following the procedure of Example 111. LC-MS Anal. Calc'd for $C_{26}H_{29}F_5N_2O_4$: 528, found [M+H] 529.2. $^1$H NMR (500 MHz, DMSO-d$_6$) δ 7.00 (dd, J=12.4, 8.8 Hz, 1H), 6.95-6.84 (m, 2H), 6.76 (dd, J=8.5, 2.5 Hz, 1H), 6.53 (dd, J=7.4, 2.8 Hz, 1H), 6.49-6.44 (m, 1H), 4.46 (dt, J=7.8, 4.0 Hz, 1H), 4.05-3.92 (m, 3H), 3.54-3.12 (m, 4H), 2.96-2.67 (m, 3H), 2.44 (dd, J=15.4, 3.0 Hz, 1H), 2.27-1.94 (m, 4H), 1.80-1.68 (m, 3H), 1.29 (t, J=6.9 Hz, 3H). Analytical HPLC (Acquity): RT=2.07 min, HI: 98.8%. hGPR40 $EC_{50}$=360 nM.

EXAMPLE 144

2-((2R,4R)-1-(4-((3,4-trans)-1-(5-Chloro-2-methoxypyridin-4-yl)-3-methylpiperidin-4-yloxy)-2,6-difluorophenyl)-4-methoxypyrrolidin-2-yl)acetic acid, TFA

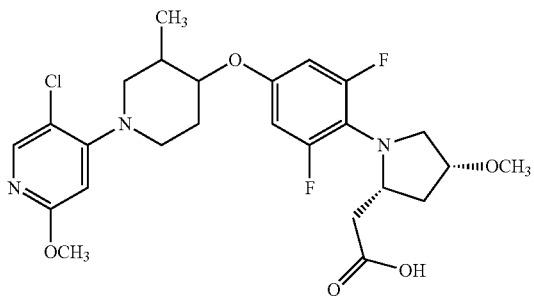 [SMILES: COc1cc(N2CCC(Oc3cc(F)c(N4C[C@H](OC)C[C@@H]4CC(=O)O)c(F)c3)C(C)C2)c(Cl)cn1]

Example 144 (21 mg) was prepared as a single isomer from 3,5-difluoro-4-iodophenol and 4A following the procedure of Example 111. LC-MS Anal. Calc'd for $C_{25}H_{30}ClF_2N_3O_5$: 525, found [M+H] 526.1. $^1$H NMR (400 MHz, $CDCl_3$) δ 8.13 (s, 1H), 6.51 (d, J=10.6 Hz, 2H), 6.30 (s, 1H), 4.28-4.07 (m, 1H), 4.03 (s, 4H), 3.96-3.87 (m, 1H), 3.85-3.66 (m, 2H), 3.49 (dd, J=10.3, 3.1 Hz, 1H), 3.40-3.29 (m, 4H), 3.26-3.16 (m, 1H), 2.96 (dd, J=12.8, 8.6 Hz, 1H), 2.63-2.43 (m, 3H), 2.37-2.10 (m, 2H), 1.98-1.77 (m, 2H), 1.14 (d, J=6.8 Hz, 3H). Analytical HPLC (ZORBAX®, 8 min gradient, 0% Solvent B start): RT=8.3 min, HI: 97.5%. hGPR40 $EC_{50}$=3400 nM. hGPR40 IP1 $EC_{50}$=2500 nM.

EXAMPLE 145

2-((2S,3S,4R)-1-(4-(3,4-trans)-1-(5-Chloro-2-methoxypyridin-4-yl)-3-methylpiperidin-4-yloxy)phenyl)-4-fluoro-3-methylpyrrolidin-2-yl)acetic acid

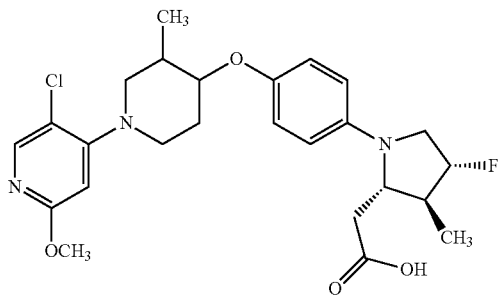 [SMILES: COc1cc(N2CCC(Oc3ccc(N4C[C@H](F)[C@@H](C)[C@@H]4CC(=O)O)cc3)C(C)C2)c(Cl)cn1]

145A. (2R,3S,4S)-1-Benzyl 2-methyl 4-(benzyloxy)-3-methylpyrrolidine-1,2-dicarboxylate: To a stirring solution of 118C (600 mg, 2.05 mmol), $Ph_3P$ (644 mg, 2.46 mmol), and benzoic acid (300 mg, 2.46 mmol) in THF (10 mL) at rt was slowly added DIAD (496 mg, 2.46 mmol) dropwise over 5 min. After the addition, the reaction mixture was stirred at rt for 1 h. The reaction mixture was concentrated. The crude product was purified by silica chromatography to provide 145A (800 mg, 2.01 mmol, 98% yield) as an oil. LC-MS Anal. Calc'd for $C_{22}H_{23}NO_6$: 397, found [M+H] 398.1.

145B. (2R,3S,4S)-1-Benzyl 2-methyl 4-hydroxy-3-methylpyrrolidine-1,2-dicarboxylate: To a solution of 145A (800 mg, 2.01 mmol) in a mixed solvent system of THF (4 mL), MeOH (1 mL), and water (3 mL) was added LiOH monohydrate (845 mg, 20.1 mmol) in one portion. The resulting yellow solution was stirred at rt under argon for 3 h. The reaction mixture was partially concentrated to remove the THF/MeOH and then cooled to 0° C. 3 M aq. HCl was added to adjust the pH to ~3-4. The reaction mixture was extracted with $CH_2Cl_2$ (3×). The combined organic extracts were washed with brine, dried ($MgSO_4$), filtered, and concentrated. The residue was dissolved in MeOH (2 mL) and toluene (4 mL) at rt and a 2 M solution of trimethylsilyldiazomethane in hexanes (4.1 mL, 8.1 mmol) was added. The reaction mixture was stirred at rt for 16 h. The solution was evaporated. The residue was purified by silica chromatography to afford (2R,3S,4S)-1-benzyl 2-methyl 4-hydroxy-3-methylpyrrolidine-1,2-dicarboxylate (450 mg, 1.53 mmol, 76% yield) as a white foam. LC-MS Anal. Calc'd for $C_{15}H_{19}NO_5$: 293, found [M+H] 294.1. $^1$H NMR (400 MHz, $CDCl_3$) δ 7.44-7.23 (m, 5H), 5.22-4.95 (m, 2H), 4.30-4.20 (m, 1H), 4.10-3.95 (dd, J=14.2, 9.4 Hz, 1H), 3.80 and 3.50 (2 s, 3H), 3.78-3.54 (m, 2H), 2.41-2.19 (m, 1H), 2.06-1.83 (m, 1H), 1.19 and 1.17 (2 d, J=7.0 Hz, 3H).

145C. (2R,3S,4R)-1-Benzyl 2-methyl 4-fluoro-3-methylpyrrolidine-1,2-dicarboxylate: To a solution of 145B (450 mg, 1.53 mmol) in $CH_2Cl_2$ (4 mL) at –78° C. was added DAST (0.41 mL, 3.1 mmol) dropwise. After the addition, the reaction mixture was stirred at rt for 16 h. The reaction mixture was diluted with $CH_2Cl_2$ and carefully quenched with sat. aq. $NaHCO_3$. The layers were separated and the aqueous layer was extracted with $CH_2Cl_2$ (2×). The combined organic layers were washed with brine, dried ($MgSO_4$), and concentrated. Purification via silica chromatography yielded 145C (120 mg, 0.406 mmol, 27% yield) as a colorless oil. LC-MS Anal. Calc'd for $C_{15}H_{18}FNO_4$: 295, found [M+Na] 318.1. $^1$H NMR (400 MHz, $CDCl_3$) δ 7.43-7.28 (m, 5H), 5.27-5.02 (m, 2H), 4.86-4.72 (m, 1H), 4.40-4.21 (m, 1H), 3.91-3.61 (m, 4H), 2.85-2.69 (m, 1H), 1.72-1.62 (m, 1H), 1.13 (d, J=7.3 Hz, 3H).

145D. (2R,3S,4R)-Benzyl 4-fluoro-2-(hydroxymethyl)-3-methylpyrrolidine-1-carboxylate: To a solution of 145C (125 mg, 0.423 mmol) in THF (4.5 mL) at 0° C. was added a 2 M solution of $LiBH_4$ (0.32 mL, 0.64 mmol) in THF. The reaction mixture was warmed to rt and stirred at rt for 16 h. The reaction was quenched with sat. aq. $NH_4Cl$ and diluted with EtOAc/water. The layers were separated and the organic layer was washed with brine, dried ($MgSO_4$), and concentrated. Purification via silica chromatography yielded 145D (60 mg, 0.22 mmol, 53% yield) as a colorless oil. LC-MS Anal. Calc'd for $C_{14}H_{18}FNO_3$: 267, found [M+H] 268.1. $^1$H NMR (400 MHz, $CDCl_3$) δ 7.45-7.33 (m, 5H), 5.17 (s, 2H), 4.90-4.60 (m, 1H), 4.02-3.60 (m, 6H), 2.70-2.20 (m, 1H), 1.11 (d, J=7.3 Hz, 3H).

145E. ((2R,3S,4R)-4-Fluoro-3-methylpyrrolidin-2-yl)methanol: A solution of 145D (56 mg, 0.21 mmol) in MeOH (2 mL) was purged with argon for 2 min and then 10% Pd/C (20 mg, 0.019 mmol) was added. The reaction mixture was stirred under $H_2$ (1 atm) for 16 h. The reaction mixture was filtered through a pad of CELITE® and the filtrate was concentrated to give 145E (28 mg, 0.210 mmol, 100% yield) as a colorless oil. LC-MS Anal. Calc'd for $C_6H_{12}FNO$: 133, found [M+H] 134.1.

Example 145 (off-white powder, 15 mg) was prepared as a single isomer from 145E and 119B following the procedure of Example 111. LC-MS Anal. Calc'd for $C_{25}H_{31}ClFN_3O_4$: 491, found [M+H] 492.1. $^1$H NMR (500 MHz, CDCl$_3$) δ 8.00 (s, 1H), 6.92 (d, J=8.0 Hz, 2H), 6.57 (d, J=8.0 Hz, 2H), 6.28 (s, 1H), 5.03 and 4.92 (2 m, 1H), 3.91 (s, 3H), 3.87-3.77 (m, 2H), 3.75-3.47 (m, 4H), 2.98-2.80 (m, 2H), 2.76-2.52 (m, 3H), 2.26-2.10 (m, 2H), 1.90-1.76 (m, 1H), 1.15 (d, J=6.8 Hz, 3H), 1.06 (d, J=7.3 Hz, 3H). Analytical HPLC: RT=10.4 min, HI: 98.9%. hGPR40 EC$_{50}$=26 nM.

EXAMPLE 146

2-((2S,3S,4R)-1-(6-(3,4-trans)-1-(5-Chloro-2-methoxypyridin-4-yl)-3-methylpiperidin-4-yloxy)pyridin-3-yl)-4-fluoro-3-methylpyrrolidin-2-yl)acetic acid

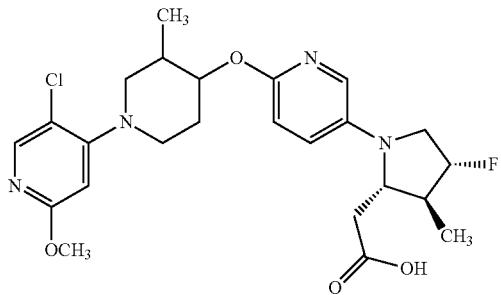 [SMILES: COc1cc(N2CCC(Oc3ccc(N4C[C@H](F)[C@@H](C)[C@@H]4CC(=O)O)cn3)C(C)C2)c(Cl)cn1]

Example 146 (white powder, 13 mg) was prepared as a single isomer from 145E and 132A following the procedure of Example 111. LC-MS Anal. Calc'd for $C_{24}H_{30}ClFN_4O_4$: 492, found [M+H] 493.2. $^1$H NMR (400 MHz, CDCl$_3$) δ 8.0 (s, 1H), 7.56 (d, J=3.1 Hz, 1H), 7.06-6.99 (m, 1H), 6.74 (d, J=8 Hz, 1H), 6.29 (s, 1H), 5.06-4.93 (m, 1H), 4.80-4.69 (m, 1H), 3.90 (s, 3H), 3.88-3.83 (m, 1H), 3.85-3.45 (m, 4H), 2.98-2.82 (m, 2H), 2.79-2.53 (m, 3H), 2.38-2.25 (m, 1H), 2.19-2.10 (m, 1H), 1.89-1.73 (m, 1H), 1.07 (d, J=2.2 Hz, 3H), 1.06 (d, J=2.9 Hz, 3H). Analytical HPLC: RT=6.94 min, HI: 97.5%. hGPR40 EC$_{50}$=90 nM.

EXAMPLE 147

Isomer 1

2-((2S,3S,4S)-1-(4-((3,4-trans)-1-(5-Chloro-2-methoxypyridin-4-yl)-3-methylpiperidin-4-yloxy)phenyl)-3-fluoro-4-methoxypyrrolidin-2-yl)acetic acid, HCl

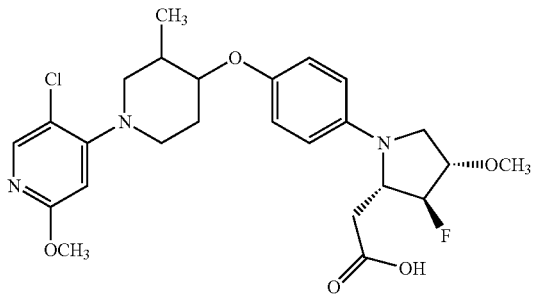 [SMILES: COc1cc(N2CCC(Oc3ccc(N4C[C@H](OC)[C@@H](F)[C@@H]4CC(=O)O)cc3)C(C)C2)c(Cl)cn1]

and

EXAMPLE 147

Isomer 2

2-((2S,3R,4R)-1-(4-(((3,4-trans)-1-(5-Chloro-2-methoxypyridin-4-yl)-3-methylpiperidin-4-yl)oxy)phenyl)-4-fluoro-3-methoxypyrrolidin-2-yl)acetic acid, HCl

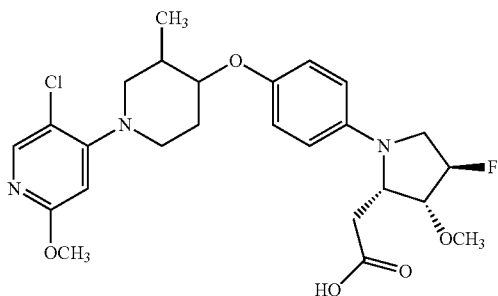 [SMILES: COc1cc(N2CCC(Oc3ccc(N4C[C@@H](F)[C@H](OC)[C@@H]4CC(=O)O)cc3)C(C)C2)c(Cl)cn1]

147A. (R)-1-Benzyl 2-methyl 4-(((trifluoromethyl)sulfonyl)oxy)-1H-pyrrole-1,2(2H,5H)-dicarboxylate: To a solution of 122A (8.35 g, 30.1 mmol) in CH$_2$Cl$_2$ (150 mL) at 0° C. was added DMAP (11.0 g, 90.0 mmol) and Tf$_2$O (8.05 mL, 45.2 mmol) dropwise. The reaction mixture was slowly warmed to rt and stirred for 16 h. The reaction mixture was diluted with CH$_2$Cl$_2$ and washed with water and brine, dried (MgSO$_4$), and concentrated. The crude material was purified by silica chromatography to 147A (10.0 g, 24.4 mmol, 81% yield) as a colorless oil. LC-MS Anal. Calc'd for $C_{15}H_{14}F_3NO_7S$: 409, found [M+H] 410.0.

147B. (R)-1-Benzyl 2-methyl 1H-pyrrole-1,2(2H,5H)-dicarboxylate: To a stirred solution of 147A (10.0 g, 24.4 mmol) in DMF (50 mL) was added tributylamine (17.5 mL, 73.3 mmol), formic acid (1.84 mL, 48.9 mmol), and PdCl$_2$(Ph$_3$P)$_2$ (1.715 g, 2.443 mmol) sequentially. The reaction mixture was stirred under argon at 60° C. for 4 h. After cooling to rt, the reaction mixture was diluted with water and extracted with EtOAc (2×). The combined organic layers were washed with brine, dried (MgSO$_4$), and concentrated. The crude product was purified by silica chromatography to give 147B (4.70 g, 18.0 mmol, 74% yield) as a light yellow oil. LC-MS Anal. Calc'd for $C_{14}H_{15}NO_4$: 261, found [M+Na] 284.1.

147C. (1S,2R,5R)-3-Benzyl 2-methyl 6-oxa-3-azabicyclo[3.1.0]hexane-2,3-dicarboxylate and (1R,2R,5S)-3-benzyl 2-methyl 6-oxa-3-azabicyclo[3.1.0]hexane-2,3-dicarboxylate: To a stirred solution of 147B (4.70 g, 18.0 mmol) in ClCH$_2$CH$_2$Cl (100 mL) was added 4,4'-thiobis(2-(tert-butyl)-6-methylphenol) (7.74 g, 21.6 mmol) and 3-chlorobenzoperoxoic acid (0.186 g, 1.08 mmol). The reaction mixture was stirred in a sealed flask at 65° C. for 16 h. The reaction mixture was diluted with CH$_2$Cl$_2$, washed with 5% aq. Na$_2$S$_2$O$_3$, sat. aq. NaHCO$_3$, and brine, dried (Na$_2$SO$_4$), filtered, and concentrated. The resulting residue was purified by silica chromatography to separate the two products. (1S,2R,5R)-3-Benzyl 2-methyl 6-oxa-3-azabicyclo[3.1.0] hexane-2,3-dicarboxylate (0.87 g, 3.1 mmol, 17% yield). LC-MS Anal. Calc'd for $C_{14}H_{15}NO_5$: 277. found [M+H] 278.0. (1R,2R,5S)-3-Benzyl 2-methyl 6-oxa-3-azabicyclo[3.1.0]hexane-2,3-dicarboxylate (590 mg, 2.13 mmol, 12% yield). LC-MS Anal. Calc'd for $C_{14}H_{15}NO_5$: 277, found [M+H] 278.1.

147D. (2R,3S,4S)-1-Benzyl 2-methyl 3-hydroxy-4-methoxypyrrolidine-1,2-dicarboxylate and (2R,3R,4R)-1-benzyl 2-methyl 4-hydroxy-3-methoxypyrrolidine-1,2-dicarboxylate: To a solution of (1S,2R,5R)-3-benzyl 2-methyl 6-oxa-3-azabicyclo[3.1.0]hexane-2,3-dicarboxylate (400 mg, 1.44 mmol) in MeOH (8 mL) was added AMBERLYST® 15 (400 mg), which was pre-washed with MeOH. The reaction mixture was heated to 65° C. for 16 h. After cooling to rt, the reaction mixture was filtered. The AMBERLYST® residue was washed with MeOH (4×) and the combined filtrates were concentrated. The crude residue was purified by silica chromatography to give 147D (210 mg) as an isomeric mixture. LC-MS Anal. Calc'd for $C_{15}H_{19}NO_6$: 309. found [M+H] 310.1. $^1$H NMR (400 MHz, $CDCl_3$) δ 7.43-7.28 (m, 5H), 5.26-5.00 (m, 2H), 4.60-4.45 (m, 1H), 4.44-4.26 (m, 1H), 3.96-3.80 (m, 1H), 3.80-3.60 (m, 4H), 3.60-3.5 (m, 1H), 3.34 and 3.33 (2 s, 3H), 2.40 and 2.35 (2 d, J=4.3 Hz, 1H).

147E. (2S,3S,4S)-1-Benzyl 2-methyl 3-fluoro-4-methoxypyrrolidine-1,2-dicarboxylate and (2R,3R,4R)-1-benzyl 2-methyl 4-fluoro-3-methoxypyrrolidine-1,2-dicarboxylate: To a solution of 147D as an isomeric mixture (220 mg, 0.711 mmol) in $CH_2Cl_2$ (4 mL) at −78° C. was added DAST (0.38 mL, 2.9 mmol) dropwise. After the addition, the reaction mixture was slowly warmed to rt and stirred for 16 h. The reaction mixture was diluted with $CH_2Cl_2$ and carefully quenched with sat. aq. $NaHCO_3$. The layers were separated and the aqueous layer was extracted with $CH_2Cl_2$ (2×). The combined organic layers were washed with brine, dried ($MgSO_4$), and concentrated. The crude product was purified by silica chromatography to provide 147E as an isomeric mixture (160 mg, 0.514 mmol, 72% yield) as a colorless oil. LC-MS Anal. Calc'd for $C_{15}H_{18}FNO_5$: 311, found [M+Na] 334.1.

147F. (2S,3S,4S)-Benzyl 3-fluoro-2-(hydroxymethyl)-4-methoxypyrrolidine-1-carboxylate and (2S,3R,4R)-benzyl 4-fluoro-2-(hydroxymethyl)-3-methoxypyrrolidine-1-carboxylate: To a solution of the isomeric mixture 147E (270 mg, 0.867 mmol) in THF (4.5 mL) at 0° C. was added a 2 M solution of $LiBH_4$ (0.43 mL, 0.87 mmol) in THF dropwise. After the addition, the reaction mixture was warmed to rt and stirred for 16 h. The reaction was quenched with sat. aq. $NH_4Cl$ and diluted with EtOAc/water. The layers were separated and the organic layer was washed with brine, dried ($MgSO_4$), and concentrated. The crude product was purified by silica chromatography to provide 147F as an isomeric mixture (160 mg, 0.565 mmol, 65% yield) as a colorless oil. LC-MS Anal. Calc'd for $C_{14}H_{18}FNO_4$:283, found [M+H] 284.1.

147G. (2S,3S,4S)-Benzyl 3-fluoro-4-methoxy-2-((tetrahydro-2H-pyran-2-yloxy)methyl)pyrrolidine-1-carboxylate and (2S,3R,4R)-benzyl 4-fluoro-3-methoxy-2-((tetrahydro-2H-pyran-2-yloxy)methyl)pyrrolidine-1-carboxylate: An isomeric mixture of 147F (160 mg, 0.565 mmol), 3,4-dihydro-2H-pyran (0.103 mL, 1.13 mmol), and pyridine 4-methylbenzenesulfonate (14 mg, 0.056 mmol) in $CH_2Cl_2$ (4 mL) was stirred at 60° C. for 16 h. The reaction mixture was concentrated. The crude oil was purified by silica chromatography to give 147G as an isomeric mixture (143 mg, 0.389 mmol, 69% yield) as a colorless oil. LC-MS Anal. Calc'd for $C_{19}H_{26}FNO_5$: 367, found [M+Na] 390.0.

147H. (2S,3S,4S)-3-Fluoro-4-methoxy-2-((tetrahydro-2H-pyran-2-yloxy)methyl)pyrrolidine and (2S,3R,4R)-4-fluoro-3-methoxy-2-((tetrahydro-2H-pyran-2-yloxy)methyl)pyrrolidine: A solution of an isomeric mixture of 147G (140 mg, 0.381 mmol) in MeOH (5 mL) was purged with argon for 2 min and then 10% Pd/C (50 mg, 0.47 mmol) was added. The reaction mixture was stirred under $H_2$ (1 atm) for 2 h. The reaction mixture was filtered through a pad of CELITE® and the filtrate was concentrated to provide 147H as an isomeric mixture (97 mg, 0.42 mmol, 89% yield) as a colorless oil. LC-MS Anal. Calc'd for $C_{11}H_{20}FNO_3$: 233, found [M+H] 234.1.

147I. 5-Chloro-4-(3,4-trans)-4-(4-((2S,3S,4S)-3-fluoro-4-methoxy-2-((tetrahydro-2H-pyran-2-yloxy)methyl) pyrrolidin-1-yl)phenoxy)-3-methylpiperidin-1-yl)-2-methoxypyridine and 5-chloro-4-(3,4-trans)-4-(4-((2S,3R,4R)-4-fluoro-3-methoxy-2-((tetrahydro-2H-pyran-2-yloxy) methyl)pyrrolidin-1-yl)phenoxy)-3-methylpiperidin-1-yl)-2-methoxypyridine: 119B (98 mg, 0.21 mmol) and an isomeric mixture of 147H (50 mg, 0.21 mmol), NaOtBu (28.8 mg, 0.300 mmol), SPhos (7.5 mg, 0.021 mmol), and $Pd_2(dba)_3$ chloroform adduct (5.9 mg, 6.4 µmol) were combined in a 2 dram pressure vial, which was purged with argon. Toluene (1 mL) was added and the reaction mixture was stirred at 90° C. for 8 h. The reaction mixture was cooled to rt and diluted with water. The product was extracted with $CH_2Cl_2$ (3×). The combined organic layers were washed with brine, dried ($MgSO_4$), and concentrated. The crude product was purified by silica chromatography to provide 147I as an isomeric mixture (20 mg, 0.035 mmol, 17% yield) as a white foam. LC-MS Anal. Calc'd for $C_{29}H_{35}ClFN_3O_5$: 563. found [M+H] 564.3.

147J. 2-((2S,3S,4S)-1-(4-(3,4-trans)-1-(5-Chloro-2-methoxypyridin-4-yl)-3-methylpiperidin-4-yloxy)phenyl)-3-fluoro-4-methoxypyrrolidin-2-yl)methanol and 2-((2S,3R,4R)-1-(4-(3,4-trans)-1-(5-chloro-2-methoxypyridin-4-yl)-3-methylpiperidin-4-yloxy)phenyl)-3-fluoro-4-methoxypyrrolidin-2-yl)methanol: An isomeric mixture of 147I (20 mg, 0.035 mmol) and PPTS (1.8 mg, 7.1 µmol) in MeOH (1 mL) was stirred at 60° C. for 16 h and then concentrated. The crude oil was purified by silica chromatography to provide 147J as an isomeric mixture (12 mg, 0.026 mmol, 71% yield) as a white foam. LC-MS Anal. Calc'd for $C_{24}H_{31}ClFN_3O_4$: 479, found [M+H] 480.1.

Example 147, Isomer 1 and Isomer 2 were prepared from an isomeric mixture of 147J following the procedure of Example 111. The two products were separated as single isomers by chiral SFC. Example 147, Isomer 1 (off-white powder, 1.6 mg). LC-MS Anal. Calc'd for $C_{25}H_{31}ClFN_3O_5$: 507, found [M+H] 508.1. $^1$H NMR (400 MHz, $CDCl_3$) δ 7.98 (s, 1H), 6.91 (d, J=8.6 Hz, 2H), 6.59 (d, J=8.8 Hz, 2H), 6.27 (s, 1H), 5.23-4.99 (m, 1H), 4.34-3.99 (m, 2H), 3.89 (s, 3H), 3.86-3.72 (m, 1H), 3.60-3.39 (m, 5H), 3.10-2.95 (m, 2H), 2.90-2.50 (m, 4H), 2.25-2.05 (m, 2H), 1.90-1.75 (m, 1H), 1.14 (d, J=6.8 Hz, 3H). Analytical HPLC: RT=8.9 min, HI: 96.2%. hGPR40 $EC_{50}$=170 nM. Example 147, Isomer 2 (off-white powder, 1.4 mg). LC-MS Anal. Calc'd for $C_{25}H_{31}ClFN_3O_5$: 507, found [M+H] 508.1. $^1$H NMR (400 MHz, $CDCl_3$) δ 7.98 (s, 1H), 6.91 (d, J=8.6 Hz, 2H), 6.59 (d, J=8.8 Hz, 2H), 6.27 (s, 1H), 5.23-5.04 (m, 1H), 4.45-4.30 (m, 1H), 4.20-4.10 (m, 1H), 3.89 (s, 3H), 3.86-3.72 (m, 2H), 3.60-3.35 (m, 6H), 3.10-2.95 (m, 1H), 2.90-2.78 (m, 1H), 2.70-2.50 (m, 2H), 2.25-2.05 (m, 2H), 1.90-1.75 (m, 1H), 1.14 (d, J=6.8 Hz, 3H). Analytical HPLC: RT=8.6 min, HI: 94.2%. hGPR40 $EC_{50}$=870 nM.

EXAMPLE 148

2-((2S,3S,4S)-1-(4-(((3,4-trans)-1-(5-Chloro-2-methoxypyridin-4-yl)-3-methylpiperidin-4-yloxy)phenyl)-4-fluoro-3-methoxypyrrolidin-2-yl)acetic acid

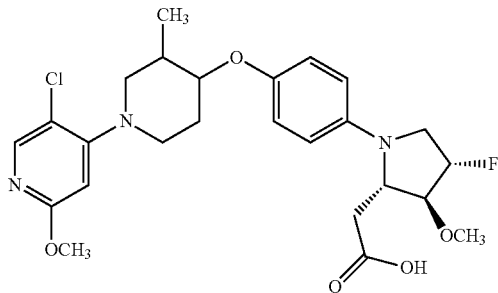 [SMILES: COc1cc(N2CCC(Oc3ccc(N4C[C@H](F)[C@@H](OC)[C@@H]4CC(=O)O)cc3)C(C)C2)c(Cl)cn1]

Example 148 (0.8 mg) was prepared as a single isomer from 147D [(1R,2R,5S)-3-benzyl-2-methyl-6-oxa-6-azabicyclo[3,1,0]hexane-2,3-dicarboxylate] following the procedure of Example 147. LC-MS Anal. Calc'd for $C_{25}H_{31}ClFN_3O_5$: 507. found [M+H] 508.2. $^1H$ NMR (500 MHz, DMSO-$d_6$) δ 8.02 (s, 1H), 6.91 (d, J=7.7 Hz, 2H), 6.53 (d, J=7.7 Hz, 2H), 6.40 (s, 1H), 5.39-5.15 (m, 1H), 4.00-3.85 (m, 3H), 3.80 (br. s, 3H), 3.71-3.40 (m, 4H), 2.93-2.57 (m, 5H), 2.20-1.88 (m, 3H), 1.83-1.44 (m, 2H), 1.18 (d, J=6.6 Hz, 3H). Analytical HPLC (Acquity): RT=1.86 min, HI: 99%. hGPR40 $EC_{50}$=120 nM.

EXAMPLE 149

2-((2R,4R)-1-(6-(((3,4-trans)-1-(5-Cyclopentyl-2-methoxypyridin-4-yl)-3-methylpiperidin-4-yl)oxy)pyridin-3-yl)-4-methoxypyrrolidin-2-yl)acetic acid

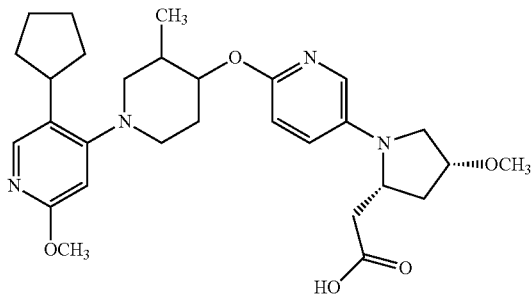 [SMILES: COc1cc(N2CCC(Oc3ccc(N4C[C@H](OC)C[C@@H]4CC(=O)O)cn3)C(C)C2)c(C2CCCC2)cn1]

149A. 4-((3R,4S)-4-((tert-Butyldimethylsilyl)oxy)-3-methylpiperidin-1-yl)-5-chloro-2-methoxypyridine: To a round bottom flask was added 119A, Isomer 1 (3.00 g, 11.7 mmol), DMF (20 mL), imidazole (1.59 g, 23.4 mmol) and TBS-Cl (2.11 g, 14.0 mmol). The reaction mixture was stirred at rt overnight. The reaction mixture was diluted with EtOAc (70 mL) and washed with water (3×40 mL) and brine (40 mL). The organic layer was dried over $MgSO_4$, filtered, and concentrated. The residue was purified by silica chromatography to give 149A (4.25 g, 11.5 mmol, 98% yield) as a colorless oil. LC-MS Anal. Calc'd for $C_{18}H_{31}ClN_2O_2Si$: 370.2, found [M+H] 371.3, 373.3. $^1H$ NMR (400 MHz, $CDCl_3$) δ 7.94 (s, 1H), 6.28 (s, 1H), 3.88 (s, 4H), 3.33-3.20 (m, 1H), 3.13-3.00 (m, 2H), 2.85 (t, J=11.0 Hz, 1H), 1.94 (td, J=6.7, 2.9 Hz, 1H), 1.88-1.81 (m, 1H), 1.80-1.70 (m, 1H), 0.94-0.90 (m, 9H), 0.10-0.04 (m, 9H).

149B. 4-((3R,4S)-4-((tert-Butyldimethylsilyl)oxy)-3-methylpiperidin-1-yl)-5-(cyclopent-1-en-1-yl)-2-methoxypyridine: To a sealed tube was added 149A (300 mg, 0.809 mmol), 2-(cyclopent-1-en-1-yl)-4,4,5,5-tetramethyl-1,3,2-dioxaborolane (157 mg, 0.809 mmol), $PdCl_2$(dppf) (53 mg, 0.081 mmol), 3 M aq. $K_3PO_4$ (0.54 mL, 1.6 mmol), and THF (5 mL). The reaction vessel was purged with argon for 2 min and then sealed. The reaction mixture was heated to 90° C. overnight. The reaction mixture was partitioned between EtOAc (50 mL) and water (30 mL). The organic layer was separated, washed with water (30 mL) and brine (30 mL), dried over $MgSO_4$, filtered, and concentrated. The residue was purified by silica chromatography to give 149B (250 mg, 0.621 mmol, 77% yield) as a colorless oil. LC-MS Anal. Calc'd for $C_{23}H_{38}N_2O_2Si$: 402.3, found [M+H] 403.3.

149C. 4-((3R,4S)-4-((tert-Butyldimethylsilyl)oxy)-3-methylpiperidin-1-yl)-5-cyclopentyl-2-methoxypyridine: To a 3-neck round bottom flask was added 149B (254 mg, 0.631 mmol), EtOH (5 mL), and $PtO_2$ (35.8 mg, 0.158 mmol). The reaction mixture was stirred under $H_2$ (1 atm) at rt for 8 h. The reaction mixture was filtered and the filtrate was concentrated. The residue was purified by silica chromatography to give 149C (150 mg, 0.371 mmol, 59% yield) as a colorless oil. LC-MS Anal. Calc'd for $C_{23}H_{40}N_2O_2Si$: 404.3, found [M+H] 405.4.

149D. (3R,4S)-1-(5-Cyclopentyl-2-methoxypyridin-4-yl)-3-methylpiperidin-4-ol: To a round bottom flask was added 149C (150 mg, 0.371 mmol), THF (3 mL), and TBAF (1.11 mL, 1.11 mmol). The reaction mixture was stirred at rt overnight. The reaction mixture was concentrated and the residue was purified by silica chromatography to give 149D (105 mg, 0.362 mmol, 98% yield) as a colorless oil. LC-MS Anal. Calc'd for $C_{17}H_{26}N_2O_2Si$: 290.2, found [M+H] 291.2.

149E. 5-Cyclopentyl-4-((3R,4R)-4-((5-iodopyridin-2-yl)oxy)-3-methylpiperidin-1-yl)-2-methoxypyridine: To a round bottom flask was added 149D (105 mg, 0.362 mmol), 5-iodopyridin-2-ol (88 mg, 0.40 mmol), toluene (3 mL), $Bu_3P$ (0.14 mL, 0.58 mmol) and ADDP (146 mg, 0.579 mmol). The reaction mixture was stirred at 60° C. for 1.5 h. The reaction mixture was concentrated and purified by silica chromatography to give 149E (155 mg, 0.314 mmol, 87% yield) as a colorless oil. LC-MS Anal. Calc'd for $C_{22}H_{28}IN_3O_2$: 493.1, found [M+H] 494.1. $^1H$ NMR (400 MHz, $CDCl_3$) δ 8.35-8.20 (m, 1H), 8.03-7.94 (m, 1H), 7.78 (dd, J=8.6, 2.4 Hz, 1H), 6.64-6.53 (m, 1H), 6.32-6.23 (m, 1H), 4.89-4.70 (m, 1H), 3.93-3.86 (m, 3H), 3.24-3.15 (m, 3H), 3.06 (s, 1H), 2.83 (s, 1H), 2.59-2.47 (m, 1H), 2.27 (dd, J=12.5, 2.6 Hz, 1H), 2.13-2.04 (m, 3H), 1.89-1.80 (m, 3H), 1.70-1.62 (m, 2H), 1.60 (br. s, 1H), 1.03-0.98 (m, 3H).

149F. ((2R,4R)-1-(6-(((3R,4R)-1-(5-Cyclopentyl-2-methoxypyridin-4-yl)-3-methylpiperidin-4-yl)oxy)pyridin-3-yl)-4-methoxypyrrolidin-2-yl)methanol: To a round bottom flask was added 149E (153 mg, 0.310 mmol), 4A (47.6 mg, 0.310 mmol), CuI (12 mg, 0.062 mmol), NaOH (37.2 mg, 0.930 mmol), and n-BuOH (2 mL). The reaction vessel was purged with argon and then stirred under argon at 90° C. for 5 h. The reaction mixture was partitioned between EtOAc (50 mL) and water (20 mL). The organic layer was separated, washed with water (2×20 mL) and brine (20 mL), dried over $MgSO_4$, filtered, and concentrated. The residue was purified by silica chromatography to give 149F (40 mg, 0.081 mmol, 26% yield) as a beige solid. LC-MS Anal. Calc'd for $C_{28}H_{40}N_4O_4$: 496.3, found [M+H] 497.3.

149G. 2-((2S,4R)-1-(6-(((3R,4R)-1-(5-Cyclopentyl-2-methoxypyridin-4-yl)-3-methylpiperidin-4-yl)oxy)pyridin-3-yl)-4-methoxypyrrolidin-2-yl)acetonitrile: To a round bottom flask was added 149F (40 mg, 0.081 mmol), MsCl (11 µL, 0.14 mmol), $CH_2Cl_2$ (2 mL), and $NEt_3$ (0.028 mL, 0.20 mmol). The reaction mixture was stirred at rt for 1.5 h. The reaction mixture was diluted with $CH_2Cl_2$ (20 mL) and washed with water (15 mL) and brine (15 mL), dried over $MgSO_4$, filtered, and concentrated. To this residue was added NaCN (11.8 mg, 0.240 mmol) and DMSO (1 mL). The reaction mixture was heated to 55° C. overnight. The reaction mixture was partitioned between EtOAc (50 mL) and water (25 mL). The organic layer was separated, washed with water (30 mL) and brine (30 mL), dried over $MgSO_4$, filtered, and concentrated. The residue was purified by silica chromatography to 149G (19 mg, 0.038 mmol, 47% yield) as a light colored oil. LC-MS Anal. Calc'd for $C_{29}H_{39}N_5O_3$: 505.3, found [M+H] 506.3.

Example 149: To a vial was added 149G (10 mg, 0.020 mmol), EtOH (0.5 mL), and 6 M aq. KOH (0.066 mL, 0.40 mmol). The reaction mixture was stirred at 130° C. for 1.5 h. The pH of the reaction mixture was adjusted to 4. The reaction mixture was then partitioned between EtOAc (10 mL) and water (5 mL). The organic layer was separated, washed with brine (5 mL), dried over $MgSO_4$, filtered, and concentrated. The residue was purified by RP-Prep. HPLC to give Example 149 (0.8 mg, 0.001 mmol, 8% yield) as an off-white solid as a single isomer. LC-MS Anal. Calc'd for $C_{29}H_{40}N_4O_5$: 524.3, found [M+H] 525.3. $^1$H NMR (500 MHz, DMSO-$d_6$) δ 7.97 (s, 1H), 7.47 (d, J=2.8 Hz, 1H), 7.07 (dd, J=8.9, 2.9 Hz, 1H), 6.71 (d, J=9.1 Hz, 1H), 6.32 (s, 1H), 4.65 (td, J=9.4, 4.3 Hz, 1H), 4.06 (t, J=4.8 Hz, 1H), 3.99 (t, J=8.7 Hz, 1H), 3.85-3.73 (m, 4H), 3.29-3.26 (m, 5H), 3.18-3.10 (m, 4H), 2.79 (t, J=10.7 Hz, 1H), 2.57-2.49 (m, 2H), 2.30 (dd, J=14.9, 10.5 Hz, 1H), 2.23-2.17 (m, 1H), 2.16-2.11 (m, 1H), 2.06-1.96 (m, 3H), 1.86-1.75 (m, 2H), 1.72-1.58 (m, 3H), 1.57-1.44 (m, 2H), 1.02-0.89 (m, 3H). Analytical HPLC (Acquity): RT=1.9 min, HI: 97.9%. hGPR40 $EC_{50}$=160 nM.

EXAMPLE 150

Isomer 1 and Isomer 2

2-((2S,3S,4R)-1-(6-(((3,4-trans)-1-(5-(2,2-Dimethylcyclopentyl)-2-methoxypyridin-4-yl)-3-methylpiperidin-4-yl)oxy)pyridin-3-yl)-4-methoxy-3-methylpyrrolidin-2-yl)acetic acid, HCl 150A: 2-((2S,3S,4R)-1-(6-(((3R,4R)-1-(5-(2,2-Dimethylcyclopentyl)-2-methoxypyridin-4-yl)-3-methylpiperidin-4-yl)oxy)pyridin-3-yl)-4-methoxy-3-methylpyrrolidin-2-yl)acetonitrile, Isomer 1 and Isomer 2: 150A was prepared from 65B following the procedure of Example 149. The diastereomers were separated by chiral SFC to provide the products as single isomers. Example 150A, Isomer 1 (9 mg) was recovered as a colorless oil. LC-MS Anal. Calc'd for $C_{32}H_{45}N_5O_3$: 547.3, found [M+H] 548.3. Example 2A, isomer 2somer 2 (8 mg) was recovered as a colorless oil. LC-MS Anal. Calc'd for $C_{32}H_{45}N_5O_3$: 547.3, found [M+H] 548.3.

Example 150 was prepared as single isomers from 2A, Isomer 1 and Isomer 2 following the procedure of Example 149. Example 150, Isomer 1 (beige solid, 8.2 mg). LC-MS Anal. Calc'd for $C_{32}H_{46}N_4O_5$: 566.3, found [M+H] 567.3. $^1$H NMR (400 MHz, acetonitrile-$d_3$) δ 7.75 (s, 1H), 7.47 (d, J=3.1 Hz, 1H), 7.40 (dd, J=9.1, 3.0 Hz, 1H), 7.30-7.11 (m, 2H), 7.02 (d, J=9.0 Hz, 1H), 6.59 (s, 1H), 4.68 (td, J=8.7, 4.0 Hz, 1H), 4.08 (s, 3H), 3.80-3.69 (m, 2H), 3.57 (d, J=12.1 Hz, 1H), 3.51-3.40 (m, 3H), 3.37-3.27 (m, 4H), 3.10-2.99 (m, 1H), 2.81 (dd, J=13.4, 9.7 Hz, 1H), 2.42 (q, J=7.2 Hz, 1H), 2.36-2.28 (m, 2H), 2.26-2.08 (m, 3H), 1.90-1.69 (m, 4H), 1.65-1.59 (m, 2H), 1.05 (d, J=6.8 Hz, 3H), 0.99 (d, J=7.3 Hz, 3H), 0.94 (s, 3H), 0.67 (s, 3H). Analytical HPLC: RT=6.6 min, HI: 95.0%. hGPR40 $EC_{50}$=320 nM. Example 150, Isomer 2 (beige solid, 8.3 mg) was prepared 2A isomer 2 following the procedure of Example 1. LC-MS Anal. Calc'd for $C_{32}H_{46}N_4O_5$: 566.3, found [M+H] 567.4. $^1$H NMR (400 MHz, acetonitrile-$d_3$) δ 7.82-7.75 (m, 1H), 7.57 (dd, J=9.4, 3.2 Hz, 1H), 7.50 (d, J=3.1 Hz, 1H), 7.33-7.24 (m, 1H), 7.23-7.14 (m, 2H), 6.69-6.62 (m, 1H), 4.66 (td, J=9.2, 4.3 Hz, 1H), 4.14-4.09 (m, 3H), 3.87-3.72 (m, 2H), 3.66 (d, J=13.9 Hz, 1H), 3.58-3.43 (m, 3H), 3.37-3.33 (m, 3H), 3.16-2.99 (m, 3H), 2.46 (q, J=7.1 Hz, 1H), 2.34 (s, 1H), 2.32-2.26 (m, 1H), 2.23-2.01 (m, 3H), 1.93-1.75 (m, 4H), 1.67-1.58 (m, 2H), 1.16-1.11 (m, 3H), 1.04-0.98 (m, 3H), 0.96 (s, 3H), 0.73-0.66 (m, 3H). Analytical HPLC: RT=6.6 min, HI: 95.0%. hGPR40 $EC_{50}$=110 nM.

EXAMPLE 151

Isomer 1 and Isomer 2

2-((2S,3S,4R)-1-(6-((1-(5-(2,2-Dimethylcyclopentyl)-2-methoxypyridin-4-yl)piperidin-4-yl)oxy)pyridin-3-yl)-4-methoxy-3-methylpyrrolidin-2-yl)acetic acid, HCl

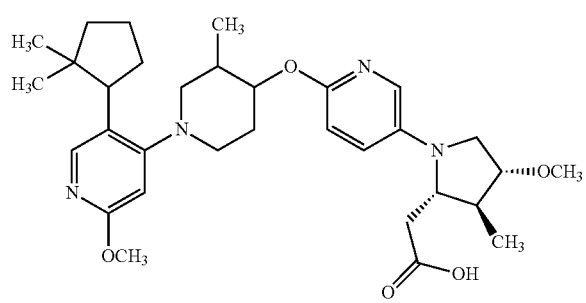 [SMILES: COc1cc(N2CCC(Oc3ccc(N4C[C@H](OC)[C@@H](C)[C@@H]4CC(=O)O)cn3)C(C)C2)c(C2CCCC2(C)C)cn1]

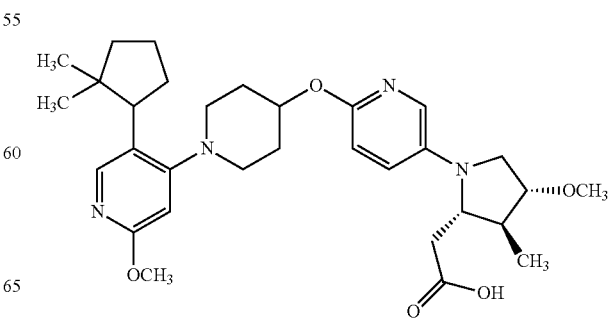

Example 151, Isomer 1 and Isomer 2 were prepared as single isomers from 150A, Isomer 1 and Isomer 2 and 118F following the procedure of Example 150.

Example 151, Isomer 1 (beige solid, 24 mg). LC-MS Anal. Calc'd for $C_{31}H_{44}N_4O_5$: 552.3, found [M+H] 553.3. $^1$H NMR (400 MHz, acetonitrile-$d_3$) δ 7.73 (s, 1H), 7.48 (dd, J=9.4, 3.2 Hz, 1H), 7.43 (d, J=3.1 Hz, 1H), 7.28-7.21 (m, 1H), 7.19-7.15 (m, 1H), 7.14-7.08 (m, 1H), 6.60 (s, 1H), 4.98 (dt, J=7.0, 3.5 Hz, 1H), 4.09-4.00 (m, 3H), 3.77-3.69 (m, 2H), 3.56-3.39 (m, 3H), 3.38-3.26 (m, 5H), 3.17-3.07 (m, 1H), 3.05-2.97 (m, 1H), 2.74-2.53 (m, 2H), 2.41 (q, J=7.3 Hz, 1H), 2.26-2.17 (m, 1H), 2.14-2.06 (m, 2H), 2.00 (d, J=3.5 Hz, 1H), 1.89-1.70 (m, 4H), 1.63-1.51 (m, 2H), 1.00-0.95 (m, 3H), 0.92 (s, 3H), 0.62 (s, 3H). Analytical HPLC: RT=6.1 min, HI: 95.0%. hGPR40 $EC_{50}$=38 nM. hGPR40 IP1 $EC_{50}$=4 nM. Example 151, Isomer 2 (beige solid, 15 mg) was. LC-MS Anal. Calc'd for $C_{31}H_{44}N_4O_5$: 552.3, found [M+H] 553.3. $^1$H NMR (400 MHz, acetonitrile-$d_3$) δ 7.72 (s, 1H), 7.50-7.40 (m, 2H), 7.29-7.21 (m, 1H), 7.21-7.13 (m, 1H), 7.11-7.02 (m, 1H), 6.60 (s, 1H), 5.10-4.95 (m, 1H), 4.06 (m, 3H), 3.72 (br. s, 2H), 3.61-3.52 (m, 1H), 3.50-3.41 (m, 2H), 3.38-3.29 (m, 5H), 3.12-2.99 (m, 2H), 2.75-2.55 (m, 2H), 2.41 (q, J=7.3 Hz, 1H), 2.27-2.18 (m, 1H), 2.17-2.04 (m, 3H), 1.91-1.72 (m, 4H), 1.60 (d, J=7.9 Hz, 2H), 0.97 (d, J=7.3 Hz, 3H), 0.93 (s, 3H), 0.63 (s, 3H). Analytical HPLC: RT=6.6 min, HI: 95.0%. hGPR40 $EC_{50}$=140 nM.

EXAMPLE 152

2-((2S,3S,4R)-1-(6-((1-(5-(5,5-Dimethylcyclopent-1-en-1-yl)-2-methoxypyridin-4-yl)piperidin-4-yl)oxy)pyridin-3-yl)-4-methoxy-3-methylpyrrolidin-2-yl)acetic acid, HCl

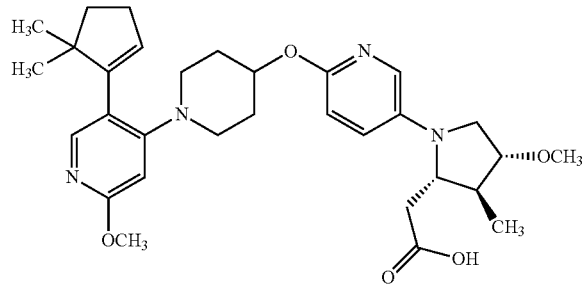 [SMILES: COc1cc(N2CCC(Oc3ccc(N4C[C@H](OC)[C@@H](C)[C@@H]4CC(=O)O)cn3)CC2)c(C2=CCCC2(C)C)cn1]

Example 152 (beige solid, 23 mg) was prepared from 65B and 118F following the procedure of Example 149. LC-MS Anal. Calc'd for $C_{31}H_{42}N_4O_5$: 550.3, found [M+H] 551.3. $^1$H NMR (400 MHz, acetonitrile-$d_3$) δ 7.60 (dd, J=9.4, 3.2 Hz, 1H), 7.50 (d, J=3.1 Hz, 1H), 7.43-7.37 (m, 1H), 7.32-7.11 (m, 3H), 6.42 (s, 1H), 5.87 (t, J=2.3 Hz, 1H), 5.06 (dt, J=6.8, 3.3 Hz, 1H), 4.16-4.03 (m, 3H), 3.95-3.85 (m, 2H), 3.82-3.73 (m, 2H), 3.72-3.60 (m, 2H), 3.56-3.45 (m, 2H), 3.35 (s, 3H), 2.74-2.63 (m, 2H), 2.53-2.40 (m, 3H), 2.18-2.04 (m, 2H), 1.90 (t, J=6.8 Hz, 4H), 1.05 (s, 6H), 1.01 (d, J=7.3 Hz, 3H). Analytical HPLC: RT=5.9 min, HI: 95.0%. hGPR40 $EC_{50}$=68 nM.

EXAMPLE 153

2-((2S,3S,4R)-1-(6-(((3R,4R)-1-(5-(5,5-Dimethylcyclopent-1-en-1-yl)-2-methoxypyridin-4-yl)-3-methylpiperidin-4-yl)oxy)pyridin-3-yl)-4-methoxy-3-methylpyrrolidin-2-yl)acetic acid, HCl

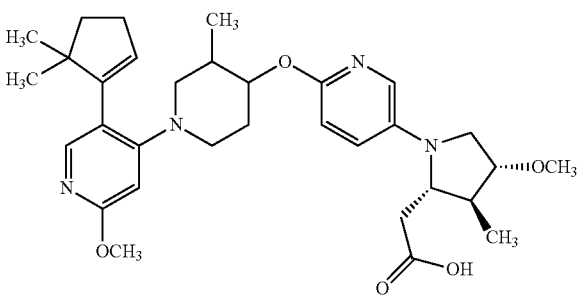 [SMILES: COc1cc(N2CCC(Oc3ccc(N4C[C@H](OC)[C@@H](C)[C@@H]4CC(=O)O)cn3)C(C)C2)c(C2=CCCC2(C)C)cn1]

Example 153 (brown solid, 5 mg) was prepared as a single isomer from 65B and 118F following the procedure of Example 149. LC-MS Anal. Calc'd for $C_{32}H_{44}N_4O_5$: 564.3, found [M+H] 565.3. $^1$H NMR (400 MHz, acetonitrile-$d_3$) δ 7.59-7.53 (m, 1H), 7.47-7.33 (m, 3H), 7.26-7.14 (m, 3H), 6.36 (br. s, 1H), 5.83 (br. s, 1H), 4.57 (br. s, 1H), 4.04 (d, J=2.0 Hz, 6H), 3.74 (br. s, 2H), 3.32 (d, J=2.0 Hz, 4H), 3.11 (br. s, 2H), 2.72-2.58 (m, 2H), 2.41 (br. s, 3H), 2.25-2.09 (m, 1H), 1.86 (d, J=2.6 Hz, 3H), 1.69 (br. s, 1H), 1.04-0.93 (m, 12H). Analytical HPLC: RT=6.3 min, HI: 95.0%. hGPR40 $EC_{50}$=200 nM.

EXAMPLE 154

2-((2S,3R)-1-(4-(((3,4-trans)-1-(5-Chloro-2-methoxypyridin-4-yl)-3-methylpiperidin-4-yl)oxy)phenyl)-3-methylpyrrolidin-2-yl)acetic acid, TFA

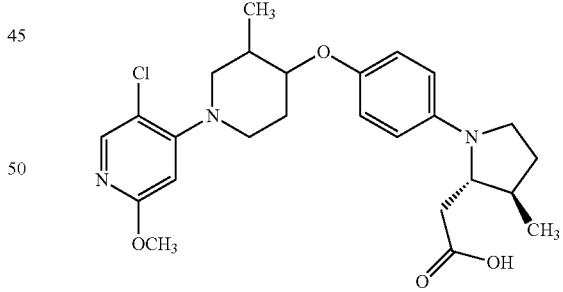

Example 154 (brown oil, 34.8 mg) was prepared as a single isomer from (2R,3R)-1-(tert-butoxycarbonyl)-3-methylpyrrolidine-2-carboxylic acid following the procedure of Example 119. LC-MS Anal. Calc'd for $C_{25}H_{32}ClN_3O_4$: 473.99, found [M+H] 474.4. $^1$H NMR (400 MHz, DMSO-$d_6$) δ 8.01 (s, 1H), 6.87 (d, J=9.0 Hz, 2H), 6.47 (d, J=9.0 Hz, 2H), 6.40 (s, 1H), 3.89-3.82 (m, 1H), 3.80 (s, 3H), 3.55 (d, J=8.0 Hz, 1H), 3.48-3.42 (m, 2H), 3.29-3.21 (m, 1H), 3.20-3.09 (m, 1H), 2.86 (t, J=10.3 Hz, 1H), 2.65 (dd, J=12.0, 9.5 Hz, 1H), 2.55 (dd, J=15.1, 2.5 Hz, 1H), 2.23-2.04 (m, 4H), 1.93 (dd, J=9.5, 7.0 Hz, 1H), 1.64-1.52

(m, 2H), 1.05 (d, J=6.5 Hz, 3H), 0.95 (d, J=6.5 Hz, 3H). Analytical HPLC: RT=9.1 min, HI: 98.0%. hGPR40 EC$_{50}$=110 nM.

EXAMPLE 155

2-((2S,3S,4R)-4-Butoxy-1-(4-(((3,4-trans)-1-(5-chloro-2-methoxypyridin-4-yl)-3-methylpiperidin-4-yl)oxy)phenyl)-3-methylpyrrolidin-2-yl)acetic acid

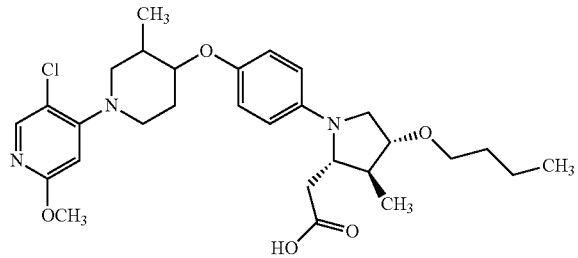 [SMILES: CCCCO[C@H]1CN(c2ccc(OC3CCN(c4cc(OC)ncc4Cl)CC3C)cc2)[C@@H](CC(=O)O)[C@@H]1C]

Example 155 (brown oil, 13.2 mg) was prepared as a single isomer from 1-bromobutane following the procedure of Example 119. LC-MS Anal. Calc'd for C$_{29}$H$_{40}$ClN$_3$O$_5$: 546.10, found [M$^+$] 546.0. $^1$H NMR (400 MHz, DMSO-d$_6$) δ 8.06-7.97 (m, 1H), 6.88 (d, J=9.0 Hz, 2H), 6.49 (d, J=9.0 Hz, 2H), 6.40 (s, 1H), 3.86 (td, J=8.8, 4.0 Hz, 1H), 3.81 (s, 3H), 3.49-3.30 (m, 8H), 2.87 (t, J=10.3 Hz, 1H), 2.70-2.52 (m, 2H), 2.27 (q, J=7.2 Hz, 1H), 2.12-2.02 (m, 1H), 2.00-1.87 (m, 2H), 1.64-1.52 (m, 1H), 1.52-1.43 (m, 2H), 1.39-1.27 (m, 2H), 1.05 (d, J=6.5 Hz, 3H), 0.93 (d, J=7.5 Hz, 3H), 0.91-0.85 (m, 3H). Analytical HPLC (XBridge Phenyl, 25 min gradient): RT=19.7 min, HI: 99.0%. hGPR40 EC$_{50}$=240 nM.

EXAMPLE 156

2-((2S,3S,4R)-1-(4-(((3,4-trans)-1-(5-Chloro-2-methoxypyridin-4-yl)-3-methylpiperidin-4-yl)oxy)-3-fluorophenyl)-4-fluoro-3-methylpyrrolidin-2-yl)acetic acid

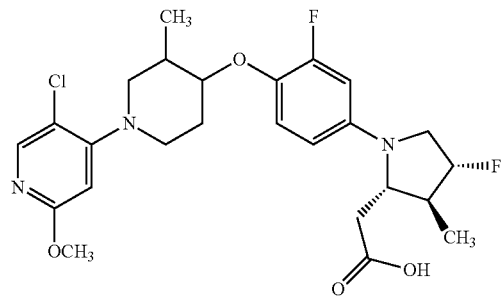 [SMILES: COc1cc(N2CCC(Oc3ccc(N4C[C@H](F)[C@@H](C)[C@@H]4CC(=O)O)cc3F)C(C)C2)c(Cl)cn1]

Example 156 (white solid, 14 mg) was prepared as a single isomer from 145E and 98A following the procedure of Example 98. LC-MS Anal. Calc'd for C$_{25}$H$_{30}$ClF$_2$N$_3$O$_4$: 509.97, found [M+H] 510.2. $^1$H NMR (500 MHz, CDCl$_3$) δ 8.00 (s, 1H), 6.96 (t, J=9.1 Hz, 1H), 6.34 (dd, J=13.8, 2.8 Hz, 1H), 6.29-6.21 (m, 2H), 5.08-4.86 (m, 1H), 3.92 (s, 3H), 3.84 (dd, J=10.7, 2.8 Hz, 1H), 3.74 (td, J=8.5, 4.1 Hz, 1H), 3.70-3.61 (m, 1H), 3.61-3.48 (m, 3H), 2.90 (dd, J=16.8, 3.0 Hz, 1H), 2.87-2.80 (m, 1H), 2.76-2.63 (m, 2H), 2.63-2.54 (m, 1H), 2.21-2.06 (m, 2H), 1.91-1.82 (m, 1H), 1.18 (d, J=6.6 Hz, 3H), 1.04 (d, J=7.4 Hz, 3H). Analytical HPLC: RT=10.8 min, HI: 99.0%. hGPR40 EC$_{50}$=63 nM.

EXAMPLE 157

2-((2S,3R,4R)-1-(4-(((3,4-trans)-1-(5-Chloro-2-methoxypyridin-4-yl)-3-methylpiperidin-4-yl)oxy)phenyl)-3-methyl-4-(trifluoromethyl)pyrrolidin-2-yl)acetic acid

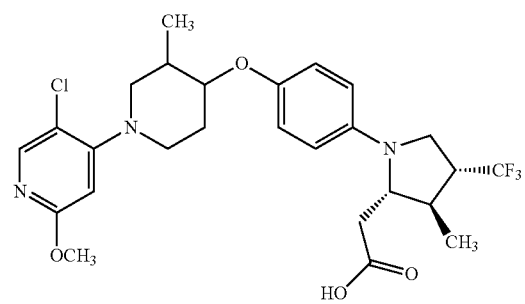 [SMILES: COc1cc(N2CCC(Oc3ccc(N4C[C@H](C(F)(F)F)[C@@H](C)[C@@H]4CC(=O)O)cc3)C(C)C2)c(Cl)cn1]

157A. (2R,3S,4R)-Methyl 4-hydroxy-3-methylpyrrolidine-2-carboxylate: A solution of 118C (3.00 g, 10.2 mmol) in MeOH (30 mL) was purged with argon for 2 min and then 10% Pd/C (300 mg, 0.282 mmol) was added. The reaction mixture was stirred under an atmosphere of H$_2$ (1 atm) for 16 h. The reaction mixture was filtered through a pad of CELITE® and concentrated to give 157A (1.55 g, 9.74 mmol, 95% yield) as a colorless oil. LC-MS Anal. Calc'd for C$_7$H$_{13}$NO$_3$: 159.18, found [M+H] 160.1.

157B. (2R,3S,4R)-1-tert-Butyl 2-methyl 4-hydroxy-3-methylpyrrolidine-1,2-dicarboxylate: To a solution of 157A (1.55 g, 9.74 mmol) in THF (20 mL) and water (20 mL) was added Boc$_2$O (3.19 g, 14.6 mmol) and NaHCO$_3$ (2.45 g, 29.2 mmol). The reaction mixture was stirred for 72 h. The product was extracted with EtOAc (3×). The combined organic layers were washed with brine, dried (Na$_2$SO$_4$), and concentrated. The resulting residue was purified by silica chromatography to afford 157A (2.45 g, 9.45 mmol, 97% yield) as a white foam. LC-MS Anal. Calc'd for C$_{12}$H$_{21}$NO$_5$: 259.30, found [M+H] 260.0.

157C. (2R,3S)-1-tert-Butyl 2-methyl 3-methyl-4-oxopyrrolidine-1,2-dicarboxylate: To a solution of 157B (2.45 g, 9.45 mmol) in CH$_2$Cl$_2$ (25 mL) at 0° C. was added TCCA (2.20 g, 9.45 mmol), followed by the addition of TEMPO (0.015 g, 0.094 mmol). The reaction mixture was warmed to rt and stirred for 60 min. The reaction mixture was filtered and washed with sat. aq. Na$_2$CO$_3$, 0.1 M aq. HCl, and brine. The organic layer was dried (MgSO$_4$) and concentrated. The crude product was purified by silica chromatography to give 157C (2.05 g, 7.97 mmol, 84% yield) as a white solid. LC-MS Anal. Calc'd for C$_{12}$H$_{19}$NO$_5$: 257.28, found [M+H-Boc] 158.1.

157D. (2R,3S)-1-tert-Butyl 2-methyl 4-hydroxy-3-methyl-4-(trifluoromethyl)pyrrolidine-1,2-dicarboxylate: To a solution of 157C (2.05 g, 7.97 mmol) in THF (40 mL) at 0° C. was added trimethyl(trifluoromethyl)silane (1.25 mL, 8.45 mmol), followed by a solution of 1 M TBAF in THF (0.28 mL, 0.28 mmol). The mixture was warmed to rt and stirred overnight. Additional trimethyl(trifluoromethyl)silane (1.3 mL, 8.5 mmol) was added followed by 1 M TBAF in THF (8.0 mL, 8.0 mmol). The reaction mixture was stirred at rt for 6 h. Sat. aq. NH$_4$Cl (15 mL) was added and the mixture was stirred at rt for 30 min. The organic layer was separated and the aqueous layer was extracted with Et$_2$O (3×50 mL). The combined organic layers were washed with brine, dried (Na$_2$SO$_4$), concentrated, and purified by silica chromatography to give 157D (1.15 g, 3.51 mmol, 44% yield) as a colorless oil. LC-MS Anal. Calc'd for C$_{13}$H$_{20}$F$_3$NO$_5$: 327.30, found [M+H-Boc] 228.1. $^1$H NMR (400 MHz, CDCl$_3$) δ 4.13-3.98 (m, 1H), 3.95-3.82 (m, 1H), 3.78 (d, J=5.7 Hz, 3H), 3.71-3.59 (m, 1H), 2.66-2.53 (m, 1H), 1.54-1.37 (m, 9H), 1.30-1.19 (m, 3H).

157E. (2R,3S)-tert-Butyl 4-hydroxy-2-(hydroxymethyl)-3-methyl-4-(trifluoromethyl)pyrrolidine-1-carboxylate: To a solution of 157D (1.11 g, 3.39 mmol) in THF (15 mL) at 0° C. was added a 2 M solution of LiBH$_4$ (2.54 mL, 5.09 mmol) in THF. The reaction mixture was warmed to rt and stirred for 3 days. The reaction was quenched with sat. aq. NH$_4$Cl and diluted with EtOAc/water. The layers were separated and the organic layer was washed with brine, dried (MgSO$_4$), and concentrated. The crude product was purified by silica chromatography to provide 157E (980 mg, 3.27 mmol, 97% yield) as a colorless oil. LC-MS Anal. Calc'd for C$_{12}$H$_{20}$F$_3$NO$_4$: 299.29, found [M+H] 300.0.

157F. (2R,3S)-tert-Butyl 2-(((tert-butyldimethylsilyl)oxy)methyl)-4-hydroxy-3-methyl-4-(trifluoromethyl)pyrrolidine-1-carboxylate: To a solution of 157F (970 mg, 3.24 mmol) in CH$_2$Cl$_2$ (15 mL) was added TBS-Cl (488 mg, 3.24 mmol), Et$_3$N (0.95 mL, 6.8 mmol), and DMAP (39.6 mg, 0.324 mmol). The reaction mixture was stirred at rt for 16 h. The reaction mixture was diluted with water and extracted with CH$_2$Cl$_2$ (2×). The combined organic extracts were washed with brine, dried (Na$_2$SO$_4$), filtered, and concentrated. The resulting residue was purified by silica chromatography to give 157F (980 mg, 2.37 mmol, 73% yield) as a colorless oil. LC-MS Anal. Calc'd for C$_{18}$H$_{34}$F$_3$NO$_4$Si: 413.55, found [M+H] 414.0.

157G. (2R,3S)-tert-Butyl 2-(((tert-butyldimethylsilyl)oxy)methyl)-3-methyl-4-(tosyloxy)-4-(trifluoromethyl)pyrrolidine-1-carboxylate: To a solution of 157F (970 mg, 2.35 mmol) in THF (10 mL) at 0° C. was added 60% NaH (141 mg, 3.52 mmol) in several portions. After the addition, the reaction mixture was stirred at rt for 30 min and then cooled to 0° C. Ts-Cl (894 mg, 4.69 mmol) was added in several portions. The reaction mixture was stirred at rt for 16 h. The reaction mixture was diluted with water and extracted with EtOAc (2×). The combined organic layers were washed with brine, dried (MgSO$_4$), and concentrated. The crude product was purified by silica chromatography to provide 157G (1.15 g, 2.03 mmol, 86% yield) as a white foam. $^1$H NMR (400 MHz, CDCl$_3$) δ 7.80 (d, J=7.9 Hz, 2H), 7.37-7.29 (m, 2H), 4.52-4.40 (m, 1H), 4.12-3.93 (m, 1H), 3.93-3.82 (m, 1H), 3.70-3.52 (m, 1H), 3.48-3.29 (m, 1H), 3.25-3.07 (m, 1H), 2.45 (s, 3H), 1.50-1.38 (m, 9H), 1.22-1.08 (m, 3H), 0.89 (s, 9H), 0.04 (s, 6H).

157H. (2R,3R)-tert-Butyl 2-(((tert-butyldimethylsilyl)oxy)methyl)-3-methyl-4-(trifluoromethyl)-2,3-dihydro-1H-pyrrole-1-carboxylate: To a solution of 157G (1100 mg, 1.9 mmol) in THF (10 mL) at −40° C. was added KOtBu (435 mg, 3.88 mmol) in several portions. After the addition, the reaction mixture was stirred at −40° C. for 2 h. The reaction mixture was carefully quenched with sat. aq. NH$_4$Cl and extracted with EtOAc (2×). The combined organic layers were washed with brine, dried (MgSO$_4$), and concentrated. The crude product was purified by silica chromatography to provide 157H (300 mg, 0.725 mmol, 37% yield) as a white solid. LC-MS Anal. Calc'd for C$_{18}$H$_{34}$F$_3$NO$_4$Si: 395.53, found [M+H-Boc 296.0. $^1$H NMR (400 MHz, CDCl$_3$) δ 7.12-6.80 (m, 1H), 3.81 (br. s, 1H), 3.76-3.53 (m, 2H), 3.12 (br. s, 1H), 1.49 (s, 9H), 1.21 (d, J=7.0 Hz, 3H), 0.87 (s, 9H), 0.08--0.03 (m, 6H).

157I. (2R,3R,4R)-tert-Butyl 2-(hydroxymethyl)-3-methyl-4-(trifluoromethyl)pyrrolidine-1-carboxylate: A solution of 157H (75 mg, 0.19 mmol) in MeOH (2 mL) was purged with argon for 2 min and then 10% Pd/C (20 mg, 0.470 mmol) was added. The reaction mixture was stirred at rt under H$_2$ (1 atm) for 16 h. The reaction mixture was filtered through a pad of CELITE® and the filtrate was concentrated to give 157I (55 mg, 0.19 mmol, 100% yield) as a colorless oil. LC-MS Anal. Calc'd for C$_{12}$H$_{20}$F$_3$NO$_3$: 283.29, found [M+H-Boc] 184.1. $^1$H NMR (400 MHz, CDCl$_3$) δ 3.89-3.73 (m, 2H), 3.69-3.56 (m, 1H), 3.55-3.43 (m, 1H), 3.32 (t, J=10.9 Hz, 1H), 2.56-2.37 (m, 1H), 2.09-1.87 (m, 1H), 1.47 (s, 9H), 1.22 (d, J=6.6 Hz, 3H).

Example 157 (white solid, 14 mg) was prepared as a single isomer from 157I following the procedure of Example 119. LC-MS Anal. Calc'd for C$_{26}$H$_{31}$ClF$_3$N$_3$O$_4$: 541.99, found [M+H] 542.2. $^1$H NMR (500 MHz, CDCl$_3$) δ 7.99 (s, 1H), 6.91 (d, J=9.1 Hz, 2H), 6.78 (d, J=9.1 Hz, 2H), 6.27 (s, 1H), 3.90 (s, 3H), 3.87 (dt, J=8.4, 4.3 Hz, 1H), 3.74-3.65 (m, 1H), 3.59-3.44 (m, 4H), 2.93-2.83 (m, 1H), 2.76 (dd, J=16.4, 2.6 Hz, 1H), 2.71-2.59 (m, 2H), 2.51-2.38 (m, 2H), 2.23-2.09 (m, 2H), 1.88-1.76 (m, 1H), 1.31 (d, J=6.9 Hz, 3H), 1.13 (d, J=6.6 Hz, 3H). Analytical HPLC: RT=11.3 min, HI: 99.0%. hGPR40 EC$_{50}$=300 nM.

EXAMPLE 158

2-((2S,3S,4R)-1-(4-(((3,4-trans)-1-(5-Chloro-2-methoxypyridin-4-yl)-3-methylpiperidin-4-yl)oxy)phenyl)-4-ethoxy-3-methylpyrrolidin-2-yl)acetic acid, TFA

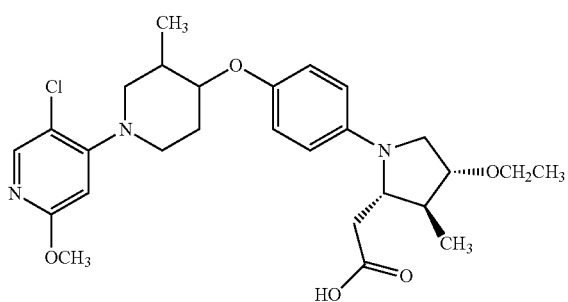 [SMILES: CCO[C@H]1CN(c2ccc(OC3CCN(c4cc(OC)ncc4Cl)CC3C)cc2)[C@@H](CC(=O)O)[C@@H]1C]

Example 158 (brown solid, 5.2 mg) was prepared as a single isomer from 1-bromoethane following the procedure of Example 119. LC-MS Anal. Calc'd for C$_{27}$H$_{36}$ClN$_3$O$_5$: 518.05, found [M$^+$] 518.0. $^1$H NMR (400 MHz, DMSO-d$_6$) δ 8.02 (s, 1H), 6.88 (d, J=8.5 Hz, 2H), 6.48 (d, J=9.0 Hz, 2H), 6.40 (s, 1H), 3.86 (td, J=8.8, 4.0 Hz, 1H), 3.80 (s, 3H), 3.74 (d, J=4.5 Hz, 1H), 3.59 (d, J=8.0 Hz, 1H), 3.53-3.41 (m, 5H), 3.31-3.26 (m, 1H), 2.92-2.80 (m, 1H), 2.71-2.53 (m, 2H), 2.27 (q, J=7.5 Hz, 2H), 2.08 (d, J=10.0 Hz, 1H), 1.93 (br. s, 1H), 1.64-1.52 (m, 1H), 1.12 (t, J=6.8 Hz, 3H), 1.05 (d, J=6.5 Hz, 3H), 0.93 (d, J=7.5 Hz, 3H). Analytical HPLC (XBridge Phenyl, 25 min gradient): RT=17.0 min, HI: 97.0%. hGPR40 EC$_{50}$=160 nM.

EXAMPLE 159

2-((2S,3S,4R)-1-(6-(((3,4-trans)-1-(5-Chloro-2-methoxypyridin-4-yl)-3-methylpiperidin-4-yl)oxy)-5-fluoropyridin-3-yl)-4-methoxy-3-methylpyrrolidin-2-yl)acetic acid

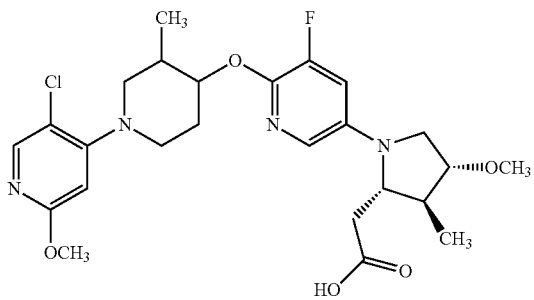 [SMILES: COc1cc(N2CCC(Oc3ncc(N4C[C@H](OC)[C@@H](C)[C@@H]4CC(=O)O)cc3F)C(C)C2)c(Cl)cn1]

159A. (3,4-trans)-1-(5-Chloro-2-methoxypyridin-4-yl)-3-methylpiperidin-4-ol, Isomer 1 and Isomer 2: 159A was prepared from 27B following the procedure of Example 83. The racemic product (13.6 g, 53.0 mmol) was separated by chiral SFC to provide the product as single isomers. 159A, Isomer 1 was isolated as a brown oil (3.00 g, 11.7 mmol, 22% yield). LC-MS Anal. Calc'd for $C_{12}H_{17}ClN_2O_2$: 256.73, found [M+H] 257.0. $^1$H NMR (300 MHz, CDCl$_3$) δ 7.96 (s, 1H), 6.25 (s, 1H), 3.88 (s, 3H), 3.62-3.53 (m, 1H), 3.49 (dt, J=12.2, 3.4 Hz, 1H), 3.34 (d, J=4.9 Hz, 1H), 2.76 (td, J=11.9, 2.6 Hz, 1H), 2.43 (dd, J=12.1, 10.2 Hz, 1H), 2.14-1.97 (m, 1H), 1.85-1.66 (m, 2H), 1.06 (d, J=6.8 Hz, 3H). 159A, Isomer 2 was isolated as a brown oil (3.70 g, 14.4 mmol, 27% yield). LC-MS Anal. Calc'd for $C_{12}H_{17}ClN_2O_2$: 256.73, found [M+H] 257.0. $^1$H NMR (400 MHz, CDCl$_3$) δ 7.96 (s, 1H), 6.25 (s, 1H), 3.88 (s, 3H), 3.62-3.53 (m, 1H), 3.49 (ddd, J=12.0, 4.0, 2.5 Hz, 1H), 3.34 (t, J=9.8 Hz, 1H), 2.76 (td, J=11.9, 2.8 Hz, 1H), 2.43 (dd, J=12.3, 10.3 Hz, 1H), 2.09-2.02 (m, 1H), 1.87-1.70 (m, 2H), 1.52 (br. s, 1H), 1.06 (d, J=6.5 Hz, 3H).

159B. 2-(((3,4-trans)-1-(5-Chloro-2-methoxypyridin-4-yl)-3-methylpiperidin-4-yl)oxy)-3-fluoro-5-iodopyridine: To a solution of 159A, Isomer 2 (410 mg, 1.60 mmol) in DMF (7 mL) at 0° C. was added 60% NaH (96 mg, 2.4 mmol) and the reaction mixture was stirred at 0° C. for 10 min and then rt for 20 min. The reaction mixture was recooled to 0° C. and 2,3-difluoro-5-iodopyridine (385 mg, 1.60 mmol) was added. The reaction mixture was warmed to rt and stirred for 1 h 45 min. The reaction mixture was cooled to 0° C. and quenched with sat. aq. NH$_4$Cl. The reaction mixture was partitioned between EtOAc/water. The aqueous phase was extracted with EtOAc (2×). The combined organic extracts were washed with water and brine, dried (MgSO$_4$), and concentrated. The crude product was purified by silica chromatography to give 159B (532 mg, 1.114 mmol, 69.7% yield) as a beige solid. LC-MS Anal. Calc'd for $C_{17}H_{18}ClFIN_3O_2$: 477.70. found [M+H] 478.0. $^1$H NMR (400 MHz, chloroform-d) δ 8.08 (d, J=1.8 Hz, 1H), 7.99 (s, 1H), 7.61 (dd, J=9.1, 1.9 Hz, 1H), 6.28 (s, 1H), 4.91 (td, J=9.2, 4.4 Hz, 1H), 3.92 (s, 3H), 3.66-3.52 (m, 2H), 3.02-2.89 (m, 1H), 2.68 (dd, J=12.3, 9.7 Hz, 1H), 2.37-2.17 (m, 2H), 1.94-1.79 (m, 1H), 1.06 (d, J=6.6 Hz, 3H).

Example 159 (off-white solid, 44.3 mg) was prepared as a single isomer from 159B following the procedure of Example 17. LC-MS Anal. Calc'd for $C_{25}H_{32}ClFN_4O_5$: 523.00, found [M$^+$] 523.3. $^1$H NMR (400 MHz, CDCl$_3$) δ 7.97 (s, 1H), 7.29 (d, J=2.6 Hz, 1H), 6.77 (dd, J=12.3, 2.6 Hz, 1H), 6.28 (s, 1H), 4.75 (td, J=9.1, 4.1 Hz, 1H), 3.89 (s, 3H), 3.72 (t, J=6.7 Hz, 1H), 3.68 (br. s, 1H), 3.60-3.56 (m, 1H), 3.55-3.52 (m, 1H), 3.47-3.42 (m, 2H), 3.38 (s, 3H), 2.98-2.89 (m, 1H), 2.83-2.78 (m, 2H), 2.65 (dd, J=12.3, 9.7 Hz, 1H), 2.47 (q, J=7.3 Hz, 1H), 2.32-2.15 (m, 2H), 1.92-1.80 (m, 1H), 1.07 (d, J=6.6 Hz, 3H), 1.04 (d, J=7.3 Hz, 3H). Analytical HPLC (ZORBAX®, 50% B start): RT=6.8 min, HI: 98.5%. hGPR40 EC$_{50}$=85 nM.

EXAMPLE 160

2-((2S,3S,4R)-1-(5-Butoxy-6-(((3,4-trans)-1-(5-chloro-2-methoxypyridin-4-yl)-3-methylpiperidin-4-yl)oxy)pyridin-3-yl)-4-methoxy-3-methylpyrrolidin-2-yl)acetic acid

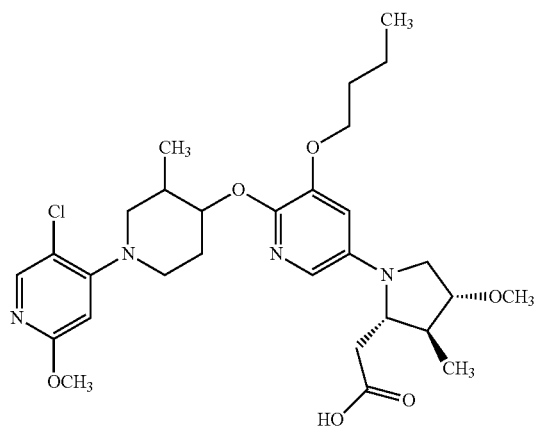 [SMILES: CCCCOc1cc(N2C[C@H](OC)[C@@H](C)[C@@H]2CC(=O)O)cnc1OC1CCN(c2cc(OC)ncc2Cl)CC1C]

Example 160 (grey solid, 2.4 mg) was isolated as a single isomer as a byproduct from the reaction sequence of Example 159. LC-MS Anal. Calc'd for $C_{29}H_{41}ClN_4O_6$: 577.11, found [M$^+$] 577.4. $^1$H NMR (400 MHz, CDCl$_3$) δ 8.13 (s, 1H), 7.23 (br. s, 1H), 6.89 (d, J=1.3 Hz, 1H), 6.32 (s, 1H), 4.77 (br. s, 1H), 4.10 (dt, J=6.4, 3.2 Hz, 1H), 4.02 (s, 3H), 4.01-3.93 (m, 1H), 3.84 (dd, J=8.0, 3.9 Hz, 1H), 3.78-3.65 (m, 3H), 3.53-3.46 (m, 2H), 3.37 (s, 3H), 3.02-2.92 (m, 1H), 2.89-2.80 (m, 1H), 2.78-2.68 (m, 1H), 2.50 (q, J=6.7 Hz, 1H), 2.30 (br. s, 2H), 1.99-1.76 (m, 4H), 1.57-1.49 (m, 2H), 1.13 (d, J=6.8 Hz, 3H), 1.06-1.02 (m, 3H), 1.01-0.98 (m, 3H). Analytical HPLC (ZORBAX®, 50% B start): RT=7.5 min, HI: 95.0%. hGPR40 EC$_{50}$=86 nM.

EXAMPLE 161

2-((2S,3S,4R)-1-(4-(((3,4-trans)-1-(5-Chloro-2-methoxypyridin-4-yl)-3-methylpiperidin-4-yl)oxy)phenyl)-3-methyl-4-(4,4,4-trifluorobutoxy)pyrrolidin-2-yl)acetic acid, TFA

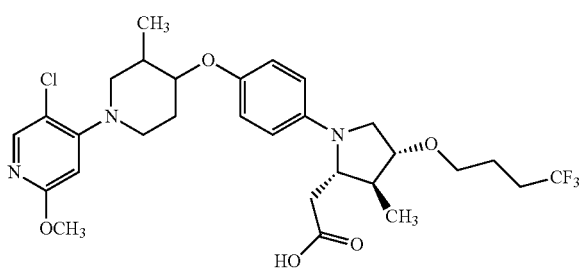 [SMILES: COc1cc(N2CCC(Oc3ccc(N4C[C@H](OCCCC(F)(F)F)[C@@H](C)[C@@H]4CC(=O)O)cc3)C(C)C2)c(Cl)cn1]

Example 161 (brown solid, 15.6 mg) was prepared as a single isomer from 4-bromo-1,1,1-trifluorobutane following the procedure of Example 119. LC-MS Anal. Calc'd for $C_{29}H_{37}ClF_3N_3O_5$: 600.1, found [M+] 599.8. $^1$H NMR (400 MHz, DMSO-d$_6$) δ 8.02 (s, 1H), 6.88 (d, J=9.0 Hz, 2H), 6.48 (d, J=9.0 Hz, 2H), 6.40 (s, 1H), 3.90-3.82 (m, 1H), 3.81 (s, 3H), 3.76 (d, J=4.5 Hz, 1H), 3.61 (d, J=10.0 Hz, 1H), 3.54-3.42 (m, 4H), 2.87 (t, J=10.0 Hz, 1H), 2.71-2.58 (m, 1H), 2.43 (br. s, 1H), 2.36-2.22 (m, 5H), 2.08 (d, J=9.5 Hz, 2H), 1.93 (br. s, 2H), 1.77-1.69 (m, 2H), 1.64-1.53 (m, 1H), 1.05 (d, J=6.5 Hz, 3H), 0.94 (d, J=7.5 Hz, 3H). Analytical HPLC (25 min gradient): RT=23.1 min, HI: 99.0%. hGPR40 EC$_{50}$=190 nM.

EXAMPLE 162

2-((2S,3S,4R)-1-(4-(((3,4-trans)-1-(5-Chloro-2-methoxypyridin-4-yl)-3-methylpiperidin-4-yl)oxy)phenyl)-3-methyl-4-(pentyloxy)pyrrolidin-2-yl)acetic acid, TFA

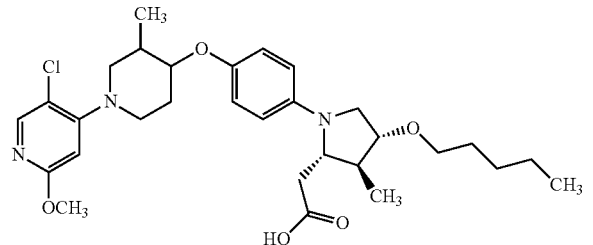 [SMILES: CCCCCO[C@H]1CN(c2ccc(OC3CCN(c4cc(OC)ncc4Cl)CC3C)cc2)[C@@H](CC(=O)O)[C@@H]1C]

Example 162 (brown solid, 10.9 mg) was prepared as a single isomer from 1-bromopentane following the procedure of Example 119. LC-MS Anal. Calc'd for $C_{30}H_{42}ClN_3O_5$: 560.13, found [M+] 560.0. $^1$H NMR (400 MHz, DMSO-d$_6$) δ 7.94 (s, 1H), 6.85 (d, J=9.0 Hz, 2H), 6.46 (d, J=9.0 Hz, 2H), 6.35 (s, 1H), 3.86-3.79 (m, 1H), 3.76 (s, 3H), 3.69 (d, J=4.0 Hz, 1H), 3.55 (d, J=7.5 Hz, 1H), 3.45-3.32 (m, 5H), 3.31-3.20 (m, 1H), 2.83 (t, J=10.5 Hz, 1H), 2.69-2.54 (m, 3H), 2.22 (d, J=7.0 Hz, 1H), 2.05 (d, J=9.5 Hz, 1H), 1.90 (br. s, 1H), 1.60-1.39 (m, 3H), 1.30-1.20 (m, 4H), 1.00 (d, J=6.5 Hz, 3H), 0.88 (d, J=7.0 Hz, 3H), 0.85-0.76 (m, 3H). Analytical HPLC (XBridge Phenyl): RT=20.6 min, HI: 98.5%. hGPR40 EC$_{50}$=63 nM.

EXAMPLE 163

2-((2S,3S,4R)-1-(4-(((3,4-trans)-1-(5-Chloro-2-methoxypyridin-4-yl)-3-methylpiperidin-4-yl)oxy)phenyl)-3-methyl-4-propoxypyrrolidin-2-yl)acetic acid, TFA

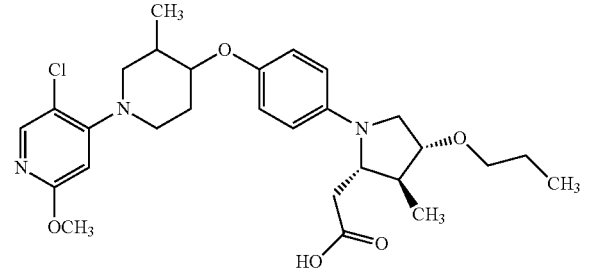 [SMILES: CCCO[C@H]1CN(c2ccc(OC3CCN(c4cc(OC)ncc4Cl)CC3C)cc2)[C@@H](CC(=O)O)[C@@H]1C]

Example 163 (brown solid, 25.2 mg) was prepared as a single isomer from 1-bromopropane following the procedure of Example 119. LC-MS Anal. Calc'd for $C_{28}H_{38}ClN_3O_5$: 532.07, found [M+] 532.2. $^1$H NMR (400 MHz, DMSO-d$_6$) δ 8.02 (s, 1H), 6.88 (d, J=9.0 Hz, 2H), 6.50 (d, J=9.0 Hz, 2H), 6.40 (s, 1H), 3.86 (td, J=8.8, 4.0 Hz, 1H), 3.81 (s, 3H), 3.73 (d, J=4.5 Hz, 1H), 3.48-3.31 (m, 8H), 2.92-2.82 (m, 1H), 2.71-2.61 (m, 1H), 2.60-2.52 (m, 1H), 2.28 (q, J=7.0 Hz, 1H), 2.13-2.03 (m, 1H), 2.01-1.89 (m, 1H), 1.64-1.56 (m, 1H), 1.51 (dq, J=13.9, 7.1 Hz, 2H), 1.05 (d, J=6.5 Hz, 3H), 0.94 (d, J=7.5 Hz, 3H), 0.88 (t, J=7.3 Hz, 3H). Analytical HPLC (25 min gradient, 5 minute hold): RT=27.3 min, HI: 99.0%. hGPR40 EC$_{50}$=120 nM.

EXAMPLE 164

2-((2S,3S,4R)-1-(6-(((3,4-trans)-1-(5-Chloro-2-methoxypyridin-4-yl)-3-methylpiperidin-4-yl)oxy)-5-fluoropyridin-3-yl)-4-fluoro-3-methylpyrrolidin-2-yl)acetic acid

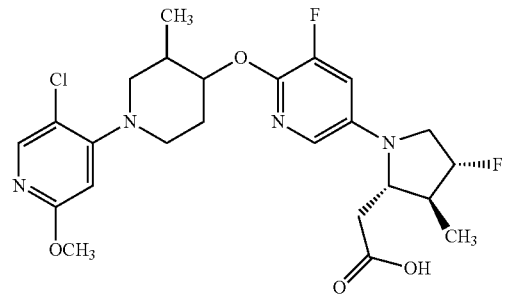

Example 164 (white solid, 13 mg) was prepared as a single isomer from 145E following the procedure of Example 159. LC-MS Anal. Calc'd for $C_{24}H_{29}ClF_2N_4O_4$: 510.96, found [M+H] 511.2. $^1$H NMR (400 MHz, CDCl$_3$) δ 8.00 (s, 1H), 7.29 (d, J=2.6 Hz, 1H), 6.78 (dd, J=12.1, 2.6 Hz, 1H), 6.28 (s, 1H), 4.99 (dd, J=52.6, 3.3 Hz, 1H), 4.78 (td, J=9.1, 4.3 Hz, 1H), 3.91 (s, 3H), 3.82 (dd, J=10.5, 3.0 Hz, 1H), 3.73-3.64 (m, 1H), 3.63-3.55 (m, 2H), 3.49 (dd, J=11.8, 4.1 Hz, 1H), 3.02-2.92 (m, 1H), 2.87 (dd, J=16.7, 3.1 Hz, 1H), 2.78-2.54 (m, 3H), 2.34-2.16 (m, 2H), 1.93-1.80 (m, 1H), 1.08 (d, J=6.6 Hz, 3H), 1.05 (d, J=7.3 Hz, 3H). Analytical HPLC (ZORBAX®, 0% B start): RT=8.1 min, HI: 98.9%. hGPR40 EC$_{50}$=110 nM.

EXAMPLE 165

2-((2S,3S,4R)-1-(6-(((3,4-trans)-1-(5-Chloro-2-methoxypyridin-4-yl)-3-methylpiperidin-4-yl)oxy)-5-(trifluoromethyl)pyridin-3-yl)-4-methoxy-3-methylpyrrolidin-2-yl)acetic acid

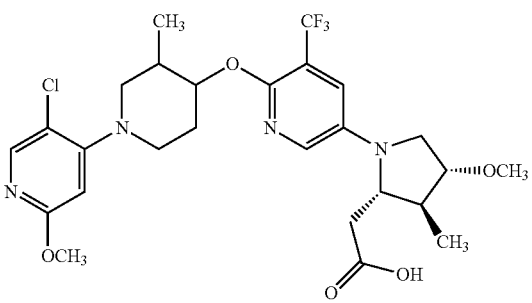 [SMILES: COc1cc(N2CCC(Oc3ncc(N4C[C@H](OC)[C@@H](C)[C@@H]4CC(=O)O)cc3C(F)(F)F)C(C)C2)c(Cl)cn1]

Example 165 (white oil, 5 mg) was prepared as a single isomer from 2-chloro-5-iodo-3-(trifluoromethyl)pyridine following the procedure of Example 159. LC-MS Anal. Calc'd for $C_{26}H_{32}ClF_3N_4O_5$: 573.00, found [M+] 573.3. $^1$H NMR (400 MHz, $CD_2Cl_2$) δ 7.95 (s, 1H), 7.68 (d, J=2.4 Hz, 1H), 7.20 (d, J=2.9 Hz, 1H), 6.29 (s, 1H), 4.84 (td, J=8.8, 4.0 Hz, 1H), 3.86 (s, 3H), 3.76 (t, J=6.6 Hz, 1H), 3.68 (d, J=4.2 Hz, 1H), 3.56-3.40 (m, 4H), 3.36 (s, 3H), 3.00-2.83 (m, 1H), 2.75 (d, J=6.4 Hz, 2H), 2.66 (dd, J=12.0, 9.4 Hz, 1H), 2.45 (q, J=7.1 Hz, 1H), 2.36-2.24 (m, 1H), 2.20-2.13 (m, 1H), 1.86-1.71 (m, 1H), 1.04 (d, J=6.8 Hz, 3H), 1.02 (d, J=7.3 Hz, 3H). Analytical HPLC: RT=12.2 min, HI: 98.3%. hGPR40 $EC_{50}$=47 nM.

EXAMPLE 166

2-((2S,3S,4R)-1-(5-(((3,4-trans)-1-(5-Chloro-2-methoxypyridin-4-yl)-3-methylpiperidin-4-yl)oxy)pyridin-2-yl)-4-methoxy-3-methylpyrrolidin-2-yl) acetic acid

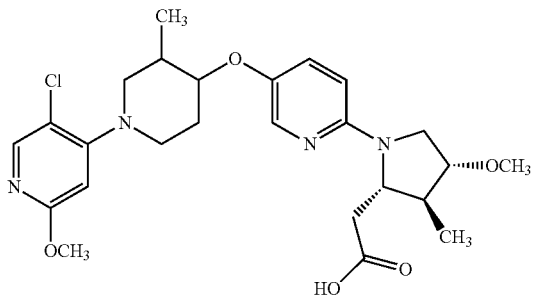 [SMILES: COc1cc(N2CCC(Oc3ccc(N4C[C@H](OC)[C@@H](C)[C@@H]4CC(=O)O)nc3)C(C)C2)c(Cl)cn1]

166A. (2R,3S,4R)-Benzyl 4-methoxy-3-methyl-2-(((methylsulfonyl)oxy)methyl)pyrrolidine-1-carboxylate: To a stirring solution of 118E (780 mg, 2.79 mmol) in $CH_2Cl_2$ (10 mL) cooled to 0° C. was added $NEt_3$ (0.78 mL, 5.6 mmol), followed by MsCl (0.33 mL, 4.2 mmol). After the addition, the cloudy solution was stirred at 0° C. for 1 h. The reaction mixture was diluted with EtOAc, washed with water (2×), sat. aq. $NaHCO_3$, and brine (2×), dried ($Na_2SO_4$), and concentrated. The light brownish oily residue was dried under high vacuum to afford 166A (1010 mg, 2.81 mmol, 100% yield), which was used in the following reaction immediately. LC-MS Anal. Calc'd for $C_{16}H_{23}NO_6S$: 357.42, found [M+Na] 380.1.

166B. (2S,3S,4R)-Benzyl 2-(cyanomethyl)-4-methoxy-3-methylpyrrolidine-1-carboxylate: To a solution of 166A (997 mg, 2.79 mmol) in DMSO (10 mL) was added NaCN (547 mg, 11.2 mmol). The reaction mixture was stirred at 50° C. for 16 h. The reaction mixture was cooled to rt and quenched with water. The product was extracted with EtOAc (3×). The combined organic layers were washed with water/brine and brine, dried ($Na_2SO_4$), and concentrated. The oily crude product was purified by silica chromatography to afford 166B (641 mg, 2.20 mmol, 79% yield) as a colorless oil. LC-MS Anal. Calc'd for $C_{16}H_{20}N_2O_3$: 288.34, found [M+H] 289.2. $^1$H NMR (400 MHz, $CDCl_3$) δ 7.44-7.29 (m, 5H), 5.24-5.04 (m, 2H), 3.81-3.62 (m, 1H), 3.57-3.42 (m, 2H), 3.33 (s, 3H), 3.00-2.70 (m, 2H), 2.46 (t, J=7.0 Hz, 1H), 1.16-0.96 (m, 3H).

166C. 2-((2S,3S,4R)-4-Methoxy-3-methylpyrrolidin-2-yl)acetonitrile: To a stirring solution of 166B (560 mg, 1.94 mmol) in EtOAc (20 mL) was added 5% Pd/C (207 mg, 0.097 mmol) and the suspension was stirred at rt under $H_2$ (1 atm) for 16 h. The reaction mixture was filtered and the filtrate was concentrated to afford 166C (264 mg, 1.71 mmol, 88% yield). LC-MS Anal. Calc'd for $C_8H_{14}N_2O$: 154.21, found [M+H] 155.1. $^1$H NMR (400 MHz, $CDCl_3$) δ 3.47 (dt, J=5.1, 3.4 Hz, 1H), 3.31 (s, 3H), 3.11-3.00 (m, 2H), 2.96 (q, J=6.2 Hz, 1H), 2.55 (dd, J=6.4, 5.5 Hz, 2H), 1.89 (ddddd, J=6.8, 3.6 Hz, 1H), 1.11 (d, J=7.3 Hz, 3H).

166D. 44(3,4-trans)-4-((6-Bromopyridin-3-yl)oxy)-3-methylpiperidin-1-yl)-5-chloro-2-methoxypyridine: To a stirring solution of 119A, Isomer 1, 6-bromopyridin-3-ol (101 mg, 0.582 mmol) and $Ph_3P$ (166 mg, 0.633 mmol) in THF (3 mL) at rt was slowly added DIAD (0.12 mL, 0.63 mmol) dropwise. The reaction mixture was stirred at rt for 4 h. Additional DIAD (0.035 mL) was added. The reaction mixture was stirred for 15 h. The reaction mixture was concentrated. The residue was purified by silica chromatography to give 166D (113 mg, 0.271 mmol, 54% yield) as a colorless oil. LC-MS Anal. Calc'd for $C_{17}H_{19}BrClN_3O_2$: 412.71, found [M+H] 412.1, 414.1. $^1$H NMR (400 MHz, $CDCl_3$) δ 8.08 (d, J=3.1 Hz, 1H), 7.98 (s, 1H), 7.38 (d, J=8.6 Hz, 1H), 7.12 (dd, J=8.6, 3.1 Hz, 1H), 6.27 (s, 1H), 3.99 (td, J=8.6, 4.1 Hz, 1H), 3.89 (s, 3H), 3.59-3.44 (m, 2H), 2.95-2.80 (m, 1H), 2.66 (dd, J=12.3, 9.2 Hz, 1H), 2.26-2.12 (m, 2H), 1.85 (dtd, J=13.1, 9.7, 3.9 Hz, 1H), 1.12 (d, J=6.8 Hz, 3H).

166E. 2-((2S,3S,4R)-1-(5-(((3,4-trans)-1-(5-Chloro-2-methoxypyridin-4-yl)-3-methylpiperidin-4-yl)oxy)pyridin-2-yl)-4-methoxy-3-methylpyrrolidin-2-yl)acetonitrile: To a microwave vial containing 166D (53 mg, 0.128 mmol) was added a solution of 166C (23.8 mg, 0.154 mmol) in dioxane (0.7 mL). $Pd(OAc)_2$ (2.9 mg, 0.013 mmol) was added, followed by DtBPF (122 mg, 0.257 mmol) and NaOtBu (30.9 mg, 0.321 mmol). The vial was flushed with argon for 1 min and then sealed and heated to 100° C. for 1 h under microwave irradiation. The reaction mixture was diluted with water and extracted with $CH_2Cl_2$ (3×). The combined organics were washed with water and brine, dried ($MgSO_4$), and concentrated. The crude product was purified by silica chromatography to provide 166E (49 mg, 0.097 mmol, 75% yield) as a brown oil. LC-MS Anal. Calc'd for $C_{25}H_{32}ClN_5O_3$: 486.01, found [M+] 486.3. $^1$H NMR (400 MHz, $CDCl_3$) δ 7.97 (s, 1H), 7.92 (d, J=2.9 Hz, 1H), 7.18 (dd, J=9.0, 2.9 Hz, 1H), 6.33 (d, J=9.0 Hz, 1H), 6.26 (s, 1H), 4.07-3.96 (m, 1H), 3.88 (s, 3H), 3.74 (td, J=8.7, 4.2 Hz, 1H), 3.66 (dt, J=4.6, 2.1 Hz, 1H), 3.59-3.46 (m, 4H), 3.39 (s, 3H), 3.08 (dd, J=16.3, 3.7 Hz, 1H), 2.87-2.76 (m, 2H), 2.65-2.53 (m, 2H), 2.20-2.09 (m, 2H), 1.88-1.76 (m, 1H), 1.15 (d, J=6.6 Hz, 3H), 1.08 (d, J=7.3 Hz, 3H).

Example 166 (off-white solid, 30.3 mg) was prepared as a single isomer from 166E following the procedure of Example 2. LC-MS Anal. Calc'd for $C_{25}H_{33}ClN_4O_5$: 505.01, found [M+] 505.3. $^1$H NMR (400 MHz, $CDCl_3$) δ 7.97 (s, 1H), 7.79 (d, J=2.9 Hz, 1H), 7.32 (dd, J=9.2, 2.9 Hz, 1H), 6.46 (d, J=9.0 Hz, 1H), 6.26 (s, 1H), 3.89 (s, 3H), 3.88-3.84 (m, 1H), 3.76 (td, J=8.9, 4.2 Hz, 1H), 3.66 (dt, J=5.2, 2.5 Hz, 1H), 3.60-3.55 (m, 1H), 3.55-3.50 (m, 1H), 3.50-3.45 (m, 1H), 3.38 (s, 3H), 2.91 (dd, J=16.1, 4.4 Hz, 1H), 2.86-2.76 (m, 2H), 2.61 (dd, J=12.3, 9.5 Hz, 1H), 2.48-2.38 (m, 1H), 2.18-2.09 (m, 3H), 1.88-1.75 (m, 1H), 1.13 (d, J=6.6 Hz, 3H), 1.05 (d, J=7.0 Hz, 3H). Analytical HPLC: RT=5.7 min, HI: 99.0%. hGPR40 $EC_{50}$=420 nM.

EXAMPLE 167

2-((2S,3S,4R)-1-(6-(((3,4-trans)-1-(5-Chloro-2-methoxypyridin-4-yl)-3-methylpiperidin-4-yl)oxy)-5-isopropoxypyridin-3-yl)-4-methoxy-3-methylpyrrolidin-2-yl)acetic acid

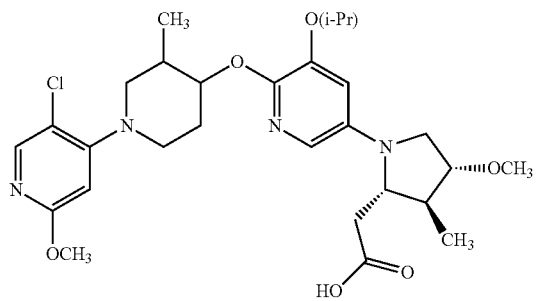

Example 167 (off-white solid, 4.0 mg) was isolated as a single isomer as a byproduct during the synthesis of Example 159 when i-PrOH was used as the solvent for the CuI-catalyzed coupling. LC-MS Anal. Calc'd for $C_{28}H_{39}ClN_4O_6$: 563.09, found [M⁺] 563.4. ¹H NMR (400 MHz, CDCl₃) δ 7.97 (s, 1H), 7.18 (d, J=2.4 Hz, 1H), 6.62 (d, J=2.6 Hz, 1H), 6.28 (s, 1H), 4.73 (td, J=9.0, 4.1 Hz, 1H), 4.52 (dt, J=12.3, 6.1 Hz, 1H), 3.89 (s, 3H), 3.77-3.61 (m, 2H), 3.59-3.50 (m, 2H), 3.48-3.40 (m, 2H), 3.37 (s, 3H), 3.00-2.90 (m, 1H), 2.85-2.72 (m, 2H), 2.66 (dd, J=12.2, 9.6 Hz, 1H), 2.43 (q, J=7.3 Hz, 1H), 2.36-2.28 (m, 1H), 2.26-2.18 (m, 1H), 1.92-1.78 (m, 1H), 1.38-1.30 (m, 6H), 1.10-1.03 (m, 6H). Analytical HPLC: RT=5.6 min, HI: 95.7%. hGPR40 EC₅₀=45 nM.

EXAMPLE 168

2-((2R,3S,4R)-1-(6-(((3,4-trans)-1-(5-Chloro-2-methoxypyridin-4-yl)-3-methylpiperidin-4-yl)oxy)-5-fluoropyridin-3-yl)-4-methoxy-3-methylpyrrolidin-2-yl)acetic acid

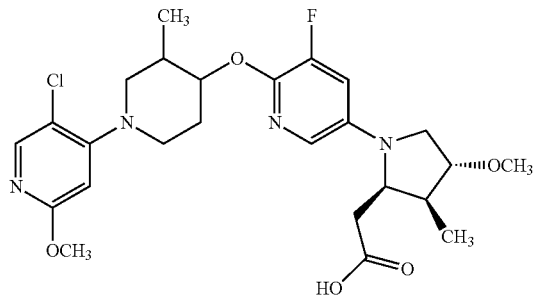 [SMILES: COc1cc(N2CCC(Oc3ncc(N4C[C@H](OC)[C@@H](C)[C@H]4CC(=O)O)cc3F)C(C)C2)c(Cl)cn1]

Example 168 (off-white solid, 1.7 mg) was isolated as a single isomer as a byproduct during the preparation of Example 159. LC-MS Anal. Calc'd for $C_{25}H_{32}ClFN_4O_5$: 522.21, found [M+H] 523.3. ¹H NMR (400 MHz, CDCl₃) δ 7.96 (br. s, 1H), 7.34 (d, J=18.9 Hz, 1H), 6.83 (d, J=12.1 Hz, 1H), 6.27 (br. s, 1H), 4.77 (d, J=3.7 Hz, 1H), 4.21 (t, J=7.3 Hz, 1H), 3.89 (s, 3H), 3.76-3.65 (m, 2H), 3.56 (d, J=11.9 Hz, 2H), 3.42 (s, 3H), 3.13-3.03 (m, 1H), 2.93 (t, J=10.7 Hz, 1H), 2.70-2.59 (m, 2H), 2.55-2.38 (m, 2H), 2.27 (d, J=13.0 Hz, 2H), 1.84 (d, J=10.6 Hz, 1H), 1.13 (d, J=7.0 Hz, 3H), 1.08 (d, J=6.6 Hz, 3H). Analytical HPLC(ZORBAX®, 50% B start): RT=6.7 min, HI: 94.0%. hGPR40 EC₅₀=500 nM.

EXAMPLE 169

Isomer 1 and Isomer 2

2-((2S,3S,4R)-1-(4-(((3,4-trans)-1-(2,4-Difluoro-5-methoxyphenyl)-3-methylpiperidin-4-yl)oxy)phenyl)-4-methoxy-3-methylpyrrolidin-2-yl)acetic acid

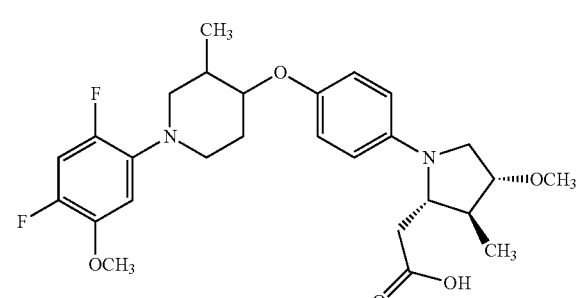

169A. 2,4-Difluoro-5-methoxyaniline: A solution of 1,5-difluoro-2-methoxy-4-nitrobenzene (2.00 g, 10.6 mmol) in EtOH (20 mL) was purged with argon for 2 min and then 10% Pd/C (200 mg, 1.88 mmol) was added. The reaction mixture was stirred at rt under H₂ (1 atm) for 3 days. The reaction mixture was filtered through a pad of CELITE® and the filtrate was concentrated to give 169A (1.60 g, 10.1 mmol, 95% yield) as a dark brown solid. LC-MS Anal. Calc'd for $C_7H_7F_2NO$: 159.13, found [M+H] 160.1.

169B. 1-Bromo-2,4-difluoro-5-methoxybenzene: To a stirred suspension of 169A (1.60 g, 10.1 mmol) in water (14 mL) was added hydrobromic acid (3.4 mL, 30 mmol). The resulting mixture was cooled to 0° C. and a solution of NaNO₂ (0.763 g, 11.1 mmol) in water (7 mL) was added dropwise over 1 h with stirring, maintaining the temperature between 0 and 5° C. The solution of the diazonium salt was then added to a suspension of copper(I) bromide (1.587 g, 11.06 mmol) in water (7 mL), which had been preheated to 75° C. The mixture was stirred thoroughly and then 48% hydrobromic acid (17 mL, 310 mmol) was added. The resulting mixture was stirred overnight at rt and then diluted with water. The product was extracted with Et₂O and the combined organic extracts were washed with brine, dried (MgSO₄), and concentrated. The resulting residue was purified by silica chromatography to afford 169B (0.180 g, 0.807 mmol, 8% yield) as a white solid. ¹H NMR (400 MHz, CDCl₃) δ 7.11 (dd, J=8.6, 6.4 Hz, 1H), 6.94 (dd, J=10.8, 8.1 Hz, 1H), 3.87 (s, 3H).

169C. (3,4-cis)-4-((tert-Butyldimethylsilyl)oxy)-1-(2,4-difluoro-5-methoxyphenyl)-3-methylpiperidine: A solution of 27E (150 mg, 0.654 mmol), 169B (160 mg, 0.719 mmol), and SPHOS precatalyst (8.8 mg, 0.013 mmol) in THF (1 mL) was purged with argon and 1 M LHMDS in THF (0.79 mL, 0.79 mmol) was added. The reaction mixture was heated to 70° C. for 2 h. Sat. aq NaHCO₃ (10 mL) was added slowly to the reaction mixture. The mixture was extracted with EtOAc (2×10 mL) and the combined organic extracts were washed with water (20 mL) and brine (20 mL), dried (Na₂SO₄), filtered, and concentrated. The crude product was purified by silica chromatography to give 169C (100 mg, 0.269 mmol, 41% yield) as an oil. LC-MS Anal. Calc'd for $C_{19}H_{31}F_2NO_2Si$: 371.54, found [M+H] 372.3.

169D. (3,4-cis)-1-(2,4-Difluoro-5-methoxyphenyl)-3-methylpiperidin-4-ol: To a solution of 169C (75 mg, 0.20 mmol) in THF (1 mL) was added a 1 M solution of TBAF (0.30 mL, 0.30 mmol) in THF and the reaction mixture was stirred at rt for 16 h. The reaction mixture was diluted with EtOAc, washed with water and brine, dried (MgSO$_4$), and concentrated. The crude product was purified by silica chromatography to give 169D (35 mg, 0.14 mmol, 67% yield) as a white foam. LC-MS Anal. Calc'd for $C_{13}H_{17}F_2NO_2$: 257.28, found [M+H] 258.2. $^1$H NMR (400 MHz, CDCl$_3$) δ 6.82 (t, J=11.3 Hz, 1H), 6.62 (t, J=8.5 Hz, 1H), 3.91 (d, J=1.3 Hz, 1H), 3.85 (s, 3H), 3.06-2.99 (m, 2H), 2.92 (dd, J=11.4, 4.0 Hz, 1H), 2.85-2.77 (m, 1H), 2.11-1.83 (m, 4H), 1.03 (d, J=6.8 Hz, 3H).

169E. Methyl 2-((2S,3S,4R)-1-(4-hydroxyphenyl)-4-methoxy-3-methylpyrrolidin-2-yl)acetate: 169D was prepared from 188F following the procedure of Example 1. LC-MS Anal. Calc'd for $C_{15}H_{21}NO4$: 279.33, found [M+H] 280.3.

Example 169, Isomer 1 and Isomer 2 were prepared as single isomers from 169D and 169F following the procedure of Example 43 followed by SFC chiral separation. Example 169, Isomer 1 (off-white solid, 8.0 mg). LC-MS Anal. Calc'd for $C_{27}H_{34}F_2N_2O_5$: 504.57, found [M+H] 505.4. $^1$H NMR (400 MHz, methanol-d$_4$) δ 6.96-6.86 (m, 3H), 6.76 (t, J=8.5 Hz, 1H), 6.60-6.51 (m, 2H), 3.85 (s, 3H), 3.79 (td, J=9.2, 4.3 Hz, 1H), 3.74-3.66 (m, 2H), 3.50-3.45 (m, 1H), 3.44-3.40 (m, 1H), 3.38 (s, 3H), 3.34 (d, J=2.9 Hz, 2H), 2.80 (td, J=11.4, 2.6 Hz, 1H), 2.76-2.69 (m, 1H), 2.64-2.53 (m, 2H), 2.39 (q, J=7.3 Hz, 1H), 2.20-2.11 (m, 1H), 2.10-1.98 (m, 1H), 1.79-1.67 (m, 1H), 1.13 (d, J=6.6 Hz, 3H), 1.02 (d, J=7.3 Hz, 3H). Analytical HPLC: RT=10.7 min, HI: 98.0%. hGPR40 EC$_{50}$=3500 nM. Example 169, Isomer 2 (off-white solid, 6.0 mg). LC-MS Anal. Calc'd for $C_{27}H_{34}F_2N_2O_5$: 504.57, found [M+H] 505.4. $^1$H NMR (400 MHz, methanol-d$_4$) δ 6.97-6.85 (m, 3H), 6.76 (t, J=8.6 Hz, 1H), 6.60-6.51 (m, 2H), 3.85 (s, 3H), 3.78 (td, J=9.2, 4.2 Hz, 1H), 3.75-3.70 (m, 1H), 3.70-3.66 (m, 1H), 3.50-3.39 (m, 2H), 3.37 (s, 3H), 3.35-3.32 (m, 2H), 2.80 (td, J=11.4, 2.6 Hz, 1H), 2.76-2.68 (m, 1H), 2.64-2.52 (m, 2H), 2.39 (q, J=7.3 Hz, 1H), 2.21-2.11 (m, 1H), 2.11-1.97 (m, 1H), 1.80-1.65 (m, 1H), 1.12 (d, J=6.8 Hz, 3H), 1.02 (d, J=7.3 Hz, 3H). Analytical HPLC: RT=10.4 min, HI: 97.0%. hGPR40 EC$_{50}$=450 nM.

EXAMPLE 170

2-((2S,3S,4R)-1-(5-(((3,4-trans)-1-(5-Chloro-2-methoxypyridin-4-yl)-3-methylpiperidin-4-yl)oxy)pyrimidin-2-yl)-4-methoxy-3-methylpyrrolidin-2-yl)acetic acid

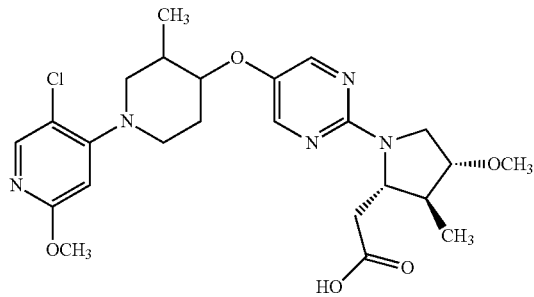 [SMILES: COc1cc(N2CCC(Oc3cnc(N4C[C@H](OC)[C@@H](C)[C@@H]4CC(=O)O)nc3)C(C)C2)c(Cl)cn1]

170A. (3,4-cis)-1-(5-Chloro-2-methoxypyridin-4-yl)-3-methylpiperidin-4-yl methanesulfonate: To a stirring solution of 119A, Isomer 1 (257 mg, 1.00 mmol) in CH$_2$Cl$_2$ (4 mL) cooled to 0° C. was added TEA (0.28 mL, 2.0 mmol) followed by the dropwise addition of MsCl (0.12 mL, 1.5 mmol) over 5 min. The resulting cloudy solution was stirred at 0° C. for 5 min and then at rt for 1 h. The reaction mixture was diluted with EtOAc, washed with water (2×), sat. aq. NaHCO$_3$, and brine (2×), dried (MgSO$_4$), and concentrated to afford 170A (339 mg, 0.982 mmol, 98% yield) as a white foam, which was used in the following reaction immediately. LC-MS Anal. Calc'd for $C_{13}H_{19}ClN_2O_4S$: 334.82, found [M+H] 335.2.

170B. 2-Chloro-5-(((3,4-trans)-1-(5-chloro-2-methoxy-pyridin-4-yl)-3-methylpiperidin-4-yl)oxy)pyrimidine: To a solution of 170A (335 mg, 1.00 mmol) in anhydrous DMF (3 mL) was added 2-chloropyrimidin-5-ol (100 mg, 0.766 mmol) followed by K$_2$CO$_3$ (159 mg, 1.15 mmol). The reaction mixture was stirred at rt for 10 min and then heated to 100° C. overnight. The reaction mixture was cooled to rt and diluted with water and EtOAc. The layers were separated and the aqueous layer was extracted with EtOAc (2×). The combined organic layers were washed with sat. aq. NaHCO$_3$, water (2×), and brine, dried (MgSO$_4$), and concentrated. The crude product was purified by silica chromatography to give 170B (75 mg, 0.19 mmol, 24% yield) as a white solid. LC-MS Anal. Calc'd for $C_{16}H_{18}Cl_2N_4O_2$: 369.25, found [M$^+$] 369.2. $^1$H NMR (400 MHz, CDCl$_3$) δ 8.31 (s, 2H), 8.01 (s, 1H), 6.27 (s, 1H), 4.06 (td, J=8.6, 4.2 Hz, 1H), 3.92 (s, 3H), 3.62-3.51 (m, 2H), 3.00-2.85 (m, 1H), 2.70 (dd, J=12.4, 9.1 Hz, 1H), 2.31-2.15 (m, 2H), 1.89 (dtd, J=13.2, 9.6, 3.9 Hz, 1H), 1.14 (d, J=6.6 Hz, 3H).

170C. 2-((2S,3S,4R)-1-(5-(((3,4-trans)-1-(5-Chloro-2-methoxypyridin-4-yl)-3-methylpiperidin-4-yl)oxy)pyrimidin-2-yl)-4-methoxy-3-methylpyrrolidin-2-yl)acetonitrile: To a microwave vial containing 170B (40 mg, 0.108 mmol) was added a solution of 166C (18.4 mg, 0.119 mmol) in dioxane (0.6 mL). DtBPF (103 mg, 0.217 mmol) and Pd(OAc)$_2$ (2.4 mg, 11 µmol) were added, followed by NaOtBu (26.0 mg, 0.271 mmol). Argon was bubbled through the reaction mixture for 1 min and then the tube was sealed and heated to 100° C. for 1 h under microwave irradiation. The reaction mixture was diluted with water and extracted with CH$_2$Cl$_2$ (3×). The combined organic layers were washed with brine, dried (MgSO$_4$), and concentrated. The crude product was purified by silica chromatography to give 170C (25 mg, 0.045 mmol, 42% yield) as a brown oil. LC-MS Anal. Calc'd for $C_{24}H_{31}ClN_6O_3$: 486.99, found [M+H] 487.2.

Example 170 (white solid, 9.9 mg) was prepared as a single isomer from 170C following the procedure of Example 1. LC-MS Anal. Calc'd for $C_{24}H_{32}ClN_5O_5$: 505.99, found [M+H] 506.1. $^1$H NMR (400 MHz, CDCl$_3$) δ 8.17 (s, 2H), 7.98 (s, 1H), 6.26 (s, 1H), 4.03-3.96 (m, 1H), 3.89 (s, 3H), 3.87-3.80 (m, 1H), 3.78-3.68 (m, 2H), 3.66-3.61 (m, 1H), 3.58-3.48 (m, 2H), 3.37 (s, 3H), 3.02 (dd, J=16.3, 4.0 Hz, 1H), 2.89-2.76 (m, 2H), 2.61 (dd, J=12.3, 9.5 Hz, 1H), 2.49 (q, J=7.3 Hz, 1H), 2.20-2.10 (m, 2H), 1.89-

1.75 (m, 1H), 1.15 (d, J=6.6 Hz, 3H), 1.07 (d, J=7.3 Hz, 3H). Analytical HPLC: RT=4.2 min, HI: 94.0%. hGPR40 $EC_{50}$=1700 nM.

EXAMPLE 171

2-((2S,3S,4R)-1-(5-(((3,4-trans)-1-(5-Chloro-2-methoxypyridin-4-yl)-3-methylpiperidin-4-yl)oxy)-3-fluoropyridin-2-yl)-4-methoxy-3-methylpyrrolidin-2-yl)acetic acid

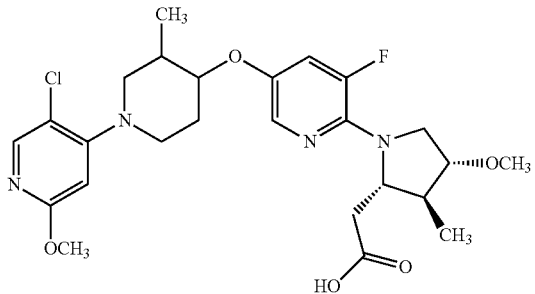 [SMILES: COc1cc(N2CCC(Oc3cnc(N4C[C@H](OC)[C@@H](C)[C@@H]4CC(=O)O)c(F)c3)C(C)C2)c(Cl)cn1]

171A. 2-((2S,3S,4R)-1-(5-(((3,4-trans)-1-(5-Chloro-2-methoxypyridin-4-yl)-3-methylpiperidin-4-yl)oxy)-3-fluoropyridin-2-yl)-4-methoxy-3-methylpyrrolidin-2-yl)acetonitrile: 171A was prepared from 6-chloro-5-fluoropyridin-3-ol following the procedure of Example 166. LC-MS Anal. Calc'd for $C_{25}H_{31}ClFN_5O_3$: 504.00, found [M+] 504.2.

Example 171 (white solid, 21.3 mg) was prepared as a single isomer from 171A following the procedure of Example 1. LC-MS Anal. Calc'd for $C_{25}H_{32}ClFN_4O_5$: 523.00, found [M+] 523.1. $^1$H NMR (400 MHz, CDCl$_3$) δ 7.98 (s, 1H), 7.65 (d, J=2.2 Hz, 1H), 7.09 (d, J=13.4 Hz, 1H), 6.26 (s, 1H), 4.03-3.96 (m, 1H), 3.89 (s, 3H), 3.87-3.78 (m, 3H), 3.60 (q, J=4.3 Hz, 1H), 3.56-3.47 (m, 2H), 3.38 (s, 3H), 2.92-2.74 (m, 3H), 2.62 (dd, J=12.2, 9.4 Hz, 1H), 2.35 (dt, J=7.2, 3.7 Hz, 1H), 2.20-2.11 (m, 2H), 1.89-1.75 (m, 1H), 1.12 (d, J=4.6 Hz, 3H), 1.10 (d, J=5.1 Hz, 3H). Analytical HPLC: RT=5.5 min, HI: 97.0%. hGPR40 $EC_{50}$=410 nM.

EXAMPLE 172

Isomer 1 and Isomer 2

2-((2R,4R)-1-(4-(((3,4-trans)-1-(5-Chloro-2-methoxypyridin-4-yl)-3-(methoxymethyl)piperidin-4-yl)oxy)phenyl)-4-(trifluoromethyl)pyrrolidin-2-yl)acetic acid, TFA

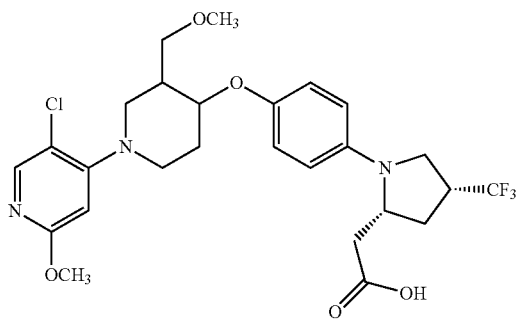 [SMILES: COCC1CN(c2cc(OC)ncc2Cl)CCC1Oc1ccc(N2C[C@H](C(F)(F)F)C[C@@H]2CC(=O)O)cc1]

172A. (3,4-cis)-tert-Butyl 4-hydroxy-3-(methoxymethyl)piperidine-1-carboxylate: To a solution of 93C (230 mg, 0.994 mmol) in THF (3.3 mL) at 0° C. was added 60% NaH (55.7 mg, 1.39 mmol). After 10 min, MeI (75 μL, 1.2 mmol) was added. After stirring for 2 h, the reaction was quenched with water and diluted with EtOAc. The organic layer was washed with water and brine, dried over Na$_2$SO$_4$, and concentrated. The crude product was purified by silica chromatography to give 17C (140 mg, 0.570 mmol, 57% yield) as a colorless oil. LC-MS Anal. Calc'd for $C_{12}H_{23}NO_4$: 245.32, found [M+H] 246.0. $^1$H NMR (400 MHz, CDCl$_3$) δ 4.04 (br. s, 1H), 3.62 (d, J=4.2 Hz, 1H), 3.59-3.50 (m, 2H), 3.51-3.40 (m, 2H), 3.32-3.26 (m, 4H), 2.35 (br. s, 1H), 1.80 (ddt, J=9.8, 7.6, 5.1 Hz, 1H), 1.70-1.47 (m, 2H), 1.38 (s, 9H).

172B. (3,4-cis)-3-(Methoxymethyl)piperidin-4-ol, TFA: To a solution of 172A (140 mg, 0.570 mmol) in CH$_2$Cl$_2$ (2.9 mL) was added TFA (440 μL, 5.7 mmol). After stirring for 3 h, the reaction mixture was concentrated to give 172B (235 mg, 0.630 mmol, 100% yield) as a beige oil. LC-MS Anal. Calc'd for $C_7H_{15}NO_2$: 145.1, found: [M+H] 146.0.

172C. (3,4-cis)-1-(5-Chloro-2-methoxypyridin-4-yl)-3-(methoxymethyl)piperidin-4-ol: To a solution of 172B (235 mg, 0.630 mmol) and K$_2$CO$_3$ (348 mg, 2.52 mmol) in DMSO (2.0 mL) was added 1J (140 mg, 0.630 mmol). The reaction mixture was stirred at 110° C. overnight. The reaction mixture was diluted with EtOAc and the organic layer was washed with water and brine, dried over Na$_2$SO$_4$, and concentrated. The crude product was purified by silica chromatography to provide 172C (120 mg, 0.418 mmol, 67% yield) as a colorless oil. LC-MS Anal. Calc'd for $C_{13}H_{19}ClN_2O_3$: 286.1, found: [M+H] 287.1. $^1$H NMR (400 MHz, CDCl$_3$) δ 8.02-7.90 (m, 1H), 6.30 (s, 1H), 4.19 (dd, J=4.1, 2.8 Hz, 1H), 3.88 (s, 3H), 3.66 (d, J=4.8 Hz, 1H), 3.39 (d, J=4.6 Hz, 1H), 3.37 (s, 3H), 3.21-3.17 (m, 3H), 3.12 (d, J=2.2 Hz, 1H), 2.22-2.00 (m, 2H), 1.94-1.87 (m, 2H).

172D. Methyl 2-((2R,4R)-1-(4-(((3,4-trans)-1-(5-chloro-2-methoxypyridin-4-yl)-3-(methoxymethyl)piperidin-4-yl)oxy)phenyl)-4-(trifluoromethyl)pyrrolidin-2-yl)acetate: To a solution of 172C (90.0 mg, 0.314 mmol), 93A (86.0 mg, 0.282 mmol), and Bu$_3$P (124 μL, 0.502 mmol) in toluene (3.9 mL) was added ADDP (127 mg, 0.502 mmol). The reaction mixture was sonicated for 2 h. The reaction mixture was poured into hexanes (10 mL), filtered, and concentrated. The crude product was purified by silica chromatography to provide 172D (100 mg, 0.175 mmol, 56% yield) as a colorless oil. LC-MS Anal. Calc'd for $C_{27}H_{33}ClF_3N_3O_5$: 571.2, found [M+H] 572.2.

Example 172, Isomer 1 and Isomer 2: To a solution of 172D (100 mg, 0.175 mmol) in THF (3.2 mL) and water (320 μL) was added 1 N aq. LiOH (874 μL, 0.874 mmol). The reaction mixture was stirred at rt for 5 h. The reaction mixture was concentrated to remove the THF and acidified to pH 1 with 1 N aq. HCl. The product was extracted with CH$_2$Cl$_2$ (3×) and the combined organic layers were dried and concentrated. The crude product was purified by RP-Prep. HPLC. The two isomers were separated by chiral SFC.

Example 172, Isomer 1 (5.1 mg, 0.0073 mmol, 4% yield) was obtained as a colorless foam. LC-MS Anal. Calc'd for $C_{26}H_{31}ClF_3N_3O_5$: 557.2, found [M+H] 558.2. $^1$H NMR (500 MHz, acetonitrile-d$_3$) δ 7.98 (s, 1H), 7.00-6.87 (m, 2H), 6.81-6.71 (m, 2H), 6.40 (s, 1H), 4.27 (d, J=4.1 Hz, 1H), 4.21-4.12 (m, 1H), 3.92 (s, 3H), 3.82-3.75 (m, 1H), 3.71-3.62 (m, 1H), 3.60-3.44 (m, 4H), 3.32-3.26 (m, 3H), 3.24-3.17 (m, 1H), 3.15-3.02 (m, 2H), 2.77 (dd, J=16.0, 3.3 Hz, 1H), 2.69-2.57 (m, 1H), 2.29 (dd, J=16.1, 9.5 Hz, 1H), 2.23-2.12 (m, 2H), 2.03-1.97 (m, 1H), 1.82-1.69 (m, 1H).

Analytical HPLC: RT=10.9 min, HI: 97.0%. hGPR40 EC$_{50}$=1800 nM. Example 172, Isomer 2 (6.2 mg, 0.0090 mmol, 5% yield) was obtained as a colorless foam. LC-MS Anal. Calc'd for C$_{26}$H$_{31}$ClF$_3$N$_3$O$_5$: 557.2, found [M+H] 558.2. $^1$H NMR (500 MHz, acetonitrile-d$_3$) δ 7.98 (s, 1H), 7.01-6.89 (m, 2H), 6.81-6.71 (m, 2H), 6.39 (s, 1H), 4.26 (d, J=4.1 Hz, 1H), 4.20-4.06 (m, 1H), 3.91 (s, 3H), 3.80-3.72 (m, 1H), 3.69-3.61 (m, 1H), 3.59-3.48 (m, 4H), 3.27 (s, 3H), 3.25-3.15 (m, 1H), 3.13-2.98 (m, 2H), 2.77 (dd, J=16.0, 3.0 Hz, 1H), 2.66-2.55 (m, 1H), 2.29 (dd, J=16.1, 9.5 Hz, 1H), 2.18 (d, J=8.8 Hz, 2H), 2.03-1.96 (m, 1H), 1.81-1.70 (m, 1H). Analytical HPLC: RT=10.9 min, HI: 98.0%. hGPR40 EC$_{50}$=460 nM.

What is claimed is:

1. A compound of Formula (I):

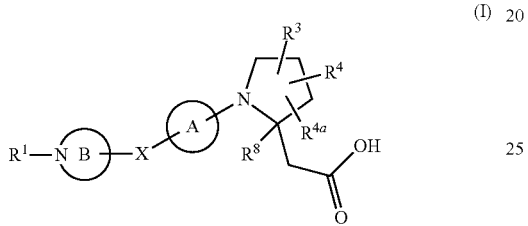

or a stereoisomer, a tautomer, or a pharmaceutically acceptable salt thereof, wherein:

X is independently selected from: a bond, O, S, NH, N(C$_{1-4}$ alkyl), CH$_2$, CH$_2$CH$_2$, CH(C$_{1-4}$ alkyl), OCH$_2$, CH$_2$O, OCH$_2$CH$_2$, and CH$_2$CH$_2$O;

ring A is independently

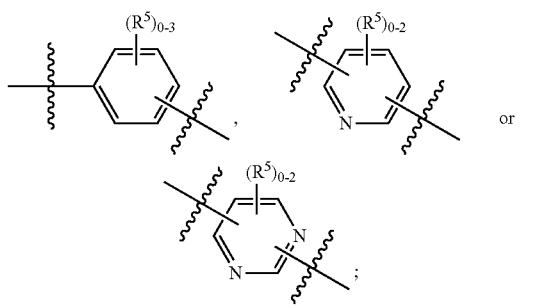

ring B is independently a 4- to 7-membered saturated heterocycle containing carbon atoms, the nitrogen atom shown in the ring B and 0-1 additional heteroatom selected from N, O, and S; and ring B is substituted with 0-4 R$^2$;

R$^1$ is independently CO$_2$R$^9$, SO$_2$R$^9$,

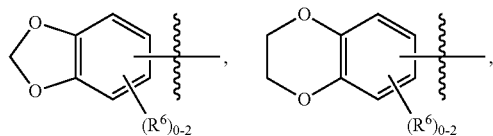

phenyl, benzyl, naphthyl or a 5- to 10-membered heteroaryl containing carbon atoms and 1-4 heteroatoms selected from N, NR$^{11}$, O, and S; wherein said phenyl, benzyl, naphthyl and heteroaryl are each substituted with 0-3 R$^6$;

R$^2$, at each occurrence, is independently selected from: =O, OH, halogen, C$_{1-6}$ alkyl substituted with 0-1 R$^{12}$, C$_{1-6}$ alkoxy substituted with 0-1 R$^{12}$, C$_{1-4}$ haloalkyl substituted with 0-1 R$^{12}$, C$_{1-4}$ haloalkoxy substituted with 0-1 R$^{12}$, —(CH$_2$)$_m$—C$_{3-6}$ carbocycle substituted with 0-1 R$^{12}$, and —(CH$_2$)$_m$-(5- to 10-membered heteroaryl containing carbon atoms and 1-4 heteroatoms selected from N, NR$^{11}$, O, and S); wherein said heteroaryl is substituted with 0-1 R$^{12}$;

when two R$^2$ groups are attached to two different carbon atoms, they may combine to form a 1- to 3-membered carbon atom bridge over ring B;

when two R$^2$ groups are attached to the same carbon, they may combine, together with the carbon atom to which they are attached, to form a 3- to 6-membered carbon atom containing spiro ring;

R$^3$, at each occurrence, is independently selected from: H, halogen, CN, C$_{1-6}$ alkyl, C$_{1-6}$ alkoxy, C$_{1-4}$ haloalkyl, C$_{1-4}$ haloalkoxy, phenyl, benzyl, phenoxy, benzoxy, 1-C$_{1-4}$ alkyl-pyrazolyl, triazolyl, tetrazolyl, pyridinyl, —O-pyridinyl, pyrimidinyl, and —O-pyrimidinyl; wherein each said ring moiety is substituted with 0-2 R$^{10}$;

R$^4$ and R$^{4a}$ are independently selected from: H, halogen, C$_{1-6}$ alkyl, C$_{1-6}$ alkoxy, and —(CH$_2$)$_m$—C$_{3-6}$ carbocycle;

R$^5$, at each occurrence, is independently selected from: halogen, C$_{1-6}$ alkyl, and C$_{1-6}$ alkoxy;

R$^6$, at each occurrence, is independently selected from: halogen, OH, C$_{1-4}$ alkylthio, CN, SO$_2$(C$_{1-2}$ alkyl), N(C$_{1-4}$ alkyl)$_2$, C$_{1-4}$ haloalkyl, C$_{1-4}$ haloalkoxy, C$_{1-8}$ alkyl substituted with 0-1 R$^7$, C$_{1-6}$ alkoxy substituted with 0-1 R$^7$, —(O)$_n$—(CH$_2$)$_m$—(C$_{3-10}$ carbocycle substituted with 0-2 R$^7$), and —(CH$_2$)$_m$-(5- to 10-membered heteroaryl containing carbon atoms and 1-4 heteroatoms selected from N, NR$^{11}$, O, and S); wherein said heteroaryl is substituted with 0-2 R$^7$;

R$^7$, at each occurrence, is independently selected from: halogen, OH, C$_{1-4}$ alkyl, C$_{2-4}$ alkenyl, C$_{1-4}$ alkoxy, C$_{1-4}$ alkylthio, C$_{1-4}$ haloalkyl, C$_{1-4}$ haloalkoxy, SCF$_3$, CN, NO$_2$, NH$_2$, NH(C$_{1-4}$ alkyl), N(C$_{1-4}$ alkyl)$_2$, SO$_2$(C$_{1-2}$ alkyl), and phenyl;

R$^8$ is independently selected from: H and C$_{1-4}$ alkyl;

R$^{10}$ and R$^{12}$, at each occurrence, is independently selected from: OH, halogen, CN, C$_{1-4}$ alkyl, C$_{1-4}$ alkoxy, C$_{1-4}$ haloalkyl, C$_{1-4}$ haloalkoxy, SCF$_3$, NO$_2$, CO$_2$(C$_{1-4}$ alkyl), SO$_2$(C$_{1-4}$ alkyl), and tetrazolyl;

R$^{11}$, at each occurrence, is independently selected from: H, C$_{1-4}$ alkyl and benzyl;

m, at each occurrence, is independently 0, 1, or 2; and n, at each occurrence, is independently 0 or 1.

2. A compound according to claim 1, wherein the compound is of Formula (II):

(II)

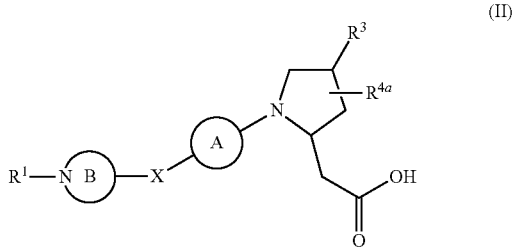

or a stereoisomer, a tautomer, or a pharmaceutically acceptable salt thereof, wherein:

X is independently selected from: a bond, O, S, NH, $N(C_{1-4}$ alkyl), $CH_2$, $CH_2CH_2$, $CH(C_{1-4}$ alkyl), $OCH_2$, $CH_2O$, $OCH_2CH_2$, and $CH_2CH_2O$;

ring A is independently

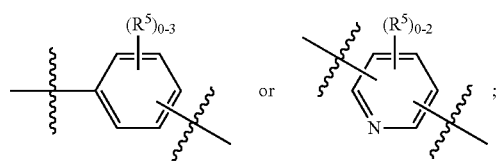

ring B is independently a 4- to 7-membered saturated heterocycle containing carbon atoms and the nitrogen atom shown in ring B; and ring B is substituted with 0-4 $R^2$;

$R^1$ is independently $CO_2(C_{1-4}$ alkyl), $CO_2Bn$,

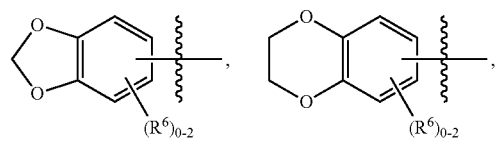

phenyl, benzyl, naphthyl or a 5- to 10-membered heteroaryl containing carbon atoms and 1-4 heteroatoms selected from N, $NR^{11}$, O, and S; wherein said phenyl, benzyl, naphthyl and heteroaryl are each substituted with 0-3 $R^6$;

$R^2$, at each occurrence, is independently selected from: =O, OH, halogen, $C_{1-6}$ alkyl substituted with 0-1 $R^{12}$, $C_{1-6}$ alkoxy substituted with 0-1 $R^{12}$, $C_{1-4}$haloalkyl, $C_{1-4}$haloalkoxy, and benzyl;

when two $R^2$ groups are attached to two different carbon atoms, they may combine to form a 1- to 3-membered carbon atom bridge over ring B;

when two $R^2$ groups are attached to the same carbon, they may combine, together with the carbon atom to which they are attached, to form a 3- to 6-membered carbon atom containing spiro ring;

$R^3$, at each occurrence, is independently selected from: H, halogen, CN, $C_{1-6}$ alkyl, $C_{1-6}$ alkoxy, $C_{1-4}$ haloalkyl, $C_{1-4}$ haloalkoxy, phenyl, benzyl, phenoxy, benzoxy, 1—$C_{1-4}$ alkyl-pyrazolyl, triazolyl, tetrazolyl, pyridinyl, —O-pyridinyl, pyrimidinyl, and —O-pyrimidinyl; wherein each said ring moiety is substituted with 0-2 $R^{10}$;

$R^{4a}$ is independently selected from: H, halogen, $C_{1-4}$ alkyl, $C_{1-4}$ alkoxy, and —$(CH_2)_m$—$C_{3-6}$ carbocycle;

$R^5$, at each occurrence, is independently selected from: halogen, $C_{1-6}$ alkyl, and $C_{1-6}$ alkoxy;

$R^6$, at each occurrence, is independently selected from: halogen, OH, $C_{1-4}$ alkylthio, CN, $SO_2(C_{1-2}$ alkyl), $N(C_{1-4}$ alkyl)$_2$, $C_{1-4}$ haloalkyl, $C_{1-4}$ haloalkoxy, $C_{1-8}$ alkyl substituted with 0-1 $R^7$, $C_{1-4}$ alkoxy substituted with 0-1 $R^7$, —$(O)_n$—$CH_2)_m$—$(C_{3-6}$ carbocycle substituted with 0-2 $R^7$), —$(CH_2)_m$-(naphthyl substituted with 0-2 $R^7$), and —$(CH_2)_m$-(5- to 10-membered heteroaryl containing carbon atoms and 1-4 heteroatoms selected from N, $NR^{11}$, O, and S; wherein said heteroaryl is substituted with 0-2 $R^7$);

$R^7$, at each occurrence, is independently selected from: halogen, OH, $C_{1-4}$ alkyl, $C_{2-4}$ alkenyl, $C_{1-4}$ alkoxy, $C_{1-4}$ alkylthio, $C_{1-4}$ haloalkyl, $C_{1-4}$ haloalkoxy, $SCF_3$, CN, $NO_2$, $NH_2$, $NH(C_{1-4}$ alkyl), $N(C_{1-4}$ alkyl)$_2$, $SO_2(C_{1-2}$ alkyl), and phenyl;

$R^{10}$ and $R^{12}$, at each occurrence, are independently selected from: OH, halogen, CN, $C_{1-4}$ alkyl, $C_{1-4}$ alkoxy, $C_{1-4}$ haloalkyl, $C_{1-4}$ haloalkoxy, $SCF_3$, $NO_2$, $CO_2(C_{1-4}$ alkyl), $SO_2(C_{1-4}$ alkyl), and tetrazolyl;

$R^{11}$, at each occurrence, is independently selected from: H, $C_{1-4}$ alkyl and benzyl;

m, at each occurrence, is independently 0, 1, or 2; and n, at each occurrence, is independently 0 or 1.

3. A compound according to claim 1, wherein:

X is independently selected from: a bond, O, NH, $N(CH_3)$, $CH_2$, $CH_2CH_2$, $CH(CH_3)$, $OCH_2$, $CH_2O$, $OCH_2CH_2$, and $CH_2CH_2O$;

ring A is independently

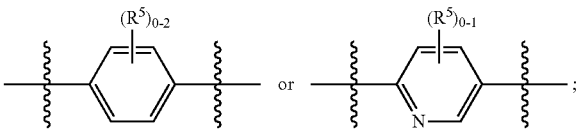

ring B is independently selected from:

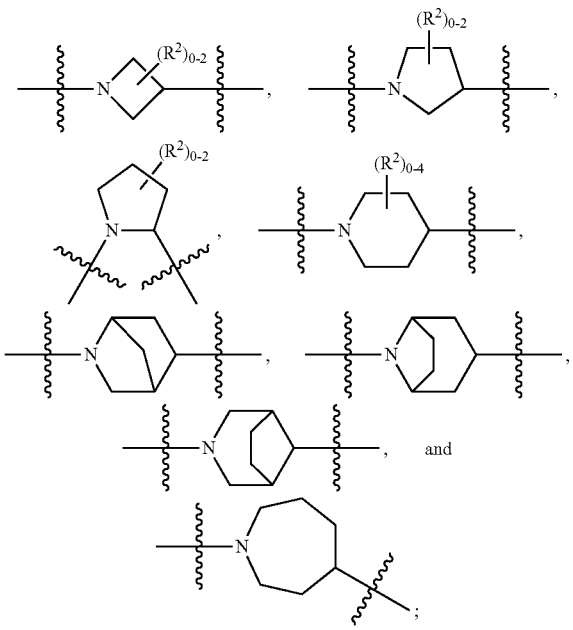

$R^1$ is independently $CO_2(C_{1-4}$ alkyl), $CO_2Bn$,

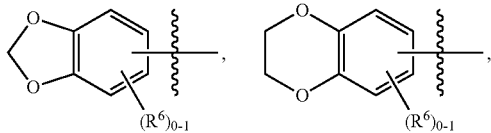

phenyl substituted with 0-3 $R^6$ or a heteroaryl substituted with 0-2 $R^6$; wherein said heteroaryl is selected from: furanyl, oxazolyl, thiazolyl, pyrazolyl, oxadiazolyl, pyridinyl, pyrimidinyl, pyrazinyl,

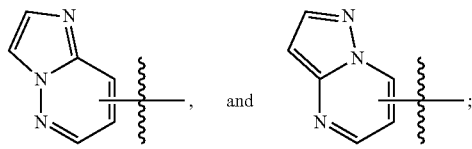

$R^2$, at each occurrence, is independently selected from: OH, halogen, $C_{1-4}$ alkyl substituted with 0-1 $R^{12}$, $C_{1-4}$ alkoxy substituted with 0-1 $R^{12}$, and benzyl;

$R^3$ is independently selected from: H, halogen, CN, $C_{1-6}$ alkyl, $C_{1-6}$ alkoxy, $C_{1-4}$ haloalkyl, $C_{1-4}$ haloalkoxy, phenyl, benzyl, phenoxy, benzoxy, oxazolyl, 1-$C_{1-4}$ alkyl-pyrazolyl, triazolyl, tetrazolyl, pyridinyl, —O-pyridinyl, pyrimidinyl, —O-pyrimidinyl, and

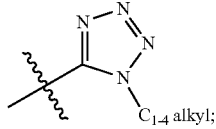

wherein each said ring moiety is substituted with 0-2 $R^{10}$;

$R^{4a}$ is independently selected from: H, halogen $C_{1-4}$ alkyl, $C_{1-4}$ alkoxy, and $C_{3-6}$ cycloalkyl;

$R^6$, at each occurrence, is independently selected from: halogen, OH, $C_{1-8}$ alkyl substituted with 0-1 OH, $C_{1-4}$ alkoxy, $C_{1-4}$ alkylthio, $C_{1-4}$ haloalkyl, $C_{1-4}$ haloalkoxy, CN, $SO_2(C_{1-2}$ alkyl), $N(C_{1-4}$ alkyl)$_2$, $C_{3-6}$ cycloalkyl substituted with 0-2 $C_{1-4}$ alkyl, $C_{5-6}$ cycloalkenyl substituted with 0-2 $C_{1-4}$ alkyl, —O—$C_{3-6}$ cycloalkyl, benzyl, and oxazolyl; and $R^{10}$ and $R^{12}$, at each occurrence, are independently selected from: halogen, CN, $C_{1-4}$ alkyl, $C_{1-4}$ alkoxy, $C_{1-4}$ haloalkyl, $C_{1-4}$ haloalkoxy, $SO_2(C_{1-4}$ alkyl), and $CO_2(C_{1-2}$ alkyl), and tetrazolyl.

4. A compound according to claim 1, wherein:
$R^1$ is independently

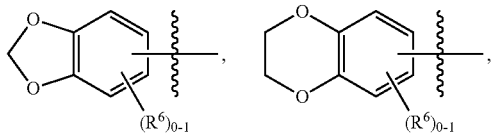

phenyl substituted with 0-3 $R^6$ or a heteroaryl substituted with 0-2 $R^6$; wherein said heteroaryl is selected from: thiazolyl, pyridinyl, pyrimidinyl, pyrazinyl,

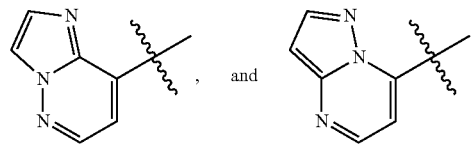

5. A compound according to claim 1, wherein:
X is independently selected from: O, N(CH$_3$), CH$_2$, CH$_2$O, and CH$_2$CH$_2$O;
ring B is independently selected from:

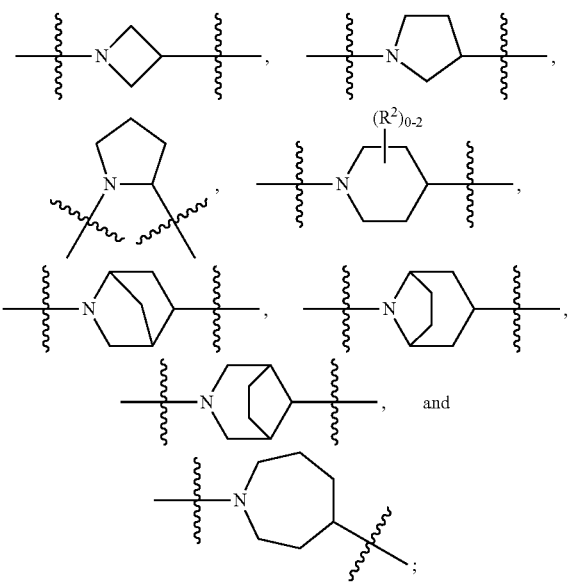

$R^1$, at each occurrence, is independently phenyl substituted with 0-3 $R^6$, pyridinyl substituted with 0-2 $R^6$, pyrazinyl substituted with 0-2 $R^6$, pyrimidinyl substituted with 0-2 $R^6$, thiazolyl substituted with 0-2 $R^6$,

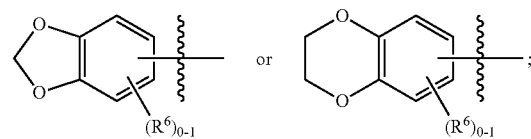

$R^2$, at each occurrence, is independently selected from: OH, halogen, $C_{1-6}$ alkyl substituted with 0-1 CN, $C_{1-6}$ alkoxy, benzyl, and tetrazolylmethyl;

$R^3$, at each occurrence, is independently selected from: H, halogen, CN, $C_{1-6}$ alkyl, $C_{1-6}$ alkoxy, $C_{1-4}$ haloalkyl, $C_{1-4}$ haloalkoxy, phenyl, benzyl, phenoxy, benzoxy, 1—$C_{1-4}$ alkyl-pyrazolyl, triazolyl, tetrazolyl, pyridinyl, —O-pyridinyl, pyrimidinyl, and —O-pyrimidinyl; wherein each said ring moiety is substituted with 0-2 $R^{10}$;

$R^6$, at each occurrence, is independently selected from: halogen, CN, $C_{1-8}$ alkyl, $C_{1-4}$ alkoxy, $C_{1-4}$ haloalkyl, $C_{1-4}$ haloalkoxy, $C_{3-6}$ cycloalkyl substituted with 0-2 $C_{1-4}$ alkyl, $C_{5-6}$ cycloalkenyl substituted with 0-2 $C_{1-4}$ alkyl, —O—$C_{3-6}$ cycloalkyl, benzyl, and oxazolyl; and $R^{10}$, at each occurrence, is independently selected from: halogen, CN, $C_{1-4}$ alkyl, $C_{1-4}$ alkoxy, $C_{1-4}$ haloalkyl, $C_{1-4}$ haloalkoxy, and $CO_2(C_{1-2}$ alkyl).

6. A compound according to claim 1, wherein:
ring B is independently selected from:

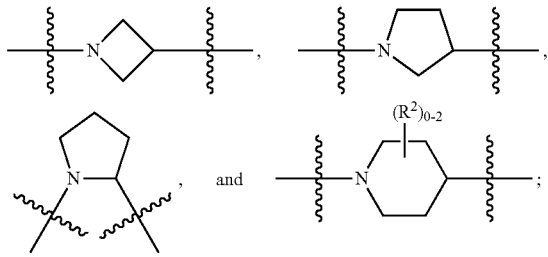

R$^1$, at each occurrence, is independently phenyl substituted with 0-3 R$^6$ or pyridinyl substituted with 0-2 R$^6$;
R$^2$, at each occurrence, is independently selected from: halogen, C$_{1-6}$ alkyl, and C$_{1-6}$ alkoxy;
R$^3$, at each occurrence, is independently selected from: H, halogen, CN, C$_{1-6}$ alkyl, C$_{1-6}$ alkoxy, C$_{1-4}$ haloalkyl, C$_{1-4}$ haloalkoxy, phenyl, benzyl, phenoxy, benzoxy, 1-C$_{1-4}$ alkyl-pyrazolyl, triazolyl, tetrazolyl, pyridinyl, —O-pyridinyl, and —O-pyrimidinyl; wherein said phenyl, benzyl, phenoxy —O-pyridinyl, and —O-pyrimidinyl are each substituted with 0-2 R$^{10}$;
R$^6$, at each occurrence, is independently selected from: halogen, C$_{1-6}$ alkyl, C$_{1-4}$ alkoxy, C$_{1-4}$ haloalkyl, C$_{1-4}$ haloalkoxy, C$_{3-6}$ cycloalkyl substituted with 0-2 C$_{1-4}$ alkyl, C$_{5-6}$ cycloalkenyl substituted with 0-2 C$_{1-4}$ alkyl, and benzyl; and
R$^{10}$, at each occurrence, is independently selected from: halogen, CN, C$_{1-4}$ alkyl, C$_{1-4}$ alkoxy, C$_{1-4}$ haloalkyl, and C$_{1-4}$ haloalkoxy.

7. A compound according to claim 1, wherein the compound is of Formula (III), (IIIa), (IIIb) or (IIIc):

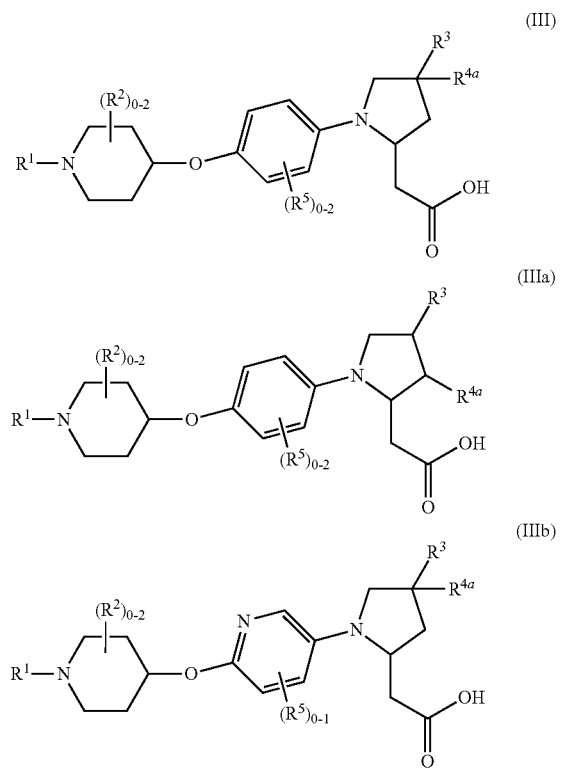

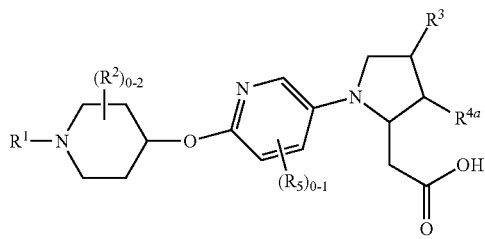

or a stereoisomer, a tautomer, a pharmaceutically acceptable salt, or a solvate thereof, wherein:
R$^1$, at each occurrence, is independently phenyl substituted with 0-3 R$^6$ or pyridinyl substituted with 0-2 R$^6$;
R$^2$, at each occurrence, is independently selected from: halogen, C$_{1-4}$ alkyl, and C$_{1-6}$ alkoxy;
R$^3$, at each occurrence, is independently selected from: H, halogen, C$_{1-4}$ alkyl, C$_{1-4}$ alkoxy, C$_{1-4}$ haloalkyl, C$_{1-4}$ haloalkoxy, phenyl, benzyl, phenoxy, pyridinyl, and —O-pyridinyl; wherein said phenyl, benzyl, phenoxy, pyridinyl and —O-pyridinyl are each substituted with 0-1 R$^{10}$;
R$^{4a}$, at each occurrence, is independently selected from: H, halogen, C$_{1-4}$ alkyl, C$_{1-4}$ alkoxy, and cyclopropyl;
R$^5$, at each occurrence, is independently halogen and C$_{1-6}$ alkoxy;
R$^6$, at each occurrence, is independently selected from: halogen, C$_{1-6}$ alkyl, C$_{1-4}$ alkoxy, C$_{3-6}$ cycloalkyl substituted with 0-2 C$_{1-4}$ alkyl, and C$_{5-6}$ cycloalkenyl substituted with 0-2 C$_{1-4}$ alkyl; and
R$^{10}$ is independently selected from: halogen, CF$_3$, OCF$_3$, CN, C$_{1-4}$ alkyl, and C$_{1-4}$ alkoxy.

8. A compound according to claim 7, wherein the compound is of Formula (IV) or (IVa):

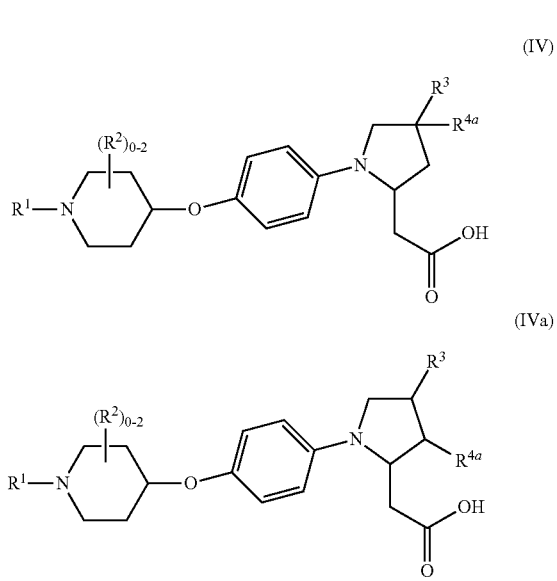

or a stereoisomer, a tautomer, or a pharmaceutically acceptable salt thereof.

9. A compound according to claim 7, wherein:
R$^1$ is independently phenyl substituted with 0-3 R$^6$ or pyridinyl substituted with 0-2 R$^6$;
R$^2$ is independently halogen or C$_{1-4}$ alkyl;

R³ is independently selected from: halogen, C₁₋₄ alkyl, C₁₋₄ alkoxy, CF₃, phenyl, benzyl, and phenoxy;
R⁴ᵃ is independently selected from: H, halogen and C₁₋₄ alkyl; and
R⁶, at each occurrence, is independently selected from: halogen, C₁₋₄ alkyl, and C₁₋₄ alkoxy.
10. A compound according to claim 1, wherein the compound is selected from the the group consisting of
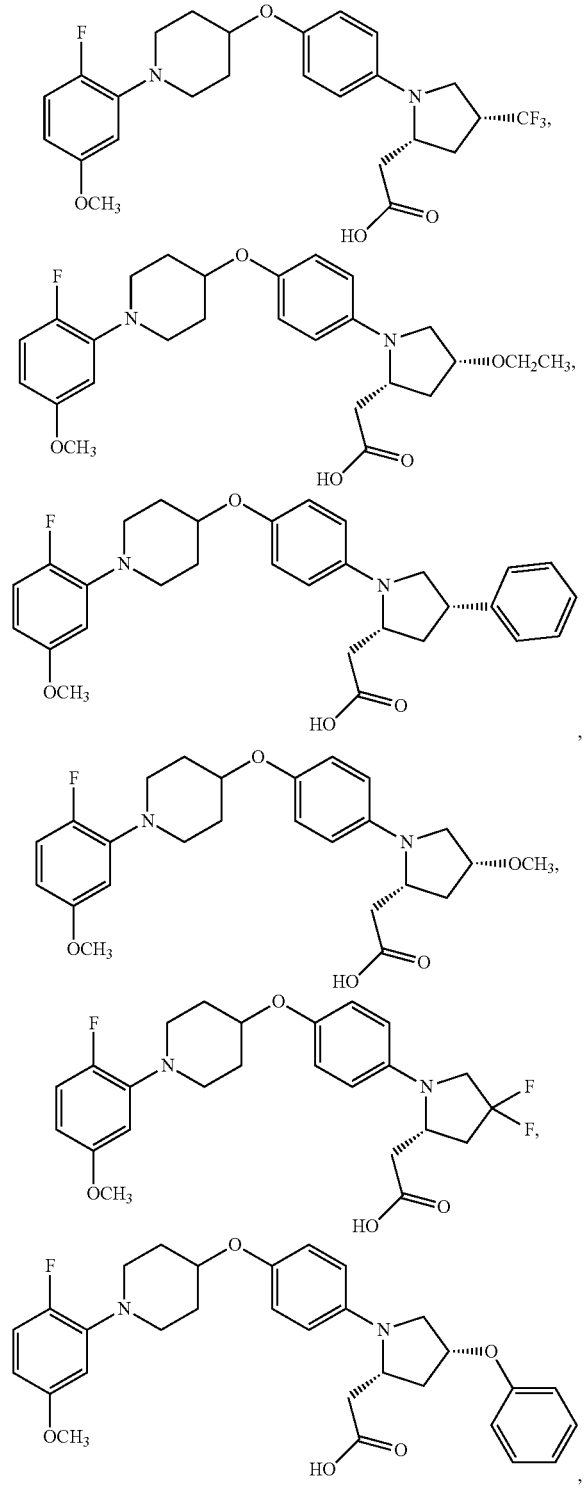
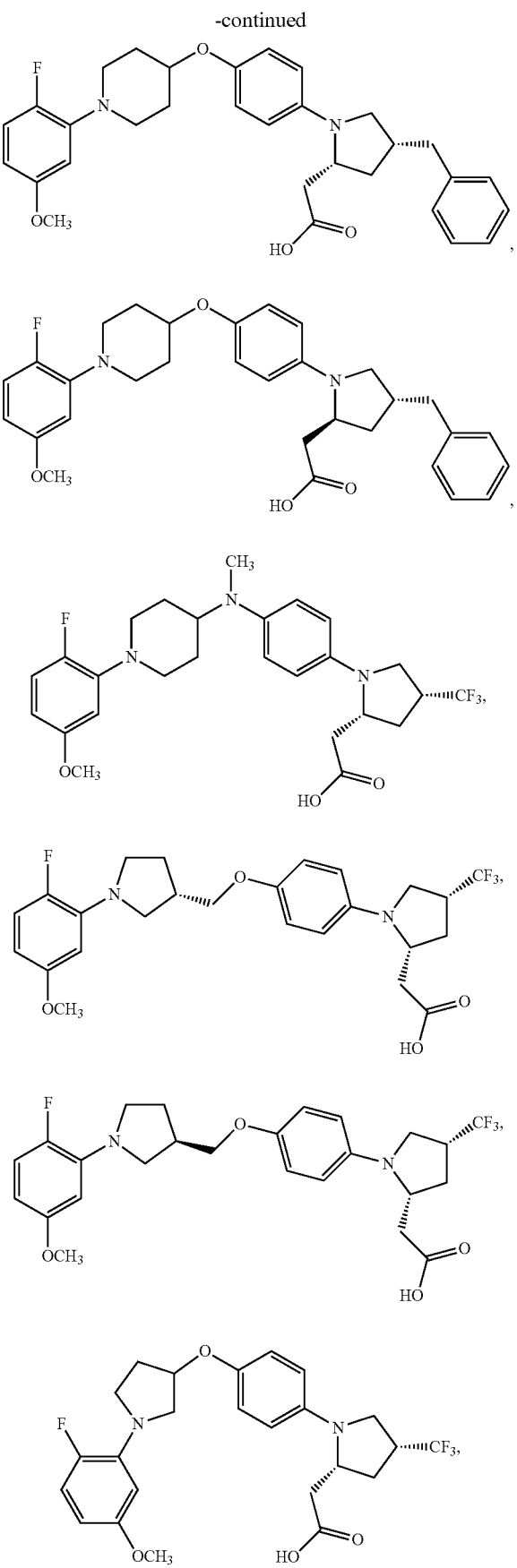

209
-continued
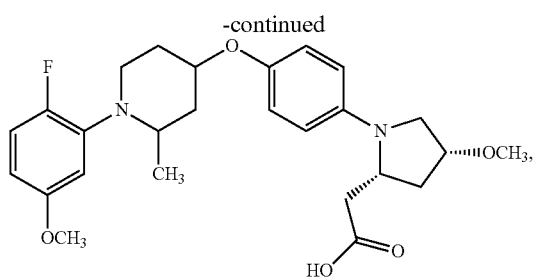
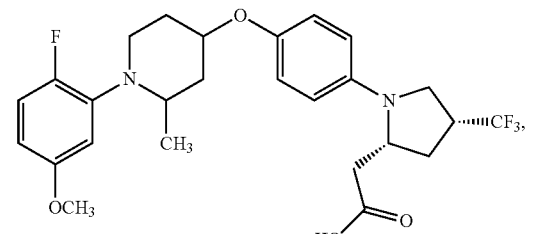
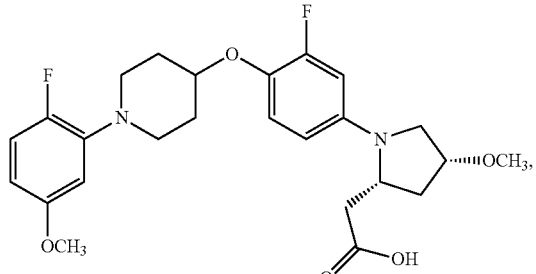
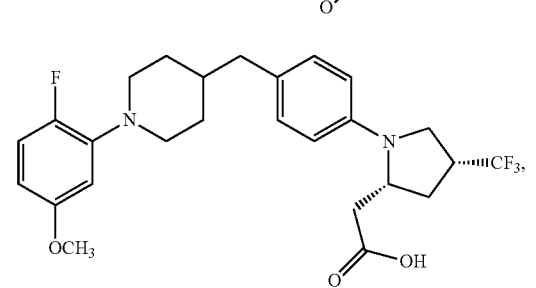
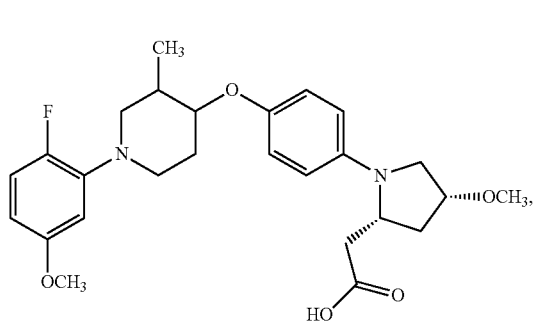
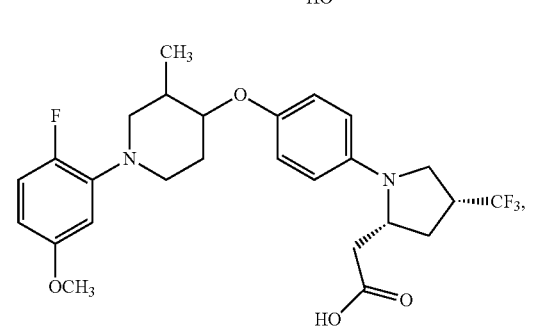
210
-continued
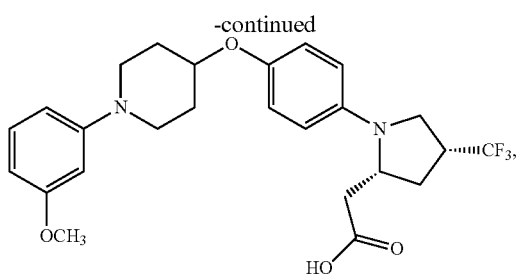
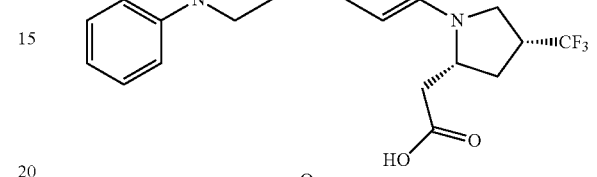
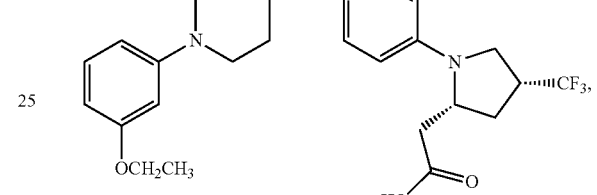
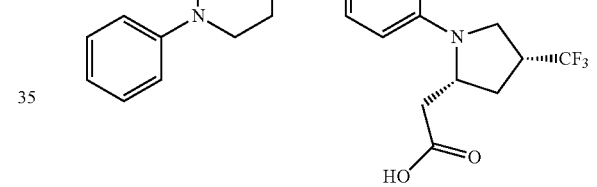
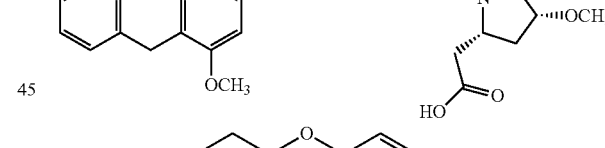
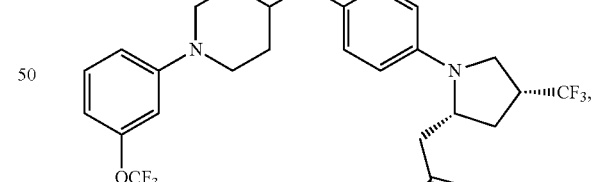
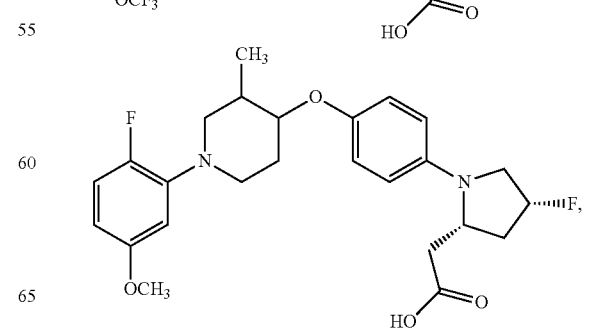

211
-continued
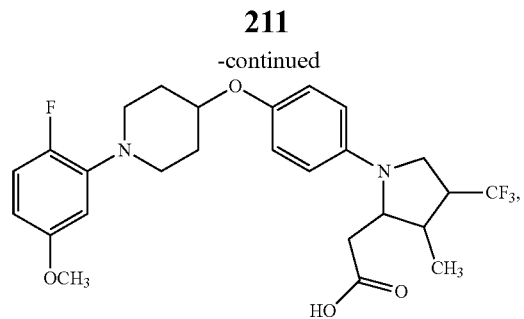
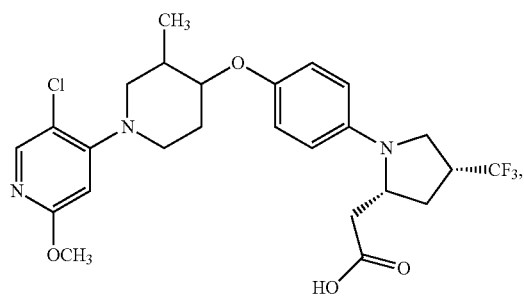
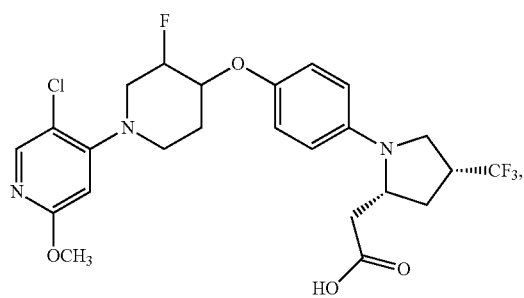
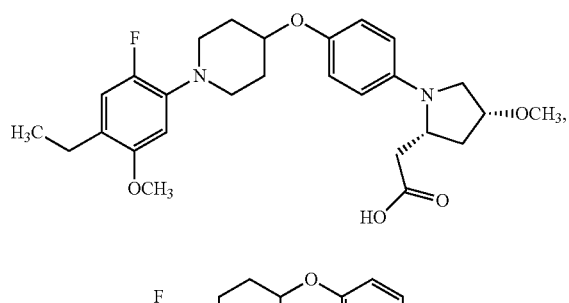
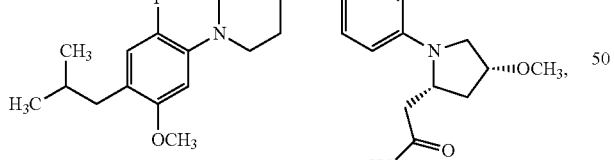
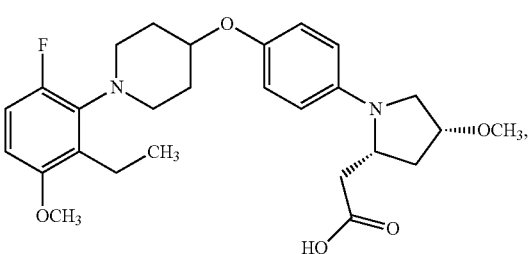
212
-continued
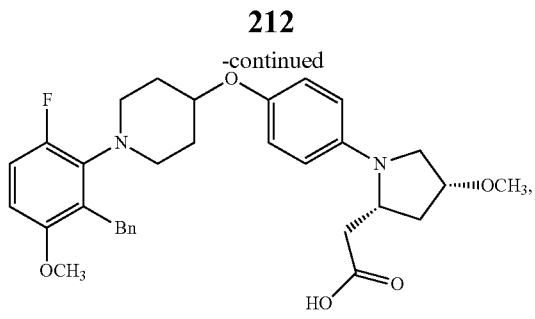
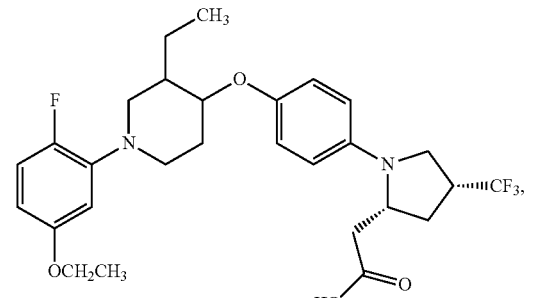
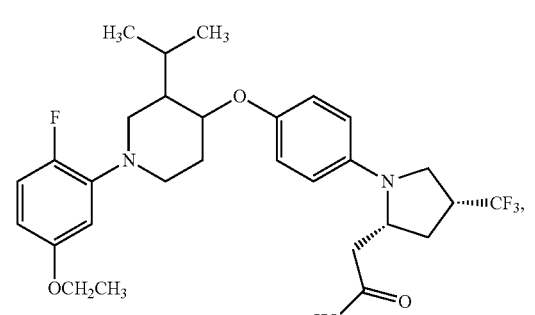
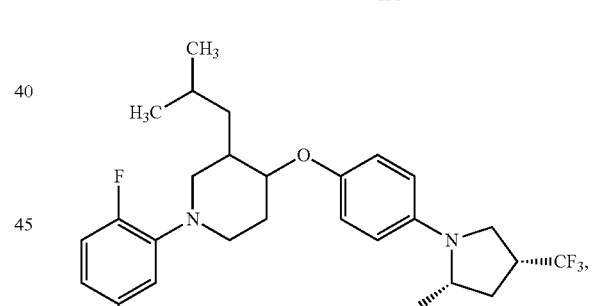
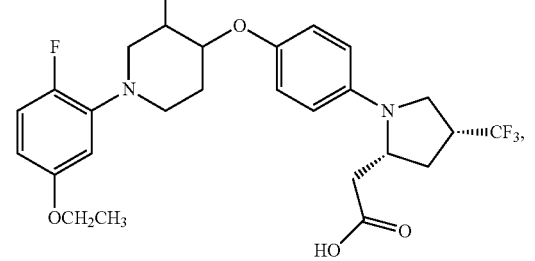

213
-continued
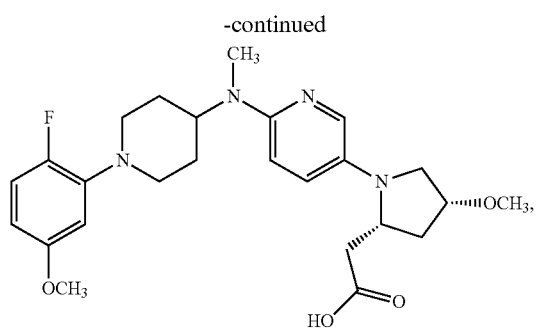
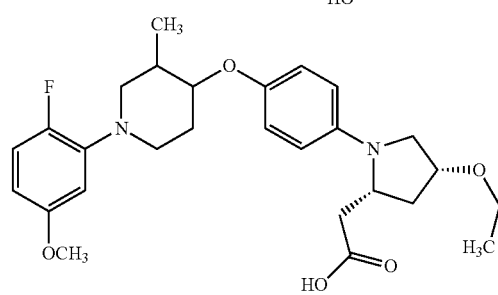
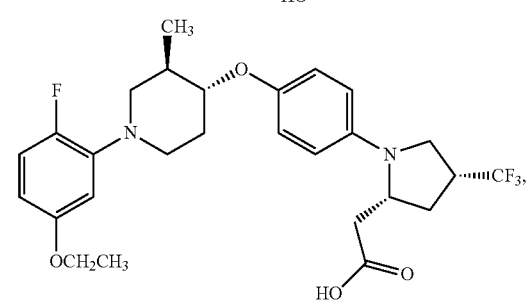
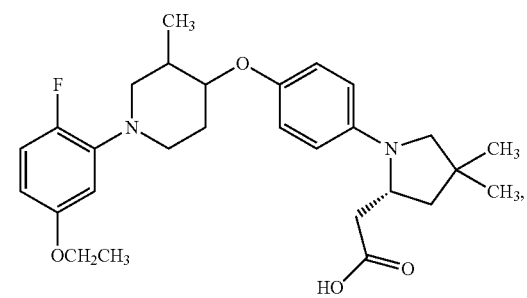
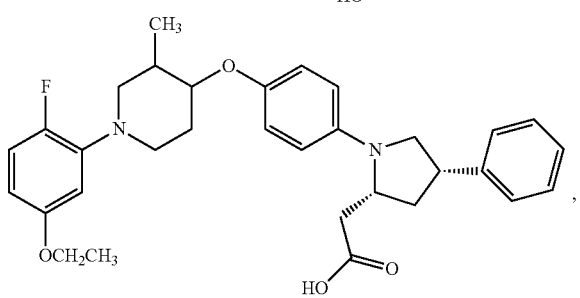
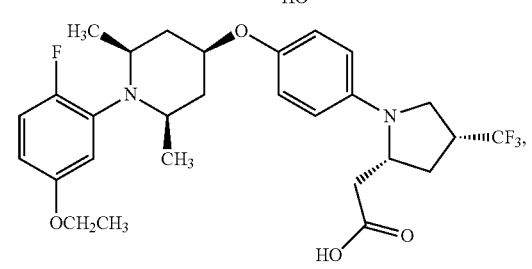
214
-continued
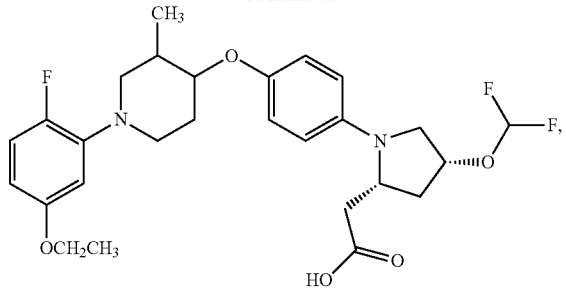
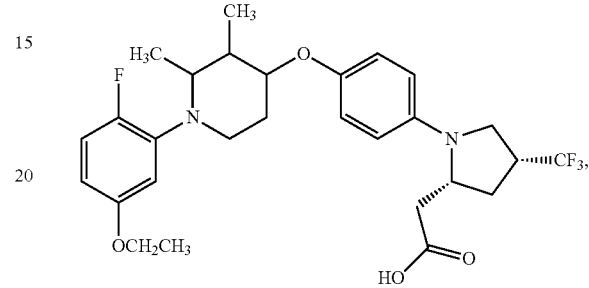
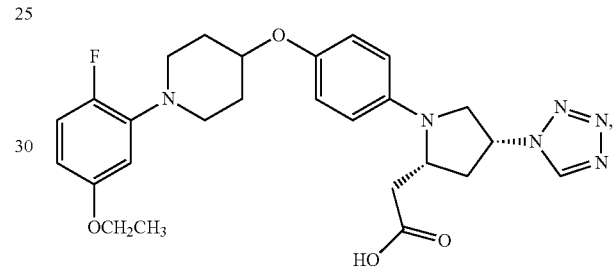
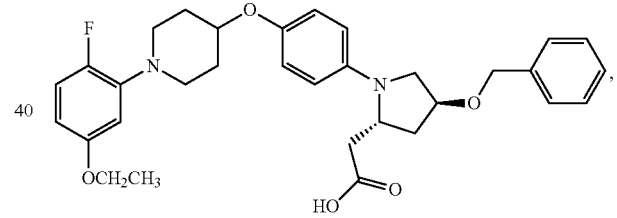
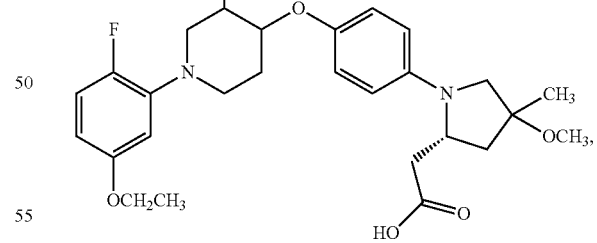
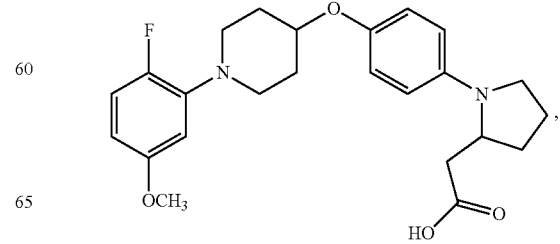

215
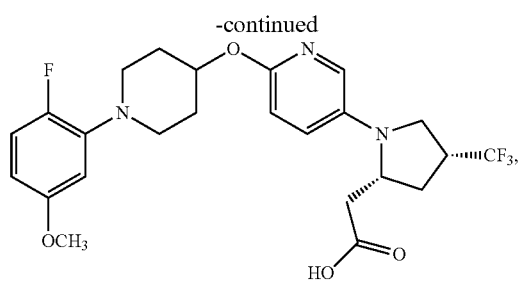
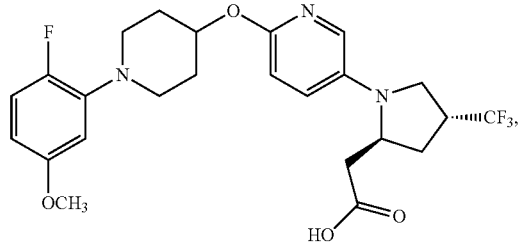
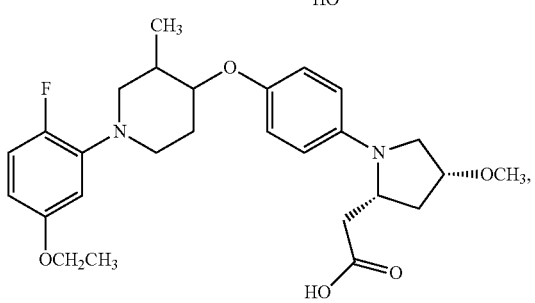
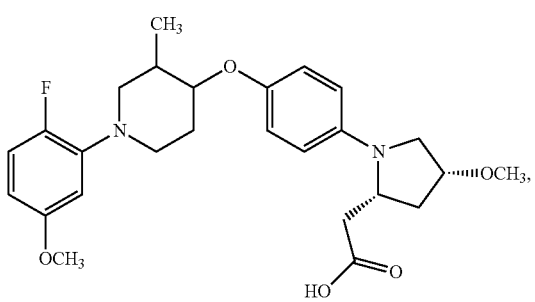
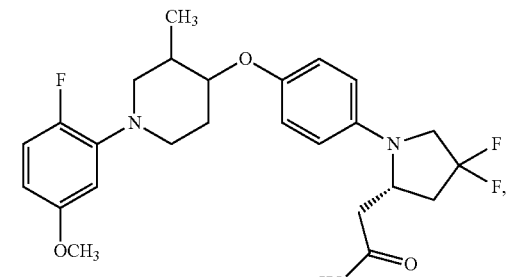
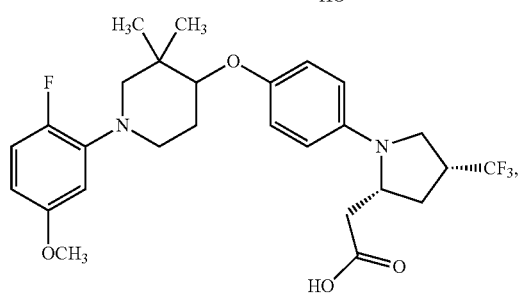
216
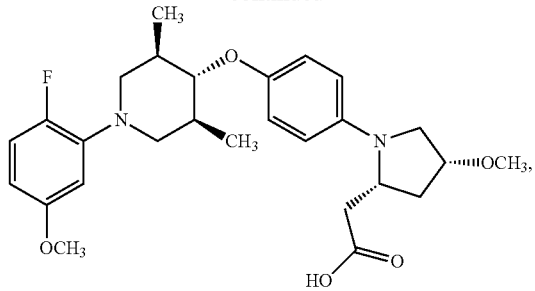
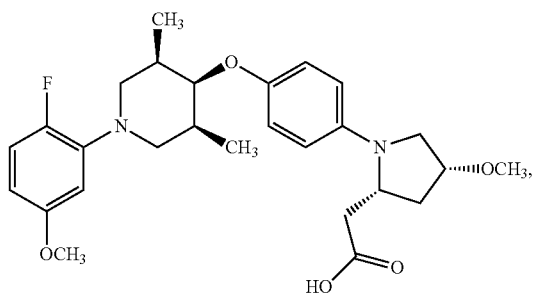
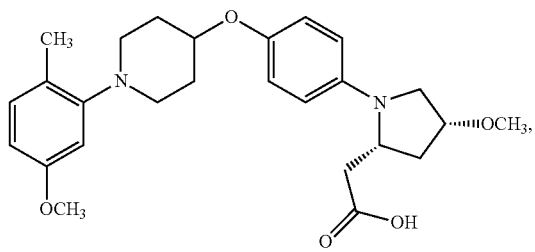
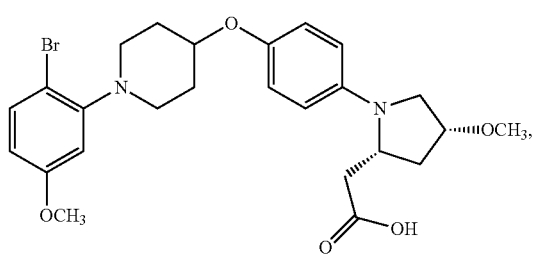
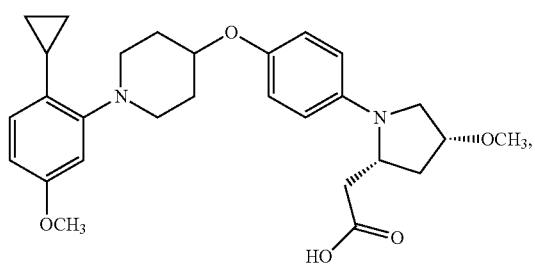
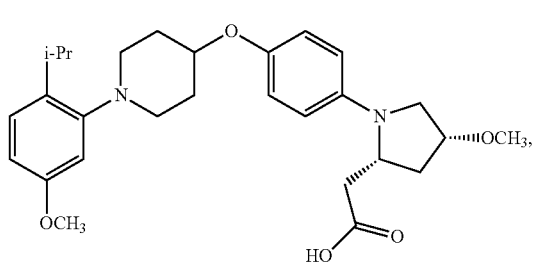

217
-continued
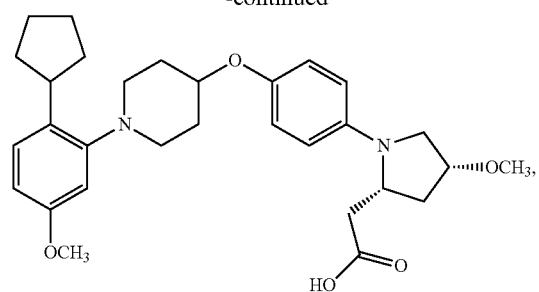
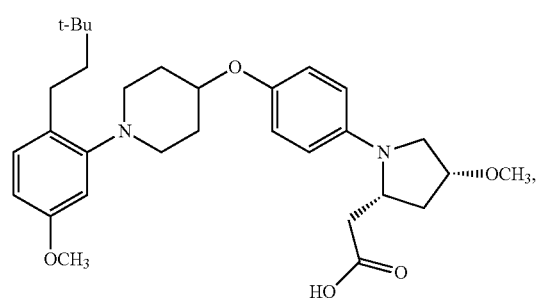
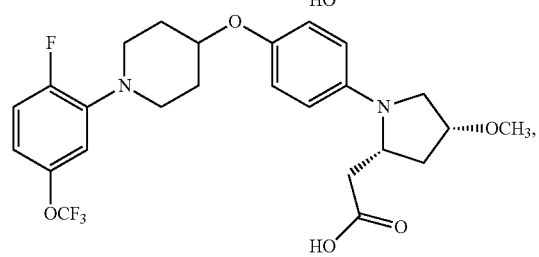
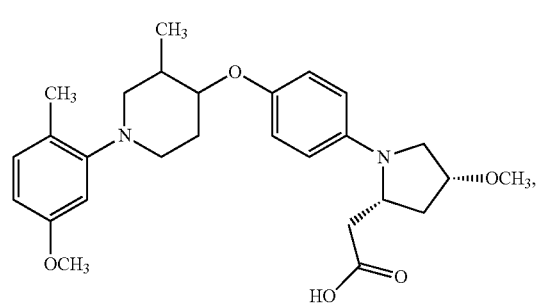
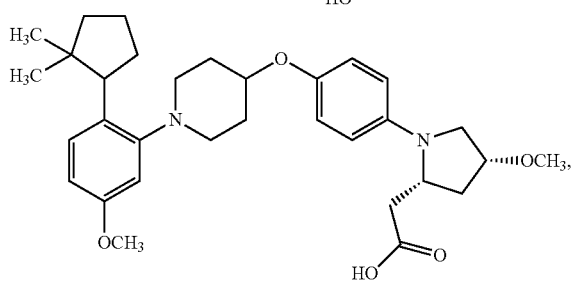
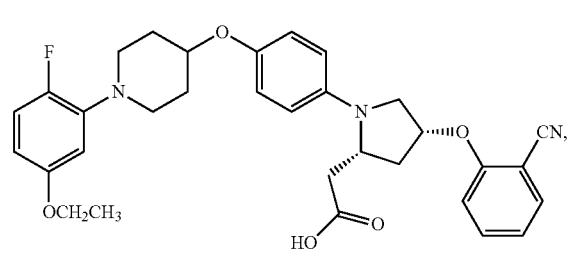
218
-continued
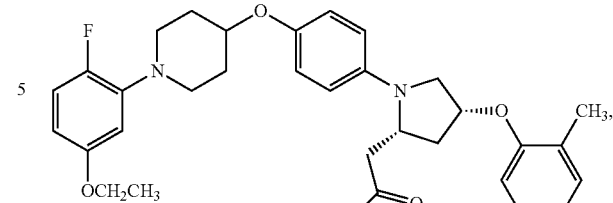
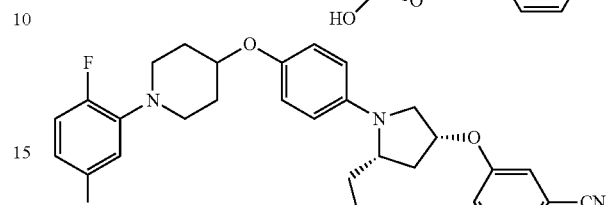
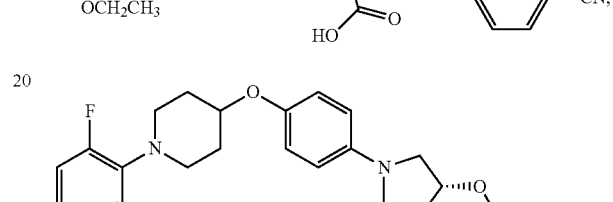
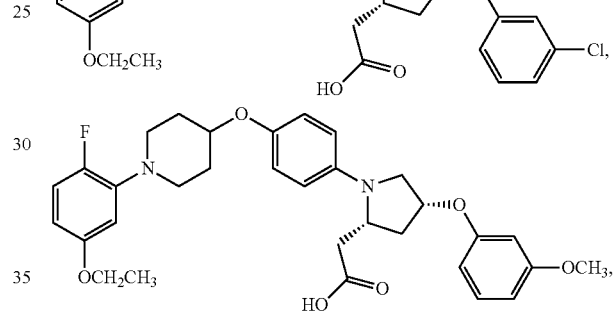
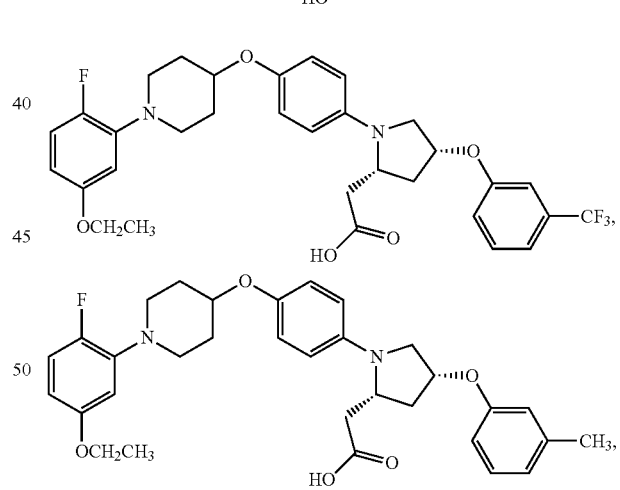
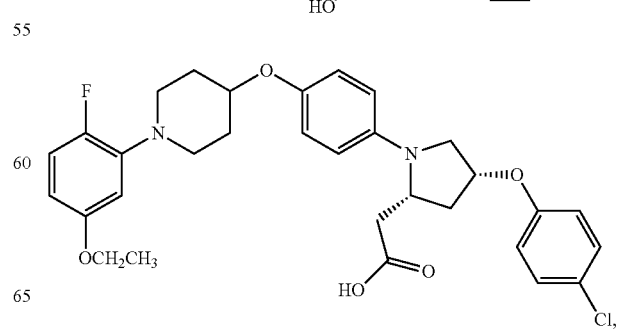

-continued
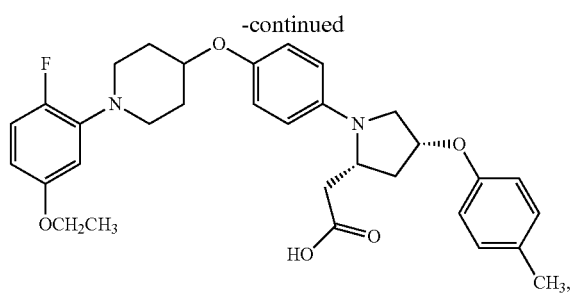
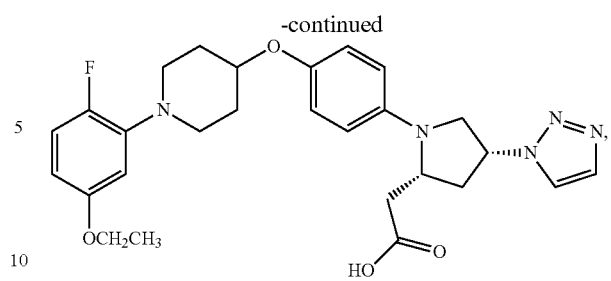
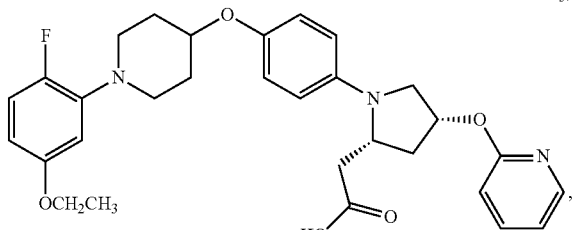
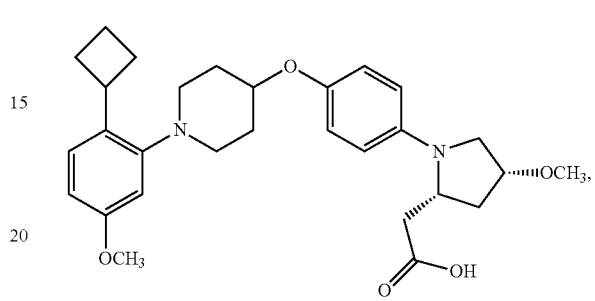
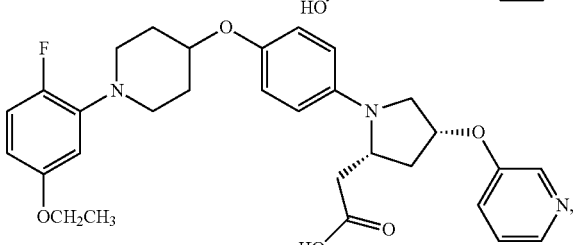
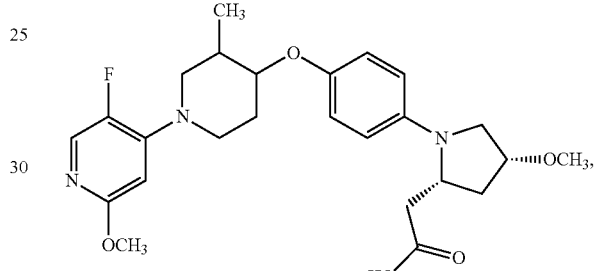
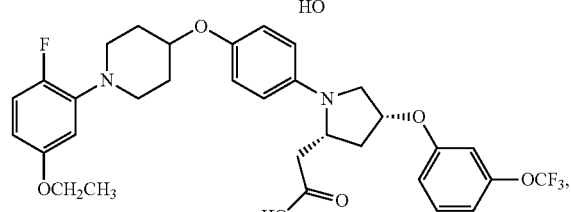
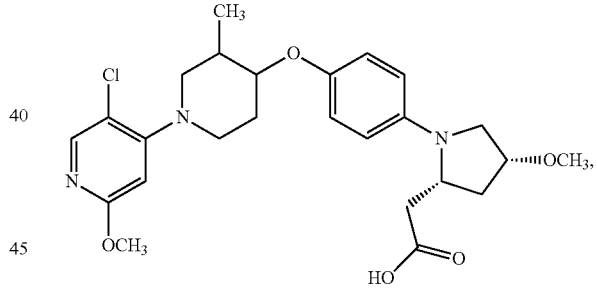
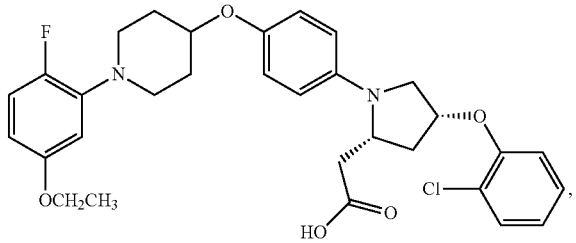
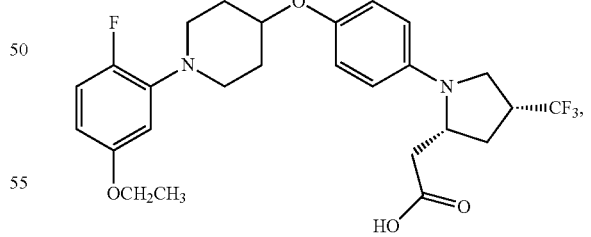
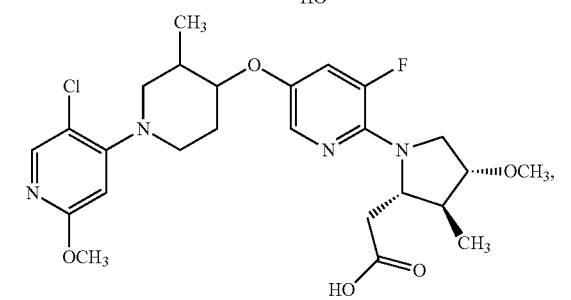
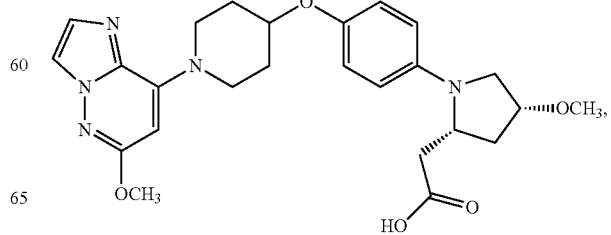

221
-continued
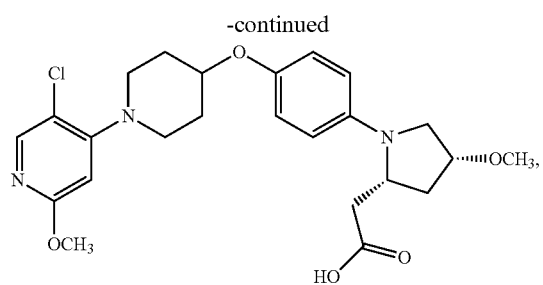
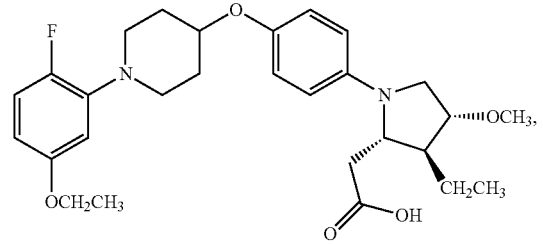
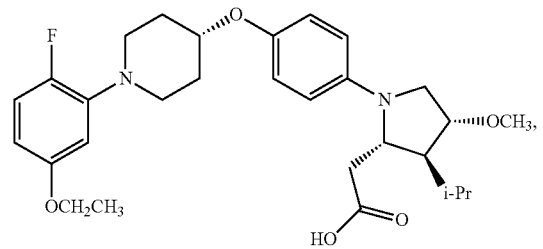
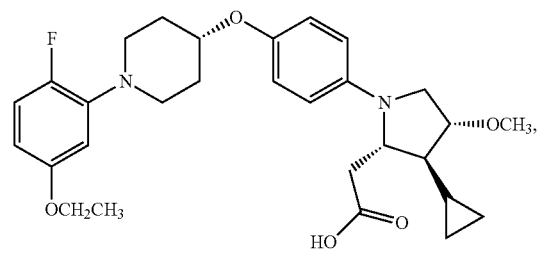
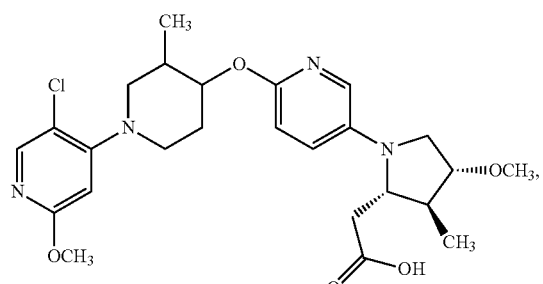
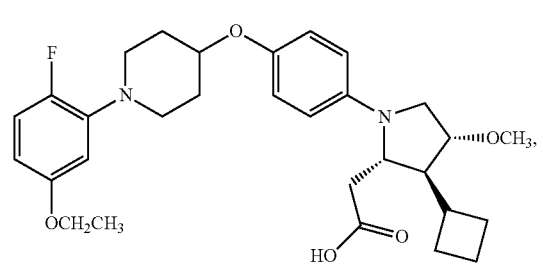
222
-continued
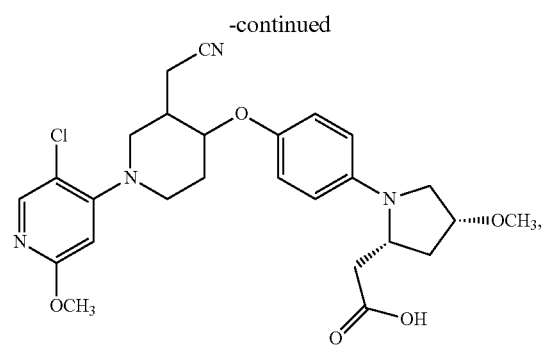
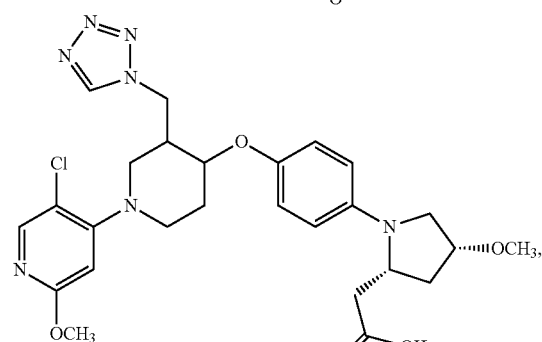
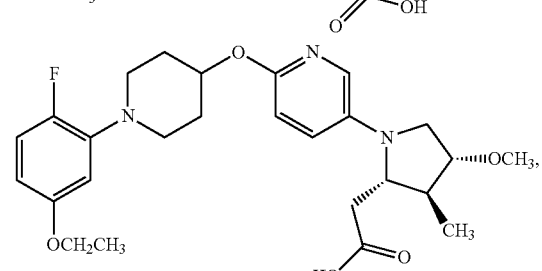
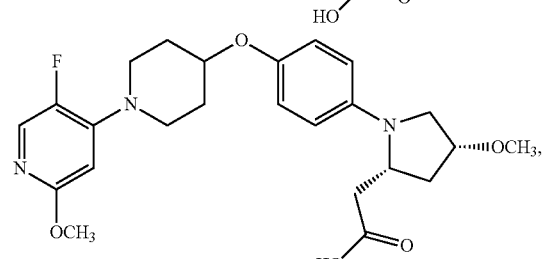
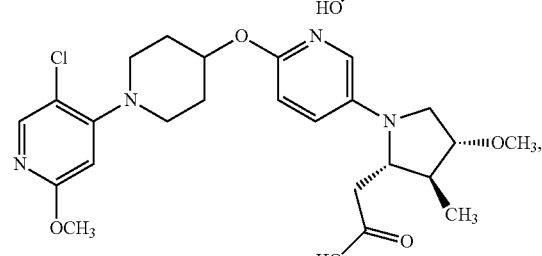
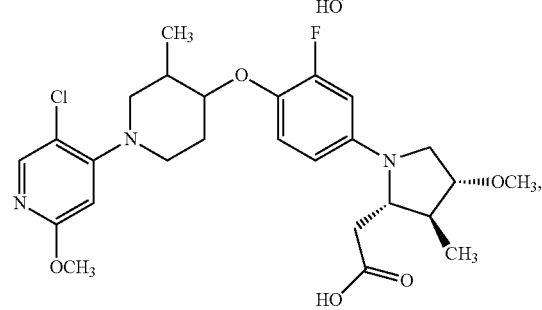

223
-continued
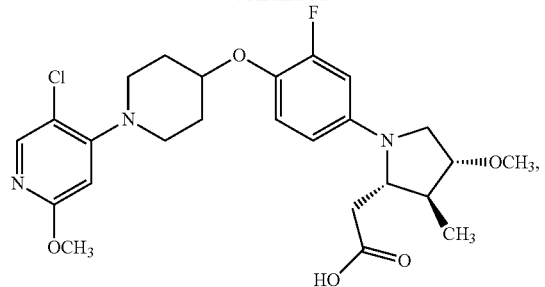
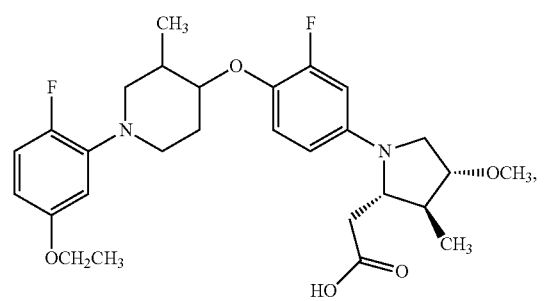
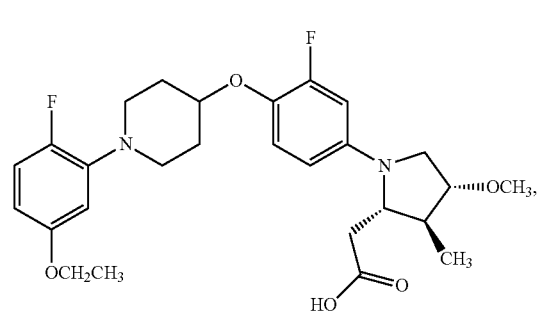
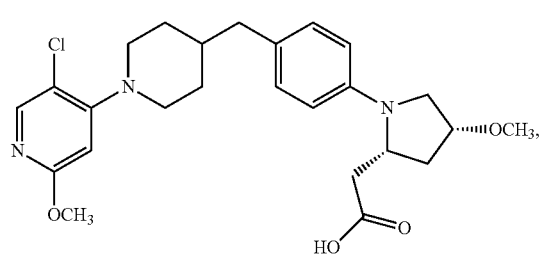
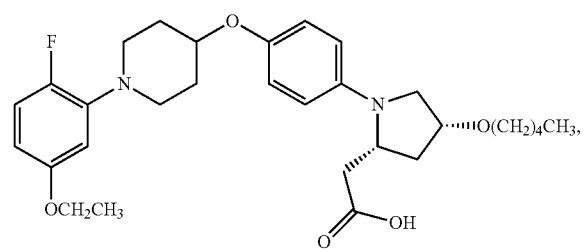
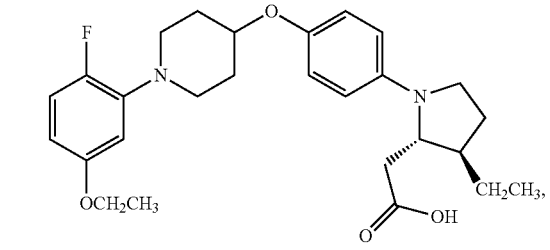
224
-continued
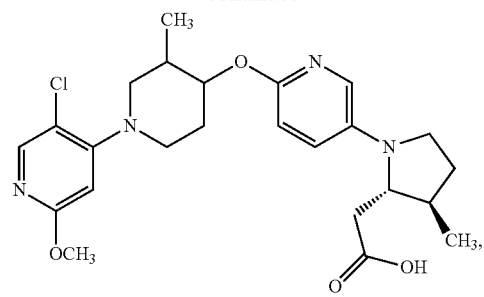
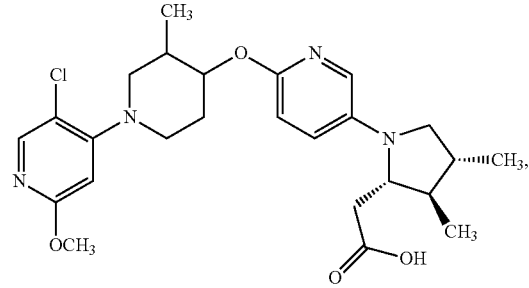
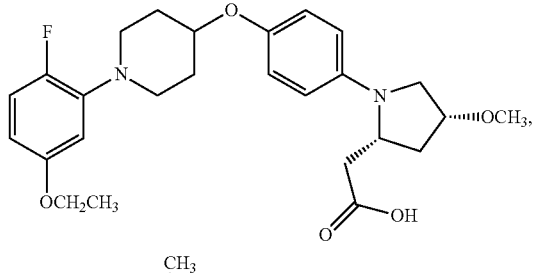
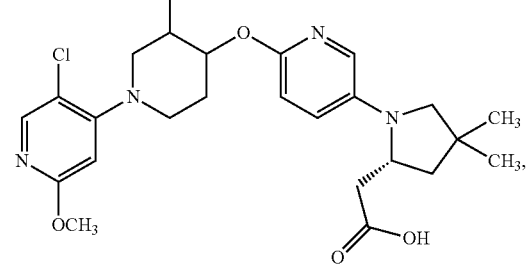
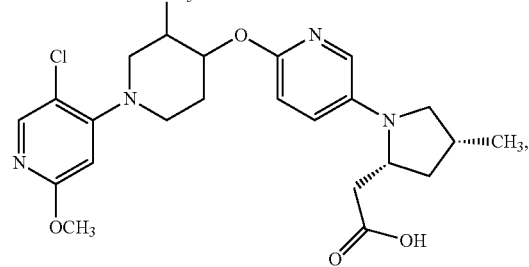
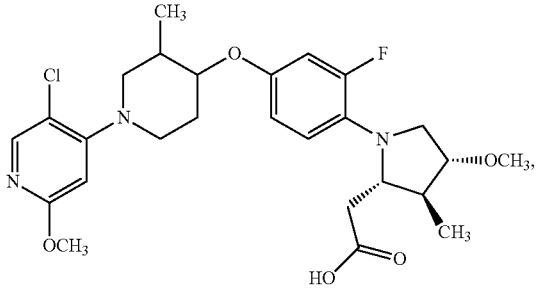

225
-continued
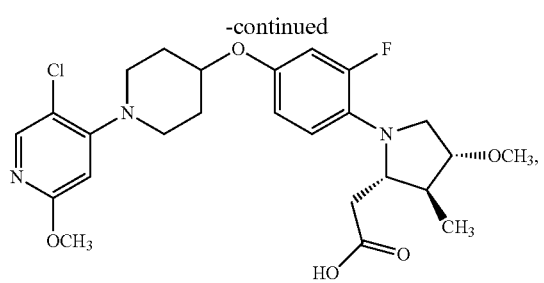
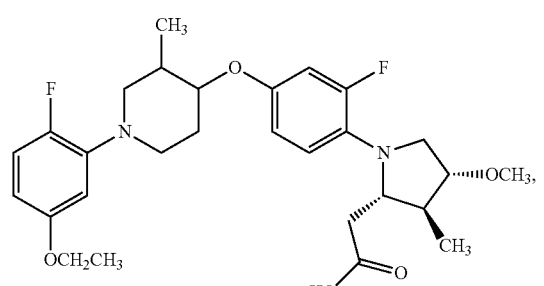
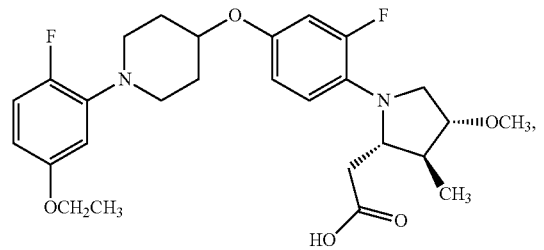
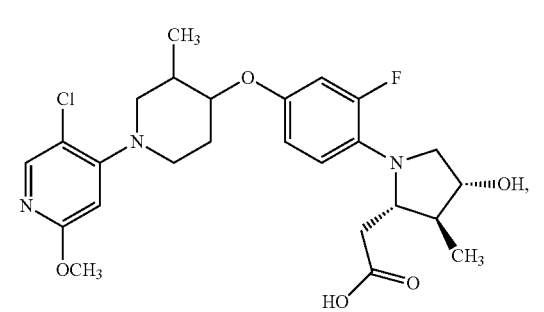
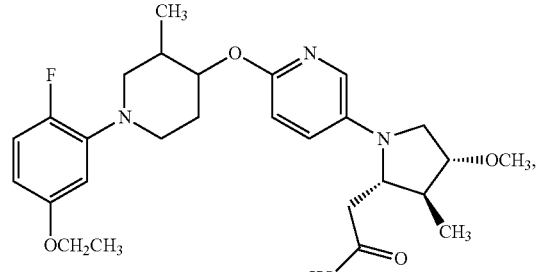
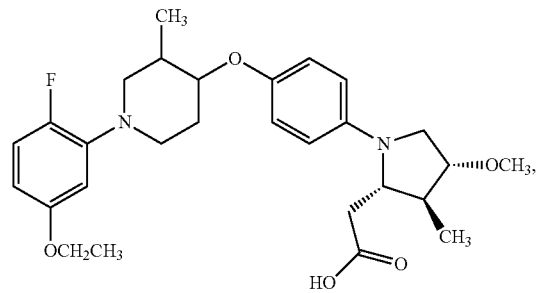
226
-continued
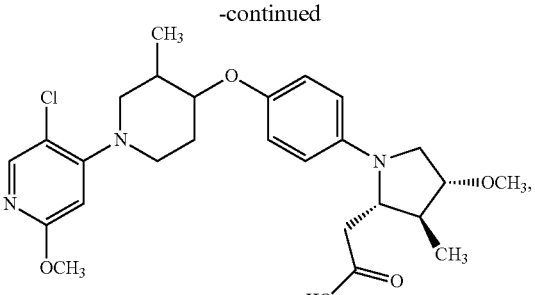
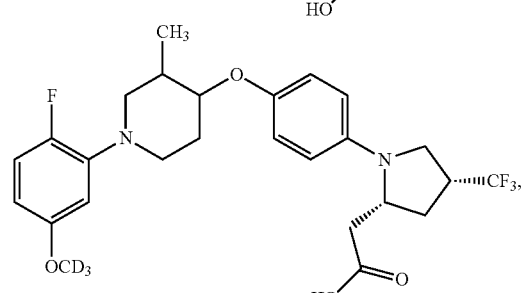
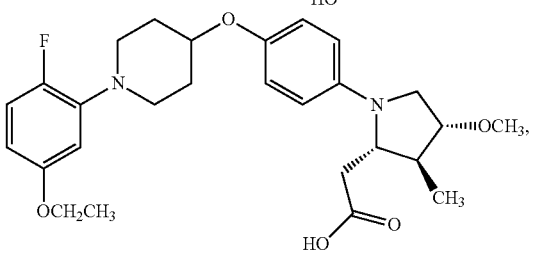
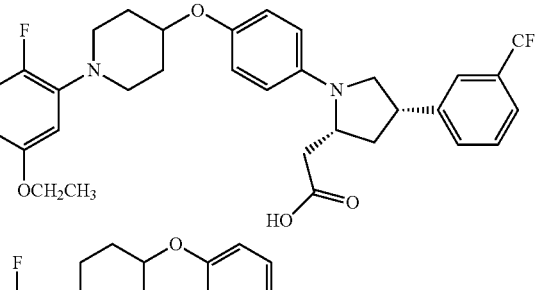
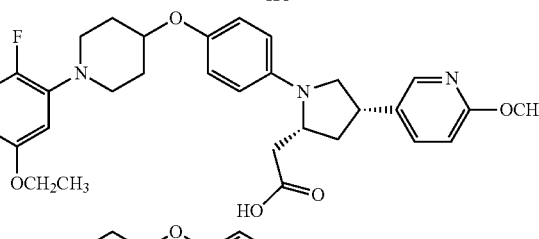
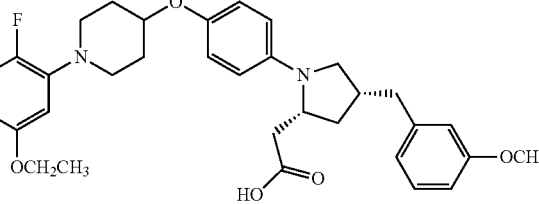
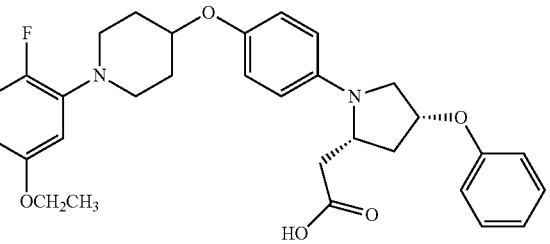

227
-continued
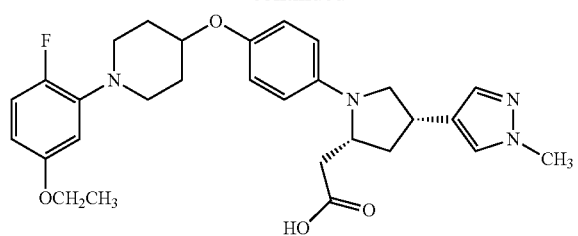
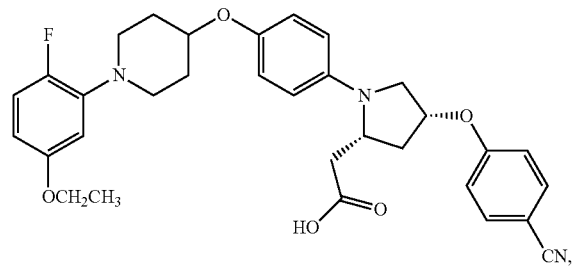
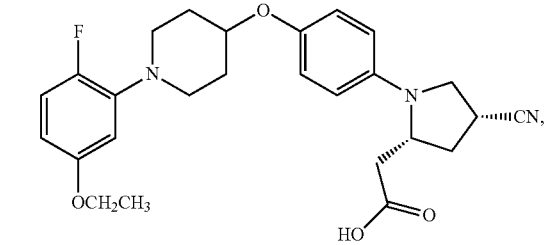
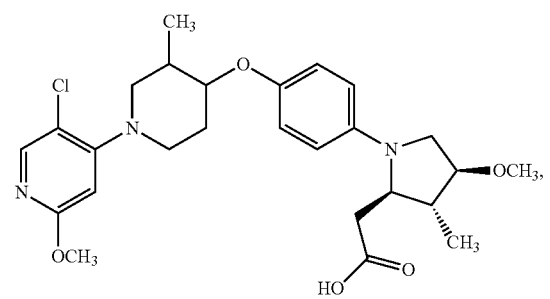
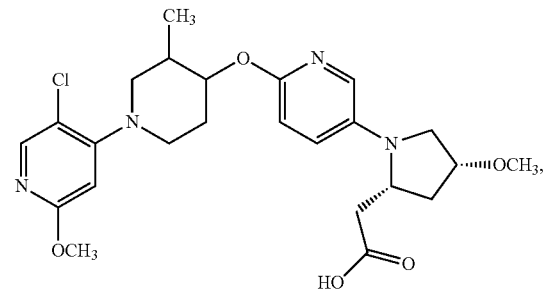
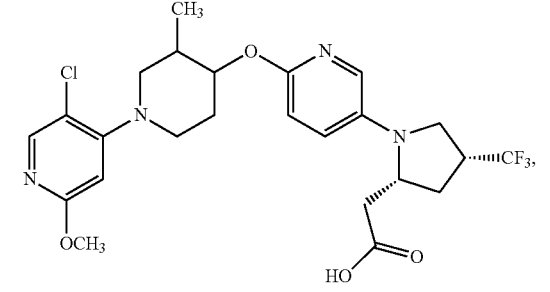
228
-continued
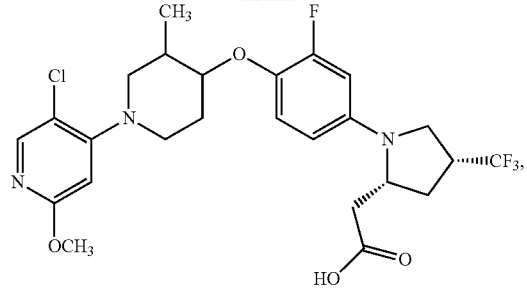
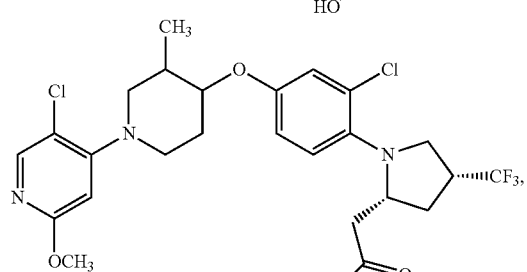
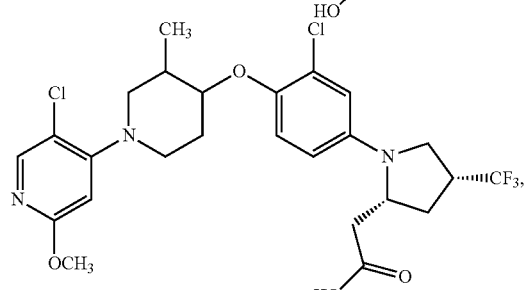
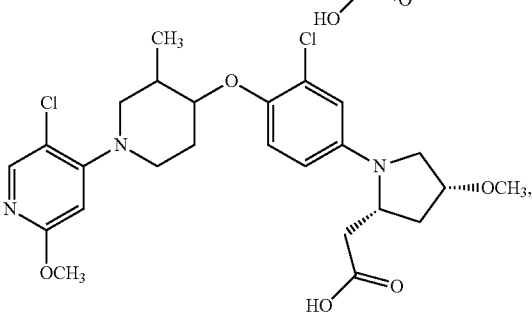
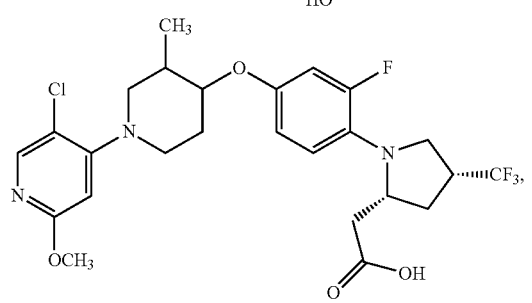
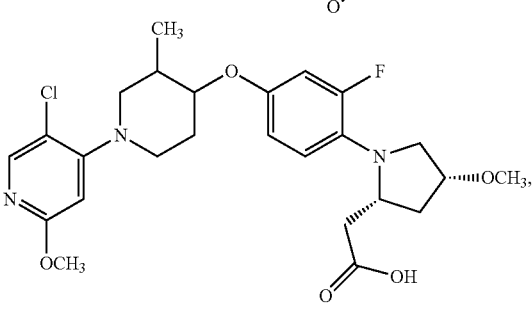

229
-continued
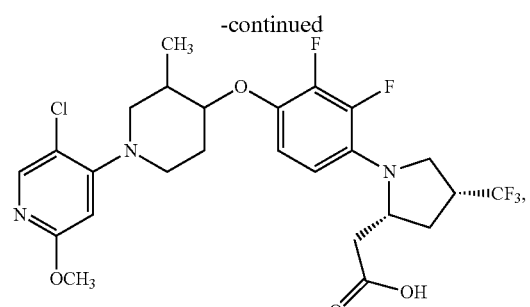
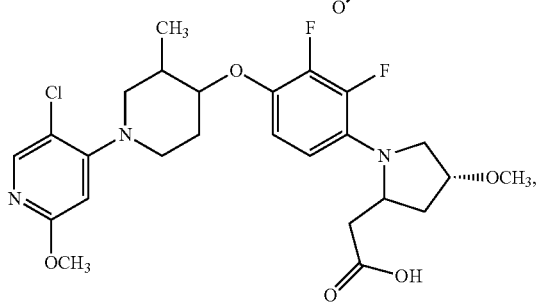
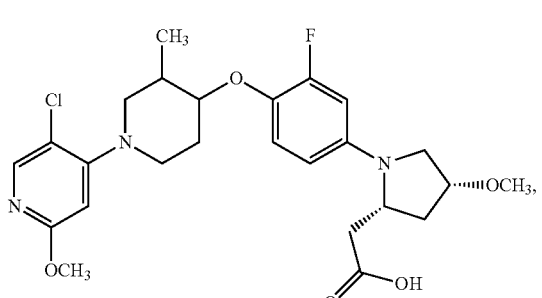
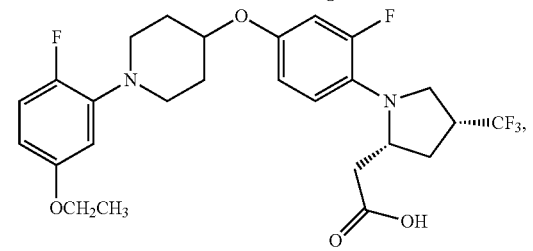
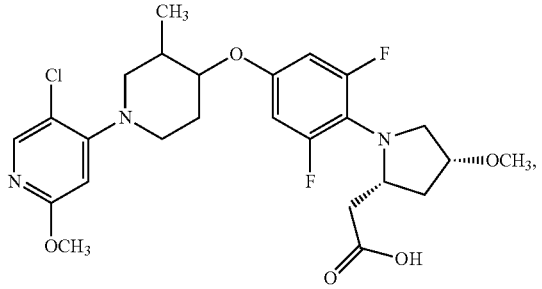
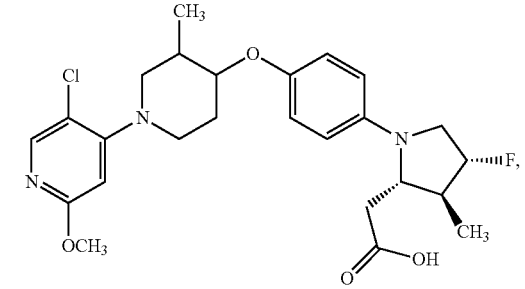
230
-continued
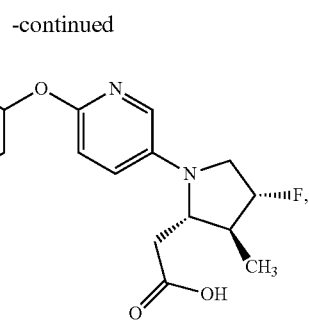
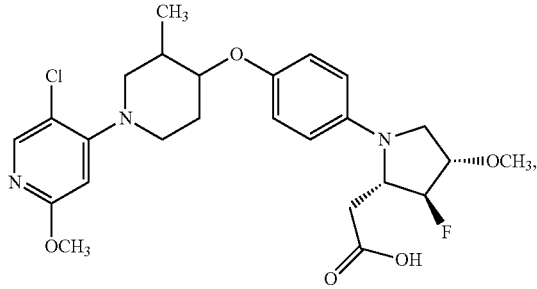
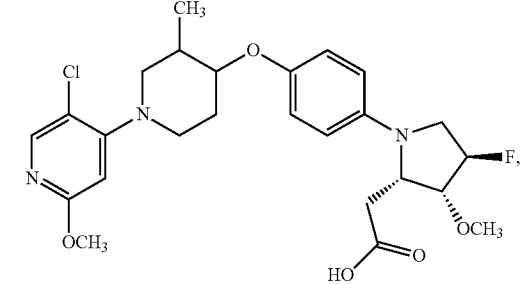
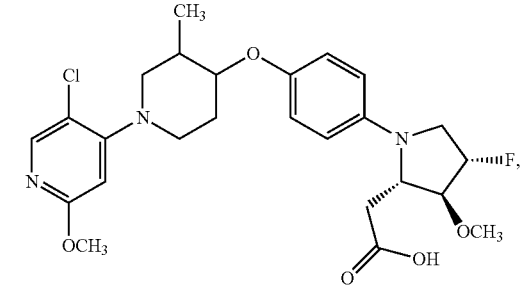
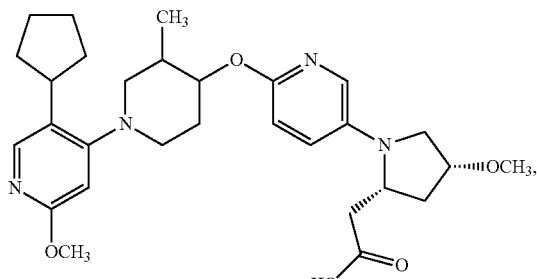
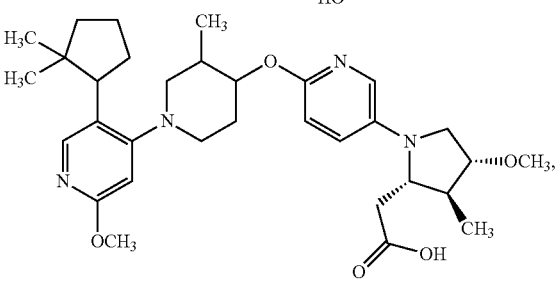

231
-continued
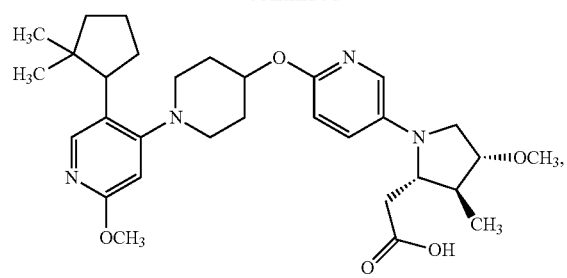
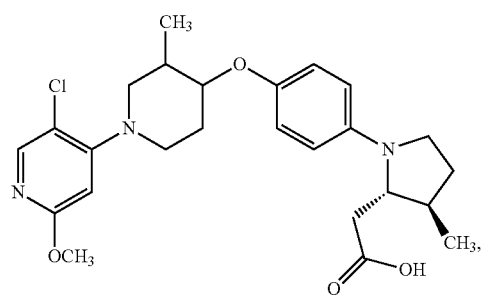
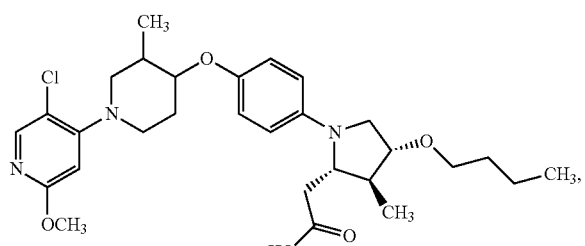
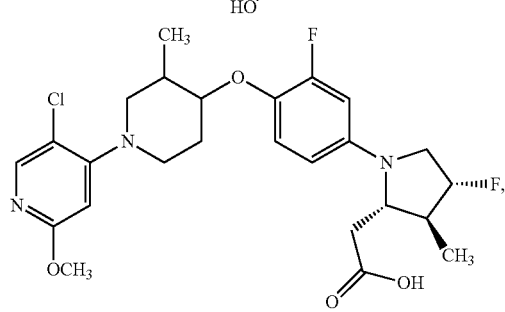
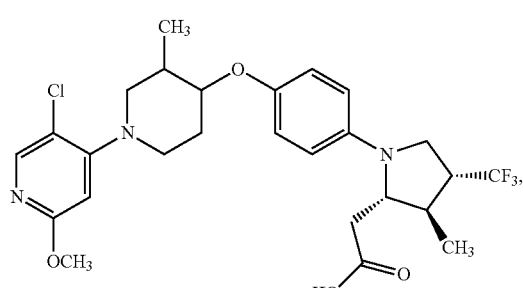
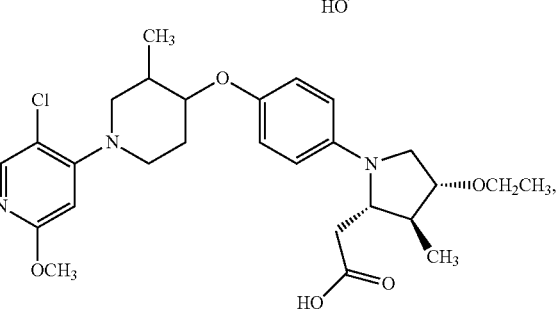
232
-continued

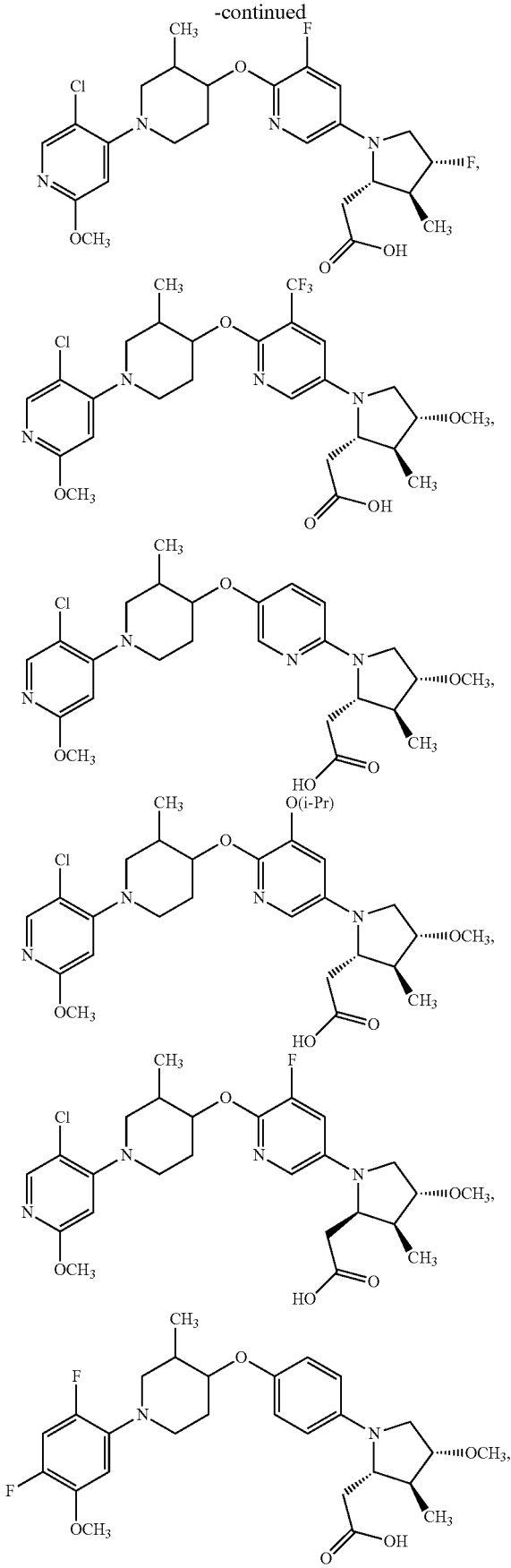
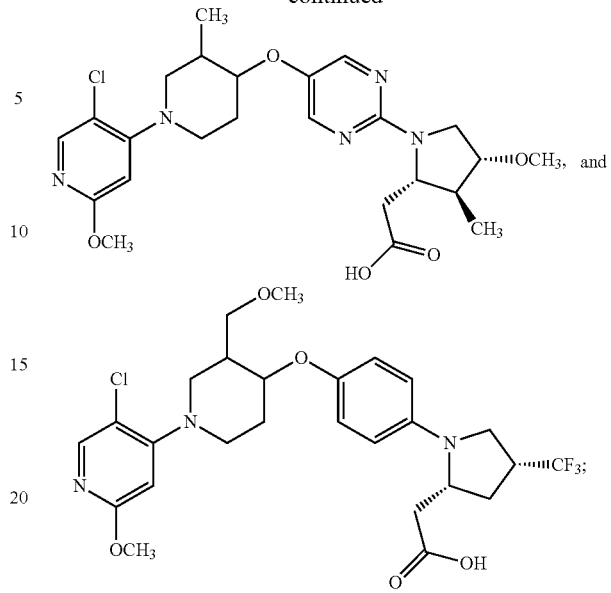

or a stereoisomer, a tautomer, or a pharmaceutically acceptable salt thereof.

11. A pharmaceutical composition, comprising a pharmaceutically acceptable carrier and a compound of claim 1, or a stereoisomer, a tautomer, or a pharmaceutically acceptable salt thereof.

12. The pharmaceutical composition according to claim 11, further comprising one or more other suitable therapeutic agents selected from the group consisting of anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease and anti-inflammatory agents.

13. The pharmaceutical composition according to claim 11, further comprising a dipeptidyl peptidase-IV inhibitor and/or a sodium-glucose transporter-2 inhibitor.

14. A method for modulating or treating a disease comprising administering a therapeutically effective amount of a compound of claim 1, or a stereoisomer, a tautomer, or a pharmaceutically acceptable salt thereof, to a patient in need thereof; and the disease is selected from the group consisting of diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, acute coronary syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), non-cardiac ischemia, pancreatitis, lipid disorders, neurodegenerative disease, cognitive impairment, dementia, NASH (Non-Alcoholic Steato-Hepatitis), NAFLD (Non-Alcoholic Fatty Liver Disease) and liver cirrhosis.

15. The method of claim 14, wherein the compound, or a stereoisomer, a tautomer, or a pharmaceutically acceptable salt thereof, was administered simultaneously, separately or sequentially with an additional therapeutic agent.

* * * * *